US012428472B2

(12) United States Patent
Scheid et al.

(10) Patent No.: US 12,428,472 B2
(45) **Date of Patent: *Sep. 30, 2025**

(54) HUMAN IMMUNODEFICIENCY VIRUS NEUTRALIZING ANTIBODIES AND METHODS OF USE THEREOF

(71) Applicants: The Rockefeller University, New York, NY (US); California Institute of Technology, Pasadena, CA (US)

(72) Inventors: Johannes Scheid, New York, NY (US); Michel Nussenzweig, New York, NY (US); Pamela J. Bjorkman, Altadena, CA (US); Ron Diskin, Rehovot (IL)

(73) Assignees: The Rockefeller University, New York, NY (US); California Institute of Technology, Pasadena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/597,018

(22) Filed: Mar. 6, 2024

(65) Prior Publication Data

US 2024/0254206 A1 Aug. 1, 2024

Related U.S. Application Data

(60) Continuation of application No. 18/172,836, filed on Feb. 22, 2023, now Pat. No. 12,071,470, which is a continuation of application No. 17/248,143, filed on Jan. 11, 2021, now Pat. No. 11,634,478, which is a continuation of application No. 15/719,738, filed on Sep. 29, 2017, now Pat. No. 10,889,633, which is a division of application No. 14/118,496, filed as application No. PCT/US2012/038400 on May 17, 2012, now Pat. No. 9,783,594.

(60) Provisional application No. 61/486,960, filed on May 17, 2011.

(51) Int. Cl.

| | |
|---|---|
| ***G01N 33/569*** | (2006.01) |
| ***C07K 16/10*** | (2006.01) |
| *A61K 39/00* | (2006.01) |

(52) U.S. Cl.

CPC ...... *C07K 16/1045* (2013.01); *C07K 16/1063* (2013.01); *G01N 33/56983* (2013.01); *A61K 2039/505* (2013.01); *C07K 2317/10* (2013.01); *C07K 2317/21* (2013.01); *C07K 2317/34* (2013.01); *C07K 2317/55* (2013.01); *C07K 2317/56* (2013.01); *C07K 2317/76* (2013.01); *C07K 2317/92* (2013.01)

(58) Field of Classification Search

CPC .... A61K 2039/505; A61P 31/12; A61P 31/18; C07K 16/1045; C07K 16/1063; C07K 2317/55; C07K 2317/76; C07K 2317/56; C07K 2317/10

See application file for complete search history.

(56) References Cited

U.S. PATENT DOCUMENTS

| | | | |
|---|---|---|---|
| 5,750,105 A | 5/1998 | Newman et al. | |
| 5,830,663 A | 11/1998 | Embleton et al. | |
| 6,114,143 A | 9/2000 | Eda et al. | |
| 6,228,361 B1 | 5/2001 | Posner | |
| 6,465,172 B1 | 10/2002 | Devico et al. | |
| 7,585,961 B2 | 9/2009 | Van De Winkel et al. | |
| 7,763,247 B2 | 7/2010 | Watkins et al. | |
| 9,493,549 B2 | 11/2016 | Diskin et al. | |
| 9,695,230 B2 | 7/2017 | Kwong et al. | |
| 9,783,594 B2 | 10/2017 | Scheid et al. | |
| 9,890,207 B2 | 2/2018 | Diskin et al. | |
| 10,035,844 B2 | 7/2018 | Kwong et al. | |
| 10,676,521 B2 | 6/2020 | Nussenzweig et al. | |
| 12,071,470 B2 * | 8/2024 | Scheid | C07K 16/1045 |
| 2003/0223994 A1 | 12/2003 | Hoogenboom et al. | |
| 2004/0005667 A1 | 1/2004 | Ratti et al. | |
| 2005/0288864 A1 | 12/2005 | Cattaneo et al. | |
| 2007/0264265 A1 | 11/2007 | Goldenberg et al. | |
| 2008/0050754 A1 | 2/2008 | Yamada et al. | |
| 2008/0193465 A1 | 8/2008 | Dimitrov et al. | |
| 2009/0155164 A1 | 6/2009 | Brasel et al. | |
| 2009/0170792 A1 | 7/2009 | Hart et al. | |
| 2009/0202568 A1 | 8/2009 | Eriksson et al. | |
| 2009/0226922 A1 | 9/2009 | Grawunder et al. | |
| 2011/0091475 A1 | 4/2011 | Pass et al. | |

FOREIGN PATENT DOCUMENTS

| | | |
|---|---|---|
| EP | 1728864 A1 | 12/2006 |
| EP | 2186888 A1 | 5/2010 |
| EP | 2281845 A1 | 2/2011 |
| WO | 2002/068649 A2 | 9/2002 |
| WO | 03044036 A1 | 5/2003 |
| WO | 03106478 A2 | 12/2003 |
| WO | 2010136598 A1 | 12/2010 |
| WO | 2011020079 A1 | 2/2011 |

(Continued)

OTHER PUBLICATIONS

2011ScheidEA_Science-Sequence and Structural Convergence of Broad and Potent HIV Antibodies That Mimic CD4 Binding.
Adamczyk et al., "Sequencing of anti-thyroxine monoclonal antibody fab fragment by ion trap mass spectrometry," Rapid Commun Mass Spectrom (2000): vol. 14, No. 11, pp. 999-1007 Abstract Only.
Brekke et al., "Therapeutic Antibodies for Human Diseases at the Dawn of the Twenty-First Century" Nature (Jan. 2003); 2:52-62.
Butler, Declan, "First trials of blood-based Ebola therapy kick off," Nature News (2014)—3 pages.
Caskey et al., "Broadly neutralizing anti-HIV-1 monoclonal antibodies in the clinic", Nature Medicine, vol. 25, 2019, pp. 547-553.
Dashti et al., "Broadly Neutralizing Antibodies against HIV: Back to Blood", Trends in Molecular Medicine, vol. 25, No. 3, 2019.
Eurasian Search Report published Apr. 30, 2023 in Eurasian Application No. 202292902, 2 pages.

(Continued)

*Primary Examiner* — Bao Q Li
(74) *Attorney, Agent, or Firm* — Fox Rothschild LLP

(57) ABSTRACT

The invention provides broadly neutralizing antibodies directed to epitopes of Human Immunodeficiency Virus, or HIV. The invention further provides compositions containing HIV antibodies used for prophylaxis, and methods for diagnosis and treatment of HIV infection.

23 Claims, 32 Drawing Sheets

Specification includes a Sequence Listing.

(56) References Cited

FOREIGN PATENT DOCUMENTS

| WO | 2011038290 A2 | 3/2011 |
| WO | 2012154312 A1 | 11/2012 |
| WO | 2013/86533 A1 | 6/2013 |
| WO | 2014/063059 A1 | 4/2014 |

OTHER PUBLICATIONS

European Extended Search Report mailed Jul. 20, 2021 based on related European Application No. 21151942.6, 6 pages.
Extended European Search Report issued in Application No. 12785929.6 dated Mar. 20, 2015.
Gautam et al., "A single injection of anti-HIV-1 antibodies protects against repeated SHIV challenges," Nature (2016); 000:1-12.
Genbank Accession No. DQ029980 "*Homo sapiens* HC1446 gene, Virtual Transcript, partial sequence, genomic survey sequence" [online] <https://www.ncbi.nlm.nih.gov/nucgss/66881184/>, uploaded Dec. 6, 2006.
GenBank Accession No. AF013625 "*Homo sapiens* cone T1-2 immunoglobulin heavy chain variable region (VH4) gene, partial cds," [online] <http://www.ncbi.nlm.nih.gov/nuccore/3135412>, uploaded: May 16, 1998.
GenBank Accession No. AF062279 "*Homo sapiens* clone Xu-51 immunoglobulin heavy chain variable region (IGH) mRNA, partial cds," [online] <http://www.ncbi.nlm.nih.gov/nuccore/3171030>, uploaded: May 9, 2001.
GenBank Accession No. AF174028 "*Homo sapiens* clone 77u-c10 immunoglobulin heavy chain variable region precursor (IgH) mRNA, partial cds," [online] <http://www.ncbi.nlm.nih.gov/nuccore/5834015>, uploaded: May 8, 2001.
GenBank Accession No. AF283787 "*Homo sapiens* isolate B-DLCL0018 clone 1 immunoglobulin heavy chain variable region mRNA, partial cds," [online] <http://www.ncbi.nlm.nih.gov/nuccore/12006441>, uploaded: Jan. 2, 2001.
GenBank Accession No. AJ234179 "*Homo sapiens* mRNA for Ig heavy chain variable region, clone C6," [online] <http://www.ncbi.nlm.nih.gov/nucleotide/3821120>, uploaded: Dec. 10, 1999.
GenBank Accession No. AK130825.1 "*Homo sapiens* cDNA FLJ27315 fis, clone TMS06851, highly similar to Ig epsilon chain C region," [online] <http://www.ncbi.nlm.nih.gov/nucleodide/34527715>, uploaded: Sep. 14, 2006.
GenBank Accession No. AY452137 "*Homo sapiens* clone G14F7E5 immunoglobin heavy chain mRNA, partical cds," [online] <http://www.ncbi.nlm.nih.gov/nuccore/42415708>, uploaded: Jul. 16, 2004.
GenBank Accession No. AY996339 "*Homo sapiens* clone MM25 immunoglobin heavy chain variable region mRNA, partical cds," [online] <http://www.ncbi.nlm.nih.gov/nuccore/62911028>, uploaded: May 2, 2005.
GenBank Accession No. BC073765 "*Homo sapiens* immunoglobulin heavy constant alpha 2 (A2m marker), mRNA (cDNA clone IMAGE:4765168)," [online] <http://www.ncbi.nlm.nih.gov/nucleodide/49258099>, uploaded: Mar. 24, 2009.
GenBank Accession No. DQ459436 "*Homo sapiens* isolate MM42 immunoglobulin heavy chain variable region gene, partial cds," [online] <http://www.ncbi.nlm.nih.gov/nuccore/92111210>, uploaded: Apr. 22, 2006.
GenBank Accession No. HQ650795 "*Homo sapiens* isolate pateitn 5b B-cell receptor immunoglobulin heavy chain variable region (IGVH) gene, partial sequence," [online] <http://www.ncbi.nlm.nih.gov/nuccore/320117094>, uploaded: Apr. 11, 2011.
GenBank Accession No. U43756 "Human immunoglobulin heavy chain variable region mRNA, cell line 28e4, anti-RhD, partial cds," [online] <http://www.ncbi.nlm.nih.gov/nucleodide/1353797>, uploaded: Jun. 5, 1996.
International Preliminary Report on the Patentability for Application No. PCT/US2012/038400 mailed Nov. 19, 2013.
International Search Report for Application No. PCT/US2012/038400 mailed Aug. 31, 2012.
Larrick et al., "Rapid cloning of rearranged immunoglobulin genes from human hybridoma cells using mixed primers and the polymerase chain reaction," Biochem Biophys Res Commun (May 15, 1989): vol. 160, No. 3 pp. 1250-1256 Abstract Only.
Liu et al., "Broadly neutralizing antibodies for HIV-1: effecacies, challenges and opportunities", Emerging Microbes & Infections, 2020, vol. 9.
Liu et al., "Heterogeneity of Monoclonal Antibodies," Journal of Pharmaceutical Sciences (Jul. 2008); 97(7):2426-2447.
Mahomed et al., "Clinical Trials of Broadly Neutralizing Monoclonal Antibodies for Human Immunodeficiency Virus Prevention: A Review", The Journal of Infectious Diseases, 2021, 13;223(3), pp. 370-380.
McCoy, "The expanding array of HIV broadly neutralizing antibodies", Retrovirology, 2018, 15:70.
Parsons et al., "Importance of Fc-mediated functions of anti-HIV-1 broadly neutralizing antibodies", Retrovirology, 2018, 15:58.
Possas et al., "HIV cure: global overview of bNAbs' patents and related scientific publications", Expert Opinion on Therapeutic Patents, 2018, vol. 28, No. 7, pp. 551-560.
Progress Toward an HIV vaccine p. 1 published by NIH, National Cancer Institute, Jun. 28, 2022.
Robert-Guroff et al. "Vaccine Protection against a Heterologous, Non-Syncytium-Inducing, Primary Human Immunodeficiency Virus", J. Viral. 1998, vol. 72, pp. 10275-10280.
Scheid et al., "Sequence and structural convergence of broad and potent HIV antibodies that mimic CD4 binding," Scien ePub (Jul. 14, 2011): vol. 333, No. 6049, pp. 1633-1637.
Shingai et al., "Passive transfer of modest titers of potent and broadly neutralizing anti-HIV monoclonal antibodies block SHIV infection in macaques," J. Exp. Med. (2014); 10-2061-2074.
Sok et al., "Recent progress in broadly neutralizing antibodies to HIV", Nature Immunology, 2018, vol. 19, pp. 1179-1188.
Tiller et al., "Efficient generation of monoclonal antibodies from single human B cells by single cell RT-PCR and expression vector cloning," J. Immunol. Methods (Jan. 1, 2008); 329(1-2):112-124.
Tomaras, Georgia D. et al., "HIV-1-specific antibody responses during acute and chronic HIV-1 infection", Curr Opin HIV AIDS. Sep. 2009;4(5):373-379.
Written Opinion of the International Searching Authority for Application No. PCT/US2012/038400 mailed Aug. 31, 2012.
Wu et al., "Rational Design of Envelope Identifies Broadly Neutralizing Human Monoclonal Antibodies to HIV-1," Science (Aug. 13, 2010); 329:856-861.
Wu et al: "Focused Evolution of HIV-1 1-7 Neutralizing Antibodies Revealed by Structures and Deep Sequencing", Science, vol. 333, No. 6049, Aug. 11, 2011 (Aug. 11, 2011), pp. 1593-1602.
Zhou et al., "Structural basis for broad and potent neutralization of HIV-1 by antibody VRC01," Science, American Association for the Advancement of Science, US., Aug. 2010, vol. 329, No. 5993, pp. 811-817.

\* cited by examiner

C

D

3BNC60

FR 1 / CDR 1 / FR 2 / CDR 2

QVHLSQSGAAVTKPGASVRVSCEASGYKISDHFIHWWRQAPGQGLQWVGWINPKTGQPNNPRQFQG

FR 3 / CDR 3

RVSLTRQASWDFDTYSFYMDLKAVRSDDTAIYFCARQRSDFWDFDV

Figure 4A:
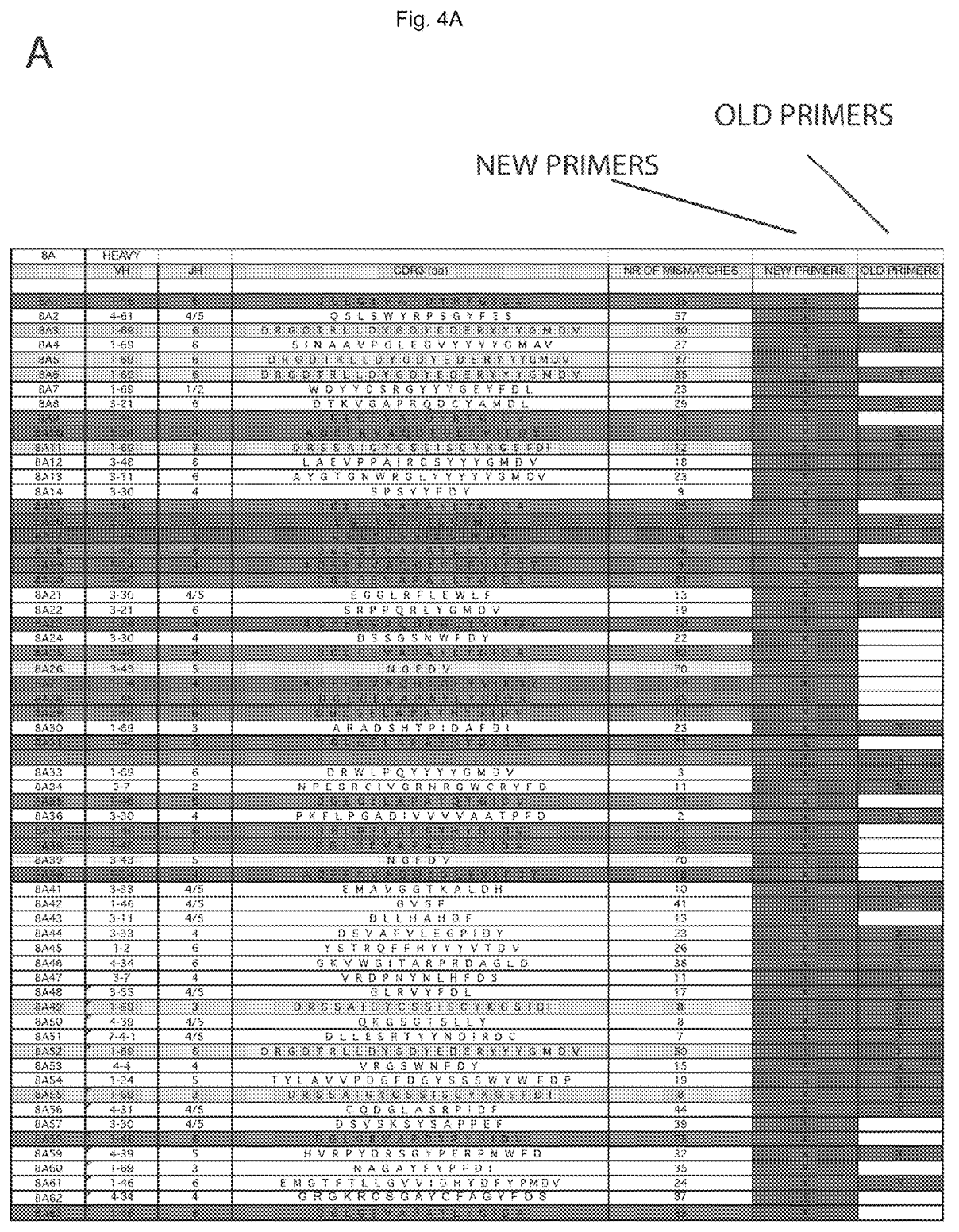

NEW PRIMERS

OLD PRIMERS

| 8A | HEAVY | | | | | |
|---|---|---|---|---|---|---|
| | VH | JH | CDR3 (aa) | NR OF MISMATCHES | NEW PRIMERS | OLD PRIMERS |
| | | | | | | |
| [illegible] | [illegible] | [illegible] | [illegible] | [illegible] | | |
| 8A2 | 4-61 | 4/5 | Q S L S W Y R P S G Y F E S | 57 | | |
| 8A3 | 1-69 | 6 | D R G D T R L L D Y G D Y E D E R Y Y Y G M D V | 40 | | |
| 8A4 | 1-69 | 6 | S I N A A V P G L E G V Y Y Y Y G M A V | 27 | | |
| 8A5 | 1-69 | 6 | D R G D T R L L D Y G D Y E D E R Y Y Y G M D V | 37 | | |
| 8A6 | 1-69 | 6 | D R G D T R L L D Y G D Y E D E R Y Y Y G M D V | 35 | | |
| 8A7 | 1-69 | 1/2 | W D Y Y D S R G Y Y Y G E Y F D L | 23 | | |
| 8A8 | 3-21 | 6 | D T K V G A P R Q D C Y A M D L | 29 | | |
| [illegible] | [illegible] | [illegible] | [illegible] | [illegible] | | |
| [illegible] | [illegible] | [illegible] | [illegible] | [illegible] | | |
| 8A11 | 1-69 | 3 | D R S S A I G Y C S S I S C Y K G S F D I | 12 | | |
| 8A12 | 3-48 | 6 | L A E V P P A I R G S Y Y Y G M D V | 18 | | |
| 8A13 | 3-11 | 6 | A Y G T G N W R G L Y Y Y Y Y G M D V | 23 | | |
| 8A14 | 3-30 | 4 | S P S Y Y F D Y | 9 | | |
| [illegible] | [illegible] | [illegible] | [illegible] | [illegible] | | |
| [illegible] | [illegible] | [illegible] | [illegible] | [illegible] | | |
| [illegible] | [illegible] | [illegible] | [illegible] | [illegible] | | |
| [illegible] | [illegible] | [illegible] | [illegible] | [illegible] | | |
| [illegible] | [illegible] | [illegible] | [illegible] | [illegible] | | |
| [illegible] | [illegible] | [illegible] | [illegible] | [illegible] | | |
| 8A21 | 3-30 | 4/5 | E G G L R F L E W L F | 13 | | |
| 8A22 | 3-21 | 6 | S R P P Q R L Y G M D V | 19 | | |
| [illegible] | [illegible] | [illegible] | [illegible] | [illegible] | | |
| 8A24 | 3-30 | 4 | D S S G S N W F D Y | 22 | | |
| [illegible] | [illegible] | [illegible] | [illegible] | [illegible] | | |
| 8A26 | 3-43 | 5 | N G F D V | 70 | | |
| [illegible] | [illegible] | [illegible] | [illegible] | [illegible] | | |
| [illegible] | [illegible] | [illegible] | [illegible] | [illegible] | | |
| [illegible] | [illegible] | [illegible] | [illegible] | [illegible] | | |
| 8A30 | 1-69 | 3 | A R A D S H T P I D A F D I | 23 | | |
| [illegible] | [illegible] | [illegible] | [illegible] | [illegible] | | |
| | | | | | | |
| 8A33 | 1-69 | 6 | D R W L P Q Y Y Y Y G M D V | 3 | | |
| 8A34 | 3-7 | 2 | N P E S R C I V G R N R G W C R Y F D | 11 | | |
| [illegible] | [illegible] | [illegible] | [illegible] | [illegible] | | |
| 8A36 | 3-30 | 4 | P K F L P G A D I V V V V A A T P F D | 2 | | |
| [illegible] | [illegible] | [illegible] | [illegible] | [illegible] | | |
| [illegible] | [illegible] | [illegible] | [illegible] | [illegible] | | |
| 8A39 | 3-43 | 5 | N G F D V | 70 | | |
| [illegible] | [illegible] | [illegible] | [illegible] | [illegible] | | |
| 8A41 | 3-33 | 4/5 | E M A V G G T K A L D H | 10 | | |
| 8A42 | 1-46 | 4/5 | G V S F | 41 | | |
| 8A43 | 3-11 | 4/5 | D L L H A H D F | 13 | | |
| 8A44 | 3-33 | 4 | D S V A F V L E G P I D Y | 23 | | |
| 8A45 | 1-2 | 6 | Y S T R Q F F H Y Y Y V T D V | 26 | | |
| 8A46 | 4-34 | 6 | G K V W G I T A R P R D A G L D | 38 | | |
| 8A47 | 3-7 | 4 | V R D P N Y N L H F D S | 11 | | |
| 8A48 | 3-53 | 4/5 | G L R V Y F D L | 17 | | |
| 8A49 | 1-69 | 3 | D R S S A I G Y C S S I S C Y K G S F D I | 8 | | |
| 8A50 | 4-39 | 4/5 | Q K G S G T S L L Y | 8 | | |
| 8A51 | 7-4-1 | 4/5 | D L L E S R T Y Y N D I R D C | 7 | | |
| 8A52 | 1-69 | 6 | D R G D T R L L D Y G D Y E D E R Y Y Y G M D V | 30 | | |
| 8A53 | 4-4 | 4 | V R G S W N F D Y | 15 | | |
| 8A54 | 1-24 | 5 | T Y L A V V P D G F D G Y S S S W Y W F D P | 19 | | |
| 8A55 | 1-69 | 3 | D R S S A I N Y C S S I S C Y K G S F D I | 8 | | |
| 8A56 | 4-31 | 4/5 | C Q D G L A S R P I D F | 44 | | |
| 8A57 | 3-30 | 4/5 | D S V S K S Y S A P P E F | 39 | | |
| [illegible] | [illegible] | [illegible] | [illegible] | [illegible] | | |
| 8A59 | 4-39 | 5 | H V R P Y D R S G Y P E R P N W F D | 32 | | |
| 8A60 | 1-69 | 3 | N A G A Y F Y P F D I | 35 | | |
| 8A61 | 1-46 | 6 | E M G T F T L L G V V I D H Y D F Y P M D V | 24 | | |
| 8A62 | 4-34 | 4 | G R G K R C S G A Y C F A G Y F D S | 37 | | |
| [illegible] | [illegible] | [illegible] | [illegible] | [illegible] | | |

B

Pt 8 Clones

```
                FR 1                          CDR 1        FR 2
                                              *  *            ●  * * ●●
VRC01      QVQLVQSGGQMKKPGESMRISCRASGYEFIDCTLNWIRLAPGKRPEWMGWLKPRG
VRC02      QVQLVQSGGQMKKPGESMRISCQASGYEFIDCTLNWVRLAPGRRPEWMGWLKPRG
NIH45-46   QVRLSQSGGQMKKPGESMRLSCRASGYEFLNCPINWIRLAPGRRPEWMGWLKPRG
NIH45-177  QVRLSQSGGQMKKPGESMRISCRASGYEFIDCTLNWIRLAPGRRPEWMGWLKPRG
NIH45-243  QVRLSQSGGQMKKPGESMRISCRASGYEFIDCTLNWIRLAPGRRPEWMGWLKPRG
```

```
             CDR 2                 FR 3                      CDR 3
           ○●●*●*●*  *    ○ * *●                           ●     ●●*
VRC01      GAVNYARPLQGRVTMTRDVYSDTAFLELRSLTVDDTAVYFCTRGKNCD----YNWDFEHWG
VRC02      GAVNYARPLQGRVTMTRDVYSDTAFLELRSLTADDTAVYYCTRGKNCD----YNWDFEHWG
NIH45-46   GAVNYARKFQGRVTMTRDVYSDTAFLELRSLTSD TAVYFCTRGKYCTARDYYNWDFEHWG
NIH45-177  GAVNYARPLQGRVTMTRDVYSDTAFLELRSLTADDTAVYFCTRGKNCN----YNWDFEHWG
NIH45-243  GAVNYARSFQGRVTMTRDVYSDTAFLELRSLTADDTAVYFCARGKNCD----YNWDFEHWG
```

B

```
                 FR 1                    CDR 1        FR 2       CDR 2
            ●                            *●○●
VRC01      EIVLTQSPGTLSLSPGETAIISCRTSQYGSLAWYQQRPGQAPRLVIYSGSTRAA
VRC02      EIVLTQSPGTLSLSPGETAIISCRTSQYGSLAWYQQRPGQAPRLVIYSGSTRAA
NIH45-46   EIVLTQSPATLSLSPGETAIISCRTSQSGSLAWYQQRPGQAPRLVIYSGSTRAA
NIH45-177  EIVLTQSPATLSLSPGETAIISCRTSQYGSLAWYQQRPGQAPRLVIYSGSTRAA
NIH45-243  EIVLTQSPATLSLSPGETAIISCRTSQYGSLAWYQQRPGQAPRLVIYSGSTRAA
```

```
                      FR 3                  CDR 3
                                             ***
VRC01      GIPDRFSGSRWGPDYNLTISNLESGDFGVYYCQQYEFFGQ
VRC02      GIPDRFSGSRWGPDYNLTIRNLESGDFGLYYCQQYEFFGQ
NIH45-46   GIPDRFSGSRWGADYNLSISNLESGDFGVYYCQQYEFFGQ
NIH45-177  GIPDRFSGSRWGPDYNLTISNLESGDFGVYYCQQYEFFGQ
NIH45-243  GIPDRFSGSRWGPDYNLTISNLESGDFGVYYCQQYEFFGQ
```

| | $IC_{50}$ | Pt 1 | Pt 3B | Pt 8 | NIH45 | Pt 12A |
|---|---|---|---|---|---|---|
| Clade B | 6535.3 | 88 | 400.4 | 23.2 | 61 | 101.3 |
| | RHPA4259.7 | 113 | 16.6 | 154.1 | 30 | 30.1 |
| | SC422661.8 | 49 | 25.9 | 16.6 | 107 | 62.7 |
| | PVO.4 | 89 | 78.1 | 74.1 | 195 | 116.3 |
| | TRO.11 | 72 | 24.5 | 62.2 | 208 | 53.6 |
| | YU2.DG | 131 | 25.4 | 32.7 | 92 | 50.6 |
| | H086.8 | >132 | >132 | >132 | 37 | |
| Clade C | Du172.17 | 228.42 | 418.62 | 86.463 | 349 | |
| | ZM53M.PB12 | 60.70 | 383.37 | >227 | 317 | |
| | ZM109F.PB4 | 86.82 | 12.97 | >227 | 73 | |
| Clade A | Q842.d12 | 12.196 | 6.158 | 4.056 | 50 | |
| | 3415.v1.c1 | 43.28 | 38.88 | 16.53 | 54 | |
| | 3365.v2.c20 | 111.54 | 28.46 | >227 | 94 | |
| CRF02_AG | 250-4 | >132 | 560.58 | 55.39 | 90 | |
| | 251-18 | >340 | 104.58 | 92.28 | 841 | |
| | 278-50 | >132 | >132 | >132 | >1000 | |
| CRF01_AE | 620345.c1 | >132 | >132 | >132 | >1000 | |
| Clade D | 3016.v5.c45 | >340 | 185.62 | >227 | ND | |
| | 231965.c1 | 304.48 | 86.54 | 171.56 | ND | |
| Clade G | X1254_c3 | 222.01 | 81.48 | >227 | ND | |
| CRF01_AE | R1166.c1 | >340 | 52.01 | >227 | ND | |

FIGURE 10A

```
            FR 1                       CDR 1     FR 2        CDR 2   To FIGURE 10A Cont'd
                10        20        30        40        50        60        70
1B2530    QVRLEQSGAAMRKPGASVTLSCQASGYNFVKYIIHWVRQKPGLGFEWVGMIDPYRGRPWSAHKFQGRLSLS
1B2586    QVRLEQSGAAMRKPGASVTLSCQASGYNFVKYIVHWVRQKPGLGFEWVGMIDPYRGRPWSAHKFQGRLSLS
1B2612  * QVRLEQSGTAMRKPGASVTLSCQASGYNFVKYIVHWVRQKPGLGFEWVGMIDPYRGRPWSAHKFQGRLSLS
1B2339    QVRLEQSGAAMRKPGASVTLSCQASGYNFVKYIVHWVRQKPGLGFEWVGMIDPYRGRPWSAHKFQGRLSLS
1B2680    QVRLEQSGVAMRKPGASVTLSCQASGYNFVKYIIHWVRQKPGLGFEWVGMIDPYRGRPWSAHKFQGRLSLS
1NC89   * QVRLEQSGGALRKPGASVTLSCQASGYNFVKYIIHWVRQRPGLGFEWVGMIDPYRGRPWYAHSFAGRLSLS
1NC3    * QVRLEQSGAAVRTPGASVTLSCQASGYKFVNYIIHWVRQRPGLAFEWVGMIDPYRGRPWSAHSFEGRLSLS
1B2364    QVRLEQSGAAVRKPGASVTLSCQASGYNFVNYIIHWVRQRPGLDFEWVGMIDPYRGRPWSAHKFQGRLSLS
1NC7    * QVRLEQSGAAVRKPGASVTLSCQASGYNFVNYIIHWVRQRPGLDFEWVGMIDPYRGRPWSAHKFQGRLSLS
1NC123  * QVRLEQSGAAVRKPGASVTLSCQASGYNFVNYIIHWVRQRPGLDFEWVGMIDPYRGRPWSAHKFEGRLSLS
1B2503    QVRLEQSGAAVRKPGASVTLSCQASGYNFVRYIIHWVRQRPGLDFEWVGMIDPYRGRPWSAHKFGGRLSLT
1B2351    QVRLEQSGTAVRKPGASVTISCQASGYNFVKFFIHWVRQRPGQGFEWVGMIEPFRGRPWSAGNFQGRLSLS
1B344     QVRLEQSGTAVRKPGASVTISCQASGYNFVKFFIHWVRQRPGQGFEWVGMIEPFRGRPWSAGNFQGRLSLS
1B2525    QVRLEQSGNAVRKPGASVTISCQASGYNFVKFFIHWVRQRPGQGFEWVGMIEPFRGRPWSAGNFQGRLSLS
1NC60   * QVRLEQSGAAVKKPGASVTISCQASGYNFVKFFIHWVRQRPGQGFEWVGMIEPYRGRPWSAGNFQGRLSLS
1NC82     QVRLFQSGAAMRKPGASVTISCEASGYNFMNYFVHWVRQRPGRGFEWLGMINPRGGRPWSAQSVQGRLTLT
1B2578    QVQLFQSGAAMRKPGASVTISCEASGYNFMNYFVHWVRQRPGRGFEWLGMINPRGGRPWSAQSVQGRLTLT
1B2538    QVRLFQSGAAMRKPGASVTISCEASGYNFLNYFVHWVRQRPGRGFEWLGMINPRGGRPWSAQSVQGRLTLT
1B2609  * QVRLFQSGAAMKKPGASVTISCEASGYNFMNYFVHWVRQRPGRGFEWLGMINPRGGRPWSAQSVQGRLTLT
1B2367    QVRLSQSGAAIKKPGASVTISCETEGYTFINYIIHWVRQPPGRGFEWLGMIDPRNGRPWFGQSVQGRLSLR
1NC24   * QVRLSQSGAAMKKPGASVTISCETEGYTFINYIIHWVRQPPGRGFEWLGMIDPRNGRPWFGQSVQGRLSLR
1B2573    QVRLSQSGAAIKKPGASVTISCETEGYTFINYIIHWVRQPPGRGFEWLGMIDPRNGRPWFGQSVQGRLSLR
1NC116  * QVRLSQSGAAVVKTGASVTISCETEGYNFVNYIIHWVRRPPGRGFEWLGMIDPRNGHPWFAQTVRGRLSLR
1NC18   * QVRLSQSGAAVMKTGASVTISCETEGFNFVNYIIHWVRRPPGRGFEWLGMIDPRNGHPWFAQTVRGRLSLR
1NC66   * QVRLSQSGAAVMKTGASVTISCETEGYNFVNYIIHWVRRPPGRGFEWLGMIDPKNGHPWFAQAVRGRLSLR
1NC48   * QVRLSQSGAAVVKTGASVTISCETEGYTFVNHIIHWVRQPPGRGFEWLGMIDPRNGHPWFGQRLRGRLSLR
1NC70     QVRLSQSGAAVVKTGASVTISCETEGYTFVNYIIHWVRQPPGRGFEWLGMIDPRNGHPWFGQRFRGRLSLR
1NC52     QVRLSQSGAAVVKTGASVTISCETEGYTFVNYIIHWVRQPPGRGFEWLGMIDPRNGHPWFGQRLQGRLSLR
1NC29   * QVRLSQSGAAVVKTGASVTISCETEGYTFVNYIIHWVRQSPGRGFEWLGMIDPRNGHPWFGQRLRGRLSLR
1B2416    QVRLSQSGAAVKKPGASVTIVCETEGYNFIDYIIHWVRQPPGRGFEWLGMIDPRNGRPWSGQKVHGRLSLW
1NC108    QVHTFQSGSSMKKSGASVTISCEATGYNIKNYILHWVRQKPGRGFEWVGMIDPINGRPWFGQPFRGRLTLT
1NC46   * QVQFFQSGSSMKKSGASVTISCEATGYNIKNHILHWVRQKPGRGFEWVGMIDPINGRPWFGQAFRGRLTLT
1NC117  * QVRLVQSGAQLKKPGASVTVSCEASGYNFVNYIINWVRQTPGQGFEWVGMIDPRRGRPWSAQKFQGRLTLT
1NC9    * QVRLVQSGAQLKKPGASVTVSCEASGYNFVNYIINWVRQTPGRSFEWVGMIDPRRGRPWSAQKFQGRLTLT
1NC107    QVRLVQSGPQVKTAGASMRVSCEASGYRFLDYIIVWIRQTHGQHFEYVGMINPRGGTPWPSSKFRDRLTLT
1NC109  * QVSLVQSGPQVKTPGASMRVSCETSGYRFLDYIIVWIRQTHGQHFEYVGMINPRGGTPWPSSKFRDRLTMT
1NC56   * QVRLVQSGPQVKTPGASMRVSCEASGYRFLDYIIVWIRQTHGQHFEYVGMINPRGGTPWPSSKFRDRLSLT
1NC118    QVRLVQSGPQVKTPGASMRISCEASGYRFQDYIIVWIRQTHGQGFEYVGMINPRGGTPWSSSKFRDRLSLT
1NC110  * QVRLVQSGPQMKTPGASLRLSCEVSGYRFLDYFIVWVRQTGGQGFEYVGMINPRGGRPWSSWKFRDRLSLT
1NC33   * QVRLVQSGPQVKTPGASIRLSCEASGYRFLDYFIVWVRQTPGQGFEYVGMINPRGGRPWSSWKFRDRLSLT
1NC122  * QVRLVQSGPQVKRPGASIRLSCETSGYRFQDYIVAWIRQTRGQRFEFVGMVNPRGGRPWPSSKFRDRVTLT
1NC95     QVRLVQSGPQVKRPGASIRLSCESSGYRFQDYIVAWIRQTRGQGFEFVGMVNPRGGRPWPSSRFRDRVTLT
```

FIGURE 10A Cont'd

From FIGURE 10A

FR 3 CDR 3

80 90 100 110 120 130

```
RDTSMEILYMTLTSLKSDDTATYFCARAEAASDS---HSRPIMFD--------------HWGQGSRVTVSSASTKG
RDTSMEILYMTLTSLKSDDTATYFCARAEAASDS---HSRPIMFD--------------HWGQGSRVTVSSASTKG
RDTSMEILYMTLTSLKSDDTATYFCARAEAASDS---HSRPIMFD--------------HWGQGSRVTVSSASTKG
RDTSMEILYMTLTSLTSDDTATYFCARAEAASDS---HSRPIMFD--------------HWGQGSRVTVSSASTKG
RDTSMEILYMTLTSLKSDDTATYFCARAEAASDI---HSRPIILTGPGEYGLDLEHMDWTWRILCLLAVAPGCHSQ
RDTSTETLYMTLSSLKSDDTATYFCARAEAASDS---HSRPI-------------MDWTWRILCLLAVVPASTKG
RDVSMEILYMTLTSLRSDDTATYFCARAEAESQS---HSRPIIS------------------------TSGAR--
RDVSTEILYMTLSSLRSDDTATYFCARAEAESQS---HSRPIMFD--------------FWGQGSRVTVSSASTKG
RDVSTEILYMTLNSLRSDDTATYFCARAEAESQS---HSRPIMFD--------------SWGQGSRVTVSSASTKG
RDVSTEVLYMTLSSLRSDDTATYFCARAEAESQS---HSRPIMFD--------------YWGQGSRVTVSSASTKG
RDVSTEILYMTLTSLRSDDTATYFCARAEAESQS---HSRPIMFD--------------SWGQGSRVTVSSASTKG
RDVSTETLYMTLNNLRSDDTAVYFCARLEAESDS---HSRPIMFD--------------HWGHGSLVTVSSASTKG
RDVSTETLYMTLNNLRSDDTAVYFCARLEAESDS---HSRPIMFD--------------HWGHGSLVTVSSASTKG
RDVSTETLYMTLNNLRSDDTAVYFCARLEAESDS---HSRPIMFD--------------HWGHGSLVTVSSASTKG
RDVSTETLYMTLNNLRSDDTAVYFCARLEAESDS---HSRPIMFD--------------HWGHGSLVTVSSASTKG
RDTSTEMFYMRLDGLRSDDTATYFCARNEADYHDGNGHSLRGMFD--------------YWGQGSLITVSSASTKG
RDTSTEMFYMRLDGLRSDDTATYFCARNEADYHDGNGHSLRGMFD--------------YWGQGSLITVSSASTKG
RDTSTEMFYMRLDGLRSDDTATYFCARNEADYHDGNGHSLRGMFD--------------YWGQGSLITVSSASTKG
RDISTEMFYMRLDGLRSDDTATYFCARNEADYHDGNGHSLRGMFD--------------YWGQGSLITVSSASTKG
RDTYTEVVYMTLSGLTSDDAGHYFCARNEPQYHDGNGHSLPGMFD--------------YWGQGTLVAVSSASTKG
RDTYTEVVYMTLSGLTSDDAGLYFCARNEPQYHDGNGHSLPGMFD--------------YWGQGTLVAVSSASTKG
RDTYTEVVYMTLSGLTSDDTGLYFCARNEPQYHDGNGHSLPGMFD--------------SWGQGTLVAVSSASTKG
RDTFKETVYMTLSGLTSDDTGVYFCARNEPQYH-----SLPGMFD--------------YWGHGTPVTVSSASTKG
RDTFNEIVYMTLSGLTTDDTGLYFCARNEPQYH-----SLPGMFD--------------YWGQGTPVTVSSASTKG
RDTFNEVVYMTLSGLTSDDTGLYFCARNEPQYHDGNGHSLPGMFD--------------FWGQGTLVTVSSASTKG
RDRSTETVFMTLSGLTSDDIGIYFCARNEPQYFDGSGHSLPGMFD--------------YWGQGTRVVVSSASTKG
RDRSTETVFMTLSGLTSDDNGIYFCARNEPQYYDGSGHSLPGMFD--------------YWGQGTRVVVSSASTKG
RDRSTETVFMTLSGLTSDDTGIYFCARNEPQYYDGSGHSLPGMFD--------------YWGQGTRVVVSSASTKG
RDRSTETVFMTLSGLTSDDTAIYFCARNEPQYYDGSGHSLPGMFD--------------YWGQGTRVVVSSASTKG
RDTSTEKVYMTLTGLTSDDTGLYFCGRNEPQYHDDNGHSLPGMID--------------YWGQGTMVTVSSASTKG
RDLSTETFYMSLSGLTSDDTATYFCARREADYHDGNGHTLPGMFD--------------FWGPGTLITVSSASTKG
RDLSTETFYMSLSGLTSDDTATYFCARREADYHDGNGHTLPGMFD--------------FWGPGTLVTVSSASTKG
RDIDSEKLYMHLSGLRGDDTAVYYCARQDSDFHDGHGHTLRGMFD--------------SWGQGSPVTVSSASTKG
RDIDSEKLYMHLSGLRGDDTAVYYCARQDSDFHDGHGHTLRGMFD--------------SWGQGSPVTVSSASTKG
RDIYTDTFYLGLNNLGSGDTAIYFCARLEADGDD----YSPKMFD--------------YWGQGTRIIVSAASTKG
RDIHTDTFYLGLNNLRSDDTAIYFCARLEADGDD----YSPKMFD--------------YWGQGTRIIVSAASTKG
RDIHTDTFYLGLNNLGSDDTAIYFCARLEADGDD----YSPKMFD--------------HWGQGTRIIVSAASTKG
RDIYTDTFYLGLNNLGSDDTAIYFCARLEADGGD----YSPKMFD--------------YWGQGTRIIVSAASTKG
RDIETDTFYLGLNNLRSDDTAIYFCARLEADGDN----YSPKMVD--------------YWGQGTKIIVSPASTKG
REIDTDTFYLGLSNLRSDDTAIYFCARLEADGDD----YSPKMVD--------------YWGQGTKIIVSAASTKG
RDIESETFHLGLNDLTSDDTATYFCARLEADGAD----YSPKMFD--------------FWGQGTKIVVSPASTKG
RDIESETFYLGLNDLTSDDTATYFCARLEADGSD----YSPKMFD--------------FWGQGTKIVVSPASTKG
```

FIGURE 10A Cont'd

| Protein | SEQ ID NO: |
|---|---|
| 1B2530 | 1020 |
| 1B2586 | 1021 |
| 1B2612 | 1022 |
| 1B2339 | 1023 |
| 1B2680 | 1024 |
| 1NC89 | 1025 |
| 1NC3 | 1026 |
| 1B2364 | 1027 |
| 1NC7 | 1028 |
| 1NC123 | 1029 |
| 1B2503 | 1030 |
| 1B2351 | 1031 |
| 1B344 | 1032 |
| 1B2525 | 1033 |
| 1NC60 | 1034 |
| 1NC82 | 1035 |
| 1B2578 | 1036 |
| 1B2538 | 1037 |
| 1B2609 | 1038 |
| 1B2367 | 1039 |
| 1NC24 | 1040 |
| 1B2573 | 1041 |
| 1NC116 | 1042 |
| 1NC18 | 1043 |
| 1NC66 | 1044 |
| 1NC48 | 1045 |
| 1NC70 | 1046 |
| 1NC52 | 1047 |
| 1NC29 | 1048 |
| 1B2416 | 1049 |
| 1NC108 | 1050 |
| 1NC46 | 1051 |
| 1NC117 | 1052 |
| 1NC9 | 1053 |
| 1NC107 | 1054 |
| 1NC109 | 1055 |
| 1NC56 | 1056 |
| 1NC118 | 1057 |
| 1NC110 | 1058 |
| 1NC33 | 1059 |
| 1NC122 | 1060 |
| 1NC95 | 1061 |

```
              FR 1                      CDR 1     FR 2        CDR 2
                   10        20         30        40        50        60
                    .         .          .         .         .         .
3BNC75    QVQLLQSG--AAVTKPGASVRVSCEASG----YNIRDYFIHWWRQAPGQGLQWVGWINPKTGQPNNPRQF
3B16      QVQLLQSG--AAVTKPGASVRVSCEASG----YNIRDYFIHWWRQAPGQGLQWVGWINPKTGQPNNPCQF
3BNC95    QVQLLQSG--AAVTKPGASVRVSCEASG----YNIRDYFIHWWRQAPGQGLQWVGWINPKTGQPNNPRLF
3BNC176   QVQLLQSG--AAVTKPGASVRVSCEASG----YNIRDYFIHWWRQAPGQGLQWVGWINPKTGQPNNPRQF
3B188     QAQLLQSG--AAVTKPGASVRVSCEASG----YNIRDYFIHWWRQAPGQGLQWVGWINPKTGQPNNPRQF
3B180     QVQLLQSG--AAVTKPGASVRVSCEASG----YNIRDYFIHWWRQAPGQGLQWVGWINPKTGQPNNPCQF
3BNC65    QVQLLPFG--GAVTKPGASVRVSCEASG----YNIRDYFIHWWRQAPGQGLQWVGWINPKTGQPNNPCQF
3BNC79*   QVQLLQSG--AAVTKPGASVRVSCEASG----YNIRDYFIHWWRQAPGQGLQWVGWINPKTGQPNNPRQF
3BNC105   HVQLLQSG--AAVTKPGASVRVSCEASG----YNIRDYFIHWWRQAPGQGLQWVGWINPKTGQPNNPRQF
3B183     QVRLLQSG--AAVTKPGASVRVSCEASG----YEIRDYFIHWWRQAPGQGLQWVGWINPKTGQPNNPRQF
3B21      QVRLLQSG--AAVTKPGASVRVSCEASG----YEIRDYFIHWWRQAPGQGLQWVGWINPKTGQPNNPRQF
3B191     QVRLLQSG--AAVTKPGASVRVSCEASG----YEIRDYFIHWWRQAPGQGLQWVGWINPKTGQPNNPRQF
3BNC128   QVHLSQSG--AAVTKPGASVRVSCEASG----YKISDHFIHWWRQAPGQGLQWVGWINPKTGQPNNPRQF
3BNC23    QVHLSQSG--AAVTKPGASVRVSCEASG----YKISDHFIHWWRQAPGQGLQWVGWINPKTGQPNNPRQF
3BNC196   QVQLLQSG--AAVTKPGASVRVSCEASG----YKISDHFIHWWRQAPGQGLQWVGWINPKTGQPNNPRQF
3BNC91*   QVQLLQSG--AVVSKPGASVRVSCEASG----YKIRDYFIHWWRQAPGQGLQWVGWINPQTGQPNIPRPF
3BNC134   QVQLVQSG--AALKKPGASLRISCQAYG----YKFTDHLIYWWRQAPGQGLEWIGWIKPETGQPSYSYKF
3BNC81    QVQLVQSG--AALKKPGASLRISCQAYG----YKFTDHLIYWWRQAPGQGLEWIGWIKPETGQPSYSYKF
3BNC84    QVQLVQSG--AALKKPGASLRISCQAYG----YKFTDHLIYWWRQAPGQGLEWIGWIKPETGQPSYSYKF
3BNC107   QVQLVQSG--AALKKPGASLRISCQAYG----YKFTDYLIHWWRQAPGQGLEWIGWIKPETGQPSYSYKF
3BNC42    QVQLVQSG--AALKKPGASVRISCQAYG----YKFTDYLIHWWRQAPGQGLEWIGWIKPETGQPSYSYKF
3BNC142*  QVQLVQSG--AALKKPGASVRISCQAYG----YKFTDHLIYWWRQAPGQGLEWIGWIKPETGQPSYSYKF
3BNC53*   QVQLVQSG--AALKKPGASVRISCQAYG----YKFTDHLIYWWRQAPGQGLEWIGWIKPETGQPSYAYKF
3BNC123   QVQLVQSG--AALKKPGASVRISCQTYG----YKFTDHLIYWWRQAPGQGLEWIGWIKPETGQPSYSYRF
3BNC153   QVQLVQSG--AALKKPGASLRISCLTYG----YKFTDHLIYWWRQAPGQGLEWIGWIKPETGQPSYSYRF
3BNC156*  QVQLVQSG--AALKKPGASLRISCQTYG----YKFTDHLIYWWRQAPGQGLEWIGWIKPETGQPSYSYRF
3BNC72    QVQLVQSG--AALKKPGASLRISCQTYG----YKFTDHLIYWWRQAPGQGLEWMGWIKPETGQPSYSYRF
3BNC158   QVQLVQSG--AALKKPGASLRISCQTYG----YKFTDHLIYWWRQAPGQGLEWIGWIKPETGQPSYSYRF
3BNC66    QVQLVQSG--AALKKPGASLRISCQTYG----YKFTDHLIYWWRQAPGQGLEWIGWIKPETGQPSYSYRF
3BNC159   QVQLVQSG--AALKKPGASVRISCQTYG----YKFTDHLIHWWRQAPGQGLEWIGWIKPETGQPSYSSRF
3BNC151   QVQLVQSG--ATLKKPGASVRISCQAYG----YKFTDHLIHWWRQAPGQGLEWIGWIKPETGQPSYAYKF
3BNC108*  QVQLVQSG--TAVKKPGASVRVSCQASG----YTFTDYFIYWWRQAPGQGLEWLGWINPRTSQPSYPYRF
3BNC55    QVQLVQSG--TAVKRPGASVRVSCQASG----YTFTDYFIYWWRQAPGQGLEWLGWINPLTSQPSYPSRF
3BNC89    QVQLVQSG--TAVKRPGASVRVSCQASG----YTFIDHFIYWWRQAPGQGLEWLGWINPLTSQPSYPSRF
3ANC41    QVQLVQSG--AAVKKPGASVKVSCETYG----YTFTDHFMHWWRQAPGQGLEWMGWINPYSSAVSYSPRY
3ANC87    QVQLVQSG--GAVKKPGASVKVSCETYG----YTFTDHFMHWWRQAPGQGLEWMGWINPYSSAVSYSPRY
3ANC66*   QVQLVQSG--AAVKKPGASVKVSCETYG----YKFTDHFMHWWRQAPGQGLEWMGWINPYSSAVSYSPRY
3ANC79    QVQLVQSG--AAVKKPGASVKVSCEAYG----YKFTDHFMHWWRQAPGQGLEWMGWINPYTSAVNYSPKY
3BNC126   QPQLVQSGSGAEVKKPGASVRISCEASE----YNVFDHFMQWVRQAPGQGLEWMGWINPRGGYPSYSPTF
3BNC149   QPQLVQSGSGAEVKKPGASVRISCEASE----YNVFDHFMQWVRQAPMEGLEWMGWINPRGGYPSYSPTF
3BNC102   QPQLVQSGSGAEVKKPGASVRISCEASE----YNVFDHFMQWVRQAPGQGLEWMGWINPRGGYPSYSPRF
```

FIGURE 10B Cont'd

From FIGURE 10B

FR 3 CDR 3

```
         70        80        90        100          110        120
         .         .         .         .            .          .
QGRVSLTRHASWDFDTFSFYMDLKALRSDDTAVYFCARQRS--DYWDFDVWGSGTQVTVSSASTKG
QGRVSLTRHASWDFDTFSFYMDLKALRSDDTAVYFCARQRS--DYWDFDVWGSGTQVTVSSASTK-
QGRVSLTRHASWDFDTFSFYMDLKAVRSDDTAVYFCARQRS--DYWDFDVWGSGTQVTVSSASTKG
QGRVSLTRHASWDFDTFSFYMDLKGLRSDDTAIYFCARQRS--DYWDFDVWGSGTQVTVSSASTKG
QGRVSLTRHASWDFDTFSFYMDLKGLRSDDTAIYFCARQRS--DYWDFDVWGSGTQVTVSSASTKG
QGRVSLTRQASWDFDTISFYMDLKALRLDDTAVYFCARQRS--DYWDFDVWGSGTQVTVSSASTKG
QGRVSLTRPASWDFDTISFYMDLKALRLDDTAVYFCARQRS--DYWDFDVWGSGTQVTVSSASTKG
QGRVSLTRQASWDFDTISFYMDLKALRLDDTAVYFCARQRS--DYWDFDVWGSGTQVTVSSASTKG
QGRVSLTRQASWDFDTFSFYMDLKALRLDDTAIYFCARQRS--DYWDFDVWGSGTQVTVSSASTKG
QGRVSLTRQASWDFDSYSFYMDLKALRSDDTAVYFCARQRS--DYWDFDVWGSGSQVTVSSASTKG
QGRVSLTRQASWDFDSYSFYMDLKALRSDDTAVYFCARQRS--DYWDFDVWGSGTQVTVSSASTKG
QGRVSLTRQASWDFDSYSFYMDLKALRSDDTGVYFCARQRS--DYWDFDVWGSGTQVTVSSASTKG
QGRVSLTRQASWDFDTYSFYMDLKVLRSDDTAIYFCARQRS--DFWDFDVWGSGTQVTVSSASTKG
QGRVSLTRQASWDFDTYSFYMDLKALRSDDTAIYFCARQRS--DFWDFDVWGSGTQVTVSSASTKG
QGRISLTRQASWDFDTFSFYMDLKALRSDDTAVYFCARQRS--DYWDFDVWGSGTQVTVSSASTKG
QGRVTLTRHASWDFDTFSFYMDLKALRSDDTAIYFCARRRS--DYCDFDVWGSGTHVTVSSASTKG
QGRVSLTRDTF---QEI-LFMNLRGLRSDDTAIYFCARRHS--DYCDFDVWGSGSQILVSSASTKG
QGRVSLTRDTF---QEI-LFMDLRGLRSDDTAIYFCARRHS--DYCDFDVWGSGSQILVSSASTKG
QGRVSLTRDTF---QEI-LFMDLRGLRSDDTAIYFCARRHS--DYCDFDVWGSGSQVIVSSASTKG
QGRVSLTRDTF---EEI-LFMDLRGLRSDDTAIYFCARRHS--DYCDFDVWGGGSQVLVSSASTKG
QGRVTLTRDTF---EEI-LFMDLRGLRSDDTAIYFCARRHS--DYCDFDVWGSGSQVIVSSASTKG
QGRVTLTRDTF---EEI-HFMDLRGLRYDDTATYFCARRHS--DYCDFDVWGSGSQVSVSSASTKG
QGRVTLTRDTF---EEI-HFMDLRGVRNDDTATYFCARRHS--DYCDFDVWGSGSQVIVSSASTKG
QGRVSLTRDTF---EEI-VFMDLRGLRSDDTAIYFCARRHS--DYCDFDVWGSGSQVLVSSASTKG
QGRVSLTRDTF---EEI-VFMDLRGLRSDDTAIYFCARRHS--DYCDFDVWGSGSQVIVSSASTKG
QGRVSLTRDTF---EEI-VFMDLRGLRSDDTAIYFCARRHS--DYCDFDVWGGPSQVIVSSASTKG
QGRVSLTRDTF---EEI-VFMDLRGLRSDDTAIYFCARRHS--DYCDFDVWGSGSQVIVSSASTKG
QGRVSLTRDTF---EEI-VFMDLRGLRSDDTAIYFCARRHS--DYCDFDVWGSGSQVLVSSASTKG
QGRVSLTRDTF---EEI-AFMDLRGLRSDDTAIYFCARRHT--DYCVFDVWGSGSQIIVSSASTKG
QGRVSLTRDTF---EEI-VFMDLRGLRSDDTAIYFCARRHS--DYCDFDVWGSGSQVLVSSASTKG
QGRVSLTRDTF---EEI-LFMDLRGLRSDDTAIYFCARRHS--DYCDLDVWGGGTQLLVSSASTKG
QGRVTLTRDIF---EEM-LYMDLRGLRSDDTGIYFCARRHS--DYCDFDIWGSGTQIIVSSASTKG
QGRLTLTRDTF---DEM-LYMDLRGLRSDDTGIYFCARRHS--DYCDFDIWGSGTQIIVSSASTKG
QGRLTLTRDTF---DEM-LYMDLRGLRSDDTGIYFCARRHS--DYCDFDIWGSGTQIIVSSASTKG
QGRVTMTRDTF---LET-VYMELRGLKFDDTAIYYCATRKSGRDYWSFDIWGQGTLVTVSSASTKG
QGRVTMTRDTF---LET-VYMELRGLKFDDTAIYYCATPKSGRDYWSFDLWGQGTLVTVSSASTKG
QGRVTMTRDTF---LET-VYMELRGLRFDDTAIYYCATPKSGRDYWSFDLWGQGTLVTVSSASTKG
QGRVTMTRDTF---LET-VYMELRGLRVDDTAIYYCATPKSGRDYWSFDLWGQGTLVTVSSASTKG
QGRLTFTRQPSWDDSTITFHMELRGLGHDDTAVYYCARPHSPDDAWSLDVWGRGTLVTVSSASTKG
QGRLTFTRQPSWDDSTITFHMELRGLRHDDTAVYYCARPHSPDDAWSLDVWGRGTLVTVSSASTKG
QGRLTFTRQPSWDDSSVTFHMELRGLRHDDTAVYYCARPHSPDDAWSLDVWGRGTLVTVSSASTKG
```

```
                FR 1                   CDR 1    FR 2        CDR 3
                 10        20        30        40        50        60
                  .         .         .         .         .         .
3ANC3    QVQLVQSG--ADVKKPGASVTVSCKTDEDEDDFRAH--LVQWMRQAPGQRLEWVGWIKPQTGQPSYAQKF
3ANC32   QVQLVQSG--ADVKKPGAAVTVSCKTDEDEDDFRAH--LMQWMRQAPGQRLEWVGWIKPQTGQPSYGQKF
3BNC104  EVQLVQSG--SDVRKPGAAVTVSCKADEDEDDFTAYNYFMHWVRQAPGHGLEWIGWINPRTGQPNHAKQF
3BNC106  VVQLVQSG--SDVRKPGAAVTVSCKADEDEDDFTAYNYFMHWVRQAPGHGLEWIGWINPRTGQPNHAKQF
3BNC44   EVQLVESG--SDVRKPGAAVTVSCKADEDEDDFTAYNYFMHWVRQAPGHGLEWIGWINPRTGQPNHAKQF
3BNC127  EVQLVESG--SDVRKPGAAVTVSCKADEDEDDFTAYNYFMHWVRQAPGQGLEWIGWINPRTGQPNHAKQF
3BNC6    QVQLVESG--SDVRKPGAAVTVSCKADEDEDDFTAYNYFMHWVRQAPGHGLEWIGWINPRTGQPNHAKQF
3BNC148  QVQLVQSG--SDVRKPGAAVTVSCKADEDEDDFTAYNYFMHWVRQAPGHGLEWIGWINPRTGQPNHAKQF
3BNC173  QVQLVQSG--SDVRKPGAAVTVSCKADEDEDDFTAYNYFMHWVRQAPGHGLEWIGWINPRTGQPNHAKQF
3BNC181  EVQLVQSG--SDVRKPGAAVTVSCKADEDEDDFTAYDYFMHWVRQAPGHGLEWIGWINPRTGQPNHAKQF
3BNC101  EVQLVQSG--SDVKKPGTTVTISCKADEDEDDFTAYNYFMHWVRQAPGQGLEWIGWINPRTGQPNHAKQL
```

FIGURE 10B Cont'd

From FIGURE 10B Cont'd

FR 3 CDR 3

```
      70        80        90        100       110       120
      .         .         .         .         .         .
QGRVTLTREVS----TSTVFLQLRNLRSDDTAVYYCARPRGGRDNWSFHVWGRGTLVTVSSASTKG
QGRVTLTREVS----TSTVFLQLRNLRSDDTAVYYCARPRGGRDNWSFHVWGRGTLVTVSSASTKG
QGRVTLTRERS----TSTVFMKLTNLRLDDTAVYFCARPLRGGDTWHYHSWGRGTSLTVSSASTKG
QGRVTLTRERS----TSTVFMKLTNLRLDDTAVYFCARPLRGGDTWHYHSWGRGTSLTVSSASTKG
QGRVTLTRERS----TSTVFMKLTNLRLDDTAVYFCARPLRGGDTWHYHSWGRGTSLTVSSASTKG
QGRVTLTRERS----TSTVFMKLTNLRLDDTAVYFCARPLRGGDTWHYHSWGRGTSLTVSSASTKG
QGRVTLTRERS----TSTVFMKLTNLRLDDTAVYFCARRLRGGDTWHYHSWGRGTSLTVSSASTKG
QGRVTLTRERS----TSTVFMKLTNLRLDDTAVYFCARRLRGGDTWHYHSRGRGTSLTVSSASTKG
QGRVTLTRERS----TSTVFMKLTNLRLDDTAVYFCARRLRGGDTWHYHSWGRGTSLTVSSASTKG
QGRVTLTRERS----TSTVFMKLTNLRLDDTAVYFCARRLRGGDTWHYHSWGRGTSLTVSSASTKG
QGRVTLTRERS----TSTVFMKLTNLRLDDTAVYFCARRLRGGDTWHYHSWGRGTSLIVSSASTKG
```

FIGURE 10B Cont'd

| Protein | SEQ ID NO: |
|---|---|
| 3BNC75 | 1062 |
| 3B16 | 1063 |
| 3BNC95 | 1064 |
| 3BNC176 | 1065 |
| 3B188 | 1066 |
| 3B180 | 1067 |
| 3BNC65 | 1068 |
| 3BNC79* | 1069 |
| 3BNC105 | 1070 |
| 3B183 | 1071 |
| 3B21 | 1072 |
| 3B191 | 1073 |
| 3BNC128 | 1074 |
| 3BNC23 | 1075 |
| 3BNC196 | 1076 |
| 3BNC91* | 1077 |
| 3BNC134 | 1078 |
| 3BNC81 | 1079 |
| 3BNC84 | 1080 |
| 3BNC107 | 1081 |
| 3BNC42 | 1082 |
| 3BNC142* | 1083 |
| 3BNC53* | 1084 |
| 3BNC123 | 1085 |
| 3BNC153 | 1086 |
| 3BNC156* | 1087 |
| 3BNC72 | 1088 |
| 3BNC158 | 1089 |
| 3BNC66 | 1090 |
| 3BNC159 | 1091 |
| 3BNC151 | 1092 |
| 3BNC108* | 1093 |
| 3BNC55 | 1094 |
| 3BNC89 | 1095 |
| 3ANC41 | 1096 |
| 3ANC87 | 1097 |
| 3ANC66* | 1098 |
| 3ANC79 | 1099 |
| 3BNC126 | 1100 |
| 3BNC149 | 1101 |
| 3BNC102 | 1102 |
| 3ANC3 | 1103 |
| 3ANC32 | 1104 |

| Protein | SEQ ID NO: |
|---|---|
| 3BNC104 | 1105 |
| 3BNC106 | 1106 |
| 3BNC44 | 1107 |
| 3BNC127 | 1108 |
| 3BNC6 | 1109 |
| 3BNC148 | 1110 |
| 3BNC173 | 1111 |
| 3BNC181 | 1112 |
| 3BNC101 | 1113 |

| | | FR 1 (1–29) · CDR 1 (30–34) · FR 2 (35–48) · CDR 2 (49–60) |
|---|---|---|
| | | 10 · 20 · 30 · 40 · 50 · 60 |
| 8ABM1 | | -GHLVQSGGGXKKPGTSVTISCLASEYTFTEFTIHRIRQAPGQGPLWLG-LIKGSGRLMTSY |
| 8ABM24 | | QGQLVQSGGGVKKPGSSVTISCLASEYTFTEFTIHWIRQAPGQGPLWLG-LIKRSGRLMTSY |
| 8ABM11 | | QGHLVQSGGGVKKPGTSVTLSCLASEYTFTEFTIHWIRQAPGQGPLWLG-LIKRSGRLMTSY |
| 8A253 | | QGQLVQSGGGLKKPGTSVTISCLASEYTFNEFVIHWIRQAPGQGPLWLG-LIKRSGRLMTAY |
| 8ANC131 | * | QGQLVQSGGGLKKPGTSVTISCLASEYTFNEFVIHWIRQAPGQGPLWLG-LIKRSGRLMTAY |
| 8ANC13 | * | QGQLVQSGGGVKKPGASVTISCLASEYTFNEFVIHWIRQAPGQGPLWLG-LIKRSGRLMTAY |
| 8ANC88 | | QGQLVQSGGGVKKPGTSVTISCLASEYTFNEFVIHWIRQAPGQGPLWLG-LIKRSGRLMTSY |
| 8ANC134 | * | QGQLVQSGGGVKKPGTSVTISCLASEYTFNEFVIHWIRQAPGQGPVWLG-LIKRSGRLMTSY |
| 8ANC26 | * | QGQLVQSGGGVKKPGTSVTISCLASEYTFNEFVIHWIRQAPGQGPVWLG-LIKRSGRLMTSY |
| 8ANC127 | | QGHLVQSGGGVKKLGTSVTISCLVSEYTFNEFVIHWIRQAPGQGPLWLG-LIKRSGRLMTSY |
| 8ANC40 | | QGHLVQSGGGVKKLGTSVTISCLASEYTFNEFVIHWIRQAPGQGPLWLG-LIKRSGRLMTSY |
| 8ABM13 | | QGHLVQSGGGVKKLGTSVTISCLASEDTFNEFVIHWIRQAPGQGPLWLG-LIKRSGRLMTSY |
| 8ANC22 | | QGHLVQSGGGVKKLGTSVTISCLASEDTFNEFVIHWIRQAPGQGPLWLG-LIKRSGRLMTSY |
| 8ABM12 | | QGHLVQSGGGVKKLGTSVTISCLASEYTFNEFVIHWIRQAPGQGPLWLG-LIKRSGRLMTSY |
| 8A275 | * | QGLLVQSGGGVKKLGTSVTISCLASEYTFNEFVIHWIRQAPGQGPLWLG-LIKRSGRLMTSY |
| 8ANC116 | | QGQLVQSGGGVKKLGTSVTISCLASEYTFNEFVIHWIRQAPGQGPLWLG-LIKRSGRLMTSY |
| 8ANC53 | | QGQLVQSGGGGKKLGTSVTISCLASEYTFNEFVIHWIRQAPGQGPLWLG-LIKRSGRLMTSY |
| 8ANC2 | | QGQLVQSGGGVKKLGTSVTIPCLASEYTFNEFVTHWIRQAPGQGPLWLG-LIKRSGRLMTSY |
| 8ANC30 | * | QGQLVQSGGGVKKLGTSVTISCLASEYTFNEFVIHWIRQALGQGLLWLG-LIKRSGRLMTSY |
| 8ABM26 | | QGQLVQSGGGVKKLGTSVTISCLASEYTFNEFVIHWIRQAPGQGPLWLG-LIKRSGRLMTSY |
| 8ABM20 | | QGHLVQSGGGVKKPGSSVTISCLASEYTFTEFTIHWIRQAPGQGPLWLG-LIKRSGRLMTSY |
| 8ANC18 | | QGHLVQSGGGVKKPGSSVTISCLASEYTFTEFTIHWIRQAPGQGPLWLG-LIKRSGRLMTSY |
| 8ANC182 | * | QGQLVQSGGGVKKPGTSVTISCLASEYTFTEFTIHWIRQAPGQGPLWLG-LIKRSGRLMTAY |
| 8ANC41 | | QGQLVQSGGGVKKTGTSVTISCLASEYTFTEFTIHWIRQAPGQGPLWLG-LIKRSGRLMTAN |
| 8ABM27 | | QGHLVQSGXEVKKPGSSVKVSCKASGGTFSXYAIGWVRQAPGQGLEWMGGIIPILGTTNYAQ |

FIGURE 10C Cont'd

From FIGURE 10C

FR3 CDR3

70 80 90 100 110 120

GFQDRLSLRRDRSTGTVFMELRSLRTDDTAVYYCARDGLGELAP-AYHYGIDVWGQGTTVIVTSASTS-
GFQDRLSVRRDRSTGTVFMELRSLRTDDTAVYYCARDGLGELAP-AYHYGIDVWGQGTTVIVTSASTS-
RFQDRLSLRRDRSTGTVFMELRSLRTDDTAVYYCARDGLGELAP-AYHYGIDAWGQGTTVIVTSASTS-
NFQDRLSLRRDRSTGTVFMELRGLRPDDTAVYYCARDGLGEVAP-DYRYGIDVWGQGSTVIVTAASTKG
NFQDRLRLRRDRSTGTVFMELRGLRPDDTAVYYCARDGLGEVAP-DYRYGIDVWGQGSTVIVTAASTKG
NFQDRLSLRRDRSTGTVFMELRGLRPDDTAVYYCARDGLGEVAP-DYRYGIDVWGQGSTVIVSAASTKG
KFQDRLNLRRDRSTGTVFMELRGLRPDDTAVYYCARDGLGEVAP-DYRYGIDVWGQGSTVIVTAASTKG
KFQDRLSLRRDRSTGTVFMELRGLRLDDTAVYYCARDGLGEVAP-AYHYGIDAWGQGSTVIVTSASTKG
KFQDRLSLRRDRSTGTVFMELRGLRLDDTAVYYCARDGLGEVAP-AYLYGIDAWGQGSKVIVTPASTKG
QFQDRLSLRRDRSTGTVFMELRGLRVDDTAVYYCARDGLGEVAP-AYLYGIDAWGQGTTVIVTSASTKG
QFQDRLSLRRDRSTGTVFMELRGLRVDDTAVYYCARDGLGEVAP-AYLYGIDAWGQGTTVIVTSASTKG
QFQDRLSLRRDRSTGTVFMELRGLRVDDTAVYYCARDGLGEVAP-AYLYGIDAWGQGTTVIVTSASTS-
QFQDRLSLRRDRSTGTVFMELRGLRVDDTAVYYCARDGLGEVAP-AYLYGIDAWGQGTTVIVTSASTKG
QFQDRLSLRRDRSTGTVFMELRGLRVDDTAVYYCARDGLGEVAP-AYLYGIDAWGQGTTVIVTSAST--
QFQDRLSLRRDRSTGTVFMELRGLRVDDTAVYYCARDGLGEVAP-AYLYGIDAWGQGTTVIVTSASTKG
QFQDRLSLRRDRSTGTVFMELRGLRVDDTAVYYCARDGLGEVAP-AYLYGIDAWGQGTTVIVSSASTKG
QFQDRLSLRRDRSTGTVFMELRGLRVDDTAVYYCARDGLGEVAP-AYLYGIDAWGQGTTVIVSSASTKG
QFQDRLSLRRDRSTGTVFMELRGLRVDDTAVYYCARDGLGEVAP-AYLYGIDAWGQGTTVIVTSASTKG
QFQDRLSLRRDRSTGTVFMELRGLRVDDTAVYYCARDGLGEVAL-AYLYGIDAWGQGTTVIVTSASTKG
QFQDRLSLRRDRSTGTVFMELRGLRVDDTAVYYCARDGLGEVAP-AYLYGIDAWGQGTTVIVTSASTS-
RFQDRLSLRRDRSTGTVFMELRGLRIDDTAVYYCARDGLGEVAP-AYLYGIDVWGQGTTVIVTSASTS-
RFQDRLSLRRDRSTGTVFMELRGLRIDDTAVYYCARDGLGEVAP-AYLYGIDVWGQGSTVIVTSASTS-
RFQDRLSLRRDRSTGTVFMELRNLRMDDTAVYYCARDGLGELAP-AYQYGIDVWGQGTTVIVSSASTKG
RFQDRLSLRRDRSTGTVFMELRSLRIDDTAVYYCARDGLGELAP-AYHYGIDVWGQGTTIIVTSASTKG
RFQGGVTITADESTNTAYMDVSSLRSDDTAVYYCAKAPYRPRGSGNYYYAMDVWGQGTTVIVSSASTS-

FIGURE 10C Cont'd

| Protein | SEQ ID NO: |
|---|---|
| 8ABM1 | 1114 |
| 8ABM24 | 1115 |
| 8ABM11 | 1116 |
| 8A253 | 1117 |
| 8ANC131 | 1118 |
| 8ANC13 | 1119 |
| 8ANC88 | 1120 |
| 8ANC134 | 1121 |
| 8ANC26 | 1122 |
| 8ANC127 | 1123 |
| 8ANC40 | 1124 |
| 8ABM13 | 1125 |
| 8ANC22 | 1126 |
| 8ABM12 | 1127 |
| 8A275 | 1128 |
| 8ANC116 | 1129 |
| 8ANC53 | 1130 |
| 8ANC2 | 1131 |
| 8ANC30 | 1132 |
| 8ABM26 | 1133 |
| 8ABM20 | 1134 |
| 8ANC18 | 1135 |
| 8ANC182 | 1136 |
| 8ANC41 | 1137 |
| 8ABM27 | 1138 |

HUMAN IMMUNODEFICIENCY VIRUS NEUTRALIZING ANTIBODIES AND METHODS OF USE THEREOF

CROSS-REFERENCE TO RELATED APPLICATIONS

This application is a Continuation of U.S. patent application Ser. No. 18/172,836, filed Feb. 22, 2023, which is a Continuation of U.S. patent application Ser. No. 17/248,143, filed Jan. 11, 2021, issued as U.S. Pat. No. 11,634,478 on Apr. 25, 2023, which is a Continuation of U.S. patent application Ser. No. 15/719,738, filed Sep. 29, 2017, issued as U.S. Pat. No. 10,889,633, on Jan. 12, 2021, which is a Divisional of U.S. patent application Ser. No. 14/118,496, filed Jul. 25, 2014, issued as U.S. Pat. No. 9,783,594 on Oct. 10, 2017, which is a U.S. National Phase of International Application No. PCT/US2012/038400, filed May 17, 2012, which claims priority under 35 U.S.C. § 119(e) to U.S. Provisional Application No. 61/486,960, filed on May 17, 2011. The disclosures of which are hereby incorporated in their entirety.

STATEMENT REGARDING FEDERALLY FUNDED RESEARCH

The research leading to the present invention was supported in part, by National Institutes of Health Grant No. P01 A108677-01. Accordingly, the U.S. Government has certain rights in this invention.

SEQUENCE LISTING

This application contains a Sequence Listing which has been submitted electronically in xml format and is hereby incorporated by reference in its entirety. Said xml copy, created on Mar. 1, 2024, is named SeqList-070413-20790 and is 1,165,685 bytes in size.

FIELD OF THE INVENTION

The present invention relates to antibodies directed to epitopes of Human Immunodeficiency Virus ("HIV"). The present invention further relates to the preparation and use of broadly neutralizing antibodies directed to the HIV gp120 envelope protein for the prevention and treatment of HIV infection.

BACKGROUND OF THE INVENTION

HIV causes Acquired Immunodeficiency Syndrome ("AIDS"). The immune response to HIV infection in long-term non-progressors suggests that specific viral immunity may limit infection and the symptoms of disease. Some HIV infected individuals show broadly neutralizing IgG antibodies in their serum; little is known regarding the specificity and activity of these antibodies, despite their potential importance in designing effective vaccines, and no single characteristic has of yet been correlated with protective immunity. In animal models, passive transfer of neutralizing antibodies can contribute to protection against virus challenge. Neutralizing antibody responses also can be developed in HIV-infected individuals but the detailed composition of the serologic response is yet to be fully uncovered.

A number of immunologic abnormalities have been described in AIDS. These include, but are not limited to, abnormalities in B-cell function, abnormal antibody response, defective monocyte cell function, impaired cytokine production, depressed natural killer and cytotoxic cell function, defective ability of lymphocytes to recognize and respond to soluble antigens, and the depletion of the T4 helper/inducer lymphocyte population.

The amino acid and RNA sequences encoding HIV env from a number of HIV strains are known (Modrow, S. et al., J. Virology 61(2): 570 (1987)). The HIV virion is covered by a membrane or envelope derived from the outer membrane of host cells. This membrane contains a population of envelope glycoproteins (gp 160) anchored in the membrane bilayer at their carboxyl terminal region. Each glycoprotein contains two segments: the N-terminal segment, and the C-terminal segment. The N-terminal segment, called gp120 by virtue of its relative molecular weight of about 120 kD, protrudes into the aqueous environment surrounding the virion. The C-terminal segment, called gp41, spans the membrane. The N-terminal gp120 and the C-terminal gp41 are covalently linked by a peptide bond that is particularly susceptible to proteolytic cleavage. See European Patent Application Publication No. 0 335 635 to McCune et al and the references cited therein, each incorporated herein by reference in its entirety.

Several approaches to an AIDS vaccine have been proposed, including, but not limited to, inactivated and attenuated virus vaccines, subunit vaccines from virus-infected cells, recombinantly produced viral antigens, vaccines based on synthetic peptides, anti-idiotypic vaccines, and viral carrier-based vaccines. An additional approach to HIV therapeutic and prophylactic treatment includes making highly potent, broadly neutralizing monoclonal antibodies. Multiple studies have reported cloning and making monoclonal antibodies by various techniques for targeting the CD4 binding site as well as other parts of the virion spike and for neutralizing HIV. Generally, these techniques involve self-fusion or phage display techniques. Typically, in making HIV neutralizing antibodies using phage display techniques, random combinations of heavy and light chains are combined and a random pair is selected. Studies have reported a limited number of monoclonal antibodies, such as, for example, the phage display antibody b12, that are broadly highly potent, and broadly neutralizing (meaning antibodies that can neutralize multiple strains of HIV in sera) against HIV. The monoclonal antibody b12 is a broadly neutralizing antibody which has been reported to prevent HIV infection in macaques. Another broadly neutralizing antibody includes 2G12, which, atypically, has a structure which has yet to be seen in any other antibody with three combining sites. VRC01 is recently discovered broadly neutralizing antibody that targets the CD4 binding site (CD4bs) on the HIV spike. VRC01 was isolated by purifying single B cells that bind to a soluble, biotin labeled, stabilized, and resurfaced core fragment of HIV gp120 (X. Wu et al., Science 329, 856 (Aug. 13, 2010)). Although successful, the isolation was inefficient, producing only 3 closely related HIV-binding antibodies from 25 million peripheral blood mononuclear cells from one individual. Like other anti-HIV antibodies obtained by the single cell antigen capture method, VRC01-3 showed very high levels of somatic mutations that were essential for potency and breadth. This high frequency of mutation is a potential impediment to antibody cloning because the mutated sequences may no longer be complementary to the primers used for cloning.

Some studies have reported that certain patients develop antibodies to HIV that are broadly neutralizing. Studies have reported that antibodies can be protective against initial HIV infection in passive transfer experiments in non-human primates and can modulate viral load during infection. See, for example, Mascola, 2000; Shibata, 1999; Veazey, 2003; Parren, 2001; Mascola, 1999; Trkola, 2005; Wei, 2003; Frost, 2005; Burton, 2004; Mascola, 2007; Karlsson Hedestam, 2008; McMichael, 2006; Zolla-Pazner, 2004.

BRIEF SUMMARY OF THE INVENTION

The present invention, in one embodiment, provides broadly neutralizing antibodies against HIV. In one embodiment, the present invention provides an isolated HIV antibody comprising a heavy chain comprising the consensus amino acid sequence: QXXLXQSGGXVKKPGXSVXVSCXAS-GYXXFXXYXIHWXRQAPGXGXXWVGXIX-PRXGXXXXAXXFQGRLSLT RDXXXXXXTXXXFMDLXGLRXDD-TAVYFCARXXXXXXXXXXXXXXXXXXDX (SEQ ID NO:1) wherein X indicates any amino acid or no amino acid.

In another embodiment, the present invention provides an isolated HIV antibody comprising a light chain comprising the consensus amino sequence: EIXLTQSPXSLSXSXGEXX-TISCXXXQXXXXXXXLXWYQQRXGXAPRL-LIXXXSXXXXGVPXRFSGXXXGXXYXL XISXLXXDDXAXYFCXXYEXXXXXXX (SEQ ID NO:2) wherein X indicates any amino acid or no amino acid.

In another embodiment, the present invention provides an isolated HIV antibody comprising a heavy chain comprising a highly conserved consensus sequence and a light chain comprising a highly conserved consensus sequence. The present invention further provides a method of producing an isolated HIV antibody comprising a heavy chain comprising a highly conserved consensus sequence and a light chain comprising a highly conserved consensus sequence.

In another embodiment, the present invention provides an isolated HIV antibody comprising the heavy chain consensus sequence of SEQ ID NO:1 and the light chain sequence of SEQ ID NO:2. In a further embodiment, the present invention provides an isolated HIV antibody comprising one or both of the heavy chain consensus sequence of SEQ ID NO:1 and the light chain sequence of SEQ ID NO:2, or sequences having at least 70%, or at least 80%, or at least 85%, or at least 90%, or at least 95%, or at least 97%, or at least 98%, or at least 99% identity thereto, with the proviso that the antibody does not have the amino acid sequence of VRC01.

In another embodiment, the present invention provides an isolated HIV antibody comprising one or both of the heavy chain consensus sequence of SEQ ID NO:1 and the light chain consensus sequence of SEQ ID NO:2 and wherein the antibody neutralizes HIV virus ZM53M.PB12 at an $IC_{50}$ concentration of less than 1.0 µg/ml, or HIV virus R1166.c1 at an $IC_{50}$ concentration of less than 1.0 µg/ml, or DU172.17 at an $IC_{50}$ concentration of less than 30 µg/ml. In another embodiment, the present invention provides an isolated HIV antibody comprising one or both of the heavy chain consensus sequence of SEQ ID NO:1 and the light chain consensus sequence of SEQ ID NO:2, wherein the antibody neutralizes a VRC01-resistant HIV virus at an $IC_{50}$ concentration of less than 30 µg/ml.

In another embodiment, the present invention provides an isolated HIV antibody selected from the group consisting of 3BNC117, 3BNC60, 12A12, 12A21, NIH45-46, 8ANC131, 8ANC134, 182530, INC9 and 8ANC196.

In another embodiment, the present invention provides an isolated HIV antibody comprising heavy chain CDR1, CDR2 and CDR3 regions and light chain CDR1, CDR2 and CDR3 regions comprising the amino acid sequences of the corresponding regions of an HIV antibody selected from the group consisting of 3BNC117, 3BNC60, 12A12, 12A21, NIH45-46, bANC131, 8ANC134, 182530, INC9 and 8ANC196.

In another embodiment, the present invention provides an isolated HIV antibody comprising a heavy chain comprising an amino acid sequence selected from the group consisting of SEQ ID NOs: 5-438.

In another embodiment, the present invention provides an isolated HIV antibody comprising a light chain comprising an amino acid sequence selected from the group consisting of SEQ ID NOs: 439-583.

In another embodiment, the present invention provides an isolated HIV antibody comprising a heavy chain and a light chain comprising an amino acid sequence set forth in Table A or Table B.

In another embodiment, the present invention provides an isolated HIV antibody comprising an insertion sequence comprising the amino acid sequence: ASWDFDF (SEQ ID NO:3).

In another embodiment, the present invention provides an isolated HIV antibody comprising an insertion sequence comprising the amino acid sequence: TARDY (SEQ ID NO:4).

In another embodiment, the present invention provides an isolated HIV antibody comprising insertion sequences SEQ ID No: 3 and SEQ ID No: 4.

In another embodiment, the present invention provides a method to improve the HIV neutralization potency and breadth of an isolated HIV antibody comprising inserting at least one of insertion sequences SEQ ID No: 3 and SEQ ID No: 4.

According to another embodiment, the present invention provides compositions comprising an isolated HIV antibody of the invention.

According to another embodiment, the present invention provides pharmaceutical compositions comprising an antibody of the invention and a pharmaceutically acceptable carrier.

According to another embodiment, the present invention provides nucleic acid molecules encoding an isolated HIV antibody of the invention.

According to other embodiments, the present invention provides vectors comprising nucleic acid molecules encoding an isolated HIV antibody of the invention, and cells comprising such vectors.

According to another embodiment, the present invention provides a method of preventing or treating HIV infection or an HIV-related disease comprising the steps of: identifying a mammalian subject in need of such prevention or treatment, and administering to said subject a therapeutically effective amount of at least one HIV antibody of the invention.

According to another embodiment, the method further comprises the administration of a second therapeutic agent. According to another embodiment, the second therapeutic agent is an antiviral agent.

Another embodiment of the present invention provides a method of reducing virus replication or spread of infection to additional host cells or tissues comprising contacting a mammalian cell with at least one antibody of the invention. According to another aspect, the present invention provides for a method for treating a mammalian subject infected with HIV, the method comprising administering to said subject a pharmaceutical composition comprising at least one antibody according to the invention.

According to another embodiment, the present invention provides a method for the preparation and administration of an HIV antibody preparation which is suitable for administration to a mammalian subject having or at risk of HIV infection, in an amount and according to a schedule sufficient to induce a protective immune response against HIV or reduction of the HIV virus in a mammalian subject. In another embodiment, the present invention provides a method for detecting an HIV antibody comprising a heavy chain comprising a highly conserved consensus sequence and a light chain comprising a highly conserved consensus sequence in a biological sample.

In another embodiment, the present invention provides the isolated antibodies of the invention for use in the treatment of HIV.

In another embodiment, the present invention provides a kit comprising a pharmaceutically acceptable dose unit of a pharmaceutically effective amount of at isolated HIV antibody of the invention, and a pharmaceutically acceptable dose unit of a pharmaceutically effective amount of an HIV agent selected from the group consisting of a non-nucleoside reverse transcriptase inhibitor, a protease inhibitor, a entry or fusion inhibitor and an integrase inhibitors, wherein the two pharmaceutically acceptable dose units can optionally take the form of a single pharmaceutically acceptable dose unit.

In another embodiment, the present invention provides a kit for the diagnosis, prognosis or monitoring the treatment of HIV in a subject comprising one or more detection reagents which specifically bind to anti-HIV neutralizing antibodies in a biological sample from a subject. In another aspect of the invention, the kit further provides reagents for performing PCR or mass spectrometry.

BRIEF DESCRIPTION OF THE DRAWINGS

FIGS. 4A and 4B show recovery of highly mutated immunoglobulin heavy chains with specific primers. (A) side by side comparison of new and old primer set. Red boxes indicate successful amplification of $IgV_H$ genes. FIG. 4A discloses SEQ ID NOS 917-979, respectively, in order of appearance). (B) HIV antibodies that bind to 2CC-core from Pt 8. Clonal families are shown by differently expanded slices. Two highly mutated clones that were not amplified with the old primer set are shown in striped pie slices.

FIGS. 5A and 5B show Ig V heavy (A) (SEQ ID NOS 980-984, respectively, in order of appearance) and light chain (B) (SEQ ID NOS 985-989, respectively, in order of appearance) sequences of new VRC01 clonal members.

FIGS. 6A and 6B show patient serum neutralizing activity. (A) Table summarizes purified serum IgG neutralizing activity against a panel of Tier 2 viruses in a Tzm-bl assay. Dark red boxes indicate $IC_{50}$ values below 1⍰ g/ml, orange between 10 and 100⍰ g/ml and yellow above 100⍰ g/ml. (B) dot plot summarizes the $IC_{50}$ values shown in A for the 4 more extensively tested patients.

FIG. 9A discloses SEQ ID NOS 991, 990, and 992-997; FIG. 9A Cont'd discloses SEQ ID NOS 999, 998, and 1000-1003; FIG. 9B discloses SEQ ID NOS 1005, 1004, and 1006-1009; FIG. 9B Cont'd discloses SEQ ID NOS 1011, 1010, and 1012-1015; and FIG. 9C discloses SEQ ID NOS 1017, 1016, and 1018-1019, all respectively, in order of appearance.

FIGS. 10A, 10B and 10C show antibody sequences from one expanded neutralizing clone in each (A) Patient (Pt)1, (B) Pt3 and (C) Pt8. Peptides identified by mass spectrometry are indicated in color. The variants marked with an asterisk are uniquely defined by one or more mass spectrometrically observed peptides (shown in light grey). The remaining mass spectrometrically observed peptides map non-uniquely to multiple variants as shown in dark grey. Underlined amino acids indicate non-tryptic cleavage sites in the variants shown. The cleavages are presumed to occur through chymotryptic cleavage or additional mutations (not observed among the cloned variants) that place a lysine or arginine residue at these sites. FIG. 10A discloses SEQ ID NOS 1020-1061; FIG. 10B discloses SEQ ID NOS 1062-1113; and FIG. 10C discloses SEQ ID NOS 1114-1138, all respectively, in order of appearance.

DETAILED DESCRIPTION OF THE INVENTION

I. HIV Neutralizing Antibodies

Figures 1A, 1B:
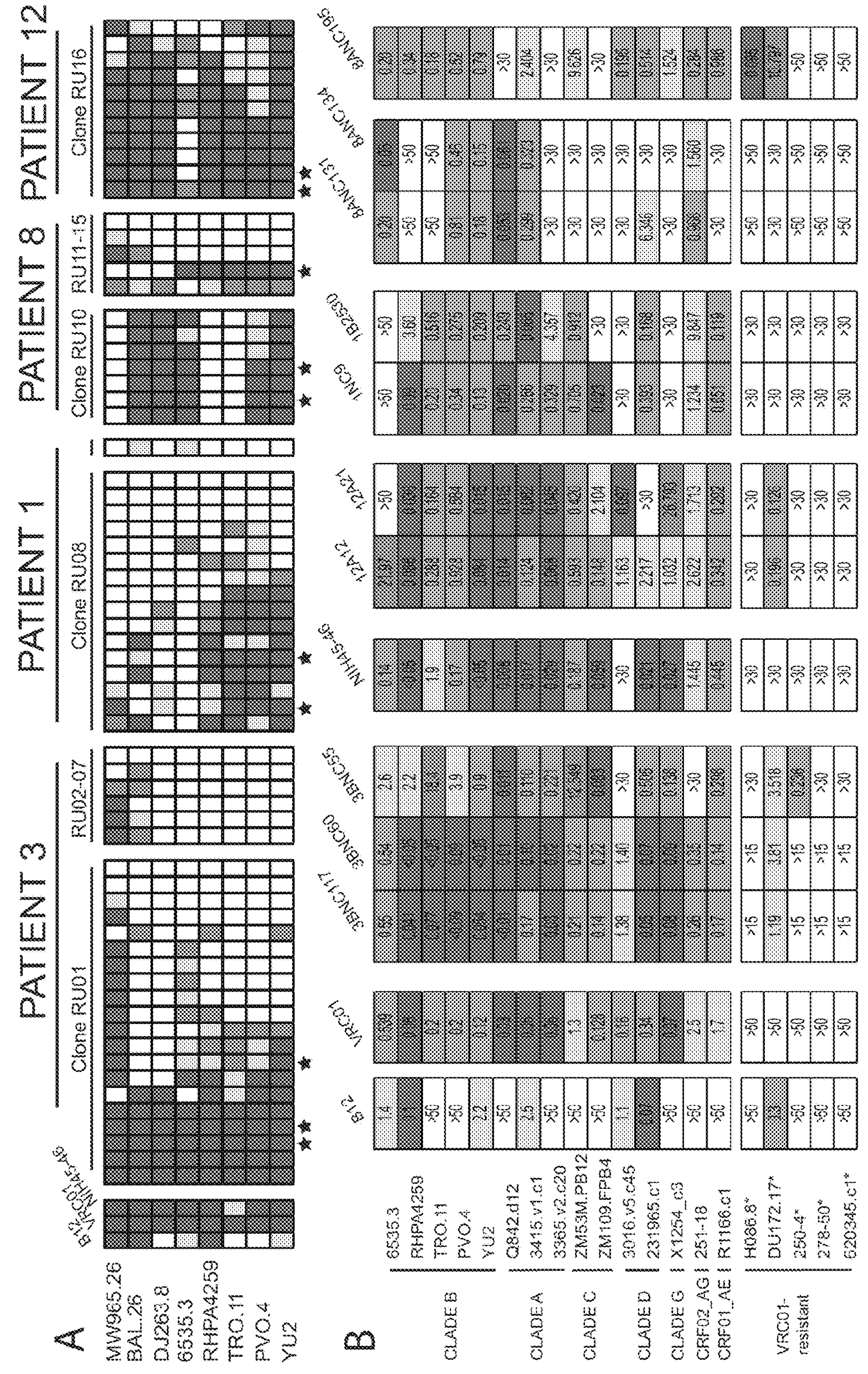
FIGS. 1A, 1B, 1C and 1D show the HIV antibody neutralizing activity $IC_{50}$. (A) Limited panel. Top line indicates the donor number, then clone or antibody (Table 4); viruses are shown on the left. Colors indicate concentration at $IC_{50}$: red≤0.1⍰ g/ml; orange 0.1-1⍰ ⍰ g/ml; yellow 1-10 ⍰ g/ml; green≥10⍰ g/ml; white not neutralized at any concentration tested. (B) Extended panel. (C) Neutralization summary graph comparing VRC01, NIH45-46, 3BNC117. Length of lines and size of circles inversely proportional to $IC_{50}$. Colors indicate viral clades: red A; blue B; green C; fucia D; black AE; gold AG. (D) Sequence of 3BNC60 (SEQ ID NO: 893), 1B2530 and 8ANC134 heavy chains with coverage by peptides found by Mass Spec in light grey. Red dots indicate differences from respective germline sequences.

The present invention, in one embodiment, provides broadly neutralizing antibodies against HIV. In one embodiment, the present invention provides an isolated HIV antibody comprising a heavy chain comprising the consensus amino acid sequence: QXXLXQSGGXVKKPGXSVXVSCXAS-GYXXFXXYXIHWXRQAPGXGXXWVGXIX-PRXGXXXXAXXFQGRLSLT RDXXXXXXTXXXFMDLXGLRXDD-TAVYFCARXXXXXXXXXXXXXXXXXXXDX (SEQ ID NO:1) wherein X indicates any amino acid or no amino acid.

In another embodiment, the present invention provides an isolated HIV antibody comprising a light chain comprising the consensus amino sequence: EIXLTQSPXSLSXSXGEXX-TISCXXXQXXXXXXXLXWYQQRXGXAPRL-LIXXXSXXXXGVPXRFSGXXXGXXYXL XISXLXXDDXAXYFCXXYEXXXXXXX (SEQ ID NO:2) wherein X indicates any amino acid or no amino acid.

In another embodiment, the present invention provides an isolated HIV antibody comprising the heavy chain sequence of SEQ ID NO:1 and the light chain sequence of SEQ ID NO:2. In a further embodiment, the present invention provides an isolated HIV antibody comprising one or both of the heavy chain sequence of SEQ ID NO:1 and the light chain sequence of SEQ ID NO:2, or sequences having at least 70%, or at least 80%, or at least 85%, or at least 90%, or at least 95%, or at least 97%, or at least 98%, or at least 99% identity thereto, with the proviso that the antibody does not have the amino acid sequence of VRC01. Percentage identity is determined as disclosed hereinbelow.

The present invention provides, in other embodiments, an isolated HIV antibody comprising a heavy chain comprising an highly conserved heavy chain amino acid sequence and a light chain comprising a highly conserved light chain amino acid sequence. A highly conserved heavy chain amino acid sequence is defined herein as an amino acid sequence having at least 70%, or at least 80%, or at least 85%, or at least 90%, or at least 95%, or at least 97%, or at least 98%, or at least 99% identity with the sequence of SEQ ID NO:1. A highly conserved light chain amino acid sequence is defined herein as an amino acid sequence having at least 70%, or at least 80%, or at least 85%, or at least 90%, or at least 95%, or at least 97%, or at least 98%, or at least 99% identity with the sequence of SEQ ID NO:2. Percentage identity is determined as disclosed hereinbelow.

In another embodiment, present invention provides an isolated HIV antibody comprising a heavy chain comprising an highly conserved heavy chain amino acid sequence and a light chain comprising a highly conserved light chain amino acid sequence, with the proviso that the antibody does not have the sequence of VRC01.

In another embodiment, the present invention provides an isolated HIV antibody comprising one or both of the heavy chain sequence of SEQ ID NO:1 and the light chain sequence of SEQ ID NO:2 and wherein the antibody neutralizes HIV virus ZM53M.PB12 at an $IC_{50}$ concentration of less than 1.0 µg/ml, or HIV virus R1166.c1 at an $IC_{50}$ concentration of less than 1.0 µg/ml, or DU172.17 at an $IC_{50}$ concentration of less than 30 µg/ml. In another embodiment, the present invention provides an isolated HIV antibody comprising one or both of the heavy chain sequence of SEQ ID NO:1 and the light chain sequence of SEQ ID NO:2, wherein the antibody neutralizes a VRC01-resistant HIV virus at an $IC_{50}$ concentration of less than 30 µg/ml. A VRC01-resistant HIV virus is defined herein as an HIV virus that is resistant to neutralization by VRC01 at an $IC_{50}$ value of 50 µg/ml. VRC01-resistant HIV viruses include, for example, H086.8, DU172.17, 250-4, 278-50, and 620345.c1.

In another embodiment, the present invention provides an isolated HIV antibody selected from the group consisting of 3BNC117, 3BNC60, 12A12, 12A21, NIH45-46, bANC131, 8ANC134, 182530, INC9 and 8ANC196.

In another embodiment, the present invention provides an isolated HIV antibody comprising heavy chain CDR1, CDR2 and CDR3 regions and light chain CDR1, CDR2 and CDR3 regions comprising the amino acids sequences of the corresponding regions of an HIV antibody selected from the group consisting of 3BNC117, 3BNC60, 12A12, 12A21, NIH45-46, bANC131, 8ANC134, 182530, INC9 and 8ANC196.

In another embodiment, the present invention provides an isolated HIV antibody comprising a heavy chain comprising an amino acid sequence selected from the group consisting of SEQ ID NOs: 5-438.

In another embodiment, the present invention provides an isolated HIV antibody comprising a light chain comprising an amino acid sequence selected from the group consisting of SEQ ID NOs: 439-583.

In another embodiment, the present invention provides an isolated HIV antibody comprising a heavy chain and a light chain comprising an amino acid sequence set forth in Table A or Table B.

In another embodiment, the present invention provides an isolated HIV antibody comprising an insertion sequence comprising the amino acid sequence: ASWDFDF (SEQ ID NO:3). In a further embodiment, the present invention provides an isolated HIV antibody wherein insertion sequence SEQ ID No: 3, which corresponds to the FR3 region of the heavy chain commencing at amino acid 74 of 3BNC117 and 3BNC60 as shown in FIG. 5A, is substituted for the corresponding region, as determined by sequence alignment, of an HIV antibody of the invention. For example, SEQ ID No: 3 may be inserted after the seventh amino acid of FR3 of the heavy chain.

In another embodiment, the present invention provides an isolated HIV antibody comprising an insertion sequence comprising the amino acid sequence: TARDY (SEQ ID NO:4). In a further embodiment, the present invention provides an isolated HIV antibody wherein insertion sequence SEQ ID No: 4, which corresponds to the CDR3 region of the heavy chain commencing at amino acid 103 of NIH45-46 as shown in FIG. 5A, is substituted for the corresponding region, as determined by sequence alignment, of an HIV antibody of the invention. For example, SEQ ID No: 4 may be inserted after the fourth amino acid of CDR3 of the heavy chain.

In another embodiment, the present invention provides an isolated HIV antibody wherein insertion sequence SEQ ID No: 3, which corresponds to the FR3 region of the heavy chain commencing at amino acid 74 of 3BNC117 and 3BNC60 as shown in FIG. 5A, is substituted for the corresponding region, as determined by sequence alignment, of an HIV antibody of the invention, and insertion sequence SEQ ID No: 4, which corresponds to the CDR3 region of the heavy chain commencing at amino acid 103 of NIH45-46 as shown in FIG. 5A, is substituted for the corresponding region, as determined by sequence alignment, of an HIV antibody of the invention. For example, SEQ ID No: 3 may be inserted after the seventh amino acid of FR3 of the heavy chain and SEQ ID No: 4 may be inserted after the fourth amino acid of CDR3 of the heavy chain.

In another embodiment, the present invention provides a therapeutic composition comprising: i) a recombinantly produced monoclonal anti-HIV antibody or a gp120-derived antigen-binding fragment thereof comprising the CDR1, CDR2, and CDR3 regions of SEQ ID NO: 896, which corresponds to the variable heavy chain of NIH45-46 and the CDR1, CDR2, and CDR3 regions of SEQ ID NO: 910, which corresponds to the variable light chain of NIH45-46; and ii) a pharmaceutically acceptable carrier.

In a further embodiment, the present invention provides a method to improve the HIV neutralization potency and breadth of an isolated HIV antibody comprising making an isolated HIV antibody wherein insertion sequence SEQ ID No: 3, which corresponds to the FR3 region of the heavy commencing at amino acid 74 of 3BNC117 and 3BNC60 as shown in FIG. 5A, is substituted for the corresponding region, as determined by sequence alignment, of an HIV antibody of the invention and/or the insertion sequence SEQ ID No: 4, which corresponds to the CDR3 region of the heavy chain commencing at amino acid 103 of NIH45-46 as shown in FIG. 5A, is substituted for the corresponding region, as determined by sequence alignment, of an HIV antibody of the invention. For example, SEQ ID No: 3 may be inserted after the seventh amino acid of FR3 of the heavy chain, and/or SEQ ID No: 4 may be inserted after the fourth amino acid of CDR3 of the heavy chain. One skilled in this art can modify the amino acid sequence of an antibody utilizing recombinant methods and/or synthetic chemistry techniques for the production of a polypeptide or an antibody. Also, one skilled in the art can identify an improved HIV antibody with greater neutralization potency and breadth by using a HIV neutralization assay, as described below.

In another embodiment, the present invention provides an improved isolated HIV antibody comprising at least one of insertion sequences SEQ ID NO: 3 and SEQ ID NO: 4, wherein the improved isolated HIV antibody has greater HIV neutralization potency and breadth, than said isolated HIV antibody without insertion sequences SEQ ID NO: 3 and SEQ ID NO: 4. One skilled in the art can identify the improved HIV antibody with greater HIV neutralization potency and breadth by using the HIV neutralization assay, as described below.

One skilled in this art can modify the amino acid sequence of an antibody utilizing recombinant methods and/or synthetic chemistry techniques for the production of a polypeptide or an antibody.

In another embodiment, the present invention provides for a method to make an isolated HIV antibody comprising the heavy chain consensus sequence of SEQ ID NO:1 and the light chain sequence of SEQ ID NO:2. In a further embodiment, the present invention provides for a method of producing an isolated HIV antibody comprising one or both of the heavy chain consensus sequence of SEQ ID NO:1 and the light chain sequence of SEQ ID NO:2, or sequences having at least 70%, or at least 80%, or at least 85%, or at least 90%, or at least 95%, or at least 97%, or at least 98%, or at least 99% identity thereto, with the proviso that the antibody does not have the amino acid sequence of VRC01. Percentage identity is determined as disclosed hereinbelow.

In another embodiment, the present invention provides a method for detecting an isolated HIV antibody comprising obtaining an immunoglobulin-containing biological sample from a mammalian subject, isolating an HIV antibody from said sample, determining the amino sequence of the HIV antibody and identifying the presence of the heavy chain sequence of SEQ ID NO:1 and the light chain sequence of SEQ ID NO:2. In a further embodiment, the present invention provides for a method of selecting an isolated HIV antibody comprising determining the presence of one or both of the heavy chain consensus sequence of SEQ ID NO:1 and the light chain sequence of SEQ ID NO:2, or sequences having at least 70%, or at least 80%, or at least 85%, or at least 90%, or at least 95%, or at least 97%, or at least 98%, or at least 99% identity thereto, with the proviso that the antibody does not have the amino acid sequence of VRC01. Percentage identity is determined as disclosed herein below. The biological sample may be blood, serum, saliva, urine, sputum, a cell swab sample, or a tissue biopsy. The amino acid sequences may be determined by methods known in the art including, for example, PCR and mass spectrometry.

The term "antibody" (Ab) as used herein includes monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). It is understood in the art that an antibody is a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, FWR4. The variable regions of the heavy and light chains contain a binding domain that interacts with an antigen while, depending of the isotype, the constant region(s) may mediate the binding of the immunoglobulin to host tissues or factors.

Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan.

The term "variable" refers to the fact that certain segments of the variable (V) domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta sheet configuration, connected by three hypervariable regions, which form loops connecting, and in some cases forming part of, the beta sheet structure. The hypervariable regions in each chain are held together in close proximity by the FRs and, with the hypervariable regions from the other chain, contribute to the formation of the antigen-binding site of antibodies (see, for example, Kabat et al., Sequences of Proteins of Immunological Interest, 5th Ed. Public Health Service, National Institutes of Health, Bethesda, Md. (1991)).

The term "hypervariable region" as used herein refers to the amino acid residues of an antibody that are responsible for antigen binding. The hypervariable region generally comprises amino acid residues from a "complementarity determining region" ("CDR").

The term "monoclonal antibody" as used herein refers to an antibody obtained from a population of substantially homogeneous antibodies, i.e., the individual antibodies comprising the population are identical except for possible naturally occurring mutations that may be present in minor amounts. The term "polyclonal antibody" refers to preparations that include different antibodies directed against different determinants ("epitopes").

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with, or homologous to, corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., Proc. Natl. Acad. Sci. USA, 81:6851-6855 (1984)). The described invention provides variable region antigen-binding sequences derived from human antibodies. Accordingly, chimeric antibodies of primary interest herein include antibodies having one or more human antigen binding sequences (for example, CDRs) and containing one or more sequences derived from a non-human antibody, for example, an FR or C region sequence. In addition, chimeric antibodies included herein are those comprising a human variable region antigen binding sequence of one antibody class or subclass and another sequence, for example, FR or C region sequence, derived from another antibody class or subclass.

A "humanized antibody" generally is considered to be a human antibody that has one or more amino acid residues introduced into it from a source that is non-human. These non human amino acid residues often are referred to as "import" residues, which typically are taken from an "import" variable region. Humanization may be performed following the method of Winter and co-workers (see, for example, Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (see, for example, U.S. Pat. No. 4,816,567), wherein substantially less than an intact human variable region has been substituted by the corresponding sequence from a non-human species.

An "antibody fragment" comprises a portion of an intact antibody, such as the antigen binding or variable region of the intact antibody. Examples of antibody fragments include, but are not limited to, Fab, Fab', F(ab')2, and Fv fragments; diabodies; linear antibodies (see, for example, U.S. Pat. No. 5,641,870; Zapata et al., Protein Eng. 8(10): 1057-1062 [1995]); single-chain antibody molecules; and multispecific antibodies formed from antibody fragments.

"Fv" is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

"Single-chain Fv" ("sFv" or "scFv") are antibody fragments that comprise the VH and VL antibody domains connected into a single polypeptide chain. The sFv polypeptide can further comprise a polypeptide linker between the VH and VL domains that enables the sFv to form the desired structure for antigen binding. For a review of sFv, see, for example, Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from about 11 kDa to about 15 kDa. dAbs are the robust variable regions of the heavy and light chains of immunoglobulins (VH and VL, respectively). They are highly expressed in microbial cell culture, show favorable biophysical properties including, for example, but not limited to, solubility and temperature stability, and are well suited to selection and affinity maturation by in vitro selection systems such as, for example, phage display. dAbs are bioactive as monomers and, owing to their small size and inherent stability, can be formatted into larger molecules to create drugs with prolonged serum half-lives or other pharmacological activities. Examples of this technology have been described in, for example, WO9425591 for antibodies derived from Camelidae heavy chain Ig, as well in US20030130496 describing the isolation of single domain fully human antibodies from phage libraries.

Fv and sFv are the only species with intact combining sites that are devoid of constant regions. Thus, they are suitable for reduced nonspecific binding during in vivo use. sFv fusion proteins can be constructed to yield fusion of an effector protein at either the amino or the carboxy terminus of an sFv. See, for example, Antibody Engineering, ed. Borrebaeck, supra. The antibody fragment also can be a "linear antibody", for example, as described in U.S. Pat. No. 5,641,870 for example. Such linear antibody fragments can be monospecific or bispecific.

In certain embodiments, antibodies of the described invention are bispecific or multi-specific. Bispecific antibodies are antibodies that have binding specificities for at least two different epitopes. Exemplary bispecific antibodies can bind to two different epitopes of a single antigen. Other such antibodies can combine a first antigen binding site with a binding site for a second antigen. Alternatively, an anti-HIV arm can be combined with an arm that binds to a triggering molecule on a leukocyte, such as a T-cell receptor molecule (for example, CD3), or Fc receptors for IgG (Fc gamma R), such as Fc gamma RI (CD64), Fc gamma RII (CD32) and Fc gamma RIII (CD16), so as to focus and localize cellular defense mechanisms to the infected cell. Bispecific antibodies also can be used to localize cytotoxic agents to infected cells. Bispecific antibodies can be prepared as full length antibodies or antibody fragments (for example, F(ab')2 bispecific antibodies). For example, WO 96/16673 describes a bispecific anti-ErbB2/anti-Fc gamma RIII antibody and U.S. Pat. No. 5,837,234 discloses a bispecific anti-ErbB2/anti-Fc gamma RI antibody. For example, a bispecific anti-ErbB2/Fc alpha antibody is reported in WO98/02463; U.S. Pat. No. 5,821,337 teaches a bispecific anti-ErbB2/anti-CD3 antibody. See also, for example, Mouquet et al., Polyreactivity Increases The Apparent Affinity Of Anti-HIV Antibodies By Heteroligation. *NATURE.* 467, 591-5 (2010).

Methods for making bispecific antibodies are known in the art. Traditional production of full length bispecific antibodies is based on the co-expression of two immunoglobulin heavy chain-light chain pairs, where the two chains have different specificities (see, for example, Millstein et al., Nature, 305:537-539 (1983)). Similar procedures are disclosed in, for example, WO 93/08829, Traunecker et al., EMBO J., 10:3655-3659 (1991) and see also; Mouquet et al., Polyreactivity Increases The Apparent Affinity Of Anti-HIV Antibodies By Heteroligation. NATURE. 467, 591-5 (2010).

Alternatively, antibody variable regions with the desired binding specificities (antibody-antigen combining sites) are fused to immunoglobulin constant domain sequences. The fusion is with an Ig heavy chain constant domain, comprising at least part of the hinge, CH2, and CH3 regions. According to some embodiments, the first heavy-chain constant region (CH1) containing the site necessary for light chain bonding, is present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Techniques for generating bispecific antibodies from antibody fragments also have been described in the literature. For example, bispecific antibodies can be prepared using chemical linkage. For example, Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated then are converted to thionitrobenzoate (TNB) derivatives. One of the Fab'-TNB derivatives then is reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Other modifications of the antibody are contemplated herein. For example, the antibody can be linked to one of a variety of nonproteinaceous polymers, for example, polyethylene glycol, polypropylene glycol, polyoxyalkylenes, or copolymers of polyethylene glycol and polypropylene glycol. The antibody also can be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in, for example, Remington's Pharmaceutical Sciences, 16th edition, Oslo, A., Ed., (1980).

Typically, the antibodies of the described invention are produced recombinantly, using vectors and methods available in the art. Human antibodies also can be generated by in vitro activated B cells (see, for example, U.S. Pat. Nos. 5,567,610 and 5,229,275). General methods in molecular genetics and genetic engineering useful in the present invention are described in the current editions of Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, CA), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, CA), Culture of Animal Cells: A Manual of Basic Technique, 2nd Ed. (R. I. Freshney. 1987. Liss, Inc. New York, NY), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

Human antibodies also can be produced in transgenic animals (for example, mice) that are capable of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice results in the production of human antibodies upon antigen challenge. See, for example, Jakobovits et al., Proc. Natl.

Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals can be genetically engineered to produce human antibodies comprising a polypeptide of the described invention.

Various techniques have been developed for the production of antibody fragments. Traditionally, these fragments were derived via proteolytic digestion of intact antibodies (see, for example, Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Fab'-SH fragments can be directly recovered from *E. coli* and chemically coupled to form F(ab')2 fragments (see, for example, Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner.

Other techniques that are known in the art for the selection of antibody fragments from libraries using enrichment technologies, including but not limited to phage display, ribosome display (Hanes and Pluckthun, 1997, *Proc. Nat. Acad. Sci.* 94: 4937-4942), bacterial display (Georgiou, et al., 1997, *Nature Biotechnology* 15: 29-34) and/or yeast display (Kieke, et al., 1997, *Protein Engineering* 10: 1303-1310) may be utilized as alternatives to previously discussed technologies to select single chain antibodies. Single-chain antibodies are selected from a library of single chain antibodies produced directly utilizing filamentous phage technology. Phage display technology is known in the art (e.g., see technology from Cambridge Antibody Technology (CAT)) as disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members, or applications which rely on priority filing GB 9206318, filed 24 May 1992; see also Vaughn, et al. 1996, *Nature Biotechnology* 14: 309-314). Single chain antibodies may also be designed and constructed using available recombinant DNA technology, such as a DNA amplification method (e.g., PCR), or possibly by using a respective hybridoma cDNA as a template.

Variant antibodies also are included within the scope of the invention. Thus, variants of the sequences recited in the application also are included within the scope of the invention. Further variants of the antibody sequences having improved affinity can be obtained using methods known in the art and are included within the scope of the invention. For example, amino acid substitutions can be used to obtain antibodies with further improved affinity. Alternatively, codon optimization of the nucleotide sequence can be used to improve the efficiency of translation in expression systems for the production of the antibody.

Such variant antibody sequences will share 70% or more (i.e., 80%, 85%, 90%, 95%, 97%, 98%, 99% or greater) sequence identity with the sequences recited in the application. Such sequence identity is calculated with regard to the full length of the reference sequence (i.e., the sequence recited in the application). Percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1]. For example, peptide sequences are provided by this invention that comprise at least about 5, 10, 15, 20, 30, 40, 50, 75, 100, 150, or more contiguous peptides of one or more of the sequences disclosed herein as well as all intermediate lengths there between. As used herein, the term "intermediate lengths" is meant to describe any length between the quoted values, such as 7, 8, 9, 10, 11, 12, 13, 14, 15, 16, 17, 18, 19, etc.; 21, 22, 23, etc.; 30, 31, 32, etc.; 50, 51, 52, 53, etc.; 100, 101, 102, 103, etc.; 150, 151, 152, 153, etc.

The present invention provides for antibodies, either alone or in combination with other antibodies, such as, but not limited to, VRC01 and PG9, that have broad neutralizing activity in serum.

According to another embodiment, the present invention provides methods for the preparation and administration of an HIV antibody composition that is suitable for administration to a human or non-human primate patient having HIV infection, or at risk of HIV infection, in an amount and according to a schedule sufficient to induce a protective immune response against HIV, or reduction of the HIV virus, in a human.

According to another embodiment, the present invention provides a vaccine comprising at least one antibody of the invention and a pharmaceutically acceptable carrier. According to one embodiment, the vaccine is a vaccine comprising at least one antibody described herein and a pharmaceutically acceptable carrier. The vaccine can include a plurality of the antibodies having the characteristics described herein in any combination and can further include antibodies neutralizing to HIV as are known in the art.

It is to be understood that compositions can be a single or a combination of antibodies disclosed herein, which can be the same or different, in order to prophylactically or therapeutically treat the progression of various subtypes of HIV infection after vaccination. Such combinations can be selected according to the desired immunity. When an antibody is administered to an animal or a human, it can be combined with one or more pharmaceutically acceptable carriers, excipients or adjuvants as are known to one of ordinary skilled in the art. The composition can further include broadly neutralizing antibodies known in the art, including but not limited to, VRC01, PG9 and b12.

Further, with respect to determining the effective level in a patient for treatment of HIV, in particular, suitable animal models are available and have been widely implemented for evaluating the in vivo efficacy against HIV of various gene therapy protocols (Sarver et al. (1993b), supra). These models include mice, monkeys and cats. Even though these animals are not naturally susceptible to HIV disease, chimeric mice models (for example, SCID, bg/nu/xid, NOD/SCID, SCID-hu, immunocompetent SCID-hu, bone marrow-ablated BALB/c) reconstituted with human peripheral blood mononuclear cells (PBMCs), lymph nodes, fetal liver/thymus or other tissues can be infected with lentiviral vector or HIV, and employed as models for HIV pathogenesis. Similarly, the simian immune deficiency virus (SIV)/monkey model can be employed, as can the feline immune deficiency virus (FIV)/cat model. The pharmaceutical composition can contain other pharmaceuticals, in conjunction with a vector according to the invention, when used to therapeutically treat AIDS. These other pharmaceuticals can be used in their traditional fashion (i.e., as antiviral agents to treat HIV infection). Examples of HIV agents include without limitation non-nucleoside reverse transcriptase inhibitors, protease inhibitors, entry or fusion inhibitors and integrase inhibitors According to another embodiment, the present invention provides an antibody-based pharmaceutical composition comprising an effective amount of an isolated HIV antibody, or an affinity matured version, which provides a prophylactic or therapeutic treatment choice to reduce infection of the HIV virus. The antibody-based pharmaceutical composition of the present invention may be formulated by any number of strategies known in the art (e.g., see McGoff and Scher, 2000, Solution Formulation of Proteins/Peptides: In McNally, E. J., ed. Protein Formulation and Delivery. New York, NY: Marcel Dekker; pp. 139-158; Akers and Defilippis, 2000, Peptides and Proteins as Parenteral Solutions. In: Pharmaceutical Formulation Development of Peptides and Proteins. Philadelphia, PA: Talyor and Francis; pp. 145-177; Akers, et al., 2002, Pharm. Biotechnol. 14:47-127). A pharmaceutically acceptable composition suitable for patient administration will contain an effective amount of the antibody in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody to a concentration which provides the desired beneficial palliative or curative results while at the same time minimizing any adverse side effects that might occur from too high a concentration. It may also have a preservative effect. Thus, for the antibody having a high physiological activity, more of the excipient will be employed. On the other hand, for any active ingredient(s) that exhibit a lower physiological activity, a lesser quantity of the excipient will be employed.

The above described antibodies and antibody compositions or vaccine compositions, comprising at least one or a combination of the antibodies described herein, can be administered for the prophylactic and therapeutic treatment of HIV viral infection.

The present invention also relates to isolated polypeptides comprising the amino acid sequences of the light chains and heavy chains listed in Tables A, B and FIGS. 10 A-C; the consensus sequences for the heavy and light chains of SEQ ID NOs: 1 and 2; and insertion sequences SEQ ID NOs:3 and 4.

In other related embodiments, the invention provides polypeptide variants that encode the amino acid sequences of the HIV antibodies listed in Tables A, B and FIGS. 10 A-C; the consensus sequences for the heavy and light chains of SEQ ID NOs: 1 and 2; and insertion sequences SEQ ID NOs:3 and 4. These polypeptide variants have at least 70%, at least 75%, at least 80%, at least 85%, at least 90%, at least 95%, at least 96%, at least 97%, at least 98%, or at least 99%, or greater, sequence identity compared to a polypeptide sequence of this invention, as determined using the methods described herein, (for example, BLAST analysis using standard parameters). One skilled in this art will recognize that these values can be appropriately adjusted to determine corresponding identity of proteins encoded by taking into amino acid similarity and the like.

The term "polypeptide" is used in its conventional meaning, i.e., as a sequence of amino acids. The polypeptides are not limited to a specific length of the product. Peptides, oligopeptides, and proteins are included within the definition of polypeptide, and such terms can be used interchangeably herein unless specifically indicated otherwise. This term also includes post-expression modifications of the polypeptide, for example, glycosylations, acetylations, phosphorylations and the like, as well as other modifications known in the art, both naturally occurring and non-naturally occurring. A polypeptide can be an entire protein, or a subsequence thereof. Particular polypeptides of interest in the context of this invention are amino acid subsequences comprising CDRs, VH and VL, being capable of binding an antigen or HIV-infected cell.

A polypeptide "variant," as the term is used herein, is a polypeptide that typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of techniques well known in the art.

For example, certain amino acids can be substituted for other amino acids in a protein structure without appreciable loss of its ability to bind other polypeptides (for example, antigens) or cells. Since it is the binding capacity and nature of a protein that defines that protein's biological functional activity, certain amino acid sequence substitutions can be made in a protein sequence, and, accordingly, its underlying DNA coding sequence, whereby a protein with like properties is obtained. It is thus contemplated that various changes can be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

Amino acid substitutions generally are based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

"Homology" or "sequence identity" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least about 70%, at least about 75%, at least about 80%, at least about 90%, at least about 95%, at least about 98%, or at least about 99% polynucleotide or polypeptide homology with a polynucleotide or polypeptide described herein.

Such variant polypeptide sequences will share 70% or more (i.e. 80%, 85%, 90%, 95%, 97%, 98%, 99% or more) sequence identity with the sequences recited in the application. In additional embodiments, the described invention provides polypeptide fragments comprising various lengths of contiguous stretches of amino acid sequences disclosed herein. For example, peptide sequences are provided by this invention that comprise at least about 5, 10, 15, 20, 30, 40, 50, 75, 100, 150, or more contiguous peptides of one or more of the sequences disclosed herein as well as all intermediate lengths there between.

The invention also includes nucleic acid sequences encoding part or all of the light and heavy chains of the described inventive antibodies, and fragments thereof. Due to redundancy of the genetic code, variants of these sequences will exist that encode the same amino acid sequences.

The present invention also includes isolated nucleic acid sequences encoding the polypeptides for the heavy and light chains of the HIV antibodies listed in Tables A, B and FIG. 10 A-C; the consensus sequences for the heavy and light chains of SEQ ID NOs: 1 and 2; and insertion sequences SEQ ID NOs:3 and 4.

In other related embodiments, the described invention provides polynucleotide variants that encode the peptide sequences of the heavy and light chains of the HIV antibodies listed in Tables A, B and FIGS. 10 A-C; the consensus sequences for the heavy and light chains of SEQ ID NOs: 1 and 2; and insertion sequences SEQ ID NOs:3 and 4. These polynucleotide variants have at least 70%, at least 75%, at least 80%, at least 85%, at least 90%, at least 95%, at least 96%, at least 97%, at least 98%, or at least 99%, or greater, sequence identity compared to a polynucleotide sequence of this invention, as determined using the methods described herein, (for example, BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

The terms "nucleic acid" and "polynucleotide" are used interchangeably herein to refer to single-stranded or double-stranded RNA, DNA, or mixed polymers. Polynucleotides can include genomic sequences, extra-genomic and plasmid sequences, and smaller engineered gene segments that express, or can be adapted to express polypeptides.

An "isolated nucleic acid" is a nucleic acid that is substantially separated from other genome DNA sequences as well as proteins or complexes such as ribosomes and polymerases, which naturally accompany a native sequence. The term encompasses a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Accordingly, this refers to the nucleic acid as originally isolated and does not exclude genes or sequences later added to the isolated nucleic acid by the hand of man.

A polynucleotide "variant," as the term is used herein, is a polynucleotide that typically differs from a polynucleotide specifically disclosed herein in one or more substitutions, deletions, additions and/or insertions. Such variants can be naturally occurring or can be synthetically generated, for example, by modifying one or more of the polynucleotide sequences of the invention and evaluating one or more biological activities of the encoded polypeptide as described herein and/or using any of a number of techniques well known in the art.

Modifications can be made in the structure of the polynucleotides of the described invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art typically will change one or more of the codons of the encoding DNA sequence.

Typically, polynucleotide variants contain one or more substitutions, additions, deletions and/or insertions, such that the immunogenic binding properties of the polypeptide encoded by the variant polynucleotide is not substantially diminished relative to a polypeptide encoded by a polynucleotide sequence specifically set forth herein.

In additional embodiments, the described invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between and encompass any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; and including all integers through 200-500; 500-1,000.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderate stringent conditions for testing the hybridization of a polynucleotide of this invention with other polynucleotides include prewashing in a solution of 5×SSC, 0.5% SDS, 1.0 mM EDTA (pH 8.0); hybridizing at 50-60° C., 5×SSC, overnight; followed by washing twice at 65° C. for 20 minutes with each of 2×, 0.5×. and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, for example, to 60-65° C. or 65-70° C.

In some embodiments, the polypeptide encoded by the polynucleotide variant or fragment has the same binding specificity (i.e., specifically or preferentially binds to the same epitope or HIV strain) as the polypeptide encoded by the native polynucleotide. In some embodiments, the described polynucleotides, polynucleotide variants, fragments and hybridizing sequences, encode polypeptides that have a level of binding activity of at least about 50%, at least about 70%, and at least about 90% of that for a polypeptide sequence specifically set forth herein.

The polynucleotides of the described invention, or fragments thereof, regardless of the length of the coding sequence itself, can be combined with other DNA sequences, such as promoters, polyadenylation signals, additional restriction enzyme sites, multiple cloning sites, other coding segments, and the like, such that their overall length can vary considerably. A nucleic acid fragment of almost any length is employed. For example, illustrative polynucleotide segments with total lengths of about 10000, about 5000, about 3000, about 2000, about 1000, about 500, about 200, about 100, about 50 base pairs in length, and the like, (including all intermediate lengths) are included in many implementations of this invention.

In some embodiments, the polynucleotide sequences provided herein are used as probes or primers for nucleic acid hybridization, for example, as PCR primers. The ability of such nucleic acid probes to specifically hybridize to a sequence of interest enables them to detect the presence of complementary sequences in a given sample. However, other uses also are encompassed by the described invention, such as the use of the sequence information for the preparation of mutant species primers, or primers for use in preparing other genetic constructions. As such, nucleic acid segments of the described invention that include a sequence region of at least about a 15 nucleotide long contiguous sequence that has the same sequence as, or is complementary to, a 15 nucleotide long contiguous sequence disclosed herein is particularly useful. Longer contiguous identical or complementary sequences, for example, those of about 20, 30, 40, 50, 100, 200, 500, 1000 (including all intermediate lengths) including full length sequences, and all lengths in between, also are used in some embodiments.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, for example, Southern and Northern blotting, and/or primers for use in, for example, PCR. The total size of fragment, as well as the size of the complementary stretch(es), ultimately depends on the intended use or application of the particular nucleic acid segment. Smaller fragments generally are used in hybridization embodiments, wherein the length of the contiguous complementary region can be varied, such as between about 15 and about 100 nucleotides, but larger contiguous complementarity stretches can be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 12 bases in length can be utilized, though, in order to increase stability and selectivity of the hybrid, and thereby improve the quality and degree of specific hybrid molecules obtained. Nucleic acid molecules having gene-complementary stretches of 15 to 25 contiguous nucleotides, or even longer where desired, can be utilized.

Hybridization probes are selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences is governed by various factors. For example, one may wish to employ primers from towards the termini of the total sequence.

Further included within the scope of the invention are vectors such as expression vectors, comprising a nucleic acid sequence according to the invention. Cells transformed with such vectors also are included within the scope of the invention.

The present invention also provides vectors and host cells comprising a nucleic acid of the invention, as well as recombinant techniques for the production of a polypeptide of the invention. Vectors of the invention include those capable of replication in any type of cell or organism, including, for example, plasmids, phage, cosmids, and mini chromosomes. In some embodiments, vectors comprising a polynucleotide of the described invention are vectors suitable for propagation or replication of the polynucleotide, or vectors suitable for expressing a polypeptide of the described invention. Such vectors are known in the art and commercially available.

"Vector" includes shuttle and expression vectors. Typically, the plasmid construct also will include an origin of replication (for example, the ColE1 origin of replication) and a selectable marker (for example, ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells.

As used herein, the term "cell" can be any cell, including, but not limited to, that of a eukaryotic, multicellular species (for example, as opposed to a unicellular yeast cell), such as, but not limited to, a mammalian cell or a human cell. A cell can be present as a single entity, or can be part of a larger collection of cells. Such a "larger collection of cells" can comprise, for example, a cell culture (either mixed or pure), a tissue (for example, endothelial, epithelial, mucosa or other tissue), an organ (for example, lung, liver, muscle and other organs), an organ system (for example, circulatory system, respiratory system, gastrointestinal system, urinary system, nervous system, integumentary system or other organ system), or an organism (e.g., a bird, mammal, or the like).

Polynucleotides of the invention may synthesized, whole or in parts that then are combined, and inserted into a vector using routine molecular and cell biology techniques, including, for example, subcloning the polynucleotide into a linearized vector using appropriate restriction sites and restriction enzymes. Polynucleotides of the described invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the invention, the nucleotide sequences encoding the polypeptide, or functional equivalents, may be inserted into an appropriate expression vector, i.e., a vector that contains the necessary elements for the transcription and translation of the inserted coding sequence. Methods well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F.

M. et al. (1989) Current Protocols in Molecular Biology, John Wiley & Sons, New York. N.Y.

The present invention also provides kits useful in performing diagnostic and prognostic assays using the antibodies, polypeptides and nucleic acids of the present invention. Kits of the present invention include a suitable container comprising an HIV antibody, a polypeptide or a nucleic acid of the invention in either labeled or unlabeled form. In addition, when the antibody, polypeptide or nucleic acid is supplied in a labeled form suitable for an indirect binding assay, the kit further includes reagents for performing the appropriate indirect assay. For example, the kit may include one or more suitable containers including enzyme substrates or derivatizing agents, depending on the nature of the label. Control samples and/or instructions may also be included. The present invention also provide kits for detecting the presence of the HIV antibodies or the nucleotide sequence of the HIV antibody of the present invention in a biological sample by PCR or mass spectrometry.

"Label" as used herein refers to a detectable compound or composition that is conjugated directly or indirectly to the antibody so as to generate a "labeled" antibody. A label can also be conjugated to a polypeptide and/or a nucleic acid sequence disclosed herein. The label can be detectable by itself (for example, radioisotope labels or fluorescent labels) or, in the case of an enzymatic label, can catalyze chemical alteration of a substrate compound or composition that is detectable. Antibodies and polypeptides of the described invention also can be modified to include an epitope tag or label, for example, for use in purification or diagnostic applications. Suitable detection means include the use of labels such as, but not limited to, radionucleotides, enzymes, coenzymes, fluorescers, chemiluminescers, chromogens, enzyme substrates or co-factors, enzyme inhibitors, prosthetic group complexes, free radicals, particles, dyes, and the like.

According to another embodiment, the present invention provides diagnostic methods. Diagnostic methods generally involve contacting a biological sample obtained from a patient, such as, for example, blood, serum, saliva, urine, sputum, a cell swab sample, or a tissue biopsy, with an HIV antibody and determining whether the antibody preferentially binds to the sample as compared to a control sample or predetermined cut-off value, thereby indicating the presence of the HIV virus.

According to another embodiment, the present invention provides methods to detect the presence of the HIV antibodies of the present invention in a biological sample from a patient. Detection methods generally involve obtaining a biological sample from a patient, such as, for example, blood, serum, saliva, urine, sputum, a cell swab sample, or a tissue biopsy and isolating HIV antibodies or fragments thereof, or the nucleic acids that encode an HIV antibody, and assaying for the presence of an HIV antibody in the biological sample. Also, the present invention provides methods to detect the nucleotide sequence of an HIV antibody in a cell. The nucleotide sequence of an HIV antibody may also be detected using the primers disclosed herein. The presence of the HIV antibody in a biological sample from a patient may be determined utilizing known recombinant techniques and/or the use of a mass spectrometer.

In another embodiment, the present invention provides a method for detecting an HIV antibody comprising a heavy chain comprising a highly conserved consensus sequence and a light chain comprising a highly conserved consensus sequence in a biological sample, comprising obtaining an immunoglobulin-containing biological sample from a mammalian subject, isolating an HIV antibody from said sample, and identifying the highly conserved consensus sequences of the heavy chain and the light chain. The biological sample may be blood, serum, saliva, urine, sputum, a cell swab sample, or a tissue biopsy. The amino acid sequences may be determined by methods known in the art including, for example, PCR and mass spectrometry.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

II. Method of Reducing Viral Replication

Methods for reducing an increase in HIV virus titer, virus replication, virus proliferation or an amount of an HIV viral protein in a subject are further provided. According to another aspect, a method includes administering to the subject an amount of an HIV antibody effective to reduce an increase in HIV titer, virus replication or an amount of an HIV protein of one or more HIV strains or isolates in the subject.

According to another embodiment, the present invention provides a method of reducing viral replication or spread of HIV infection to additional host cells or tissues comprising contacting a mammalian cell with the antibody, or a portion thereof, which binds to an antigenic epitope on gp120.

III. Method of Treatment

According to another embodiment, the present invention provides a method for treating a mammal infected with a virus infection, such as, for example, HIV, comprising administering to said mammal a pharmaceutical composition comprising the HIV antibodies disclosed herein. According to one embodiment, the method for treating a mammal infected with HIV comprises administering to said mammal a pharmaceutical composition that comprises an antibody of the present invention, or a fragment thereof. The compositions of the invention can include more than one antibody having the characteristics disclosed (for example, a plurality or pool of antibodies). It also can include other HIV neutralizing antibodies as are known in the art, for example, but not limited to, VRC01, PG9 and b12.

Passive immunization has proven to be an effective and safe strategy for the prevention and treatment of viral diseases. (See, for example, Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference). Passive immunization using human monoclonal antibodies provides an immediate treatment strategy for emergency prophylaxis and treatment of HIV.

Subjects at risk for HIV-related diseases or disorders include patients who have come into contact with an infected person or who have been exposed to HIV in some other way. Administration of a prophylactic agent can occur prior to the manifestation of symptoms characteristic of HIV-related disease or disorder, such that a disease or disorder is prevented or, alternatively, delayed in its progression.

For in vivo treatment of human and non-human patients, the patient is administered or provided a pharmaceutical formulation including an HIV antibody of the invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral, topical, or inhalation routes. The antibodies can be administered parenterally, when possible, at the target cell site, or intravenously. In some embodiments, antibody is administered by intravenous or subcutaneous administration. Therapeutic compositions of the invention may be administered to a patient or subject systemically, parenterally, or locally. The above parameters for assessing successful treatment and improvement in the disease are readily measurable by routine procedures familiar to a physician.

For parenteral administration, the antibodies may formulated in a unit dosage injectable form (solution, suspension, emulsion) in association with a pharmaceutically acceptable, parenteral vehicle. Examples of such vehicles include, but are not limited, water, saline, Ringer's solution, dextrose solution, and 5% human serum albumin. Nonaqueous vehicles include, but are not limited to, fixed oils and ethyl oleate. Liposomes can be used as carriers. The vehicle may contain minor amounts of additives such as substances that enhance isotonicity and chemical stability, such as, for example, buffers and preservatives. The antibodies can be formulated in such vehicles at concentrations of about 1 mg/ml to 10 mg/ml.

The dose and dosage regimen depends upon a variety of factors readily determined by a physician, such as the nature of the infection, for example, its therapeutic index, the patient, and the patient's history. Generally, a therapeutically effective amount of an antibody is administered to a patient. In some embodiments, the amount of antibody administered is in the range of about 0.1 mg/kg to about 50 mg/kg of patient body weight. Depending on the type and severity of the infection, about 0.1 mg/kg to about 50 mg/kg body weight (for example, about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art. The above parameters for assessing successful treatment and improvement in the disease are readily measurable by routine procedures familiar to a physician.

Other therapeutic regimens may be combined with the administration of the HIV antibody of the present invention. The combined administration includes co-administration, using separate formulations or a single pharmaceutical formulation, and consecutive administration in either order, wherein preferably there is a time period while both (or all) active agents simultaneously exert their biological activities. Such combined therapy can result in a synergistic therapeutic effect. The above parameters for assessing successful treatment and improvement in the disease are readily measurable by routine procedures familiar to a physician.

The terms "treating" or "treatment" or "alleviation" are used interchangeably and refer to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to treat a disease or disorder in a subject or mammal.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, polyoxyethylenesorbitan monolaurate (e. g. TWEEN); polyethylene glycol (PEG), and poloxamers (e.g. PLURONICS).

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference in their entireties.

As used herein and in the appended claims, the singular forms "a", "and" and "the" include plural references unless the context clearly dictates otherwise Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

Each of the applications and patents cited in this text, as well as each document or reference, patient or non-patient literature, cited in each of the applications and patents (including during the prosecution of each issued patent; “application cited documents”), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references (“herein-cited references”), as well as each document or reference cited in each of the herein-cited references (including any manufacturer’s specifications, instructions, etc.), is hereby expressly incorporated herein by reference.

The following non-limiting examples serve to further illustrate the present invention.

Example 1

Materials, Methods and Instrumentation

Samples. Human samples were collected after signed informed consent in accordance with Institutional Review Board (IRB)-reviewed protocols by all participating institutions. Patient 1 was selected from a cohort of long-term non-progressors followed at the Aaron Diamod Aids Research Center, New York. Patients 3 and 8 were selected from a group of elite controllers that were followed at the Ragon Institute in Boston. Patients 1, 3 and 8 were selected based on their broad neutralizing serum activity against a standard panel of HIV isolates. Patient 12 was selected from the Protocol G Cohort of the “International Aids Vaccine Initiative” based on broad serum neutralizing activity.

Staining, single-cell sorting and antibody cloning. Staining and single cell sorting of 2CC-Core and gp140 specific Ig+ memory B cells was performed (J. F. Scheid et al., Nature 458, 636 (Apr. 2, 2009)). Briefly, CD19+ B cells were enriched from peripheral blood mononuclear cells using anti human CD19 magnetic MACS beads (Miltenyi Biotec) and subsequently stained with anti human CD20 and anti human IgG antibodies (Becton Dickinson) as well as biotinylated 2CC-Core (B. Dey et al., PLoS Pathog 5, e1000445 (May, 2009)) or YU2-gp140 trimer (R. Diskin, P. M. Marcovecchio, P. J. Bjorkman, Nat Struct Mol Biol 17, 608 (May, 2010)) followed by detection with streptavidin coupled phycoerythrin (PE, Beckton Dickinson). Single cells were sorted on a FACSAria III cell sorter (Becton Dickinson), excluding cell doublets, into 96-well PCR plates (Denville) containing 4 μl/well of ice-cold 0.5× phosphate-buffered saline (PBS) containing 10 mM DTT, 8 U RNAsin® (Promega), 0.4 U 5'-3' Prime RNAse Inhibitor™ (Eppendorf). Plates were sealed with Microseal® ‘F’ Film (BioRad), immediately frozen on dry ice before storage at −80° C.

cDNA synthesis and Ig amplification were performed (H. Wardemann et al., Science 301, 1374 (Sep. 5, 2003)) with following modifications:

Instead of using the original primer sets, first and second immunoglobulin specific PCRs were carried out using the primers described in Table 1 in a semi-nested approach. Cloning of heavy and light chain PCR products into their respective expression vectors was performed and 100% identity of cloned expression plasmids with the original PCR product confirmed by sequencing before expression of the antibodies in HEK 293 cells.

ELISAs. High-binding 96-well ELISA plates (Costar) were coated overnight with 100 ng/well of purified antigens (gp140, gp120, gp41, $gp120^{core}$ and 2CC-core) (B. Dey et al., PLoS Pathog 5, e1000445 (May, 2009)) and mutant proteins (gp120 D368R, gp120 1420R) in PBS. After washing, plates were blocked 2 h with 2% BSA, 1 μM EDTA, 0.05% Tween-PBS (Blocking buffer) and then, incubated 2 h with IgG antibodies diluted at 4 μg/ml and several consecutive 1:4 dilutions in PBS. After washing, the plates were developed by incubation for 1 h with goat HRP-conjugated anti-mouse IgG (Jackson ImmunoReseach) (at 0.8 μg/ml in blocking buffer) and by adding 100 μl of HRP chromogenic substrate (ABTS solution, Invitrogen). Optical densities were measured at 405 nm ($OD_{405\ nm}$) using an ELISA microplate reader (Molecular Devices). Background values given by incubation of PBS alone in coated wells were subtracted. IgG Antibodies were tested for polyreactivity (H. Mouquet et al., Nature 467, 591 (Sep. 30, 2010)) and considered polyreactive when they recognized at least two structurally different antigens out of the four tested; ssDNA, dsDNA, insulin, and LPS. Threshold values for reactivity were determined by using control antibodies mGO53 (negative), eiJB40 (low positive), and ED38 (high positive).

Neutralization assays: Neutralization screens were performed (D. C. Montefiori, *Curr Protoc Immunol* Chapter 12, Unit 12 11 (January, 2005)). In brief, neutralization was detected as reduction in luciferase reporter gene expression after single round infection in Tzm-bl cells. In order to rule out unspecific antiviral activity in antibody samples MuLV (murine leukemia virus) was used as a negative control.

Clone specific identification of bone marrow plasma cells. Bone marrow plasma cells were stained with anti human CD138 and anti CD19 antibodies (Becton Dickinson) after Ficoll purification of mononuclear cells from bone marrow aspirates using Ficoll-Paque (GE Healthcare). CD138+ CD19+ human plasma cells were bulk sorted on a FACSAriaIII cell sorter (Becton Dickinson) and RNA isolation performed on 100.000 cells using Trizol LS reagent (Invitrogen) according to the manufacturers instructions. RNA was reverse transcribed using Superscript III reverse transcriptase (Invitrogen) according to manufacturers instructions. cDNA was then subjected to Immunoglobulin specific PCR with following modifications: 1□1 of cDNA was amplified in 2 rounds of nested immunoglobulin heavy chain clone specific PCR using first round forward leader and constant region reverse primers shown in Table 1 followed by clone specific forward and reverse primers designed based on sequencing results from single cell analysis. PCR products were gel purified and cloned into TOPO TA vectors (Invitrogen) according to the manufacturers instructions. Colonies were screened by PCR with clone specific primers and sequenced.

Figure 8A:
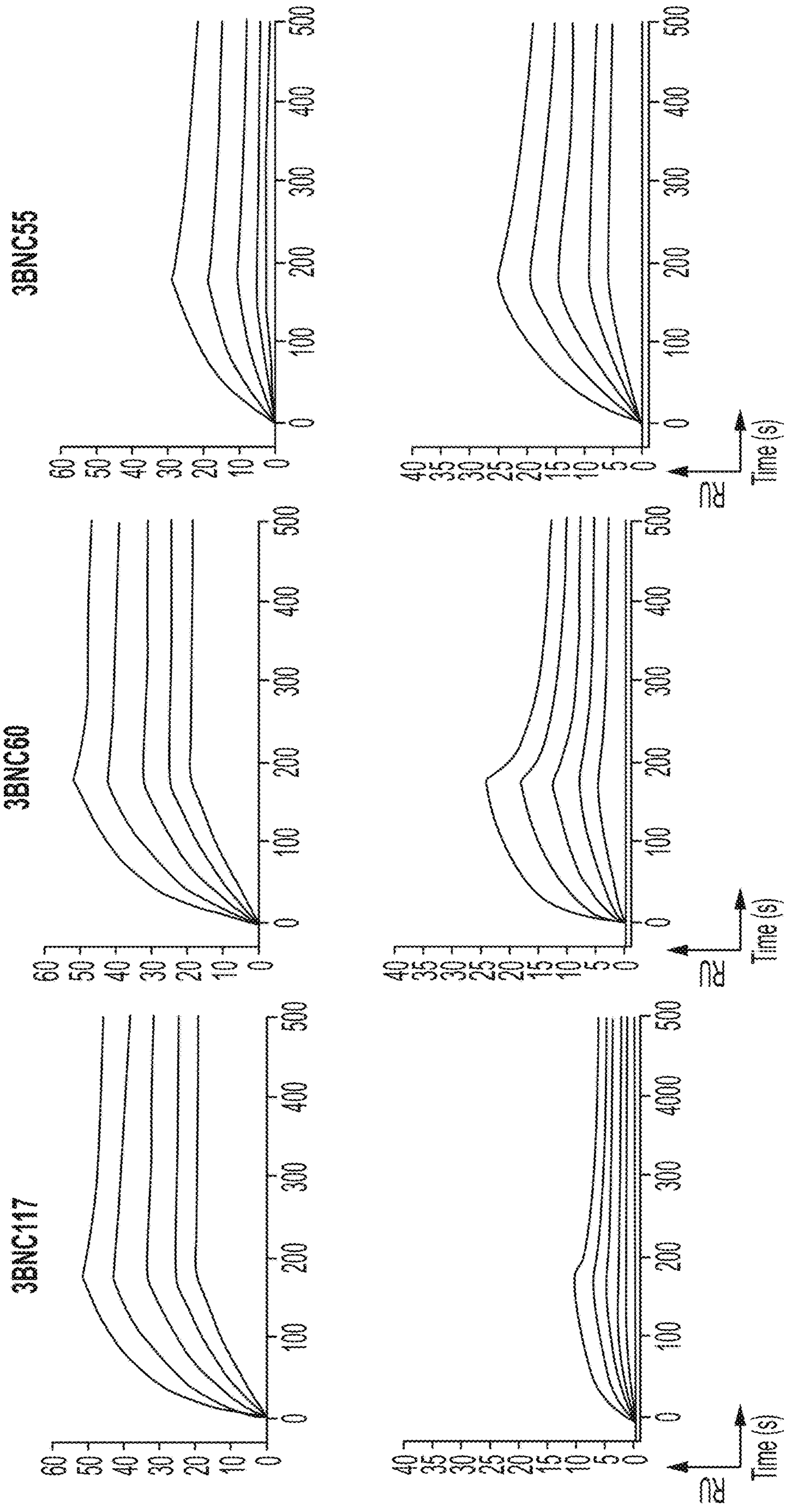
FIGS. 8A and B demonstrate affinity of HIV antibodies. (A) Antibody binding to gp140 and 2CC-core measured by surface plasmon resonance (SPR). The SPR sensograms for antibody binding of the selected 3BNC-antibody clones are shown over time. (B) Bar graphs show the binding affinity ($K_A$) for gp140 and 2CC-core antigens for the selected IgG antibodies shown in A. RU, response units.
Figure 8A:
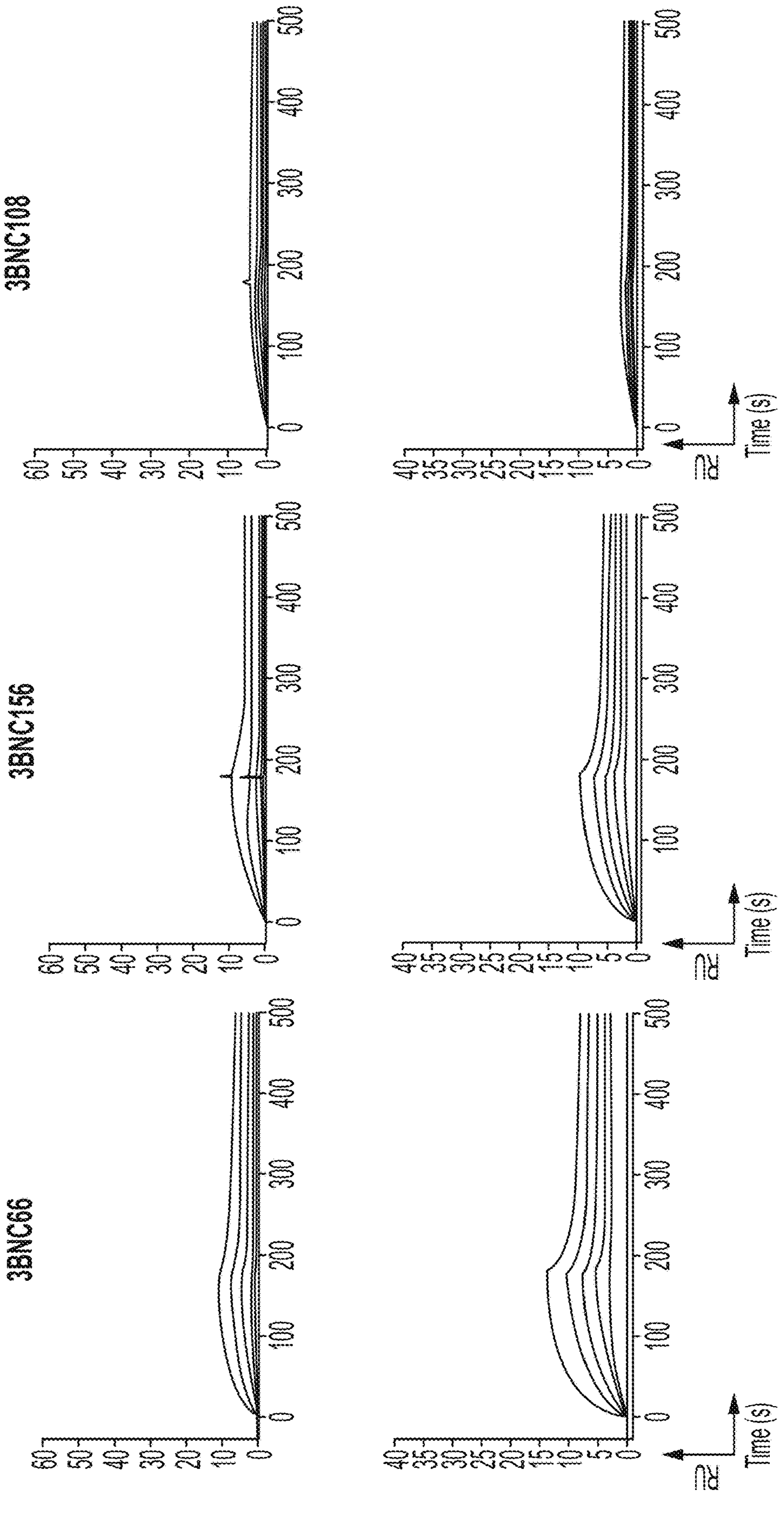
Figure 8B:
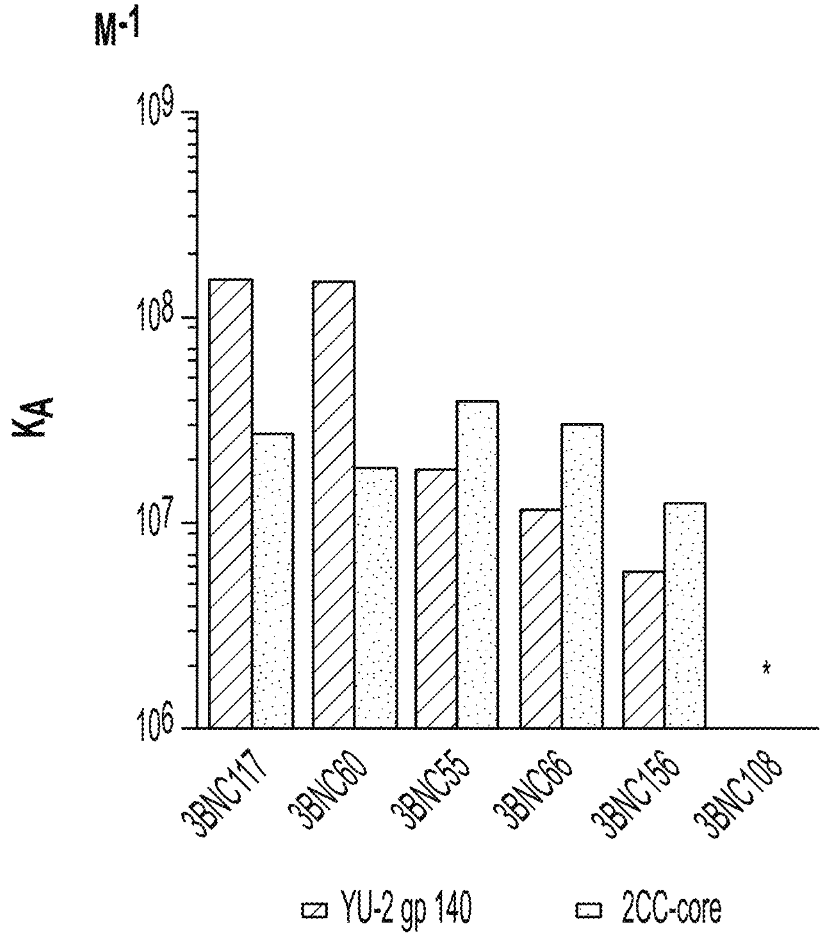
Figure 9A:
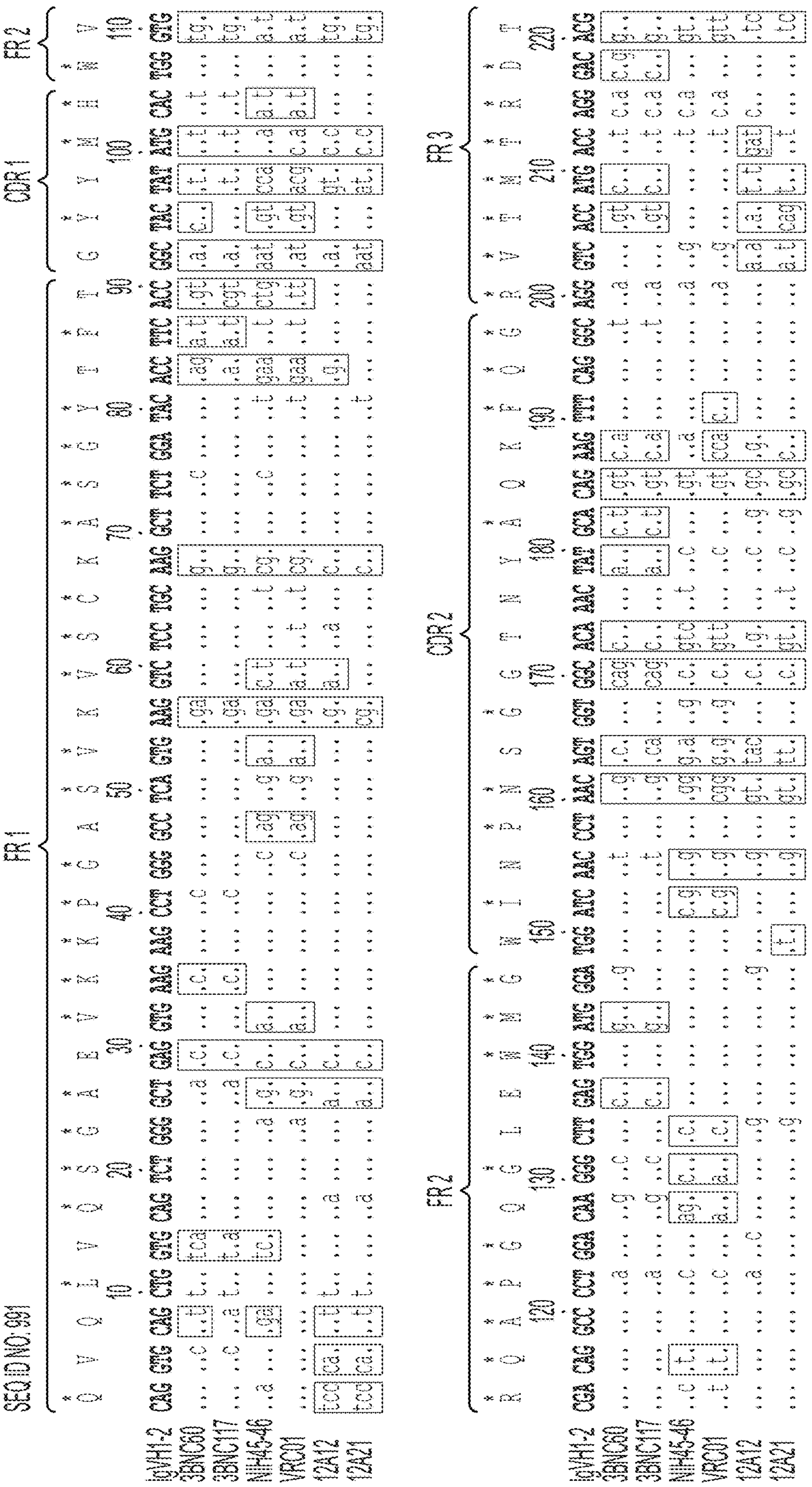
FIGS. 9A, 9B and 9C illustrate the somatic hypermutation analysis of selected HIV antibodies for (A) immunoglobulin heavy chain gene, (B) light chain kappa and (C) light chain lambda gene sequences. Sequences are aligned with their respective germline nucleotide sequences. Somatic mutations are shown in red letters, additionally gray boxes designate replacement mutations. Germline amino acid sequences with ✱ indicating consensus residues are shown above the nucleotide alignment.
Figure 9A:
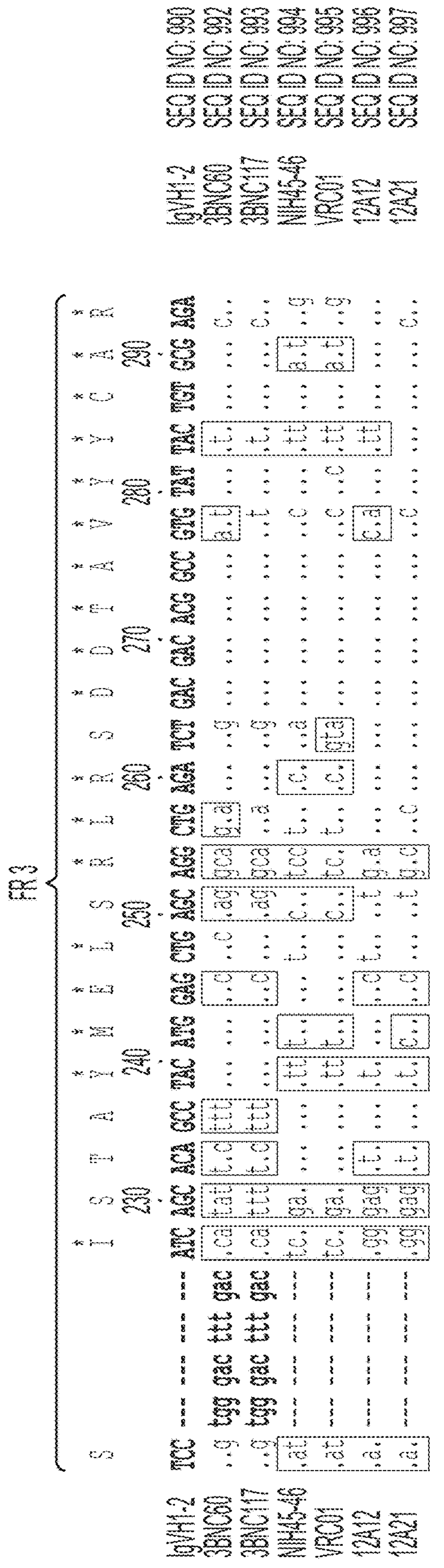
Figure 9A:
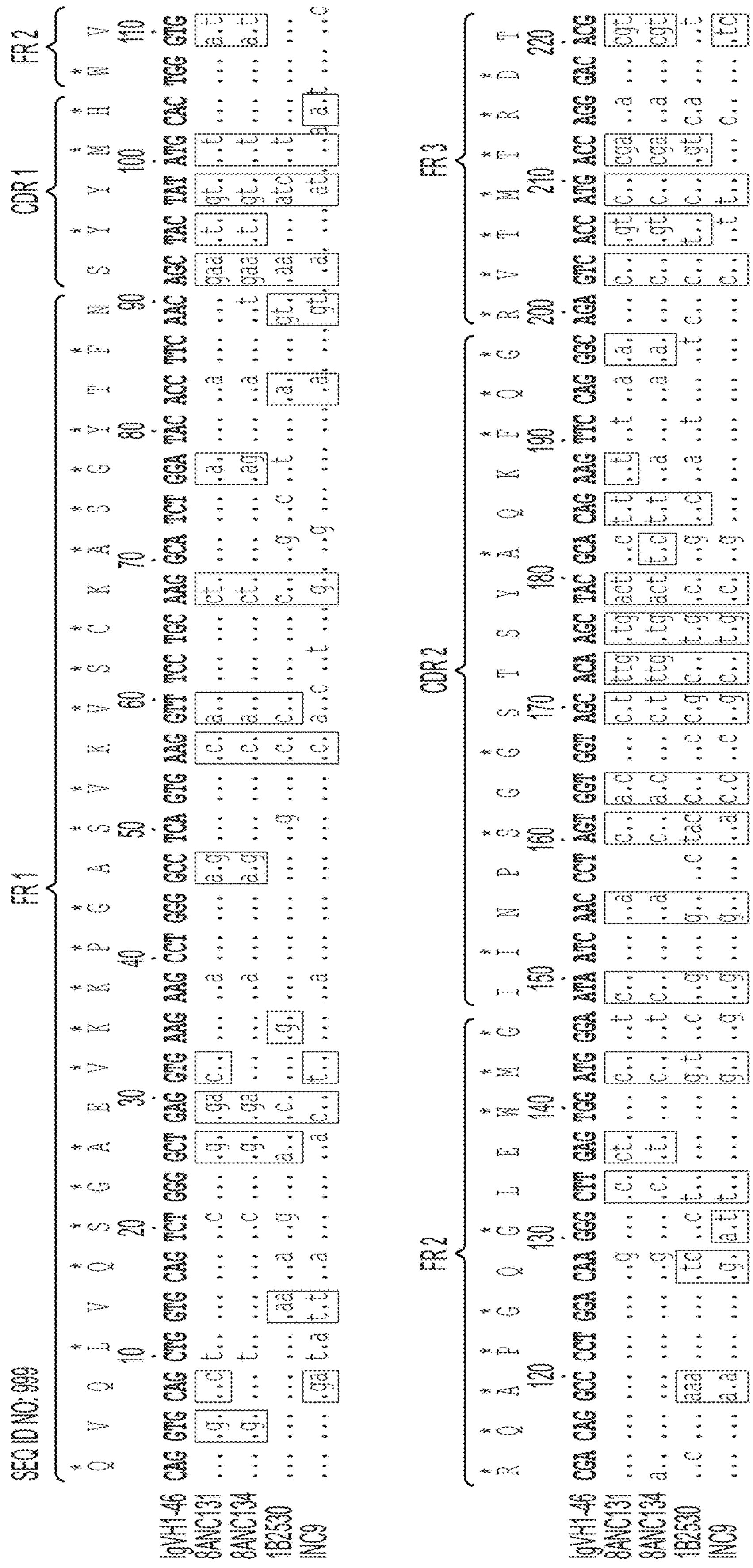
Figure 9A:
Figure 9B:
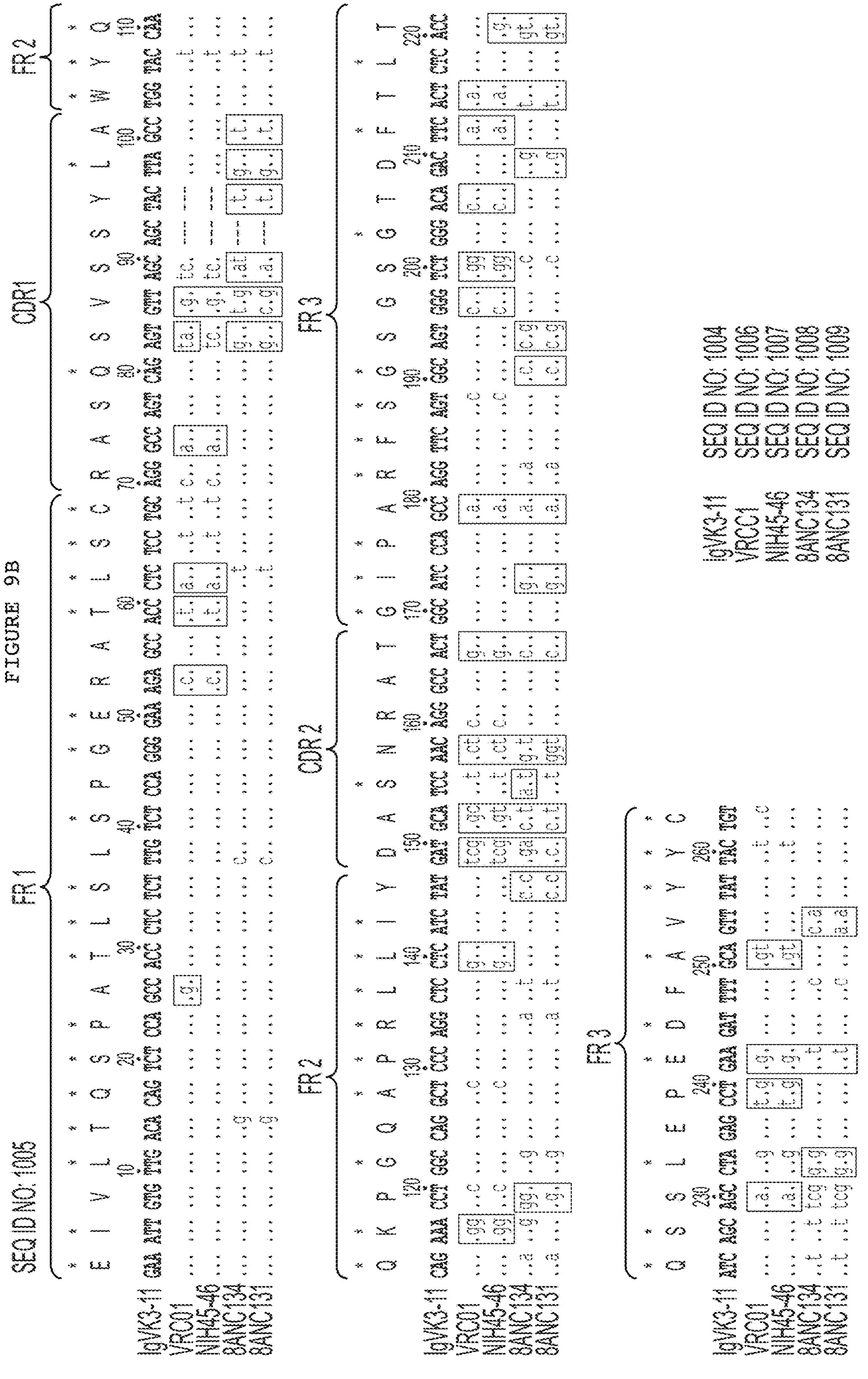
Figure 9B:
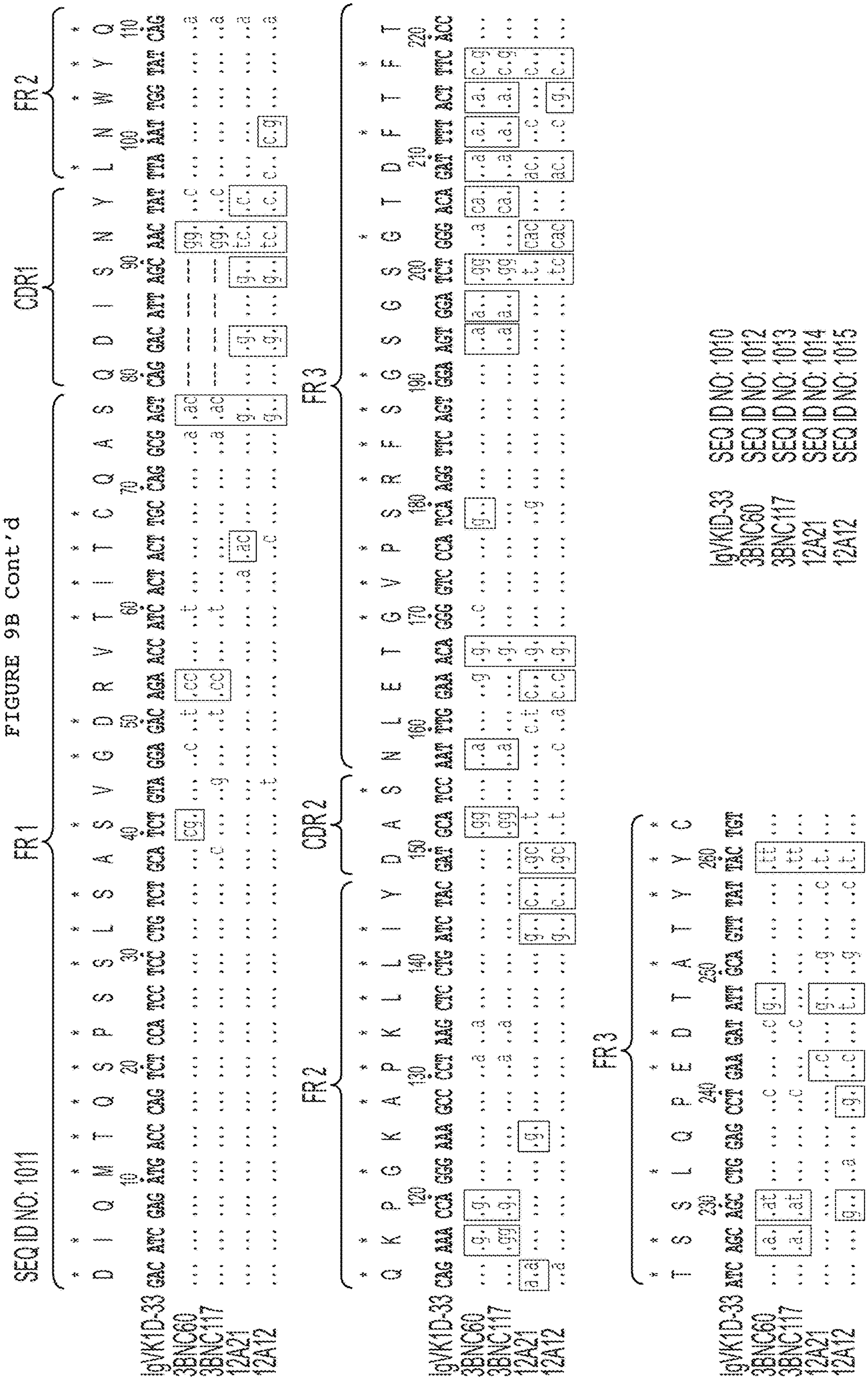
Figure 9C:
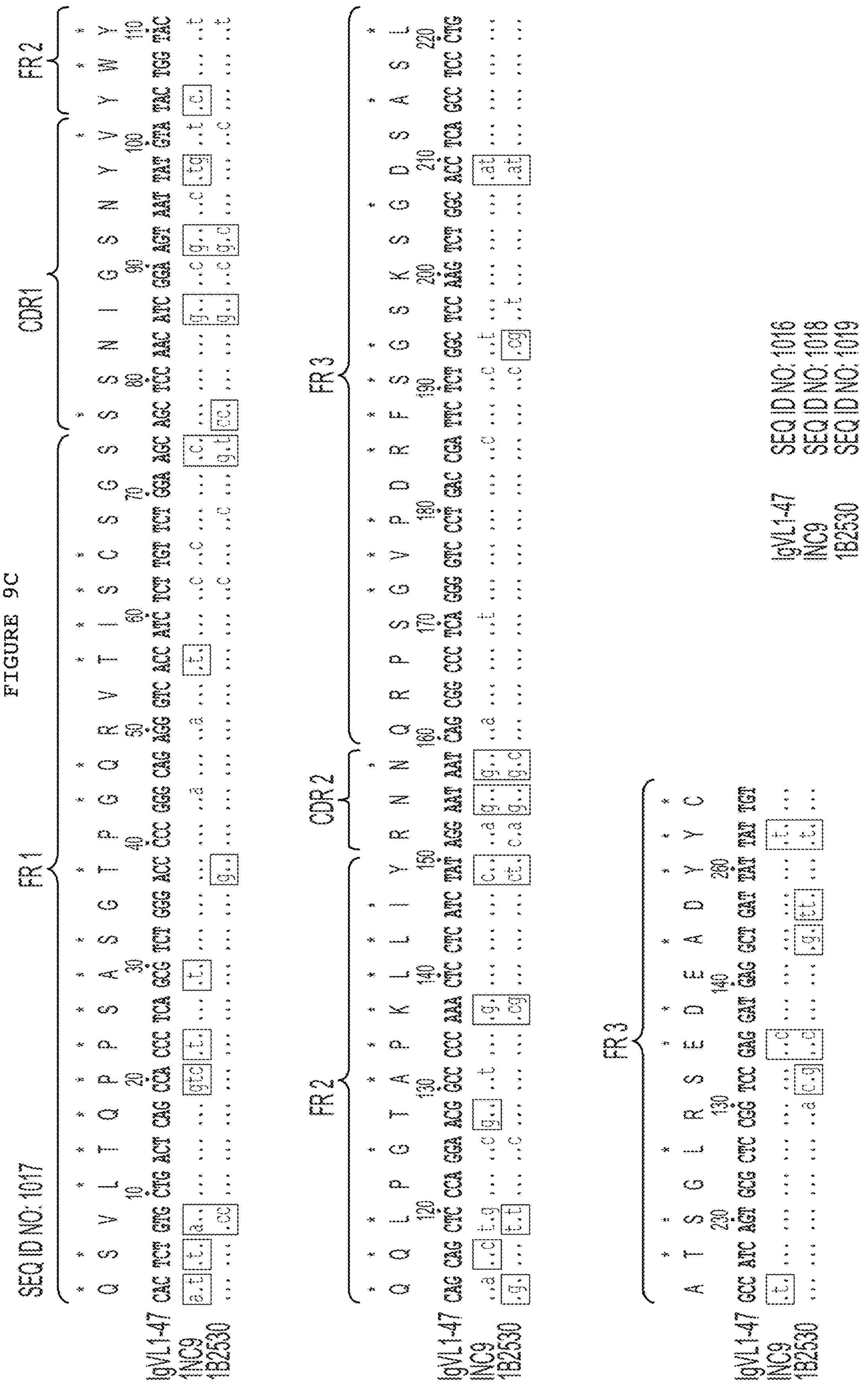

Surface plasmon resonance. All experiments were performed with a Biacore T100 (Biacore, Inc) in HBS-EP+ running buffer (Biacore, Inc) at 25° C. as described previously (Mouquet2010). YU-2 gp140 and 2CC-core proteins at 12.5 μg/mL were immobilized on CM5 chips (Biacore, Inc.) by amine coupling at pH 4.5 resulting in an immobilization level of 100 RUs. For kinetic measurements on the gp140- and 2CC-core-derivatized chips, IgGs were injected through flow cells at 700 nM and 4 successive 1:2-dilutions in HBS-EP+ running buffer (Biacore, Inc.) at flow rates of 40 μL/min with 3 min association and 5 min dissociation. The sensor surface was regenerated between each experiment with a 30 second injection of 10 mM glycine-HCl pH 2.5 at a flow rate of 50 μL/min. Off rate ($k_d$ ($s^{-1}$)), on rate ($k_a$ ($M^{-1}$ $s^{-1}$) and binding constants ($K_D$ (M) or $K_A$ ($M^{-1}$) were calculated after subtraction of backgrounds (binding to control flow cells and signal of the HBS-EP+ running buffer) using Biacore T100 Evaluation software using the kinetic analysis and the 1:1 binding model. The sensorgrams showed in FIG. 2 and FIG. 8 are derived from the Biacore data processing using Scrubber 2 sofware (Center for Biomolecular Interaction Analysis, University of Utah).

CD4i site induction. 293T cells were transfected with $gp160^{BAL.26}\Delta c$ or $gp160^{YU.2}\Delta c$ in a pMX-IRES-GFP construct (Pietzsch et al. 2010) using Fugene™ 6 (Roche) at a 1:2 plasmid:Fugene ratio. After 48 hours 293T cells were washed with PBS and detached with Trypsin-free cell dissociation buffer (Gibco) and resuspended at a concentration of $10^7$ cells/mi in FACS buffer (1×PBS, 2% FBS, 2 mM EDTA). sCD4 (Progenics Pharmaceuticals, Inc.) and mAbs were added to gp160-expressing 293T cells in a 1:4 dilution series starting with a final concentration of 40 μg/ml. mGO is a negative control antibody that does not bind to gp160Δc (H. Mouquet et al., Nature 467, 591 (Sep. 30, 2010)). After incubation for 15 min on ice cells were split and stained for 25 min on ice with an Alexa647-labeled CD4-induced site mAb (3-67; (J. F. Scheid et al., Nature 458, 636 (Apr. 2, 2009)) or an Alexa647-labeled control mAb (i.e. PG16; L. M. Walker et al., Science 326, 285 (Oct. 9, 2009)) or 2G12 for $gp160^{YU.2}$ and 2G12 for $gp160^{BAL.26}$). Antibody labeling was performed by using Alexa Fluor® 647 Microscale Protein Labeling Kit (Invitrogen). Cells were analyzed on an LSRFortessa cell analyzer (BD Bioscience).

Crystallization. The 3BNC60 IgG was expressed by transient expression in HEK293-6E cells and prepared the Fab fragment was prepared by papain cleavage (R. Diskin, P. M. Marcovecchio, P. J. Bjorkman, Nat Struct Mol Biol 17, 608 (May, 2010). Crystallization screens were conducted at 20° C. by vapor diffusion in nL sitting drops using a Mosquito™ (TTP LabTech) crystallization robot on MRC crystallization plates (Jena Bioscience). We combined 3BNC60 Fab at a concentration of 9.5 mg/ml with reservoir solution in a 1:1 ratio to create 400 nL drops. Initial crystallization hits were obtained using the PEGRx HT™ (Hampton Research) crystallization screen and further optimized manually. Crystals suitable for data collection grew after several weeks in 11.7% polyethylene glycol 20,000, 0.1 M sodium acetate pH 5.0, 100 mM potassium/sodium tartrate, 20 mM lithium sulfate, 10 mM N-Cyclohexyl-2-aminoethanesulfonic acid (CHES) pH 9.5 in the monoclinic space group $P2_1$ with two Fabs in the asymmetric unit. Crystals were soaked in reservoir solution supplemented with 15% glycerol for 2 hours before immersing in reservoir solution supplemented with 30% glycerol and flash cooling in liquid nitrogen. Diffraction data were collected at the Stanford Synchrotron Radiation Lightsource (SSRL) beam-line 12-2 at 100 K using a Pilatus 6M detector. Data were indexed, integrated, and scaled using XDS W. Kabsch, *Acta Crystallogr D Biol Crystallogr* 66, 125 (February, 2010) (Table 8). Molecular replacement was conducted using Phaser with the $V_H$ and $C_H1$ domains from the anti-tumor antibody CTM01 (PDB code 1AD9) and with the $V_L$ and $C_L$ domains of the anti-gp120 b13 antibody (PDB code 31DX) as search models. Model building and refinement to 2.65 Å resolution was done iteratively using Phenix P. Emsley, B. Lohkamp, W. G. Scott, K. Cowtan, Acta Crystallogr D Biol Crystallogr 66, 486 (April, 2010) and Coot (P. Emsley, B. Lohkamp, W. G. Scott, K. Cowtan, Acta Crystallogr D Biol Crystallogr 66, 486 (April, 2010)). The structure was refined using a maximum-likelihood target function and non-crystallographic symmetry restraints. The final model ($R_{work}$=20.7%; $R_{free}$=25.7%) includes 6478 protein atoms, 146 water molecules and 28 sugar atoms (Table 8). 91.9%, 7.6% and 0.5% of the residues were in the favored, allowed, and disallowed regions, respectively, of the Ramachandran plot. Structural analyses and visualization were done using PyMol (The PyMOL Molecular Graphics System, Version 1.3, Schrödinger, LLC). The 3BNC60 structure consists of residues 3-205 for the light chain (including the first N-acetylglucosamine within an N-linked carbohydrate attached to Asn72) and 2-217 for the heavy-chain. Residues at the termini residues and residues 133-140 within the $C_H1$ domain are disordered.

Mass Spectrometry. IgG was purified from serum using ProteinG Sepharose (GE Healthcare) according to the manufacturers instructions. IgGs were then digested with immobilized papain (Pierce) and digested Fab-Fc fragment mixes incubated with saturating quantities of biotinylated 2CC-Core protein. Streptavidin coupled Dynabeads (Invitrogen) were added after incubation for 15 minutes at room temperature and subjected to 10 rounds of washing with Phosphate Buffered Saline (Gibco). Bound Fab fragments were eluted with lithium dodecyl sulfate buffer (Invitrogen) at 95 C and sample purity confirmed with SDS-polyacrylamide gel electrophoresis followed by silver stain or coomassie staining before analysis by mass spectrometry.

Isolated Fab fragments were reduced with dithiothreitol, alkylated using iodoacetamide, resolved by 1D gel electrophoresis on a 4-12% NuPAGE Novex Bis-Tris gel (Invitrogen), and stained with Coomassie Blue (Thermo Fisher). The Fab fragments were excised from the gel, and digested using 200 ng of trypsin (Promega). The resulting peptides were isolated using reverse phase resin (PORS 20 R2, Applied Biosystem) and eluted using an aliquot of 40% acetonitrile in 0.5% acetic acid and a second aliquot of 80% acetonitrile in 0.5% acetic acid. Acetonitrile was removed using a speedvac (Thermo Fisher Scientific) and aliquots of the remaining solution pressure loaded onto self-packed PicoFrit® column (New Objective, Woburn, MA) with integrated emitter tip (360 μm O.D., 50 μm I.D., 10 μm tip), packed with 6 cm of reverse-phase C18 material (ReproSil-Pur C18-AQ, 3 μm beads from Dr. Maisch GmbH) and interfaced to a Agilent 1200 series HPLC system (Agilent) with either a LTQ Orbitrap™ XL mass spectrometer or a LTQ Orbitrap Velos™ mass spectrometer (Thermo Fisher Scientific) using a home-built micro electrospray source. The peptides were eluted into the mass spectrometer with the following gradient: 0 to 5% B in 5 min, 40% B in 125 min, 60% B in 150 min, 100% B in 165 min (A=0.1 M acetic acid, B=70% acetonitrile in 0.1 M acetic acid, flow rate 90 nL/min). Both instruments were operated in the data dependent mode and for both mass spectrometers the target value was set to 5e5 ions and a resolution of 60,000 (at 400 m/z). For analysis on the LTQ Orbitrap™ XL a full scan was followed by 8 MS/MS scans on the 8 most abundant ions from that full scan. The peptides (only charge states>1) were isolated with a 2 Da window, target window of 1e4 ions, dissociated via CAD (normalized collision energy=35, activation Q=0.25, activation time 30 msec) and mass analyzed in the LTQ. For analysis on the LTQ Orbitrap™ Velos a full scan was followed by 10 MS/MS scans at 7,500 resolution on the 10 most abundant ions from the immediate preceding full scan. The peptides (only charge state>2) were isolated with a 3 Da window, target window of 2e5 ions, dissociated via HCD (normalized collision energy=40, activation time 0.100 msec) and mass analyzed in the Orbitrap. For either instrument the ions selected for MS/MS were set on an exclusion list for 30 seconds. The resulting MS/MS spectra were searched against the Human IPI and in-house patient specific IgG database using Xtandem!, peptides were automatically compared to tryptic peptides in the human IPI and our in-house patient specific database. Peptide hits corresponding to patient specific IgG were manually confirmed.

Multiple sequence alignments. All multiple sequence alignments were conducted using CLUSTALW2 with default parameters (weight matrix: GONNET for proteins and UIB for DNA, gap open=10, gap extension 0.1). Alignments shading were generated using TeXshade package.

Alignment consensus. The consensus sequences for multiple alignments were generated based on identity and similarity between residues (>=70%). The amino acids were grouping due similarity as: FYW, ILVM, RK, DE, GA, ST and NQ.

Phylogenetic Germline Trees. The relationship between sequences was generated using the Neighbor-Joining method. The bootstrap consensus tree inferred from 1000 replicates was taken to represent the relationship. Branches corresponding to partitions reproduced in less than 50% bootstrap replicates are collapsed. The percentage of replicate trees in which the associated sequence clustered together in the bootstrap test (1000 replicates) are shown next to the branches. The tree is drawn to scale, with branch lengths in the same units as those of the evolutionary distances used to infer the phylogenetic tree. The evolutionary distances were computed using the number of differences method and are in the units of the number of amino acid differences per sequence. All ambiguous positions were removed for each sequence pair. Evolutionary analyses were conducted in MEGA5.

R/S Ratio Calculation. DNA sequences were superposed over the proteins alignments to replacement/substitution calculation. All gaps positions were removed from the analysis. The R/S ratio analysis was conducted using Perl scripts.

Example 2

Isolating HIV Antibodies

To determine whether HIV antibody cloning is limited because of somatic mutation, a new series of primers was designed to avert this potential problem (Table 1). The new primer set was tested by sorting B cells that bind to an HIV-gp120 core protein lacking the V1-3 loops and containing a pair of stabilizing disulfide bonds (2CC-core). In contrast to the re-surfaced bait used to clone VRC01, the 2CC-core bait also allows capture of antibodies to the CD4-induced co-receptor binding site (CD4i).

Figure 4B:
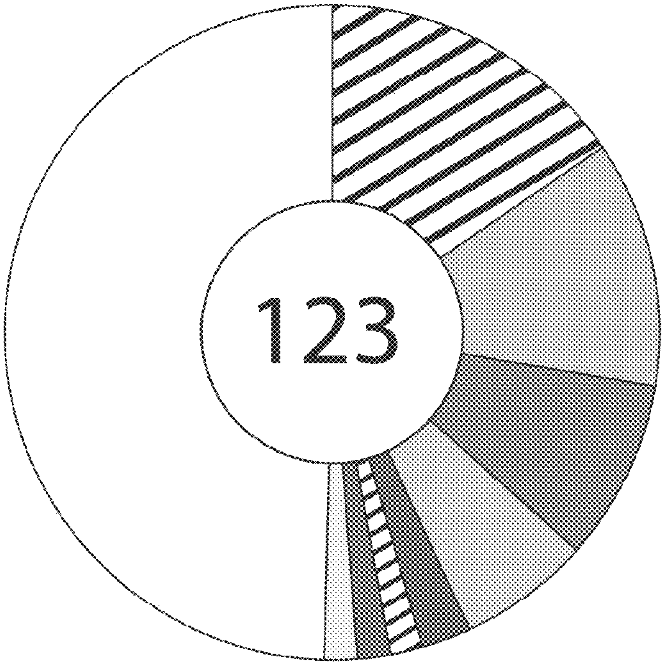

In side-by-side comparisons, the new primer set increased recovery of IgH chains when compared to the initial primer set (FIG. 4(*a*)). The antibodies obtained with the new primer set were more mutated (average 35.6 vs. 19.8 p=<0.0001 and maximum 85 vs. 50 for IgH) and included clones that were not found with the original primer set (FIG. 4(*a*)). To determine whether the new primers rescue VRC01-like antibodies from cells that had been sorted with YU2 gp140, frozen cDNA samples from that individual which had already been examined exhaustively with the original primer set without producing any VRC01 related clones were examined. In 80 wells, 3 antibodies corresponding to VRC01 variants as determined by the IgH and IgL sequences were found (FIGS. 5A and B). It was concluded that VRC01-like antibodies were captured by the gp140 trimer, and that primers that were specifically designed to clone highly mutated antibodies captured a larger fraction of anti-HIV antibodies from the memory B cells of patients with high titers of broadly neutralizing antibodies.

Four unrelated HIV infected individuals, including 2 Caucasians, 1 Hispanic and 1 African donor, showing high titers of broadly neutralizing antibodies were examined using the 2CC-core bait, including 2 individuals whose previously cloned antibodies could not account for their serologic activity (Table 2 and FIGS. 6A and B). 576 antibodies representing 201 different unique and diversified clones were obtained from a starting population of $1.5\times10^5$ $IgG^+$ memory B cells (Table 3).

Example 3

Binding Specificity of HIV Antibodies

The size of the antibody clones captured by 2CC-core bait differed widely ranging from 2-76 diversified members (Table 3). To determine whether the antibodies captured by the 2CC-core bind to the HIV spike, ELISAs were performed using YU2 gp120 on representative members of each expanded clone. All of the antibodies tested bound to gp120 (Table 3).

The site of antibody binding on the HIV spike was mapped using mutant proteins that interfere with either the CD4bs (gp120(D368R)), or the CD4-induced co-receptor binding site (CD4i, gp120(1420R)). As reported, X. Wu et al., *Science* 329, 856 (Aug. 13, 2010), VRC01 is classified as a CD4bs antibody since it is sensitive to the D368R mutation, but because of the proximity of the CD4i site, it also shows some sensitivity to the 1420R mutation. NIH45-46, which is a VRC01 variant, and antibodies 3BNC60, 8ANC131, and 12A12 showed ELISA patterns that were similar to VRC01 (These clonal members were selected based on neutralizing activity, Table 3). Other clones, including 1B2530, and 8ANC195, were equally sensitive to both mutations and could not be classified precisely based solely on ELISA.

To determine whether the antibodies are polyreactive, ELISAs were performed on purified ssDNA, dsDNA, insulin, and LPS. 63% of the anti-2CC Core antibodies tested were polyreactive. It was concluded that the majority of the antibodies captured by the 2CC-bait recognize either the CD4bs or the CD4i site on gp120 and many are also polyreactive.

Example 4

Somatic Hypermutation

Somatic hypermutation is required for development of high affinity antigen binding and in some cases contributes to polyreactivity of anti-HIV antibodies. To test if this is the case for highly mutated 2CC-core specific antibodies, 4 representative antibodies were reverted to the corresponding germline. Reversion led to complete loss of antigen binding in ELISA for all 4 clones tested and to loss of polyreactivity.

Example 5

HIV Neutralization

Figures 1C, 1D:
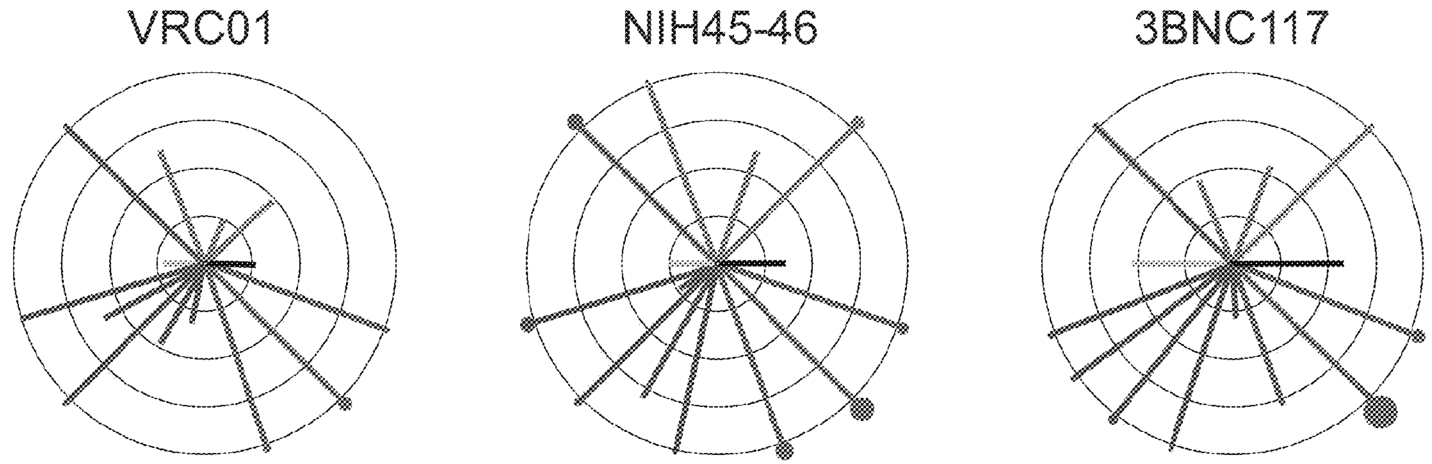
Figure 6B:
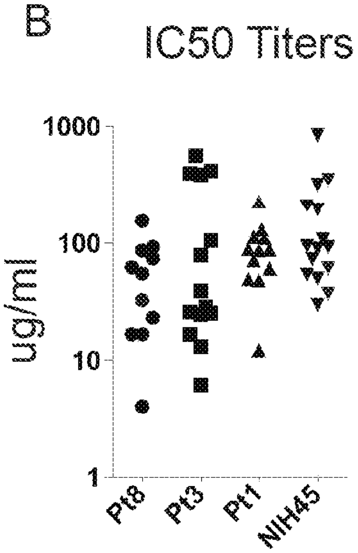
Figure 7A:
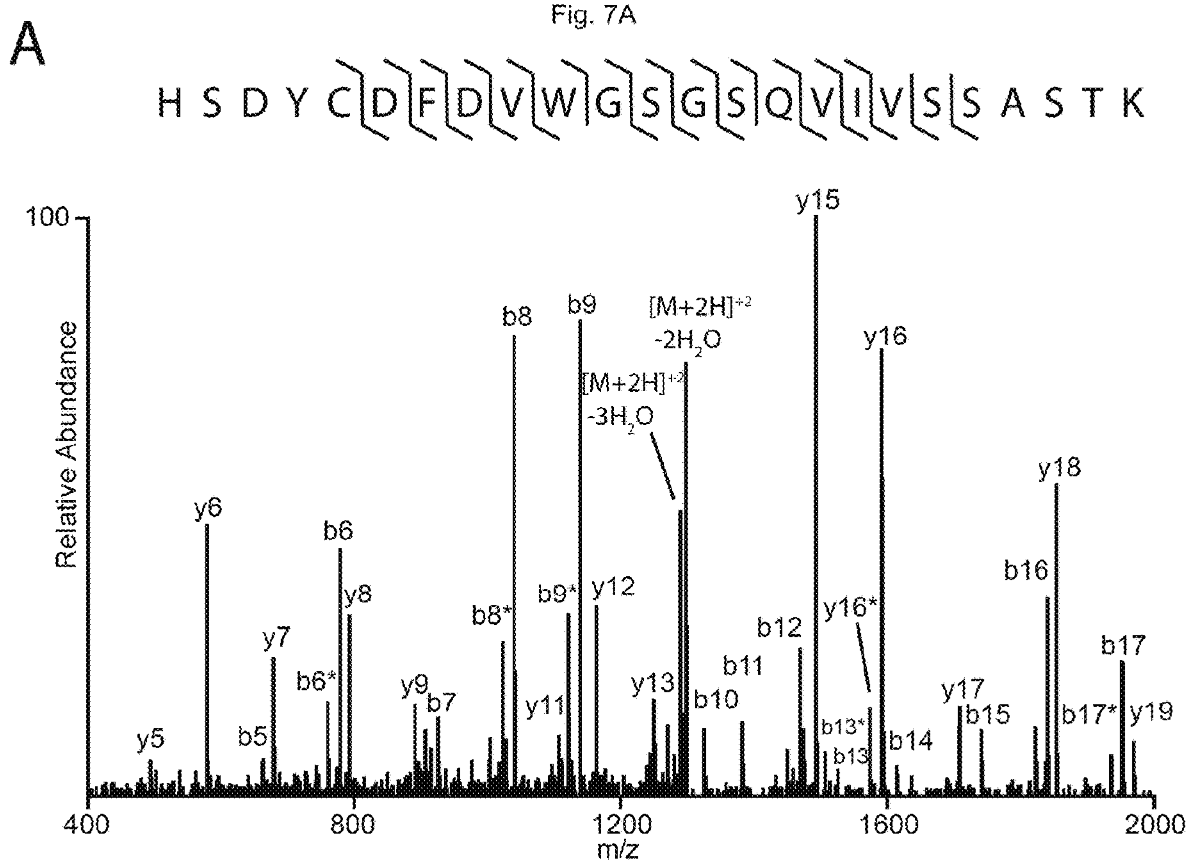
FIGS. 7A and 7B demonstrate detection of antibodies by mass spectrometry. Collision activated dissociation MS/MS spectrum recorded on the doubly charged peptides HSDYCDFDVWGSGSQVIVSSASTK (SEQ ID NO: 888) from 3BNC153HC (A) and DGLGEVAPAYLYGIDAWGQGTTVIVTSASTK (SEQ ID NO: 889) from 8ANC134HC. (B. Observed b-type fragment ions (containing the N-terminus) and y-type fragment ions (containing the C-terminus) are labeled in the spectrum. Loss of water from fragment ions is indicated by *. Ions corresponding to the loss of water from the parent ion are labeled in the spectrum. Observed backbone cleavages are indicated in the sequence with ⌉ for b-type ions and ⌊ for y type ions.
Figure 7B:
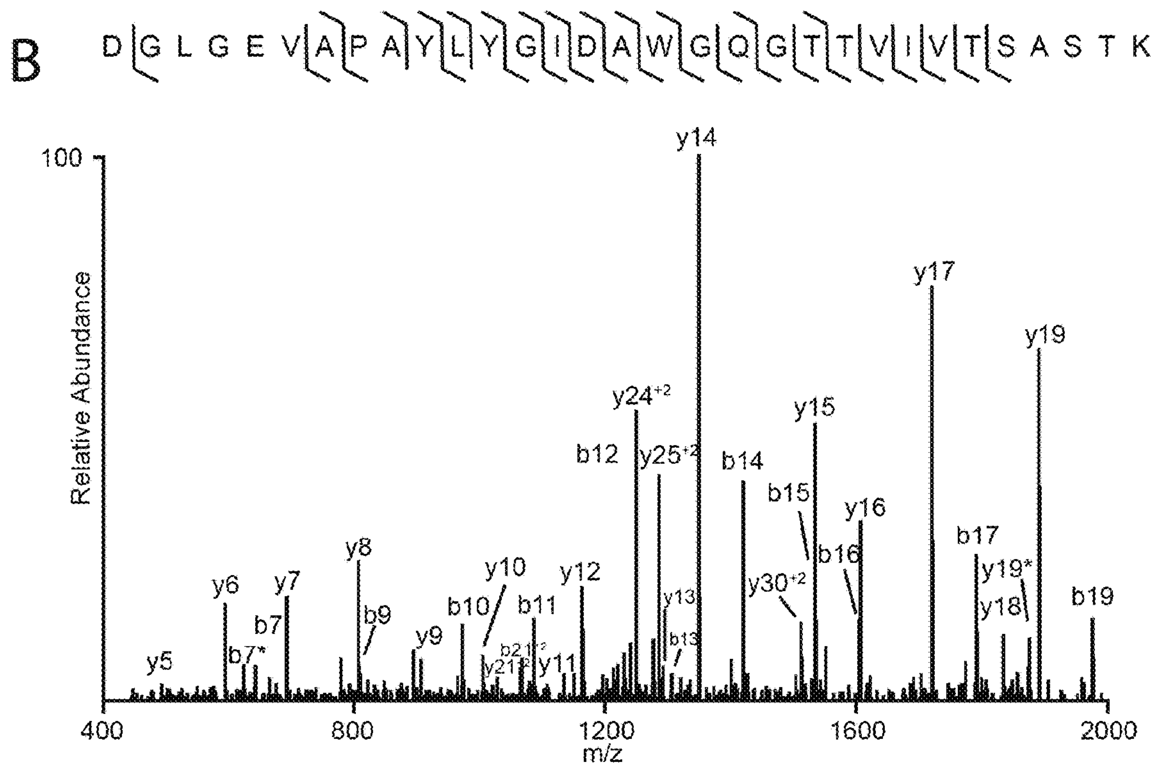

HIV neutralizing activity was measured in standardized in vitro assays using an initial panel of 8 viruses including 3 tier 1 Clade A, B and C, and 5 tier 2 Clade B Env pseudovirus variants (M. S. Seaman et al., J Virol 84, 1439 (February, 2010)). The neutralizing activity of the antibodies was compared to VRC01 and purified serum IgG from the donors (FIG. 1A, Table 4 and FIG. 6). Antibodies showing high levels of neutralizing activity were further tested on a panel of 15 additional tier 2 Clade A, B, C, D, G, AG and AE Env pseudovirus variants (FIG. 1B, Table 5) including 5 viruses that are resistant to VRC01 (FIG. 1B and Table 5). 90% of all of the antibodies tested showed some neutralizing activity and 6 clones contained antibody variants that showed high levels of potency and breadth (FIGS. 1A, B and C and Tables 4 and 5). These clones were also the most abundant among those captured by the 2CC-bait in each of the four patients studied (Table 3). The most impressive of the new antibodies, 3BNC117 belonging to a clone with 76 members, showed an average $IC_{80}$ on a combined group of 14 tier 2 viruses of 0.5□ g/ml as compared to 1.8□□ g/ml for VRC01 (FIG. 1C, Tables 4 and 5).

Only 4 of the 20 viruses tested were more sensitive to VRC01 than 3BNC117, whereas 14 were more sensitive to 3BNC117 including DU172.17 which is completely resistant to VRC01 but sensitive to 3BNC117 (FIGS. 1B and C). NIH45-46, a new variant of VRC01, is more potent than VRC01 on 15 of the 20 viruses tested but still less potent than 3BNC117 (FIGS. 1B and C and Tables 4, and 5).

There was substantial variation in neutralizing breadth and potency among the members of the 5 most potent neutralizing antibody clones. For example, 3BNC156, a variant of 3BNC117, neutralized only 2 of the viruses in the initial panel and at much higher concentrations than 3BNC117 (FIG. 1A and Table 4) and 3BNC55, another variant, was intermediate between the two showing activity against 6 viruses at an average $IC_{50}$ of 4□ g/ml (FIG. 1 and Table 4). Finally, the most active antibodies were highly hypermutated. The average number of mutations for the top 10 antibodies was 72 for $V_H$ and 45 for $V_L$, and this was associated with their breadth and potency (Tables 4 and 5). Reversion of the mutated residues to germline resulted in a complete loss of neutralizing activity for all of the antibodies tested.

Example 6

Identification of Diagnostic Peptides

The foregoing cloning strategy captured antibodies produced by antigen binding memory B cells, but circulating antibodies are not produced by these cells, and originate instead from plasma cells in the bone marrow. However, cognate antigen cannot be used as bait to capture plasma cells because they do not express surface Ig A. (Radbruch et al., Nat Rev Immunol 6, 741 (October, 2006)). In addition, the relationship between plasma cells in the bone marrow and circulating memory B cells is not defined precisely. To determine whether the antibodies cloned from memory B cells are also found in the bone marrow plasma cell compartment, CD138-expressing plasma cells were purified from paired bone marrow samples from 2 of the 4 individuals studied and used PCR to specifically amplify $IgV_H$ genes for the more potent antibodies cloned from memory B cells in these individuals. The following were the clone specific primers for RU01: CTGCAACCGGTGTACATTCT-CAAGTGCAACTGGTGC (FWRD) (SEQ ID NO. 584), CTGCAACCGGTGTACATTCTCAGGTCCATTTGT-CACAG (FWRD), (SEQ ID NO. 585) TGCGAAGTCGACGCTGACGAGACAGTGACCTGC (REV) (SEQ ID NO. 586), TGCGAAGTCGACGCT-GAAGAGACAATAATTTG (REV) (SEQ ID NO. 587), TGCGAAGTCGACGCTGACGAGACAATAACT (REV) (SEQ ID NO. 588) and for RU10: CTGCAACCGGTGTA-CATTTTCAGGGGCACTTGGTG (FWRD) (SEQ ID NO. 589), TGCGAAGTCGACGCTGAGGTGAC-GATGACCGTG (REV) (SEQ ID NO. 590). Members of the selected clones and large numbers of additional variants were readily identified in both patients.

To verify that these antibodies can also be found in serum, IgG purified from the serum of the same 2 and one additional individual were adsorbed on the 2CC-core bait and mass spectrometry was performed on the eluted IgG (FIG. 1D, FIG. 7 and FIGS. 10A-C). Diagnostic peptides were found for the highly active antibody variants in all cases (FIG. 7, FIG. 10A-C). It was concluded that broad and potent anti-HIV antibodies cloned from memory B cells were also found in the bone marrow plasma cell compartment, and in the circulating IgGs of patients with high serum titers of broadly neutralizing antibodies.

Example 7

HIV Antibody Binding Characteristics

Figures 2A, 2B, 2C:
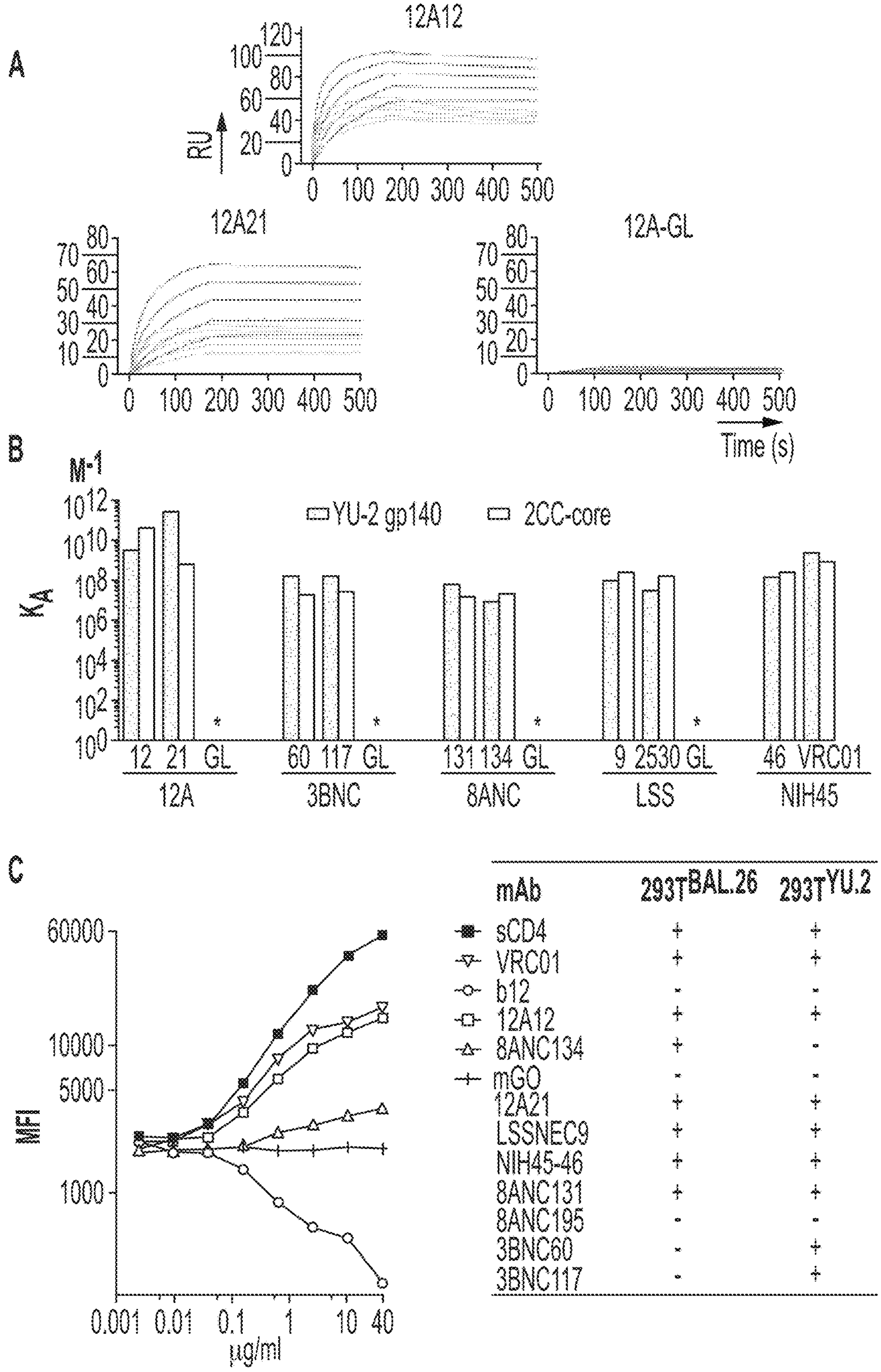
FIGS. 2A, 2B and 2C show the binding properties of the HIV antibodies. (A) Representative SPR sensograms for binding to YU2-gp140 and 2CC-core by 12A12, 12A21 and 12A-germline (GL) reverted antibodies. (B) Graph shows $K_A$ for representative antibodies. (C) Graph shows mean fluorescence intensity of anti-CD4i antibody binding to Bal.26 expressing 293T cells after incubation with the indicated antibodies. Table indicates whether or not an antibody induces CD4i site accessibility.

To determine whether antibody affinity to gp120 is related to neutralizing activity, the binding of the highly active antibodies, selected clonal relatives and germline reverted progenitors were compared using Surface Plasmon Resonance (SPR) (FIGS. 2A and B, FIG. 8 and Table 6).

The top neutralizing antibodies showed affinities ($K_A$) ranging from $\cong 10^7$-$10^{12}$ ($M^{-1}$) on YU2 gp140 trimers and $\cong 10^7$-$10^{11}$ ($M^{-1}$) on the 2CC-core (FIGS. 2A and B and Table 6). Consistent with their decreased neutralizing potency and breadth, 3BNC66, 3BNC156 and 3BNC55 displayed lower affinities on YU2 gp140 trimers than 3BNC117, but surprisingly, affinities to 2CC-core did not correlate with neutralizing activity (FIG. 1, FIG. 8, Table 4 and Table 6). Binding by SPR was not detected for any of the germline reverted antibodies tested (FIG. 2B, Table 6). It was concluded that the anti-HIV antibodies captured by the YU2 2CC-core tended to show higher affinity to the corresponding gp140 trimer than to the 2CC-core.

When VRC01 binds to the HIV spike it produces large conformational changes that mimic CD4 binding and expose the CD4i site. By contrast, b12 and most other known anti-CD4bs antibodies do not.

To determine whether this is a shared feature of the highly active antibodies, HIV-BAL.26Δc or -YU2 gp160Δc was expressed on the surface of HEK 293T cells and CD4i antibody binding measured in the presence or absence of CD4 or anti-CD4bs antibodies (FIG. 2C). With one exception, all of the highly active antibodies tested resembled CD4 and VRC01 in that they facilitated anti-CD4i antibody binding to either HIV-BAL.26 or YU2 gp160Δc or both (FIG. 2C).

The only highly active antibody that did not share this characteristic, 8ANC195, was not a traditional anti-CD4bs antibody in that it was equally sensitive to the D368R and I420R mutations (Table 3). In addition, it differed from the other highly active antibodies in its neutralization pattern: it did not neutralize any of the tier 1 viruses and showed potent activity against H086.8, a Glade B virus resistant to all other antibodies tested including 3BNC117, VRC01 and b12 (FIGS. 1 A and B and Tables 4 and 5).

Example 8

HIV Antibody Sequence Identity

Figure 3A:
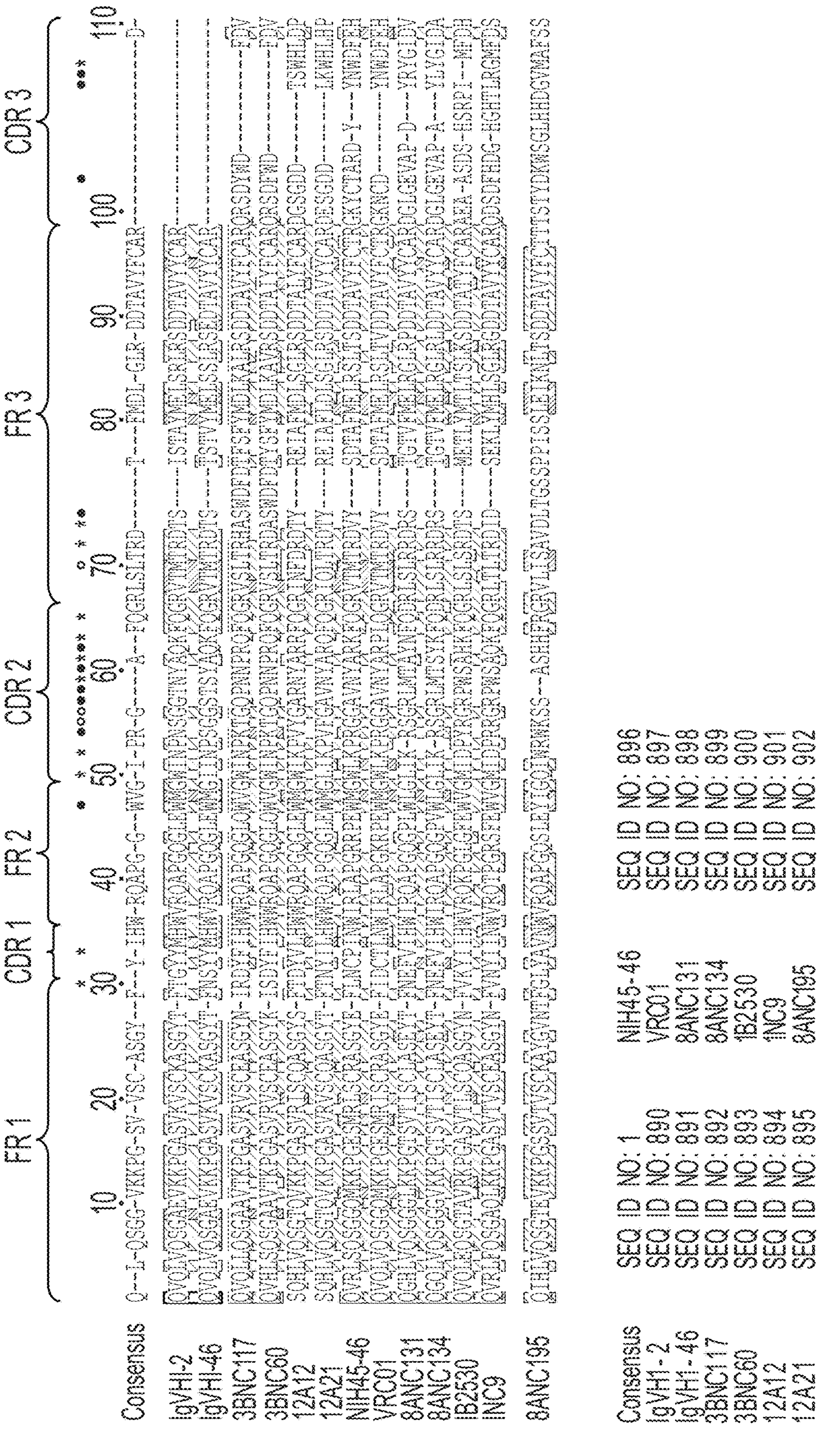
FIGS. 3A and 3B show the HIV antibody consensus sequence, and HIV antibody amino acid sequences. (A) Amino acid alignment relative to framework (FR) and CDR regions for consensus, germline genes, 10 selected antibodies and 8ANC195 (SEQ ID NOS 1 and 890-902, respectively, in order of appearance). Residues are numbered according to the 3BNC60 structure. (B) As in (A) for light chains (SEQ ID NOS 2 and 903-916, respectively, in order of appearance). (C, D, and E) Crystal structure of 3BNC60 Fab.

To determine whether highly active anti-CD4bs antibodies share common sequence features, the 10 best antibodies: 2 variants each from 5 independently derived antibody clones from 5 different patients were aligned (FIG. 3). Comparison of the $IgV_H$ regions revealed a highly conserved consensus sequence covering 68 $IgV_H$ residues (FIG. 3A). The $IgV_H$ consensus included 6 of VRC01-gp120 contact residues, including VRC01-Arg 71, which mimics the key interaction of $Arg59_{CD4}$ and $Asp368_{gp120}$ (FIG. 3A). Moreover, the consensus, including the 6 contact residues, was entirely conserved in both of the closely related germline $IgV_H$ genes ($V_H$1-2 and $V_H$1-46) that give rise to all of the antibodies in this class (FIGS. 3A and B).

Figure 3B:
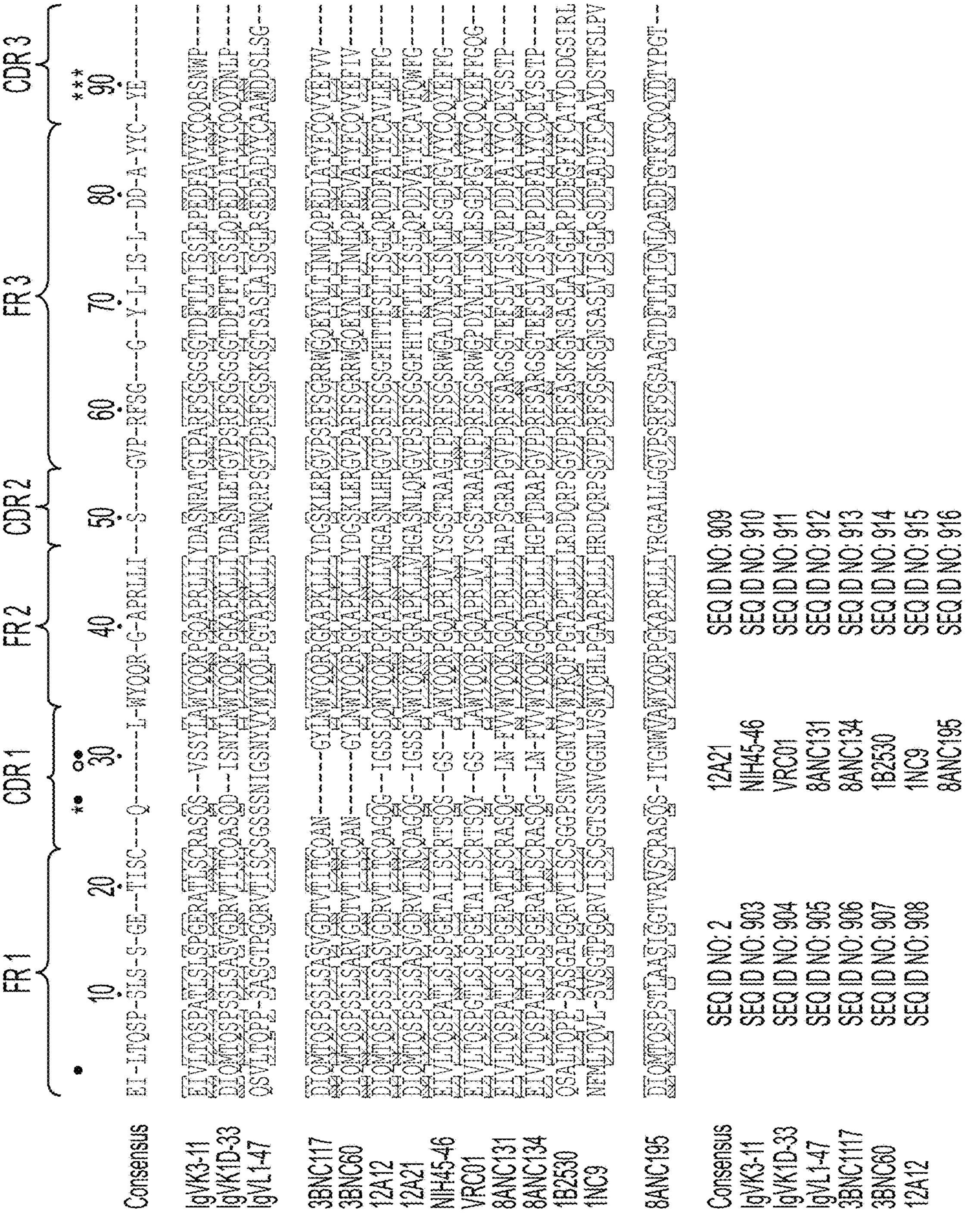

The codons encoding the consensus residues were highly somatically mutated in the 10 selected antibodies, nevertheless the amino acid sequence was conserved (FIG. 9). The ratio of replacement to silent mutations in the consensus residues ranged from 0.7-1.7, whereas it was 3.5-22 in the non-consensus residues indicating that conservation of the consensus is strongly selected (Table 7). In contrast to the heavy chain, the light chain of VRC01 made only 8 out of a total of 32 contacts with gp120. Consistent with its more limited role, comparison of the light chain sequences of the same antibodies uncovered a less extensive consensus covering 53 $IgV_L$ residues including 3 VRC01-gp120 contact residues (FIG. 3B). Finally, like the heavy chains, the light chains arose from a limited set of germline genes: 2 were derived from IgK1D-33, 2 from IgK3-11, and one from IgL1-47 (FIG. 3B and Table 3). Antibody 8ANC195, which differed from the others in several important respects did not entirely conform to the consensus and did not arise from related heavy or light chains (FIGS. 3A and B) It was concluded that there is significant sequence convergence among highly active agonistic anti-CD4bs antibodies (HAADs).

Example 9

Crystal Structure of 3BNC60 Fab

To determine whether the structure of the antibodies in different patients is also conserved, the crystal structure of the 3BNC60 Fab was solved to 2.65 Å resolution and compared it to VRC01. The structure revealed the four domains, $V_H$, $C_H1$, $V_L$, and $C_L$, of a canonical Fab and the complementarity-determining regions (CDRs) within $V_H$ and $V_L$ that form the antigen binding site. The two Fabs in the 3BNC60 asymmetric unit were almost identical; however, the conformation of residues 74-78 in the loop connecting strands D and E varied slightly due to different chemical environments formed by crystal lattice contacts.

Superimposition of the $V_H$ domains from 3BNC60 and VRC01 in the VRC01-gp120 co-crystal structure (T. Zhou et al., Science 329, 811 (Aug. 13, 2010)) yielded a root mean square deviation (rmsd) of 1.3 Å (calculated for 111 Cα atoms) with major differences confined to CDR2 residues 58-65 (3BNC60 numbering). Superimposing the structures indicated conservation of the recognition interface with gp120. For example, $Arg72_{3BNC60}$ adopted a similar conformation as $Arg71_{VRC01}$, which mimics an important salt bridge normally formed between $Arg59_{CD4}$ and $Asp368_{gp120}$. In addition, $Trp47_{3BNC60}$ adopted the same conformation as $Trp47_{VRC01}$, a residue that contacts gp120 and is involved with a complex network of interactions of aromatic and aliphatic residues that stabilize the conformations of CDRH3 and CDRL3. $Gln65_{3BNC60}$, which corresponds to $Gln64_{VRC01}$, is within the residue segment (residues 58-65) that differs in structure from VRC01. The conformation of this region of 3BNC60, which is involved in a lattice contact in the crystals, is likely to change upon binding gp120, as it would clash with the CD4-binding loop on gp120.

Superimposing the 3BNC60 and VRC01 $V_L$ domains yielded an rmsd of 0.9 Å (calculated for 95 Ca atoms) and showed that some of gp120-contacting residues are structurally conserved; $Tyr91_{3BNC60}$ and $Glu91a_{3BNC60}$ adopted similar conformations as $Tyr91_{VRC01}$ and $Glu96_{VRC01}$, which engaged loop D of gp120 via polar interactions. Overall, these structural comparisons suggested that 3BNC60 binds gp120 with the same architecture as observed for the binding of VRC01.

Example 10

HIV Antibody Consensus Sequence

The foregoing experiments defined a class of agonistic anti-CD4bs antibodies, HAADs, that shares $IgV_H$ and $IgV_L$ consensus sequences including 8 of the contact residues between VRC01 and the HIV spike (FIGS. 3A and B). In five different donors, selected for their high level serologic anti-HIV activity, these antibodies originated from only 2 closely related $IgV_H$ and 3 $IgV_L$ germline genes that conform to the HAAD consensus: $V_H$1-2 and $V_H$1-46 differ by only 7 amino acids, none of which are part of the consensus (FIG. 3A). Despite extensive somatic hypermutation, the consensus residues were retained in their germline form.

The only exception to the consensus, 8ANC195, differed from the others in a number of ways that suggest that it may have a unique mode of antigen recognition: absence of the Arg in the heavy chain that mimics the critical $Arg59_{CD4}$ and $Asp368_{gp120}$ contact site; unique neutralizing pattern; and inability to facilitate anti-CD4i antibody binding. This antibody is one of two distinct highly active antibodies arising in one patient, lending additional support to the idea that serologic neutralizing activity is combinatorial.

TABLE A

| Seq ID No. | Antibody | Heavy Chain Amino Acid Sequence |
|---|---|---|
| 5 | 8A253HC | QGQLVQSGGGLKKPGTSVTISCLASEYTFNEFVIHWIRQAPGQGPLWLGLIKRSGRLMTAY NFQDRLSLRRDRSTGTVFMELRGLRPDDTAVYYCARDGLGEVAPDYRYGIDVWGQGSTVI VTAASTKG |

TABLE A-continued

| Seq ID No. | Antibody | Heavy Chain Amino Acid Sequence |
|---|---|---|
| 6 | 8A275HC | QGLLVQSGGGVKKLGTSVTISCLASEYTFNEFVIHWIRQAPGQGPLWLGLIKRSGRLMTSYQFQDRLSLRRDRSTGTVFMELRGLRVDDTAVYYCARDGLGEVAPAYLYGIDAWGQGTTVIVTSASTKG |
| 7 | 8ABM11 | FQGHLVQSGGGVKKPGTSVTLSCLASEYTFTEFTIHWIRQAPGQGPLWLGLIKRSGRLMTSYRFQDRLSLRRDRSTGTVFMELRSLRTDDTAVYYCARDGLGELAPAYHYGIDAWGQGTTVIVTSASTS |
| 8 | 8ABM12 | QGHLVQSGGGVKKLGTSVTISCLASEYTFNEFVIHWIRQAPGQGPLWLGLIKRSGRLMTSYQFQDRLSLRRDRSTGTVFMELRGLRVDDTAVYYCARDGLGEVAPAYLYGIDAWGQGTTVIVTSAST |
| 9 | 8ABM13 | QGHLVQSGGGVKKLGTSVTISCLASEDTFNEFVIHWIRQAPGQGPLWLGLIKRSGRLMTSYQFQDRLSLRRDRSTGTVFMELRGLRVDDTAVYYCARDGLGEVAPAYLYGIDAWGQGTTVIVTSASTS |
| 10 | 8ABM14 | GHLVQSGGGXKKPGTSVTISCLASEYTFTEFTIHRIRQAPGQGPLWLGLIKGSGRLMTSYGFQDRLSLRRDRSTGTVFMELRSLRTDDTAVYYCARDGLGELAPAYHYGIDVWGQGTTVIVTSASTS |
| 11 | 8ABM20 | GVHFQGHLVQSGGGVKKPGSSVTISCLASEYTFTEFTIHWIRQAPGQGPLWLGLIKRSGRLMTSYRFQDRLSLRRDRSTGTVFMELRGLRIDDTAVYYCARDGLGEVAPAYLYGIDVWGQGTTVIVTSASTS |
| 12 | 8ABM24 | FQGQLVQSGGGVKKPGSSVTISCLASEYTFTEFTIHWIRQAPGQGPLWLGLIKRSGRLMTSYGFQDRLSVRRDRSTGTVFMELRSLRTDDTAVYYCARDGLGELAPAYHYGIDVWGQGTTVIVTSASTS |
| 13 | 8ABM26 | QGQLVQSGGGVKKLGTSVTISCLASEYTFNEFVIHWIRQAPGQGPLWLGLIKRSGRLMTSYQFQDRLSLRRDRSTGTVFMELRGLRVDDTAVYYCARDGLGEVAPAYLYGIDAWGQGTTVIVTSASTS |
| 14 | 8ABM27 | QGHLVQSGXEVKKPGSSVKVSCKASGGTFSXYAIGWVRQAPGQGLEWMGGIIPILGTTNYAQRFQGGVTITADESTNTAYMDVSSLRSDDTAVYYCAKAPYRPRGSGNYYYAMDVWGQGTTVIVSSASTS |
| 15 | 8ANC105HC | QGHLVQSGGGVKKLGTSVTISCLASEYTFNEFVIHWIRQAPGQGPLWLGLIKRSGRLMTSYQFQDRLSLRRDRSTGTVFMELRGLRVDDTAVYYCARDGLGEVAPAYLYGIDAWGQGTTVIVTSASTKG |
| 16 | 8ANC116HC | QGQLVQSGGGVKKLGTSVTISCLASEYTFNEFVIHWIRQAPGQGPLWLGLIKRSGRLMTSYQFQDRLSLRRDRSTGTVFMELRGLRVDDTAVYYCARDGLGEVAPAYLYGIDAWGQGTTVIVSSASTKG |
| 17 | 8ANC127HC | QGHLVQSGGGVKKLGTSVTISCLVSEYTFNEFVIHWIRQAPGQGPLWLGLIKRSGRLMTSYQFQDRLSLRRDRSTGTVFMELRGLRVDDTAVYYCARDGLGEVAPAYLYGIDAWGQGTTVIVTSASTKG |
| 18 | 8ANC131HC | QGQLVQSGGGLKKPGTSVTISCLASEYTFNEFVIHWIRQAPGQGPLWLGLIKRSGRLMTAYNFQDRLRLRRDRSTGTVFMELRGLRPDDTAVYYCARDGLGEVAPDYRYGIDVWGQGSTVIVTAASTKG |
| 19 | 8ANC134HC | QGQLVQSGGGVKKPGTSVTISCLASEYTFNEFVIHWIRQAPGQGPVWLGLIKRSGRLMTSYKFQDRLSLRRDRSTGTVFMELRGLRLDDTAVYYCARDGLGEVAPAYLYGIDAWGQGSTVIVTSASTKG |
| 20 | 8ANC13HC | QGQLVQSGGGVKKPGASVTISCLASEYTFNEFVIHWIRQAPGQGPLWLGLIKRSGRLMTAYKFQDRLSLRRDRSTGTVFMELRGLRPEDTAVYYCARDGLGEVAPDYRYGIDVWGQGSTVIVSAASTKG |
| 21 | 8ANC171HC | QGHLVQSGGGVKKLGTSVTISCLASEYTFNEFVIHWIRQAPGQGPLWLGLIKRSGRLMTSYQFQDRLSLRRDRSTGTVFMELRGLRVDDTAVYYCARDGLGEVAPAYLYGIDAWGQGTTVIVTSASTKG |
| 22 | 8ANC18 | GVHFQGHLVQSGGGVKKPGSSVTISCLASEYTFTEFTIHWIRQAPGQGPLWLGLIKRSGRLMTSYRFQDRLSLRRDRSTGTVFMELRGLRIDDTAVYYCARDGLGEVAPAYLYGIDVWGQGSTVIVTSASTS |
| 23 | 8ANC182HC | QGQLVQSGGGVKKPGTSVTISCLASEYTFTEFTIHWIRQAPGQGPLWLGLIKRSGRLMTAYRFQDRLSLRRDRSTGTVFMELRNLRMDDTAVYYCARDGLGELAPAYQYGIDVWGQGTTVIVSSASTKG |
| 24 | 8ANC192HC | QGHLVQSGGGVKKLGTSVTISCLASEYTFNEFVIHWIRQAPGQGPLWLGLIKRSGRLMTSYQFQDRLSLRRDRSTGTVFMELRGLRVDDTAVYYCARDGLGEVAPAYLYGIDAWGQGTTVIVTSASTKG |

TABLE A-continued

| Seq ID No. | Antibody | Heavy Chain Amino Acid Sequence |
|---|---|---|
| 25 | 8ANC22HC | QGHLVQSGGGVKKLGTSVTISCLASEDTFNEFVIHWIRQAPGQGPLWLGLIKRSGRLMTSY QFQDRLSLRRDRSTGTVFMELRGLRVDDTAVYYCARDGLGEVAPAYLYGIDAWGQGTTVI VTSASTKG |
| 26 | 8ANC26HC | QGQLVQSGGGVKKPGTSVTISCLASEYTFNEFVIHWIRQAPGQGPVWLGLIKRSGRLMTSY KFQDRLSLRRDRSTGTVFMELRGLRLDDTAVYYCARDGLGEVAPAYLYGIDAWGQGSKVIV TPASTKG |
| 27 | 8ANC2HC | QGQLVQSGGGVKKLGTSVTIPCLASEYTFNEFVIHWIRQAPGQGPLWLGLIKRSGRLMTSY QFQDRLSLRRDRSTGTVFMELRGLRVDDTAVYYCARDGLGEVAPAYLYGIDAWGQGTTVI VTSASTKG |
| 28 | 8ANC30HC | QGQLVQSGGGVKKLGTSVTISCLASEYTFNEFVIHWIRQAPGQGPLWLGLIKRSGRLMTSY QFQDRLSLRRDRSTGTVFMELRGLRVDDTAVYYCARDGLGEVAPAYLYGIDAWGQGTTVI VTSASTKG |
| 29 | 8ANC37HC | QGHLVQSGGGVKKLGTSVTISCLASEYTFNEFVIHWIRQAPGQGPLWLGLIKRSGRLMTSY QFQDRLSLRRDRSTGTVFMELRGLRVDDTAVYYCARDGLGEVAPAYLYGIDAWGQGTTVI VTSASTKG |
| 30 | 8ANC40HC | QGHLVQSGGGVKKLGTSVTISCLASEYTFNEFVIHWIRQAPGQGPLWLGLIKRSGRLMTSY QFQDRLSLRRDRSTGTVFMELRGLRVDDTAVYYCARDGLGEVAPAYLYGIDAWGQGTTVI VTSASTKG |
| 31 | 8ANC41HC | QGQLVQSGGGVKKTGTSVTISCLASEYTFTEFTIHWIRQAPGQGPLWLGLIKRSGRLMTAN RFQDRLSLRRDRSTGTVFMELRSLRIDDTAVYYCARDGLGELAPAYHYGIDVWGQGTTIIVT SASTKG |
| 32 | 8ANC45HC | QGQLVQSGGGVKKTGTSVTISCLASEYTFTEFTIHWIRQAPGQGPLWLGLIKRSGRLMTAN RFQDRLSLRRDRSTGTVFMELRSLRIDDTAVYYCARDGLGELAPAYHYGIDVWGQGTTIIVT SASTKG |
| 33 | 8ANC50HC | QGQLVQSGGGVKKPGTSVTISCLASEYTFTEFTIHWIRQAPGQGPLWLGLIKRSGRLMTAY RFQDRLSLRRDRSTGTVFMELRNLRMDDTAVYYCARDGLGELAPAYQYGIDVWGQGTTVI VSSASTKG |
| 34 | 8ANC53HC | QGQLVQSGGGGKKLGTSVTISCLASEYTFNEFVIHWIRQAPGQGPLWLGLIKRSGRLMTSY QFQDRLSLRRDRSTGTVFMELRGLRVDDTAVYYCARDGLGEVAPAYLYGIDAWGQGTTVI VSSASTKG |
| 35 | 8ANC88HC | QGQLVQSGGGVKKPGTSVTISCLASEYTFNEFVIHWIRQAPGQGPLWLGLIKRSGRLMTSY KFQDRLNLRRDRSTGTVFMELRGLRPDDTAVYYCARDGLGEVAPDYRYGIDVWGQGSTVI VTAASTKG |
| 36 | 8ANC103HC | QVQLQQWGSGLLKPSETLSLTCAVYGGSFRSYYWNWIRQSPGKGLEWIGEVSHSGSTNYN PALKSRVTISVDTSKNQFSLKVKSVTAADTALYYCSRGRGKRCSGAYCFAGYFDSWGQGGL VVVSSASTKG |
| 37 | 8ANC106HC | EVQLVESGGGVVEPGESLRLSCAASGFTFRSYDMFWVRQATGKSLEWVSAIGIAGDTYYSG SVKGRFTISRENARTSLYLQLSGLRVEDSAVYFCVRGSPPRIAATEYNYYYGLDVWGQGTTV SVFSASTKG |
| 38 | 8ANC107HC | VVQLVQSGAEVRKPGSSLKVSCKSSGGTFSRYVVNWVRQAPGQGLEWMGGMIPIFGIAK YAQKFQDRVTMTADESKNTVYLDFSSLRSDDTAVYYCARDRGDTRLLDYGDYEDERYYYG MDVWGQGTTVIVSSASTKG |
| 39 | 8ANC108HC | QVQLVQSGAEVRKPGSSLKVSCKSSGGTFSRYVVNWVRQAPGQGLEWMGGIIPIFGIAKY AQKFQDRVTMTADEPKNTVYLDFNSLRSDDTAVYYCARDRGDTRLLDYGDYEDERYYYGM DVWGQGTTVIVSSASTKG |
| 40 | 8ANC109HC | EVQLVESGGGLVKPGGSLRLSCAASGFSFSEHYMSWIRLAPGKGLEWLSYISSSTRTTYSADS VRGRFTISRDTAKQLLFLHMSSLRAEDTAVYYCVRLYGGINGWFDQWGQGTLVSVSSASTK G |
| 41 | 8ANC10HC | QVQLVQSGAEVKKPGSSVKVSCKTSGGSFSNYAFSWVRQAPGEGLEWMGRIIPIFGTAKYT QKLQGRVTITADKFTSTVYMELSSLRSEDTAIYYCASLHQGPIGYTPWHPPPRAPLGQSVCG |
| 42 | 8ANC111HC | QVQLVESGAEVKKPGASVKVSCKASGYTFTSHDINWVRQATGQGLEWMGWMNPNSGD TGYAHKFQGRVTMTRNTPISTAYMELSSLRSEDTAVYYCARGRATSRNTPWAHYYDSSGYY GAGDYWGQGTLVTVSSASTKG |
| 43 | 8ANC112HC | QVQLVESGGGVVQPGRSLRLFCAASGFAFNTYGMHWVRQAPGKGLEWVAVTWHDGSQ KYYADSVKGRFTISRDNSKNTLYLQMNSLRAEDTAIYYCASDQGGFDDSSGYFAPGGMDV WGRGTTVIVSSAPTKG |

TABLE A-continued

| Seq ID No. | Antibody | Heavy Chain Amino Acid Sequence |
|---|---|---|
| 44 | 8ANC113HC | QVQLVESGAELRKPGESLEISCKASGYSFSSHWIGWARQMPGKGLEWMGIIYPGDSNTIYS PSFQGQVTISADKSINTAYLQWSSLKASDTAMYFCASNYHDYFYWGQGTLVTVSSASTKG |
| 45 | 8ANC114HC | EVQLVESGAEVKKPGSSVKVSCKASGGTFSTYAFSWVRQAPGQGLEWMGGIIPIFGTENYA QKFQGRVTITADKSTSTAYMELSSLRSEDTAVYYCARDRSSAIGYCSSISCYKGSFDIWGQGT MVTVSSASTKG |
| 46 | 8ANC115HC | QVQLVQSGAEVRKPGSSLKVSCKSSGGTFSRYVVNWVRQAPGQGLEWMGGIIPIFGIAKY AQKFQDRVTMTADEPKNTVYLDFNSLRSDDTAVYYCARDRGDTRLLDYGDYEDERYYYGM DVWGQGTTVIVSSASTKG |
| 47 | 8ANC117HC | EVQLVQSGAEVKKPGSSVKVSCKASGGTFSTYAFSWVRQAPGQGLEWMGGIIPIFGTENY AQKFQGRVTITADKSTSTAYMELSSLRSEDTAVYYCARDRSSAIGYCSSISCYKGSFDIWGQG TMVTVSSASTKG |
| 48 | 8ANC11HC | QVFVQLVQSGGGLVQPGGSVRLSCTASGFLFSTYSMNWVRQAPGKGLEWVSSISTTSNYIY YADSVKGRFTISRSNGQGSLYLQLNSLRVEDTAVYYCARDTKVGAPRQDCYAMDLWGQRD HGHRLLSFHQGPIGLPPGALLQ |
| 49 | 8ANC121HC | QVQLLESGPGLVTPSGTLSLACAVSGASISSSHWWTWVRQSPGKGLEWIGEIDRRGTTNY NPSLRSRVTILLDNSKNQFSLSLRSVTAADTAVYYCTKVYAGLFNERTYGMDVWGHGTTVL VSSASTKG |
| 50 | 8ANC126HC | QVQLVESGAEVRKPGSSLKVSCKSSGGTFSRYVVNWVRQAPGQGLEWMGGIIPIFGIAKYA QKFQDRVTMTADESKNTVYLDFSSLRSDDTAVYYCARDRGDTRLLDYGDYEDERYYYGMD VWGQGTTVIVSSASTKG |
| 51 | 8ANC130HC | QVQLLQSGAEVKKPGASVKVSCKVSGYTLTELSINWVRQAPGKGLEWMGGFDPEDDEAIY EPKFQGRLTMTEDTSTDTAYMELSSLRSEDTAVYYCATADPFKVAQDEGLYVIFDYWGQGT LVTVSSASTKG |
| 52 | 8ANC132HC | QVQLVQSGTEVQKPGASVKVSCKTSGYTFSKYYIHWVRQAPGQGLEWVGRINTDSGGTD YAEKFQGRVTMTRDTSITTVYLEMRGLTSDDTAAFYCARGPPHAGGWTIYYYGLDVWGQ GTSVIVSSASTKG |
| 53 | 8ANC133HC | QVQLVQSGAEVKKPGASVKVSCKVSGHTLSELSINWVRHVPGKGLEWMGGLDPEDGEAI HEPKFQGRLTMTEDTSTDTAYVELSSLRSEDTAMYYCATADPFKVAQDEGLYVIFDYWGQ GTLVTVSSASTKG |
| 54 | 8ANC136HC | EVQLVESGGGVVQPGRSLRLSCAASGFTFSHHGIHWVRQAPGEGLEWVAVISEDGTNIHY EDSVRGRFTISRDNSKNTVDLQMNSLRAEDTAVYYCASLISMRDGDAFDLWGQGTRVTVS SASTKG |
| 55 | 8ANC137HC | QVQLVQSGAEVRKPGSSLKVSCKSSGGTFSRYVVNWVRQAPGQGLEWMGGIIPIFGIAKY AQKFQDRVTMTADESKNTVYLDFSSLRSDDTAVYYCARDRGDTRLLDYGDYEDERYYYGM DVWGQGTTVIVSSASTKG |
| 56 | 8ANC139HC | QVQLVQSGGGLVKPGGSLRLSCAASGFTFSSYSMNWVRQAPGKGLEWVSSISSSSSYIYYA DSVKGRFTISRDNAKNSLYLQMNSLRAEDTAVYYCAREGSYYYGMDVWGQGTTVTVSSAS TKG |
| 57 | 8ANC140HC | EVQLVQSGGGLVQPGRSLRLSCAASGFTFDDYAMHWVRQAPGKGLEWVSGISWNSGTIG YADSVRGRFTISRDDAKSSLYLQMNSLRTEDTALYYCAKDGWVGSGSSTLRGSDYWGQGT LVTVSSASTKG |
| 58 | 8ANC142HC | QIHLVQSGTDVKKPGSSVTVSCKAYGVNTFGLYAVNWVRQAPGQSLEYIGQIWRWKSSAS HHFRGRVLISAVDLTGSSPPISSLEIKNLTSDDTAVYFCTTTSTYDQWSGLHHDGVMAFSSR GQGTLISVSAASTKGPSVFPLAPSSKSTYGLAHVL |
| 59 | 8ANC143HC | QVQLVQSGAEVRKPGSSLKVSCKSSGGTFSRYVVNWVRQAPGQGLEWMGGIIPIFGIAKY AQKFQDRVTMTADEPKNTVYLDFNSLRSDDTAVYYCARDRGDTRLLDYGDYEDERYYYGM DVWGQGTTVIVSSASTKG |
| 60 | 8ANC144HC | QLQLQESGPGLVKPWETLVLTCSVSGGSISSGDYYWGWIRQSPGKGPEWIGNIFYSSGNTY YNTSLKSRVTISVDVSKNRFSLKLTSMTAADTAVYYCGRLSNKGWFDPWGQGTLVSVSSAS TKG |
| 61 | 8ANC145HC | QVQLLESGGGLVQRGGSLRLSCTASGFVFNNYWMTWVRQAPGNGLEWVANIDQDGSEK HYLDSVKGRFTISRDNAKNSLYLQMNSLRAEDTAIYYCARVRFKVTAWHRFDSWGQGDLV TVSSTSTKG |
| 62 | 8ANC146HC | LVQLLQSGAEVKKPGASVKVSCKVSGYTLTELSIHWVRQAPGKGLEWMGGFDPEDDEAIY EPKFQGRLTMTEDTSTDTAYMELSSLRSEDTAVYYCATADPFKVAQDEGLYVIFDYWGQGT LVTVSSASTKG |

TABLE A-continued

| Seq ID No. | Antibody | Heavy Chain Amino Acid Sequence |
|---|---|---|
| 63 | 8ANC147HC | QVQLVESGGGLGQPGGSLRLSCAASGFTFRNYAMSWVRQAAGKGLEWVSGVSGGGDTT YYGDSVKGRFTISRDNSKNTLYLQMNNLRAEDTAVYYCAKDKGVWGSSDFDYWGQGTLV TVSSASTKG |
| 64 | 8ANC148HC | QVHLVQSGAEVKKPGASVRVSCKASGYTFTTYGISWVRQAPGQGLEWMGWISAHSGDT NYAQKLQARVTMTTDTSTNTAYMELRSLTSDDTAVYYCARDRPRHYYDRGGYYSPFDYW GQGTLVTVSSASTKG |
| 65 | 8ANC149HC | QVQLVESGAEVKKPGSSVKVSCKASGGTFNIFAFSWVRQAPGQGLEWMGGIIPIFASPNYA QRFQGRVTITADESTSTVHMELSSLRSEDTAIYYCAKDAHMHIEEPRDYDYIWGTSPYYFDY WGQGTLVTVSSASTKG |
| 66 | 8ANC14HC | QVQLVQSGAEVKKPGASVKVSCKVSGYTLTELSIHWVRQAPGKGLEWMGGFDSEDGEAF YKQNFQGRVTMTEDTSTDTAYMELRRLRSEDTAVYYCATADRFKVAQDEGLFVIFDYWGQ GTLVTVSSASTKG |
| 67 | 8ANC150HC | QVQLLQSGGEVKKPGASVKVSCKVSGYTLTELSIHWVRQAPGKGLEWMGGFDPEDDEAIY EPKFQGRLTMTEDTSTDTAYMELSSLRSEDTAVYYCATADPFKVAQDEGLYVIFDYWGQGT LVTVSSASTKG |
| 68 | 8ANC151HC | EVQLVESGGGLVQPGGSLRLSCAASGFTFSSYSMNWVRQAPGKGLEWVSYISGSSYTIYYA DSVRGRFTISRDNAKNSLYLQMNSLRDEDTAVYFCARATPPNPLNLYNYDSSGSSFDYWGQ GTLVTVSSASTKG |
| 69 | 8ANC153HC | QVQLVQSGAEVRKPGSSLKVSCKSSGGTFSRYVVNWVRQAPGQGLEWMGGMIPIFGIAK YAQKFQDRVTMTADESKNTVYLDFSSLRSDDTAVYYCARDRGDTRLLDYGDYEDERYYYG MDVWGQGTTVIVSSASTKG |
| 70 | 8ANC154HC | QVQLVESGAEVRKPGSSLKVSCKSSGGTFSRYVVNWVRQAPGQGLEWMGGIIPIFGIAKYA QKFQDRVTMTADEPKNTVYLDFNSLRSDDTAVYYCARDRGDTRLLDYGDYEDERYYYGMD VWGQGTTVIVSSASTKG |
| 71 | 8ANC155HC | QVQLVQSGAEIKKPGESLKISCKASGYTFNDYWIGWVRQMPGKGLEWMGIFYPDDSDSN YSPSFQGRVTISADKSITTAYLQWSTLKASDSAMYFCARLLGDSGAFDIWGQGTMVIVSSAS TKG |
| 72 | 8ANC156HC | EVQLVESGAEVRKPGSSLKVSCKSSGGTFSRFVVNWVRQAPGQGLEWMGGMIPIFGIAKY AQKFQDRVTMTADESKNTVYLDFSSLRSDDTAVYYCARDRGDTRLLDYGDYEDERYYYGM DVWGQGTTVIVSSASTKG |
| 73 | 8ANC157HC | QVQLVQSGAEVKKPGSSVKVSCKASGGTFSTYAFSWVRQAPGQGLEWMGGIIPIFGTENY AQKFQGRVTITADKSTSTAYMELSSLRSEDTAVYYCARDRSSAIGYCSSISCYKGSFDIWGQG TMVTVSSASTKG |
| 74 | 8ANC158HC | QVQLVQSGAEVRKPGSSLKVSCKSSGGTFSRFVVNWVRQAPGQGLEWMGGMIPIFGIAK YAQKFQDRVTMTADESKNTVYLDFSSLRSDDTAVYYCARDRGDTRLLDYGDYEDERYYYG MDVWGQGTTVIVSSASTKG |
| 75 | 8ANC160HC | QVQLVQSGGGVVQPGRSLRLSCAASGFTFSHHGIHWVRQAPGEGLEWVAVISEDGTNIHY EDSVRGRFTISRDNSKNTVDLQMNSLRAEDTAVYYCASLISMRDGDAFDLWGQGTRVTVS SASTKG |
| 76 | 8ANC161HC | EVQLVQSGGGLVKPGGSLRLSCAASGFTFKNAWMSWVRQAPGKGLEWVGHIKSKTDGG TIDYAAPVKGRFTISRDDSKNTLYLQMNSLKIEDTAVYYCTTDIGSGRGWDFHYYDSNDWG QGTLVTVSSASTKG |
| 77 | 8ANC162HC | EVQLVQSGGGVVQPGRSLRLSCVVSGFTFSSFTFHWVRQAPGKGLEWVAGMSFHATYIYY ADSVKGRFTISRDDSQDTLYLEMDSLRSEDTAIYYCARDPGIHDYGDYAPGAFDYWGQGSP VTVSSASTKG |
| 78 | 8ANC163HC | LVQLVQSGAEVKKPGASVKVSCKVSGHTLSELSINWVRHVPGKGLEWMGGLDPEDGEAIH EPKFQGRLTMTEDTSTDTAYSTLSVWAPVAAAMYYCATADPFKVAQDEGLYVIFDYWGQ GTLVTVSSASTKG |
| 79 | 8ANC164HC | EVQLVESGAEVKKPGSSVKVSCKASGGTFSSYSISWVRQAPGQGLEWMGGIIPIFATTHYG QKFQGRIKITADKSTSTAYMELSRLRSEDTAVYYCARDREFYFYGMDVWGQGTTVTVSSAS TKG |
| 80 | 8ANC165HC | QVQLQQWGAGLLKPSETLSLTCAVYAGSFSGYYWTWIRQPPGKGLEWIGEVNHGGSTNY NPSLKSRVTLSVDTSKNQFSLKLTSVTAADTAVYYCARVSRYDFWSGNYGSYGLDVWGQG TTVTVSSASTKG |
| 81 | 8ANC166HC | VVQLVQSGAEVRKPGSSLKVSCKSSGGTFSRFVVNWVRQAPGQGLEWMGGMIPIFGIAK YAQKFQDRVTMTADESKNTVYLDFSSLRSDDTAVYYCARDRGDTRLLDYGDYEDERYYYG MDVWGQGTTVIVSSASTKG |

TABLE A-continued

| Seq ID No. | Antibody | Heavy Chain Amino Acid Sequence |
|---|---|---|
| 82 | 8ANC168HC | LVQLVQSGAEVKKPGASVKVSCKVSGYSLTELSIHWVRQAPGKGLEWMGGFDSEDGEAIY KQNFQGRVTMTEDTSTDTAYMELSRLRSEDTAVYYCATADPFKVAQDEGLFVIFDYWGQG TTGHRLLSLHQGPHRLYSLGTLLSRAPIVQTHMA |
| 83 | 8ANC169HC | QVQLVQSGAEVKKPGSSVKVSCKASGGTFSTYAFSWVRQAPGQGLEWMGGIIPIFGTENY AQKFQGRVTITADKSTSTAYMELSSLRSEDTAVYYCARDRSSAIGYCSSISCYKGSFDIWGQG TMVTVSSASTKG |
| 84 | 8ANC16HC | QVQLVQSGAEVKKPGSSVKVSCKASGGTFSTYAFSWVRQAPIEGLEWMGGIIPIFGTENYA QKFQGRVTITADKSTSTAYMELSSLRSEDTAVYYCARDRSSAIGYCSSISCYKGSFDIWGQGT MVTVSSASTKG |
| 85 | 8ANC173HC | QVQLVQWGAGLLKPLETLSLTCAVYGGSFNGYFWSWIRQTPGKGLEWIGEINHGGSANF NPSLKSRVTMSVDTSKNQFSLKLASVTAADTAIYYCARGRITMVRGDPQRGGVRMDVWG QGTSVTVSSASTKG |
| 86 | 8ANC174HC | QVQLMQSGAEVKRPGASVKVSCKAFRHSLNNLGISWIRRAPGRGLEWLGWINVYEGNTK YGRRFQGRVTMTTDRSTNTVSMELRSLTSDDTAVYYCARDNHFWSGSSRYYYFGMDVW GQGTTVIVSSASTKG |
| 87 | 8ANC175HC | QVQLVQSGGGLVQPGESLRLSCTASGFTFSSYNMNWVRQAPGKGLEWISYISDKSKNKYY ADSVRGRFTISRDNAQNSLFLQMSSLRDEDTAVYYCTREGPQRSFYFDYWGQGIQVTVSSA STKG |
| 88 | 8ANC176HC | QVQLQESGPGLVKPSETLSLTCTVSGGSISNHYWSWIRQPPGKGLEWIGYIYHSGNINYKSS LKSRATISIDTSNNQFSLKLSSVIAADTAVYYCARNFGPGSPNYGMDVWGQGTTVTVSSAST KG |
| 89 | 8ANC177HC | VVQLVQSGPGLVKPSQTLSLTCTVSGGSISSGDFYWSWIRQPPGKGLEWIGYIYYSGSTYYN PSLKSRLTISVDTSKNQFSLRLSSVTAADTAVYYCARDLNSRIVGALDAFDIWGQGTMVTVS SASTKG |
| 90 | 8ANC178HC | QVQLVESGGALVQPGGSLRLSCAASGFSFSSYAMSWVRQAPGKGLEWVSAISRSGGSTYY ADSVKGRFTISIDNSNNTLYLQMNSLRVEDTAVYYCAKREAFYYGAGGYGMDVWGQGTT VTVSSASTKG |
| 91 | 8ANC179HC | EVQLVESGGGLVKPGGSLRLSCEASGFTFTNAWMNWVRQAPGKGLEWVGRIKSQTHGG TTRYAAPVKGRFTISRDDSKHTLYLQMDRLTTEDTAVYYCTGTITGSTFYYYGMDVWGQGT TVTVSPASTKG |
| 92 | 8ANC17HC | EVQLVESGGGLLQPGGSLRLSCAASGFSFNDFEMNWVRQAPGKGLEWVSYISNDGTMIH YADSVKGRFTISRDNAKKSLFLQMNSLRAEDTAVYYCARLAEVPPAIRGSYYYGMDVWGQ GTTVTVASASTKG |
| 93 | 8ANC180HC | QVQLQESGPGLLRPLETLSLTCSVSGGSIRGYFWSWVRQPAGRGLEWIGRIYSSGTTRENPS LKSRVRLSIDTAKSEVSLNITSVTAADSASYFCAGTSPVHGGLDLWGLGLRVTVSSASTKG |
| 94 | 8ANC181HC | HLVQSGTEVKKPGSSVTVSCKAYGVNTFGLYAVNWVRQAPGQSLEYIGQIWRWKSSASH HFRGRVLISAVDLTGSSPPISSLEIKNLTSDDTAVYFCTTTSTYDQWSGLHHDGVMAFSSWG QGTLISVSAASTKG |
| 95 | 8ANC184HC | EVQLVQSGAEVKKPGASVKVSCKVSGYTLTELSIHWVRQAPGKGLEWMGGFDPEDDEAIY EPKFQGRLTMTEDTSTDTAYMELSSLRSEDTAVYYCATADPFKVAQDEGLYVIFDYWGQGT LVTVSSASTKG |
| 96 | 8ANC185HC | QVQLVESGGGLVQPGGSLRLSCAASGFTFSTHWMHWVRQAPGKGLVWVSRIHSDGRST SYADSVKGRFTISRDNAKNTLYLQMNSLRAEDTAVYYCARGAAVFGVVIIGGMDLWGQGT TVTVSSASTKG |
| 97 | 8ANC186HC | EVQLVESGGGVVQPGGSLRLSCAASGFMFKNYAMHWVRQPPGKGLEWVAVIWYGGRD QNYADSVKGRFTISRDDSDNTLYLQMNSLRAGDTAVYFCARNSQVGRLMPAAGVWGQG TLVTVSSASTKG |
| 98 | 8ANC187HC | EVQLVESGGGLIQRGGSLRLSCVASGFPVSDNHMSWVRQAPGKGLEWVSIIYSDGGTYYA DSVKGRFTISRDNSKNTVYLQMNSLRATDTAVYYCARDPGFHYGLDVWGQGTTVTVSSAS TKG |
| 99 | 8ANC188HC | VVQLVESGGGLVQPGGSLRLSCAASGFAFRSYWMSWVRQAPGRGLEWVANIKQDGSEK YYADSVKGRFTISRDNTKNSLYLQMNSLRAEDTAVFYCASRGDRYGPIDYWGQGTLVTVSS ASTKG |
| 100 | 8ANC191HC | VVQLVESGTEVKKPGSSVKVSCKASGGTFSGSDISWVRQAPGQGLEWMGGIIPMFDIENH AEKFRGRLTITAVKSTGAAYMELSSLRSEDAAVYYCARSSGNYDFAYDIWGQGTRVIVSSAS TKG |

TABLE A-continued

| Seq ID No. | Antibody | Heavy Chain Amino Acid Sequence |
|---|---|---|
| 101 | 8ANC193HC | EVQLVQSGAEVKKPGSSVKVSCKASGGTFSTYAFSWVRQAPGQGLEWMGGIIPIFGTENYAQKFQGRVTITADKSTSTAYMELSSLRSEDTAVYYCARDRSSAIGYCSSISCYKGSFDIWGQGTMVTVSSASTKG |
| 102 | 8ANC194HC | EVQLVQSGGGLVQPGGSLRLSCAASGLTFRNFAMSWVRQAPGKGLEWVSSISGSGGSTYYADSVKGRFTISRDNSKNTLYLQMNSLRGEDTAVYFCAKGVGYDILTGLGDAFDIWGQGTVVAVSSASTKG |
| 103 | 8ANC195HC | QIHLVQSGTEVKKPGSSVTVSCKAYGVNTFGLYAVNWVRQAPGQSLEYIGQIWRWKSSASHHFRGRVLISAVDLTGSSPPISSLEIKNLTSDDTAVYFCTTTSTYDKWSGLHHDGVMAFSSWGQGTLISVSAASTKG |
| 104 | 8ANC196HC | VVQLVQSGTEVKKPGSSVKVSCKASGGTFSGSDISWVRQAPGQGLEWMGGIIPMFDIEDHAQKFRGRLTITADKSTGAAYMELSSLRSEDAAVYYCARSSGNYDFAFDIWGQGTRLIVSSASTKG |
| 105 | 8ANC20HC | QVQLGESGGGLVEPGGSLRLSCAASGFLFSDYQMSWIRLAPGKGLEWISFISGFGSVYYADSVEGRFTISRDNARNSLYLQMNNLRAEDTAVYYCARAYGTGNWRGLYYYYYGMDVWGHGTTVTVSSASTKG |
| 106 | 8ANC21HC | QLQLVESGGGVVQPGRSLRLSCAASGFTFSTYTMHWVRQAPGKGLEWVAVISYDGTNKYYADSVKGRFTISRDNSKNTLYLQMNSLRGEDTAVYYCARSPSYYFDYWGQGTLVTVSAASTKG |
| 107 | 8ANC24HC | QVQLVQSGAEVKMPGASVKVSCKVSGYSLTELSIHWVRQAPGKRLEWMGGFDPEDDERIYAQKFQDRVTMTEDTSTDTAYMDLNSLRSEDTAVYYCTTGGLYCSSISCIMDVWGQGTTVIVSSASTKG |
| 108 | 8ANC25HC | QVQLVQSGAEVKKPGASVKVSCKVSGYTLTELSIHWVRQAPGKRLEWMGGFDPEDGERIYAQKFQGRVTMTEDTSTDTAYMELNSLRSDDTAVYYCATGGLYCSSISCIMDVWGQGTTVTVSSASTKG |
| 109 | 8ANC27HC | QVQLVQSGAEVKKPGASVKVSCKVSGYTLTELSIHWVRQAPGKGLEWMGGFDSEDGEAIYKQNFQGRVTMTEDTSTDTAYMELSRLRSEDTAVYYCATADRFKVAQDEGLFVIFDYWGQGNPGHRLLSLHQGPIGLPPGTLPPKATSGHAARR |
| 110 | 8ANC31HC | QVQLVESGGGVVQPGRSLRLSCAASGFTFSSYAMHWVRQAPGKGLEWVAVISYDGSNKYYADSVKGRFTISRDDSKSTVYLQINSLRAADTAVYFCAREGGLRFLEWLFWGQGTLVTVSSGESSASTKG |
| 111 | 8ANC33HC | EFQLVQSGGGLVKPGGSLRLSCTGSTFSFSSDDMNWVRQAPGKGLEWVSSMSDSGSHIYYADFVKGRFTISRDNAKKSLYLQMNSLRAEDTAVYYCAQSRPPQRLYGMDVWGQGTTVTVSSASTKG |
| 112 | 8ANC34HC | QVQLVQSGAEVKKPGASVKVSCKVSGYTLTELSIHWVRQAPGKGLEWMGGFDPEDGEASFEPKFQGRLTMTEDTSTDTAYMELSSLRSEDTAVYYCATADPFKVAQDEGLYVIFDYWGQGTLVTVSSASTKG |
| 113 | 8ANC36HC | QVQLVESGGGVVQPGKSLRLSCAASGFTFSTHAMHWVRQAPGKGLDWVAVISHDGDNQYYADAVKGRFTISRDDSRDTVFLQMNSLRTEDTGVYYCAADSSGSNWFDYWGQGILVTVSSASTKG |
| 114 | 8ANC38HC | EPMFQPGQSGGVVVQSGESLHLSCEASGFKFASQMMHWVRHVPGRGLEWVALISWDGSGKLFADSVRGRFTIHRWNDRNSLYLDVKNVRPEDAAIYYCTRNGFDVWGQGILVTVSSASTKG |
| 115 | 8ANC39HC | QVQLLQSGAEVKKPGASVKVSCKVSGYTLTELSIHWVRQAPGKGLEWMGGFDPEDDEAIYEPKFQGRLTMTEDTSTDTAYMELSSLRSEDTAVYYCATADPFKVAQDEGLYVIFDYWGQGTLVTVSSASTKG |
| 116 | 8ANC3HC | QVHLQESGPRLVRSSETLSLTCSVPGGSIVNPITNYYWSWIRQSPRKGLQWIGDIYYTGTSSRNPSLDSRVSISMDVSRKQISLTLYSVTAADTAVHYCASQSLSWYRPSGYFESWGQGILVTVSSASTKG |
| 117 | 8ANC43HC | QVQLVQSGAEVKKPGSSMKVSCKSSGGTFSNHAISWVRQAPGKGLEWMGGIIPMSGTTNYLQKFQGRVTITADEFATTAYMELSSLTSEDTAVYYCARARADSHTPIDAFDIWGPGTRVIVSSASTKG |
| 118 | 8ANC46HC | QVQLVQSGTEVKKPGSSVKVSCKASGGTFSDSDIAWVRQAPGQGLEWMGGITPMFDMAKSAQKFRGRLIITADKSTGTAYMELSSLRYEDAAVYFCARSSGNFEFAFEIWGQGTKIIVSLASTKG |
| 119 | 8ANC48HC | QVQLVQSGAEVKKPGASVKVSCKASGYTFTSYDINWVRQATGQGLEWMGWMNPNSGNTGYAQTFQGRVTMTRNTSISTAYMELSSLRSEDTAVYYCARDRWLPQYYYYGMDVWGQGTTVTVSSASTKG |

TABLE A-continued

| Seq ID No. | Antibody | Heavy Chain Amino Acid Sequence |
|---|---|---|
| 120 | 8ANC49HC | FVQLVESGGGLVQPGGSLRLSCAASGFNFNTYWMNWVRQAPGKGLEWVANMKEDGSE KYYVDSVKGRFTISRDNAKNSLYLQMNSLRAEDTAVYYCARNPESRCIVGRNRGWCRYFDL WGRGSLVTVSPASTKG |
| 121 | 8ANC51HC | LVQLVESGGGVVQPGRSLRLSCAASGFTFSTYAMHWVRQAPGKGLEWVAVISYDGSNKFY ADSVKGRFTISRDNSKNTLYLQMNSLRAEDTAVYYCARPKFLPGADIVVVVAATPFDYWGQ GNPGHRLLSFHQGPIGLPPG |
| 122 | 8ANC57HC | PMFQPGQSGGVVVQSGESLHLSCEASGFKFASQMMHWVRHVPGRGLEWVALISWDGS GKLFADSVRGRFTIHRWNDRNSLYLDVKNVRPEDAAIYYCTRNGFDVWGQGILVTVSSAST KG |
| 123 | 8ANC58HC | QVQLVQSGAEVKKPGASVKVSCKVSGHTLSELSINWVRHVPGKGLEWMGGLDPEDGEAI HEPKFQGRLTMTEDTSTDTAYVELSSLRSEDTAMYYCATADPFKVAQDEGLYVIFDYWGQ GTLVTVSSASTKG |
| 124 | 8ANC5HC | QVQLVQSGAEVRKPGSSLKVSCKSSGGTFSRFVVNWVRQAPGQGLEWMGGMIPIFGIAK YAQKFQDRVTMTADESKNTVYLDFSSLRSDDTAVYYCARDRGDTRLLDYGDYEDERYYYG MDVWGQGTTVIVSSASTKG |
| 125 | 8ANC60HC | LVQLVESGGGVVQPGKSLRLSCATSGFTFSTYGMHWVRQAPGKGLEWVAVIWYDGSYKY YADSVKGRFTISRDNSKNTLFLQMNSLRAEDTAMYYCGREMAVGGTKALDHWGQGTLVT VSSASTKG |
| 126 | 8ANC63HC | QVQLVQSGAEAKRPGDSVKVSCKASGYTFTEYYIHWVRQTPGQGFEWMGIITPGAGNTTY AQKFQGRITVTRDTSAATVYMELSNLTSEDTAVYFCSRGVSFWGQGTLVTVSSASTKG |
| 127 | 8ANC65HC | QVQMVASGGGLVKPGGSLRLSCEASGFTFSDYYMSWVRQAPGKGLEWISYITSGGNALYY ADSVKGRFTISRDNAKNSLYLQMNSLRAEDTAVYYCARDLLHAHDFGRQGTLVTVSSASTK G |
| 128 | 8ANC67HC | QVQLVESGGGVVQPGRSLRLSCATSGFTSKNYGVHWVRQAPGKGLEWVAVIWYDGSNK FYADSVKGRFTISRDRSKNMVYLQMNSLRVEDTAIYYCARDSVAFVLEGPIDYWGQGTLVT VSSASTKG |
| 129 | 8ANC69HC | QVQLVQSGAEVKKPGASVKVSCKASGYTFTDYYIHWVRQAPGQGLEWMGWINPSTGGT NFVQKFLGRVTMTSDTSINTAYMELRRLKNDDAAIYYCATYSTRQFFHYYYVTDVWGQGT TVTVSSASTKG |
| 130 | 8ANC6HC | QVQLVQSGAEVKKPGSSVKVSCRASGGSFGNYAINWVRQAPMQGLEWMGGIIPIFGTTN YAQNFRGRVTINADTFTNTVNMDLSSLRSEDTAVYYCGRSINAAVPGLEGVYYYYGMAVW GQGTTVTVSSASTKG |
| 131 | 8ANC70HC | QVQLHQWGAGLLKPSDTLSLTCGILGVSPPGSLTGYYWTWIRQPPGKGLEWIGEVYHSGS TNYNPSLASRVTISMGTTKTQFSLRLTSVTAADSAVYYCASGKVWGITARPRDAGLDVWG QGTTVTVTSASTKG |
| 132 | 8ANC71HC | EVQVVESGGGLVQPGGSLRLSCVASGFTFSEYWMSWVRQAPGKGLEWVATIKRDGSEES YVDSVKGRFTISRDNAKNSLYLQMNSLRAEDTAVYYCARVRDPNYNLHFDSWGQGTLVTV SSASTKG |
| 133 | 8ANC72HC | QVQLVESGGGLIQPGGSLRLSCEASGFAVGDINYMSWVRQAPGKGLEWVSVLYSGGSSQY ADSVKGRFTISRDNSRNTLYLQMDNLRAEDTAVYYCARGLRVYFDLWGQGILVTVSSASTK G |
| 134 | 8ANC74HC | QVQLVQSGAEVKKPGSSVKVSCKASGGTFSTYAFSWVRQAPGQGLEWMGGIIPIFGTENY AQKFQGRVTITADKSTSTAYMELSSLRSEDTAVYYCARDRSSAIGYCSSISCYKGSFDIWGQG TMVTVSSASTKG |
| 135 | 8ANC75HC | QVQLQESGPGLVKPSETLSLTCTVSGGSISSRSYYWGWIRQPPGKGLEWVGSIYYTGSTYYS PSLKSRVTISVDTSQNQFSLKLNSVTAADTAVYYCARQKGSGTSLLYWGQGTLVTVSSASTK G |
| 136 | 8ANC76HC | QVQLVQSGSELKKPGASVKVSCKASGYTFTSYAINWVRQAPGQGLEWMGWINTNTGNPT YAQGFTGRFVFSLETSVSTAYLQINSLKAEDTAVYYCARDLLESRTYYNDIRDCWGQGTLVT VSSASTKG |
| 137 | 8ANC78HC | QVQLQESGSGLVKPSGTLSLTCAVSNGPISSGNWWSWVRQTPEKGLEWIGEVYHSGSTN HNPSLKSRATILVDKSKNQFSLNLRSVTAADTAVYYCARVRGSWNFDYWGQGILVTVSSAS TKG |
| 138 | 8ANC79HC | QHQLVPCVAEVRKPGASVKVSCKVSGYTLTEISMHWVRQAPGKGLEWMGGFDREDGETI YAQKFQGRVTMTEDTSTDTAYMELSSLRSEDTAVYYCATTYLAVVPDGFDGYSSSWYWFD PWGQGTLVTVSSASMQGPMLLSPTGTLLPRAPLVQTRPGP |

TABLE A-continued

| Seq ID No. | Antibody | Heavy Chain Amino Acid Sequence |
|---|---|---|
| 139 | 8ANC7HC | QVQLVQSGAEVRKPGSSLKVSCKSSGGTFSRYVVNWVRQAPGQGLEWMGGIIPIFGIAKYAQKFQDRVTMTADESKNTVYLDFSSLRSDDTAVYYCARDRGDTRLLDYGDYEDERYYYGMDVWGQGTTVIVSSASTKG |
| 140 | 8ANC80HC | QVQLVQSGAEVKKPGSSVKVSCKASGGTFSTYAFSWVRQAPGQGLEWMGGIIPIFGTENYAQKFQGRVTITADKSTSTAYMELSSLRSEDTAVYYCARDRSSAIGYCSSISCYKGSFDIWGQGTMVTVSSASTKG |
| 141 | 8ANC82HC | QVHLEESGPGLVKTSQTLSLTCSVSSYSISRSGYFWTWIRQRPGKGLEWIGYIYFNGRTTYNPSLKSRITISRDTSHSQFSLTLNSLSAADTAVYYCGRCQDGLASRPIDFWGQGTLVTVSSASTKG |
| 142 | 8ANC83HC | QVQLVESGGGVVQPGKSLRLSCAISGFLFNNYGGQWVRQAPGKGLEWVAAISYDGNNRYYADSAKGRFLISRDTPKNILYLQIYSLRLDDTAVYYCARDSVSKSYSAPPEFWGQGTVVTVSSASTKG |
| 143 | 8ANC91HC | QLQLQESGPGLVKPSETLSLTCSVSDGSINSNSYYWAWIRQSPGKGLEWIGSVYYFGGTYYSPSLKSRVTMSVDRSKNQFSLNVSSVTAADTAIYYCARHVRPYDRSGYPERPNWFDPWGRGTLVTVSSASTKG |
| 144 | 8ANC92HC | RVQLVQSGAEVKKPGSSVTVSCKASGGSFSSYAISWVRQAPGQGLEWVGGVKVMFGTVHYSQKVQGRVTITADDSTGTSYLELSGLRSADTAVYYCARNAGAYFYPFDIWGQGTLIIVSSASTKG |
| 145 | 8ANC93HC | QVQLVQSGAEVKKPGASVKVSCKASGYTFTRYHIHWVRHAPGQGLEWMGKINPSRASTKYAKKFQDRVTMTRDTSTSTVYMELSSLRGDDTAVYYCGREMGTFTLLGVVIDHYDFYPMDVWGQGTPVTVSSASTKG |
| 146 | 8ANC9HC | QVQLVQSGAEVRKPGSSLKVSCKSSGGTFSRYVVNWVRQAPGQGLEWMGGIIPIFGIAKYAQKFQDRVTMTADESKNTVYLDFSSLRSGDTAVYYCARDRGDTRLLDYGDYEDERYYYGMDVWGQGTTVTVSSASTKG |
| 147 | 12A10HC | SQHLVQSGTQVKKPGASVRVSCQASGYTFTNYILHWWRQAPGQGLEWMGLIKPVFGAVNYARQFQGRIQLTRDIYREIAFLDLSGLRSDDTAVYYCARDESGDDLKWHLHPWGQGTQVIVSPASTKG |
| 148 | 12A12HC | SQQLVQSGTQVKKPGASVRISCQASGYSFTDYVLHWWRQAPGQGLEWMGWIKPVYGARNYARRFQGRINFDRDIYREIAFMDLSGLRSDDTALYFCARDGSGDDTSWHLDPWGQGTLVIVSAASTKG |
| 149 | 12A13HC | SQQLVQSGTQVKKPGASVRISCQASGYSFTDYVLHWYRQAPGQGLEWMGWIKPVYGARNYARRFQGRINFDRDIYREIAFMDLSGLRSDDTALYFCARDGSGDDTSWYLDPWGQGTLVIVSAASTKG |
| 150 | 12A16HC | SQQLVQSGTQVKKPGASVRISCQASGYTFTDYVLHWWRQAPGQGLEWMGWIKPVYGARNYARRFQGRINFDRDIYREIAYMDLSGLRSDDTARYFCARDGSGDDTSWHLHPWGQGTLVIVSAASTKG |
| 151 | 12A17HC | SQQLVQSGTQVKKPGASVRVSCQASGYTFMNYIIHWWRQAPGQRLEWMGWINPVFGARNYAHRFQGRINFDRDINRETFQMELTGLRSDDTAVYYCARDGSGDARDWHLDPWGQGTLVIVSSASTKG |
| 152 | 12A1HC | SQHLVQSGTQVKKPGASVRVSCQASGYTFTNYILHWWRQAPGQGLEWMGLIKPVFGAVNYARQFQGRIQLTRDINREIAFLDLSGLRSDDTAVYYCARDESGDDLKWHLHPWGQGTQVIVSPASTKG |
| 153 | 12A20HC | SQQLVQSGTQVKKPGASVRVSCQASGYTFMNYIIHWWRQAPGQRLEWMGWINPVFGARNYAHRFQGRINFDRDINRETFQMDLTGLRSDDTAVYYCARDGSGDARDWHLHPWGQGTLVIVSSASTKG |
| 154 | 12A21HC | SQHLVQSGTQVKKPGASVRVSCQASGYTFTNYILHWWRQAPGQGLEWMGLIKPVFGAVNYARQFQGRIQLTRDIYREIAFLDLSGLRSDDTAVYYCARDESGDDLKWHLHPWGQGTQVIVSPASTKG |
| 155 | 12A22HC | SQQLVQSGTQVKKTGASVRVSCQASGYDFTKYLIHWWRQAPGQGLEWMGWMKPVYGATNYAHRFQGRISFTRDIYREIAFMDLNGLRSDDTAVYFCARDGGGDDRTWLLDAWGQGTLVIVSSASTKG |
| 156 | 12A23HC | SQHLVQSGTQVKKPGASVRVSCQASGYTFTNYILHWWRQAPGQGLEWMGLIKPVFGAVNYARQFQGRIQLTRDINREIAFLDLSGLRSDDTAVYYCARDESGDDLKWHLHPWGQGTQVIVSPASTKG |
| 157 | 12A27HC | SQQLVQSGTQVKKPGASVRISCQASGYTFTDYVLHWWRQAPGQGLEWMGWIKPVYGARNYARRFQGRINFDRDIYREIAFLDLSGLRSDDTARYFCARDGSGDDTSWHLHPWGQGTLVIVSAASTKG |

TABLE A-continued

| Seq ID No. | Antibody | Heavy Chain Amino Acid Sequence |
|---|---|---|
| 158 | 12A2HC | SQQLVQSGTQVKKPGASVRISCQASGYTFTDYVLHWWRQAPGQGLEWMGWIKPVYGA RNYARRFQGRINFDRDIYREIAYMDLSGLRSDDTARYFCARDGSGDDTSWHLHPWGQGTL VIVSAASTKG |
| 159 | 12A30HC | SQQLVQSGTQVKKPGASVRISCQASGYTFTDYVLHWWRQAPGQGLEWMGWIKPVYGA RNYARRFQGRINFDRDIYREIAYMDLSGLRSDDTARYFCARDGSGDDTSWHLHPWGQGTL VIVSAASTKG |
| 160 | 12A37HC | SQQLVQSGTQVKKTGASVRVSCQASGYDFTKYLIHWWRQAPGQGLEWMGWMKPVYG ATNYAHRFQGRISFTRDIYREIAFMDLNGLRSDDTAVYFCARDGGGDDRTWLLDAWGQG TLVIVSSASTKG |
| 161 | 12A46HC | SQQLVQSGAQVKKPGASVRVSCQASGYTFTNHFLHWWRQAPRQGLEWMGWINPVHG GRNYARRFQGRINFGRDVYQETAYMELSGLRNDDTATYFCARGGGDGRNWHLHPWGQ GTLVIVSAASTKG |
| 162 | 12A4HC | SQHLVQSGTQVKKPGASVRVSCQASGYTFTNYILHWWRQAPGQGLEWMGLIKPVFGAV NYARQFQGRIQLTRDIYREIAFLDLSGLRSDDTAVYYCARDESGDDLKWHLHPWGQGTQVI VSPASTKG |
| 163 | 12A55HC | SQQLVQSGAQVKKPGASLRVSCQASGYTFMNYLLHWWRQAPGQGLEWMGWINPVYG AVNYAHRFQGRLTFSRDVYREIAYMDLNGLRSDDTAVYFCARDGSGDDRNWHLDPWGQ GTLVIVSSASTKG |
| 164 | 12A56HC | SQQLVQSGTQVKKPGASVRVSCQASGYTFTNYILHWWRQAPGRGLEWMGLIKPVYGAV NYARQFQGRIQLTRDIYREIAFLDLSGLRPDDTAVYYCARDESGYDLNWHLDSWGQGTQVI VSPASTKG |
| 165 | 12A6HC | SQQLVQSGTQVKKPGASVRVSCQASGYTFTDYVLHWWRQAPGQGLEWMGWIKPVYGA RNYAHRFQGRINFDRDVYREIAYMDLSGLRSDDTAVYFCARDGSGDATSWHLHPWGQGT LVIVSSASTKG |
| 166 | 12A7HC | SQQLVQSGTQVKKPGASVRVSCQASGYTFMNYIIHWWRQAPGQRLEWMGWINPVFGA RNYAHRFQGRINFDRDINRETFQMELTGLRSDDTAVYYCARDGSGDARDWHLDPWGQG TLVIVSSASTKG |
| 167 | 12A9HC | QVTLVQSGAEVKKPGASVRISCRASGFTFDDYSDYSFIPTTYLIHWFRQAPGQGLEWMAWI NSVNGGRNIARQFQGRVTVARDRSNSIAFLEFSGLRHDDTAVYFCARDRRDDDRAWLLDP WGQGTRVTVSSASTKG |
| 168 | LSSB2339HC | QVRLEQSGAAMRKPGASVTLSCQASGYNFVKYIVHWVRQKPGLGFEWVGMIDPYRGRP WSAHKFQGRLSLSRDTSMEILYMTLTSLTSDDTATYFCARAEAASDSHSRPIMFDHWGQG SRVTVSSASTKG |
| 169 | LSSB2351HC | QVRLEQSGTAVRKPGASVTISCQASGYNFVKFFIHWVRQRPGQGFEWVGMIEPFRGRPW SAGNFQGRLSLSRDVSTETLYMTLNNLRSDDTAVYFCARLEAESDSHSRPIMFDHWGHGSL VTVSSASTKG |
| 170 | LSSB2361HC | QVRLFQSGAAMRKPGASVTISCEASGYNFMNYFVHWVRQRPGRGFEWLGMINPRGGRP WSAQSVQGRLTLTRDTSTEMFYMRLDGLRSDDTATYFCARNEADYHDGNGHSLRGMFDY WGQGSLITVSSASTKG |
| 171 | LSSB2364HC | QVRLEQSGAAVRKPGASVTLSCQASGYNFVNYIIHWVRQRPGLDFEWVGMIDPYRGRPW SAHKFQGRLSLSRDVSTEILYMTLSSLRSDDTATYFCARAEAESQSHSRPIMFDFWGQGSRV TVSSASTKG |
| 172 | LSSB2367HC | QVRLSQSGAAIKKPGASVTISCETEGYTFINYIIHWVRQPPGRGFEWLGMIDPRNGRPWFG QSVQGRLSLRRDTYTEVVYMTLSGLTSDDAGHYFCARNEPQYHDGNGHSLPGMFDYWG QGTLVAVSSASTKG |
| 173 | LSSB2416HC | QVRLSQSGAAVKKPGASVTIVCETEGYNFIDYIIHWVRQPPGRGFEWLGMIDPRNGRPWS GQKVHGRLSLWRDTSTEKVYMTLTGLTSDDTGLYFCGRNEPQYHDDNGHSLPGMIDYWG QGTMVTVSSASTKG |
| 174 | LSSB2434HC | QVRLFQSGAAMRKPGASVTISCEASGYNFMNYFVHWVRQRPGRGFEWLGMINPRGGRP WSAQSVQGRLTLTRDTSTEMFYMRLDGLRSDDTATYFCARNEADYHDGNGHSLRGMFDY WGQGSLITVSSASTKG |
| 175 | LSSB2483HC | QVRLFQSGAAMRKPGASVTISCEASGYNFMNYFVHWVRQRPGRGFEWLGMINPRGGRP WSAQSVQGRLTLTRDTSTEMFYMRLDGLRSDDTATYFCARNEADYHDGNGHSLRGMFDY WGQGSLITVSSASTKG |
| 176 | LSSB2490HC | QVRLFQSGAAMRKPGASVTISCEASGYNFMNYFVHWVRQRPGRGFEWLGMINPRGGRP WSAQSVQGRLTLTRDTSTEMFYMRLDGLRSDDTATYFCARNEADYHDGNGHSLRGMFDY WGQGSLITVSSASTKG |

TABLE A-continued

| Seq ID No. | Antibody | Heavy Chain Amino Acid Sequence |
|---|---|---|
| 177 | LSSB2503HC | QVRLEQSGAAVRKPGASVTLSCQASGYNFVRYIIHWVRQRPGLDFEWVGMIDPYRGRPWSAHKFGGRLSLTRDVSTEILYMTLTSLRSDDTATYFCARAEAESQSHSRPIMFDSWGQGSRVTVSSASTKG |
| 178 | LSSB2525HC | QVRLEQSGNAVRKPGASVTISCQASGYNFVKFFIHWVRQRPGQGFEWVGMIEPFRGRPWSAGNFQGRLSLSRDVSTETLYMTLNNLRSDDTAVYFCARLEAESDSHSRPIMFDHWGHGSLVTVSSASTKG |
| 179 | LSSB2530HC | QVRLEQSGAAMRKPGASVTLSCQASGYNFVKYIIHWVRQKPGLGFEWVGMIDPYRGRPWSAHKFQGRLSLSRDTSMEILYMTLTSLKSDDTATYFCARAEAASDSHSRPIMFDHWGQGSRVTVSSASTKG |
| 180 | LSSB2538HC | QVRLFQSGAAMRKPGASVTISCEASGYNFLNYFVHWVRQRPGRGFEWLGMINPRGGRPWSAQSVQGRLTLTRDTSTEMFYMRLDGLRSDDTATYFCARNEADYHDGNGHSLRGMFDYWGQGSLITVSSASTKG |
| 181 | LSSB2554HC | QVRLEQSGAAMRKPGASVTLSCQASGYNFVKYIIHWVRQKPGLGFEWVGMIDPYRGRPWSAHKFQGRLSLSRDTSMEILYMTLTSLKSDDTATYFCARAEAASDSHSRPIMFDHWGQGSRVTVSSASTKG |
| 182 | LSSB2573HC | QVRLSQSGAAIKKPGASVTISCETEGYTFINYIIHWVRQPPGRGFEWLGMIDPRNGRPWFGQSVQGRLSLRRDTYTEVVYMTLSGLTSDDTGLYFCARNEPQYHDGNGHSLPGMFDSWGQGTLVAVSSASTKG |
| 183 | LSSB2578HC | QVQLFQSGAAMRKPGASVTISCEASGYNFMNYFVHWVRQRPGRGFEWLGMINPRGGRPWSAQSVQGRLTLTRDTSTEMFYMRLDGLRSDDTATYFCARNEADYHDGNGHSLRGMFDYWGQGSLITVSSASTKG |
| 184 | LSSB2586HC | QVRLEQSGAAMRKPGASVTLSCQASGYNFVKYIVHWVRQKPGLGFEWVGMIDPYRGRPWSAHKFQGRLSLSRDTSMEILYMTLTSLKSDDTATYFCARAEAASDSHSRPIMFDHWGQGSRVTVSSASTKG |
| 185 | LSSB2609HC | QVRLFQSGAAMKKPGASVTISCEASGYNFMNYFVHWVRQRPGRGFEWLGMINPRGGRPWSAQSVQGRLTLTRDISTEMFYMRLDGLRSDDTATYFCARNEADYHDGNGHSLRGMFDYWGQGSLITVSSASTKG |
| 186 | LSSB2612HC | QVRLEQSGTAMRKPGASVTLSCQASGYNFVKYIVHWVRQKPGLGFEWVGMIDPYRGRPWSAHKFQGRLSLSRDTSMEILYMTLTSLKSDDTATYFCARAEAASDSHSRPIMFDHWGQGSRVTVSSASTKG |
| 187 | LSSB2630HC | QVRLFQSGAAMRKPGASVTISCEASGYNFMNYFVHWVRQRPGRGFEWLGMINPRGGRPWSAQSVQGRLTLTRDTSTEMFYMRLDGLRSDDTATYFCARNEADYHDGNGHSLRGMFDYWGQGSLITVSSASTKG |
| 188 | LSSB2640HC | QVRLFQSGAAMRKPGASVTISCEASGYNFMNYFVHWVRQRPGRGFEWLGMINPRGGRPWSAQSVQGRLTLTRDTSTEMFYMRLDGLRSDDTATYFCARNEADYHDGNGHSLRGMFDYWGQGSLITVSSASTKG |
| 189 | LSSB2644HC | QVRLSQSGAAIKKPGASVTISCETEGYTFINYIIHWVRQPPGRGFEWLGMIDPRNGRPWFGQSVQGRLSLRRDTYTEVVYMTLSGLTSDDTGLYFCARNEPQYHDGNGHSLPGMFDSWGQGTLVAVSSASTKG |
| 190 | LSSB2665HC | QVRLFQSGAAMRKPGASVTISCEASGYNFMNYFVHWVRQRPGRGFEWLGMINPRGGRPWSAQSVQGRLTLTRDTSTEMFYMRLDGLRSDDTATYFCARNEADYHDGNGHSLRGMFDYWGQGSLITVSSASTKG |
| 191 | LSSB2666HC | QVRLEQSGAAMRKPGASVTLSCQASGYNFVKYIIHWVRQKPGLGFEWVGMIDPYRGRPWSAHKFQGRLSLSRDTSMEILYMTLTSLKSDDTATYFCARAEAASDSHSRPIMFDHWGQGSRVTVSSASTKG |
| 192 | LSSB2669HC | QVRLEQSGAAMRKPGASVTLSCQASGYNFVKYIIHWVRQKPGLGFEWVGMIDPYRGRPWSAHKFQGRLSLSRDTSMEILYMTLTSLKSDDTATYFCARAEAASDSHSRPIMFDHWGQGSRVTVSSASTKG |
| 193 | LSSB2680HC | QVRLEQSGVAMRKPGASVTLSCQASGYNFVKYIIHWVRQKPGLGFEWVGMIDPYRGRPWSAHKFQGRLSLSRDTSMEILYMTLTSLKSDDTATYFCARAEAASDIHSRPIILTGPGEYGLDLEHMDWTWRILCLLAVAPGCHSQ |
| 194 | LSSB2683HC | QVRLEQSGAAMRKPGASVTLSCQASGYNFVKYIVHWVRQKPGLGFEWVGMIDPYRGRPWSAHKFQGRLSLSRDTSMEILYMTLTSLKSDDTATYFCARAEAASDSHSRPIMFDHWGQGSRVTVSSASTKG |
| 195 | LSSB344HC | QVRLEQSGTAVRKPGASVTISCQASGYNFVKFFIHGVRQRPGQGFEWVGMIEPFRGRPWSAGNFQGRLSLSRDVSTETLYMTLNNLRSDDTAVYFCARLEAESDSHSRPIMFDHWGHGSLVTVSSASTKG |

TABLE A-continued

| Seq ID No. | Antibody | Heavy Chain Amino Acid Sequence |
|---|---|---|
| 196 | LSSNEC107HC | QVRLVQSGPQVKTAGASMRVSCEASGYRFLDYIIVWIRQTHGQHFEYVGMINPRGGTPW PSSKFRDRLTLTRDIYTDTFYLGLNNLGSGDTAIYFCARLEADGDDYSPKMFDYWGQGTRIIV SAASTKG |
| 197 | LSSNEC108HC | QVHTFQSGSSMKKSGASVTISCEATGYNIKNYILHWVRQKPGRGFEWVGMIDPINGRPWF GQPFRGRLTLTRDLSTETFYMSLSGLTSDDTATYFCARREADYHDGNGHTLPGMFDFWGP GTLITVSSASTKG |
| 198 | LSSNEC109HC | QVSLVQSGPQVKTPGASMRVSCETSGYRFLDYIIVWIRQTHGQHFEYVGMINPRGGTPWP SSKFRDRLTMTRDIHTDTFYLGLNNLRSDDTAIYFCARLEADGDDYSPKMFDYWGQGTRIIV SAASTKG |
| 199 | LSSNEC110HC | QVRLVQSGPQMKTPGASLRLSCEVSGYRFLDYFIVWVRQTGGQGFEYVGMINPRGGRPW SSWKFRDRLSLTRDIETDTFYLGLNNLRSDDTAIYFCARLEADGDNYSPKMVDYWGQGTKII VSPASTKG |
| 200 | LSSNEC116HC | QVRLSQSGAAVVKTGASVTISCETEGYNFVNYIIHWVRRPPGRGFEWLGMIDPRNGHPWF AQTVRGRLSLRRDTFKETVYMTLSGLTSDDTGVYFCARNEPQYHSLPGMFDYWGHGTPVT VSSASTKG |
| 201 | LSSNEC117HC | QVRLVQSGAQLKKPGASVTVSCEASGYNFVNYIINWVRQTPGRGFEWVGMIDPRRGRPW SAQKFQGRLTLTRDIDSEKLYMHLSGLRGDDTAVYYCARQDSDFHDGHGHTLRGMFDSW GQGSPVTVSSASTKG |
| 202 | LSSNEC118HC | QVRLVQSGPQVKTPGASMRISCEASGYRFQDYIIVWIRQTHGQGFEYVGMINPRGGTPWS SSKFRDRLSLTRDIYTDTFYLGLNNLGSDDTAIYFCARLEADGGDYSPKMFDYWGQGTRIIVS AASTKG |
| 203 | LSSNEC11HC | QVRLFQSGAAMRKPGASVTISCEASGYNFMNYFVHWVRQRPGRGFEWLGMINPRGGRP WSAQSVQGRLTLTRDTSTEMFYMRLDGLRSDDTATYFCARNEADYHDGNGHSLRGMFDY WGQGSLITVSSASTKG |
| 204 | LSSNEC122HC | QVRLVQSGPQVKRPGASIRLSCETSGYRFQDYIVAWIRQTRGQRFEFVGMVNPRGGRPW PSSKFRDRVTLTRDIESETFHLGLNDLTSDDTATYFCARLEADGADYSPKMFDFWGQGTKIV VSPASTKG |
| 205 | LSSNEC123HC | QVRLEQSGAAVRKPGASVTLSCQASGYNFVNYIIHWVRQRPGLDFEWVGMIDPYRGRPW SAHKFEGRLSLSRDVSTEVLYMTLSSLRSDDTATYFCARAEAESQSHSRPIMFDYWGQGSRV TVSSASTKG |
| 206 | LSSNEC127HC | QVRLEQSGAAMRKPGASVTLSCQASGYNFVKYIIHWVRQKPGLGFEWVGMIDPYRGRPW SAHKFQGRLSLSRDTSMEILYMTLTSLKSDDTATYFCARAEAASDSHSRPIMFDHWGQGSR VTVSSASTKG |
| 207 | LSSNEC18HC | QVRLSQSGAAVMKTGASVTISCETEGFNFVNYIIHWVRRPPGRGFEWLGMIDPRNGHPW FAQTVRGRLSLRRDTFNEIVYMTLSGLTTDDTGLYFCARNEPQYHSLPGMFDYWGQGTPV TVSSASTKG |
| 208 | LSSNEC24HC | QVRLSQSGAAMKKPGASVTISCETEGYTFINYIIHWVRQPPGRGFEWLGMIDPRNGRPWF GQSVQGRLSLRRDTYTEVVYMTLSGLTSDDAGLYFCARNEPQYHDGNGHSLPGMFDYWG QGTLVAVSSASTKG |
| 209 | LSSNEC29HC | QVRLSQSGAAVVKTGASVTISCETEGYTFVNYIIHWVRQSPGRGFEWLGMIDPRNGHPWF GQRLRGRLSLRRDRSTETVFMTLSGLTSDDTAIYFCARNEPQYYDGSGHSLPGMFDYWGQ GTRVVVSSASTKG |
| 210 | LSSNEC2HC | QVRLFQSGAAMRKPGASVTISCEASGYNFMNYFVHWVRQRPGRGFEWLGMINPRGGRP WSAQSVQGRLTLTRDTSTEMFYMRLDGLRSDDTATYFCARNEADYHDGNGHSLRGMFDY WGQGSLITVSSASTKG |
| 211 | LSSNEC33HC | QVRLVQSGPQVKTPGASIRLSCEASGYRFLDYFIVWVRQTPGQGFEYVGMINPRGGRPWS SWKFRDRLSLTREIDTDTFYLGLSNLRSDDTAIYFCARLEADGDDYSPKMVDYWGQGTKIIV SAASTKG |
| 212 | LSSNEC34HC | QVRLFQSGAAMRKPGASVTISCEASGYNFMNYFVHWVRQRPGRGFEWLGMINPRGGRP WSAQSVQGRLTLTRDTSTEMFYMRLDGLRSDDTATYFCARNEADYHDGNGHSLRGMFDY WGQGSLITVSSASTKG |
| 213 | LSSNEC3HC | QVRLEQSGAAVRTPGASVTLSCQASGYKFVNYIIHWVRQRPGLAFEWVGMIDPYRGRPW SAHSFEGRLSLSRDVSMEILYMTLTSLRSDDTATYFCARAEAESQSHSRPIISTSGAR |
| 214 | LSSNEC46HC | QVQFFQSGSSMKKSGASVTISCEATGYNIKNHILHWVRQKPGRGFEWVGMIDPINGRPW FGQAFRGRLTLTRDLSTETFYMSLSGLTSDDTATYFCARREADYHDGNGHTLPGMFDFWG PGTLVTVSSASTKG |

TABLE A-continued

| Seq ID No. | Antibody | Heavy Chain Amino Acid Sequence |
|---|---|---|
| 215 | LSSNEC48HC | QVRLSQSGAAVVKTGASVTISCETEGYTFVNHIIHWVRQPPGRGFEWLGMIDPRNGHPWFGQRLRGRLSLRRDRSTETVFMTLSGLTSDDIGIYFCARNEPQYFDGSGHSLPGMFDYWGQGTRVVVSSASTKG |
| 216 | LSSNEC52HC | QVRLSQSGAAVVKTGASVTISCETEGYTFVNYIIHWVRQPPGRGFEWLGMIDPRNGHPWFGQRLQGRLSLRRDRSTETVFMTLSGLTSDDTGIYFCARNEPQYYDGSGHSLPGMFDYWGQGTRVVVSSASTKG |
| 217 | LSSNEC56HC | QVRLVQSGPQVKTPGASMRVSCEASGYRFLDYIIVWIRQTHGQHFEYVGMINPRGGTPWPSSKFRDRLSLTRDIHTDTFYLGLNNLGSDDTAIYFCARLEADGDDYSPKMFDHWGQGTRIIVSAASTKG |
| 218 | LSSNEC60HC | QVRLEQSGAAVKKPGASVTISCQASGYNFVKFFIHWVRQRPGQGFEWVGMIEPYRGRPWSAGNFQGRLSLSRDVSTETLYMTLNNLRSDDTAVYFCARLEAESDSHSRPIMFDHWGHGSLVTVSSASTKG |
| 219 | LSSNEC66HC | QVRLSQSGAAVMKTGASVTISCETEGYNFVNYIIHWVRRPPGRGFEWLGMIDPKNGHPWFAQAVRGRLSLRRDTFNEVVYMTLSGLTSDDTGLYFCARNEPQYHDGNGHSLPGMFDFWGQGTLVTVSSASTKG |
| 220 | LSSNEC70HC | QVRLSQSGAAVVKTGASVTISCETEGYTFVNYIIHWVRQPPGRGFEWLGMIDPRNGHPWFGQRFRGRLSLRRDRSTETVFMTLSGLTSDDNGIYFCARNEPQYYDGSGHSLPGMFDYWGQGTRVVVSSASTKG |
| 221 | LSSNEC72HC | QVRLEQSGAAVRKPGASVTLSCQASGYNFVNYIIHWVRQRPGLDFEWVGMIDPYRGRPWSAHKFQGRLSLSRDVSTEILYMTLSSLRSDDTATYFCARAEAESQSHSRPIMFDFWGQGSRVTVSSASTKG |
| 222 | LSSNEC7HC | QVRLEQSGAAVRKPGASVTLSCQASGYNFVNYIIHWVRQRPGLDFEWVGMIDPYRGRPWSAHKFQGRLSLSRDVSTEILYMTLNSLRSDDTATYFCARAEAESQSHSRPIMFDSWGQGSRVTVSSASTKG |
| 223 | LSSNEC82HC | QVRLFQSGAAMRKPGASVTISCEASGYNFMNYFVHWVRQRPGRGFEWLGMINPRGGRPWSAQSVQGRLTLTRDTSTEMFYMRLDGLRSDDTATYFCARNEADYHDGNGHSLRGMFDYWGQGSLITVSSASTKG |
| 224 | LSSNEC89HC | QVRLEQSGGALRKPGASVTLSCQASGYNFVKYIIHWVRQRPGLGFEWVGMIDPYRGRPWYAHSFAGRLSLSRDTSTETLYMTLSSLKSDDTATYFCARAEAASDSHSRPIMDWTWRILCLLAVVPASTKG |
| 225 | LSSNEC8HC | QVRLFQSGAAMRKPGASVTISCEASGYNFMNYFVHWVRQRPGRGFEWLGMINPRGGRPWSAQSVQGRLTLTRDTSTEMFYMRLDGLRSDDTATYFCARNEADYHDGNGHSLRGMFDYWGQGSLITVSSASTKG |
| 226 | LSSNEC94HC | QVRLEQSGAAMRKPGASVTLSCQASGYNFVKYIVHWVRQKPGLGFEWVGMIDPYRGRPWSAHKFQGRLSLSRDTSMEILYMTLTSLKSDDTATYFCARAEAASDSHSRPIMFDHWGQGSRVTVSSASTKG |
| 227 | LSSNEC95HC | QVRLVQSGPQVKRPGASIRLSCESSGYRFQDYIVAWIRQTRGQGFEFVGMVNPRGGRPWPSSRFRDRVTLTRDIESETFYLGLNDLTSDDTATYFCARLEADGSDYSPKMFDFWGQGTKIVVSPASTKG |
| 228 | LSSNEC9HC | QVRLVQSGAQLKKPGASVTVSCEASGYNFVNYIINWVRQTPGRSFEWVGMIDPRRGRPWSAQKFQGRLTLTRDIDSEKLYMHLSGLRGDDTAVYYCARQDSDFHDGHGHTLRGMFDSWGQGSPVTVSSASTKG |
| 229 | LSSB2055HC | QVQLVQSGPELMKPGSSVKVSCRASGDNFLTSTFNWLRQAPGQRLEWMGRFIPSLGLITSAPKFSDRLTITADQATLTAYMELTGLTSEDTALYYCARGLCRGGNCRLGPSGWLDPWGRGTQVTVSSASTKG |
| 230 | LSSB2066HC | QVVLIQSGAEVKRPGSSVKVSCKASGGSFPITWVRQAPGHGLEWMGGINPFFGTTNYAQKFQGRVSITADESTSTTYLHLSDLRSEDTAVYFCARENREKWLVLRSWFAPWGQGTLVTVSSASTKG |
| 231 | LSSB2068HC | EESGPGLVKPSQTLSLTCSVSGDSVSSGGYFWSWIRQHPTKGLECLGYVYYTGNTYYNPSLKSPPTIEVAMANNQVSLKLGSVTAADTAVYYCARIKRFRGGNYFDTWGHGLLVTVSSASTKG |
| 232 | LSSB2080HC | LAQLEQSGGGVVKPGGSLRLPCAASGFTFIDYYMAWIRLAPGKGLEWLSYISKNGDYTKYSESLKGRFTISRDNAKNLVILQLNRLRADDTAIYFCARADGLTYFGELLQYIFDLWGQGARVIVSSASTKGPSVFPLAPSSKSTSGHASV |

TABLE A-continued

| Seq ID No. | Antibody | Heavy Chain Amino Acid Sequence |
|---|---|---|
| 233 | LSSB2133HC | QVQLVQSGAEVKKPGASVKISCKASGYSFRNYAVHWVRQAPGQGLEWMGEINGGNGNT EYSQKSQGRLTITRDISATTAYMELSSLRSDDTAVYYCARVAYVHVVTTRSLDNWGQGTLVT VSSASTKG |
| 234 | LSSB2182HC | QVQIRQSGPGLVKPLETLSLSCIVFGGSFIAYHWTWIRQAPLKGLEWIGDIDQGGDITYSPSL KSRVTMSVDRSKSQFSLKLSSVTAADAAVYYCVRGPPNRYAVTSFTSGTHRERSSYYFDYW GPGTLVTVSSASTKG |
| 235 | LSSB218HC | KAPATLSLSPGERATLSCRASQSVGSDLAWYQQKPGQAPRLLIYDASNRATAIPARFSGSGS GTDFTLSISSLEPEDFAVYFCQQRYDKITFGQGTRLEIQRTVAAPSVFIFPPSDEQ |
| 236 | LSSB2277HC | FVQLVESGGGVVQPGTSLRLSCTTSGFIFSDYGMHWVRQAAGKGLEWVAVIWHDGSNRF YADSVKGRFTISRDNSKNAVYLEMNNLRVEDTALYYCARTSMDIDYWGQGTPVTVSSASTK G |
| 237 | LSSB2288HC | QVYLVQSGPELKKPGASVKISCKASGYNFPKYAIHWVRQAPGQGLQWMGWINGDNGDA RYSQKLQGRVTPSTDTSASVVYMELKRLRSEDTAVYYCARALYPWEIGGVPSTMGDDYWG QGTLITVSSASTKG |
| 238 | LSSB331HC | QVHLQQWGAGLLKPSETLSLTCAVSGGSFSGFFWTWIRQSPGKGLEWIGEVNHSGFTHSN PSLESRATISVAASNTQFSLRLASVTAADTAIYFCALRYFDWSPFRRDTYGTDVWGQGTTVI VSSASTKG |
| 239 | LSSNEC101HC | QVQLVQSGAELKKPGSSVKVSCKASGGTFNNHTFNWVRQAPGQGLEWMGRTIPILGSRD YAKTFQDRVTIIADKSTSTVYLELRRLKSEDTGVYYCATSMYYFDSGGYYRNTDLDKWGQGS LVTVSSASTKG |
| 240 | LSSNEC106HC | GLDLEHDGHHKEEPRASVTVSCEASGYNFVNYIIHWVRLTPGRGFEWMGMIDPRRGRPW SAQKFQGRLTLTRDIDSERLYMQLSGLRGDDTAVYFCARQEPDFHDGHGHTLRGMFDSW GQGSPVSVSSASTKG |
| 241 | LSSNEC112HC | QVQLVQSGAELKKPGSSVKVSCKASGGTFSNYAINWVRQAPGQGFEWMGGIIPLFATPTY AQKFQGRVRITADDSTSTAYMELSSLRSDDTAVYFCARPNVVRSALDYWGQGTLVTVSSAS TKG |
| 242 | LSSNEC115HC | QARLDQWGTGLLKPSETLSLKCAVFGVLFTDYNWTWVRQSPGKGLEWIGHLDHRGGGNY NPSLESRVTISLDYSKAQFSLHLKSVTVADTALYYCAGAVKGFWFDEVYNWFGPWSQGTLV TVASASTKG |
| 243 | LSSNEC124HC | QVQLQESGPGLVKPSGTLSLTCAVSGASISSRNWWTWVRQPPGKGLEWIGEIYESGATNY NPSLKSRVTISVDKSKNQFSLRLTSVTAADTAVYFCARLMTFGGLIGTLDYWGQGTLVTVLQ PPPRAHRYHPRNLLQEHLCARVMP |
| 244 | LSSNEC125HC | QVQLVQSGAEVKKPGSSVKVSCKASGGTFSTYAISWVRQAPGQGLEWMGGIIPSFSMSNY AQDFQGRLTITADESTSSVYMELNSLRSEDTAVYYCARDFPRFHRLVGNYDFWRGTLDRFS YMDLWGRGTAVTVSSASTKG |
| 245 | LSSNEC126HC | QVHLVQSGAEAKRPGSSVRVSCRASGGDFSSYTLSWVRQAPGQGIEWMGGVVPMLDTV HYAQKFQGRLTLSVDEGTSTAYMELSSLRSEDTAMYYCTRGRQTFRAIWSGPPAVFDIWG QGTLVIVSSASTKG |
| 246 | LSSNEC14HC | NGGSLRLSCRVSGFGFHLYEMNWVRQAPGKGLEWISSISGSGESTHYSDSITGRFSMSRDE AKDSLYLQMNNLRVEDTAVYYCTRGFSMGDGTGFSFDTWGRGTMVTVSSGLDTVSLAST KGPSVFPLAPCSRSTSDARLS |
| 247 | LSSNEC16HC | AARLDQWGTGLVKPSETLSLKCAVFGVDFPDYTWTWARQAPGKGLEWIGHRDHRGGSSY NPSLSGRATISLDTSKAQFSLHIKSVTVADTATYYCAGAVAGLWFEDAYNWFGPWSQGTLV TVAAASTKGPSVFPLAPSSKSTSGHASVL |
| 248 | LSSNEC21HC | QARLDQWGTGLLKPSETLSLKCAVFGVLFTDYNWTWVRQSPGKGLEWIGHLDHRGGGNY NPSLESRVTISLDYSKAQFSLHLKSVTVADTALYYCAGAVKGLWFDETYTWFGPWSQGTRV TVASASTKGPSVFPLAPSSKSTSGTRDLS |
| 249 | LSSNEC30HC | QVQLVQSEAEVKKPGSSVKVSCKASGGTFRGYTISWVRQAPGQGLEWMGRIIPILGKAIYA PSFQGRVTLTADKSTGTAYMELSRLRSDDTAVYYCAKVKMRGSSGYYYLFDDWGQGTLVT VSSASTKG |
| 250 | LSSNEC49HC | QVHLVQSGAEVKKPGASVKVSCKVSGYTLSELSIHWVRQGPGRGLEWMANFDPEDGETIY APQFQGRVTLTEDTSTDTAYMQLTSLRSEDTAVYYCATDRYTDTGRWGPGTLVTVSSASTK G |

TABLE A-continued

| Seq ID No. | Antibody | Heavy Chain Amino Acid Sequence |
|---|---|---|
| 251 | LSSNEC54HC | QARLDQWGTGLLKPSETLSLKCAVFGVLFTDYNWTWVRQSPGKGLEWIGHLDHRGGGSY NPSLESRVSISLDYSKAQFSLHLKSVTVADTALYYCAGAVKGFWFDEPSTWFGPWSQGTM VTVASASTKG |
| 252 | LSSNEC55HC | QARLDQWGTGLLKPSETLSLKCAVFGVLFTDYNWTWVRQSPGKGLEWIGHLDHRGGGNY NPSLESRVTISLDYSKAQFSLHLKSVTVADTALYYCAGAVKGFWFDEVYNWFGPGVREPWL PSPQPPPRAHRSSPWHPPPRAPLVTATVP |
| 253 | LSSNEC57HC | QARLDQWGTGLLKPSETLSLKCAVFGVLFTDYNWTWVRQSPGKELEWIGHLDHRGGGNY NPSLESRVTISLDYSKAQFSLHLKSVTVADTARYYCAGAVKGFWFDDPYTWFGPWSQGTLV TVASASTKG |
| 254 | LSSNEC5HC | QVHLVQSGAEAKRPGSSVRVSCRASGGDFSSYTLSWVRQAPGQGLERMGGVVPMLDTV HYAQKFQGRLTLSVDEGTSTAYMELSSLRSEDTAMYYCTRGRQTFRAIWSGPPVVFDIWG QGTLVSVSSASTKG |
| 255 | LSSNEC67HC | QFRLVQSGPEVKNPGSSVTVSCKASGGTFSGLGINWVRQAPGQGLEWLGDIKTMYGTTN YAPKFQGRVTITADESTSTSYMELSGLRSEDTAVFYCVRELFGHHPAFGVWGQGTSVIVSSA STKG |
| 256 | LSSNEC74HC | QVQLVQSGAEVKKPGASVKVSCKASGYTFTNYGVSWVRQAPGQGLEWMGWISPYSGNT NYAQRLQDRVTMTTDTSTNTAYMELRSLRSDDTAVYYCAARSYYYYSMDVWGQGTTVTV SSASTKG |
| 257 | LSSNEC77HC | QVQLVQSGADVKKPGASVKVSCKVSGYTVSELSIHWVRQAPGKGLEWMGGFDPEDGKTV SAQNFQGRVTMTEDKSTGTANMELRSLRSEDTAVYYCATTVQLIVDFCNGGPCYNFDDW GQGTLVTVSSASTKG |
| 258 | LSSNEC85HC | QVQLVQSGAEVKKPGSSVKVSCKASGGTLSSYTISWVRQAPGQGLEWMGRLIPLVDITTYA QKFQGRVTITADTSTNTAYMELSNLRSEDTAIYHCATSTMIAAVINDAFDLWGQGTTVTVS SASTKG |
| 259 | LSSNEC91HC | QVQLVQSGAEVKKPGASVKVSCKASGNTFTSYGITWVRQAPGQGLEWMGWISAYNGNT NYAQKLQDRLTMTTDTSTSTAYMELRSLRSDDTAVYYCAFSRHYGSGNYDYWGQGTLVTV SSASTKG |
| 260 | LSSNEC92HC | QVQLQQWGAGLLKPSETLSLTCAVYGGSFSGYYWSWIRQPPGKGLEWIGEINHSGSTNYN PSLKSRVTISVDTSKNQFSLKLSSVTAADTAVYYCARLPIGSGWYGRDYWGQGTLVTVSSAS TKG |
| 261 | 3A124HC | EVQLLESGGGLVRPGGSLXLSCSASGFTFNSYAMSWVRQAPGKGLEWVSSVSASGEMTYY ADSVRGRFTISRDNANNALHLQMNSLRAEXTAVYYCAKVGGTVWSGYSNYLDYWGPGTL VTVSSASTKG |
| 262 | 3A125HC | QVQLVQSGAEVKKPGASVKVSCKPSSNTFTSHYIHWVRQAPGQGLEWMGMINPGGSTR YAPKFQGRVTLTRDTSTRTVYMELSSLRSEDTAVYYCARPQYNLGRDPLDVWGLGTMVTV SSASTKG |
| 263 | 3A140HC | EVQLVESGGGLVKPGGSLRLSCADSGFTFRSYSMHWVRQAPGKGLAWVSSISSTSNYIYYA DSVKGRFTISRDNAKNSLYLQMNSLRAEDTAVYYCARTFITASWFDSWGQGTLVTVSSAST KG |
| 264 | 3A144HC | VSGGRFSNYGLSWVRQAPGQGLEWMGRIVPAINRAKYAQKFQGRVILTADKITDTAYMEL RSLRSEDTAIFYCARDPQIEIRGNAFDIWGQGTVVTVSSASTKG |
| 265 | 3A160HC | QVQLQESGPGLVKPSGTLSLTCNVYGGSMISYYWSWIRQPPGKGLEWIGHVYNSGNTKYS PSLKNRVTISMDTSRNLFSLKVTSVTPADTAVYYCARADYDNIWDSRGGFDLWGQGTLVTV SSASTKG |
| 266 | 3A18HC | QVQLVQLLQSGAEVKKPGSSVKVSCQISGYGFSNYAISWVRQAPGQGLEWLGRIVPAVGM TEYAQKFQGRVTFTADRSTITAYMDLRGLRSDDTAVYYCVRDPQVEVRGNAFDIWGQGT MVTVSSASTKG |
| 267 | 3A204HC | QVQLVQSGAEMKKPGASVKVSCKASGHTFTNYYMHWVRQAPGQGLEWMGMINPTGD STRYAQRFQGRVTMTRDTSTRTVYMELSSLRSDDTAVYYCARAHHDFWRAPVDVWGKGT TVTVSSASTKG |
| 268 | 3A228HC | EVQLVQSGAEVKKPGESLRISCKTSGYNFNDDWIAWVRQRPDKGPEWMGIFYPGDSQAT YSPSFQGHVTFSADTSISTAYLQWTSLKASDTAIYYCARTRCFGANCFNFMDVWGKGTALT VTVSSASTKG |
| 269 | 3A233HC | QVQLQESGPGPVKPSETLSLTCTVSGGSMISYYWSWIRQPPGKGLEWIGYIFTNGRTTYSPS LRSRVTISLDTSTNHFSLRLKSVTAADTAIYYCARLDGEAFRYYLDLWGQGNLVTVSSASTKG |
| 270 | 3A244HC | IRSFYWHWIRQSPGKGLEWLGSVFDNGLTTHNPSLKSRLTISEDPSRNQISLKLRSMTAADT AVYYCARGDYDILTSSYQFDYWGQGTLVAVSSASTKG |

TABLE A-continued

| Seq ID No. | Antibody | Heavy Chain Amino Acid Sequence |
|---|---|---|
| 271 | 3A255HC | QVQLQESGPGLVKPSETLSLTCTVFGASIRSFYWHWIRQSPGKGLEWLGSVFDNGLTTYNPSLKNRLSISEDPSRNQISLNLRSMTAADTAVYYCARADYDLLTSSYHFDSWGQGTLVTVSSASTKG |
| 272 | 3A296HC | QVQLQESGPGLVKPSETLSLTCTVSGGSISYYYWSWIRQPPGKGLEWIGDIYYSGTTDYNPSLKSRVTISVDTSKNQFSLKLSSVTAADTAVYYCARRRGQRLLAYFDYWGQGSLVTVSSASTKG |
| 273 | 3A334HC | QVQLVQSGAEVKKPGASVKVSCKAPGYTFIGHYMHWIRQAPGQGLEWMGWINPNSGDTNYAQTFQGRVTMTRDTSISTAYMELTRLRSDDTAVYYCARDLRPMRGNWAMHVWGEGTTVTVSSASTKG |
| 274 | 3A366HC | CTVSGGSISSAGYYWTWIRQHPGKGLEFIGYIYYIGTTYYNPSLKSRLTISIDTSKNQFSLKLSSVTAADTAIYYCARDYTARGRHFFDYWGQGALVTVSSASTKG |
| 275 | 3A381HC | SSFAISWVRQAPGQGLEWMGGIIPIFEATSYAQKFQDRLTITTDESTTTAYMDLSSLRSEDTAVYYCARAQGDILTEGYFDYWGQGTLVTVSSASTKG |
| 276 | 3A384HC | QVQLVQSGAEVKKPGSSVKVSCKVSFFSNYGISWVRQRPGQGLEWMGRIIPAIDDMTYAQTFRGRVTFSADKFTTTAYMELTGLTFEDTATYFCARDPQVNRRGNCFDHWGQGTLVTVSSASTKG |
| 277 | 3A419HC | LEWMGRIIPAIDDVTYAQTFRGRVTFSADKFTTTAYMDLTGLRSEDTATYFCARDPQVNRRGNCFDHWGQGTLVTVSSASTKG |
| 278 | 3A461HC | QVQLVQSGAEVKKPGAAVKISCKASRFTFSSYYIHWVRQAPGQGLEWMGIINPSGGSTSNAQKFQDRVTLTRDMSTGTVYMELSRLTSEDTAVYYCATPEPSSIVAPLYYWGQGTLVTVSSASTKG |
| 279 | 3A474HC | EVQLLESGGGLVQPGGSLRLSCAVSGFTFGGHAVSWVRQAPGKGLEWLSQISGTGSRTDYADAVKGRFTVSRDNSKKTVYLQMNSLRVEDTALFYCATRSPGGGYAFDIWGQGAMVTVSSASTKG |
| 280 | 3A518HC | QVQLQESGPGLVKPSETLSLTCTVSGGSISSAGYYWSWIRQHPEKGLEFIGYIYYLGTTYYNPSLKSRVSISIDTSNNQFSLELSSVSAADTAIYYCARDYTASGRHFFDYWGQGTLVTVSSASTKG |
| 281 | 3A539HC | EVQLLESGGALVQPGGSLRLSCAASGFTFSTSSMSWVRQAPGKGLEWVSAIGSGRGSTFYADSVKGRFTISRDNSKNTLSLQMNSLTAEDTATYYCTKTGGLLRFPEVWGKGTTVTVSSASTKG |
| 282 | 3A576HC | QVQLVQSGAEVKKPGSSVKVSCKASGGTFSNYAISWVRQAPGQGLEWMGGIIPIFEAASYAQKFQDRLTITTDESTTTAYMDLSSLRSEDTAIYYCARAQGDILTEGYFDYWGQGTLVTVSSASTKG |
| 283 | 3A613HC | QVQLQESGPGLVKPSETLSLTCTVSGGSISTYYWSWIRQPPGKGLEWIGYISYSGSTNYNPSLKSRVTISVDTSKNQFSLKLSSVTAADTAVYYCARHKSVLLWFRELDYWGQGTLVTVSSASTKG |
| 284 | 3A64HC | QVQLVQSGAEVKKPGSSVKVSCKTSGVRFSSNAISWVRQAPGQGLEWMGRTTPMLGGANHAPSFKGRVTISADESTRTVYMEMSSLRYEDTAVYYCASGRREGLNFLLDYWGQGTLVTVSSASTKG |
| 285 | 3A650HC | QVQLVQSGAEVRKPGASVKVSCKTSGYTFTNSYIHWVRQAPGQGLEWMGIINPPGGNTYYAQKFHGRVTLTRDTSTSTVYMELNSLRSEDTAVYFCARPHSPTNIPSRPLDYWGQGTLVTVSSASTKG |
| 286 | 3A67HC | QVQLVQSGAEVKKPGASVKVSCKVSGYPLAELSVHWVRQVPGKGLEWVGGFDPEEGKTVYAQKFQGRVTMTEDRSTDTVYMELISLRYEDTAVYYCATDNPVLQLGELSSSLDYWGQGTLVTVSSASTKG |
| 287 | 3A779HC | PSETLSLTCRVSGASISNFYWTWIRQPAGKGLEWIGRLYSSDKTNYNPSLNGRVTMSLDTSKNQFSLRLTSMTDADTAIYYCAREKGQWVTLPPYYFDSWGQGILVTVSSASTKG |
| 288 | 3A816HC | NTFTSHYVHWVRQAPGQGLEWMGMINPGGTTRYAPKFQDRVTLTRDTSTRTVYMELRSLRSEDTAVYYCARPQYNLGREPLNVWGQGTMVTVSSASTKG |
| 289 | 3A869HC | QVQLQESGPGLVKPSETLSLTCSVSGASISNFYWTWIRQPAGKGLEWVGRLYSSDRTNYNPSLNGRVTMSLDTSKNQFSLRLTSMTDADTAIYFCAREKGQWLTVPPYYFDSWGQGILVTVSSASTKG |

TABLE A-continued

| Seq ID No. | Antibody | Heavy Chain Amino Acid Sequence |
|---|---|---|
| 290 | 3A93HC | CTVSGGSIISYYWNWIRQSPGKGLEWLGYIFDGGRANYNPSLRSRLTMSVDTSKNQISLKVKSVTAADSAIYYCARLDGEAFRYYFDSWGQGTLVTVSSASTKG |
| 291 | 3A966HC | QTLSLTCSVSGGSISSAGYYWGWIRQHPGKGLEWIGHIYYSGNTNYNPSLKSRLSMSVETSKNQFSLNLASVTAADTAVYFCARDYSAAGRHLFDSWGQGILVTVSSASTKG |
| 292 | 3A978HC | KPSQTLSLTCTVSGGSISSAGYYWTWIRHHPGKGLEFIGYIYHIGTPYYNPSLKSRLTISIDTSKNQFSLKLSSVTAADTAIYYCARDYTARGRHFFDYWGQGALVTVSSASTKG |
| 293 | 3ANC3HC | QVQLVQSGADVKKPGASVTVSCKTDEDEDDFRAHLVQWMRQAPGQRLEWVGWIKPQTGQPSYAQKFQGRVTLTREVSTSTVFLQLRNLRSDDTAVYYCARPRGGRDNWSFHVWGRGTLVTVSSASTKG |
| 294 | 3ANC42HC | QVQLVQSGAAVKKPGASVKVSCETYGYTFTDHFMHWWRQAPGQGLEWMGWINPYSSAVSYSPRYQGRVTMTRDTFLETVYMELRGLKFDDTAIYYCATPKSGRDYWSFDLWGQGTLVTVSSASTKG |
| 295 | 3ANC66HC | QVQLVQSGAAVKKPGASVKVSCETYGYKFTDHFMHWWRQAPGQGLEWMGWINPYSSAVSYSPRYQGRVTMTRDTFLETVYMELRGLRFDDTAIYYCATPKSGRDYWSFDLWGQGTLVTVSSASTKG |
| 296 | 3ANC79HC | QVQLVQSGAAVKKPGASVKVSCEAYGYKFTDHFMHWWRQAPGQGLEWMGWINPYTSAVNYSPKYQGRVTMTRDTFLETVYMELRGLRVDDTAIYYCATPKSGRDYWSFDLWGQGTLVTVSSASTKG |
| 297 | 3B10HC | QVQLQESGPGLVKPSETLSLTCSVSNGSISSGGYYWSWLRQFPGKGLEWIGSIHYTGRTMYNPSLMGRPALSMDTSNNQFSLKLRSVTAADTALYFCARDLQWIFVVDPWGQGTLVTVSSASTKG |
| 298 | 3B120HC | LQQLQVPRLSMWRVFKVAAATGAQTLTVEEPGSSVKVSCKASGGSSTAYGYSWVRQAPGQGFEWMGRIIPFYGIITYAPKFQGRVTITADRSTSTVYMELTSLTFADTALFFCARDFGDPRNGYYFDSWDQGLWLTVSSASTKG |
| 299 | 3B126HC | QVHLVQSGAEVKKPGSSVRVSCKASGWTFGDSVNSAITWVRQAPGQGLEWMGRFIPILGLSNYAQKFQDRVTINVDRSTNTAYMELSGLRSEDTAVYYCARLITGMNAPWFYYMDVWGKGTTITVSSASTKG |
| 300 | 3B129HC | FICFSVVVRLLEFGGRLVQPGGSLRLSCSASGFTFSNSAMSWVRQAPGKGLEWVSSILSSGVGTFYADSVKGRFTVSRDNSRNTLYLQMKSLRAEDTALYYCAKVQIQQLNFGVITDAGLDVWGKGTTLIVSSASTKG |
| 301 | 3B142HC | QVQLGQSGTEVKKPGFSVKVSCKASGGSSTAYGYSWVRQAPGQGFEWMGRIIPFYGIITYAPKFQGRVTITADRSTSTVYMELTSLTFADTALFFCARDFGDPRNGYYFDSWDQGLWLTVSSASTKG |
| 302 | 3B154HC | QVQLVQSGGEVRKPGSSVKVPCKISGNAFSNYGVNWVRQAPGQGLEWVGRIIPVIGVAQHAPKFQGRVTITADKSTTTAYLELSSLRSDDTAVYFCAKDHGDPRTGYYFDYWGQGALVTVSSASTKG |
| 303 | 3B165HC | QVQLLQSGTEVKKPGSSVKVSCRASGWTLGNSPNSAIGWVRQAPGQGLEWIGRIIPILDVTNYAQKFQGRVTISADKSTNIAYMEISSLGSEDTAFYYCARVITGMTSPWYFYMDVWGEGTTVIVSSASTKG |
| 304 | 3B171HC | VQSQVYLVQSGGEVKKPGSSVKVSCKASGDSFSSSVITWVRQAPGQGPEWMGRIIPVLGVAAYAQNFYGRVTISADTSSNTAYMELSSLRFEDTAVFYCARETGRGGNLALRQYFFDSWGQGTLVTVSSPSTKG |
| 305 | 3B17HC | EVQLVESGGGLVQPGGSLRISCSATGFTFSTHAMHWVRQAPGKGLEYVSAINSNGRSAFYADSVKGRVTISRDNSKNTLFLQMTSLRAEDTAVYYCVKGPLLRYLDSWGQGTLVTVSSASTKG |
| 306 | 3B186HC | QVQLVESGGGLVKPGGSLRLSCAASGFSFNEYYMSWIRQAPGQGLEWVANIGSSDAYTIYADSVKGRFTISRDNAENTVYLQMNSLRGEDTAVYYCARIEGYCSNSRCSNYFDPWGQGALVTVSSASTKG |
| 307 | 3B193HC | MFLFLVAGATGVQSQVYLVPFGPEVKKPGSSVKVSCKASGDSFTSSVITWVRQAPGQGPEWMGRVIPVLGVAAYAQKFYGRVTITADTSSNTAYMEVNSLRFEDTAVYYCARETGRGGNLALRQYFFDSWGQGTLVTVSSPSTKG |
| 308 | 3B22HC | CQVQLVESGGGVVQPGRSLRLSCVGSGFTFSSSGMHWVRQAPGKGLEWVAVISSDGSDEYYGDSVEGRFTISRDNSKNTLFLQLDSLEAEDSAVYYCAKTPPHYDALTGYPSSVLEFWGLGTLVTVSSASTKG |
| 309 | 3B27HC | EVQLVESGGGLVQPGGSLRISCSATGFTFSTHAMHWVRQAPGKGLEYVSAINSNGRSAFYADSVKGRVTISRDNSKNTLFLQMTSLRAEDTAVYYCVKGPLLRYLDSWGQGTLVTVSSASTKG |

TABLE A-continued

| Seq ID No. | Antibody | Heavy Chain Amino Acid Sequence |
|---|---|---|
| 310 | 3B29HC | QVHLVQSGAEVKKPGSSVRVSCKASGWTFGDSVNSAITWVRQAPGQGLEWMGRFIPILGLSNYAQKFQDRVTINVDRSTNTAYMELSGLRSEDTAVYYCARLITGMNAPWFYYMDVWGKGTTITVSSASTKG |
| 311 | 3B2HC | SGGRLVQPGGSLRLSCSASGFTLSNSAMSWVRQAPGKGLEWVSSILSSGVGTFYADSVKGRFTVSRDNSRNTLYLQMKSLRAEDTALYYCAKVQIQQLNFGVITDAGLDVWGKGTTLIVSSASTKG |
| 312 | 3B31HC | EVQLVQSGAEVKKPGSSVKVSCKASGGTFTTYDISWVRQAPGQGLEWIGGILPDFGAPSYAQKFQDRVTITTDESSRTAYMELNSLRSEDTAIYYCARGRGDDFWSGESPSWYFDYWGQGTQVTVSSASTKG |
| 313 | 3B33HC | PLVQLEPSGVEVKKRGASVKVSCKVSGYSLTELSMHWVRQAPGKGLEWMGSFDPLDGDTIYAQKFQGRVTMTVDTSTDTAYMDLSSLRFEDTAVYYCATPSKAYYYDSPNYEGDFYMDVWGKGTTVIVSSASTKG |
| 314 | 3B40HC | QVQLVESGGGVVQPGRSLRLSCVGSGFTFSSSGMHWVRQAPGKGLEWVAVISSDGSDEYYGDSVEGRFTISRDNSKNTLFLQLDSLEAEDSAVYYCAKTPPHYDALTGYPSSVLEFWGLGTLVTVSSASTKG |
| 315 | 3B41HC | EVQLVQSGAEVKKPGASVKVSCKVSGYTLTELSMHWVRQAPGKGLEWMGVFDPLEGDGVYAEKFRGRVIMTEDTSTDTGYMELTSLRSEDTAIYYCATKAKDYYYESSDYSPYYYYYMDVWGKGTTVTVSSASTKG |
| 316 | 3B44HC | EVRLLESGGGLVQPGGSLRLSCSASGFTFSNSALSWVRQAPGKGLEWVSSVVSSGGDTFYADSVKGRFTISRDNSRNTLYLQMKSLRAEDTALYYCAKVQIQQLNFGVITDAGMDVWGKGTTVIVSSASTKG |
| 317 | 3B45HC | VEEPGSSVKVSCKASGGSSTAYGYSWVRQAPGQGFEWMGRIIPFYGIITYAPKFQGRVTITADRSTSTVYMELTRLTFADTALFFCARDYGDPRNGYYFDSWDQGLWLTVSSASTKG |
| 318 | 3B48HC | QVQLVESGGGLVQPGGSLRISCSATGFTFSTHAMHWVRQAPGKGLEYVSAINSNGRSAFYADSVKGRVTISRDNSKNTLFLQMTSLRAEDTAVYYCVKGPLLRYLDSWGQGTLVTVSSASTKG |
| 319 | 3B50HC | QVQLVQSGPGLVKPSETLSLTCSVSNGSISSGGYYWSWLRQFPGKGLEWIGSIHYTGRTFYNPSLMGRTALSMDTSNNQFSLKVSSVTAADTALYYCARELQWMFVVDPWGQGTLVTVSSASTKG |
| 320 | 3B51HC | QVQLLQSGTEVKKPGSSVKVSCRASGWTLGNSPNSAIGWVRQAPGQGLEWIGRIIPILDVTNYAQKFQGRVTISADKSTNIAYMEISSLGSEDTAFYYCARVITGMTSPWYFYMDVWGEGTTVIVSSASTKG |
| 321 | 3B56HC | QVQLVQSGGEVKKPGASVKVSCKVSGYSLTELSMHWVRQAPGKGLEWMGVFDPLEGDGVYVQKFRGRVIMTEDTSTDTAYMELTSLRSEDTAIYYCATKAKDYYYESSDYSPYYYYYMDVWGKGTTVTVSSASTKG |
| 322 | 3B57HC | GSEVQLVESGAEVKKRGASVKVSCKVSGYSLTELSMHWVRQAPGKGLEWMGSFDPLDGDTIYAQKFQGRVTMTVDTSTDTAYMDLSSLRFEDTAVYYCATPSKAYYYDSPNYEGDFYMDVWGKGTTVIVSSASTKG |
| 323 | 3B5HC | SVVQLVESGPGLVKPSETLSLTCSVSNGSISSGGYYWSWLRQFPGKGLEWIGSIHYTGRTMYNPSLMGRPALSMDTSNNQFSLKLRSVTAADTALYFCARDLQWIFVVDPWGQGTLVTVSSASTKG |
| 324 | 3B61HC | SVDERLLEFGGRLVQPGGSLRLSCSASGFTFSNSAMSWVRQAPGKGLEWVSSILSSGVGTFYADSVKGRFTVSRDNSRNTLYLQMKSLRAEDTALYYCAKVQIQQLNFGVITDAGLDVWGKGTTLIVSSASTKG |
| 325 | 3B6HC | QLQLKESGPGMVKPSETLSLTCSVSGASVVSANDYWGWIRQAPGKGLECIGIILYTGSTFYNPSLQSRVTISRDPSKNHVSLTLTSVTAADSAVYYCARIPYHSESYYNVVIGGFDVWGQGTRVTVSSASTKG |
| 326 | 3B77HC | QVHLVQSGAEVKKPGSSVRVSCKASGWTFGDSVNSAITWVRQAPGQGLEWMGRFIPILGLSNYAQKFQDRVTINVDRSTNTAYMELSGLRSEDTAVYYCARLITGMNAPWFYYMDVWGKGTTITVSSASTKG |
| 327 | 3B79HC | QVQLGQSGTEVKKPGFSVKVSCKASGGSSTAYGYSWVRQAPGQGFEWMGRIIPFYGIITYAPKFQGRVTITADRSTSTVYMELTSLTFADTALFFCARDFGDPRNGYYFDSWDQGLWLTVSSASTKG |
| 328 | 3B84HC | SQVQLVESGPGLVKPSETLSLTCSVSNGSISSGGYYWSWLRQFPGKGLEWIGSIHYTGRTMYNPSLMGRPALSMDTSNNQFSLKLSSVTAADTALYFCARDLQWIFVVDPWGQGTLVTVSSASTKG |

TABLE A-continued

| Seq ID No. | Antibody | Heavy Chain Amino Acid Sequence |
|---|---|---|
| 329 | 3B86HC | RVHSQVQLVESGPGLVKPSQTLSLTCTVSGGSISNGGHYWNWIRQHPGKGLEWIGHIYNIA TTYYNPSLKSRVSISVDTSKNQFSLKLSSVTAADTAVYYCARGSGRWTIGARIYFDNWGQGA LVAVSSASTKG |
| 330 | 3B8HC | QVQLVQSGGEVRKPGSSVKVPCKISGNAFSNYGVNWVRQAPGQGLEWVGRIIPVIGVAQ HAPKFQGRVTITADKSTTTAYLELSSLRSDDTAVYFCAKDHGDPRTGYYFDYWGQGALVTV SSASTKG |
| 331 | 3B93HC | QVHLVQSGAEVKKPGSSVRVSCEASGWTFGSVNSAITWVRQAPGQGLEWMGRTIPFLGIS NYAQKFQGRVTITADKSTNIAYVDVTSLTSQDTAVYYCARLITGMTAPWFYYMDVWGKGT TVTVSSASTKG |
| 332 | 3BNC101HC | EVQLVQSGSDVKKPGTTVTISCKADEDEDDFTAYNYFMHWVRQAPGQGLEWIGWINPRT GQPNHAKQLQGRVTLTRERSTSTVFMKLTNLRLDDTAVYFCARPLRGGDTWHYHSWGRG TSLIVSSASTKG |
| 333 | 3BNC124HC | QSQVHLVQSGAEVKKPGSSVKVSCQASGGTFNTFAINWVRQAPGQGLEWVGGIIPVFGT ASYAQKFQGRVTVTTDESRGTAYMELNSLRSEDTAVYYCARGQTDLNDDLWSDYSTPGFD YWGQGTLVTVSSASTKG |
| 334 | 3BNC130HC | RVQLGQSGAEVKKPGASVKVSCKVSGNSLTEFSIHWVRQAPGKGLEWMGGFDPEEGETV PAQKFKGRVTMTEDTSTNTAYMELSSLRSEDTAVYYCSTEPREMGTLTAGFEYWGQGTLVI VSSASTKG |
| 335 | 3BNC149HC | QPQLVQSGSGAEVKKPGASVRISCEASEYNVFDHFMQWVRQAPMEGLEWMGWINPRG GYPSYSPTFQGRLTFTRQPSWDDSTITFHMELRGLRHDDTAVYYCARPHSPDDAWSLDVW GRGTLVTVSSASTKG |
| 336 | 3BNC177HC | LQPRVHSEVQLVESGAEVKKPGASVKVSCKVSGYTLSDLSMHWVRQAPGKGLEWMGGF DEEDGEITYAQKFQGRVSMTEDTSRDTAYMELSSLRSEDTAVYYCATAPRLELGELSSGFHY WGLGTLVTVSSASTKG |
| 337 | 3BNC17HC | RVQLGQSGAEVKKPGASVKVSCKVSGNSLTEFSIHWVRQAPGKGLEWMGGFDPEEGETV PAQKFKGRVTMTEDTSTNTAYMELSSLRSEDTAVYYCSTEPREMGTLTAGFEYWGQGTLVI VSSASTKG |
| 338 | 3BNC48HC | IWAPLIAVTFLVLHCESLGTCCCCQASGGTFNTFAINWVRQAPGQGLEWVGGIIPVFGTAS YAQKFQGRVTVTTDESRGTAYMELNSLRSEDTAVYYCARGQTDLNDDLWSDYSTPGFDY WGQGTLVTVSSASTKG |
| 339 | 3BNC58HC | EVQLVESGAEVKKPGASVKVSCKVSGYTLSDLSMHWVRQAPGKGLEWMGGFDEEDGEIT YAQKFQGRVSMTEDTSRDTAYMELSSLRSEDTAVYYCATAPRLELGELSSGFHYWGLGTLV TVSSASTKG |
| 340 | 3BNC78HC | EVQLVESGAEVKKPGASVKVACKVSGKKLSDLSIHWVRQAPGKGLEWMGGFDEEDGKISY ERKFQGRVTMTEDTARDTAFMEMSSLRSDDTAVYFCAAAPRLDLGELSSGFHFWGLGTLV SVSSASTKG |
| 341 | 3BNC82HC | CNPRVHSEVQLVESGAEVKKPGASVKVACKVSGKKLSDLSIHWVRQAPGKGLEWMGGFD EEDGKISYERKFQGRVSMTEDTARDTAFMEMSSLRSDDTAVYFCAAAPRLDLGELSSGFHF WGLGTLVTVSSASTKG |
| 342 | 3BNC8HC | EVQLVESGAEVKKPGASVKVSCKVSGNSLTEFSIHWVRQAPGKGLEWMGGFDPEEGETVP AQKFKGRLTMTEDTSTNTAYMELSSLRSEDTAVYYCSTEPREMGTLTAGFEYWGQGTLVT VSSASTKG |
| 343 | 3a426hc | QVQLQESGPGLVKPSETXSLTCSVSNGSISSGGYYWSWLRQFPGKGLEWIGSIHYTGRTMY NPSLMGRPALSMDTSNNQFSLKLSSVTAADTALYFCARDLQWIFVVDPWGQGTLVTVSSA STKG |
| 344 | 3a515hc | QVQLVQSGAEVKKPGSSVKVSCKASGGTFTTYDISWVRQAPGQGLEWMGGILPDFGAPS YAQKFQDRVTITTDESSSTAYMELNSLRSEDTAIYYCARGRGDDFWSGESPSWYFDYWGQ GTLVTVSSASTKG |
| 345 | 3b46HC | GYSEVQLVQSGPGLVKPSQTLSLTCTVSGGSISNGGHYWNWIRQHPGKGLEWIGHIYNIAT TYYNPSLKSRVSISVDTSKNQFSLKLSSVTAADTAVYYCARGSGRWTIGARIYFDNWGQGAL VAVSSASTKG |
| 346 | 3ANC32HC | QVQLVQSGADVKKPGATVTVSCKTDEDEDDFRAHLMQWMRQAPGQRLEWVGWIKPQ TGQPSYGQKFQGRVTLTREVSTSTVFLQLRNLRSDDTAVYYCARPRGGRDNWSFHVWGR GTLVTVSSASTKG |
| 347 | 3ANC3HC | QVQLVQSGADVKKPGASVTVSCKTDEDEDDFRAHLVQWMRQAPGQRLEWVGWIKPQT GQPSYAQKFQGRVTLTREVSTSTVFLQLRNLRSDDTAVYYCARPRGGRDNWSFHVWGRG TLVTVSSASTKG |

TABLE A-continued

| Seq ID No. | Antibody | Heavy Chain Amino Acid Sequence |
|---|---|---|
| 348 | 3ANC41HC | QVQLVQSGAAVKKPGASVKVSCETYGYTFTDHFMHWWRQAPGQGLEWMGWINPYSSA VSYSPRYQGRVTMTRDTFLETVYMELRGLKFDDTAIYYCATPKSGRDYWSFDLWGQGTLV TVSSASTKG |
| 349 | 3ANC42HC | QVQLVQSGAAVKKPGASVKVSCETYGYTFTDHFMHWWRQAPGQGLEWMGWINPYSSA VSYSPRYQGRVTMTRDTFLETVYMELRGLKFDDTAIYYCATPKSGRDYWSFDLWGQGTLV TVSSASTKG |
| 350 | 3ANC66HC | QVQLVQSGAAVKKPGASVKVSCETYGYKFTDHFMHWWRQAPGQGLEWMGWINPYSSA VSYSPRYQGRVTMTRDTFLETVYMELRGLRFDDTAIYYCATPKSGRDYWSFDLWGQGTLV TVSSASTKG |
| 351 | 3ANC70HC | QVQLVQSGAAVKKPGASVKVSCETYGYKFTDHFMHWWRQAPGQGLEWMGWINPYSSA VSYSPRYQGRVTMTRDTFLETVYMELRGLRFDDTAIYYCATPKSGRDYWSFDLWGQGTLV TVSSASTKG |
| 352 | 3ANC75HC | QVQLVQSGAAVKKPGASVKVSCETYGYTFTDHFMHWWRQAPGQGLEWMGWINPYSSA VSYSPRYQGRVTMTRDTFLETVYMELRGLKFDDTAIYYCATPKSGRDYWSFDLWGQGTLV TVSSASTKG |
| 353 | 3ANC79HC | QVQLVQSGAAVKKPGASVKVSCEAYGYKFTDHFMHWWRQAPGQGLEWMGWINPYTS AVNYSPKYQGRVTMTRDTFLETVYMELRGLRVDDTAIYYCATPKSGRDYWSFDLWGQGTL VTVSSASTKG |
| 354 | 3ANC87HC | QVQLVQSGGAVKKPGASVKVSCETYGYTFTDHFMHWWRQAPGQGLEWMGWINPYSSA VSYSPRYQGRVTMTRDTFLETVYMELRGLKFDDTAIYYCATPKSGRDYWSFDLWGQGTLV TVSSASTKG |
| 355 | 3ANC8HC | QVQLVQSGADVKKPGASVTVSCKTDEDEDDFRAHLVQWMRQAPGQRLEWVGWIKPQT GQPSYAQKFQGRVTLTREVSTSTVFLQLRNLRSDDTAVYYCARPRGGRDNWSFHVWGRG TLVTVSSASTKG |
| 356 | 3ANC96HC | QVQLVQSGADVKKPGASVTVSCKTDEDEDDFRAHLVQWMRQAPGQRLEWVGWIKPQT GQPSYAQKFQGRVTLTREVSTSTVFLQLRNLRSDDTAVYYCARPRGGRDNWSFHVWGRG TLVTVSSASTKG |
| 357 | 3B106HC | QVQLLQSGAAVTKPGASVRVSCEASGYNIRDYFIHWWRQAPGQGLQWVGWINPKTGQP NNPRQFQGRVSLTRHASWDFDTFSFYMDLKALRSDDTAVYFCARQRSDYWDFDVWGSG TQVIVSSASTKG |
| 358 | 3B16HC | QVQLLQSGAAVTKPGASVRVSCEASGYNIRDYFIHWWRQAPGQGLQWVGWINPKTGQP NNPCQFQGRVSLTRHASWDFDTFSFYMDLKALRSDDTAVYFCARQRSDYWDFDVWGSG TQVTVSSASTK |
| 359 | 3B180HC | QVQLLQSGAAVTKPGASVRVSCEASGYNIRDYFIHWWRQAPGQGLQWVGWINPKTGQP NNPCQFQGRVSLTRQASWDFDTISFYMDLKALRLDDTAVYFCARQRSDYWDFDVWGSGT QVTVSSASTKG |
| 360 | 3B183HC | QVRLLQSGAAVTKPGASVRVSCEASGYEIRDYFIHWWRQAPGQGLQWVGWINPKTGQP NNPRQFQGRVSLTRQASWDFDSYSFYMDLKALRSDDTAVYFCARQRSDYWDFDVWGSG SQVTVSSASTKG |
| 361 | 3B191HC | QVRLLQSGAAVTKPGASVRVSCEASGYEIRDYFIHWWRQAPGQGLQWVGWINPKTGQP NNPRQFQGRVSLTRQASWDFDSYSFYMDLKALRSDDTGVYFCARQRSDYWDFDVWGSG TQVTVSSASTKG |
| 362 | 3B21HC | QVRLLQSGAAVTKPGASVRVSCEASGYEIRDYFIHWWRQAPGQGLQWVGWINPKTGQP NNPRQFQGRVSLTRQASWDFDSYSFYMDLKALRSDDTAVYFCARQRSDYWDFDVWGSG TQVTVSSASTKG |
| 363 | 3BBM60 | QVHLSQSGAVVTKPGASVRVSCEASGYKISDHFIHWWRQAPGQGPQWVGWINPKTGQP NNPRQFQGRISLTRQASWDFDTFSFYMDLKALRSDDTAVYFCARHRSDYWDFDVWGSGT QVTVSSASTKG |
| 364 | 3BBM60 | QVHLSQSGAAVTKPGASVRVSCEASGYKISDHFIHWWRQAPGQGLQWVGWINPKTGQP NNPRQFQGRISLTRQASWDFDTFSFYMDLKALRSDDTAVYFCARQRSDYRDFDVWGSGT QVTVSSASTKG |
| 365 | 3BBM60 | QVHLSQSGAAVTKPGASVRVSCEASGYKIRDYSIHWWRQAPGQGLQWVGWINPQTGQP NIPRPFQGRISLTRQASWDFDTFSFYMDLEALRSDDTAVYFCARQRSDYWDFDVWGSGT QVTVSSASTKG |
| 366 | 3BBM60 | QVHLSQSGAVVTKPGASVRVSCEASGYKISDHFIHWWRQAPGQGLQWVGWINPKTGQP NNPRQFQGRISLTRQASWDFDTFSFYMDLEALRSDDTAVYFCARQRSDYWDFDVWGSGT QVTVSSASTKG |

TABLE A-continued

| Seq ID No. | Antibody | Heavy Chain Amino Acid Sequence |
|---|---|---|
| 367 | 3BBM60 | QVHLSQSGAVVTKPGASVRVSCEASGYKISDHFIHWWRQAPGQGLQWVGWINPKTGQP NNPRQFQGRISLTRQASWDFDTFSFYMDLKALRSDDTAVYFCARHRSDYWDFDVWGSGT QVTVSSASTKG |
| 368 | 3BBM60 | QVHLSQSGAAVTKPGASVRVSCEASGYKISDHFIHWWRQAPGQGLQWVGWINPKTGQP NNPRQFQGRVSLTRQASWDFDTYSFYMGLKAVRSDDTAIYFCARQRSDFWDFDVWGSG TQVTVSSASTKG |
| 369 | 3BBM60 | QVHLSQSGAAVTKPGASVRVSCEASGYKISDHFIHWWRQAPGQGLQWVGWINPKTGQP NNPRQFQGRISLTRQASWDFDTFSFYMDLKALRSDDTAVYFCARHRSDYWDFDVWGSGT QVTVSSASTKG |
| 370 | 3BBM60 | QVHLSQSGAVVTKPGASVRVSCEASGYKISGHFIHWWRQAPGQGLQWVGWINPKTGQP NNPRQFQGRISLTRQASWDFDTFSFYMDLKALRSDDTAVYFCARHRSDYWDFDVWGSGT QVTVSSASTKG |
| 371 | 3BBM60 | QVHLSQSGAVVTKPGASVRVSCEASGYKISDHFIHWWRQAPGQGLQWVGWINPKTGQP NIPRQFQGRISLTRQASGDFDTFSFYMDLKALRSDDTAVYFCARQRSDYWDFGVWGSGTQ VTVSSASTKG |
| 372 | 3BBM60 | QVHLSQSGAVVTKPGASVRVSCEASGYKISDHFIHWWRQAPGQGLQWVGWINPKTGQP NNPRQFQGRISLTRQASWDIDTFSFYMDLKALRSDDTAVYFCARHRSDYWDFDVWGSGT QVTVSSASTKG |
| 373 | 3BBM60 | QVHLSQSGAVVTKPGASVRVSCEASGYKISDHFIHWWRQAPGQGLQWVGWINPKTGQP NNPRQFQGRISLTRQASWDFDTFSFYMDLKALRSDDTAVYFCARQRSDYWDFDVWGSGT QVTVSSASTKG |
| 374 | 3BBM60 | QVHLSHSGAAVTKPGASVRVSCEASGYKISDHFIHWWRQAPGQGLQWVGWINPKTGQP NNPRQFQGRISLTRQASWDFDTFSFYMDLKALRSDDTAVYFCARQRSDYWDFDVWGSGT QVTVSSASTKG |
| 375 | 3BBM60 | QVHLSQSGAVVTKPGASVRVSCEASGYKISDHFIHWWRQAPGQGLQWVGWINPKTGQP NNPRQFQGRISLTRQASWDFDTFSFYMDLKALRSDDTAVYFCARHRSDYWDFDVWGSGT QVTVSSASTKG |
| 376 | 3BBM60 | QVHLSQSGAVVTKPGASVRVSCEASGYKISDHFIHWWRQAPGQGLQWVGWINPKTGQP NNPRQFQGRISLTRQASWDFDTFSFYMDLKALRSDDTAVYFCARHRSDYWDFDVWGSGT QVTVSSASTKG |
| 377 | 3BBM60 | QVHLSQSGAAVTKPGASVRVSCEASGYKISDHFIHWWRQAPGQGLQWVGWINPKTGQP NNPRQFQGRISLTRQASWDFDTFSFYMDLKALRSDDTAVYFCARHRSDYWDFDVWGSGT QVTVSSASTKG |
| 378 | 3BNC101HC | EVQLVQSGSDVKKPGTTVTISCKADEDEDDFTAYNYFMHWVRQAPGQGLEWIGWINPRT GQPNHAKQLQGRVTLTRERSTSTVFMKLTNLRLDDTAVYFCARPLRGGDTWHYHSWGRG TSLIVSSASTKG |
| 379 | 3BNC102HC | QPQLVQSGSGAEVKKPGASVRISCEASEYNVFDHFMQWVRQAPGQGLEWMGWINPRG GYPSYSPRFQGRLTFTRQPSWDDSSVTFHMELRGLRHDDTAVYYCARPHSPDDAWSLDV WGRGTLVTVSSASTKG |
| 380 | 3BNC104HC | EVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 381 | 3BNC105HC | HVQLLQSGAAVTKPGASVRVSCEASGYNIRDYFIHWWRQAPGQGLQWVGWINPKTGQP NNPRQFQGRVSLTRQASWDFDTFSFYMDLKALRLDDTAIYFCARQRSDYWDFDVWGSGT QVTVSSASTKG |
| 382 | 3BNC106HC | VVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 383 | 3BNC107HC | QVQLVQSGAALKKPGASLRISCQAYGYKFTDYLIHWWRQAPGQGLEWIGWIKPETGQPSY SYKFQGRVSLTRDTFEEILFMDLRGLRSDDTAIYFCARRHSDYCDFDVWGGGSQVLVSSAST KG |
| 384 | 3BNC108HC | QVQLVQSGTAVKKPGASVRVSCQASGYTFTDYFIYWWRQAPGQGLEWLGWINPRTSQPS YPYRFQGRVTLTRDIFEEMLYMDLRGLRSDDTGIYFCARRHSDYCDFDIWGSGTQIIVSSAST KG |
| 385 | 3BNC10HC | EVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |

TABLE A-continued

| Seq ID No. | Antibody | Heavy Chain Amino Acid Sequence |
|---|---|---|
| 386 | 3BNC114HC | EVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 387 | 3BNC117HC | QVQLLQSGAAVTKPGASVRVSCEASGYNIRDYFIHWWRQAPGQGLQWVGWINPKTGQP NNPRQFQGRVSLTRHASWDFDTFSFYMDLKALRSDDTAVYFCARQRSDYWDFDVWGSG TQVTVSSASTKG |
| 388 | 3BNC126HC | QPQLVQSGSGAEVKKPGASVRISCEASEYNVFDHFMQWVRQAPGQGLEWMGWINPRG GYPSYSPTFQGRLTFTRQPSWDDSTITFHMELRGLGHDDTAVYYCARPHSPDDAWSLDV WGRGTLVTVSSASTKG |
| 389 | 3BNC127HC | EVQLVESGSDVRKPGATVTVSCKADEDEDDFTAYNYFMHWVRQAPGQGLEWIGWINPR TGQPNHAKQFQGRVTLTRERSTSTVFMKLTNLRLDDTAVYFCARPLRGGDTWHYHSWGR GTSLTVSSASTKG |
| 390 | 3BNC134HC | QVQLVQSGAALKKPGASLRISCQAYGYKFTDHLIYWWRQAPGQGLEWIGWIKPETGQPSY SYKFQGRVSLTRDTFQEILFMNLRGLRSDDTAIYFCARRHSDYCDFDVWGSGSQILVSSAST KG |
| 391 | 3BNC140HC | EVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 392 | 3BNC141HC | VVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 393 | 3BNC142HC | QVQLVQSGAALKKPGASVRISCQAYGYKFTDHLIYWWRQAPGQGLEWIGWIKPETGQPS YSYKFQGRVTLTRDTFEEIHFMDLRGLRYDDTATYFCARRHSDYCDFDVWGSGSQVSVSSA STKG |
| 394 | 3BNC148HC | QVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSRGR GTSLTVSSASTKG |
| 395 | 3BNC149HC | QPQLVQSGSGAEVKKPGASVRISCEASEYNVFDHFMQWVRQAPMEGLEWMGWINPRG GYPSYSPTFQGRLTFTRQPSWDDSTITFHMELRGLRHDDTAVYYCARPHSPDDAWSLDVW GRGTLVTVSSASTKG |
| 396 | 3BNC151HC | QVQLVQSGATLKKPGASVRISCQAYGYKFTDHLIHWWRQAPGQGLEWIGWIKPETGQPS YAYKFQGRVSLTRDTFEEILFMDLRGLRSDDTAIYFCARRHSDYCDLDVWGGGTQLLVSSAS TKG |
| 397 | 3BNC153HC | QVQLVQSGAALKKPGASLRISCLTYGYKFTDHLIYWWRQAPGQGLEWIGWIKPETGQPSY SYRFQGRVSLTRDTFEEIVFMDLRGLRSDDTAIYFCARRHSDYCDFDVWGSGSQVIVSSAST KG |
| 398 | 3BNC156HC | QVQLVQSGAALKKPGASLRISCQTYGYKFTDHLIYWWRQAPGQGLEWIGWIKPETGQPSY SYRFQGRVSLTRDTFEEIVFMDLRGLRSDDTAIYFCARRHSDYCDFDVWGGGSQVIVSSAST KG |
| 399 | 3BNC158HC | QVQLVQSGAALKKPGASLRISCQTYGYKFTDHLIYWWRQAPGQGLEWIGWIKPETGQPSY SYRFQGRVSLTRDTFEEIVFMDLRGLRSDDTAIYFCARRHSDYCDFDVWGSGSQVIVSSAST KG |
| 400 | 3BNC159HC | QVQLVQSGAALKKPGASVRISCQTYGYKFTDHLIHWWRQAPGQGLEWIGWIKPDTGQPS YSSRFQGRVSLTRDTFEEIVFMDLRGLRSDDTAIYFCARRHSDYCDFDVWGSGSQVLVSSAS TKG |
| 401 | 3BNC15HC | QVQLVQSGAALKKPGASLRISCQTYGYKFTDHLIYWWRQAPGQGLEWIGWIKPETGQPSY SYRFQGRVSLTRDTFEEIVFMDLRGLRSDDTAIYFCARRHSDYCDFDVWGSGSQVLVSSAST KG |
| 402 | 3BNC173HC | QVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 403 | 3BNC175HC | EVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 404 | 3BNC176HC | QVQLLQSGAAVTKPGASVRVSCEASGYNIRDYFIHWWRQAPGQGLQWVGWINPKTGQP NNPRQFQGRVSLTRHASWDFDTFSFYMDLKGLRSDDTAIYFCARQRSDYWDFDVWGSGT QVTVSSASTKG |

TABLE A-continued

| Seq ID No. | Antibody | Heavy Chain Amino Acid Sequence |
|---|---|---|
| 405 | 3BNC181HC | EVQLVQSGSDVRKPGATVTVSCKADEDEDDFTAYDYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 406 | 3BNC186HC | EVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 407 | 3BNC18HC | EVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 408 | 3BNC193HC | QVQLVQSGTAVKKPGASVRVSCQASGYTFTDYFIYWWRQAPGQGLEWLGWINPRTSQPS YPYRFQGRVTLTRDIFEEMLYMDLRGLRSDDTGIYFCARRHSDYCDFDIWGSGTQIIVSSAST KG |
| 409 | 3BNC196HC | QVQLLQSGAAVTKPGASVRVSCEASGYKISDHFIHWWRQAPGQGLQWVGWINPKTGQP NNPRQFQGRISLTRQASWDFDTFSFYMDLKALRSDDTAVYFCARQRSDYWDFDVWGSGT QVTVSSASTKG |
| 410 | 3BNC20HC | QVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 411 | 3BNC29HC | VVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 412 | 3BNC31HC | QVQLVQSGAALKKPGASVRISCQTYGYKFTDHLIYWWRQAPGQGLEWIGWIKPETGQPSY SYRFQGRVSLTRDTFEEIVFMDLRGLRSDDTAIYFCARRHSDYCDFDVWGSGSQVLVSSAST KG |
| 413 | 3BNC33HC | VVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 414 | 3BNC42HC | QVQLVQSGAALKKPGASVRISCQAYGYKFTDYLIHWWRQAPGQGLEWIGWIKPETGQPS YSYKFQGRVTLTRDTFEEILFMDLRGLRSDDTAIYFCARRHSDYCDFDVWGSGSQVIVSSAS TKGA |
| 415 | 3BNC44HC | EVQLVESGSDVRKPGATVTVSCKADEDEDDFTAYNYFMHWVRQAPGHGLEWIGWINPRT GQPNHAKQFQGRVTLTRERSTSTVFMKLTNLRLDDTAVYFCARPLRGGDTWHYHSWGRG TSLTVSSASTKG |
| 416 | 3BNC45HC | VVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 417 | 3BNC53HC | QVQLVQSGAALKKPGASVRISCQAYGYKFTDHLIYWWRQAPGQGLEWIGWIKPETGQPS YAYKFQGRVTLTRDTFEEIHFMDLRGVRNDDTATYFCARRHSDYCDFDVWGSGSQVIVSSA STKG |
| 418 | 3BNC54HC | EVQLVESGSDVRKPGATVTVSCKADEDEDDFTAYNYFMHWVRQAPGHGLEWIGWINPRT GQPNHAKQFQGRVTLTRERSTSTVFMKLTNLRLDDTAVYFCARPLRGGDTWHYHSWGRG TSLTVSSASTKG |
| 419 | 3BNC55HC | QVQLVQSGTAVKRPGASVRVSCQASGYTFTDYFIYWWRQAPGQGLEWLGWINPLTSQPS YPSRFQGRLTLTRDTFDEMLYMDLRGLRSDDTGIYFCARRHSDYCDFDIWGSGTQIIVSSAS TKG |
| 420 | 3BNC59HC | EVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 421 | 3BNC60HC | QVHLSQSGAAVTKPGASVRVSCEASGYKISDHFIHWWRQAPGQGLQWVGWINPKTGQP NNPRQFQGRVSLTRQASWDFDTYSFYMDLKAVRSDDTAIYFCARQRSDFWDFDVWGSG TQVTVSSASTKG |
| 422 | 3BNC62HC | QVRLLQSGAAVTKPGASVRVSCEASGYEIRDYFIHWWRQAPGQGLQWVGWINPKTGQP NNPRQFQGRVSLTRQASWDFDSYSFYMDLKALRSDDTGVYFCARQRSDYWDFDVWGSG TQVTVSSASTKG |
| 423 | 3BNC64HC | QVHLSQSGAAVTKPGASVRVSCEASGYKISDHFIHWWRQAPGQGLQWVGWINPKTGQP NNPRQFQGRVSLTRQASWDFDTYSFYMDLKALRSDDTAIYFCARQRSDFWDFDVWGSGT QVTVSSASTKG |

TABLE A-continued

| Seq ID No. | Antibody | Heavy Chain Amino Acid Sequence |
|---|---|---|
| 424 | 3BNC65HC | QVQLLPFGGAVTKPGASVRVSCEASGYNIRDYFIHWWRQAPGQGLQWVGWINPKTGQP NNPCQFQGRVSLTRPASWDFDTISFYMDLKALRLDDTAVYFCARQRSDYWDFDVWGSGT QVTVSSASTKG |
| 425 | 3BNC66HC | QVQLVQSGAALKKPGASLRISCQTYGYKFTDHLIYWWRQAPGQGLEWIGWIKPETGQPSY SYRFQGRVSLTRDTFEEIAFMDLRGLRSDDTAIYFCARRHTDYCVFDVWGSGSQIIVSSASTK G |
| 426 | 3BNC6HC | QVQLVESGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 427 | 3BNC72HC | QVQLVQSGAALKKPGASLRISCQTYGYKFTDHLIYWWRQAPGQGLEWMGWIKPETGQPS YSYRFQGRVSLTRDTFEEIVFMDLRGLRSDDTAIYFCARRHSDYCDFDVWGSGSQVIVSSAS TKG |
| 428 | 3BNC75HC | QVQLLQSGAAVTKPGASVRVSCEASGYNIRDYFIHWWRQAPGQGLQWVGWINPKTGQP NNPRQFQGRVSLTRHASWDFDTFSFYMDLKALRSDDTAVYFCARQRSDYWDFDVWGSG TQVTVYSASTKG |
| 429 | 3BNC79HC | QVQLLQSGAAVTKPGASVRVSCEASGYNIRDYFIHWWRQAPGQGLQWVGWINPKTGQP NNPRQFQGRVSLTRQASWDFDTISFYMDLKALRLDDTAVYFCARQRSDYWDFDVWGSGT QVTVSSASTKG |
| 430 | 3BNC81HC | RQVQLVQSGAALKKPGASLRISCQAYGYKFTDHLIYWWRQAPGQGLEWIGWIKPETGQPS YSYKFQGRVSLTRDTFQEILFMDLRGLRSDDTAIYFCARRHSDYCDFDVWGSGSQILVSSAS TKG |
| 431 | 3BNC84HC | QVQLVQSGAALKKPGASLRISCQAYGYKFTDHLIYWWRQAPGQGLEWIGWIKPETGQPSY SYKFQGRVSLTRDTFQEILFMDLRGLRSDDTAIYFCARRHSDYCDFDVWGSGSQVIVSSAST KG |
| 432 | 3BNC86HC | QVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 433 | 3BNC87HC | QVQLLQSGAAVTKPGASVRVSCEASGYNIRDYFIHWWRQAPGQGLQWVGWINPKTGQP NNPRQFQGRVSLTRHASWDFDTFSFYMDLKALRSDDTAVYFCARQRSDYWDFDVWGSG TQVTVSSASTKG |
| 434 | 3BNC89HC | QVQLVQSGTAVKRPGASVRVSCQASGYTFIDHFIYWWRQAPGQGLEWLGWINPLTSQPS YPSRFQGRLTLTRDTFDEMLYMDLRGLRSDDTGIYFCARRHSDYCDFDIWGSGTQIIVSSAS TKG |
| 435 | 3BNC91HC | QVQLLQSGAVVTKPGASVRVSCEASGYKIRDYFIHWWRQAPGQGLQWVGWINPQTGQP NIPRPFQGRVTLTRHASWDFDTFSFYMDLKALRSDDTAIYFCARRRSDYCDFDVWGSGTH VTVSSASTKG |
| 436 | 3BNC92HC | EVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 437 | 3BNC94HC | QVQLVQSGSDVRKPGATVTVSCKADEDEDDFTAYNYFMHWVRQAPGHGLEWIGWINPR TGQPNHAKQFQGRVTLTRERSTSTVFMKLTNLRLDDTAVYFCARPLRGGDTWHYHSWGR GTSLTVSSASTKG |
| 438 | 3BNC95HC | QVQLLQSGAAVTKPGASVRVSCEASGYNIRDYFIHWWRQAPGQGLQWVGWINPKTGQP NNPRLFQGRVSLTRHASWDFDTFSFYMDLKAVRSDDTAVYFCARQRSDYWDFDVWGSG TQVTVSSASTKG |

TABLE B

| Seq ID No. | Antibody | Light Chain Amino Acid Sequence |
|---|---|---|
| 439 | 8ANC131KC | EIVLTQSPATLSLSPGERATLSCRASQGLNFVVWYQQKRGQAPRLLIHAPSGRAPGVPDR FSARGSGTEFSLVISSVEPDDFAIYYCQEYSSTPYNFGPGTRVDRKRTVAAPSVFIFPPSDE Q |
| 440 | 8ANC134KC | EIVLTQSPATLSLSPGERATLSCRASQGLNFVVWYQQKGGQAPRLLIHGPTDRAPGVPDR FSARGSGTEFSLVISSVEPDDFALYYCQEYSSTPYNFGPGTRVDRKRTVAAPSVFIFPPSDE Q |

TABLE B-continued

| Seq ID No. | Antibody | Light Chain Amino Acid Sequence |
|---|---|---|
| 441 | 8ANC13KC | EIVLTQSPATLSLSPGERATLSCRASQGLNFVVWYQQKRGQAPRLLIHGPSHRAPGVPDRFSARGSGTEFSLVISSVEPDDFAIYYCQEYSSTPYNFGPGTRVDRKRTVAAPSVFIFPPSDEQ |
| 442 | 8ANC45KC | EIVLTQSPATLSLSPGERATLSCRASQGVNFVVWYQQKRGQAPRLLIYGPSNRAPGVPDRFSARGSGTEFSLVISSVEPDDFALYYCQEYSSTPYNFGPGTRVDRKRTVAAPSVFIFPPSDEQ |
| 443 | 8ANC50KC | EIVLTQSPTTLSLSPGERATLSCRASQGVNLVVWYQQKRGQAPRLLIYGPSDRAPGVPDRFSARGSGTEFSLVISSVEPDDFALYYCQEYSSTPYNFGTGTRVDRKRTVAAPSVFIFPPSDEQ |
| 444 | 8ANC88KC | EIVLTQSPATLSLSPGERATLSCRASQGLNFVVWYQQKRGQAPRLLIHAPSDRAPGVPDRFSARGSGTDFSLVISSVEPDDFAIYYCQEYSSTPYNFGPGTRVDRKRTVAAPSVFIFPPSDEQ |
| 445 | 8anc182kc | EIVLTQSPATLSLSPGERATLSCRASQGVNFVVWYQQKRGQAPRLLIYGPSDRAPGVPDRFSARGSGTEFSLVISSVEPDDFALYYCQEYSSTPYNFGTGTRVDRKRTVAAP |
| 446 | 8anc192kc | EIVLTQSPATLSLSPGERATLSCRASQGVNFVVWYQQKRGQAPRLLIYGNSDRVPGVPDRFSARGSGTEFSLVISSVEPDDFALYYCQEYSSTPYNFGPGTRVDRKRTVAA |
| 447 | 8ANC14KC | SEIVLTQSPATLSLSPGERATLSCRASQSINNYLAWYQQKPGQAPRLLIYDASNRATGIPARFSGGGSGTDFTLTISSLEPEDFAVYYCQQRANWRLLTFGGGTKVEIKRTVAAPSVFIFPPSDEQ |
| 448 | 8ANC16KC | EIVMTQSPDTLSVSPGERATLSCRASQSVNSNLAWYQQKPGQAPRLLIYGASTRATAVPARFSGSGSGTEFTLTISSLQSEDSAVYYCQQYYQWLSYTFGQGTKLEIKRTVAAPSVFIFPPSDEQ |
| 449 | 8ANC195KC | DIQMTQSPSTLAASIGGTVRVSCRASQSITGNWVAWYQQRPGKAPRLLIYRGAALLGGVPSRFSGSAAGTDFTLTIGNLQAEDFGTFYCQQYDTYPGTFGQGTKVEVKRTVAAPSVFIFPPSDEQ |
| 450 | 8ANC24KC | SEIVMTQSPATLSMSPGERATLSCRASLSVNTNLAWYQQKPGQAPRLLIYGASTRATGIPARFSGSGSGTEFTLTISSLQSEDFALYYCQQYNHWPQTFGQGTKVEIKRTVAAPSVFIFPPSDEQK |
| 451 | 8ANC5KC | DIQMTQSPPSLSASVGDRVTITCQASQDINNFLNWYQQKPGKAPRLLIYDASNLESGVSSRFSGSRSGTDFTLTISSLLPEDIATYSCQQYSNLPYTFSQGTKLEIKRTVAAPSVFIFPPSDEQ |
| 452 | 12a12kc | DIQMTQSPSSLSASVGDRVTITCQAGQGIGSSLQWYQQKPGKAPKLLVHGASNLHRGVPSRFSGSGFHTTFSLTISGLQRDDFATYFCAVLEFFGPGTKVEIKRTVAAPSVFIFPPSDEQLKS |
| 453 | 12a13kc | DIQMTQSPSSLSASVGDRVTITCQAGQGIGSSLQWYQQKPGKAPKLLVHGASNLHRGVPSRFSGSGFHTTFSLTISGLQRDDFATYFCAVVEFFGPGTKVDIKRTVAAPSVFIFPPSDEQL |
| 454 | 12a16kc | DIQMTQSPSSLSASVGDRVTITCQASQGIGSSLQWYQQKPGRAPNLLVHGASKLHRGVPSRFSGSGFHTTFSLTISGLQRDDFATYFCAVLEFFGPGTKVEIKRTVAAPSVFIFPPSDEQLK |
| 455 | 12a1kc | DIQMTQSPSSLSASVGDRVSINCQAGQGLGSSLNWYQQKPGRAPKLLVHGASNLQRGVPSRFSGSGFHTTFTLTISSLQPDDVATYFCAAFQWFGPGTKVEIKRT |
| 456 | 12a20kc | DIQMTQSPSSLSASVGDRVSIHCQAGQGIGSSLNWYQQKPGRAPRLLVHGASNLQRGVPSRFSGSGFHTTFTLTISSLQPDDVATYWCAALEFFGPGTKVEI |
| 457 | 12a21kc | DIQMTQSPSSLSASVGDRVTINCQAGQGIGSSLNWYQKKPGRAPKLLVHGASNLQRGVPSRFSGSGFHTTFTLTISSLQPDDVATYFCAVFQWFGPGTKVDIKRTVAAPSVFIFPPSDEQLK |
| 458 | 12a22kc | DIQMTQSPSSLSASVGDRVTITCQAGQGIGSSLNWYQQKPGRAPKLLVYGASNLQRGVPSRFSGSGFHTTFTLTISSLQPEDFATYFCSVYEFLGPGTKVEIKRTVAAPSVFIFPPSDEQ |
| 459 | 12a23kc | DIQMTQSPSSLSVSVGDRVSITCRATQGIGNSLNWYQQKPGKAPKVLIYGTTKLHGGVPSRFSGGGSGSTGTLTIDSLQPEDIATYFCQLFEFFGPGTKVEIKRTVAAPSVFIFPPSDEQ |
| 460 | 12a27kc | DIQMTQSPSSLSASVGDRVTITCQASQGIGSSLQWYQQKPGRAPNLLVHGASNLHRGVPSRFSGSGFHTTFSLTISGLQRDDFATYFCAVLEFFGPGTKVDIKRTVAAPSVFIFPPSDEQ |
| 461 | 12a46kc | DIQMTQSPSSLPASVGDTVTITCQAGQGIGSSLQWYQQRPGRAPNLLVYDASNLQRGVPSRFTGTGFHTTFTLTIRGLRPEDFGTYFCASLEFFGPGTKVDIKRTVAAPSVFIFPPSDEQ |
| 462 | 12a55kc | YIQMTQSPSSLSASIGDRVTITCQAGQGIGSSLNWYQQKPGKAPKLLVHGASNLQRGVSSRFSGSGFHTTFTLTISSLRPEDVGTYFCEVYEFIGPGTKVDIKRTVAAPSVFIFPPSDEQ |

TABLE B-continued

| Seq ID No. | Antibody | Light Chain Amino Acid Sequence |
|---|---|---|
| 463 | 12a56kc | DIQMTQSPSSLSASVGDRVSINCQAGQGIGSSLNWYQQKRGKAPKLLVHGASTLQRGV PSRFSGSGFHTTFTLTISSLQPDDVATYFCESFQWFGPGTKVEIKRTVAAPSVFIFPPSDEQ |
| 464 | 12a6kc | DIQMTQSPSSLSASVGDRVTITCQASQGIGSSLQWYQQKPGRAPKLLVHGASNLHRGVP SRFSGSGFHTSFTLTISSLQPDDVATYFCAVLEFFGPGTKVEIKRTVAAPSVFIFPPSDEQ |
| 465 | 12a7kc | DIQMTQSPSSLSASVGDRVSIHCQAGQGIGSSLKWYQQKSGRAPRLLVHGASNLQRGV PSRFSGSGFHTTFTLTISSLQPDDVATYWCAVLEFFGPGTKVEIKRTVAAPSVFIFPPSDEQ |
| 466 | LSSB2339LC | QSVLTQPPSASGAPGQRVTISCSGGPSNVGGNYVYWYRQFPGTAPNLLILRDDQRPSGV PDRFSASKSGNSASLAISGLRPDDEAFYFCATYDSDGSVRLFGGGTTLTVLSQPKAAPSVT LFPPSNGGR |
| 467 | LSSB2351LC | QSALTQTPSVSGAPGQRVTISCSGGPSNVGGNYVYWYQQFPGAAPKLLIRRDDQRPSG VPDRFSGSKSGNSASLAISGLRLDDEAYYFCATYDSGWSIRLFGGGTRLTVLSQPKAAPSV TLFPPSSEEL |
| 468 | LSSB2364LC | SQAVVTQPPSVSGAPGQRVTISCSGGPSNVGGNLVYWYKQFPGTAPKLLIRRDDQRPSG VPDRFSGSKSGNSASLAISGLRPDDEAFYFCATYDSHGSIRLFGGGTLLTVLSQPKAAPSVT LFPP |
| 469 | LSSB2367LC | QTVVTQPPSASGTPGQRVTISCSGGGSNIGGNLVSWYQHFPGAAPKLLIYRNDQRPSGV PDRFSGSKSGTSASLTISGLRSDDEATYFCAAYDCTLSLRLFGGGTTLNVLSQPKAAPSVTL FPPSSEEL |
| 470 | LSSB2490LC | QSALTQPPSVSGTPGQNVTISCSGGGSNVGGNLVSWYQHFPGAAPKLLIHRDNQRPSG VPDRFSVLKSGNSASLAISGPRSDDEAFYFCAVYDSSLSLGLFGGGTKLTVLSQPKAAPSVT LFPPSSEEL |
| 471 | LSSB2530LC | QSALTQPPSASGAPGQRVTISCSGGPSNVGGNYVYWYRQFPGTAPTLLILRDDQRPSGV PDRFSASKSGNSASLAISGLRPDDEGFYFCATYDSDGSIRLFGGGTALTVLSQPKAAPSVTL FPPSSEELK |
| 472 | LSSB2554LC | NFMLTQAPSASGAPGQRVTISCSGGPSNVGGNYVYWYRQYPGTAPKLLILRDDQRPSG VPDRFSASKSGNSASLAISELRPDDEAFYFCATYDSDGSIRLFGGGTALTVLSQPKAAPSV |
| 473 | LSSB2586LC | NFMLTQPPSASGAPGQRVTISCSGGPSNVGGNYVYWYRQFPGTAPNLLILRDDQRPSG VPDRFSASKSGNSASLAISGLRPDDEAFYFCATYDSDGSIRLFGGGTTLTVLSQPKAAPSVT LFPP |
| 474 | LSSB2612LC | QSVLTQPPSASGAPGQRVTISCSGGPSNVGGNYVYWYRQFPGTAPKLLILRDDQRPSGV PDRFSASKSGNSASLAISGLRPDDEAFYFCATYDSDGSIRLFGGGTALTVLSQPKAAPS |
| 475 | LSSB2640LC | QLVLTQPPSVSGTPGQNVTISCSGGGSHVGGNLVSWYQHFPGAAPKLLIHRDNQRPSG VPDRFSALKSGNSASLAISGLRSDDEAFYFCAVYDSSLSLGLFGGGTKLTVLSQPKAAPSVT |
| 476 | LSSB2644LC | RTVVTQPPSVSGAPGQRVTISCTGSSSNIGAGYDVHWYQQLPGTAPKLLIYGNSNRPSG VPDRFSGSKSGTSASLAITGLQAEDEADYYCQSYDSSLSGSGVFGTGTKVTVLGQPKANP TVTLFPPSSEEL |
| 477 | LSSB2666LC | QSALTQPPSASGAPGQRVTISCSGGPSNVGGNYVYWYRQFPGTAPKLLILRDDQRPSGV PDRFSASKSGNSASLAISGLRPDDEALYFCATYDSDGSIRLFGGGTALTVLSQPKAAPSVTL FPPGWEE |
| 478 | LSSB2680LC | QPVLTQPPSASGAPGQRVTISCSGGPSNVGGNYVYWYRQFPGTAPNLLILRDDQRPSGV PDRFSASKSGNSASLAITGLRPDDEAFYFCATYDSDGSIRLFGGGTALTVLSQPKAAPSVTL FPP |
| 479 | LSSB2683LC | QSALTQPPSASGAPGQRVTISCSGGPSNVGGNYVYWYRQFPGTAPNLLILRDDQRPSGV PDRFSASKSGNSASLAISGLRPDDEAFYFCATYDSDGSIRLFGGGTTLTVLSQPKAAPSVTL F |
| 480 | LSSB344LC | QSALTQTPSVSGAPGQRVTISCSGGPSNVGGNYVYWYQQFPGAAPKLLIRRDDQRPSG VPDRFSGSKSGNSASLAISGLRLDDEAYYFCATYDSGWSIRLFGGGTRLTVLSQPKAAPSV TLFPPSSEEL |
| 481 | LSSNEC107LC | QLVLTQPPSVSATPGQTVTISCSGSGSNVGGNHVYWYRQLPGAAPTLVISKTDHRPSRV PDRFSGSKSGNSASLAISGLRPDDEAAYFCATYDTGLSLRLFGGGTRLAVLSQPKAAPSVT LFPPSSEEL |
| 482 | LSSNEC108LC | QSALTQPPATSGTPGQRVTISCSGGGSNVGGNLVSWYQQFPGAAPKLILHRDGQRPSG VPDRFSASKSGTSASLTISGLRSDDEATYFCAAFDSALSLPLFGGGTKLTVLSQPKAAPSVT LFPPSSEEL |
| 483 | LSSNEC117LC | QSVLTQVLSVSGTPGQRVIISCSGTSSNVGGNLVSWYQHLPGAAPRLLIHRDDQRPSGVP DRFSGSKSGNSASLVISGLRSDDEADYFCGAYDSTFSLPVFGGGTRLTVLSQPKAAPSVTL FPPSSEEL |

TABLE B-continued

| Seq ID No. | Antibody | Light Chain Amino Acid Sequence |
|---|---|---|
| 484 | LSSNEC118LC | NFMLTQPPSVSATPGQTVTISCSGSGSNVGGNHVYWYRQLPGAAPTLVISKTDHRPSRV PDRFSGSKSGNSASLAISGLRPDDEAVYFCATYDTGLSLRLFGGGTRLTVLSQPKAAPSVT QFPPSSEE |
| 485 | LSSNEC122LC | QSALTQPPSVSATPGQTVTISCSGSGSNVGGNHVYWYRQLPGAAPTLLISKTNHRPSQV PDRFSASKSGNSASLAISGLRPDDEADYFCGTYDTSLSLRLFGGGTRLTVLSQPKAAPSVTL FPPSSEEL |
| 486 | LSSNEC24LC | QSALTQPPSASGTPGQRVTISCSGGGSNIGGNLVSWYQHFPGTAPKLLIYRNDQRPSGV PDRFSGSKSGTSASLTISGLRSDDEATYFCAAYDSSLSLRLFGGGTTLNVLSQPKAAPSVTL FPPSSEEL |
| 487 | LSSNEC2LC | QSALTQPPSVSGTPGQNVTISCSGGGSDVGGNLVSWYQHFPGAAPKLLIHRDNQRPSG VPDRFSALKSGNSASLAISGLRSDDEAFYFCAVYDSSLSLGLFGGGTKLTVLSQPKAAPSVT LFPPSSEEL |
| 488 | LSSNEC33LC | QAVVTQPPSVSATPGQTVTISCSGSGSNVGGNHVYWYRQLPGAAPTLLISKTNRRPSQV PDRFSGSKSGNSASLAISGLRPDDEADYFCATYDTDLSLRLFGGGTRLTVLSQPKAAPSVT LFPPSSEEL |
| 489 | LSSNEC46LC | QSALTQPPAASGAPGQRVTISCSGGGSNVGGNLVSWYQQFPGAAPKLILHRDGQRPSG VPDRFSASKSGTSASLTISGLRSDDEATYFCAAYDSAVSLPVFGGGTKLTVLSQPKAAPLVT |
| 490 | LSSNEC48LC | NFMLTQPPSASGTPGQRVTISCSGGGSNIGGNLVSWYQHFPGAAPKLLIYRNDQRPSGV PDRFSGSKSGTSASLAISGLRSDDKATYFCAAYDSTLSLRLFGGGTTLTVLSQPKAAPSVTL FPPSSEE |
| 491 | LSSNEC52LC | QSVLTQVLSVSGTPGQRVIISCSGTSSNVGGNLVSWYQHLPGAAPRLLIHRDDQRPSGVP DRFSGSKSGNSASLVISGLRSDDEADYFCAAYDSTFSLPVFGGGTRLTVLSQPKAAPSVTLF PPSSE |
| 492 | LSSNEC56LC | QSALTQPPSVSATPGQTVTISCSGSGSNVGGNHVYWYRQLPGAAPTLLISKTDHRPSRVP DRFSASKSGNSASLAISGLRPDDEAIYFCATYDTGLSLRLFGGGTRLTVLSQPKAAPSVTLF PPSSEEL |
| 493 | LSSNEC60LC | QSALTRTPSVSGAPGQRVTISCSGGPSNVGGNYVYWYQQFPGAAPKLLIRRDDQRPSGV PDRFSGSKSGNSASLAISGLRLDDEAYYFCATYDSGWSIRLFGGGTRLTVLSQPKAAPSVT LFPPSSEEL |
| 494 | LSSNEC70LC | QSALTQAPSASGTPGQRVTISCSGGGSNIGGNLVSWYQHFPGAAPKLLIYRNDQRPSGV PDRFSASKSGTSASLAISGLRSDDEATYFCAAYDSTLSLRLFGGGTTLAVLSQPKA |
| 495 | LSSNEC72LC | NFMLTQPPSVSGAPGQRVTISCSGGPSNVGGNLVYWYKQFPGTAPKLLIRRDDQRPSG VPDRFSGSKSGNSASLAISGLRPDDEAFYFCATYDSHGSIRLFGGGTLLTVLSQPKAAPSVT LFPPSSEEL |
| 496 | LSSNEC7LC | QLVLTQPPSVSGAPGQRVTISCSGGPSNVGGNLVYWYKQFPGTAPKLLIRRDDQRPSGV PDRFSGSKSGNSASLTISGLRPDDEAFYFCATYDSQGSTRLFGGGTVLTVLSQPKAAPSVT LFPPSSEEL |
| 497 | LSSNEC89LC | QSALTQPPSVSGAPGQRVTISCSGGPSNVGGNYVYWYRQFPGTAPKLLILRDDQRPSGV PDRFSASKSGNSASLAISGLRPDDEAFYFCATYDSQGSFRVFGGGTALTVLSQPKAAPSVT LYPPSSEE |
| 498 | LSSNEC94LC | NFMLTQPPSASGAPGQRVTISCSGGPSNVGGNYVYWYRQFPGTAPNLLILRDDQRPSG VPDRFSASKSGNSASLAISGLRPDDEAFYFCATYDSDGSIRLFGGGTTLTVLSQPKAAPSVT LFPPSSEEL |
| 499 | LSSNEC9LC | QVLSVSGTPGQRVIISCSGTSSNVGGNLVSWYQHLPGAAPRLLIHRDDQRPSGVPDRFS GSKSGNSASLVISGLRSDDEADYFCAAYDSTFSLPVFGGGTRLTVLSQPKAAPSVTLYAPSS EE |
| 500 | LSSB2066KC | PVTLSASVGDRVTITCRASEDISKYLNWYQHKPGKAPKLLIYTASSLETGVPSRFSGSGSGT DFSLTISSLQPDDFATYYCQQSYTSSVTFGQGTRVEVKRTVAAPSVFIFPPSDEQ |
| 501 | LSSB2080KC | PATLAVSPGERATISCKSSQNLLYSANNQHSLAWYQQRPGQPPKLLLYWASTRLSGVPD RFSGSGSGTDFTLTISNLQAEDVAVYYCQQYYSPPPTFGQGTKVEIRRTVAAPSVFIFPPS DEQL |
| 502 | LSSB2133KC | TLSASVGDRVTITCRASQSINNYLNWYQQKPGKAPKLLIYAASSLQSGVPSRFSGSGSGTD FTLTISSLQPEDFVTYYCQQTYSNPRMFGQGTKVEIKRTVAAPSVFIFPPSDEQ |

TABLE B-continued

| Seq ID No. | Antibody | Light Chain Amino Acid Sequence |
|---|---|---|
| 503 | LSSB2182KC | KAPATLSLSPGERATLSCRASQSVGSDLAWYQQKPGQAPRLLIYDASNRATAIPARFSGS GSGTDFTLSISSLEPEDFAVYFCQQRYDKITFGQGTRLEIQRTVAAPSVFIFPPSDEQ |
| 504 | LSSB331KC | RGPVTLAVSLGERATITCKSSQSVLVHSNNKNYLSWYQQKPGQPPKLLIYWASTRESGVP ERFSGSGSGTDFTLSISSLQAEDVAVYYCHQYFSTPRTFGQGTKVEIKGTVAAPSVFIFPPS DEQL |
| 505 | 3A124KC | SEIVLTQSPATLSLSPGESATLSCRASQSLSSSLAWYQQKPGQAPRLLIYDTSDRATGIPAR FSGRGSGTDFTLTISSLEPEDFAVYYCQQRSNWAITFGQGTRLEIKRTVAAPSVFIFPPSD |
| 506 | 3A125KC | EIVLTQSPGTLSLSPGEXATLSCRASQTISNNYLXWYQQKAGQAPRLLIYGASSGATGIPD RFSGSGSGTDFTLTISRLEPEDFAVYYCQQYGLSPWTFGRGTKVEIKRTVAAPSVFIFPPSD |
| 507 | 3A140LC | QSALTQPRSVSGSPGQSVTISCTGTSSDVGAYNYVSWYRQHPGKAPKLMINDVSKRPSG VPDRFSGSKSGNTASLTISGLQAEDEADYYCCSYAGTYSYVFGTGTKVTVLGQPKANPTV TLFPPSSEEL |
| 508 | 3A144KC | APVTLSASVGDTVTITCRASQPIATFLNWYQHKPGQAPKLLIYAASTFQRGAPSRYSGSGS GTDFTLTINSLQPEDLATYYCQQTFTDPVTFGQGTRLEIKRTVAAPSVFIFPPSD |
| 509 | 3A160KC | DIQMTQSPASLSASVGDRVTITCRASQGISHYLAWYQQKPGKVPRLLIYAASRLQSGVTS RFSGSGSGTEFTLTISSLLPEDAAVYFCQKYDTDPMTFGQGTRLEIKRTVAAPSVFIFPPSD |
| 510 | 3A18KC | DIQMTQSPSSLSASIGDRVTITCRANQHIRSFLNWYQQTPGKAPKLLIYAASTLQRGVPSR FSGSGSGTDFTLTITSLEREDLATYYCQQTYTSPITFGQGTRLEIKRTVAAPSVFIFPPSDE |
| 511 | 3A204KC | EIVLTQSPGTLSLSPGERATLSCRASQSVSNNYLAWYQQKPGQAPRLLIYGASSRATGIPD RFSGSGSGTDFTLTISRLEPEDFAVYYCQQYATSSLYTFGQGTKLEIKRTVAAPSVFIFPPSD |
| 512 | 3A228KC | LSVSLGERATINCKSSQSILYSSDKKNYLAWYQQKIGQPPKLLLYWASTRESGIPDRFSGSG SGSDFTLTISSLQPEDVAVYYCQQYYISPFTFGPGTKVDLKRTVAAPSVFIFPPSD |
| 513 | 3A233LC | NFMLTQPASVSGSPGQSITLSCTGTTSDVRDSNFVSWYQQVPGKAPKLIIYDVSARPSGV SFRFSGSKSGNTASLTISGLQAEDEALYYCSSFTPTNTLVFGGGTKLTVLGQPKAAPSVT |
| 514 | 3A244LC | SQSVVTQEPSLTVSPGGTVTLTCGPSTGAVTSGFYPHWFQQKPGQAPRALIYSTSNKYS WTPARFSGSLLGGKAVLTLSDVQPDDEAEYYCLLLLYYGGPWIFGGGTKLTVLVS |
| 515 | 3A255LC | QAVVTQEPSLTVSPGGTVTLTCASSTGAVTSGFYPHWFQQKPGQAPRALIYSTSNRYSW TPARFSGSLLGGKAALTLSGVQPEDEAEYYCLLLPYYGGPWIFGGGTKLTVLGQPKAAPS VTLFPPSSEEL |
| 516 | 3A296KC | EIVMTQSPATLSVSPGDRATLSCRASQSVSTNLAWYQQKPGQAPRLLIYGASTRATGIPA TFSGSGFATEFTLTISSLQSEDFAVYYCQQYNNWPPAFGQGTKVEIKRTVAAPSVFIFPPS D |
| 517 | 3A334LC | QSVLTQPPSASGSPGQSITISCTGTSSDVGGYNYVSWYQQPPGKAPKVIIYEVSKRPSGVP DRFSGSKSGNTASLTVSGLQAEDEADYYCSSYAGSNNFVFGTGTEVTVVGQPKANPTVT LFPPSSEELL |
| 518 | 3A366KC | SLSASVGDRVTITCRASESISFYLNWYQQKPGKAPELLIFATSTLHSGVPSRFSGSGSGTDF TLTISSLQLEDFATYYCQQSSSTPFTFGGGTKVEIKRTVAAPSVFIFPPSD |
| 519 | 3A384KC | DIQMTQSPSSLSAYVGDRVTITCRASQNINTYLNWYQQRPGKAPKLLIYAASTLQSGVPS RFSGSGSGTDFTLTISNLETEDFAVYYCQQTYRSVTFGQGTKLEIKRTVAAPSVFIFPPSD |
| 520 | 3A419KC | LSAYVGDRVTITCRASQNINTYLNWYQQRPGKAPKLLIYAASTLQSGVPSRFSGSGSGTD FTLTISNLETEDFAVYYCQQTYSSVTFGQGTKLETRRTVAAPSVFIFPPSD |
| 521 | 3A461KC | SEIVLTQSPGTLSLSPGERATLSCRASQSVSSSYLAWYQQKPVQAPRLLIYGASSRATGIPD RFSGSGSGTDFTLTISRLEPEDFAVYYCQQYGTLHPRTFGQGTKVEIKRTVAAPSVFIFPPS D |
| 522 | 3A474KC | EIVLTQSPGTLSLSPGERATLSCRASQSISSNYLAWYQQKPGQAPRLLIYGASTRATGIPDR FSGSGSGTDFTLSISRLEPEDIAVYYCHQYGSSQRFGQGTKVEIKRTVAAPSVFIFPPSD |
| 523 | 3A518KC | DIQMTQSPSSLSASVGDRVTITCRASQSISRYLNWYQQKPGKAPKLLIYAASSLQGGVPSR FSGSGSGTDFTLTISSLQPEDFATYYCQQSSSKPFTFGGGTKVEIKRTVAAPSVFIFPPSD |
| 524 | 3A539LC | NFMLTQPASVSGSPGQSITISCSGTGSDIGVYNYVSWYQQHPGKAPRLMIYDVTNRPSG VSNRFSGSKSGFTASLTISGLQGDDEADYYCSSYSSTNTYVFGTGTHVTVLGQPKANPTVT LFPPSSEEL |
| 525 | 3A576LC | QSALTQPPSASGTPGQRVTISCSGSYHNIGSNAVNWYQQLPGTAPKLLIYSNDQRPSGV PDRFSGSKSGTSASLAISGLQSEDEADYYCAAWDDSLHVFGTGTKVTVLGQPKANPTVTL FPPSSEEL |

TABLE B-continued

| Seq ID No. | Antibody | Light Chain Amino Acid Sequence |
|---|---|---|
| 526 | 3A613LC | QSALTQPPSASGTPGQRVTISCSGSYHNIGSNAVNWYQQLPGTAPKLLIYSNDQRPSGV PDRFSGSKSGTSASLAISGLQSEDEADYYCAAWDDSLHVFGTGTKVTVLGQPKANPTVTL FPPSSEEL |
| 527 | 3A64KC | DIQMTQSPSSLSASVGDRVTITCRASQDITTYLAWLQQKPGKAPKSLIYSASTVQSGVPSR FSGSGSGTEFTLTISGLQPEDFATYYCQQYNYYPITFGLGTRLEIKRTVAAPSVFIFPPSDE |
| 528 | 3A650KC | IILFLVATATGSWAQSALTQPRSVSGSLGQSVTISCTGSSSDVGRYNYVSWYQHHPGKAP KLMISDVNKRPSGVPDRFSGSKSGNTASLTISGLQAEDETDYYCCSYAGSYIWVFGG |
| 529 | 3A67KC | EIVLTQSPATLSLSPGERATLSCRASQSVSSYLAWYQQKPGQAPRLLIYDASNRATGIPARF SGSGSDTDFTLTISSLEPEDFAVYYCQQRGIWPLQITFGQGTRLEIKRTVAAPSVFIFPPSDE |
| 530 | 3A779KC | LSASVGDRVTITCRASQSIDRYLNWYQQKPGKAPKLLIYAASSLHTDVPSRFSGSGAGTYF TLTITSLQPEDFATYYCQQSHSPSFGQESYSITFGQGTRLEIKRTVAAPSVFIFPPSD |
| 531 | 3A816KC | VTLSLSPGERATLSCRASQTISNNYLAWYQQKPGQAPRLLIYGASSGATGLPDRFSGSGS GTDFTLTISRLEPEDFAVYYCHQYALSPWTFGRGTKVEIKRTVAAPSVFIFPPSD |
| 532 | 3A869KC | IILFLVATATGVHSDIQMTQSPSSLSASVGDRVTITCRASQSIDRYLNWYQHKPGKAPKLLI YAASNLHTDVPSRFSGSGAGTYFTLTITSLQPEDFATYYCQQSHSPSFGQESYSIAFGQGT RLEIKRTVAAPSVFIFPPSDE |
| 533 | 3A93LC | QSVLTQPASVSGSPGQSITISCTGTNSDVGYSYVSWFQQHPGKVPKLLIYDVSRRSSGVS NRFSGSRSGNTASLTISGLRAEDEADYYCGSFTTSLTLVFGGGTKLAVLVSPS |
| 534 | 3a426kc | EIVLTQSPGTLSLSPGERATLSCRASQSVSSRYLAWYQQKPGQAPRLIIYDASSRASGIPDR FSGSGSETDFTLTITRLEPEDFAVYYCQLYGTSPKFTFGQGTKLEIKRTVAAPSVFIFPPSD |
| 535 | 3a515kc | DVVMTQSPLSLPVTLGQPASISCRSSQSLVYSHGDTYLKCFQQRPGQSPRRPIYKVSNRD SGVPDRFSGSGSGTDFTLKISRVEAEDVGV |
| 536 | 3b129kc | GPATLSVSPGERATLSCRASQSLRNNLAWYQQKTGQSPRLLIYAVSTRATGIPPRFSGGG SGTEFTLTIDSLQSEDFAVYFCQQYDSPQWTFGQGTKVEIKRTVAAPSVFIFPPSD |
| 537 | 3b171lc | QSVLTQPASVSGSPGQSITISCTGTSNDVGGQNFVSWYQQHPGTAPQLLIYDVTNRPAG VSSRFSGSKSGNTASLTISGLRTEDEADYYCASFTILNGVDYVFGTGTKVTVLLSPSQPYL |
| 538 | 3b27kc | EIVLTQSPATLSVSPGERATLSCRAGQSVSSDLAWYQHKPGQAPRLLIYDASKRATGIPAR FSGSGSGTDFTLTISSLEPEDFAVYYCQHRTNWPPSITFGQGTRLEIKRTVAAPSVFIFPPS D |
| 539 | 3b41kc | EIVLTQSPGTLSLSPGERATLSCRASQSVSSNYLAWYQQKPGQAPRLLIYGASSRATGIPD RFSGSGSGTDFTLSISRLEPEDFAVYYCQQYGTSSCTFGQGTKLEIKRTVAAPSVFIF |
| 540 | 3b45kc | EIVLTQSPGTLSLSPGDRAALSCRASETLSGNSLAWYQQKRGQPPRLLIFAASSRATGIPER FSGGGSGTDFTLTITRLEPEDFAVYFCQQYVDAPITFGQGTRLEIKRTVAAPSVFIFPPSD |
| 541 | 3b46kc | EIVLTQSPGTLSLSPGERATLSCRASQSVSSNNLAWYQQKPGQAPRLLMSGASSRATGIP DRFSGSGSGTDFTLTISRLEPEDFAVYHCQQYGSSPPTFGQGTKVEIKRTVAAPSVFIFPP |
| 542 | 3b57lc | QSVLTQPRSVSGSPGQSVTISCTGTSSDVGGYNYVSWYQQHPGKAPKTMIFDVTKRPSG VPDRFSGSKSGNTASLTISGLQAEDEADYYCSSYAGRNTFYVFGTGTTVTVQVSPSQPPP |
| 543 | 3b8kc | EIVLTQSPGTLSLSPGERATLSCRASQSVSSNLAWYAQKPGQAPRLIIYGASSRASAIPDRF RGSGSGTDFTLTISRLEPEDFAVYYCQQYDDAPITFGHGTRLEIKRTVAAPSVFIFPPSDE |
| 544 | 3BNC55KC | DIQMTQSPSSLSASVGDKVTITCQTSAGYLNWYQQRRGRAPKLLMYDGSRLVTGVPSRF SGRRWGTQYNLTIGSLQPEDIATYYCQVYEFFGPGTRLDLKSTVAA |
| 545 | 3BNC60KC | DIQMTQSPSSLSARVGDTVTITCQANGYLNWYQQRRGKAPKLLIYDGSKLERGVPARFS GRRWGQEYNLTINNLQPEDVATYFCQVYEFIVPGTRLDLKRTVAA |
| 546 | 3anc3kc | DIQMTQSPSSVSASVGDRVTITCQASRDTDNSLTWYQQKPGRPPKLLIYHVVNLGPGVP SRFSGSASSATQSTLIISDFQPDDVATYFCQNYEFFGPGTKVEIKRTVAAPSVFIFPPSDEQ |
| 547 | 3b106kc | DIQMTQSPSSLSASVGDTVTITCQANGYLNWYQQRRGKAPKLLIYDGSKLERGVPSRFSG RRWGQEYNLTINNLQPEDIATYFCQVYEFVVPGTRLDLKRTVAAPSVFIFPPSD |
| 548 | 3b16kc | DIQMTQSPSSLSASVGDTVTITCQANGYLNWYQQRRGKAPKLLIYDGSKLERGVPSRFSG RRWGQEYNLTINNLQPEDIATYFCQVYEFVVPGTRLDLKRTVAAPSVFIFPPSD |
| 549 | 3b180kc | DIQMTQSPSSLSARVGDTVTFTCQANGYLNWYQQRRGKAPKLLIYDGSKLERGVPSRFS GRGWGQEYNLTINNLQPEDIATYFCQVYEFAVPGTRLDLKRTVAAPSVFIFPPSD |
| 550 | 3b183kc | DIQMTQSPSSLSARVGDTVTITCQANGYLNWYQQRRGKAPKLLIYDGSKLETGVPSRFT GRRWGQEYNLTINNLQPEDIATYFCQVYEFIVPGTRLDLKRTVAAPSVFIFPPSD |

TABLE B-continued

| Seq ID No. | Antibody | Light Chain Amino Acid Sequence |
|---|---|---|
| 551 | 3b191kc | DIQMTHSPSSLSASVGDTVTITCQANGYLNWYQQRRGKAPKLLIYDGSKLETGVPSRFTGRRWGQEYNLTINNLQPEDIATYFCQVYEFIVPGTRLDLKRTVAAPSVFIFPPSD |
| 552 | 3b21kc | DIQMTQSPSSLSARVGDTVTITCQANGYLNWYQQRRGKAPKLLIYDGSKLETGVPSRFTGRRWGQEYNLTINNLQPEDIATYFCQVYEFIVPGTRLDLKRTVAAPSVFIFPPSD |
| 553 | 3bnc102kc | DIQMTQSPSSLSASVGDRVTITCQASQGISNSLNWYQQKPGKAPRLLIYGTSTLQRGVPSRFSGSGSGTRFTVTINSLQPEDIATYFCQHNEFFGRGTKVDIKRTVAAPSVFIFPPSDEQL |
| 554 | 3bnc104kc | DIQMTQSPSSLSASIGDRVNITCQASRDTGSALNWYQQKVGRPPRLLISAVSNLGAGVPSRFSGRRSGTQSTLTINTLQPEDIATYFCQHYEFFGPGTKVDIKRTVAAPSVFIFPPSDEQ |
| 555 | 3bnc105kc | DIQMTQSPSSLSASVGDTVTFTCQANGYLNWYQQRRGKAPKLLIYDGSRLERGVPSRFSGRRWGQEYNLTINNLQPEDIATYFCQVYEFAVPGTRLDLKRTVAAPSVFIFPPSD |
| 556 | 3bnc107kc | DIQMTQSPSSLSASVGDTVTITCQTNKGYLNWYQQRRGRAPKLLMYDGSKLVTGVPSRFSGRRWGTQYNLTIGSLQPEDIATYYCQVYEFFGPGTRLDLKRTVAAPSVFIFPPSD |
| 557 | 3bnc108kc | DIQMTQSPSSLSARVGDKVTITYQTSAGYLNWYQQRRGRAPKLLMYDGSRLVTGAPSRFSGRRWGTQYNLTIGSLQPEDIATYYCQVYEFFGPGTRLDLKRTVAAPSVFIFPPSD |
| 558 | 3bnc117kc | DIQMTQSPSSLSASVGDTVTITCQANGYLNWYQQRRGKAPKLLIYDGSKLERGVPSRFSGRRWGQEYNLTINNLQPEDIATYFCQVYEFVVPGTRLDLKRTVAAPSVFIFPPSD |
| 559 | 3bnc134kc | DIQMTQSPSSLSASVGDTVTINCQTNKGYLNWYQQRRGRAPKLLMYDGSKLVTGVPSRFSGRRWGTQYNLTIGSLQPEDIATYYCQVYEFFGPGTRLDLKRTVAAPSVFIFPPSD |
| 560 | 3bnc142kc | DIQMTQSPSSLSASVGDTVTITCHTNKGYLNWYQQRRGRAPKLLMFDGSKLVTGVPSRFSGRRWGTQYNLTIGSLQPEDIATYYCQVYEVFGPGTRLDLKRTVAAPSVFIFPPSD |
| 561 | 3bnc151kc | DIQMTQSPSSLSASVGDTVTITCQTNKGYLNWYQQRRGRAPKLLMYDGSKLVTGVPSRFSGRRWGTQYNLTIGSLQPEDIATYYCQVYEFFGPGTRLDLKRTVAAPSVFIFPPSD |
| 562 | 3bnc153kc | DIQMTQSPSSLSASVGDTVTITCQTNKGYLNWYQQRRGRAPKLLMYDGSKLVTGVPSRLSGRRWGTQYNLTIGSLQPEDIATYYCQVYEFFGPGTRLDLKRTVAAPSVFIFPPSD |
| 563 | 3bnc156kc | DIQMTQSPSSLSASVGDTVTITCQTNKGYLNWYQQKRGRAPKLLMYDGSKLVTGVPSRLSGRRWGTQYNLTIGSLQPEDIATYYCQVYEFFGPGTRLDLKRTVAAPSVFIFPPSD |
| 564 | 3bnc158kc | DIQMTQSPSSLSASVGDTVTITCQTNKGYLNWYQQRRGRAPKLLMYDGSKLVTGVPSRLSGRRWGTQYNLTIGSLQPEDIATYYCQVYEFFGPGTRLDLKRTVAAPSVFIFPPSD |
| 565 | 3bnc159kc | DIQMTQSPSSLSASVGDTVTITCQTNKGYLNWYQQRRGRAPKLLMYDGSKLVTGVPSRFSGRRWGTQYNLTIGSLQPEDIATYYCQVYEFFGPGTRLDLKRTVAAPSVFIFPPSD |
| 566 | 3bnc15kc | DIQMTQSPSSLSASVGDTVTITCQTNKGYLNWYQQRRGRAPKLLMYDGSKLVTGVPSRLSGRRWGTQYNLTIGSLQPEDIATYYCQVYEFFGPGTRLDLKRTVAAPSVFIFPPSD |
| 567 | 3bnc176kc | DIQMTQSPSSLSASVGDTVTITCQANGYLNWYQQRRGKAPKLLIYDGSKLERGVPSRFSGRRWGQEYNLTINNLQAEDIATYFCQVYEFAVPGTRLDLKRTVAAPSVFIFPPSD |
| 568 | 3bnc193kc | DIQMTQSPSSLSARVGDKVTITCQTSAGYLNWYQQRRGRAPKLLMYDGSRLVTGVPSRFSGRRWGTQYNLTIGSLQPEDIATYYCQVYEFFGPGTRLDLKRTVAAPSVFIFPPSD |
| 569 | 3bnc196kc | DIQMTQSPSSLSASVGDTVTITCQANGYLNWYQQRRGKAPKLLMYDGSTLERGVPARFSGRRWGQEYNLTINNLQPEDVATYFCQVYEFIVPGTRLDLKRTVAAPSVFIFPPSD |
| 570 | 3bnc31kc | DIQMTQSPSSLSASVGDTVTITCQTNKGYLNWYQQRRGRAPKLLMCDGSKLVTGVPSRFSGRRWGTQYNLTIGSLQPEDIATYYCQVYEFFGPGTRLDLKRTVAAPSVFIFPPSD |
| 571 | 3bnc42kc | DIQMTQSPSSLSASVGDTVTITCQTTKGYLNWYQQRRGRAPKLLMFDGSKLVTGVPSRFSGRRWGTQYNLTIGSLQPEDLATYYCQVYEFFGPGTRLDLKRTVAAPSVFIFPPSD |
| 572 | 3bnc53kc | DIQMTQSPSSLSASVGDTVTITCHTNKGYLNWYQQRRGRAPKLLMFDGSKLVTGVPSRFSGRRWGTQYNLTIGSLQPEDIATYYCQVYEVFGPGTRLDLKRTVAAPSVFIFPPSD |
| 573 | 3bnc62kc | DIQMTQSPSSLSARVGDTVTITCQANGYLNWYQQRRGKAPKLLIYDGSKLETGVPSRFTGRRWGQEYNLTINNLQPEDIATYFCQVYEFIVPGTRLDLKRTVAAPSVFIFPPSD |
| 574 | 3bnc65kc | DIQMTQSPSSLSARVGDTVTFTCQANGYLNWYQQRRGKAPKLLIYDGSKLERGVPSRFSGRRWGQEYNLTINNLQPEDIATYFCQVYEFAVPGTRLDLKRTVAAPSVFIFPPSD |
| 575 | 3bnc66kc | DIQMTQSPSSLSASVGDTVTITCQTNKGYLNWYQQRRGRAPKLLMYDGSKLVTGVPSRLSGRRWGTQYNLTIGSLQPEDIATYYCQVYEFFGPGTRLDLKRTVAAPSVFIFPPSD |

TABLE B-continued

| Seq ID No. | Antibody | Light Chain Amino Acid Sequence |
|---|---|---|
| 576 | 3bnc75kc | DIQMTQSPSSLSARVGDTVTITCQANGYLNWYQQRRGKAPKLLIYDGSKLERGVPSRFS GRRWGQEYNLTINNLQPEDIATYFCQVYEFVVPGTRLDLKRTVAAPSVFIFPPSD |
| 577 | 3bnc79kc | DIQMTQSPSSLSARVGDTVTFTCQANGYLNWYQQRRGKAPKLLIYDGSKLERGVPSRFS GRRWGQEYNLTINNLQPEDIATYFCQVYEFAVPGTRLDLKRTVAAPSVFIFPPSD |
| 578 | 3bnc81kc | DIQMTQSPSSLSASVGDTVTINCQTNKGYLNWYQQRRGRAPKLLMYDGSKLVTGVPSR FSGRRWGTQYNLTIGSLQPEDIATYYCQVYEFFGPGTRLDLKRTVAAPSD |
| 579 | 3bnc84kc | DIQMTQSPSSLSASVGDTVTINCQTNKGYLNWYQQRRGRAPKLLMYDGSKLVTGVPSR FSGRRWGTQYNLTIGSLQPEDIATYYCQVYEFFGPGTRLDLKRTVAAPSVFIFPPSD |
| 580 | 3bnc87kc | DIQMTQSPSSLSARVGDTVTITCQANGYLNWYQQRRGKAPKLLIYDGSKLERGVPSRFS GRRWGQEYNLTINNLQPEDIATYFCQVYEFVVPGTRLDLKRTVAAPSVFIFPPSD |
| 581 | 3bnc89kc | DIQMTQSPSSLSASVGDKVTITCQTSAGYLNWYQQRRGRAPKLLMYDGSRLVTGVPSRF SGRRWGTQYNLTIGSLQPEDVATYYCQVYEFFGPGTRLDLKRTVAAPSVFIFPPSD |
| 582 | 3bnc91kc | DIQMTQSPSSLSARVGDTVTITCQANGYLNWYQQRRGKAPKLLIYDGSKLERGVPSRFS GRRWGQEYNLTINNLQPEDIATYFCQVYEFAVPGTRLDLKRTVAAPSVFIFPPSD |
| 583 | 3bnc95kc | DIQMTQSPSSLSASVGDTVTITCQANGYLNWYQQRRGKAPKLLIYDGSKLERGVPSRFSG RRWGQEYNLTINNLQPEDIATYFCQVYEFIVPGTRLDLKRTVAAPSVFIFPPSD |

TABLE 1

| Forward Leader Sequence Primers | | |
|---|---|---|
| VH1 LEADER-A | ATGGACTGGACCTGGAGGAT | SEQ ID NO 591 |
| VH1 LEADER-B | ATGGACTGGACCTGGAGCAT | SEQ ID NO 592 |
| VH1 LEADER-C | ATGGACTGGACCTGGACAAT | SEQ ID NO 593 |
| VH1 LEADER-D | GGCCTTCTCTTTGTGGTGGC | SEQ ID NO 594 |
| VH1 LEADER-E | ATGGACTGGACCTGGAGGGT | SEQ ID NO 595 |
| VH1 LEADER-F | ATGGACTGGATTTGGAGGAT | SEQ ID NO 596 |
| VH1 LEADER-G | AGGTTCCTCTTTGTGGTGGCAG | SEQ ID NO 597 |
| VH3 LEADER-A | TAAAAGGTGTCCAGTGT | SEQ ID NO 598 |
| VH3 LEADER-B | TAAGAGGTGTCCAGTGT | SEQ ID NO 599 |
| VH3 LEADER-C | TAGAAGGTGTCCAGTGT | SEQ ID NO 600 |
| VH3 LEADER-D | GCTATTTTTAAAGGTGTCCAGTGT | SEQ ID NO 601 |
| VH3 LEADER-E | TACAAGGTGTCCAGTGT | SEQ ID NO 602 |
| VH3 LEADER-F | TTAAAGCTGTCCAGTGT | SEQ ID NO 603 |
| VH4 LEADER-A | ATGAAACACCTGTGGTTCTTCC | SEQ ID NO 604 |
| VH4 LEADER-B | ATGAAACACCTGTTTCTT | SEQ ID NO 605 |
| VH4 LEADER-C | ATGAAGCACCTGTGGTTCTT | SEQ ID NO 606 |
| VH4 LEADER-D | ATGAAACATCTGTGGTTCTT | SEQ ID NO 607 |
| VH5 LEADER-A | TTCTCCAAGGAGTCTGT | SEQ ID NO 608 |
| VH5 LEADER-B | CCTCCACAGTGAGAGTCTG | SEQ ID NO 609 |
| VH6 LEADER-A | ATGTCTGTCTCCTTCCTCATC | SEQ ID NO 610 |
| VH7 LEADER-A | GGCAGCAGCAACAGGTGCCCA | SEQ ID NO 611 |

TABLE 1-continued

| Reverse Constant Region Primers | | |
|---|---|---|
| 3' Cg CH1 (gamma) | GGAAGGTGTGCACGCCGCTGGTC | SEQ ID NO 612 |
| 3' IgG (internal) | GTTCGGGGAAGTAGTCCTTGAC | SEQ ID NO 613 |

TABLE 2

| | gender | clade | year of birth | year of diagnosis | CD4+ T cells/ul | Virus copies/ml | clinical status |
|---|---|---|---|---|---|---|---|
| pt1 | male | B | 1948 | 1985 | 354 | 4722 | non progressor |
| pt3 | male | B | 1965 | 2002 | 427 | 880 | non progressor |
| pt8 | male | B | 1962 | 1989 | 580 | <50 | elite controller |
| pt12 | male | ND | ND | ND | ND | ND | ND |

TABLE 3A

| Ab Name | VH | D | JH | (-) | CDR3 (aa) | SEQ ID NO |
|---|---|---|---|---|---|---|
| 3BNC4 | 1-2 | 7-27 | 2/6 | 3 | R H S D Y C D F D V | 614 |
| 3BNC23 | 1-2 | 6-25/3-3 | 2/6 | 3 | Q R S D F W D F D V | 615 |
| 3BNC42 | 1-2 | 7-27 | 2/6 | 3 | R H S D Y C D F D V | 616 |
| 3BNC53 | 1-2 | 3-3 | 2/6 | 3 | R H S D Y C D F D V | 617 |
| 3BNC55 | 1-2 | 3-3/6-19/5-12 | 2/6 | 3 | R H S D Y C D F D I | 618 |
| 3BNC62 | 1-2 | 6-25/6-13/6-6 | 2/6 | 3 | Q R S D Y W D F D V | 619 |
| 3BNC65 | 1-2 | 6-25/6-6 | 2/6 | 3 | Q R S D Y W D F D V | 620 |

TABLE 3A-continued

| | | | | | | |
|---|---|---|---|---|---|---|
| 3BNC66 | 1-2 | 7-27 | 2/6 | 3 | R H T D Y C D F D V | 621 |
| 3BNC72 | 1-2 | 7-27 | 2/6 | 3 | R H S D Y C D F D V | 622 |
| 3BNC79 | 1-2 | 6-25/6-6 | 2/6 | 3 | Q R S D Y W D F D V | 623 |
| 3BNC81 | 1-2 | 7-27 | 2/6 | 3 | R H S D Y C D F D V | 624 |
| 3BNC89 | 1-2 | 3-3/6-19/5-12 | 2/6 | 3 | R H S D Y C D F D I | 625 |
| 3BNC91 | 1-2 | 2-21/6-25 | 2/6 | 3 | R R S D Y C D F D V | 626 |
| 3BNC95 | 1-2 | 6-25/2-8 | 2/6 | 3 | Q R S D Y W D F D V | 627 |
| 3BNC105 | 1-2 | 6-6/6-25 | 2/6 | 3 | Q R S D Y W D F D V | 628 |
| 3BNC107 | 1-2 | 7-27/3-3 | 2/6 | 3 | R H S D Y C D F D V | 629 |
| 3BNC108 | 1-2 | 3-3/6-19/6-25 | 2/6 | 3 | R H S D Y C D F D I | 630 |
| 3BNC117 | 1-2 | 6-25/2-8 | 2/6 | 3 | Q R S D Y W D F D V | 631 |
| 3BNC134 | 1-2 | 7-27 | 2/6 | 3 | R H S D Y C D F D V | 632 |
| 3BNC142 | 1-2 | 3-3 | 2/6 | 3 | R H S D Y C D F D V | 633 |
| 3BNC151 | 1-2 | 7-27/4-17/3-3 | 2/6 | 3 | R H S D Y C D L D V | 634 |
| 3BNC156 | 1-2 | 3-3/7-27 | 2/6 | 3 | R H S D Y C D F D V | 635 |
| 3BNC159 | 1-2 | 7-27 | 2/6 | 3 | R H S D Y C D F D V | 636 |
| 3BNC176 | 1-2 | 6-25/6-6 | 2/6 | 3 | Q R S D Y W D F D V | 637 |
| 3BNC196 | 1-2 | 6-25/6-6/6-13 | 2/6 | 3 | Q R S D Y W D F D V | 638 |
| 3BNC6 | 1-2 | 3-16/1-7 | 2 | 1 | P L R G G D T W H Y H S | 639 |
| 3BNC101 | 1-2 | 1-7/3-16 | 2 | 1 | P L R G G D T W H Y H S | 640 |
| 3BNC102 | 1-2 | 3-22/1-26/1-20 | 2 | 3 | P H S P D D A W S L D V | 641 |
| 3BNC126 | 1-2 | 3-22/1-26/1-20 | 2 | 3 | P H S P D D A W S L D V | 642 |
| 3BNC149 | 1-2 | 3-22/1-26/1-20 | 2 | 3 | P H S P D D A W S L D V | 643 |
| 3ANC3 | 1-2 | 2-21/2-15 | 1/2 | 1 | P R G G R D N W S F H V | 644 |
| 3ANC42 | 1-2 | ND | 2 | 2 | P K S G R D Y W S F D L | 645 |
| 3BNC3 | 1-69 | 5-5/5-18/5-24 | 3 | 2 | A T G Y S Y G Y L D A F D I | 646 |
| 3BNC8 | 1-24 | 5-24/4-17 | 4 | 3 | E P R E M G T L T A G F E Y | 647 |
| 3BNC48 | 1-69 | 3-3 | 4 | 5 | G Q T D L N D D L W S D Y S T P G F D Y | 648 |
| 3ANC38 | 1-69 | 3-3 | 4 | 5 | G Q T D L N D D F W S E Y S T P G F D Y | 649 |
| 3BNC49 | 1-69 | 3-22/6-19/5-12 | 6 | 3 | G E F D S S G F D Y E S W Y P Y Y M D V | 650 |
| 3BNC58 | 1-24 | 3-16/3-10 | 4/5 | 2 | A P R L E L G E L S S G F H Y | 651 |
| 3BNC78 | 1-24 | | 4/5 | 2 | A P R L D L G E L S S G F H F | 652 |
| 3BNC78 | 1-24 | | 4/5 | 2 | A P R L D L G E L S S G F H F | 653 |
| 3BNC71 | 1-24 | 1-24 | 4/5 | 3 | D N P L L Q S G E F S S S L D N | 654 |

TABLE 3A-continued

| | | | | | | | | | |
|---|---|---|---|---|---|---|---|---|---|
| 3BNC71 | 1-24 1-24 | | 4/5 3 D N P L L Q S G E F S S S L E N 655 | | | | | | |
| 3BNC144 | 1-69 3-9/5-5 | | 4 3 A Q G D I L T E G Y F D Y 656 | | | | | | |

| Ab Name | (+) | Length | Mutations HC | Primer Set | k/l | Vk/l | Jk/l | (-) |
|---|---|---|---|---|---|---|---|---|
| 3BNC4 | 1 | 10 | 72 | new | k | 1D-33 | 3 | 1 |
| 3BNC23 | 1 | 10 | 79 | new | k | 1D-33 | 3 | 1 |
| 3BNC42 | 2 | 10 | 69 | new | k | 1D-33 | 3 | 1 |
| 3BNC53 | 2 | 10 | 74 | new | k | 1D-33 | 3 | 1 |
| 3BNC55 | 2 | 10 | 64 | new | k | 1D-33 | 1/3 | 1 |
| 3BNC62 | 1 | 10 | 81 | new | k | 1D-33 | 3 | 1 |
| 3BNC65 | 1 | 10 | 82 | new | k | 1D-33 | 3 | 1 |
| 3BNC66 | 2 | 10 | 69 | new | k | 1D-33 | 3 | 1 |
| 3BNC72 | 1 | 10 | 72 | new | k | 1D-33 | 3 | 1 |
| 3BNC79 | 1 | 10 | 76 | new | k | 1D-33 | 3 | 1 |
| 3BNC81 | 2 | 10 | 71 | new | k | 1D-33 | 3 | 1 |
| 3BNC89 | 2 | 10 | 68 | new | k | 1D-33 | 3 | 1 |
| 3BNC91 | 2 | 10 | 76 | new | k | 1D-33 | 3 | 1 |
| 3BNC95 | 1 | 10 | 72 | new | k | 1D-33 | 3 | 1 |
| 3BNC105 | 1 | 10 | 77 | new | k | 1D-33 | 3 | 1 |
| 3BNC107 | 2 | 10 | 69 | new | | | | |
| 3BNC108 | 2 | 10 | 62 | new | k | 1D-33 | 3 | 1 |
| 3BNC117 | 1 | 10 | 72 | new | k | 1D-33 | 3 | 1 |
| 3BNC134 | 2 | 10 | 71 | new | k | 1D-33 | 3 | 1 |
| 3BNC142 | 2 | 10 | 72 | new | k | 1D-33 | 3 | 1 |
| 3BNC151 | 2 | 10 | 69 | new | k | 1D-33 | 3 | 1 |
| 3BNC156 | 2 | 10 | 72 | new | k | 1D-33 | 3 | 1 |
| 3BNC159 | 2 | 10 | 71 | new | k | 1D-33 | 3 | 1 |
| 3BNC176 | 1 | 10 | 72 | new | k | 1D-33 | 3 | 1 |
| 3BNC196 | 1 | 10 | 78 | new | k | 1D-33 | 3 | 1 |
| 3BNC6 | 3 | 12 | 55 | new | k | 1D-33 | 1/3 | 1 |
| 3BNC101 | 3 | 12 | 54 | new | | | | |
| 3BNC102 | 1 | 12 | 63 | new | k | 1D-33 | 1/3 | 1 |
| 3BNC126 | 1 | 12 | 65 | new | | | | |
| 3BNC149 | 1 | 2 | 68 | new | | | | |
| 3ANC3 | 3 | 12 | 59 | new | k | 1D-33 | 3 | 1 |
| 3ANC42 | 2 | 12 | 53 | new | k | 1D-33 | 3 | 1 |
| 3BNC3 | 0 | 14 | 22 | new | L | 1-44 | 1 | 2 |
| 3BNC8 | 1 | 14 | 21 | old | k | 3-11 | 2 | 0 |
| 3BNC48 | 0 | 20 | 18 | new | | | | |
| 3ANC38 | 0 | 20 | 12 | new | 1 | 1-47 | 1/6 | 2 |
| 3BNC49 | 0 | 20 | 23 | old | k | 3-20 | 3 | |

TABLE 3A-continued

| | | | | | | | | |
|---|---|---|---|---|---|---|---|---|
| 3BNC58 | 1 | 15 | 16 | old | k | 3-11 | 2 | 0 |
| 3BNC78 | 2 | 15 | 38 | old | | | | |
| 3BNC78 | 2 | 15 | 39 | old | | | | |
| 3BNC71 | 0 | 16 | 22 | old | k | 3-11 | 5 | |
| 3BNC71 | 0 | 16 | 17 | old | k | 3-11 | 5 | |
| 3BNC144 | 0 | 13 | 15 | old | k/l | 1-44/1-47 | 1 | 2 |

| Ab Name | CDR3 (aa) | SEQ ID NO | (+) | Length | Mutations LC | Binding | NEUT | # of Relatives |
|---|---|---|---|---|---|---|---|---|
| 3BNC4 | Q V Y E F | 657 | 0 | 5 | 38 | | + | 7 |
| 3BNC23 | Q V Y E F | 658 | 0 | 4 | 50 | CD4BS | + | 5 |
| 3BNC42 | Q V Y E F | 659 | 0 | 5 | 42 | | − | 1 |
| 3BNC53 | Q V Y E V | 660 | 0 | 5 | 42 | | + | 1 |
| 3BNC55 | Q V Y E F | 661 | 0 | 5 | 32 | | + | 1 |
| 3BNC62 | Q V Y E F | 662 | 0 | 5 | 43 | | + | 4 |
| 3BNC65 | Q V Y E F | 663 | 0 | 5 | 44 | | ND | 1 |
| 3BNC66 | Q V Y E F | 664 | 0 | 5 | 38 | | + | 1 |
| 3BNC72 | Q V Y E F | 665 | 0 | 5 | 38 | | + | 1 |
| 3BNC79 | Q V Y E F | 666 | 0 | 5 | 44 | | ND | 2 |
| 3BNC81 | Q V Y E F | 667 | 0 | 5 | 38 | | ND | 2 |
| 3BNC89 | Q V Y E F | 668 | 0 | 5 | 35 | | + | 1 |
| 3BNC91 | Q V Y E F | 669 | 0 | 5 | 42 | | + | 1 |
| 3BNC95 | Q V Y E F | 670 | 0 | 5 | 39 | | + | 9 |
| 3BNC105 | Q V Y E F | 671 | 0 | 5 | 43 | | ND | 1 |
| 3BNC107 | ND | | | | | | ND | 1 |
| 3BNC108 | Q V Y E F | 672 | 0 | 5 | 38 | | + | 2 |
| 3BNC117 | Q V Y E F | 673 | 0 | 5 | 39 | CD4BS | + | 9 |
| 3BNC134 | Q V Y E F | 674 | 0 | 5 | 38 | | ND | 1 |
| 3BNC142 | Q V Y E V | 675 | 0 | 5 | 42 | | + | 1 |
| 3BNC151 | Q V Y E F | 676 | 0 | 5 | 40 | | ND | 1 |
| 3BNC156 | Q V Y E F | 677 | 0 | 5 | 37 | | + | 1 |
| 3BNC159 | Q V Y E F | 678 | 0 | 5 | 39 | | ND | 1 |
| 3BNC176 | Q V Y E F | 679 | 0 | 5 | 41 | | + | 3 |
| 3BNC196 | Q V Y E F | 680 | 0 | 5 | 43 | | ND | 1 |
| 3BNC6 | Q H Y E F | 681 | 1 | 5 | 44 | | + | 24 |
| 3BNC101 | ND | | | | | | ND | 1 |
| 3BNC102 | Q H Y E F | 682 | 1 | 5 | 34 | | − | 1 |
| 3BNC126 | ND | | | | | | ND | 1 |
| 3BNC149 | ND | | | | | | ND | 1 |
| 3ANC3 | Q H Y E F | 683 | 0 | 5 | 47 | | + | 1 |
| 3ANC42 | Q Q Y E F | 684 | 1 | 5 | 41 | | ND | 4 |

TABLE 3A-continued

| | | | | | | | | |
|---|---|---|---|---|---|---|---|---|
| 3BNC3 | A A W D D T L Y V | 685 | 0 | 9 | 19 | CD4i | + | 7 |
| 3BNC8 | Q H R S I W P L M C T | 686 | 2 | 11 | 10 | CD4i | + | 3 |
| 3BNC48 | ND | | | | | | ND | |
| 3ANC38 | G A W D D T L Y V | 687 | 0 | 9 | 8 | CD4i | - | 2 |
| 3BNC49 | ND | | | | | CD4i | ND | 2 |
| 3BNC58 | Q Q R T I W P P G C S | 880 | 1 | 11 | 10 | CD4i | ND | 2 |
| 3BNC78 | ND | | | | | | ND | 1 |
| 3BNC78 | ND | | | | | | ND | 2 |
| 3BNC71 | ND | | | | | CD4i | ND | 1 |
| 3BNC71 | | | | | | CD4i | ND | 1 |
| 3BNC144 | ND | | 1 | 9 | | CD4i | ND | 1 |

TABLE 3b

| Ab Name | VH | D | JH | (-) | CDR3 (aa) | SEQ ID NO |
|---|---|---|---|---|---|---|
| 1NC2 | 1-46 | 3-22/5-5 | 4/5 | 4 | N E A D Y H D G N G H S L R G M F D Y | 881 |
| 1NC3 | 1-46 | 6-19 | 4/5 | 3 | A E A E S Q S H S R P I M F D F | 688 |
| 1NC7 | 1-46 | 6-19/1-14 | 4/5 | 3 | A E A E S Q S H S R P I M F D S | 689 |
| 1NC9 | 1-46 | 5-12/2-8 | 4/5 | 4 | Q D S D F H D G H G H T L R G M F D S | 690 |
| 1NC18 | 1-46 | 1-14/2-21 | 4/5 | 2 | N E P Q Y H S L P G M F D Y | 691 |
| 1NC24 | 1-46 | 3-16 | 4/5 | 3 | N E P Q Y H D G N G H S L P G M F D Y | 692 |
| 1NC29 | 1-46 | 3-16/6-19 | 4/5 | 3 | N E P Q Y Y D G S G H S L P G M F D Y | 693 |
| 1NC33 | 1-46 | 5-12 | 4/5 | 5 | L E A D G D D Y S P K M V D Y | 694 |
| 1NC46 | 1-46 | 3-9/3-16 | 4/5 | 3 | R E A D Y H D G N G H T L P G M F D F | 695 |
| 1NC48 | 1-46 | 3-9/6-19 | 4/5 | 2 | N E P Q Y F D G S G H S L P G M F D Y | 696 |
| 1NC52 | 1-46 | 3-16/6-19 | 4/5 | 3 | N E P Q Y Y D G S G H S L P G M F D Y | 697 |
| 1NC56 | 1-46 | 5-12/3-9 | 4/5 | 5 | L E A D G D D Y S P K M F D H | 698 |
| 1NC60 | 1-46 | 3-22/1-26 | 1/5 | 4 | L E A E S D S H S R P I M F D H | 699 |
| 1NC66 | 1-46 | 3-16 | 4/5 | 2 | N E P Q Y H D G N G H S L P G M F D F | 700 |
| 1NC70 | 1-46 | 3-16/6-19 | 4/5 | 3 | N E P Q Y Y D G S G H S L P G M F D Y | 701 |
| 1NC72 | 1-46 | 6-19/1-14 | 4/5 | 3 | A E A E S Q S H S R P I M F D F | 702 |
| 1NC94 | 1-46 | 6-13/6-19 | 4/5 | 3 | A E A A S D S H S R P I M F D H | 703 |
| 1NC95 | 1-46 | 3-16/6-19 | 4/5 | 4 | L E A D G S D Y S P K M F D F | 704 |
| 1NC107 | 1-46 | 3-3/5-12 | 4/5 | 5 | L E A D G D D Y S P K M F D Y | 705 |
| 1NC108 | 1-46 | 3-9/3-16 | 4/5 | 4 | R E A D Y H D G N G H T L P G M F D F | 706 |
| 1NC109 | 1-46 | 5-1/6-19 | 4/5 | 5 | L E A D G D D Y S P K M F D Y | 707 |
| 1NC110 | 1-46 | 5-24/6-19 | 4/5 | 4 | L E A D G D N Y S P K M V D Y | 708 |
| 1NC116 | 1-46 | 2-21 | 4 | 2 | N E P Q Y H S L P G M F D Y | 709 |

TABLE 3b-continued

| | | | | | | |
|---|---|---|---|---|---|---|
| 1NC118 | 1-46 | 3-9/5-12 | 4 | 3 | L E A D G G D Y S P K M F D Y | 710 |
| 1NC122 | 1-46 | 3-16/3-3 | 4 | 4 | L E A D G A D Y S P K M F D F | 711 |
| 1NC123 | 1-46 | 6-19 | 4 | 3 | A E A E S Q S H S R P I M F D Y | 712 |
| 1NC127 | 1-46 | 6-13/6-19 | 4/5 | 3 | A E A A S D S H S R P I M F D H | 713 |
| 1B344 | 1-46 | 3-22/1-26 | 1/5 | 4 | L E A E S D S H S R P I M F D H | 714 |
| 1B2416 | 1-46 | 1-14/3-16 | 4 | 4 | N E P Q Y H D D N G H S L P G M I D Y | 715 |
| 1B2503 | 1-46 | 6-19 | 5 | 3 | A E A E S Q S H S R P I M F D S | 716 |
| 1B2573 | 1-46 | 3-22 | 4/5 | 2 | N E P Q Y H D G N G H S L P G M F D S | 717 |
| 1NC5 | 1-69 | 3-3 | 3 | 1 | G R Q T F R A I W S G P P V V F D I | 718 |
| 1NC126 | 1-69 | 3-3 | 3 | 1 | G R Q T F R A I W S G P P A V F D I | 719 |
| 1NC16 | 4-34 | 3-10 | 5 | 2 | A V A G L W F E D A Y N W F G P | 720 |
| 1NC21 | 4-34 | 3-10 | 5 | 2 | A V K G L W F D E T Y T W F G P | 721 |
| 1NC54 | 4-34 | 3-10 | 5 | 2 | A V K G F W F D E P S T W F G P | 722 |
| 1NC57 | 4-34 | 3-10 | 5 | 2 | A V K G F W F D D P Y T W F G P | 723 |
| 1NC115 | 4-34 | 3-10 | 5 | 2 | A V K G F W F D E V Y N W F G P | 724 |

| Ab Name | (+) | Length | Mutations HC | Primer Set | k/l | Vk/l | Jk/l | (-) |
|---|---|---|---|---|---|---|---|---|
| 1NC2 | 2 | 19 | 74 | new | 1 | 1-47 | 3 | 1 |
| 1NC3 | 2 | 16 | 86 | NEW | 1 | 1-47 | 6/7 | 1 |
| 1NC7 | 2 | 16 | 77 | new | 1 | 1-47 | 6/7 | 1 |
| 1NC9 | 4 | 19 | 67 | new | 1 | 1-47 | 3 | 1 |
| 1NC18 | 1 | 14 | 85 | new | | | | |
| 1NC24 | 2 | 19 | 79 | new | 1 | 1-47 | 3 | 1 |
| 1NC29 | 1 | 19 | 87 | new | | | | |
| 1NC33 | 0 | 15 | 84 | new | 1 | 1-47 | 3 | 2 |
| 1NC46 | 3 | 19 | 85 | new | 1 | 1-47 | 3 | 1 |
| 1NC48 | 1 | 19 | 88 | new | 1 | 1-47 | 3 | 1 |
| 1NC52 | 1 | 19 | 82 | new | 1 | 1-47 | 3 | 1 |
| 1NC56 | 2 | 15 | 91 | new | 1 | 1-47 | 3 | 1 |
| 1NC60 | 3 | 16 | 72 | new | 1 | 1-47 | 3 | 1 |
| 1NC66 | 2 | 19 | 91 | new | 1 | 1-47 | 3 | 1 |
| 1NC70 | 1 | 19 | 85 | new | 1 | 1-47 | 3 | 1 |
| 1NC72 | 2 | 16 | 77 | new | 1 | 1-47 | 6/7 | 1 |
| 1NC94 | 3 | 16 | 81 | new | 1 | 1-47 | 3 | 2 |
| 1NC95 | 0 | 15 | 93 | new | | | | |
| 1NC107 | 1 | 15 | 90 | new | 1 | 1-47 | 3 | 1 |
| 1NC108 | 3 | 19 | 85 | new | 1 | 1-47 | 3 | 1 |
| 1NC109 | 1 | 15 | 85 | new | | | | |
| 1NC110 | 1 | 15 | 88 | new | | | | |
| 1NC116 | 1 | 14 | 83 | new | | | | |

TABLE 3b-continued

| | | | | | | | | |
|---|---|---|---|---|---|---|---|---|
| 1NC118 | 0 | 15 | 86 | new | l | 1-47 | 3 | 1 |
| 1NC122 | 1 | 15 | 94 | new | l | 1-47 | 3 | 1 |
| 1NC123 | 2 | 16 | 78 | new | l | 1-47 | 3 | 1 |
| 1NC127 | 3 | 16 | 81 | new | l | 1-47 | 3 | 2 |
| 1B344 | 3 | 16 | 72 | new | l | 1-47 | 3 | 1 |
| 1B2416 | 2 | 19 | 81 | new | | | | |
| 1B2503 | 1 | 16 | 78 | new | l | 1-47 | 3 | 1 |
| 1B2573 | 2 | 19 | 81 | new | | | | |
| 1NC5 | 2 | 18 | 47 | new | k | 3-11 | 2 | 0 |
| 1NC126 | 2 | 18 | 47 | new | | | | |
| 1NC16 | 0 | 16 | 75 | new | k | 1D-39 | 2/3 | 0 |
| 1NC21 | 1 | 16 | 58 | new | | | | |
| 1NC54 | 1 | 16 | 59 | new | | | | |
| 1NC57 | 1 | 16 | 61 | new | | | | |
| 1NC115 | 1 | 16 | 58 | new | | | | |

| Ab Name | CDR3 (aa) | SEQ ID NO | (+) | Length | Mutations LC | Binding | NEUT | # of Relatives |
|---|---|---|---|---|---|---|---|---|
| 1NC2 | A V Y D S S L S L G L | 725 | 0 | 11 | 47 | | + | 15 |
| 1NC3 | A T Y D S Q R S I R L | 726 | 2 | 11 | 55 | | + | 1 |
| 1NC7 | A T Y D S Q G S T R L | 727 | 1 | 11 | 51 | | + | 1 |
| 1NC9 | A A Y D S T F S L P V | 728 | 0 | 11 | 53 | ? | + | 2 |
| 1NC18 | ND | | | | | | ND | 1 |
| 1NC24 | A A Y D S S L S L R L | 729 | 0 | 11 | 30 | | + | 2 |
| 1NC29 | ND | | | | | | ND | 1 |
| 1NC33 | A T Y D T D L S L R L | 730 | 1 | 11 | 49 | | + | 1 |
| 1NC46 | A A Y D S A V S L P V | 731 | 0 | 11 | 52 | | ND | 1 |
| 1NC48 | A A Y D S T L S L R L | 732 | 1 | 11 | 37 | | ND | 1 |
| 1NC52 | A A Y D S T F S L P V | 733 | 0 | 11 | 54 | | ND | 1 |
| 1NC56 | A T Y D T G L S L R L | 734 | 1 | 11 | 58 | | ND | 1 |
| 1NC60 | A T Y D S G W S I R L | 735 | 1 | 11 | 46 | | + | 3 |
| 1NC66 | A A Y D S T L S L R L | 736 | 1 | 11 | 33 | | ND | 1 |
| 1NC70 | A A Y D S T L S L R L | 737 | 1 | 11 | 40 | | ND | 1 |
| 1NC72 | A T Y D S Q G S T R L | 738 | 1 | 11 | 51 | | + | 2 |
| 1NC94 | A T Y D S D G S I R L | 739 | 1 | 11 | 41 | | − | 5 |
| 1NC95 | ND | | | | | | ND | 1 |
| 1NC107 | A T Y D T G L S L R L | 740 | 1 | 11 | 58 | | ND | 1 |
| 1NC108 | A A F D S A L S L P L | 741 | 0 | 11 | 51 | | + | 1 |
| 1NC109 | ND | | | | | | ND | 1 |
| 1NC110 | ND | | | | | | ND | 1 |
| 1NC116 | ND | | | | | | ND | 1 |
| 1NC118 | A T Y D T G L S L R L | 742 | 1 | 11 | 54 | | ND | 1 |

TABLE 3b-continued

| | | | | | | | | |
|---|---|---|---|---|---|---|---|---|
| 1NC122 | G T Y D T S L S L R L | 743 | 1 | 11 | 57 | | ND | 1 |
| 1NC123 | A T Y D S H G S I R L | 744 | 2 | 11 | 48 | | - | 1 |
| 1NC127 | A T Y D S D G S I R L | 745 | 1 | 11 | 41 | ? | + | 5 |
| 1B344 | A T Y D S G W S I R L | 746 | 1 | 11 | 46 | | + | 1 |
| 1B2416 | ND | | | | | | ND | 1 |
| 1B2503 | G T Y D S Q G S T R L | 882 | 1 | 11 | 49 | | ND | 1 |
| 1B2573 | ND | | | | | | - | 2 |
| 1NC5 | Q H R S N W P W T | 883 | 2 | 9 | | CD4BS | + | 1 |
| 1NC126 | ND | | | | | | ND | 1 |
| 1NC16 | Q Q S F A V P Y T | 884 | 0 | 9 | 35 | ND | ND | 1 |
| 1NC21 | ND | | | | | ND | ND | 1 |
| 1NC54 | ND | | | | | ND | ND | 1 |
| 1NC57 | ND | | | | | ND | ND | 1 |
| 1NC115 | ND | | | | | ND | ND | 1 |

TABLE 3c

| Ab Name | VH | D | JH | (-) | CDR3 (aa) | SEQ ID NO |
|---|---|---|---|---|---|---|
| 8ANC13 | 1-46 | 3-16 | 6 | 4 | D G L G E V A P D Y R Y G I D V | 885 |
| 8ANC22 | 1-46 | 3-16 | 6 | 3 | D G L G E V A P A Y L Y G I D A | 747 |
| 8ANC26 | 1-46 | 3-16 | 6 | 3 | D G L G E V A P A Y L Y G I D A | 748 |
| 8ANC37 | 1-46 | 3-16 | 6 | 3 | D G L G E V A P A Y L Y G I D A | 749 |
| 8ANC41 | 1-46 | 3-16 | 6 | 3 | D G L G E L A P A Y H Y G I D V | 750 |
| 8ANC50 | 1-46 | 3-16 | 6 | 3 | D G L G E L A P A Y Q Y G I D V | 751 |
| 8ANC88 | 1-46 | 3-16 | 6 | 4 | D G L G E V A P D Y R Y G I D V | 752 |
| 8ANC127 | 1-46 | 3-16 | 6 | 3 | D G L G E V A P A Y L Y G I D A | 753 |
| 8ANC131 | 1-46 | 3-16 | 6 | 3 | D G L G E V A P D Y R Y G I D V | 754 |
| 8ANC142 | 1-69 | 3-3 | ND | 2 | T S T Y D Q W S G L H H D G V M A F S S | 755 |
| 8ANC46 | 1-69 | 3-22/2-15 | 3 | 2 | S S G N F E F A F E I | 756 |
| 8ANC191 | 1-69 | 3-22/2-15 | 3 | 2 | S S G N Y D F A Y D I | 757 |
| 8ANC196 | 1-69 | 3-22/2-15 | 3 | 2 | S S G N Y D F A F D I | 758 |
| 8ANC14 | 1-24 | 6-13/5-5 | 4 | 4 | A D R F K V A Q D E G L F V I F D Y | 759 |
| 8ANC34 | 1-24 | 6-13/5-5 | 4 | 4 | A D P F K V A Q D E G L Y V I F D Y | 760 |
| 8ANC58 | 1-24 | 6-13/5-5 | 4 | 4 | A D P F K V A Q D E G L Y V I F D Y | 761 |
| 8ANC168 | 1-24 | 6-13/5-5 | 4 | 4 | A D P F K V A Q D E G L F V I F D Y | 762 |
| 8ANC5 | 1-69 | 4-17/3-10 | 6 | 8 | D R G D T R L L D Y G D Y E D E R Y Y Y G M D V | 763 |
| 8ANC7 | 1-69 | 4-17/3-10 | 6 | 8 | D R G D T R L L D Y G D Y E D E R Y Y Y G M D V | 764 |
| 8ANC9 | 1-69 | 4-17/3-10 | 6 | 8 | D R G D T R L L D Y G D Y E D E R Y Y Y G M D V | 765 |
| 8ANC77 | 1-69 | 4-17/3-10 | 6 | 8 | D R G D T R L L D Y G D Y E D E R Y Y Y G M D V | 766 |
| 8ANC107 | 1-69 | 4-17/3-10 | 6 | 8 | D R G D T R L L D Y G D Y E D E R Y Y Y G M D V | 767 |

TABLE 3c-continued

| | | | | | | |
|---|---|---|---|---|---|---|
| 8ANC108 | 1-69 | 4-17/3-10 | 6 | 8 | D R G D T R L L D Y G D Y E D E R Y Y Y G M D V | 768 |
| 8ANC137 | 1-69 | 4-17/3-10 | 6 | 8 | D R G D T R L L D Y G D Y E D E R Y Y Y G M D V | 769 |
| 8ANC16 | 1-69 | 2-2 | 3 | 2 | D R S S A I G Y C S S I S C Y K G S F D I | 770 |
| 8ANC24 | 1-24 | 2-2 | 6 | 1 | G G L Y C S S I S C I M D V | 771 |
| 8ANC25 | 1-24 | 2-2 | 6 | 1 | G G L Y C S S I S C I M D V | 772 |
| 8ANC38 | 3-43 | 3-16 | 5 | 1 | N G F D V | 773 |

| Ab Name | (+) | Length | Mutations HC | Primer Set | k/l | Vk/l | Jk/l | (−) |
|---|---|---|---|---|---|---|---|---|
| 8ANC13 | 1 | 16 | 75 | new | k | 3-11 | 2/3 | 1 |
| 8ANC22 | 0 | 16 | 85 | new | | | | |
| 8ANC26 | 0 | 16 | 76 | new | k | 3-11 | 2/3 | 1 |
| 8ANC37 | 0 | 16 | 82 | new | k | 3-11 | 2/3 | 1 |
| 8ANC41 | 1 | 16 | 71 | new | k | 3-11 | 2/3 | 1 |
| 8ANC50 | 0 | 16 | 71 | new | k | 3-11 | 2/3 | 1 |
| 8ANC88 | 0 | 16 | 73 | new | k | 3-11 | 2/3 | 1 |
| 8ANC127 | 0 | 16 | 86 | new | | | | |
| 8ANC131 | 1 | 16 | 75 | new | k | 3-11 | 2/3 | 1 |
| 8ANC142 | 2 | 20 | 72 | new | k | 1-5 | 1/5 | 1 |
| 8ANC46 | 0 | 11 | 30 | old | l | 1-40 | 3 | 1 |
| 8ANC191 | 0 | 11 | 28 | old | | | | |
| 8ANC196 | 0 | 11 | 25 | old | | | | |
| 8ANC14 | 1 | 18 | 11 | old | k | 3-11 | 4 | 0 |
| 8ANC34 | 0 | 18 | 10 | new | | | | |
| 8ANC58 | 0 | 18 | 18 | new | | | | |
| 8ANC168 | 1 | 18 | 11 | new | | | | |
| 8ANC5 | 3 | 24 | 40 | old | k | 1D-33 | 2 | 0 |
| 8ANC7 | 3 | 24 | 37 | new | | | | |
| 8ANC9 | 3 | 24 | 35 | old | | | | |
| 8ANC77 | 3 | 24 | 50 | old | | | | |
| 8ANC107 | 3 | 24 | 38 | old | | | | |
| 8ANC108 | 3 | 24 | 37 | old | | | | |
| 8ANC137 | 3 | 24 | 37 | new | | | | |
| 8ANC16 | 1 | 21 | 12 | old | k | 3-15 | 2 | 0 |
| 8ANC24 | 0 | 14 | 12 | old | k | 3-15 | 1 | 0 |
| 8ANC25 | 0 | 14 | 6 | old | | | | |
| 8ANC38 | 0 | 5 | 70 | new | l | 2-11 | 3 | 0 |

| Ab Name | CDR3 (aa) | SEQ ID NO | (+) | Length | Mutations LC | Binding | NEUT | # of Relatives |
|---|---|---|---|---|---|---|---|---|
| 8ANC13 | Q E Y S S T P Y N | 774 | 0 | 9 | 50 | | + | 1 |
| 8ANC22 | ND | | | | | | ND | 1 |
| 8ANC26 | Q E Y S S T P Y N | 775 | 0 | 9 | 55 | CD4BS | + | 2 |

TABLE 3c-continued

| | | | | | | | | |
|---|---|---|---|---|---|---|---|---|
| 8ANC37 | Q E Y S S T P Y N | 776 | 0 | 9 | 50 | CD4BS | + | 8 |
| 8ANC41 | Q E Y S S T P Y N | 777 | 0 | 9 | 42 | | + | 2 |
| 8ANC50 | Q E Y S S T P Y N | 778 | 0 | 9 | 46 | CD4BS | + | 2 |
| 8ANC88 | Q E Y S S T P Y N | 779 | 0 | 9 | 46 | | ND | 1 |
| 8ANC127 | ND | | | | | | ND | 1 |
| 8ANC131 | Q E Y S S T P Y N | 780 | 0 | 9 | 45 | CD4BS | + | 1 |
| 8ANC142 | Q Q Y D T Y P G T | 781 | 0 | 9 | 43 | ? | + | 2 |
| 8ANC46 | Q S Y D R S L R G S V | 782 | 1 | 11 | 30 | ND | ND | 1 |
| 8ANC191 | ND | | | | | | ND | 1 |
| 8ANC196 | ND | | | | | | ND | 1 |
| 8ANC14 | Q Q R A N W R L L T | 783 | 2 | 10 | 9 | CD4i | + | 2 |
| 8ANC34 | ND | | | | | | ND | 5 |
| 8ANC58 | ND | | | | | | ND | 3 |
| 8ANC168 | ND | | | | | | ND | 1 |
| 8ANC5 | Q Q Y S N L P Y T | 784 | 0 | 9 | 17 | CD4i | - | 2 |
| 8ANC7 | ND | | | | | | ND | 2 |
| 8ANC9 | ND | | | | | | ND | 1 |
| 8ANC77 | ND | | | | | | ND | 3 |
| 8ANC107 | ND | | | | | | ND | 2 |
| 8ANC108 | ND | | | | | | ND | 4 |
| 8ANC137 | ND | | | | | | ND | 1 |
| 8ANC16 | Q Q Y Y Q W L S Y T | 785 | 0 | 10 | 13 | ND | ND | 8 |
| 8ANC24 | Q Q Y N H W P Q T | 786 | 0 | 9 | 7 | CD4i | + | 1 |
| 8ANC25 | ND | | | | | | ND | 1 |
| 8ANC38 | C L K K T S S Y V | 787 | 2 | 9 | 41 | CORE | + | 2 |

TABLE 3d

| Ab Name | VH | D | JH | (-) | CDR3 (aa) | SEQ ID NO |
|---|---|---|---|---|---|---|
| 12A1 | 1-2 | 5-12/3-10 | 4/5 | 4 | D E S G D D L K W H L H P | 886 |
| 12A2 | 1-2 | 4-17 | 4/5 | 3 | D G S G D D T S W H L H P | 788 |
| 12A4 | 1-2 | 5-12/3-10 | 4/5 | 4 | D E S G D D L K W H L H P | 789 |
| 12A6 | 1-2 | 1-26/3-10 | 4/5 | 2 | D G S G D A T S W H L H P | 790 |
| 12A7 | 1-2 | 1-26 | 4/5 | 4 | D G S G D A R D W H L D P | 791 |

TABLE 3d-continued

| | | | | | | |
|---|---|---|---|---|---|---|
| 12A9 | 1-2 | 3-3 | 4/5 | 5 | D R R D D D R A W L L D P | 792 |
| 12A12 | 1-2 | 1-26/3-10 | 4/5 | 4 | D G S G D D T S W H L D P | 793 |
| 12A13 | 1-2 | 1-26 | 4/5 | 4 | D G S G D D T S W Y L D P | 794 |
| 12A20 | 1-2 | 1-26 | 4/5 | 3 | D G S G D A R D W H L H P | 795 |
| 12A22 | 1-2 | 3-16 | 4/5 | 4 | D G G G D D R T W L L D A | 796 |
| 12A23 | 1-2 | 3-3 | 4/5 | 5 | D R R D D G L D W L L D P | 797 |
| 12A27 | 1-2 | 1-26/3-10 | 4/5 | 3 | D G S G D D T S W H L H P | 798 |
| 12A46 | 1-2 | 3-10 | 4/5 | 1 | G G G D G R N W H L H P | 799 |
| 12A55 | 1-2 | 1-26 | 4/5 | 4 | D G S G D D R N W H L D P | 800 |
| 12A56 | 1-2 | 1-26 | 4/5 | 4 | D E S G Y D L N W H L D S | 801 |

| Ab Name | (+) | Length | # Mutations HC | Primer Set | k/l | Vk/l | Jk/l | (-) |
|---|---|---|---|---|---|---|---|---|
| 12A1 | 2 | 13 | 60 | new | k | 1D-33 | 3 | 0 |
| 12A2 | 2 | 13 | 67 | new | k | 1D-33 | 3 | 10 |
| 12A4 | 2 | 13 | 59 | new | k | 1D-33 | 3 | 0 |
| 12A6 | 2 | 13 | 61 | new | k | 1D-33 | 3 | 1 |
| 12A7 | 1 | 13 | 62 | new | k | 1D-33 | 3 | 1 |
| 12A9 | 3 | 13 | 62 | new | k | 1D-33 | 3 | 1 |
| 12A12 | 1 | 13 | 60 | new | k | 1D-33 | 3 | 1 |
| 12A13 | 0 | 13 | 61 | new | k | 1D-33 | 3 | 1 |
| 12A20 | 3 | 13 | 61 | new | k | 1D-33 | 3 | 1 |
| 12A22 | 1 | 13 | 61 | new | k | 1D-33 | 3 | 1 |
| 12A23 | 2 | 13 | 51 | new | k | 1D-33 | 3 | 1 |
| 12A27 | 2 | 13 | 68 | new | k | 1D-33 | 3 | 1 |
| 12A46 | 3 | 13 | 62 | new | k | 1D-33 | 3 | 1 |
| 12A55 | 1 | 13 | 63 | new | k | 1D-33 | 3 | 2 |
| 12A56 | 1 | 13 | 66 | new | k | 1D-33 | 3 | 1 |

| Ab Name | CDR3 (aa) | SEQ ID NO | (+) | Length | Mutations LC | Binding | NEUT | # of Relatives |
|---|---|---|---|---|---|---|---|---|
| 12A1 | A A F Q W | 887 | 0 | 5 | 39 | | ND | 1 |
| 12A2 | A V L E F | 802 | 0 | 5 | 44 | | + | 3 |
| 12A4 | A V F Q W | 803 | 0 | 5 | 36 | CD4BS | + | 3 |
| 12A6 | A V L E F | 804 | 0 | 5 | 39 | | + | 1 |
| 12A7 | A V L E F | 805 | 0 | 5 | 41 | | ND | 2 |
| 12A9 | Q L F E F | 806 | 0 | 5 | 39 | | ND | 1 |
| 12A12 | A V L E F | 807 | 0 | 5 | 41 | CD4BS | + | 1 |
| 12A13 | A V V E F | 808 | 0 | 5 | 41 | | ND | 1 |
| 12A20 | A A L E F | 809 | 0 | 5 | 40 | | + | 1 |
| 12A22 | S V Y E F | 810 | 0 | 5 | 39 | | + | 2 |
| 12A23 | Q L F E F | 811 | 0 | 5 | 39 | | + | 1 |

TABLE 3d-continued

| | | | | | | | |
|---|---|---|---|---|---|---|---|
| 12A27 | A V L E F | 812 | 0 | 5 | 40 | ND | 1 |
| 12A46 | A S L E F | 813 | 0 | 5 | 43 | + | 1 |
| 12A55 | E V Y E F | 814 | 0 | 5 | 37 | + | 1 |
| 12A56 | E S F Q W | 815 | 0 | 5 | 37 | ND | 1 |

TABLE 3e

| Ab Name | VH | D | JH | (−) | CDR3 (aa) | SEQ ID NO |
|---|---|---|---|---|---|---|
| 3B191 | 1-2 | 6-25/6-13/6-6 | 2/6 | 3 | Q R S D Y W D F D V | 816 |
| 3B6 | 4-39 | 3-9/3-10 | 3 | 2 | I P Y H S E S Y Y K V V I G G F D V | 817 |
| 3B8 | 1-69 | 4-17/3-22 | 4 | 3 | D H G D P R T G Y Y F D Y | 818 |
| 3B27 | 3-64 | 3-9/1-26/4-17 | 5 | 1 | G P L L R Y L D S | 819 |
| 3B41 | 1-24 | 3-16 | 6 | 4 | K A K D Y Y Y E S S D Y S P Y Y Y Y Y M D V | 820 |
| 3B46 | 4-31 | 3-3/2-8 | 4/5 | 0 | G S G R W T I G A R I Y F D N | 821 |
| 3B144 | 3-30 | 3-3/3-10/3-16 | 4/5 | 2 | T P P H Y D V L T G Y P S S V L E F | 822 |
| 3B117 | 1-69 | 5-5/5-18/5-24 | 3 | 2 | A T G Y S Y G Y L D A F D I | 823 |
| 3A869 | 4-4/4-59 | 6-19/5-12/1-26 | 4 | 2 | E K G Q W L T V P P Y Y F D S | 824 |
| 3A228 | 5-51 | 3-3/2-2 | 6 | 1 | T R C F G A N C F N F M D V | 825 |
| 3A461 | 1-46 | 2-2 | 4 | 1 | P E P S S I V A P L Y Y | 826 |
| 3A18 | 1-69 | 3-10/5-24 | 3 | 3 | D P Q V E V R G N A F D I | 827 |
| 3A125 | 1-46 | 1-20/1-7/3-10 | 3 | 2 | P Q Y N L G R D P L D V | 828 |
| 3A255 | 4-59 | 3-3/3-9 | 4 | 3 | A D Y D L L T S S Y H F D S | 829 |
| 3A233 | 4-59/4-61 | 3-3/4-17 | 4/5 | 3 | L D G E A F R Y Y L D L | 830 |

| Ab Name | (+) | Length | # Mutations HC | Primer Set | k/l | Vk/l | Jk/l | (−) |
|---|---|---|---|---|---|---|---|---|
| 3B191 | 1 | 10 | 81 | new | k | 1D-33 | 3 | 1 |
| 3B6 | 1 | 18 | 50 | new | k | 1-9 | 1/3 | 0 |
| 3B8 | 2 | 13 | 50 | new | k | 3-20 | 1/5 | 2 |
| 3B27 | 0 | 9 | 18 | old | k | 3-11 | 1/5 | 0 |
| 3B41 | 2 | 22 | 17 | old | k | 3-20 | 2 | 0 |
| 3B46 | 2 | 15 | 22 | old | k | 3-20 | 1/4 | 0 |
| 3B144 | 1 | 18 | 23 | old | k | 3-15 | 1/5 | 0 |
| 3B117 | 0 | 14 | 22 | new | l | 1-44 | 1 | 2 |
| 3A869 | 1 | 1 | 33 | old | k | 1D-39 | 5 | 0 |
| 3A228 | 1 | 1 | 34 | old | k | 4-1 | 3 | 0 |
| 3A461 | 0 | 1 | 15 | old | k | 3-20 | 1 | 0 |

TABLE 3e-continued

| | | | | | | | | |
|---|---|---|---|---|---|---|---|---|
| 3A18 | 1 | 1 | 40 | old | k | 1D-39 | 5 | 0 |
| 3A125 | 1 | 1 | 22 | old | k | 3-20 | 1 | 0 |
| 3A255 | 1 | 1 | 35 | old | l | 7-43 | 3 | 0 |
| 3A233 | 1 | 1 | 32 | old | l | 2-14 | 2/3 | 0 |

| Ab Name | CDR3 (aa) | SEQ ID NO | (+) | Length | Binding | NEUT | # of Relatives |
|---|---|---|---|---|---|---|---|
| 3B191 | Q V Y E F | 831 | 0 | 5 | CD4BS | + | 7 |
| 3B6 | Q Q L A T | 832 | 0 | 5 | GP41 | + | 11 |
| 3B8 | Q Q Y D D A P I T | 833 | 0 | 9 | GP41 | - | 9 |
| 3B27 | Q H R T N W P P S I T | 834 | 2 | 11 | CD4i | - | 3 |
| 3B41 | Q Q Y G T S S C T | 835 | 0 | 9 | CD4i | - | 2 |
| 3B46 | Q Q Y G S S P P T | 836 | 0 | 9 | GP41 | ND | 2 |
| 3B144 | Q Q Y N N W P P I T | 837 | 0 | 10 | ND | ND | 4 |
| 3B117 | A A W D D T L Y V | 838 | 0 | 9 | ND | ND | 1 |
| 3A869 | Q Q S H S P S | 839 | 1 | 7 | CD4BS | + | 1 |
| 3A228 | Q Q Y Y I S P | 840 | 0 | 7 | VAR | + | 4 |
| 3A461 | Q Q Y G T L H P R T | 841 | 2 | 10 | GP41 | - | 3 |
| 3A18 | Q Q T Y T S P I T | 842 | 0 | 9 | GP41 | - | 2 |
| 3A125 | Q Q Y G L S P W T | 843 | 0 | 9 | GP41 | - | 4 |
| 3A255 | L L L P Y Y G G P W I | 844 | 0 | 11 | GP41 | - | 2 |
| 3A233 | S S F T P T N T L V | 845 | 0 | 10 | GP41 | - | 2 |

TABLE 3f

| Ab Name | VH | D | JH | (-) | CDR3 (aa) | SEQ ID NO |
|---|---|---|---|---|---|---|
| 1B2434 | 15341 | 3-22/5-5 | 1 | 4 | N E A D Y H D G N G H S L R G M F D Y | 846 |
| 1B218 | 1-69 | 3-3 | 3 | 1 | G R Q T F R A I W S G P P V V F D I | 847 |
| 1B331 | 4-34 | 3-9/3-3 | 6 | 3 | R Y F D W S P F R R D T Y G T D V | 848 |
| 1B2174 | 4-34 | 3-9/3-3 | 6 | 3 | R Y L D W S P I G R D T Y G T D V | 849 |
| 1B2055 | 1-69 | 2-21 | 2/5 | 1 | G L C R G G N C R L G P S G W L D P | 850 |
| 1B2133 | 1-3 | 4-17/2-21 | 4 | 1 | V A Y V H V V T T R S L D N | 851 |
| 1A64 | 4-59 | 5-5/5-18 | 6 | 2 | H E A P R Y S Y A F R R Y Y H Y G L D V | 852 |
| 1A621 | 4-59 | 3-3/3-9 | 6 | 1 | V I S G R I T I F Y Y N Y I D V | 853 |
| 1A577 | 3-48 | 3-10/3-16 | 1 | 3 | G T L W F G E S G L R L D H | 854 |
| 1A732 | 3-7/3-73 | 3-22/3-10 | 6 | 2 | N R R V A M P E A M I L S F Y M D V | 855 |
| 1A74 | 4-34 | 3-3/3-9 | 4 | 1 | V V P M F S I F G V V K A N Y F D Y | 856 |
| 1A695 | 4-59 | 3-3/3-9 | 3 | 2 | A G L D Y N F W N G K G R K G A F D V | 857 |
| 1A479 | 1-69 | 3-22 | 4 | 1 | G F R G S P F S S G S L Y F D S | 858 |
| 1A182 | 1-69 | 4-17/1-26 | 6 | 6 | A V I T D L H T F G D Y E L E D P S Y Y Y M D V | 859 |
| 1A693 | 3-23 | 7-27/3-22 | 4 | 1 | R G R R Q I G D Y | 860 |

TABLE 3f-continued

| | | | | | |
|---|---|---|---|---|---|
| 1A79 | 5-51 | 3-9/3-3 | 3 | 4 S Y Y D F S I G D G N D A F D V | 861 |
| 1A27 | 3-11 | 3-6/5-5 | 5 | 2 D T T T F T T F G G G P N M G G F D P | 862 |

| Ab Name | (+) | Length | # Mutations HC | Primer Set | k/l | Vk/l | Jk/l | (−) |
|---|---|---|---|---|---|---|---|---|
| 1B2434 | 2 | 19 | 74 | new | l | 1-47 | 3 | 1 |
| 1B218 | 2 | 18 | 47 | new | k | 3-11 | 2 | 0 |
| 1B331 | 3 | 17 | 40 | new | k | 4-1 | 1/4 | 0 |
| 1B2174 | 2 | 17 | 41 | new | k | 4-1 | 1/4 | 0 |
| 1B2055 | 2 | 18 | 62 | new | k | 3-15 | 1 | 2 |
| 1B2133 | 1 | 14 | 22 | new | k | 1D-39 | 1 | 0 |
| 1A64 | 5 | 20 | 20 | old | l | 1-44 | 3 | 2 |
| 1A621 | 1 | 16 | 30 | old | l | 1-47 | 3 | 1 |
| 1A577 | 1 | 14 | 15 | old | k | 1-16 | 2 | 0 |
| 1A732 | 2 | 18 | 9 | old | k | 3-20 | 3 | 0 |
| 1A74 | 1 | 18 | 23 | old | l | 1-51 | 3 | 1 |
| 1A695 | 3 | 19 | 9 | old | k | 1-5 | 1 | 1 |
| 1A479 | 1 | 16 | 25 | old | k | 3-20 | 1 | 0 |
| 1A182 | 1 | 24 | 28 | old | k | 1-5 | 1 | 0 |
| 1A693 | 3 | 9 | 17 | old | k | 1D-39 | 2 | 0 |
| 1A79 | 0 | 16 | 30 | old | l | 1-47 | 1 | 3 |
| 1A27 | 0 | 19 | 50 | old | | 1-9 | 1 | 0 |

| Ab Name | CDR3 (aa) | SEQ ID NO | (+) | Length | Binding | NEUT | # of Relatives |
|---|---|---|---|---|---|---|---|
| 1B2434 | A V Y D S S L S L G L | 863 | 0 | 11 | CD4BS | + | 7 |
| 1B218 | Q H R S N W P W T | 864 | 2 | 9 | CD4BS | + | 10 |
| 1B331 | H Q Y F S T P R T | 865 | 2 | 9 | CORE | + | 4 |
| 1B2174 | H Q Y F N T P R T | 866 | 2 | 9 | | ND | 1 |
| 1B2055 | Q Q Y E D P P W T | 867 | 0 | 9 | ND | ND | 3 |
| 1B2133 | Q Q T Y S N P R M | 868 | 1 | 9 | CD4i | − | 2 |
| 1A64 | A S W D D S L S G W V | 869 | 0 | 11 | CD4BS | + | 24 |
| 1A621 | A S W D N S L S G P V | 870 | 0 | 11 | CD4BS | + | 3 |
| 1A577 | Q Q Y N S F P P T | 871 | 0 | 9 | CD4BS | + | 8 |
| 1A732 | Q Q Y G R S P | 872 | 1 | 7 | CD4BS | + | 1 |
| 1A74 | G T W D S S L S A V L | 873 | 0 | 11 | CORE | + | 2 |
| 1A695 | Q Q Y D S | 874 | 0 | 5 | CORE | + | 2 |
| 1A479 | H Q Y A Y S P R T | 875 | 2 | 9 | CORE | + | 11 |
| 1A182 | Q Q Y K S Y S G T | 876 | 0 | 9 | CD4i | + | 3 |
| 1A693 | Q H S F G S P P W T | 877 | 1 | 11 | CD4i | − | 1 |
| 1A79 | A A W D D S F D Y V | 878 | 0 | 10 | V3 | + | 27 |
| 1A27 | Q Q L R T | 879 | 1 | 5 | G P 41 | − | 8 |

TABLE 4a

| Patient 3, Clone RU01 | | | | | | |
|---|---|---|---|---|---|---|
| | 3BNC62 | 3BNC176 | 3BNC60 | 3BNC117 | 3BNC95 | 3BNC104 |
| MW965.26 | <0.09 | <0.10 | <0.04 | <0.09 | <0.07 | >50 |
| BaL.26 | <0.09 | <0.10 | <0.04 | <0.09 | <0.07 | 0.025 |
| DJ263.8 | <0.09 | <0.10 | <0.04 | <0.09 | <0.07 | 0.054 |
| 6535.3 | 0.68 | 0.46 | 0.54 | 0.55 | 1.0 | >50 |
| RHPA4259.7 | <0.09 | <0.10 | <0.05 | 0.041 | <0.07 | 0.0252 |
| TRO.11 | <0.09 | <0.10 | <0.05 | 0.077 | <0.07 | 3.791 |
| PVO.4 | <0.09 | <0.10 | 0.09 | <0.09 | <0.07 | 0.348 |
| YU2.DG | <0.09 | <0.10 | <0.05 | 0.054 | <0.07 | 0.034 |

| Patient 3, Clone RU01 | | | | | | |
|---|---|---|---|---|---|---|
| | 3BNC91 | 3BNC55 | 3BNC89 | 3ANC3 | 3BNC53 | 3BNC72 |
| MW965.26 | <0.08 | 0.04 | >0.05 | 0.18 | 0.09 | <0.06 |
| BaL.26 | >178 | >30 | >110 | >50 | >30 | >139 |
| DJ263.8 | >178 | >30 | >110 | >50 | >30 | >139 |
| 6535.3 | 1 | 2.6 | 1.7 | >50 | 13.6 | 8.49 |
| RHPA4259.7 | <0.08 | 2.2 | 12.4 | 7.66 | 100.6 | >139 |
| TRO.11 | 3.06 | 18.4 | 52.4 | 10.76 | >155 | >139 |
| PVO.4 | 0.44 | 3.9 | 2.7 | 36.77 | >155 | >139 |
| YU2.DG | <0.08 | 0.9 | 0.39 | 35.01 | >155 | >139 |

| Patient 3, Clone RU01 | | | | |
|---|---|---|---|---|
| | 3BNC156 | 3BNC158 | 3BNC153 | 3BNC108 |
| MW965.26 | 0.08 | 0.11 | 0.15 | ND |
| BaL.26 | >111 | >109 | >100 | 20.6 |
| DJ263.8 | >111 | >109 | >100 | >55 |
| 6535.3 | 11.1 | 9.9 | 28.9 | >55 |
| RHPA4259.7 | >111 | >109 | >100 | 45.91 |
| TRO.11 | >111 | >109 | >100 | >55 |
| PVO.4 | >111 | >109 | >100 | >55 |
| YU2.DG | >111 | >109 | >100 | 25.5 |

| Patient 3, Clone RU01 | | | | |
|---|---|---|---|---|
| | 3BNC142 | 3BNC66 | 3BNC42 | 3BNC102 |
| MW965.26 | 0.14 | 1.24 | ND | >50 |
| BaL.26 | >172 | >189 | >26 | >50 |
| DJ263.8 | >172 | >189 | >26 | >50 |
| 6535.3 | >172 | >189 | >26 | >50 |
| RHPA4259.7 | >172 | >189 | >26 | >50 |
| TRO.11 | >172 | >189 | >26 | >50 |
| PVO.4 | >172 | >189 | NF | >50 |
| YU2.DG | >172 | >189 | >26 | >50 |

| Patient 3 Clones RU02-07 | | | | | | |
|---|---|---|---|---|---|---|
| | 3A67 | 3A383 | 3BNC8 | 3ANC44 | 3A576 | 3ANC38 |
| MW965.26 | 0.1 | 0.5 | 0.74 | 25.49 | >50 | >50 |
| BaL.26 | 19.2 | 5.3 | >50 | 27.91 | 27 | >50 |
| DJ263.8 | >50 | >50 | >50 | >50 | >50 | >50 |
| 6535.3 | >50 | ND | >50 | >50 | >50 | >50 |
| RHPA4259.7 | >50 | ND | >50 | >50 | >50 | >50 |
| TRO.11 | >50 | ND | >50 | >50 | >50 | >50 |
| PVO.4 | >50 | ND | >50 | >50 | >50 | >50 |
| YU2.DG | >50 | ND | >50 | >50 | >50 | >50 |

| B12 and NIH 45 Clone | | | |
|---|---|---|---|
| | B12 | VRC01 | NIH45-46 |
| MW965.26 | 0.2 | <0.08 | 0.04 |
| BaL.26 | 0.2 | 0.1 | <0.04 |
| DJ263.8 | >50 | 0.08 | <0.04 |
| 6535.3 | 1.4 | 0.539 | 0.14 |
| RHPA4259.7 | 0.1 | 0.06 | 0.034 |

TABLE 4a-continued

| | | | |
|---|---|---|---|
| TRO.11 | >50 | 0.2 | 1.9 |
| PVO.4 | >50 | 0.2 | 0.17 |
| YU2.DG | 2.2 | 0.12 | <0.05 |

TABLE 4b

| Patient 1, Clone RU08 | | | | | | |
|---|---|---|---|---|---|---|
| | 1B2640 | 1B2530 | 1B2364 | 1NC2 | 1NC9 | 1B2490 |
| MW965.26 | 41.76 | 0.762 | 1.85 | >50 | >50 | >50 |
| BaL.26 | 0.08 | >50 | >25 | 0.11 | 1.37 | 0.058 |
| DJ263.8 | >50 | 2.71 | 3.75 | >50 | >50 | >50 |
| 6535.3 | >50 | >50 | >25 | >50 | >50 | >50 |
| RHPA4259.7 | 0.04 | 3.6 | 2.18 | 0.59 | 0.09 | 0.414 |
| TRO.11 | 0.23 | 0.516 | 0.27 | 0.17 | 0.2 | 1.06 |
| PVO.4 | 1.05 | 0.275 | 0.161 | 0.37 | 0.34 | 2.97 |
| YU2.DG | 0.2 | 0.209 | 2.46 | 0.12 | 0.13 | 0.125 |
| **Patient 1, Clone RU08** | | | | | | |
| | 1B2351 | 1B344 | 1NC24 | 1NC3 | 1NC7 | 1NC33 |
| MW965.26 | >50 | >50 | >50 | >25 | >50 | >50 |
| BaL.26 | >50 | >50 | >50 | >25 | >50 | >50 |
| DJ263.8 | 8.46 | 12.62 | >50 | >25 | >50 | >50 |
| 6535.3 | >50 | >50 | >50 | >25 | >50 | 22.04 |
| RHPA4259.7 | 36.48 | 29.98 | >50 | >25 | 34.27 | >50 |
| TRO.11 | 0.331 | 0.27 | 0.2 | 3.37 | 16.57 | >50 |
| PVO.4 | 0.25 | 0.27 | 0.19 | 6.68 | 1.39 | 1.84 |
| YU2.DG | 0.058 | 0.25 | 0.16 | 18.26 | >50 | >50 |

TABLE 4b-continued

| Patient 1, Clone RU08 | | | | |
|---|---|---|---|---|
| | 1NC108 | 1B2644 | 1B2339 | 1NC123 |
| MW965.26 | >50 | >25 | >25 | >50 |
| BaL.26 | >50 | >25 | >25 | >50 |
| DJ263.8 | >50 | >25 | >25 | >50 |
| 6535.3 | >50 | >25 | >25 | >50 |
| RHPA4259.7 | >50 | >25 | >25 | >50 |
| TRO.11 | 19.37 | >25 | >25 | >50 |
| PVO.4 | 3.13 | >25 | >25 | >50 |
| YU2.DG | >50 | >25 | >25 | >50 |

| Patient 1, Clone RU09 | |
|---|---|
| | 1B218 |
| MW965.26 | >119 |
| BaL.26 | 1.1 |
| DJ263.8 | >119 |
| 6535.3 | 3.6 |
| RHPA4259.7 | >100 |
| TRO.11 | >100 |
| PVO.4 | >100 |
| YU2.DG | >100 |

TABLE 4c

| Patient 8, Clone RU10 | | | | | | | |
|---|---|---|---|---|---|---|---|
| | 8ANC192 | 8ANC134 | 8ANC13 | 8ANC131 | 8ANC182 | 8ANC50 | 8ANC45 |
| MW965.26 | >73 | >50 | >50 | >50 | >115 | >50 | >50 |
| BaL.26 | 0.08 | 0.02 | 0.04 | 0.06 | 0.08 | 0.17 | 0.296 |
| DJ263.8 | <0.03 | 0.003 | 0.008 | 0.004 | <0.05 | 0.04 | 0.041 |
| 6535.3 | 0.34 | 0.06 | 0.27 | 0.2 | 0.89 | 2.27 | 0.813 |
| RHPA4259.7 | >50 | >50 | >50 | >50 | >100 | >50 | >50 |
| TRO.11 | >100 | >50 | >50 | >50 | >100 | >50 | >50 |
| PVO.4 | 0.89 | 0.46 | 0.63 | 0.81 | 1.2 | 3.89 | 4.259 |
| YU2.DG | 0.09 | 0.15 | 0.21 | 0.18 | 0.22 | 0.42 | 0.499 |

| Patient 8, Clones RU11-15 | | | | | |
|---|---|---|---|---|---|
| | 8ANC57 | 8ANC195 | 8ANC24 | 8ANC14 | 8ACN5 |
| MW965.26 | 24.1 | >50 | 0.29 | 2.01 | >50 |
| BaL.26 | 4.35 | >50 | 47.53 | >50 | >50 |
| DJ263.8 | 30.19 | >50 | >50 | >50 | >50 |
| 6535.3 | >103 | 0.2 | >50 | >50 | >50 |
| RHPA4259.7 | 1.65 | 0.34 | >50 | >50 | >50 |
| TRO.11 | 32.07 | 0.18 | >50 | >50 | >50 |
| PVO.4 | 101.15 | 0.52 | >50 | >50 | >50 |
| YU2.DG | 27.52 | 0.79 | >50 | >50 | >50 |

TABLE 4d

| Patient 12, Clone RU16 | | | | | | |
|---|---|---|---|---|---|---|
| | 12A12 | 12A21 | 12A4 | 12A37 | 12A22 | 12A16 |
| MW965.26 | 0.042 | 0.075 | 0.098 | 0.056 | 0.06 | 0.167 |
| BaL.26 | 0.017 | <0.001 | <0.001 | 0.005 | 0.04 | 0.042 |
| DJ263.8 | 0.002 | 0.035 | 0.017 | 0.013 | 0.08 | 0.012 |
| 6535.3 | 21.97 | >50 | >50 | >50 | >25 | 15.44 |
| RHPA4259.7 | 0.086 | 0.038 | 0.041 | 0.042 | 0.04 | 0.207 |
| TRO.11 | 0.288 | 0.164 | 0.257 | 0.827 | 0.56 | 0.751 |
| PVO.4 | 0.928 | 0.584 | 0.819 | 0.516 | 0.45 | 2.44 |
| YU2.DG | 0.084 | 0.015 | 0.018 | 0.019 | 0.11 | 0.234 |

TABLE 4d-continued

| Patient 12, Clone RU16 | | | | | |
|---|---|---|---|---|---|
| | 12A20 | 12A6 | 12A23 | 12A46 | 12A55 |
| MW965.26 | 0.192 | 0.112 | 5.1 | >50 | 0.58 |
| BaL.26 | 0.035 | 0.072 | 0.57 | 0.013 | 2.87 |
| DJ263.8 | 0.05 | 0.004 | 0.63 | 5.79 | >50 |
| 6535.3 | 48.73 | >24 | 14.73 | 48.85 | >50 |
| RHPA4259.7 | 0.109 | 0.227 | 0.496 | >50 | >50 |
| TRO.11 | 0.689 | 1.52 | 2.88 | >50 | 21.45 |
| PVO.4 | 3.04 | 3.32 | 2.24 | 2.18 | 0.99 |
| YU2.DG | 0.142 | 0.222 | 0.053 | 0.49 | 0.1 |

| B12 and NIH45 Clone | | | |
|---|---|---|---|
| | B12 | VRC01 | NIH45-46 |
| MW965.26 | 0.2 | <0.08 | 0.04 |
| BaL.26 | 0.2 | 0.1 | <0.04 |
| DJ263.8 | >50 | 0.08 | <0.04 |
| 6535.3 | 1.4 | 0.539 | 0.14 |
| RHPA4259.7 | 0.1 | 0.06 | <0.05 |
| TRO.11 | >50 | 0.2 | 1.9 |
| PVO.4 | >50 | 0.2 | 0.17 |
| YU2.DG | 2.2 | 0.12 | <0.05 |

TABLE 4e

| Patient 3, clone RU01 | | | | | | |
|---|---|---|---|---|---|---|
| | 3BNC62 | 3BNC176 | 3BNC60 | 3BNC117 | 3BNC95 | 3BNC104 |
| MW965.26 | <0.09 | <0.10 | 0.09 | <0.09 | <0.07 | >50 |
| BaL.26 | <0.09 | <0.10 | <0.04 | <0.09 | <0.07 | 0.09 |
| DJ263.8 | 0.1 | <0.10 | 0.1 | 0.1 | 0.1 | 0.187 |
| 6535.3 | 2.24 | 1.7 | 1.77 | 2.44 | 4.5 | >50 |
| RHPA4259.7 | <0.09 | <0.10 | 0.07 | 0.137 | <0.07 | 0.06 |
| TRO.11 | <0.09 | <0.10 | 0.12 | 0.077 | <0.07 | 30.847 |
| PVO.4 | 0.23 | 0.16 | 0.27 | 0.19 | 0.23 | 0.901 |
| YU2.DG | <0.09 | <0.10 | 0.07 | 0.054 | <0.07 | 0.097 |

| Patient 3, clone RU01 | | | | | | | |
|---|---|---|---|---|---|---|---|
| | 3BNC91 | 3BNC55 | 3BNC89 | 3ANC3 | 3BNC53 | 3BNC72 | 3BNC156 |
| MW965.26 | <0.08 | 0.15 | 0.16 | 0.64 | 0.61 | 0.37 | 0.47 |
| BaL.26 | >178 | >30 | >110 | >50 | >30 | >139 | >111 |
| DJ263.8 | >178 | >30 | >110 | >50 | >30 | >139 | >111 |
| 6535.3 | 6.7 | 5.53 | 5.92 | >50 | 73.38 | 133.665 | 69.66 |
| RHPA4259.7 | 0.52 | 8.03 | >110 | >50 | >155 | >139 | >111 |
| TRO.11 | 32.31 | 41.67 | >110 | >50 | >155 | >139 | >111 |
| PVO.4 | 2.65 | 6.5 | 10.18 | >50 | >155 | >139 | >111 |
| YU2.DG | <0.08 | 1.07 | 1.49 | >50 | >155 | >139 | >111 |

| Patient 3, clone RU01 | | | | | | | |
|---|---|---|---|---|---|---|---|
| | 3BNC158 | 3BNC153 | 3BNC108 | 3BNC142 | 3BNC66 | 3BNC42 | 3BNC102 |
| MW965.26 | 0.6 | 0.63 | ND | 0.8 | 29.98 | ND | >50 |
| BaL.26 | >109 | >100 | >55 | >172 | >189 | >26 | >50 |
| DJ263.8 | >109 | >100 | >55 | >172 | >189 | >26 | >50 |
| 6535.3 | 97.75 | >100 | >55 | >172 | >189 | >26 | >50 |
| RHPA4259.7 | >109 | >100 | >55 | >172 | >189 | >26 | >50 |
| TRO.11 | >109 | >100 | >55 | >172 | >189 | >26 | >50 |
| PVO.4 | >109 | >100 | >55 | >172 | >189 | ND | >50 |
| YU2.DG | >109 | >100 | >55 | >172 | >189 | >26 | >50 |

| Patient 3, Clones RU02-07 | | | | | | |
|---|---|---|---|---|---|---|
| | 3A67 | 3A383 | 3BNC8 | 3ANC44 | 3A576 | 3ANC38 |
| MW965.26 | 16 | >25 | 0.74 | >50 | >50 | >50 |
| BaL.26 | >50 | >25 | >50 | >50 | >50 | >50 |
| DJ263.8 | >50 | >25 | >50 | >50 | >50 | >50 |
| 6535.3 | >50 | ND | >50 | >50 | >50 | >50 |

TABLE 4e-continued

| | | | | | | |
|---|---|---|---|---|---|---|
| RHPA4259.7 | >50 | ND | >50 | >50 | >50 | >50 |
| TRO.11 | >50 | ND | >50 | >50 | >50 | >50 |
| PVO.4 | >50 | ND | >50 | >50 | >50 | >50 |
| YU2.DG | >50 | ND | >50 | >50 | >50 | >50 |

B12 and NIH 45 Clone

| | B12 | VRC01 | 45-46 |
|---|---|---|---|
| MW965.26 | ND | <0.08 | 0.21 |
| BaL.26 | ND | 0.1 | 0.06 |
| DJ263.8 | ND | 0.553 | 0.06 |
| 6535.3 | ND | 2.7 | 0.28 |
| RHPA4259.7 | 0.39 | 0.185 | 0.146 |
| TRO.11 | >50 | 0.832 | 9.56 |
| PVO.4 | >50 | 1.2 | 0.47 |
| YU2.DG | 7.8 | 0.372 | 0.08 |

TABLE 4f

Patient 1, Clone RU08

| | 1B2640 | 1B2530 | 1B2364 | 1NC2 | 1NC9 | 1B2490 | 1B2351 |
|---|---|---|---|---|---|---|---|
| MW965.26 | >50 | >50 | >25 | >50 | >50 | >50 | >50 |
| BaL.26 | 0.32 | >50 | >25 | 0.51 | 19.92 | 0.3 | >50 |
| DJ263.8 | >50 | >50 | >25 | >50 | >50 | >50 | >50 |
| 6535.3 | >50 | >50 | >25 | >50 | >50 | >50 | >50 |
| RHPA4259.7 | 0.25 | >50 | >25 | 4.33 | 0.4 | 1.97 | >50 |
| TRO.11 | 1.62 | 2.46 | 1.77 | 0.55 | 0.65 | 3.58 | 1.13 |
| PVO.4 | 2.97 | 1.25 | 0.65 | 1.08 | 1.32 | 10.57 | 0.88 |
| YU2.DG | 0.7 | 7.74 | >25 | 0.39 | 0.56 | 0.59 | 0.48 |

Patient 1, Clone RU08

| | 1B344 | 1NC24 | 1NC3 | 1NC7 | 1NC33 | 1NC108 | 1B2644 |
|---|---|---|---|---|---|---|---|
| MW965.26 | >50 | >50 | >25 | >50 | >50 | >50 | >25 |
| BaL.26 | >50 | >50 | >25 | >50 | >50 | >50 | >25 |
| DJ263.8 | >50 | >50 | >25 | >50 | >50 | >50 | >25 |
| 6535.3 | >50 | >50 | >25 | >50 | >50 | >50 | >25 |
| RHPA4259.7 | >50 | >50 | >25 | >50 | >50 | >50 | >25 |
| TRO.11 | 0.89 | 0.66 | >25 | >50 | >50 | >50 | >25 |
| PVO.4 | 0.94 | 0.6 | >25 | 7.17 | 10.12 | 25.08 | >25 |
| YU2.DG | 1.29 | 0.55 | >25 | >50 | >50 | >50 | >25 |

Patient 1, Clone RU08

| | 1B2339 | 1NC123 |
|---|---|---|
| MW965.26 | >25 | >50 |
| BaL.26 | >25 | >50 |
| DJ263.8 | >25 | >50 |
| 6535.3 | >25 | >50 |
| RHPA4259.7 | >25 | >50 |
| TRO.11 | >25 | >50 |
| PVO.4 | >25 | >50 |
| YU2.DG | >25 | >50 |

Patient 1, Clone RU09

| | 1B218 |
|---|---|
| MW965.26 | >119 |
| BaL.26 | 5.61 |
| DJ263.8 | >119 |
| 6535.3 | 35.12 |
| RHPA4259.7 | >100 |
| TRO.11 | >100 |
| PVO.4 | >100 |
| YU2.DG | >100 |

TABLE 4g

| Patient 8, Clone RU 10 | | | | | | | |
|---|---|---|---|---|---|---|---|
| | 8ANC192 | 8ANC134 | 8ANC13 | 8ANC131 | 8ANC182 | 8ANC50 | 8ANC45 |
| TRO.11 | >73 | >50 | >50 | >50 | >115 | >50 | >50 |
| BaL.26 | 0.43 | 0.11 | 0.18 | 0.31 | 0.73 | 0.77 | 7.45 |
| DJ263.8 | 0.1 | 0.044 | 0.069 | 0.046 | 0.11 | 0.15 | 0.166 |
| 6535.3 | 1.43 | 2 | 2.3 | 1.9 | 3.93 | 13.65 | 10.473 |
| RHPA4259.7 | >100 | >50 | >50 | >50 | >100 | >50 | >50 |
| TRO.11 | >100 | >50 | >50 | >50 | >100 | >50 | >50 |
| PVO.4 | 3.94 | 2.5 | 3.7 | 4.9 | 4.43 | 14.99 | 17.315 |
| YU2.DG | 0.51 | 0.616 | 1.07 | 0.92 | 1.46 | 1.59 | 2.942 |

| Patient 8, Clones RU11-15 | | | | | |
|---|---|---|---|---|---|
| | 8AN57 | 8AN195 | 8AN24 | 8AN14 | 8AN5 |
| TRO.11 | >103 | >50 | 0.76 | 6.64 | >50 |
| BaL.26 | 24.76 | >50 | >50 | >50 | >50 |
| DJ263.8 | >103 | >50 | >50 | >50 | >50 |
| 6535.3 | >103 | 0.91 | >50 | >50 | >50 |
| RHPA4259.7 | 14.44 | 1.56 | >50 | >50 | >50 |
| TRO.11 | >103 | 0.89 | >50 | >50 | >50 |
| PVO.4 | >103 | 1.87 | >50 | >50 | >50 |
| YU2.DG | 91.49 | 2.77 | >50 | >50 | >50 |

TABLE 4h

| Patient 12, Clone RU16 | | | | | | |
|---|---|---|---|---|---|---|
| | 12A12 | 12A21 | 12A4 | 12A37 | 12A22 | 12A16 |
| MW965.26 | 0.2 | 0.85 | 1.24 | 0.3 | 0.21 | 0.58 |
| BaL.26 | 0.08 | 0.004 | 0.007 | 0.03 | 0.14 | 0.25 |
| DJ263.8 | 0.31 | 0.42 | 1.06 | 0.57 | 1.86 | 0.12 |
| 6535.3 | >50 | >50 | >50 | >50 | >25 | >42 |
| RHPA4259.7 | 0.4 | 0.13 | 0.19 | 0.19 | 0.13 | 0.93 |
| TRO.11 | 0.98 | 0.57 | 1.12 | 3.81 | 1.94 | 2.57 |
| PVO.4 | 3.15 | 2.09 | 2.95 | 1.8 | 1.49 | 8.72 |
| YU2.DG | 0.31 | 0.06 | 0.1 | 0.07 | 0.36 | 1.13 |

| Patient 12, Clone RU16 | | | | | |
|---|---|---|---|---|---|
| | 12A20 | 12A6 | 12A23 | 12A46 | 12A55 |
| MW965.26 | 2.2 | 0.52 | >50 | >50 | 4.49 |
| BaL.26 | 0.23 | 0.47 | 3.47 | 0.08 | >50 |
| DJ263.8 | ND | 0.08 | 30.81 | >50 | >50 |

TABLE 4h-continued

| | | | | | |
|---|---|---|---|---|---|
| 6535.3 | ND | >24 | >50 | >50 | >50 |
| RHPA4259.7 | 0.49 | 1.02 | 1.69 | >50 | >50 |
| TRO.11 | 2.41 | 5.15 | 10.11 | >50 | >50 |
| PVO.4 | 11.2 | 17.34 | 7.81 | 797 | 4.3 |
| YU2.DG | 0.67 | 1.2 | 0.19 | 0.25 | 0.29 |

| B12 and NIH45 Clone | | | |
|---|---|---|---|
| | B12 | VRC01 | NIH45-46 |
| MW965.26 | 0.2 | <0.08 | 0.04 |
| BaL.26 | 0.2 | 0.1 | <0.04 |
| DJ263.8 | >50 | 0.08 | <0.04 |
| 6535.3 | 1.4 | 0.539 | 0.14 |
| RHPA4259.7 | 0.1 | 0.06 | <0.05 |
| TRO.11 | >50 | 0.2 | 1.9 |
| PVO.4 | >50 | 0.2 | 0.17 |
| YU2.DG | 2.2 | 0.12 | <0.05 |

TABLE 5a

| In vitro Tzm-bl neutralization assay, extended panel IC50 values | | | | | | | |
|---|---|---|---|---|---|---|---|
| | B12 | VRC01 | NIH45-46 | 3BNC60 | 3BNC62 | 3BNC117 | 3BNC55 |
| Q842.d12 | >50 | 0.03 | 0.008 | 0.01 | <0.01 | <0.01 | 0.011 |
| 3415.v1.c1 | 2.5 | 0.06 | 0.017 | 0.1 | 0.17 | 0.17 | 0.11 |
| 3365.v2.c20 | >50 | 0.03 | 0.029 | 0.02 | 0.03 | 0.03 | 0.221 |
| H086.8* | >50 | >50 | >30 | >15 | >15 | >15 | >30 |
| ZM53M.PB12 | >50 | 1.3 | 0.187 | 0.22 | 0.3 | 0.21 | 12.549 |
| Du172.17* | 0.3 | >50 | >30 | 3.81 | 1.72 | 1.19 | 3.518 |
| ZM109F.PB4 | >50 | 0.128 | 0.059 | 0.22 | 0.14 | 0.14 | 0.083 |
| 3016.v5.c45 | 1.1 | 0.16 | >30 | 1.4 | 0.42 | 1.38 | >30 |
| 231965.c1 | 0.07 | 0.34 | 0.021 | 0.07 | 0.05 | 0.05 | 0.505 |
| X1254_c3 | >50 | 0.07 | 0.027 | 0.09 | 0.08 | 0.08 | 0.138 |
| 250-4* | >50 | >50 | >30 | >15 | >15 | >15 | 0.236 |
| 251-18 | >50 | 2.5 | 1.445 | 0.35 | 0.32 | 0.26 | >30 |

TABLE 5a-continued

| | | | | | | | |
|---|---|---|---|---|---|---|---|
| 278-50* | >50 | >50 | >30 | >15 | >15 | >15 | >30 |
| 620345.c1* | >50 | >50 | >30 | >15 | >15 | >15 | >30 |
| R1166.c1 | >50 | 1.7 | 0.445 | 0.14 | 0.32 | 0.17 | 0.298 |

In vitro Tzm-bl neutralization assay, extended panel IC50 values

| | 1NC9 | 1B2530 | 8ANC131 | 8ANC134 | 8ANC195 | 12A12 | 12A21 |
|---|---|---|---|---|---|---|---|
| Q842.d12 | 0.02 | 0.249 | 0.053 | 0.061 | >30 | 0.014 | 0.015 |
| 3415.v1.c1 | 0.266 | 0.065 | 0.299 | 0.323 | 2.404 | 0.121 | 0.82 |
| 3365.v2.c20 | 0.329 | 4.357 | >30 | >30 | >30 | 0.068 | 0.045 |
| H086.8* | >30 | >30 | >50 | >50 | 0.095 | >30 | >30 |
| ZM53M.PB12 | 0.705 | 0.912 | >30 | >30 | 9.626 | 0.593 | 0.42 |
| Du172.17* | >30 | >30 | >30 | >30 | 10.797 | 0.196 | 0.126 |
| ZM109F.PB4 | 0.023 | >30 | >30 | >30 | >30 | 0.148 | 2.104 |
| 3016.v5.c45 | >30 | >30 | >30 | >30 | 0.195 | 1.163 | 0.097 |
| 231965.c1 | 0.393 | 0.168 | 6.346 | >30 | 0.514 | 2.217 | >30 |
| X1254_c3 | >30 | >30 | >30 | >30 | 1.524 | 1.032 | 26.793 |
| 250-4* | >30 | >30 | >50 | >50 | >50 | >30 | >30 |
| 251-18 | 1.234 | 9.847 | 0.968 | 1.56 | 0.284 | 2.622 | 1.713 |
| 278-50* | >30 | >30 | >50 | >50 | >50 | >30 | >30 |
| 620345.c1* | >30 | >30 | >50 | >50 | >50 | >30 | >30 |
| R1166.c1 | 0.651 | 0.119 | >30 | >30 | 0.986 | 0.342 | 0.292 |

TABLE 5b

In vitro Tzm-bl neutralization assay, extended panel IC80 values

| | B12 | VRC01 | 45-46 | 3BNC60 | 3BNC62 | 3BNC117 | 3BNC55 |
|---|---|---|---|---|---|---|---|
| Q842.d12 | >50 | 0.096 | 0.026 | 0.03 | 0.03 | 0.01 | 0.062 |
| 3415.v1.c1 | 14.1 | 0.15 | 0.069 | 0.37 | 0.4 | 0.47 | 0.388 |
| 3365.v2.c20 | >50 | 0.17 | 0.114 | 0.08 | 0.09 | 0.1 | 2.341 |
| H086.8* | >50 | >50 | >30 | >15 | >15 | >15 | >30 |
| ZM53M.PB12 | >50 | 4 | 0.652 | 0.76 | 1.1 | 0.85 | >30 |
| Du172.17* | 2.6 | >50 | >30 | >15 | 12.18 | 8.9 | >30 |
| ZM109F.PB4 | >50 | 0.754 | 0.22 | 1.23 | 0.78 | 0.88 | 0.396 |
| 3016.v5.c45 | 4 | 0.42 | >30 | 7.38 | 2.35 | >15 | >30 |
| 231965.c1 | 0.16 | 1.2 | 0.1 | 0.25 | 0.22 | 0.22 | 2.78 |
| X1254_c3 | >50 | 0.19 | 0.078 | 0.29 | 0.27 | 0.27 | 0.571 |
| 250-4* | >50 | >50 | >30 | >15 | >15 | >15 | 1.922 |
| 251-18 | >50 | 11.2 | 5.255 | 0.96 | 1 | 0.82 | >30 |
| 278-50* | >50 | >50 | >30 | >15 | >15 | >15 | >30 |
| 620345.c1* | >50 | >50 | >30 | >15 | >15 | >15 | >30 |
| R1166.c1 | >50 | 4.6 | 1.679 | 0.51 | 0.89 | 0.64 | 2.351 |

In vitro Tzm-bl neutralization assay, extended panel IC80 values

| | 1NC9 | 1B2530 | 8ANC131 | 8ANC134 | 8ANC195 | 12A12 | 12A21 |
|---|---|---|---|---|---|---|---|
| Q842.d12 | 0.133 | 2.191 | 0.179 | 0.205 | >30 | 0.06 | 0.066 |
| 3415.v1.c1 | 1.002 | 0.35 | 1.555 | 2.643 | 17.743 | 0.418 | 0.296 |
| 3365.v2.c20 | 2.163 | >30 | >30 | >30 | >30 | 0.192 | 0.166 |
| H086.8* | >30 | >30 | >50 | >50 | 5.328 | >30 | >30 |
| ZM53M.PB12 | 2.771 | 4.022 | >30 | >30 | >30 | 2.069 | 1.458 |
| Du172.17* | >30 | >30 | >30 | >30 | >30 | 0.992 | 0.037 |
| ZM109F.PB4 | 0.146 | >30 | >30 | >30 | >30 | 0.698 | 13.686 |
| 3016.v5.c45 | >30 | >30 | >30 | >30 | 0.872 | 11.864 | 0.358 |
| 231965.c1 | 2.276 | 0.963 | >30 | >30 | 2.355 | 15.102 | >30 |
| X1254_c3 | >30 | >30 | >30 | >30 | 6.949 | 5.777 | >30 |
| 250-4* | >30 | >30 | >50 | >50 | >50 | >30 | >30 |
| 251-18 | 6.291 | >30 | 5.55 | 6.281 | 1.511 | 9.39 | 6.063 |
| 278-50* | >30 | >30 | >50 | >50 | >50 | >30 | >30 |
| 620345.c1* | >30 | >30 | >50 | >50 | >50 | >30 | >30 |
| R1166.c1 | 2.669 | 0.684 | >30 | >30 | 4.83 | 1.85 | 2.137 |

TABLE 6

Affinity of IgG Antibodies to YU-2 gp140 and 2CC-core Ligands Measured by Surface Plasmon Resonance

| | gp140 $k_a$ ($M^{-1}s^{-1}$) | $k_d$ ($s^{-1}$) | $K_D$ (M) | 2CC-Core ka ($M^{-1}s^{-1}$) | $k_d$ ($s^{-1}$) | $K_D$ (M) |
|---|---|---|---|---|---|---|
| 12A12 | 4.59E+04 | 1.44E−05 | 3.15E−10 | 6.33E+04 | 1.70E−06 | 2.69E−11 |
| 12A21 | 9.18E+04 | 3.44E−07 | 3.75E12 | 1.82E+05 | 3.30E−04 | 1.81E−09 |
| 12AGL | / | / | / | / | / | / |
| 3BNC60 | 2.73E+04 | 1.86E−04 | 6.81E−09 | 3.02E+04 | 1.64E−03 | 5.45E−08 |
| 3BNC117 | 3.04E+04 | 1.99E−04 | 6.54E−09 | 1.49E−03 | 4.05E+04 | 3.68E−08 |
| 3BNC55 | 1.31E+04 | 7.55E−04 | 5.78E−08 | 8.15E−04 | 3.16E+04 | 2.57E−08 |
| 3BNC66 | 1.60E+04 | 1.41E−03 | 8.81E−08 | 3.96E+04 | 1.33E−03 | 3.36E−08 |
| 3BNC156 | 1.13E+04 | 1.98E−03 | 1.75E−07 | 1.88E+04 | 1.53E−03 | 8.12E−08 |
| 3BNC108 | / | / | / | / | / | / |
| 3BNC60GL | / | / | / | / | / | / |
| 8ANC131 | 6.59E+04 | 1.09E−03 | 1.65E−08 | 4.88E+04 | 3.23E−03 | 6.61E−08 |
| 8ANC134 | 1.55E+04 | 1.74E−03 | 1.13E−07 | 2.08E+04 | 9.57E−04 | 4.61E−08 |
| 8AGL | / | / | / | / | / | / |
| 8ANC195 | 4.88E+04 | 1.67E−03 | 3.43E−08 | 2.41E+04 | 1.32E−03 | 5.47E−08 |
| 1NC9 | 4.83E+04 | 5.81E−04 | 1.20E−08 | 5.11E+04 | 2.36E−04 | 4.61E−09 |
| 1B2530 | 4.74E+04 | 1.62E−03 | 3.42E−08 | 6.83E+04 | 4.02E−04 | 5.90E−09 |
| 1GL | / | / | / | / | / | / |
| 4546 | 4.26E+04 | 2.87E−04 | 6.75E−09 | 1.12E+05 | 4.94E−04 | 4.40E−09 |
| VRC01 | 1.83E+04 | 8.08E−06 | 4.41E−10 | 2.84E+04 | 3.25E−05 | 1.15E−09 |

TABLE 7a

Replacement/Silent mutation ratios for heavy chain sequences of 10 selected antibodies

| | All Nucleotides | Consensus Nucleotides | Non Consensus Nucleotides |
|---|---|---|---|
| 3BNC117HC | 1.8 | 1.0 | 3.5 |
| 3BNC60HC | 2.0 | 1.1 | 4.4 |
| 12A12HC | 2.8 | 1.7 | 6.3 |
| 12A21HC | 2.6 | 1.5 | 4.8 |
| NIH4546HC | 1.7 | 0.9 | 5.5 |
| VRCO1HC | 2.2 | 1.1 | 22.0 |
| 8ANC131HC | 2.7 | 1.3 | 8.0 |
| 8ANC134HC | 2.2 | 1.5 | 3.7 |
| 1B2530HC | 2.0 | 0.9 | 11.0 |
| 1NC9HC | 1.9 | 0.7 | 12.0 |

TABLE 7b

Replacement/Silent mutation ratios for light chain sequences of 10 selected antibodies

| | All Nucleotides | Consensus Nucleotides | Non Consensus Nucleotides |
|---|---|---|---|
| 3BNC117KC | 1.7 | 0.8 | 2.8 |
| 3BNC60KC | 1.7 | 0.7 | 4.0 |
| 12A12KC | 1.7 | 0.6 | 4.0 |
| 12A21KC | 2.5 | 1.4 | 4.3 |
| NIH4546KC | 1.7 | 0.9 | 3.0 |
| VRCO1KC | 1.8 | 0.8 | 4.0 |
| 8ANC131KC | 1.5 | 0.5 | 4.2 |
| 8ANC134KC | 1.5 | 0.5 | 4.2 |
| 1B2530LC | 1.9 | 2.0 | 1.8 |
| 1NC9LC | 1.2 | 0.9 | 1.8 |

TABLE 8

Crystallization data collection and refinement statistics

| Crystal | 3BN60 Fab |
|---|---|
| Data collection* | |
| Wavelength (Å) | 0.9537 |
| Space group | P21 |
| Unit Cell dimensions | |
| a (Å) | 63.6 |
| b (Å) | 155.7 |
| c (Å) | 74.8 |
| α, β, γ (Y) | 90.0, 110.4, 90.0 |
| Resolution, (Å) | 39.172.65 |
| $R_{mrgd}$-F (%)[§] | 8.3 (55.5) |
| $R_{meas}$ (%)[§] | 7.7 (53.4) |
| I/σI | 15.7 (2.5) |
| Completeness (%) | 96.0 (68.1) |
| Multiplicity | 5.0 (3.6) |
| Reflections | 192709 |
| Unique reflections | 38111 |
| Refinement | |
| Resolution (Å) | 39.172.65 |
| No. reflections | 37086 |
| $R_{work}/R_{free}$ (%)[†] | 20.7/25.7 |
| RMSD Bond lengths (Å) | 0.01 |
| RMSD Bond angles (Y) | 1.3 |
| Average B-factor $Å^2$ | 64.9 |
| Ramachandran analysis | |
| Favored (%) | 91.9 |
| Allowed (%) | 7.6 |
| Outlier (%) | 0.5 |

SEQUENCE LISTING

```
Sequence total quantity: 1197
SEQ ID NO: 1            moltype = AA  length = 123
FEATURE                 Location/Qualifiers
VARIANT                 2..3
                        note = Any naturally occurring amino acid or not present
VARIANT                 5
                        note = Any naturally occurring amino acid or not present
VARIANT                 10
                        note = Any naturally occurring amino acid or not present
VARIANT                 16
                        note = Any naturally occurring amino acid or not present
VARIANT                 19
                        note = Any naturally occurring amino acid or not present
VARIANT                 23
                        note = Any naturally occurring amino acid or not present
VARIANT                 28..29
                        note = Any naturally occurring amino acid or not present
VARIANT                 31..32
                        note = Any naturally occurring amino acid or not present
VARIANT                 34
                        note = Any naturally occurring amino acid or not present
VARIANT                 38
                        note = Any naturally occurring amino acid or not present
VARIANT                 44
                        note = Any naturally occurring amino acid or not present
VARIANT                 46..47
                        note = Any naturally occurring amino acid or not present
VARIANT                 51
                        note = Any naturally occurring amino acid or not present
VARIANT                 53
                        note = Any naturally occurring amino acid or not present
VARIANT                 56
                        note = Any naturally occurring amino acid or not present
VARIANT                 58..61
                        note = Any naturally occurring amino acid or not present
VARIANT                 63..64
                        note = Any naturally occurring amino acid or not present
VARIANT                 75..80
                        note = Any naturally occurring amino acid or not present
VARIANT                 82..84
                        note = Any naturally occurring amino acid or not present
VARIANT                 89
                        note = Any naturally occurring amino acid or not present
VARIANT                 93
                        note = Any naturally occurring amino acid or not present
VARIANT                 104..121
                        note = Any naturally occurring amino acid or not present
VARIANT                 123
                        note = Any naturally occurring amino acid or not present
source                  1..123
                        mol_type = protein
                        organism = Homo sapiens
SEQUENCE: 1
QXXLXQSGGX VKKPGXSVXV SCXASGYXXF XXYXIHWXRQ APGXGXXWVG XIXPRXGXXX  60
XAXXFQGRLS LTRDXXXXXX TXXXFMDLXG LRXDDTAVYF CARXXXXXXX XXXXXXXXXX  120
XDX                                                                123

SEQ ID NO: 2            moltype = AA  length = 101
FEATURE                 Location/Qualifiers
VARIANT                 3
                        note = Any naturally occurring amino acid or not present
VARIANT                 9
                        note = Any naturally occurring amino acid or not present
VARIANT                 13
                        note = Any naturally occurring amino acid or not present
VARIANT                 15
                        note = Any naturally occurring amino acid or not present
VARIANT                 18..19
                        note = Any naturally occurring amino acid or not present
VARIANT                 24..26
                        note = Any naturally occurring amino acid or not present
VARIANT                 28..34
                        note = Any naturally occurring amino acid or not present
VARIANT                 36
                        note = Any naturally occurring amino acid or not present
VARIANT                 42
                        note = Any naturally occurring amino acid or not present
VARIANT                 44
```

```
                         note = Any naturally occurring amino acid or not present
VARIANT                  51..53
                         note = Any naturally occurring amino acid or not present
VARIANT                  55..58
                         note = Any naturally occurring amino acid or not present
VARIANT                  62
                         note = Any naturally occurring amino acid or not present
VARIANT                  67..69
                         note = Any naturally occurring amino acid or not present
VARIANT                  71..72
                         note = Any naturally occurring amino acid or not present
VARIANT                  74
                         note = Any naturally occurring amino acid or not present
VARIANT                  76
                         note = Any naturally occurring amino acid or not present
VARIANT                  79
                         note = Any naturally occurring amino acid or not present
VARIANT                  81..82
                         note = Any naturally occurring amino acid or not present
VARIANT                  85
                         note = Any naturally occurring amino acid or not present
VARIANT                  87
                         note = Any naturally occurring amino acid or not present
VARIANT                  91..92
                         note = Any naturally occurring amino acid or not present
VARIANT                  95..101
                         note = Any naturally occurring amino acid or not present
source                   1..101
                         mol_type = protein
                         organism = Homo sapiens
SEQUENCE: 2
EIXLTQSPXS LSXSXGEXXT ISCXXXQXXX XXXXLXWYQQ RXGXAPRLLI XXXSXXXXGV  60
PXRFSGXXXG XXYXLXISXL XXDDXAXYFC XXYEXXXXXX X                      101

SEQ ID NO: 3             moltype = AA  length = 7
FEATURE                  Location/Qualifiers
source                   1..7
                         mol_type = protein
                         organism = Homo sapiens
SEQUENCE: 3
ASWDFDF                                                            7

SEQ ID NO: 4             moltype = AA  length = 5
FEATURE                  Location/Qualifiers
source                   1..5
                         mol_type = protein
                         organism = Homo sapiens
SEQUENCE: 4
TARDY                                                              5

SEQ ID NO: 5             moltype = AA  length = 129
FEATURE                  Location/Qualifiers
source                   1..129
                         mol_type = protein
                         organism = Homo sapiens
SEQUENCE: 5
QGQLVQSGGG LKKPGTSVTI SCLASEYTFN EFVIHWIRQA PGQGPLWLGL IKRSGRLMTA  60
YNFQDRLSLR RDRSTGTVFM ELRGLRPDDT AVYYCARDGL GEVAPDYRYG IDVWGQGSTV  120
IVTAASTKG                                                          129

SEQ ID NO: 6             moltype = AA  length = 129
FEATURE                  Location/Qualifiers
source                   1..129
                         mol_type = protein
                         organism = Homo sapiens
SEQUENCE: 6
QGLLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 7             moltype = AA  length = 129
FEATURE                  Location/Qualifiers
source                   1..129
                         mol_type = protein
                         organism = Homo sapiens
SEQUENCE: 7
FQGHLVQSGG GVKKPGTSVT LSCLASEYTF TEFTIHWIRQ APGQGPLWLG LIKRSGRLMT  60
SYRFQDRLSL RRDRSTGTVF MELRSLRTDD TAVYYCARDG LGELAPAYHY GIDAWGQGTT  120
VIVTSASTS                                                          129
```

-continued

```
SEQ ID NO: 8            moltype = AA  length = 127
FEATURE                 Location/Qualifiers
source                  1..127
                        mol_type = protein
                        organism = Homo sapiens
SEQUENCE: 8
QGHLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSAST                                                            127

SEQ ID NO: 9            moltype = AA  length = 128
FEATURE                 Location/Qualifiers
source                  1..128
                        mol_type = protein
                        organism = Homo sapiens
SEQUENCE: 9
QGHLVQSGGG VKKLGTSVTI SCLASEDTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTS                                                           128

SEQ ID NO: 10           moltype = AA  length = 127
FEATURE                 Location/Qualifiers
VARIANT                 10
                        note = Any naturally occurring amino acid or not present
source                  1..127
                        mol_type = protein
                        organism = Homo sapiens
SEQUENCE: 10
GHLVQSGGGX KKPGTSVTIS CLASEYTFTE FTIHRIRQAP GQGPLWLGLI KGSGRLMTSY  60
GFQDRLSLRR DRSTGTVFME LRSLRTDDTA VYYCARDGLG ELAPAYHYGI DVWGQGTTVI  120
VTSASTS                                                            127

SEQ ID NO: 11           moltype = AA  length = 132
FEATURE                 Location/Qualifiers
source                  1..132
                        mol_type = protein
                        organism = Homo sapiens
SEQUENCE: 11
GVHFQGHLVQ SGGGVKKPGS SVTISCLASE YTFTEFTIHW IRQAPGQGPL WLGLIKRSGR  60
LMTSYRFQDR LSLRRDRSTG TVFMELRGLR IDDTAVYYCA RDGLGEVAPA YLYGIDVWGQ  120
GTTVIVTSAS TS                                                      132

SEQ ID NO: 12           moltype = AA  length = 129
FEATURE                 Location/Qualifiers
source                  1..129
                        mol_type = protein
                        organism = Homo sapiens
SEQUENCE: 12
FQGQLVQSGG GVKKPGSSVT ISCLASEYTF TEFTIHWIRQ APGQGPLWLG LIKRSGRLMT  60
SYGFQDRLSV RRDRSTGTVF MELRSLRTDD TAVYYCARDG LGELAPAYHY GIDVWGQGTT  120
VIVTSASTS                                                          129

SEQ ID NO: 13           moltype = AA  length = 128
FEATURE                 Location/Qualifiers
source                  1..128
                        mol_type = protein
                        organism = Homo sapiens
SEQUENCE: 13
QGQLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTS                                                           128

SEQ ID NO: 14           moltype = AA  length = 130
FEATURE                 Location/Qualifiers
VARIANT                 9
                        note = Any naturally occurring amino acid or not present
VARIANT                 31
                        note = Any naturally occurring amino acid or not present
source                  1..130
                        mol_type = protein
                        organism = Homo sapiens
SEQUENCE: 14
QGHLVQSGXE VKKPGSSVKV SCKASGGTFS XYAIGWVRQA PGQGLEWMGG IIPILGTTNY  60
AQRFQGGVTI TADESTNTAY MDVSSLRSDD TAVYYCAKAP YRPRGSGNYY YAMDVWGQGT  120
TVIVSSASTS                                                         130

SEQ ID NO: 15           moltype = AA  length = 129
FEATURE                 Location/Qualifiers
```

```
source                  1..129
                        mol_type = protein
                        organism = Homo sapiens
SEQUENCE: 15
QGHLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 16           moltype = AA  length = 129
FEATURE                 Location/Qualifiers
source                  1..129
                        mol_type = protein
                        organism = Homo sapiens
SEQUENCE: 16
QGQLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVSSASTKG                                                          129

SEQ ID NO: 17           moltype = AA  length = 129
FEATURE                 Location/Qualifiers
source                  1..129
                        mol_type = protein
                        organism = Homo sapiens
SEQUENCE: 17
QGHLVQSGGG VKKLGTSVTI SCLVSEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 18           moltype = AA  length = 129
FEATURE                 Location/Qualifiers
source                  1..129
                        mol_type = protein
                        organism = Homo sapiens
SEQUENCE: 18
QGQLVQSGGG LKKPGTSVTI SCLASEYTFN EFVIHWIRQA PGQGPLWLGL IKRSGRLMTA  60
YNFQDRLRLR RDRSTGTVFM ELRGLRPDDT AVYYCARDGL GEVAPDYRYG IDVWGQGSTV  120
IVTAASTKG                                                          129

SEQ ID NO: 19           moltype = AA  length = 129
FEATURE                 Location/Qualifiers
source                  1..129
                        mol_type = protein
                        organism = Homo sapiens
SEQUENCE: 19
QGQLVQSGGG VKKPGTSVTI SCLASEYTFN EFVIHWIRQA PGQGPVWLGL IKRSGRLMTS  60
YKFQDRLSLR RDRSTGTVFM ELRGLRLDDT AVYYCARDGL GEVAPAYLYG IDAWGQGSTV  120
IVTSASTKG                                                          129

SEQ ID NO: 20           moltype = AA  length = 129
FEATURE                 Location/Qualifiers
source                  1..129
                        mol_type = protein
                        organism = Homo sapiens
SEQUENCE: 20
QGQLVQSGGG VKKPGASVTI SCLASEYTFN EFVIHWIRQA PGQGPLWLGL IKRSGRLMTA  60
YKFQDRLSLR RDRSTGTVFM ELRGLRPEDT AVYYCARDGL GEVAPDYRYG IDVWGQGSTV  120
IVSAASTKG                                                          129

SEQ ID NO: 21           moltype = AA  length = 129
FEATURE                 Location/Qualifiers
source                  1..129
                        mol_type = protein
                        organism = Homo sapiens
SEQUENCE: 21
QGHLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 22           moltype = AA  length = 132
FEATURE                 Location/Qualifiers
source                  1..132
                        mol_type = protein
                        organism = Homo sapiens
SEQUENCE: 22
GVHFQGHLVQ SGGGVKKPGS SVTISCLASE YTFTEFTIHW IRQAPGQGPL WLGLIKRSGR  60
LMTSYRFQDR LSLRRDRSTG TVFMELRGLR IDDTAVYYCA RDGLGEVAPA YLYGIDVWGQ  120
GSTVIVTSAS TS                                                      132

SEQ ID NO: 23           moltype = AA  length = 129
```

-continued

```
FEATURE                Location/Qualifiers
source                 1..129
                       mol_type = protein
                       organism = Homo sapiens
SEQUENCE: 23
QGQLVQSGGG VKKPGTSVTI SCLASEYTFT EFTIHWIRQA PGQGPLWLGL IKRSGRLMTA  60
YRFQDRLSLR RDRSTGTVFM ELRNLRMDDT AVYYCARDGL GELAPAYQYG IDVWGQGTTV  120
IVSSASTKG                                                          129

SEQ ID NO: 24          moltype = AA  length = 129
FEATURE                Location/Qualifiers
source                 1..129
                       mol_type = protein
                       organism = Homo sapiens
SEQUENCE: 24
QGHLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 25          moltype = AA  length = 129
FEATURE                Location/Qualifiers
source                 1..129
                       mol_type = protein
                       organism = Homo sapiens
SEQUENCE: 25
QGHLVQSGGG VKKLGTSVTI SCLASEDTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 26          moltype = AA  length = 129
FEATURE                Location/Qualifiers
source                 1..129
                       mol_type = protein
                       organism = Homo sapiens
SEQUENCE: 26
QGQLVQSGGG VKKPGTSVTI SCLASEYTFN EFVIHWIRQA PGQGPVWLGL IKRSGRLMTS  60
YKFQDRLSLR RDRSTGTVFM ELRGLRLDDT AVYYCARDGL GEVAPAYLYG IDAWGQGSKV  120
IVTPASTKG                                                          129

SEQ ID NO: 27          moltype = AA  length = 129
FEATURE                Location/Qualifiers
source                 1..129
                       mol_type = protein
                       organism = Homo sapiens
SEQUENCE: 27
QGQLVQSGGG VKKLGTSVTI PCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 28          moltype = AA  length = 129
FEATURE                Location/Qualifiers
source                 1..129
                       mol_type = protein
                       organism = Homo sapiens
SEQUENCE: 28
QGQLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 29          moltype = AA  length = 129
FEATURE                Location/Qualifiers
source                 1..129
                       mol_type = protein
                       organism = Homo sapiens
SEQUENCE: 29
QGHLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 30          moltype = AA  length = 129
FEATURE                Location/Qualifiers
source                 1..129
                       mol_type = protein
                       organism = Homo sapiens
SEQUENCE: 30
QGHLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129
```

-continued

```
SEQ ID NO: 31          moltype = AA  length = 129
FEATURE                Location/Qualifiers
source                 1..129
                       mol_type = protein
                       organism = Homo sapiens
SEQUENCE: 31
QGQLVQSGGG VKKTGTSVTI SCLASEYTFT EFTIHWIRQA PGQGPLWLGL IKRSGRLMTA  60
NRFQDRLSLR RDRSTGTVFM ELRSLRIDDT AVYYCARDGL GELAPAYHYG IDVWGQGTTI  120
IVTSASTKG                                                         129

SEQ ID NO: 32          moltype = AA  length = 129
FEATURE                Location/Qualifiers
source                 1..129
                       mol_type = protein
                       organism = Homo sapiens
SEQUENCE: 32
QGQLVQSGGG VKKTGTSVTI SCLASEYTFT EFTIHWIRQA PGQGPLWLGL IKRSGRLMTA  60
NRFQDRLSLR RDRSTGTVFM ELRSLRIDDT AVYYCARDGL GELAPAYHYG IDVWGQGTTI  120
IVTSASTKG                                                         129

SEQ ID NO: 33          moltype = AA  length = 129
FEATURE                Location/Qualifiers
source                 1..129
                       mol_type = protein
                       organism = Homo sapiens
SEQUENCE: 33
QGQLVQSGGG VKKPGTSVTI SCLASEYTFT EFTIHWIRQA PGQGPLWLGL IKRSGRLMTA  60
YRFQDRLSLR RDRSTGTVFM ELRNLRMDDT AVYYCARDGL GELAPAYQYG IDVWGQGTTV  120
IVSSASTKG                                                         129

SEQ ID NO: 34          moltype = AA  length = 129
FEATURE                Location/Qualifiers
source                 1..129
                       mol_type = protein
                       organism = Homo sapiens
SEQUENCE: 34
QGQLVQSGGG GKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVSSASTKG                                                         129

SEQ ID NO: 35          moltype = AA  length = 129
FEATURE                Location/Qualifiers
source                 1..129
                       mol_type = protein
                       organism = Homo sapiens
SEQUENCE: 35
QGQLVQSGGG VKKPGTSVTI SCLASEYTFN EFVIHWIRQA PGQGPLWLGL IKRSGRLMTS  60
YKFQDRLNLR RDRSTGTVFM ELRGLRPDDT AVYYCARDGL GEVAPDYRYG IDVWGQGSTV  120
IVTAASTKG                                                         129

SEQ ID NO: 36          moltype = AA  length = 131
FEATURE                Location/Qualifiers
source                 1..131
                       mol_type = protein
                       organism = Homo sapiens
SEQUENCE: 36
QVQLQQWGSG LLKPSETLSL TCAVYGGSFR SYYWNWIRQS PGKGLEWIGE VSHSGSTNYN  60
PALKSRVTIS VDTSKNQFSL KVKSVTAADT ALYYCSRGRG KRCSGAYCFA GYFDSWGQGG  120
LVVVSSASTK G                                                      131

SEQ ID NO: 37          moltype = AA  length = 132
FEATURE                Location/Qualifiers
source                 1..132
                       mol_type = protein
                       organism = Homo sapiens
SEQUENCE: 37
EVQLVESGGG VVEPGESLRL SCAASGFTFR SYDMFWVRQA TGKSLEWVSA IGIAGDTYYS  60
GSVKGRFTIS RENARTSLYL QLSGLRVEDS AVYFCVRGSP PRIAATEYNY YYGLDVWGQG  120
TTVSVFSAST KG                                                     132

SEQ ID NO: 38          moltype = AA  length = 138
FEATURE                Location/Qualifiers
source                 1..138
                       mol_type = protein
                       organism = Homo sapiens
SEQUENCE: 38
VVQLVQSGAE VRKPGSSLKV SCKSSGGTFS RYVVNWVRQA PGQGLEWMGG MIPIFGIAKY  60
AQKFQDRVTM TADESKNTVY LDFSSLRSDD TAVYYCARDR GDTRLLDYGD YEDERYYYGM  120
DVWGQGTTVI VSSASTKG                                               138
```

```
SEQ ID NO: 39          moltype = AA  length = 138
FEATURE                Location/Qualifiers
source                 1..138
                       mol_type = protein
                       organism = Homo sapiens
SEQUENCE: 39
QVQLVQSGAE VRKPGSSLKV SCKSSGGTFS RYVVNWVRQA PGQGLEWMGG IIPIFGIAKY  60
AQKFQDRVTM TADEPKNTVY LDFNSLRSDD TAVYYCARDR GDTRLLDYGD YEDERYYYGM  120
DVWGQGTTVI VSSASTKG                                                138

SEQ ID NO: 40          moltype = AA  length = 125
FEATURE                Location/Qualifiers
source                 1..125
                       mol_type = protein
                       organism = Homo sapiens
SEQUENCE: 40
EVQLVESGGG LVKPGGSLRL SCAASGFSFS EHYMSWIRLA PGKGLEWLSY ISSSTRTTYS  60
ADSVRGRFTI SRDTAKQLLF LHMSSLRAED TAVYYCVRLY GGINGWFDQW GQGTLVSVSS  120
ASTKG                                                              125

SEQ ID NO: 41          moltype = AA  length = 123
FEATURE                Location/Qualifiers
source                 1..123
                       mol_type = protein
                       organism = Homo sapiens
SEQUENCE: 41
QVQLVQSGAE VKKPGSSVKV SCKTSGGSFS NYAFSWVRQA PGEGLEWMGR IIPIFGTAKY  60
TQKLQGRVTI TADKFTSTVY MELSSLRSED TAIYYCASLH QGPIGYTPWH PPPRAPLGQS  120
VCG                                                                123

SEQ ID NO: 42          moltype = AA  length = 139
FEATURE                Location/Qualifiers
source                 1..139
                       mol_type = protein
                       organism = Homo sapiens
SEQUENCE: 42
QVQLVESGAE VKKPGASVKV SCKASGYTFT SHDINWVRQA TGQGLEWMGW MNPNSGDTGY  60
AHKFQGRVTM TRNTPISTAY MELSSLRSED TAVYYCARGR ATSRNTPWAH YYDSSGYYGA  120
GDYWGQGTLV TVSSASTKG                                               139

SEQ ID NO: 43          moltype = AA  length = 133
FEATURE                Location/Qualifiers
source                 1..133
                       mol_type = protein
                       organism = Homo sapiens
SEQUENCE: 43
QVQLVESGGG VVQPGRSLRL FCAASGFAFN TYGMHWVRQA PGKGLEWVAV TWHDGSQKYY  60
ADSVKGRFTI SRDNSKNTLY LQMNSLRAED TAIYYCASDQ GGFDDSSGYF APGGMDVWGR  120
GTTVIVSSAP TKG                                                     133

SEQ ID NO: 44          moltype = AA  length = 121
FEATURE                Location/Qualifiers
source                 1..121
                       mol_type = protein
                       organism = Homo sapiens
SEQUENCE: 44
QVQLVESGAE LRKPGESLEI SCKASGYSFS SHWIGWARQM PGKGLEWMGI IYPGDSNTIY  60
SPSFQGQVTI SADKSINTAY LQWSSLKASD TAMYFCASNY HDYFYWGQGT LVTVSSASTK  120
G                                                                  121

SEQ ID NO: 45          moltype = AA  length = 135
FEATURE                Location/Qualifiers
source                 1..135
                       mol_type = protein
                       organism = Homo sapiens
SEQUENCE: 45
EVQLVESGAE VKKPGSSVKV SCKASGGTFS TYAFSWVRQA PGQGLEWMGG IIPIFGTENY  60
AQKFQGRVTI TADKSTSTAY MELSSLRSED TAVYYCARDR SSAIGYCSSI SCYKGSFDIW  120
GQGTMVTVSS ASTKG                                                   135

SEQ ID NO: 46          moltype = AA  length = 138
FEATURE                Location/Qualifiers
source                 1..138
                       mol_type = protein
                       organism = Homo sapiens
SEQUENCE: 46
QVQLVQSGAE VRKPGSSLKV SCKSSGGTFS RYVVNWVRQA PGQGLEWMGG IIPIFGIAKY  60
AQKFQDRVTM TADEPKNTVY LDFNSLRSDD TAVYYCARDR GDTRLLDYGD YEDERYYYGM  120
```

```
DVWGQGTTVI VSSASTKG                                              138

SEQ ID NO: 47          moltype = AA  length = 135
FEATURE                Location/Qualifiers
source                 1..135
                       mol_type = protein
                       organism = Homo sapiens
SEQUENCE: 47
EVQLVQSGAE VKKPGSSVKV SCKASGGTFS TYAFSWVRQA PGQGLEWMGG IIPIFGTENY  60
AQKFQGRVTI TADKSTSTAY MELSSLRSED TAVYYCARDR SSAIGYCSSI SCYKGSFDIW  120
GQGTMVTVSS ASTKG                                                 135

SEQ ID NO: 48          moltype = AA  length = 143
FEATURE                Location/Qualifiers
source                 1..143
                       mol_type = protein
                       organism = Homo sapiens
SEQUENCE: 48
QVFVQLVQSG GGLVQPGGSV RLSCTASGFL FSTYSMNWVR QAPGKGLEWV SSISTTSNYI  60
YYADSVKGRF TISRSNGQGS LYLQLNSLRV EDTAVYYCAR DTKVGAPRQD CYAMDLWGQR  120
DHGHRLLSFH QGPIGLPPGA LLQ                                        143

SEQ ID NO: 49          moltype = AA  length = 129
FEATURE                Location/Qualifiers
source                 1..129
                       mol_type = protein
                       organism = Homo sapiens
SEQUENCE: 49
QVQLLESGPG LVTPSGTLSL ACAVSGASIS SSHWWTWVRQ SPGKGLEWIG EIDRRGTTNY  60
NPSLRSRVTI LLDNSKNQFS LSLRSVTAAD TAVYYCTKVY AGLFNERTYG MDVWGHGTTV  120
LVSSASTKG                                                        129

SEQ ID NO: 50          moltype = AA  length = 138
FEATURE                Location/Qualifiers
source                 1..138
                       mol_type = protein
                       organism = Homo sapiens
SEQUENCE: 50
QVQLVESGAE VRKPGSSLKV SCKSSGGTFS RYVVNWVRQA PGQGLEWMGG IIPIFGIAKY  60
AQKFQDRVTM TADESKNTVY LDFSSLRSDD TAVYYCARDR GDTRLLDYGD YEDERYYYGM  120
DVWGQGTTVI VSSASTKG                                              138

SEQ ID NO: 51          moltype = AA  length = 132
FEATURE                Location/Qualifiers
source                 1..132
                       mol_type = protein
                       organism = Homo sapiens
SEQUENCE: 51
QVQLLQSGAE VKKPGASVKV SCKVSGYTLT ELSINWVRQA PGKGLEWMGG FDPEDDEAIY  60
EPKFQGRLTM TEDTSTDTAY MELSSLRSED TAVYYCATAD PFKVAQDEGL YVIFDYWGQG  120
TLVTVSSAST KG                                                    132

SEQ ID NO: 52          moltype = AA  length = 131
FEATURE                Location/Qualifiers
source                 1..131
                       mol_type = protein
                       organism = Homo sapiens
SEQUENCE: 52
QVQLVQSGTE VQKPGASVKV SCKTSGYTFS KYYIHWVRQA PGQGLEWVGR INTDSGGTDY  60
AEKFQGRVTM TRDTSITTVY LEMRGLTSDD TAAFYCARGP PHAGGWTIYY YGLDVWGQGT  120
SVIVSSASTK G                                                     131

SEQ ID NO: 53          moltype = AA  length = 132
FEATURE                Location/Qualifiers
source                 1..132
                       mol_type = protein
                       organism = Homo sapiens
SEQUENCE: 53
QVQLVQSGAE VKKPGASVKV SCKVSGHTLS ELSINWVRHV PGKGLEWMGG LDPEDGEAIH  60
EPKFQGRLTM TEDTSTDTAY VELSSLRSED TAMYYCATAD PFKVAQDEGL YVIFDYWGQG  120
TLVTVSSAST KG                                                    132

SEQ ID NO: 54          moltype = AA  length = 126
FEATURE                Location/Qualifiers
source                 1..126
                       mol_type = protein
                       organism = Homo sapiens
SEQUENCE: 54
EVQLVESGGG VVQPGRSLRL SCAASGFTFS HHGIHWVRQA PGEGLEWVAV ISEDGTNIHY  60
```

```
EDSVRGRFTI SRDNSKNTVD LQMNSLRAED TAVYYCASLI SMRDGDAFDL WGQGTRVTVS  120
SASTKG                                                            126

SEQ ID NO: 55          moltype = AA  length = 138
FEATURE                Location/Qualifiers
source                 1..138
                       mol_type = protein
                       organism = Homo sapiens
SEQUENCE: 55
QVQLVQSGAE VRKPGSSLKV SCKSSGGTFS RYVVNWVRQA PGQGLEWMGG IIPIFGIAKY  60
AQKFQDRVTM TADESKNTVY LDFSSLRSDD TAVYYCARDR GDTRLLDYGD YEDERYYYGM  120
DVWGQGTTVI VSSASTKG                                               138

SEQ ID NO: 56          moltype = AA  length = 124
FEATURE                Location/Qualifiers
source                 1..124
                       mol_type = protein
                       organism = Homo sapiens
SEQUENCE: 56
QVQLVQSGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCAREG SYYYGMDVWG QGTTVTVSSA  120
STKG                                                              124

SEQ ID NO: 57          moltype = AA  length = 130
FEATURE                Location/Qualifiers
source                 1..130
                       mol_type = protein
                       organism = Homo sapiens
SEQUENCE: 57
EVQLVQSGGG LVQPGRSLRL SCAASGFTFD DYAMHWVRQA PGKGLEWVSG ISWNSGTIGY  60
ADSVRGRFTI SRDDAKSSLY LQMNSLRTED TALYYCAKDG WVGSGSSTLR GSDYWGQGTL  120
VTVSSASTKG                                                        130

SEQ ID NO: 58          moltype = AA  length = 157
FEATURE                Location/Qualifiers
source                 1..157
                       mol_type = protein
                       organism = Homo sapiens
SEQUENCE: 58
QIHLVQSGTD VKKPGSSVTV SCKAYGVNTF GLYAVNWVRQ APGQSLEYIG QIWRWKSSAS  60
HHFRGRVLIS AVDLTGSSPP ISSLEIKNLT SDDTAVYFCT TTSTYDQWSG LHHDGVMAFS  120
SRGQGTLISV SAASTKGPSV FPLAPSSKST YGLAHVL                           157

SEQ ID NO: 59          moltype = AA  length = 138
FEATURE                Location/Qualifiers
source                 1..138
                       mol_type = protein
                       organism = Homo sapiens
SEQUENCE: 59
QVQLVQSGAE VRKPGSSLKV SCKSSGGTFS RYVVNWVRQA PGQGLEWMGG IIPIFGIAKY  60
AQKFQDRVTM TADEPKNTVY LDFNSLRSDD TAVYYCARDR GDTRLLDYGD YEDERYYYGM  120
DVWGQGTTVI VSSASTKG                                               138

SEQ ID NO: 60          moltype = AA  length = 125
FEATURE                Location/Qualifiers
source                 1..125
                       mol_type = protein
                       organism = Homo sapiens
SEQUENCE: 60
QLQLQESGPG LVKPWETLVL TCSVSGGSIS SGDYYWGWIR QSPGKGPEWI GNIFYSSGNT  60
YYNTSLKSRV TISVDVSKNR FSLKLTSMTA ADTAVYYCGR LSNKGWFDPW GQGTLVSVSS  120
ASTKG                                                             125

SEQ ID NO: 61          moltype = AA  length = 127
FEATURE                Location/Qualifiers
source                 1..127
                       mol_type = protein
                       organism = Homo sapiens
SEQUENCE: 61
QVQLLESGGG LVQRGGSLRL SCTASGFVFN NYWMTWVRQA PGNGLEWVAN IDQDGSEKHY  60
LDSVKGRFTI SRDNAKNSLY LQMNSLRAED TAIYYCARVR FKVTAWHRFD SWGQGDLVTV  120
SSTSTKG                                                           127

SEQ ID NO: 62          moltype = AA  length = 132
FEATURE                Location/Qualifiers
source                 1..132
                       mol_type = protein
                       organism = Homo sapiens
SEQUENCE: 62
```

-continued

```
LVQLLQSGAE VKKPGASVKV SCKVSGYTLT ELSIHWVRQA PGKGLEWMGG FDPEDDEAIY  60
EPKFQGRLTM TEDTSTDTAY MELSSLRSED TAVYYCATAD PFKVAQDEGL YVIFDYWGQG  120
TLVTVSSAST KG                                                       132

SEQ ID NO: 63          moltype = AA  length = 126
FEATURE                Location/Qualifiers
source                 1..126
                       mol_type = protein
                       organism = Homo sapiens
SEQUENCE: 63
QVQLVESGGG LGQPGGSLRL SCAASGFTFR NYAMSWVRQA AGKGLEWVSG VSGGGDTTYY  60
GDSVKGRFTI SRDNSKNTLY LQMNNLRAED TAVYYCAKDK GVWGSSDFDY WGQGTLVTVS  120
SASTKG                                                              126

SEQ ID NO: 64          moltype = AA  length = 132
FEATURE                Location/Qualifiers
source                 1..132
                       mol_type = protein
                       organism = Homo sapiens
SEQUENCE: 64
QVHLVQSGAE VKKPGASVRV SCKASGYTFT TYGISWVRQA PGQGLEWMGW ISAHSGDTNY  60
AQKLQARVTM TTDTSTNTAY MELRSLTSDD TAVYYCARDR PRHYYDRGGY YSPFDYWGQG  120
TLVTVSSAST KG                                                       132

SEQ ID NO: 65          moltype = AA  length = 139
FEATURE                Location/Qualifiers
source                 1..139
                       mol_type = protein
                       organism = Homo sapiens
SEQUENCE: 65
QVQLVESGAE VKKPGSSVKV SCKASGGTFN IFAFSWVRQA PGQGLEWMGG IIPIFASPNY  60
AQRFQGRVTI TADESTSTVH MELSSLRSED TAIYYCAKDA HMHIEEPRDY DYIWGTSPYY  120
FDYWGQGTLV TVSSASTKG                                                139

SEQ ID NO: 66          moltype = AA  length = 132
FEATURE                Location/Qualifiers
source                 1..132
                       mol_type = protein
                       organism = Homo sapiens
SEQUENCE: 66
QVQLVQSGAE VKKPGASVKV SCKVSGYTLT ELSIHWVRQA PGKGLEWMGG FDSEDGEAFY  60
KQNFQGRVTM TEDTSTDTAY MELRRLRSED TAVYYCATAD RFKVAQDEGL FVIFDYWGQG  120
TLVTVSSAST KG                                                       132

SEQ ID NO: 67          moltype = AA  length = 132
FEATURE                Location/Qualifiers
source                 1..132
                       mol_type = protein
                       organism = Homo sapiens
SEQUENCE: 67
QVQLLQSGGE VKKPGASVKV SCKVSGYTLT ELSIHWVRQA PGKGLEWMGG FDPEDDEAIY  60
EPKFQGRLTM TEDTSTDTAY MELSSLRSED TAVYYCATAD PFKVAQDEGL YVIFDYWGQG  120
TLVTVSSAST KG                                                       132

SEQ ID NO: 68          moltype = AA  length = 135
FEATURE                Location/Qualifiers
source                 1..135
                       mol_type = protein
                       organism = Homo sapiens
SEQUENCE: 68
EVQLVESGGG LVQPGGSLRL SCAASGFTFS SYSMNWVRQA PGKGLEWVSY ISGSSYTIYY  60
ADSVRGRFTI SRDNAKNSLY LQMNSLRDED TAVYFCARAT PPNPLNLYNY DSSGSSFDYW  120
GQGTLVTVSS ASTKG                                                    135

SEQ ID NO: 69          moltype = AA  length = 138
FEATURE                Location/Qualifiers
source                 1..138
                       mol_type = protein
                       organism = Homo sapiens
SEQUENCE: 69
QVQLVQSGAE VRKPGSSLKV SCKSSGGTFS RYVVNWVRQA PGQGLEWMGG MIPIFGIAKY  60
AQKFQDRVTM TADESKNTVY LDFSSLRSDD TAVYYCARDR GDTRLLDYGD YEDERYYYGM  120
DVWGQGTTVI VSSASTKG                                                 138

SEQ ID NO: 70          moltype = AA  length = 138
FEATURE                Location/Qualifiers
source                 1..138
                       mol_type = protein
                       organism = Homo sapiens
```

-continued

```
SEQUENCE: 70
QVQLVESGAE VRKPGSSLKV SCKSSGGTFS RYVVNWVRQA PGQGLEWMGG IIPIFGIAKY  60
AQKFQDRVTM TADEPKNTVY LDFNSLRSDD TAVYYCARDR GDTRLLDYGD YEDERYYYGM  120
DVWGQGTTVI VSSASTKG                                                138

SEQ ID NO: 71          moltype = AA  length = 124
FEATURE                Location/Qualifiers
source                 1..124
                       mol_type = protein
                       organism = Homo sapiens
SEQUENCE: 71
QVQLVQSGAE IKKPGESLKI SCKASGYTFN DYWIGWVRQM PGKGLEWMGI FYPDDSDSNY  60
SPSFQGRVTI SADKSITTAY LQWSTLKASD SAMYFCARLL GDSGAFDIWG QGTMVIVSSA  120
STKG                                                               124

SEQ ID NO: 72          moltype = AA  length = 138
FEATURE                Location/Qualifiers
source                 1..138
                       mol_type = protein
                       organism = Homo sapiens
SEQUENCE: 72
EVQLVESGAE VRKPGSSLKV SCKSSGGTFS RFVVNWVRQA PGQGLEWMGG MIPIFGIAKY  60
AQKFQDRVTM TADESKNTVY LDFSSLRSDD TAVYYCARDR GDTRLLDYGD YEDERYYYGM  120
DVWGQGTTVI VSSASTKG                                                138

SEQ ID NO: 73          moltype = AA  length = 135
FEATURE                Location/Qualifiers
source                 1..135
                       mol_type = protein
                       organism = Homo sapiens
SEQUENCE: 73
QVQLVQSGAE VKKPGSSVKV SCKASGGTFS TYAFSWVRQA PGQGLEWMGG IIPIFGTENY  60
AQKFQGRVTI TADKSTSTAY MELSSLRSED TAVYYCARDR SSAIGYCSSI SCYKGSFDIW  120
GQGTMVTVSS ASTKG                                                   135

SEQ ID NO: 74          moltype = AA  length = 138
FEATURE                Location/Qualifiers
source                 1..138
                       mol_type = protein
                       organism = Homo sapiens
SEQUENCE: 74
QVQLVQSGAE VRKPGSSLKV SCKSSGGTFS RFVVNWVRQA PGQGLEWMGG MIPIFGIAKY  60
AQKFQDRVTM TADESKNTVY LDFSSLRSDD TAVYYCARDR GDTRLLDYGD YEDERYYYGM  120
DVWGQGTTVI VSSASTKG                                                138

SEQ ID NO: 75          moltype = AA  length = 126
FEATURE                Location/Qualifiers
source                 1..126
                       mol_type = protein
                       organism = Homo sapiens
SEQUENCE: 75
QVQLVQSGGG VVQPGRSLRL SCAASGFTFS HHGIHWVRQA PGEGLEWVAV ISEDGTNIHY  60
EDSVRGRFTI SRDNSKNTVD LQMNSLRAED TAVYYCASLI SMRDGDAFDL WGQGTRVTVS  120
SASTKG                                                             126

SEQ ID NO: 76          moltype = AA  length = 133
FEATURE                Location/Qualifiers
source                 1..133
                       mol_type = protein
                       organism = Homo sapiens
SEQUENCE: 76
EVQLVQSGGG LVKPGGSLRL SCAASGFTFK NAWMSWVRQA PGKGLEWVGH IKSKTDGGTI  60
DYAAPVKGRF TISRDDSKNT LYLQMNSLKI EDTAVYYCTT DIGSGRGWDF HYYDSNDWGQ  120
GTLVTVSSAS TKG                                                     133

SEQ ID NO: 77          moltype = AA  length = 131
FEATURE                Location/Qualifiers
source                 1..131
                       mol_type = protein
                       organism = Homo sapiens
SEQUENCE: 77
EVQLVQSGGG VVQPGRSLRL SCVVSGFTFS SFTFHWVRQA PGKGLEWVAG MSFHATYIYY  60
ADSVKGRFTI SRDDSQDTLY LEMDSLRSED TAIYYCARDP GIHDYGDYAP GAFDYWGQGS  120
PVTVSSASTK G                                                       131

SEQ ID NO: 78          moltype = AA  length = 132
FEATURE                Location/Qualifiers
source                 1..132
                       mol_type = protein
```

```
                         organism = Homo sapiens
SEQUENCE: 78
LVQLVQSGAE VKKPGASVKV SCKVSGHTLS ELSINWVRHV PGKGLEWMGG LDPEDGEAIH  60
EPKFQGRLTM TEDTSTDTAY STLSVWAPVA AAMYYCATAD PFKVAQDEGL YVIFDYWGQG  120
TLVTVSSAST KG                                                      132

SEQ ID NO: 79            moltype = AA  length = 125
FEATURE                  Location/Qualifiers
source                   1..125
                         mol_type = protein
                         organism = Homo sapiens
SEQUENCE: 79
EVQLVESGAE VKKPGSSVKV SCKASGGTFS SYSISWVRQA PGQGLEWMGG IIPIFATTHY  60
GQKFQGRIKI TADKSTSTAY MELSRLRSED TAVYYCARDR EFYFYGMDVW GQGTTVTVSS  120
ASTKG                                                              125

SEQ ID NO: 80            moltype = AA  length = 131
FEATURE                  Location/Qualifiers
source                   1..131
                         mol_type = protein
                         organism = Homo sapiens
SEQUENCE: 80
QVQLQQWGAG LLKPSETLSL TCAVYAGSFS GYYWTWIRQP PGKGLEWIGE VNHGGSTNYN  60
PSLKSRVTLS VDTSKNQFSL KLTSVTAADT AVYYCARVSR YDFWSGNYGS YGLDVWGQGT  120
TVTVSSASTK G                                                       131

SEQ ID NO: 81            moltype = AA  length = 138
FEATURE                  Location/Qualifiers
source                   1..138
                         mol_type = protein
                         organism = Homo sapiens
SEQUENCE: 81
VVQLVQSGAE VRKPGSSLKV SCKSSGGTFS RFVVNWVRQA PGQGLEWMGG MIPIFGIAKY  60
AQKFQDRVTM TADESKNTVY LDFSSLRSDD TAVYYCARDR GDTRLLDYGD YEDERYYYGM  120
DVWGQGTTVI VSSASTKG                                                138

SEQ ID NO: 82            moltype = AA  length = 154
FEATURE                  Location/Qualifiers
source                   1..154
                         mol_type = protein
                         organism = Homo sapiens
SEQUENCE: 82
LVQLVQSGAE VKKPGASVKV SCKVSGYSLT ELSIHWVRQA PGKGLEWMGG FDSEDGEAIY  60
KQNFQGRVTM TEDTSTDTAY MELSRLRSED TAVYYCATAD PFKVAQDEGL FVIFDYWGQG  120
TTGHRLLSLH QGPHRLYSLG TLLSRAPIVQ THMA                              154

SEQ ID NO: 83            moltype = AA  length = 135
FEATURE                  Location/Qualifiers
source                   1..135
                         mol_type = protein
                         organism = Homo sapiens
SEQUENCE: 83
QVQLVQSGAE VKKPGSSVKV SCKASGGTFS TYAFSWVRQA PGQGLEWMGG IIPIFGTENY  60
AQKFQGRVTI TADKSTSTAY MELSSLRSED TAVYYCARDR SSAIGYCSSI SCYKGSFDIW  120
GQGTMVTVSS ASTKG                                                   135

SEQ ID NO: 84            moltype = AA  length = 135
FEATURE                  Location/Qualifiers
source                   1..135
                         mol_type = protein
                         organism = Homo sapiens
SEQUENCE: 84
QVQLVQSGAE VKKPGSSVKV SCKASGGTFS TYAFSWVRQA PIEGLEWMGG IIPIFGTENY  60
AQKFQGRVTI TADKSTSTAY MELSSLRSED TAVYYCARDR SSAIGYCSSI SCYKGSFDIW  120
GQGTMVTVSS ASTKG                                                   135

SEQ ID NO: 85            moltype = AA  length = 132
FEATURE                  Location/Qualifiers
source                   1..132
                         mol_type = protein
                         organism = Homo sapiens
SEQUENCE: 85
QVQLVQWGAG LLKPLETLSL TCAVYGGSFN GYFWSWIRQT PGKGLEWIGE INHGGSANFN  60
PSLKSRVTMS VDTSKNQFSL KLASVTAADT AIYYCARGRI TMVRGDPQRG GVRMDVWGQG  120
TSVTVSSAST KG                                                      132

SEQ ID NO: 86            moltype = AA  length = 132
FEATURE                  Location/Qualifiers
source                   1..132
```

```
                        mol_type = protein
                        organism = Homo sapiens
SEQUENCE: 86
QVQLMQSGAE VKRPGASVKV SCKAFRHSLN NLGISWIRRA PGRGLEWLGW INVYEGNTKY  60
GRRFQGRVTM TTDRSTNTVS MELRSLTSDD TAVYYCARDN HFWSGSSRYY YFGMDVWGQG  120
TTVIVSSAST KG                                                      132

SEQ ID NO: 87           moltype = AA  length = 125
FEATURE                 Location/Qualifiers
source                  1..125
                        mol_type = protein
                        organism = Homo sapiens
SEQUENCE: 87
QVQLVQSGGG LVQPGESLRL SCTASGFTFS SYNMNWVRQA PGKGLEWISY ISDKSKNKYY  60
ADSVRGRFTI SRDNAQNSLF LQMSSLRDED TAVYYCTREG PQRSFYFDYW GQGIQVTVSS  120
ASTKG                                                              125

SEQ ID NO: 88           moltype = AA  length = 126
FEATURE                 Location/Qualifiers
source                  1..126
                        mol_type = protein
                        organism = Homo sapiens
SEQUENCE: 88
QVQLQESGPG LVKPSETLSL TCTVSGGSIS NHYWSWIRQP PGKGLEWIGY IYHSGNINYK  60
SSLKSRATIS IDTSNNQFSL KLSSVIAADT AVYYCARNFG PGSPNYGMDV WGQGTTVTVS  120
SASTKG                                                             126

SEQ ID NO: 89           moltype = AA  length = 130
FEATURE                 Location/Qualifiers
source                  1..130
                        mol_type = protein
                        organism = Homo sapiens
SEQUENCE: 89
VVQLVQSGPG LVKPSQTLSL TCTVSGGSIS SGDFYWSWIR QPPGKGLEWI GYIYYSGSTY  60
YNPSLKSRLT ISVDTSKNQF SLRLSSVTAA DTAVYYCARD LNSRIVGALD AFDIWGQGTM  120
VTVSSASTKG                                                         130

SEQ ID NO: 90           moltype = AA  length = 129
FEATURE                 Location/Qualifiers
source                  1..129
                        mol_type = protein
                        organism = Homo sapiens
SEQUENCE: 90
QVQLVESGGA LVQPGGSLRL SCAASGFSFS SYAMSWVRQA PGKGLEWVSA ISRSGGSTYY  60
ADSVKGRFTI SIDNSNNTLY LQMNSLRVED TAVYYCAKRE AFYYGAGGYG MDVWGQGTTV  120
TVSSASTKG                                                          129

SEQ ID NO: 91           moltype = AA  length = 130
FEATURE                 Location/Qualifiers
source                  1..130
                        mol_type = protein
                        organism = Homo sapiens
SEQUENCE: 91
EVQLVESGGG LVKPGGSLRL SCEASGFTFT NAWMNWVRQA PGKGLEWVGR IKSQTHGGTT  60
RYAAPVKGRF TISRDDSKHT LYLQMDRLTT EDTAVYYCTG TITGSTFYYY GMDVWGQGTT  120
VTVSPASTKG                                                         130

SEQ ID NO: 92           moltype = AA  length = 132
FEATURE                 Location/Qualifiers
source                  1..132
                        mol_type = protein
                        organism = Homo sapiens
SEQUENCE: 92
EVQLVESGGG LLQPGGSLRL SCAASGFSFN DFEMNWVRQA PGKGLEWVSY ISNDGTMIHY  60
ADSVKGRFTI SRDNAKKSLF LQMNSLRAED TAVYYCARLA EVPPAIRGSY YYGMDVWGQG  120
TTVTVASAST KG                                                      132

SEQ ID NO: 93           moltype = AA  length = 123
FEATURE                 Location/Qualifiers
source                  1..123
                        mol_type = protein
                        organism = Homo sapiens
SEQUENCE: 93
QVQLQESGPG LLRPLETLSL TCSVSGGSIR GYFWSWVRQP AGRGLEWIGR IYSSGTTRFN  60
PSLKSRVRLS IDTAKSEVSL NITSVTAADS ASYFCAGTSP VHGGLDLWGL GLRVTVSSAS  120
TKG                                                                123

SEQ ID NO: 94           moltype = AA  length = 135
FEATURE                 Location/Qualifiers
```

-continued

```
source                1..135
                      mol_type = protein
                      organism = Homo sapiens
SEQUENCE: 94
HLVQSGTEVK KPGSSVTVSC KAYGVNTFGL YAVNWVRQAP GQSLEYIGQI WRWKSSASHH  60
FRGRVLISAV DLTGSSPPIS SLEIKNLTSD DTAVYFCTTT STYDQWSGLH HDGVMAFSSW  120
GQGTLISVSA ASTKG                                                   135

SEQ ID NO: 95         moltype = AA  length = 132
FEATURE               Location/Qualifiers
source                1..132
                      mol_type = protein
                      organism = Homo sapiens
SEQUENCE: 95
EVQLVQSGAE VKKPGASVKV SCKVSGYTLT ELSIHWVRQA PGKGLEWMGG FDPEDDEAIY  60
EPKFQGRLTM TEDTSTDTAY MELSSLRSED TAVYYCATAD PFKVAQDEGL YVIFDYWGQG  120
TLVTVSSAST KG                                                      132

SEQ ID NO: 96         moltype = AA  length = 129
FEATURE               Location/Qualifiers
source                1..129
                      mol_type = protein
                      organism = Homo sapiens
SEQUENCE: 96
QVQLVESGGG LVQPGGSLRL SCAASGFTFS THWMHWVRQA PGKGLVWVSR IHSDGRSTSY  60
ADSVKGRFTI SRDNAKNTLY LQMNSLRAED TAVYYCARGA AVFGVVIIGG MDLWGQGTTV  120
TVSSASTKG                                                          129

SEQ ID NO: 97         moltype = AA  length = 127
FEATURE               Location/Qualifiers
source                1..127
                      mol_type = protein
                      organism = Homo sapiens
SEQUENCE: 97
EVQLVESGGG VVQPGGSLRL SCAASGFMFK NYAMHWVRQP PGKGLEWVAV IWYGGRDQNY  60
ADSVKGRFTI SRDDSDNTLY LQMNSLRAGD TAVYFCARNS QVGRLMPAAG VWGQGTLVTV  120
SSASTKG                                                            127

SEQ ID NO: 98         moltype = AA  length = 123
FEATURE               Location/Qualifiers
source                1..123
                      mol_type = protein
                      organism = Homo sapiens
SEQUENCE: 98
EVQLVESGGG LIQRGGSLRL SCVASGFPVS DNHMSWVRQA PGKGLEWVSI IYSDGGTYYA  60
DSVKGRFTIS RDNSKNTVYL QMNSLRATDT AVYYCARDPG FHYGLDVWGQ GTTVTVSSAS  120
TKG                                                                123

SEQ ID NO: 99         moltype = AA  length = 124
FEATURE               Location/Qualifiers
source                1..124
                      mol_type = protein
                      organism = Homo sapiens
SEQUENCE: 99
VVQLVESGGG LVQPGGSLRL SCAASGFAFR SYWMSWVRQA PGRGLEWVAN IKQDGSEKYY  60
ADSVKGRFTI SRDNTKNSLY LQMNSLRAED TAVFYCASRG DRYGPIDYWG QGTLVTVSSA  120
STKG                                                               124

SEQ ID NO: 100        moltype = AA  length = 125
FEATURE               Location/Qualifiers
source                1..125
                      mol_type = protein
                      organism = Homo sapiens
SEQUENCE: 100
VVQLVESGTE VKKPGSSVKV SCKASGGTFS GSDISWVRQA PGQGLEWMGG IIPMFDIENH  60
AEKFRGRLTI TAVKSTGAAY MELSSLRSED AAVYYCARSS GNYDFAYDIW GQGTRVIVSS  120
ASTKG                                                              125

SEQ ID NO: 101        moltype = AA  length = 135
FEATURE               Location/Qualifiers
source                1..135
                      mol_type = protein
                      organism = Homo sapiens
SEQUENCE: 101
EVQLVQSGAE VKKPGSSVKV SCKASGGTFS TYAFSWVRQA PGQGLEWMGG IIPIFGTENY  60
AQKFQGRVTI TADKSTSTAY MELSSLRSED TAVYYCARDR SSAIGYCSSI SCYKGSFDIW  120
GQGTMVTVSS ASTKG                                                   135

SEQ ID NO: 102        moltype = AA  length = 130
```

```
FEATURE                Location/Qualifiers
source                 1..130
                       mol_type = protein
                       organism = Homo sapiens
SEQUENCE: 102
EVQLVQSGGG LVQPGGSLRL SCAASGLTFR NFAMSWVRQA PGKGLEWVSS ISGSGGSTYY  60
ADSVKGRFTI SRDNSKNTLY LQMNSLRGED TAVYFCAKGV GYDILTGLGD AFDIWGQGTV  120
VAVSSASTKG                                                        130

SEQ ID NO: 103         moltype = AA  length = 137
FEATURE                Location/Qualifiers
source                 1..137
                       mol_type = protein
                       organism = Homo sapiens
SEQUENCE: 103
QIHLVQSGTE VKKPGSSVTV SCKAYGVNTF GLYAVNWVRQ APGQSLEYIG QIWRWKSSAS  60
HHFRGRVLIS AVDLTGSSPP ISSLEIKNLT SDDTAVYFCT TTSTYDKWSG LHHDGVMAFS  120
SWGQGTLISV SAASTKG                                                137

SEQ ID NO: 104         moltype = AA  length = 125
FEATURE                Location/Qualifiers
source                 1..125
                       mol_type = protein
                       organism = Homo sapiens
SEQUENCE: 104
VVQLVQSGTE VKKPGSSVKV SCKASGGTFS GSDISWVRQA PGQGLEWMGG IIPMFDIEDH  60
AQKFRGRLTI TADKSTGAAY MELSSLRSED AAVYYCARSS GNYDFAFDIW GQGTRLIVSS  120
ASTKG                                                             125

SEQ ID NO: 105         moltype = AA  length = 132
FEATURE                Location/Qualifiers
source                 1..132
                       mol_type = protein
                       organism = Homo sapiens
SEQUENCE: 105
QVQLGESGGG LVEPGGSLRL SCAASGFLFS DYQMSWIRLA PGKGLEWISF ISGFGSVYYA  60
DSVEGRFTIS RDNARNSLYL QMNNLRAEDT AVYYCARAYG TGNWRGLYYY YYGMDVWGHG  120
TTVTVSSAST KG                                                     132

SEQ ID NO: 106         moltype = AA  length = 122
FEATURE                Location/Qualifiers
source                 1..122
                       mol_type = protein
                       organism = Homo sapiens
SEQUENCE: 106
QLQLVESGGG VVQPGRSLRL SCAASGFTFS TYTMHWVRQA PGKGLEWVAV ISYDGTNKYY  60
ADSVKGRFTI SRDNSKNTLY LQMNSLRGED TAVYYCARSP SYYFDYWGQG TLVTVSAAST  120
KG                                                                122

SEQ ID NO: 107         moltype = AA  length = 128
FEATURE                Location/Qualifiers
source                 1..128
                       mol_type = protein
                       organism = Homo sapiens
SEQUENCE: 107
QVQLVQSGAE VKMPGASVKV SCKVSGYSLT ELSIHWVRQA PGKRLEWMGG FDPEDDERIY  60
AQKFQDRVTM TEDTSTDTAY MDLNSLRSED TAVYYCTTGG LYCSSISCIM DVWGQGTTVI  120
VSSASTKG                                                          128

SEQ ID NO: 108         moltype = AA  length = 128
FEATURE                Location/Qualifiers
source                 1..128
                       mol_type = protein
                       organism = Homo sapiens
SEQUENCE: 108
QVQLVQSGAE VKKPGASVKV SCKVSGYTLT ELSIHWVRQA PGKRLEWMGG FDPEDGERIY  60
AQKFQGRVTM TEDTSTDTAY MELNSLRSDD TAVYYCATGG LYCSSISCIM DVWGQGTTVT  120
VSSASTKG                                                          128

SEQ ID NO: 109         moltype = AA  length = 153
FEATURE                Location/Qualifiers
source                 1..153
                       mol_type = protein
                       organism = Homo sapiens
SEQUENCE: 109
QVQLVQSGAE VKKPGASVKV SCKVSGYTLT ELSIHWVRQA PGKGLEWMGG FDSEDGEAIY  60
KQNFQGRVTM TEDTSTDTAY MELSRLRSED TAVYYCATAD RFKVAQDEGL FVIFDYWGQG  120
NPGHRLLSLH QGPIGLPPGT LPPKATSGHA ARR                              153
```

-continued

```
SEQ ID NO: 110         moltype = AA  length = 129
FEATURE                Location/Qualifiers
source                 1..129
                       mol_type = protein
                       organism = Homo sapiens
SEQUENCE: 110
QVQLVESGGG VVQPGRSLRL SCAASGFTFS SYAMHWVRQA PGKGLEWVAV ISYDGSNKYY  60
ADSVKGRFTI SRDDSKSTVY LQINSLRAAD TAVYFCAREG GLRFLEWLFW GQGTLVTVSS  120
GESSASTKG                                                         129

SEQ ID NO: 111         moltype = AA  length = 126
FEATURE                Location/Qualifiers
source                 1..126
                       mol_type = protein
                       organism = Homo sapiens
SEQUENCE: 111
EFQLVQSGGG LVKPGGSLRL SCTGSTFSFS SDDMNWVRQA PGKGLEWVSS MSDSGSHIYY  60
ADFVKGRFTI SRDNAKKSLY LQMNSLRAED TAVYYCAQSR PPQRLYGMDV WGQGTTVTVS  120
SASTKG                                                            126

SEQ ID NO: 112         moltype = AA  length = 132
FEATURE                Location/Qualifiers
source                 1..132
                       mol_type = protein
                       organism = Homo sapiens
SEQUENCE: 112
QVQLVQSGAE VKKPGASVKV SCKVSGYTLT ELSIHWVRQA PGKGLEWMGG FDPEDGEASF  60
EPKFQGRLTM TEDTSTDTAY MELSSLRSED TAVYYCATAD PFKVAQDEGL YVIFDYWGQG  120
TLVTVSSAST KG                                                      132

SEQ ID NO: 113         moltype = AA  length = 124
FEATURE                Location/Qualifiers
source                 1..124
                       mol_type = protein
                       organism = Homo sapiens
SEQUENCE: 113
QVQLVESGGG VVQPGKSLRL SCAASGFTFS THAMHWVRQA PGKGLDWVAV ISHDGDNQYY  60
ADAVKGRFTI SRDDSRDTVF LQMNSLRTED TGVYYCAADS SGSNWFDYWG QGILVTVSSA  120
STKG                                                              124

SEQ ID NO: 114         moltype = AA  length = 121
FEATURE                Location/Qualifiers
source                 1..121
                       mol_type = protein
                       organism = Homo sapiens
SEQUENCE: 114
EPMFQPGQSG GVVVQSGESL HLSCEASGFK FASQMMHWVR HVPGRGLEWV ALISWDGSGK  60
LFADSVRGRF TIHRWNDRNS LYLDVKNVRP EDAAIYYCTR NGFDVWGQGI LVTVSSASTK  120
G                                                                 121

SEQ ID NO: 115         moltype = AA  length = 132
FEATURE                Location/Qualifiers
source                 1..132
                       mol_type = protein
                       organism = Homo sapiens
SEQUENCE: 115
QVQLLQSGAE VKKPGASVKV SCKVSGYTLT ELSIHWVRQA PGKGLEWMGG FDPEDDEAIY  60
EPKFQGRLTM TEDTSTDTAY MELSSLRSED TAVYYCATAD PFKVAQDEGL YVIFDYWGQG  120
TLVTVSSAST KG                                                      132

SEQ ID NO: 116         moltype = AA  length = 131
FEATURE                Location/Qualifiers
source                 1..131
                       mol_type = protein
                       organism = Homo sapiens
SEQUENCE: 116
QVHLQESGPR LVRSSETLSL TCSVPGGSIV NPITNYYWSW IRQSPRKGLQ WIGDIYYTGT  60
SSRNPSLDSR VSISMDVSRK QISLTLYSVT AADTAVHYCA SQSLSWYRPS GYFESWGQGI  120
LVTVSSASTK G                                                       131

SEQ ID NO: 117         moltype = AA  length = 128
FEATURE                Location/Qualifiers
source                 1..128
                       mol_type = protein
                       organism = Homo sapiens
SEQUENCE: 117
QVQLVQSGAE VKKPGSSMKV SCKSSGGTFS NHAISWVRQA PGKGLEWMGG IIPMSGTTNY  60
LQKFQGRVTI TADEFATTAY MELSSLTSED TAVYYCARAR ADSHTPIDAF DIWGPGTRVI  120
VSSASTKG                                                          128
```

```
SEQ ID NO: 118         moltype = AA  length = 125
FEATURE                Location/Qualifiers
source                 1..125
                       mol_type = protein
                       organism = Homo sapiens
SEQUENCE: 118
QVQLVQSGTE VKKPGSSVKV SCKASGGTFS DSDIAWVRQA PGQGLEWMGG ITPMFDMAKS  60
AQKFRGRLII TADKSTGTAY MELSSLRYED AAVYFCARSS GNFEFAFEIW GQGTKIIVSL  120
ASTKG                                                              125

SEQ ID NO: 119         moltype = AA  length = 128
FEATURE                Location/Qualifiers
source                 1..128
                       mol_type = protein
                       organism = Homo sapiens
SEQUENCE: 119
QVQLVQSGAE VKKPGASVKV SCKASGYTFT SYDINWVRQA TGQGLEWMGW MNPNSGNTGY  60
AQTFQGRVTM TRNTSISTAY MELSSLRSED TAVYYCARDR WLPQYYYYGM DVWGQGTTVT  120
VSSASTKG                                                           128

SEQ ID NO: 120         moltype = AA  length = 134
FEATURE                Location/Qualifiers
source                 1..134
                       mol_type = protein
                       organism = Homo sapiens
SEQUENCE: 120
FVQLVESGGG LVQPGGSLRL SCAASGFNFN TYWMNWVRQA PGKGLEWVAN MKEDGSEKYY  60
VDSVKGRFTI SRDNAKNSLY LQMNSLRAED TAVYYCARNP ESRCIVGRNR GWCRYFDLWG  120
RGSLVTVSPA STKG                                                    134

SEQ ID NO: 121         moltype = AA  length = 141
FEATURE                Location/Qualifiers
source                 1..141
                       mol_type = protein
                       organism = Homo sapiens
SEQUENCE: 121
LVQLVESGGG VVQPGRSLRL SCAASGFTFS TYAMHWVRQA PGKGLEWVAV ISYDGSNKFY  60
ADSVKGRFTI SRDNSKNTLY LQMNSLRAED TAVYYCARPK FLPGADIVVV VAATPFDYWG  120
QGNPGHRLLS FHQGPIGLPP G                                            141

SEQ ID NO: 122         moltype = AA  length = 120
FEATURE                Location/Qualifiers
source                 1..120
                       mol_type = protein
                       organism = Homo sapiens
SEQUENCE: 122
PMFQPGQSGG VVVQSGESLH LSCEASGFKF ASQMMHWVRH VPGRGLEWVA LISWDGSGKL  60
FADSVRGRFT IHRWNDRNSL YLDVKNVRPE DAAIYYCTRN GFDVWGQGIL VTVSSASTKG  120

SEQ ID NO: 123         moltype = AA  length = 132
FEATURE                Location/Qualifiers
source                 1..132
                       mol_type = protein
                       organism = Homo sapiens
SEQUENCE: 123
QVQLVQSGAE VKKPGASVKV SCKVSGHTLS ELSINWVRHV PGKGLEWMGG LDPEDGEAIH  60
EPKFQGRLTM TEDTSTDTAY VELSSLRSED TAMYYCATAD PFKVAQDEGL YVIFDYWGQG  120
TLVTVSSAST KG                                                      132

SEQ ID NO: 124         moltype = AA  length = 138
FEATURE                Location/Qualifiers
source                 1..138
                       mol_type = protein
                       organism = Homo sapiens
SEQUENCE: 124
QVQLVQSGAE VRKPGSSLKV SCKSSGGTFS RFVVNWVRQA PGQGLEWMGG MIPIFGIAKY  60
AQKFQDRVTM TADESKNTVY LDFSSLRSDD TAVYYCARDR GDTRLLDYGD YEDERYYYGM  120
DVWGQGTTVI VSSASTKG                                                138

SEQ ID NO: 125         moltype = AA  length = 126
FEATURE                Location/Qualifiers
source                 1..126
                       mol_type = protein
                       organism = Homo sapiens
SEQUENCE: 125
LVQLVESGGG VVQPGKSLRL SCATSGFTFS TYGMHWVRQA PGKGLEWVAV IWYDGSYKYY  60
ADSVKGRFTI SRDNSKNTLF LQMNSLRAED TAMYYCGREM AVGGTKALDH WGQGTLVTVS  120
SASTKG                                                             126
```

```
SEQ ID NO: 126         moltype = AA  length = 118
FEATURE                Location/Qualifiers
source                 1..118
                       mol_type = protein
                       organism = Homo sapiens
SEQUENCE: 126
QVQLVQSGAE AKRPGDSVKV SCKASGYTFT EYYIHWVRQT PGQGFEWMGI ITPGAGNTTY  60
AQKFQGRITV TRDTSAATVY MELSNLTSED TAVYFCSRGV SFWGQGTLVT VSSASTKG    118

SEQ ID NO: 127         moltype = AA  length = 122
FEATURE                Location/Qualifiers
source                 1..122
                       mol_type = protein
                       organism = Homo sapiens
SEQUENCE: 127
QVQMVASGGG LVKPGGSLRL SCEASGFTFS DYYMSWVRQA PGKGLEWISY ITSGGNALYY  60
ADSVKGRFTI SRDNAKNSLY LQMNSLRAED TAVYYCARDL LHAHDFGRQG TLVTVSSAST  120
KG                                                                 122

SEQ ID NO: 128         moltype = AA  length = 127
FEATURE                Location/Qualifiers
source                 1..127
                       mol_type = protein
                       organism = Homo sapiens
SEQUENCE: 128
QVQLVESGGG VVQPGRSLRL SCATSGFTSK NYGVHWVRQA PGKGLEWVAV IWYDGSNKFY  60
ADSVKGRFTI SRDRSKNMVY LQMNSLRVED TAIYYCARDS VAFVLEGPID YWGQGTLVTV  120
SSASTKG                                                            127

SEQ ID NO: 129         moltype = AA  length = 129
FEATURE                Location/Qualifiers
source                 1..129
                       mol_type = protein
                       organism = Homo sapiens
SEQUENCE: 129
QVQLVQSGAE VKKPGASVKV SCKASGYTFT DYYIHWVRQA PGQGLEWMGW INPSTGGTNF  60
VQKFLGRVTM TSDTSINTAY MELRRLKNDD AAIYYCATYS TRQFFHYYYV TDVWGQGTTV  120
TVSSASTKG                                                          129

SEQ ID NO: 130         moltype = AA  length = 134
FEATURE                Location/Qualifiers
source                 1..134
                       mol_type = protein
                       organism = Homo sapiens
SEQUENCE: 130
QVQLVQSGAE VKKPGSSVKV SCRASGGSFG NYAINWVRQA PMQGLEWMGG IIPIFGTTNY  60
AQNFRGRVTI NADTFTNTVN MDLSSLRSED TAVYYCGRSI NAAVPGLEGV YYYYGMAVWG  120
QGTTVTVSSA STKG                                                    134

SEQ ID NO: 131         moltype = AA  length = 134
FEATURE                Location/Qualifiers
source                 1..134
                       mol_type = protein
                       organism = Homo sapiens
SEQUENCE: 131
QVQLHQWGAG LLKPSDTLSL TCGILGVSPP GSLTGYYWTW IRQPPGKGLE WIGEVYHSGS  60
TNYNPSLASR VTISMGTTKT QFSLRLTSVT AADSAVYYCA SGKVWGITAR PRDAGLDVWG  120
QGTTVTVTSA STKG                                                    134

SEQ ID NO: 132         moltype = AA  length = 126
FEATURE                Location/Qualifiers
source                 1..126
                       mol_type = protein
                       organism = Homo sapiens
SEQUENCE: 132
EVQVVESGGG LVQPGGSLRL SCVASGFTFS EYWMSWVRQA PGKGLEWVAT IKRDGSEESY  60
VDSVKGRFTI SRDNAKNSLY LQMNSLRAED TAVYYCARVR DPNYNLHFDS WGQGTLVTVS  120
SASTKG                                                             126

SEQ ID NO: 133         moltype = AA  length = 122
FEATURE                Location/Qualifiers
source                 1..122
                       mol_type = protein
                       organism = Homo sapiens
SEQUENCE: 133
QVQLVESGGG LIQPGGSLRL SCEASGFAVG DINYMSWVRQ APGKGLEWVS VLYSGGSSQY  60
ADSVKGRFTI SRDNSRNTLY LQMDNLRAED TAVYYCARGL RVYFDLWGQG ILVTVSSAST  120
KG                                                                 122
```

-continued

```
SEQ ID NO: 134          moltype = AA  length = 135
FEATURE                 Location/Qualifiers
source                  1..135
                        mol_type = protein
                        organism = Homo sapiens
SEQUENCE: 134
QVQLVQSGAE VKKPGSSVKV SCKASGGTFS TYAFSWVRQA PGQGLEWMGG IIPIFGTENY  60
AQKFQGRVTI TADKSTSTAY MELSSLRSED TAVYYCARDR SSAIGYCSSI SCYKGSFDIW  120
GQGTMVTVSS ASTKG                                                   135

SEQ ID NO: 135          moltype = AA  length = 125
FEATURE                 Location/Qualifiers
source                  1..125
                        mol_type = protein
                        organism = Homo sapiens
SEQUENCE: 135
QVQLQESGPG LVKPSETLSL TCTVSGGSIS SRSYYWGWIR QPPGKGLEWV GSIYYTGSTY  60
YSPSLKSRVT ISVDTSQNQF SLKLNSVTAA DTAVYYCARQ KGSGTSLLYW GQGTLVTVSS  120
ASTKG                                                              125

SEQ ID NO: 136          moltype = AA  length = 129
FEATURE                 Location/Qualifiers
source                  1..129
                        mol_type = protein
                        organism = Homo sapiens
SEQUENCE: 136
QVQLVQSGSE LKKPGASVKV SCKASGYTFT SYAINWVRQA PGQGLEWMGW INTNTGNPTY  60
AQGFTGRFVF SLETSVSTAY LQINSLKAED TAVYYCARDL LESRTYYNDI RDCWGQGTLV  120
TVSSASTKG                                                          129

SEQ ID NO: 137          moltype = AA  length = 123
FEATURE                 Location/Qualifiers
source                  1..123
                        mol_type = protein
                        organism = Homo sapiens
SEQUENCE: 137
QVQLQESGSG LVKPSGTLSL TCAVSNGPIS SGNWWSWVRQ TPEKGLEWIG EVYHSGSTNH  60
NPSLKSRATI LVDKSKNQFS LNLRSVTAAD TAVYYCARVR GSWNFDYWGQ GILVTVSSAS  120
TKG                                                                123

SEQ ID NO: 138          moltype = AA  length = 159
FEATURE                 Location/Qualifiers
source                  1..159
                        mol_type = protein
                        organism = Homo sapiens
SEQUENCE: 138
QHQLVPCVAE VRKPGASVKV SCKVSGYTLT EISMHWVRQA PGKGLEWMGG FDREDGETIY  60
AQKFQGRVTM TEDTSTDTAY MELSSLRSED TAVYYCATTY LAVVPDGFDG YSSSWYWFDP  120
WGQGTLVTVS SASMQGPMLL SPTGTLLPRA PLVQTRPGP                         159

SEQ ID NO: 139          moltype = AA  length = 138
FEATURE                 Location/Qualifiers
source                  1..138
                        mol_type = protein
                        organism = Homo sapiens
SEQUENCE: 139
QVQLVQSGAE VRKPGSSLKV SCKSSGGTFS RYVVNWVRQA PGQGLEWMGG IIPIFGIAKY  60
AQKFQDRVTM TADESKNTVY LDFSSLRSDD TAVYYCARDR GDTRLLDYGD YEDERYYYGM  120
DVWGQGTTVI VSSASTKG                                                138

SEQ ID NO: 140          moltype = AA  length = 135
FEATURE                 Location/Qualifiers
source                  1..135
                        mol_type = protein
                        organism = Homo sapiens
SEQUENCE: 140
QVQLVQSGAE VKKPGSSVKV SCKASGGTFS TYAFSWVRQA PGQGLEWMGG IIPIFGTENY  60
AQKFQGRVTI TADKSTSTAY MELSSLRSED TAVYYCARDR SSAIGYCSSI SCYKGSFDIW  120
GQGTMVTVSS ASTKG                                                   135

SEQ ID NO: 141          moltype = AA  length = 127
FEATURE                 Location/Qualifiers
source                  1..127
                        mol_type = protein
                        organism = Homo sapiens
SEQUENCE: 141
QVHLEESGPG LVKTSQTLSL TCSVSSYSIS RSGYFWTWIR QRPGKGLEWI GYIYFNGRTT  60
YNPSLKSRIT ISRDTSHSQF SLTLNSLSAA DTAVYYCGRC QDGLASRPID FWGQGTLVTV  120
```

-continued

```
SSASTKG                                                     127

SEQ ID NO: 142          moltype = AA  length = 127
FEATURE                 Location/Qualifiers
source                  1..127
                        mol_type = protein
                        organism = Homo sapiens
SEQUENCE: 142
QVQLVESGGG VVQPGKSLRL SCAISGFLFN NYGGQWVRQA PGKGLEWVAA ISYDGNNRYY  60
ADSAKGRFLI SRDTPKNILY LQIYSLRLDD TAVYYCARDS VSKSYSAPPE FWGQGTVVTV  120
SSASTKG                                                     127

SEQ ID NO: 143          moltype = AA  length = 134
FEATURE                 Location/Qualifiers
source                  1..134
                        mol_type = protein
                        organism = Homo sapiens
SEQUENCE: 143
QLQLQESGPG LVKPSETLSL TCSVSDGSIN SNSYYWAWIR QSPGKGLEWI GSVYYFGGTY  60
YSPSLKSRVT MSVDRSKNQF SLNVSSVTAA DTAIYYCARH VRPYDRSGYP ERPNWFDPWG  120
RGTLVTVSSA STKG                                             134

SEQ ID NO: 144          moltype = AA  length = 125
FEATURE                 Location/Qualifiers
source                  1..125
                        mol_type = protein
                        organism = Homo sapiens
SEQUENCE: 144
RVQLVQSGAE VKKPGSSVTV SCKASGGSFS SYAISWVRQA PGQGLEWVGG VKVMFGTVHY  60
SQKVQGRVTI TADDSTGTSY LELSGLRSAD TAVYYCARNA GAYFYPFDIW GQGTLIIVSS  120
ASTKG                                                       125

SEQ ID NO: 145          moltype = AA  length = 136
FEATURE                 Location/Qualifiers
source                  1..136
                        mol_type = protein
                        organism = Homo sapiens
SEQUENCE: 145
QVQLVQSGAE VKKPGASVKV SCKASGYTFT RYHIHWVRHA PGQGLEWMGK INPSRASTKY  60
AKKFQDRVTM TRDTSTSTVY MELSSLRGDD TAVYYCGREM GTFTLLGVVI DHYDFYPMDV  120
WGQGTPVTVS SASTKG                                           136

SEQ ID NO: 146          moltype = AA  length = 138
FEATURE                 Location/Qualifiers
source                  1..138
                        mol_type = protein
                        organism = Homo sapiens
SEQUENCE: 146
QVQLVQSGAE VRKPGSSLKV SCKSSGGTFS RYVVNWVRQA PGQGLEWMGG IIPIFGIAKY  60
AQKFQDRVTM TADESKNTVY LDFSSLRSGD TAVYYCARDR GDTRLLDYGD YEDERYYYGM  120
DVWGQGTTVT VSSASTKG                                         138

SEQ ID NO: 147          moltype = AA  length = 127
FEATURE                 Location/Qualifiers
source                  1..127
                        mol_type = protein
                        organism = Homo sapiens
SEQUENCE: 147
SQHLVQSGTQ VKKPGASVRV SCQASGYTFT NYILHWWRQA PGQGLEWMGL IKPVFGAVNY  60
ARQFQGRIQL TRDIYREIAF LDLSGLRSDD TAVYYCARDE SGDDLKWHLH PWGQGTQVIV  120
SPASTKG                                                     127

SEQ ID NO: 148          moltype = AA  length = 127
FEATURE                 Location/Qualifiers
source                  1..127
                        mol_type = protein
                        organism = Homo sapiens
SEQUENCE: 148
SQQLVQSGTQ VKKPGASVRI SCQASGYSFT DYVLHWWRQA PGQGLEWMGW IKPVYGARNY  60
ARRFQGRINF DRDIYREIAF MDLSGLRSDD TALYFCARDG SGDDTSWHLD PWGQGTLVIV  120
SAASTKG                                                     127

SEQ ID NO: 149          moltype = AA  length = 127
FEATURE                 Location/Qualifiers
source                  1..127
                        mol_type = protein
                        organism = Homo sapiens
SEQUENCE: 149
SQQLVQSGTQ VKKPGASVRI SCQASGYSFT DYVLHWYRQA PGQGLEWMGW IKPVYGARNY  60
```

```
ARRFQGRINF DRDIYREIAF MDLSGLRSDD TALYFCARDG SGDDTSWYLD PWGQGTLVIV  120
SAASTKG                                                           127

SEQ ID NO: 150         moltype = AA  length = 127
FEATURE                Location/Qualifiers
source                 1..127
                       mol_type = protein
                       organism = Homo sapiens
SEQUENCE: 150
SQQLVQSGTQ VKKPGASVRI SCQASGYTFT DYVLHWWRQA PGQGLEWMGW IKPVYGARNY  60
ARRFQGRINF DRDIYREIAY MDLSGLRSDD TARYFCARDG SGDDTSWHLH PWGQGTLVIV  120
SAASTKG                                                           127

SEQ ID NO: 151         moltype = AA  length = 127
FEATURE                Location/Qualifiers
source                 1..127
                       mol_type = protein
                       organism = Homo sapiens
SEQUENCE: 151
SQQLVQSGTQ VKKPGASVRV SCQASGYTFM NYIIHWWRQA PGQRLEWMGW INPVFGARNY  60
AHRFQGRINF DRDINRETFQ MELTGLRSDD TAVYYCARDG SGDARDWHLD PWGQGTLVIV  120
SSASTKG                                                           127

SEQ ID NO: 152         moltype = AA  length = 127
FEATURE                Location/Qualifiers
source                 1..127
                       mol_type = protein
                       organism = Homo sapiens
SEQUENCE: 152
SQHLVQSGTQ VKKPGASVRV SCQASGYTFT NYILHWWRQA PGQGLEWMGL IKPVFGAVNY  60
ARQFQGRIQL TRDINREIAF LDLSGLRSDD TAVYYCARDE SGDDLKWHLH PWGQGTQVIV  120
SPASTKG                                                           127

SEQ ID NO: 153         moltype = AA  length = 127
FEATURE                Location/Qualifiers
source                 1..127
                       mol_type = protein
                       organism = Homo sapiens
SEQUENCE: 153
SQQLVQSGTQ VKKPGASVRV SCQASGYTFM NYIIHWWRQA PGQRLEWMGW INPVFGARNY  60
AHRFQGRINF DRDINRETFQ MDLTGLRSDD TAVYYCARDG SGDARDWHLH PWGQGTLVIV  120
SSASTKG                                                           127

SEQ ID NO: 154         moltype = AA  length = 127
FEATURE                Location/Qualifiers
source                 1..127
                       mol_type = protein
                       organism = Homo sapiens
SEQUENCE: 154
SQHLVQSGTQ VKKPGASVRV SCQASGYTFT NYILHWWRQA PGQGLEWMGL IKPVFGAVNY  60
ARQFQGRIQL TRDIYREIAF LDLSGLRSDD TAVYYCARDE SGDDLKWHLH PWGQGTQVIV  120
SPASTKG                                                           127

SEQ ID NO: 155         moltype = AA  length = 127
FEATURE                Location/Qualifiers
source                 1..127
                       mol_type = protein
                       organism = Homo sapiens
SEQUENCE: 155
SQQLVQSGTQ VKKTGASVRV SCQASGYDFT KYLIHWWRQA PGQGLEWMGW MKPVYGATNY  60
AHRFQGRISF TRDIYREIAF MDLNGLRSDD TAVYFCARDG GGDDRTWLLD AWGQGTLVIV  120
SSASTKG                                                           127

SEQ ID NO: 156         moltype = AA  length = 127
FEATURE                Location/Qualifiers
source                 1..127
                       mol_type = protein
                       organism = Homo sapiens
SEQUENCE: 156
SQHLVQSGTQ VKKPGASVRV SCQASGYTFT NYILHWWRQA PGQGLEWMGL IKPVFGAVNY  60
ARQFQGRIQL TRDINREIAF LDLSGLRSDD TAVYYCARDE SGDDLKWHLH PWGQGTQVIV  120
SPASTKG                                                           127

SEQ ID NO: 157         moltype = AA  length = 127
FEATURE                Location/Qualifiers
source                 1..127
                       mol_type = protein
                       organism = Homo sapiens
SEQUENCE: 157
```

-continued

```
SQQLVQSGTQ VKKPGASVRI SCQASGYTFT DYVLHWWRQA PGQGLEWMGW IKPVYGARNY  60
ARRFQGRINF DRDIYREIAF LDLSGLRSDD TARYFCARDG SGDDTSWHLH PWGQGTLVIV  120
SAASTKG                                                            127

SEQ ID NO: 158         moltype = AA  length = 127
FEATURE                Location/Qualifiers
source                 1..127
                       mol_type = protein
                       organism = Homo sapiens
SEQUENCE: 158
SQQLVQSGTQ VKKPGASVRI SCQASGYTFT DYVLHWWRQA PGQGLEWMGW IKPVYGARNY  60
ARRFQGRINF DRDIYREIAY MDLSGLRSDD TARYFCARDG SGDDTSWHLH PWGQGTLVIV  120
SAASTKG                                                            127

SEQ ID NO: 159         moltype = AA  length = 127
FEATURE                Location/Qualifiers
source                 1..127
                       mol_type = protein
                       organism = Homo sapiens
SEQUENCE: 159
SQQLVQSGTQ VKKPGASVRI SCQASGYTFT DYVLHWWRQA PGQGLEWMGW IKPVYGARNY  60
ARRFQGRINF DRDIYREIAY MDLSGLRSDD TARYFCARDG SGDDTSWHLH PWGQGTLVIV  120
SAASTKG                                                            127

SEQ ID NO: 160         moltype = AA  length = 127
FEATURE                Location/Qualifiers
source                 1..127
                       mol_type = protein
                       organism = Homo sapiens
SEQUENCE: 160
SQQLVQSGTQ VKKTGASVRV SCQASGYDFT KYLIHWWRQA PGQGLEWMGW MKPVYGATNY  60
AHRFQGRISF TRDIYREIAF MDLNGLRSDD TAVYFCARDG GGDDRTWLLD AWGQGTLVIV  120
SSASTKG                                                            127

SEQ ID NO: 161         moltype = AA  length = 126
FEATURE                Location/Qualifiers
source                 1..126
                       mol_type = protein
                       organism = Homo sapiens
SEQUENCE: 161
SQQLVQSGAQ VKKPGASVRV SCQASGYTFT NHFLHWWRQA PRQGLEWMGW INPVHGGRNY  60
ARRFQGRINF GRDVYQETAY MELSGLRNDD TATYFCARGG GDGRNWHLHP WGQGTLVIVS  120
AASTKG                                                             126

SEQ ID NO: 162         moltype = AA  length = 127
FEATURE                Location/Qualifiers
source                 1..127
                       mol_type = protein
                       organism = Homo sapiens
SEQUENCE: 162
SQHLVQSGTQ VKKPGASVRV SCQASGYTFT NYILHWWRQA PGQGLEWMGL IKPVFGAVNY  60
ARQFQGRIQL TRDIYREIAF LDLSGLRSDD TAVYYCARDE SGDDLKWHLH PWGQGTQVIV  120
SPASTKG                                                            127

SEQ ID NO: 163         moltype = AA  length = 127
FEATURE                Location/Qualifiers
source                 1..127
                       mol_type = protein
                       organism = Homo sapiens
SEQUENCE: 163
SQQLVQSGAQ VKKPGASLRV SCQASGYTFM NYLLHWWRQA PGQGLEWMGW INPVYGAVNY  60
AHRFQGRLTF SRDVYREIAY MDLNGLRSDD TAVYFCARDG SGDDRNWHLD PWGQGTLVIV  120
SSASTKG                                                            127

SEQ ID NO: 164         moltype = AA  length = 127
FEATURE                Location/Qualifiers
source                 1..127
                       mol_type = protein
                       organism = Homo sapiens
SEQUENCE: 164
SQQLVQSGTQ VKKPGASVRV SCQASGYTFT NYILHWWRQA PGRGLEWMGL IKPVYGAVNY  60
ARQFQGRIQL TRDIYREIAF LDLSGLRPDD TAVYYCARDE SGYDLNWHLD SWGQGTQVIV  120
SPASTKG                                                            127

SEQ ID NO: 165         moltype = AA  length = 127
FEATURE                Location/Qualifiers
source                 1..127
                       mol_type = protein
                       organism = Homo sapiens
```

```
SEQUENCE: 165
SQQLVQSGTQ VKKPGASVRV SCQASGYTFT DYVLHWWRQA PGQGLEWMGW IKPVYGARNY  60
AHRFQGRINF DRDVYREIAY MDLSGLRSDD TAVYFCARDG SGDATSWHLH PWGQGTLVIV  120
SSASTKG                                                           127

SEQ ID NO: 166         moltype = AA  length = 127
FEATURE                Location/Qualifiers
source                 1..127
                       mol_type = protein
                       organism = Homo sapiens
SEQUENCE: 166
SQQLVQSGTQ VKKPGASVRV SCQASGYTFM NYIIHWWRQA PGQRLEWMGW INPVFGARNY  60
AHRFQGRINF DRDINRETFQ MELTGLRSDD TAVYYCARDG SGDARDWHLD PWGQGTLVIV  120
SSASTKG                                                           127

SEQ ID NO: 167         moltype = AA  length = 137
FEATURE                Location/Qualifiers
source                 1..137
                       mol_type = protein
                       organism = Homo sapiens
SEQUENCE: 167
QVTLVQSGAE VKKPGASVRI SCRASGFTFD DYSDYSFIPT TYLIHWFRQA PGQGLEWMAW  60
INSVNGGRNI ARQFQGRVTV ARDRSNSIAF LEFSGLRHDD TAVYFCARDR RDDDRAWLLD  120
PWGQGTRVTV SSASTKG                                                137

SEQ ID NO: 168         moltype = AA  length = 130
FEATURE                Location/Qualifiers
source                 1..130
                       mol_type = protein
                       organism = Homo sapiens
SEQUENCE: 168
QVRLEQSGAA MRKPGASVTL SCQASGYNFV KYIVHWVRQK PGLGFEWVGM IDPYRGRPWS  60
AHKFQGRLSL SRDTSMEILY MTLTSLTSDD TATYFCARAE AASDSHSRPI MFDHWGQGSR  120
VTVSSASTKG                                                        130

SEQ ID NO: 169         moltype = AA  length = 130
FEATURE                Location/Qualifiers
source                 1..130
                       mol_type = protein
                       organism = Homo sapiens
SEQUENCE: 169
QVRLEQSGTA VRKPGASVTI SCQASGYNFV KFFIHWVRQR PGQGFEWVGM IEPFRGRPWS  60
AGNFQGRLSL SRDVSTETLY MTLNNLRSDD TAVYFCARLE AESDSHSRPI MFDHWGHGSL  120
VTVSSASTKG                                                        130

SEQ ID NO: 170         moltype = AA  length = 133
FEATURE                Location/Qualifiers
source                 1..133
                       mol_type = protein
                       organism = Homo sapiens
SEQUENCE: 170
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 171         moltype = AA  length = 130
FEATURE                Location/Qualifiers
source                 1..130
                       mol_type = protein
                       organism = Homo sapiens
SEQUENCE: 171
QVRLEQSGAA VRKPGASVTL SCQASGYNFV NYIIHWVRQR PGLDFEWVGM IDPYRGRPWS  60
AHKFQGRLSL SRDVSTEILY MTLSSLRSDD TATYFCARAE AESQSHSRPI MFDFWGQGSR  120
VTVSSASTKG                                                        130

SEQ ID NO: 172         moltype = AA  length = 133
FEATURE                Location/Qualifiers
source                 1..133
                       mol_type = protein
                       organism = Homo sapiens
SEQUENCE: 172
QVRLSQSGAA IKKPGASVTI SCETEGYTFI NYIIHWVRQP PGRGFEWLGM IDPRNGRPWF  60
GQSVQGRLSL RRDTYTEVVY MTLSGLTSDD AGHYFCARNE PQYHDGNGHS LPGMFDYWGQ  120
GTLVAVSSAS TKG                                                    133

SEQ ID NO: 173         moltype = AA  length = 133
FEATURE                Location/Qualifiers
source                 1..133
                       mol_type = protein
```

```
                         organism = Homo sapiens
SEQUENCE: 173
QVRLSQSGAA VKKPGASVTI VCETEGYNFI DYIIHWVRQP PGRGFEWLGM IDPRNGRPWS  60
GQKVHGRLSL WRDTSTEKVY MTLTGLTSDD TGLYFCGRNE PQYHDDNGHS LPGMIDYWGQ  120
GTMVTVSSAS TKG                                                     133

SEQ ID NO: 174           moltype = AA  length = 133
FEATURE                  Location/Qualifiers
source                   1..133
                         mol_type = protein
                         organism = Homo sapiens
SEQUENCE: 174
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                     133

SEQ ID NO: 175           moltype = AA  length = 133
FEATURE                  Location/Qualifiers
source                   1..133
                         mol_type = protein
                         organism = Homo sapiens
SEQUENCE: 175
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                     133

SEQ ID NO: 176           moltype = AA  length = 133
FEATURE                  Location/Qualifiers
source                   1..133
                         mol_type = protein
                         organism = Homo sapiens
SEQUENCE: 176
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                     133

SEQ ID NO: 177           moltype = AA  length = 130
FEATURE                  Location/Qualifiers
source                   1..130
                         mol_type = protein
                         organism = Homo sapiens
SEQUENCE: 177
QVRLEQSGAA VRKPGASVTL SCQASGYNFV RYIIHWVRQR PGLDFEWVGM IDPYRGRPWS  60
AHKFGGRLSL TRDVSTEILY MTLTSLRSDD TATYFCARAE AESQSHSRPI MFDSWGQGSR  120
VTVSSASTKG                                                         130

SEQ ID NO: 178           moltype = AA  length = 130
FEATURE                  Location/Qualifiers
source                   1..130
                         mol_type = protein
                         organism = Homo sapiens
SEQUENCE: 178
QVRLEQSGNA VRKPGASVTI SCQASGYNFV KFFIHWVRQR PGQGFEWVGM IEPFRGRPWS  60
AGNFQGRLSL SRDVSTETLY MTLNNLRSDD TAVYFCARLE AESDSHSRPI MFDHWGHGSL  120
VTVSSASTKG                                                         130

SEQ ID NO: 179           moltype = AA  length = 130
FEATURE                  Location/Qualifiers
source                   1..130
                         mol_type = protein
                         organism = Homo sapiens
SEQUENCE: 179
QVRLEQSGAA MRKPGASVTL SCQASGYNFV KYIIHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                         130

SEQ ID NO: 180           moltype = AA  length = 133
FEATURE                  Location/Qualifiers
source                   1..133
                         mol_type = protein
                         organism = Homo sapiens
SEQUENCE: 180
QVRLFQSGAA MRKPGASVTI SCEASGYNFL NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                     133

SEQ ID NO: 181           moltype = AA  length = 130
FEATURE                  Location/Qualifiers
source                   1..130
```

```
                        mol_type = protein
                        organism = Homo sapiens
SEQUENCE: 181
QVRLEQSGAA MRKPGASVTL SCQASGYNFV KYIIHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                        130

SEQ ID NO: 182          moltype = AA  length = 133
FEATURE                 Location/Qualifiers
source                  1..133
                        mol_type = protein
                        organism = Homo sapiens
SEQUENCE: 182
QVRLSQSGAA IKKPGASVTI SCETEGYTFI NYIIHWVRQP PGRGFEWLGM IDPRNGRPWF  60
GQSVQGRLSL RRDTYTEVVY MTLSGLTSDD TGLYFCARNE PQYHDGNGHS LPGMFDSWGQ  120
GTLVAVSSAS TKG                                                    133

SEQ ID NO: 183          moltype = AA  length = 133
FEATURE                 Location/Qualifiers
source                  1..133
                        mol_type = protein
                        organism = Homo sapiens
SEQUENCE: 183
QVQLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 184          moltype = AA  length = 130
FEATURE                 Location/Qualifiers
source                  1..130
                        mol_type = protein
                        organism = Homo sapiens
SEQUENCE: 184
QVRLEQSGAA MRKPGASVTL SCQASGYNFV KYIVHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                        130

SEQ ID NO: 185          moltype = AA  length = 133
FEATURE                 Location/Qualifiers
source                  1..133
                        mol_type = protein
                        organism = Homo sapiens
SEQUENCE: 185
QVRLFQSGAA MKKPGASVTI SCEASGYNFM NYFVHWVRQR PGRGFEWLGM INPRGGRPWS  60
AQSVQGRLTL TRDISTEMFY MRLDGLRSDD TATYFCARNE ADYHDGNGHS LRGMFDYWGQ  120
GSLITVSSAS TKG                                                    133

SEQ ID NO: 186          moltype = AA  length = 130
FEATURE                 Location/Qualifiers
source                  1..130
                        mol_type = protein
                        organism = Homo sapiens
SEQUENCE: 186
QVRLEQSGTA MRKPGASVTL SCQASGYNFV KYIVHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                        130

SEQ ID NO: 187          moltype = AA  length = 133
FEATURE                 Location/Qualifiers
source                  1..133
                        mol_type = protein
                        organism = Homo sapiens
SEQUENCE: 187
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 188          moltype = AA  length = 133
FEATURE                 Location/Qualifiers
source                  1..133
                        mol_type = protein
                        organism = Homo sapiens
SEQUENCE: 188
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 189          moltype = AA  length = 133
FEATURE                 Location/Qualifiers
```

-continued

```
source                1..133
                      mol_type = protein
                      organism = Homo sapiens
SEQUENCE: 189
QVRLSQSGAA IKKPGASVTI SCETEGYTFI NYIIHWVRQP PGRGFEWLGM IDPRNGRPWF  60
GQSVQGRLSL RRDTYTEVVY MTLSGLTSDD TGLYFCARNE PQYHDGNGHS LPGMFDSWGQ  120
GTLVAVSSAS TKG                                                    133

SEQ ID NO: 190        moltype = AA  length = 133
FEATURE               Location/Qualifiers
source                1..133
                      mol_type = protein
                      organism = Homo sapiens
SEQUENCE: 190
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 191        moltype = AA  length = 130
FEATURE               Location/Qualifiers
source                1..130
                      mol_type = protein
                      organism = Homo sapiens
SEQUENCE: 191
QVRLEQSGAA MRKPGASVTL SCQASGYNFV KYIIHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                        130

SEQ ID NO: 192        moltype = AA  length = 130
FEATURE               Location/Qualifiers
source                1..130
                      mol_type = protein
                      organism = Homo sapiens
SEQUENCE: 192
QVRLEQSGAA MRKPGASVTL SCQASGYNFV KYIIHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                        130

SEQ ID NO: 193        moltype = AA  length = 144
FEATURE               Location/Qualifiers
source                1..144
                      mol_type = protein
                      organism = Homo sapiens
SEQUENCE: 193
QVRLEQSGVA MRKPGASVTL SCQASGYNFV KYIIHWVRQK PGLGFEWVGM IDPYRGRPWS  60
AHKFQGRLSL SRDTSMEILY MTLTSLKSDD TATYFCARAE AASDIHSRPI ILTGPGEYGL  120
DLEHMDWTWR ILCLLAVAPG CHSQ                                        144

SEQ ID NO: 194        moltype = AA  length = 130
FEATURE               Location/Qualifiers
source                1..130
                      mol_type = protein
                      organism = Homo sapiens
SEQUENCE: 194
QVRLEQSGAA MRKPGASVTL SCQASGYNFV KYIVHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                        130

SEQ ID NO: 195        moltype = AA  length = 130
FEATURE               Location/Qualifiers
source                1..130
                      mol_type = protein
                      organism = Homo sapiens
SEQUENCE: 195
QVRLEQSGTA VRKPGASVTI SCQASGYNFV KFFIHGVRQR PGQGFEWVGM IEPFRGRPWS  60
AGNFQGRLSL SRDVSTETLY MTLNNLRSDD TAVYFCARLE AESDSHSRPI MFDHWGHGSL  120
VTVSSASTKG                                                        130

SEQ ID NO: 196        moltype = AA  length = 129
FEATURE               Location/Qualifiers
source                1..129
                      mol_type = protein
                      organism = Homo sapiens
SEQUENCE: 196
QVRLVQSGPQ VKTAGASMRV SCEASGYRFL DYIIVWIRQT HGQHFEYVGM INPRGGTPWP  60
SSKFRDRLTL TRDIYTDTFY LGLNNLGSGD TAIYFCARLE ADGDDYSPKM FDYWGQGTRI  120
IVSAASTKG                                                         129

SEQ ID NO: 197        moltype = AA  length = 133
```

```
FEATURE                 Location/Qualifiers
source                  1..133
                        mol_type = protein
                        organism = Homo sapiens
SEQUENCE: 197
QVHTFQSGSS MKKSGASVTI SCEATGYNIK NYILHWVRQK PGRGFEWVGM IDPINGRPWF  60
GQPFRGRLTL TRDLSTETFY MSLSGLTSDD TATYFCARRE ADYHDGNGHT LPGMFDFWGP  120
GTLITVSSAS TKG                                                     133

SEQ ID NO: 198          moltype = AA  length = 129
FEATURE                 Location/Qualifiers
source                  1..129
                        mol_type = protein
                        organism = Homo sapiens
SEQUENCE: 198
QVSLVQSGPQ VKTPGASMRV SCETSGYRFL DYIIVWIRQT HGQHFEYVGM INPRGGTPWP  60
SSKFRDRLTM TRDIHTDTFY LGLNNLRSDD TAIYFCARLE ADGDDYSPKM FDYWGQGTRI  120
IVSAASTKG                                                          129

SEQ ID NO: 199          moltype = AA  length = 129
FEATURE                 Location/Qualifiers
source                  1..129
                        mol_type = protein
                        organism = Homo sapiens
SEQUENCE: 199
QVRLVQSGPQ MKTPGASLRL SCEVSGYRFL DYFIVWVRQT GGQGFEYVGM INPRGGRPWS  60
SWKFRDRLSL TRDIETDTFY LGLNNLRSDD TAIYFCARLE ADGDNYSPKM VDYWGQGTKI  120
IVSPASTKG                                                          129

SEQ ID NO: 200          moltype = AA  length = 128
FEATURE                 Location/Qualifiers
source                  1..128
                        mol_type = protein
                        organism = Homo sapiens
SEQUENCE: 200
QVRLSQSGAA VVKTGASVTI SCETEGYNFV NYIIHWVRRP PGRGFEWLGM IDPRNGHPWF  60
AQTVRGRLSL RRDTFKETVY MTLSGLTSDD TGVYFCARNE PQYHSLPGMF DYWGHGTPVT  120
VSSASTKG                                                           128

SEQ ID NO: 201          moltype = AA  length = 133
FEATURE                 Location/Qualifiers
source                  1..133
                        mol_type = protein
                        organism = Homo sapiens
SEQUENCE: 201
QVRLVQSGAQ LKKPGASVTV SCEASGYNFV NYIINWVRQT PGRGFEWVGM IDPRRGRPWS  60
AQKFQGRLTL TRDIDSEKLY MHLSGLRGDD TAVYYCARQD SDFHDGHGHT LRGMFDSWGQ  120
GSPVTVSSAS TKG                                                     133

SEQ ID NO: 202          moltype = AA  length = 129
FEATURE                 Location/Qualifiers
source                  1..129
                        mol_type = protein
                        organism = Homo sapiens
SEQUENCE: 202
QVRLVQSGPQ VKTPGASMRI SCEASGYRFQ DYIIVWIRQT HGQGFEYVGM INPRGGTPWS  60
SSKFRDRLSL TRDIYTDTFY LGLNNLGSDD TAIYFCARLE ADGGDYSPKM FDYWGQGTRI  120
IVSAASTKG                                                          129

SEQ ID NO: 203          moltype = AA  length = 133
FEATURE                 Location/Qualifiers
source                  1..133
                        mol_type = protein
                        organism = Homo sapiens
SEQUENCE: 203
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                     133

SEQ ID NO: 204          moltype = AA  length = 129
FEATURE                 Location/Qualifiers
source                  1..129
                        mol_type = protein
                        organism = Homo sapiens
SEQUENCE: 204
QVRLVQSGPQ VKRPGASIRL SCETSGYRFQ DYIVAWIRQT RGQRFEFVGM VNPRGGRPWP  60
SSKFRDRVTL TRDIESETFH LGLNDLTSDD TATYFCARLE ADGADYSPKM FDFWGQGTKI  120
VVSPASTKG                                                          129
```

-continued

```
SEQ ID NO: 205         moltype = AA  length = 130
FEATURE                Location/Qualifiers
source                 1..130
                       mol_type = protein
                       organism = Homo sapiens
SEQUENCE: 205
QVRLEQSGAA VRKPGASVTL SCQASGYNFV NYIIHWVRQR PGLDFEWVGM IDPYRGRPWS  60
AHKFEGRLSL SRDVSTEVLY MTLSSLRSDD TATYFCARAE AESQSHSRPI MFDYWGQGSR  120
VTVSSASTKG                                                        130

SEQ ID NO: 206         moltype = AA  length = 130
FEATURE                Location/Qualifiers
source                 1..130
                       mol_type = protein
                       organism = Homo sapiens
SEQUENCE: 206
QVRLEQSGAA MRKPGASVTL SCQASGYNFV KYIIHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                        130

SEQ ID NO: 207         moltype = AA  length = 128
FEATURE                Location/Qualifiers
source                 1..128
                       mol_type = protein
                       organism = Homo sapiens
SEQUENCE: 207
QVRLSQSGAA VMKTGASVTI SCETEGFNFV NYIIHWVRRP PGRGFEWLGM IDPRNGHPWF  60
AQTVRGRLSL RRDTFNEIVY MTLSGLTTDD TGLYFCARNE PQYHSLPGMF DYWGQGTPVT  120
VSSASTKG                                                          128

SEQ ID NO: 208         moltype = AA  length = 133
FEATURE                Location/Qualifiers
source                 1..133
                       mol_type = protein
                       organism = Homo sapiens
SEQUENCE: 208
QVRLSQSGAA MKKPGASVTI SCETEGYTFI NYIIHWVRQP PGRGFEWLGM IDPRNGRPWF  60
GQSVQGRLSL RRDTYTEVVY MTLSGLTSDD AGLYFCARNE PQYHDGNGHS LPGMFDYWGQ  120
GTLVAVSSAS TKG                                                    133

SEQ ID NO: 209         moltype = AA  length = 133
FEATURE                Location/Qualifiers
source                 1..133
                       mol_type = protein
                       organism = Homo sapiens
SEQUENCE: 209
QVRLSQSGAA VVKTGASVTI SCETEGYTFV NYIIHWVRQS PGRGFEWLGM IDPRNGHPWF  60
GQRLRGRLSL RRDRSTETVF MTLSGLTSDD TAIYFCARNE PQYYDGSGHS LPGMFDYWGQ  120
GTRVVVSSAS TKG                                                    133

SEQ ID NO: 210         moltype = AA  length = 133
FEATURE                Location/Qualifiers
source                 1..133
                       mol_type = protein
                       organism = Homo sapiens
SEQUENCE: 210
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 211         moltype = AA  length = 129
FEATURE                Location/Qualifiers
source                 1..129
                       mol_type = protein
                       organism = Homo sapiens
SEQUENCE: 211
QVRLVQSGPQ VKTPGASIRL SCEASGYRFL DYFIVWVRQT PGQGFEYVGM INPRGGRPWS  60
SWKFRDRLSL TREIDTDTFY LGLSNLRSDD TAIYFCARLE ADGDDYSPKM VDYWGQGTKI  120
IVSAASTKG                                                         129

SEQ ID NO: 212         moltype = AA  length = 133
FEATURE                Location/Qualifiers
source                 1..133
                       mol_type = protein
                       organism = Homo sapiens
SEQUENCE: 212
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133
```

```
SEQ ID NO: 213          moltype = AA  length = 117
FEATURE                 Location/Qualifiers
source                  1..117
                        mol_type = protein
                        organism = Homo sapiens
SEQUENCE: 213
QVRLEQSGAA VRTPGASVTL SCQASGYKFV NYIIHWVRQR PGLAFEWVGM IDPYRGRPWS  60
AHSFEGRLSL SRDVSMEILY MTLTSLRSDD TATYFCARAE AESQSHSRPI ISTSGAR     117

SEQ ID NO: 214          moltype = AA  length = 133
FEATURE                 Location/Qualifiers
source                  1..133
                        mol_type = protein
                        organism = Homo sapiens
SEQUENCE: 214
QVQFFQSGSS MKKSGASVTI SCEATGYNIK NHILHWVRQK PGRGFEWVGM IDPINGRPWF  60
GQAFRGRLTL TRDLSTETFY MSLSGLTSDD TATYFCARRE ADYHDGNGHT LPGMFDFWGP  120
GTLVTVSSAS TKG                                                     133

SEQ ID NO: 215          moltype = AA  length = 133
FEATURE                 Location/Qualifiers
source                  1..133
                        mol_type = protein
                        organism = Homo sapiens
SEQUENCE: 215
QVRLSQSGAA VVKTGASVTI SCETEGYTFV NHIIHWVRQP PGRGFEWLGM IDPRNGHPWF  60
GQRLRGRLSL RRDRSTETVF MTLSGLTSDD IGIYFCARNE PQYFDGSGHS LPGMFDYWGQ  120
GTRVVVSSAS TKG                                                     133

SEQ ID NO: 216          moltype = AA  length = 133
FEATURE                 Location/Qualifiers
source                  1..133
                        mol_type = protein
                        organism = Homo sapiens
SEQUENCE: 216
QVRLSQSGAA VVKTGASVTI SCETEGYTFV NYIIHWVRQP PGRGFEWLGM IDPRNGHPWF  60
GQRLQGRLSL RRDRSTETVF MTLSGLTSDD TGIYFCARNE PQYYDGSGHS LPGMFDYWGQ  120
GTRVVVSSAS TKG                                                     133

SEQ ID NO: 217          moltype = AA  length = 129
FEATURE                 Location/Qualifiers
source                  1..129
                        mol_type = protein
                        organism = Homo sapiens
SEQUENCE: 217
QVRLVQSGPQ VKTPGASMRV SCEASGYRFL DYIIVWIRQT HGQHFEYVGM INPRGGTPWP  60
SSKFRDRLSL TRDIHTDTFY LGLNNLGSDD TAIYFCARLE ADGDDYSPKM FDHWGQGTRI  120
IVSAASTKG                                                          129

SEQ ID NO: 218          moltype = AA  length = 130
FEATURE                 Location/Qualifiers
source                  1..130
                        mol_type = protein
                        organism = Homo sapiens
SEQUENCE: 218
QVRLEQSGAA VKKPGASVTI SCQASGYNFV KFFIHWVRQR PGQGFEWVGM IEPYRGRPWS  60
AGNFQGRLSL SRDVSTETLY MTLNNLRSDD TAVYFCARLE AESDSHSRPI MFDHWGHGSL  120
VTVSSASTKG                                                         130

SEQ ID NO: 219          moltype = AA  length = 133
FEATURE                 Location/Qualifiers
source                  1..133
                        mol_type = protein
                        organism = Homo sapiens
SEQUENCE: 219
QVRLSQSGAA VMKTGASVTI SCETEGYNFV NYIIHWVRRP PGRGFEWLGM IDPKNGHPWF  60
AQAVRGRLSL RRDTFNEVVY MTLSGLTSDD TGLYFCARNE PQYHDGNGHS LPGMFDFWGQ  120
GTLVTVSSAS TKG                                                     133

SEQ ID NO: 220          moltype = AA  length = 133
FEATURE                 Location/Qualifiers
source                  1..133
                        mol_type = protein
                        organism = Homo sapiens
SEQUENCE: 220
QVRLSQSGAA VVKTGASVTI SCETEGYTFV NYIIHWVRQP PGRGFEWLGM IDPRNGHPWF  60
GQRFRGRLSL RRDRSTETVF MTLSGLTSDD NGIYFCARNE PQYYDGSGHS LPGMFDYWGQ  120
GTRVVVSSAS TKG                                                     133
```

```
SEQ ID NO: 221          moltype = AA  length = 130
FEATURE                 Location/Qualifiers
source                  1..130
                        mol_type = protein
                        organism = Homo sapiens
SEQUENCE: 221
QVRLEQSGAA VRKPGASVTL SCQASGYNFV NYIIHWVRQR PGLDFEWVGM IDPYRGRPWS  60
AHKFQGRLSL SRDVSTEILY MTLSSLRSDD TATYFCARAE AESQSHSRPI MFDFWGQGSR  120
VTVSSASTKG                                                        130

SEQ ID NO: 222          moltype = AA  length = 130
FEATURE                 Location/Qualifiers
source                  1..130
                        mol_type = protein
                        organism = Homo sapiens
SEQUENCE: 222
QVRLEQSGAA VRKPGASVTL SCQASGYNFV NYIIHWVRQR PGLDFEWVGM IDPYRGRPWS  60
AHKFQGRLSL SRDVSTEILY MTLNSLRSDD TATYFCARAE AESQSHSRPI MFDSWGQGSR  120
VTVSSASTKG                                                        130

SEQ ID NO: 223          moltype = AA  length = 133
FEATURE                 Location/Qualifiers
source                  1..133
                        mol_type = protein
                        organism = Homo sapiens
SEQUENCE: 223
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 224          moltype = AA  length = 130
FEATURE                 Location/Qualifiers
source                  1..130
                        mol_type = protein
                        organism = Homo sapiens
SEQUENCE: 224
QVRLEQSGGA LRKPGASVTL SCQASGYNFV KYIIHWVRQR PGLGFEWVGM IDPYRGRPWY  60
AHSFAGRLSL SRDTSTETLY MTLSSLKSDD TATYFCARAE AASDSHSRPI MDWTWRILCL  120
LAVVPASTKG                                                        130

SEQ ID NO: 225          moltype = AA  length = 133
FEATURE                 Location/Qualifiers
source                  1..133
                        mol_type = protein
                        organism = Homo sapiens
SEQUENCE: 225
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 226          moltype = AA  length = 130
FEATURE                 Location/Qualifiers
source                  1..130
                        mol_type = protein
                        organism = Homo sapiens
SEQUENCE: 226
QVRLEQSGAA MRKPGASVTL SCQASGYNFV KYIVHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                        130

SEQ ID NO: 227          moltype = AA  length = 129
FEATURE                 Location/Qualifiers
source                  1..129
                        mol_type = protein
                        organism = Homo sapiens
SEQUENCE: 227
QVRLVQSGPQ VKRPGASIRL SCESSGYRFQ DYIVAWIRQT RGQGFEFVGM VNPRGGRPWP  60
SSRFRDRVTL TRDIESETFY LGLNDLTSDD TATYFCARLE ADGSDYSPKM FDFWGQGTKI  120
VVSPASTKG                                                         129

SEQ ID NO: 228          moltype = AA  length = 133
FEATURE                 Location/Qualifiers
source                  1..133
                        mol_type = protein
                        organism = Homo sapiens
SEQUENCE: 228
QVRLVQSGAQ LKKPGASVTV SCEASGYNFV NYIINWVRQT PGRSFEWVGM IDPRRGRPWS  60
AQKFQGRLTL TRDIDSEKLY MHLSGLRGDD TAVYYCARQD SDFHDGHGHT LRGMFDSWGQ  120
```

```
GSPVTVSSAS TKG                                                    133

SEQ ID NO: 229          moltype = AA  length = 132
FEATURE                 Location/Qualifiers
source                  1..132
                        mol_type = protein
                        organism = Homo sapiens
SEQUENCE: 229
QVQLVQSGPE LMKPGSSVKV SCRASGDNFL TSTFNWLRQA PGQRLEWMGR FIPSLGLITS  60
APKFSDRLTI TADQATLTAY MELTGLTSED TALYYCARGL CRGGNCRLGP SGWLDPWGRG  120
TQVTVSSAST KG                                                     132

SEQ ID NO: 230          moltype = AA  length = 126
FEATURE                 Location/Qualifiers
source                  1..126
                        mol_type = protein
                        organism = Homo sapiens
SEQUENCE: 230
QVVLIQSGAE VKRPGSSVKV SCKASGGSFP ITWVRQAPGH GLEWMGGINP FFGTTNYAQK  60
FQGRVSITAD ESTSTTYLHL SDLRSEDTAV YFCARENREK WLVLRSWFAP WGQGTLVTVS  120
SASTKG                                                            126

SEQ ID NO: 231          moltype = AA  length = 123
FEATURE                 Location/Qualifiers
source                  1..123
                        mol_type = protein
                        organism = Homo sapiens
SEQUENCE: 231
EESGPGLVKP SQTLSLTCSV SGDSVSSGGY FWSWIRQHPT KGLECLGYVY YTGNTYYNPS  60
LKSPPTIEVA MANNQVSLKL GSVTAADTAV YYCARIKRFR GGNYFDTWGH GLLVTVSSAS  120
TKG                                                               123

SEQ ID NO: 232          moltype = AA  length = 150
FEATURE                 Location/Qualifiers
source                  1..150
                        mol_type = protein
                        organism = Homo sapiens
SEQUENCE: 232
LAQLEQSGGG VVKPGGSLRL PCAASGFTFI DYYMAWIRLA PGKGLEWLSY ISKNGDYTKY  60
SESLKGRFTI SRDNAKNLVI LQLNRLRADD TAIYFCARAD GLTYFGELLQ YIFDLWGQGA  120
RVIVSSASTK GPSVFPLAPS SKSTSGHASV                                  150

SEQ ID NO: 233          moltype = AA  length = 128
FEATURE                 Location/Qualifiers
source                  1..128
                        mol_type = protein
                        organism = Homo sapiens
SEQUENCE: 233
QVQLVQSGAE VKKPGASVKI SCKASGYSFR NYAVHWVRQA PGQGLEWMGE INGGNGNTEY  60
SQKSQGRLTI TRDISATTAY MELSSLRSDD TAVYYCARVA YVHVVTTRSL DNWGQGTLVT  120
VSSASTKG                                                          128

SEQ ID NO: 234          moltype = AA  length = 139
FEATURE                 Location/Qualifiers
source                  1..139
                        mol_type = protein
                        organism = Homo sapiens
SEQUENCE: 234
QVQIRQSGPG LVKPLETLSL SCIVFGGSFI AYHWTWIRQA PLKGLEWIGD IDQGGDITYS  60
PSLKSRVTMS VDRSKSQFSL KLSSVTAADA AVYYCVRGPP NRYAVTSFTS GTHRERSSYY  120
FDYWGPGTLV TVSSASTKG                                              139

SEQ ID NO: 235          moltype = AA  length = 118
FEATURE                 Location/Qualifiers
source                  1..118
                        mol_type = protein
                        organism = Homo sapiens
SEQUENCE: 235
KAPATLSLSP GERATLSCRA SQSVGSDLAW YQQKPGQAPR LLIYDASNRA TAIPARFSGS  60
GSGTDFTLSI SSLEPEDFAV YFCQQRYDKI TFGQGTRLEI QRTVAAPSVF IFPPSDEQ    118

SEQ ID NO: 236          moltype = AA  length = 121
FEATURE                 Location/Qualifiers
source                  1..121
                        mol_type = protein
                        organism = Homo sapiens
SEQUENCE: 236
FVQLVESGGG VVQPGTSLRL SCTTSGFIFS DYGMHWVRQA AGKGLEWVAV IWHDGSNRFY  60
ADSVKGRFTI SRDNSKNAVY LEMNNLRVED TALYYCARTS MDIDYWGQGT PVTVSSASTK  120
```

```
G                                                                  121

SEQ ID NO: 237          moltype = AA  length = 132
FEATURE                 Location/Qualifiers
source                  1..132
                        mol_type = protein
                        organism = Homo sapiens
SEQUENCE: 237
QVYLVQSGPE LKKPGASVKI SCKASGYNFP KYAIHWVRQA PGQGLQWMGW INGDNGDARY  60
SQKLQGRVTP STDTSASVVY MELKRLRSED TAVYYCARAL YPWEIGGVPS TMGDDYWGQG  120
TLITVSSAST KG                                                      132

SEQ ID NO: 238          moltype = AA  length = 130
FEATURE                 Location/Qualifiers
source                  1..130
                        mol_type = protein
                        organism = Homo sapiens
SEQUENCE: 238
QVHLQQWGAG LLKPSETLSL TCAVSGGSFS GFFWTWIRQS PGKGLEWIGE VNHSGFTHSN  60
PSLESRATIS VAASNTQFSL RLASVTAADT AIYFCALRYF DWSPFRRDTY GTDVWGQGTT  120
VIVSSASTKG                                                         130

SEQ ID NO: 239          moltype = AA  length = 132
FEATURE                 Location/Qualifiers
source                  1..132
                        mol_type = protein
                        organism = Homo sapiens
SEQUENCE: 239
QVQLVQSGAE LKKPGSSVKV SCKASGGTFN NHTFNWVRQA PGQGLEWMGR TIPILGSRDY  60
AKTFQDRVTI IADKSTSTVY LELRRLKSED TGVYYCATSM YYFDSGGYYR NTDLDKWGQG  120
SLVTVSSAST KG                                                      132

SEQ ID NO: 240          moltype = AA  length = 133
FEATURE                 Location/Qualifiers
source                  1..133
                        mol_type = protein
                        organism = Homo sapiens
SEQUENCE: 240
GLDLEHDGHH KEEPRASVTV SCEASGYNFV NYIIHWVRLT PGRGFEWMGM IDPRRGRPWS  60
AQKFQGRLTL TRDIDSERLY MQLSGLRGDD TAVYFCARQE PDFHDGHGHT LRGMFDSWGQ  120
GSPVSVSSAS TKG                                                     133

SEQ ID NO: 241          moltype = AA  length = 124
FEATURE                 Location/Qualifiers
source                  1..124
                        mol_type = protein
                        organism = Homo sapiens
SEQUENCE: 241
QVQLVQSGAE LKKPGSSVKV SCKASGGTFS NYAINWVRQA PGQGFEWMGG IIPLFATPTY  60
AQKFQGRVRI TADDSTSTAY MELSSLRSDD TAVYFCARPN VVRSALDYWG QGTLVTVSSA  120
STKG                                                               124

SEQ ID NO: 242          moltype = AA  length = 129
FEATURE                 Location/Qualifiers
source                  1..129
                        mol_type = protein
                        organism = Homo sapiens
SEQUENCE: 242
QARLDQWGTG LLKPSETLSL KCAVFGVLFT DYNWTWVRQS PGKGLEWIGH LDHRGGGNYN  60
PSLESRVTIS LDYSKAQFSL HLKSVTVADT ALYYCAGAVK GFWFDEVYNW FGPWSQGTLV  120
TVASASTKG                                                          129

SEQ ID NO: 243          moltype = AA  length = 146
FEATURE                 Location/Qualifiers
source                  1..146
                        mol_type = protein
                        organism = Homo sapiens
SEQUENCE: 243
QVQLQESGPG LVKPSGTLSL TCAVSGASIS SRNWWTWVRQ PPGKGLEWIG EIYESGATNY  60
NPSLKSRVTI SVDKSKNQFS LRLTSVTAAD TAVYFCARLM TFGGLIGTLD YWGQGTLVTV  120
LQPPPRAHRY HPRNLLQEHL CARVMP                                       146

SEQ ID NO: 244          moltype = AA  length = 141
FEATURE                 Location/Qualifiers
source                  1..141
                        mol_type = protein
                        organism = Homo sapiens
SEQUENCE: 244
QVQLVQSGAE VKKPGSSVKV SCKASGGTFS TYAISWVRQA PGQGLEWMGG IIPSFSMSNY  60
```

```
AQDFQGRLTI TADESTSSVY MELNSLRSED TAVYYCARDF PRFHRLVGNY DFWRGTLDRF  120
SYMDLWGRGT AVTVSSASTK G                                           141

SEQ ID NO: 245         moltype = AA  length = 132
FEATURE                Location/Qualifiers
source                 1..132
                       mol_type = protein
                       organism = Homo sapiens
SEQUENCE: 245
QVHLVQSGAE AKRPGSSVRV SCRASGGDFS SYTLSWVRQA PGQGIEWMGG VVPMLDTVHY  60
AQKFQGRLTL SVDEGTSTAY MELSSLRSED TAMYYCTRGR QTFRAIWSGP PAVFDIWGQG  120
TLVIVSSAST KG                                                     132

SEQ ID NO: 246         moltype = AA  length = 141
FEATURE                Location/Qualifiers
source                 1..141
                       mol_type = protein
                       organism = Homo sapiens
SEQUENCE: 246
NGGSLRLSCR VSGFGFHLYE MNWVRQAPGK GLEWISSISG SGESTHYSDS ITGRFSMSRD  60
EAKDSLYLQM NNLRVEDTAV YYCTRGFSMG DGTGFSFDTW GRGTMVTVSS GLDTVSLAST  120
KGPSVFPLAP CSRSTSDARL S                                           141

SEQ ID NO: 247         moltype = AA  length = 149
FEATURE                Location/Qualifiers
source                 1..149
                       mol_type = protein
                       organism = Homo sapiens
SEQUENCE: 247
AARLDQWGTG LVKPSETLSL KCAVFGVDFP DYTWTWARQA PGKGLEWIGH RDHRGGSSYN  60
PSLSGRATIS LDTSKAQFSL HIKSVTVADT ATYYCAGAVA GLWFEDAYNW FGPWSQGTLV  120
TVAAASTKGP SVFPLAPSSK STSGHASVL                                   149

SEQ ID NO: 248         moltype = AA  length = 149
FEATURE                Location/Qualifiers
source                 1..149
                       mol_type = protein
                       organism = Homo sapiens
SEQUENCE: 248
QARLDQWGTG LLKPSETLSL KCAVFGVLFT DYNWTWVRQS PGKGLEWIGH LDHRGGGNYN  60
PSLESRVTIS LDYSKAQFSL HLKSVTVADT ALYYCAGAVK GLWFDETYTW FGPWSQGTRV  120
TVASASTKGP SVFPLAPSSK STSGTRDLS                                   149

SEQ ID NO: 249         moltype = AA  length = 129
FEATURE                Location/Qualifiers
source                 1..129
                       mol_type = protein
                       organism = Homo sapiens
SEQUENCE: 249
QVQLVQSEAE VKKPGSSVKV SCKASGGTFR GYTISWVRQA PGQGLEWMGR IIPILGKAIY  60
APSFQGRVTL TADKSTGTAY MELSRLRSDD TAVYYCAKVK MRGSSGYYYL FDDWGQGTLV  120
TVSSASTKG                                                         129

SEQ ID NO: 250         moltype = AA  length = 122
FEATURE                Location/Qualifiers
source                 1..122
                       mol_type = protein
                       organism = Homo sapiens
SEQUENCE: 250
QVHLVQSGAE VKKPGASVKV SCKVSGYTLS ELSIHWVRQG PGRGLEWMAN FDPEDGETIY  60
APQFQGRVTL TEDTSTDTAY MQLTSLRSED TAVYYCATDR YTDTGRWGPG TLVTVSSAST  120
KG                                                                122

SEQ ID NO: 251         moltype = AA  length = 129
FEATURE                Location/Qualifiers
source                 1..129
                       mol_type = protein
                       organism = Homo sapiens
SEQUENCE: 251
QARLDQWGTG LLKPSETLSL KCAVFGVLFT DYNWTWVRQS PGKGLEWIGH LDHRGGGSYN  60
PSLESRVSIS LDYSKAQFSL HLKSVTVADT ALYYCAGAVK GFWFDEPSTW FGPWSQGTMV  120
TVASASTKG                                                         129

SEQ ID NO: 252         moltype = AA  length = 149
FEATURE                Location/Qualifiers
source                 1..149
                       mol_type = protein
                       organism = Homo sapiens
SEQUENCE: 252
```

-continued

```
QARLDQWGTG LLKPSETLSL KCAVFGVLFT DYNWTWVRQS PGKGLEWIGH LDHRGGGNYN  60
PSLESRVTIS LDYSKAQFSL HLKSVTVADT ALYYCAGAVK GFWFDEVYNW FGPGVREPWL  120
PSPQPPPRAH RSSPWHPPPR APLVTATVP                                   149

SEQ ID NO: 253          moltype = AA  length = 129
FEATURE                 Location/Qualifiers
source                  1..129
                        mol_type = protein
                        organism = Homo sapiens
SEQUENCE: 253
QARLDQWGTG LLKPSETLSL KCAVFGVLFT DYNWTWVRQS PGKELEWIGH LDHRGGGNYN  60
PSLESRVTIS LDYSKAQFSL HLKSVTVADT ARYYCAGAVK GFWFDDPYTW FGPWSQGTLV  120
TVASASTKG                                                         129

SEQ ID NO: 254          moltype = AA  length = 132
FEATURE                 Location/Qualifiers
source                  1..132
                        mol_type = protein
                        organism = Homo sapiens
SEQUENCE: 254
QVHLVQSGAE AKRPGSSVRV SCRASGGDFS SYTLSWVRQA PGQGLERMGG VVPMLDTVHY  60
AQKFQGRLTL SVDEGTSTAY MELSSLRSED TAMYYCTRGR QTFRAIWSGP PVVFDIWGQG  120
TLVSVSSAST KG                                                     132

SEQ ID NO: 255          moltype = AA  length = 125
FEATURE                 Location/Qualifiers
source                  1..125
                        mol_type = protein
                        organism = Homo sapiens
SEQUENCE: 255
QFRLVQSGPE VKNPGSSVTV SCKASGGTFS GLGINWVRQA PGQGLEWLGD IKTMYGTTNY  60
APKFQGRVTI TADESTSTSY MELSGLRSED TAVFYCVREL FGHHPAFGVW GQGTSVIVSS  120
ASTKG                                                             125

SEQ ID NO: 256          moltype = AA  length = 124
FEATURE                 Location/Qualifiers
source                  1..124
                        mol_type = protein
                        organism = Homo sapiens
SEQUENCE: 256
QVQLVQSGAE VKKPGASVKV SCKASGYTFT NYGVSWVRQA PGQGLEWMGW ISPYSGNTNY  60
AQRLQDRVTM TTDTSTNTAY MELRSLRSDD TAVYYCAARS YYYYSMDVWG QGTTVTVSSA  120
STKG                                                              124

SEQ ID NO: 257          moltype = AA  length = 133
FEATURE                 Location/Qualifiers
source                  1..133
                        mol_type = protein
                        organism = Homo sapiens
SEQUENCE: 257
QVQLVQSGAD VKKPGASVKV SCKVSGYTVS ELSIHWVRQA PGKGLEWMGG FDPEDGKTVS  60
AQNFQGRVTM TEDKSTGTAN MELRSLRSED TAVYYCATTV QLIVDFCNGG PCYNFDDWGQ  120
GTLVTVSSAS TKG                                                    133

SEQ ID NO: 258          moltype = AA  length = 128
FEATURE                 Location/Qualifiers
source                  1..128
                        mol_type = protein
                        organism = Homo sapiens
SEQUENCE: 258
QVQLVQSGAE VKKPGSSVKV SCKASGGTLS SYTISWVRQA PGQGLEWMGR LIPLVDITTY  60
AQKFQGRVTI TADTSTNTAY MELSNLRSED TAIYHCATST MIAAVINDAF DLWGQGTTVT  120
VSSASTKG                                                          128

SEQ ID NO: 259          moltype = AA  length = 125
FEATURE                 Location/Qualifiers
source                  1..125
                        mol_type = protein
                        organism = Homo sapiens
SEQUENCE: 259
QVQLVQSGAE VKKPGASVKV SCKASGNTFT SYGITWVRQA PGQGLEWMGW ISAYNGNTNY  60
AQKLQDRLTM TTDTSTSTAY MELRSLRSDD TAVYYCAFSR HYGSGNYDYW GQGTLVTVSS  120
ASTKG                                                             125

SEQ ID NO: 260          moltype = AA  length = 125
FEATURE                 Location/Qualifiers
source                  1..125
                        mol_type = protein
                        organism = Homo sapiens
```

```
SEQUENCE: 260
QVQLQQWGAG LLKPSETLSL TCAVYGGSFS GYYWSWIRQP PGKGLEWIGE INHSGSTNYN  60
PSLKSRVTIS VDTSKNQFSL KLSSVTAADT AVYYCARLPI GSGWYGRDYW GQGTLVTVSS  120
ASTKG                                                              125

SEQ ID NO: 261         moltype = AA  length = 129
FEATURE                Location/Qualifiers
VARIANT                19
                       note = Any naturally occurring amino acid or not present
VARIANT                90
                       note = Any naturally occurring amino acid or not present
source                 1..129
                       mol_type = protein
                       organism = Homo sapiens
SEQUENCE: 261
EVQLLESGGG LVRPGGSLXL SCSASGFTFN SYAMSWVRQA PGKGLEWVSS VSASGEMTYY  60
ADSVRGRFTI SRDNANNALH LQMNSLRAEX TAVYYCAKVG GTVWSGYSNY LDYWGPGTLV  120
TVSSASTKG                                                          129

SEQ ID NO: 262         moltype = AA  length = 125
FEATURE                Location/Qualifiers
source                 1..125
                       mol_type = protein
                       organism = Homo sapiens
SEQUENCE: 262
QVQLVQSGAE VKKPGASVKV SCKPSSNTFT SHYIHWVRQA PGQGLEWMGM INPGGSTRYA  60
PKFQGRVTLT RDTSTRTVYM ELSSLRSEDT AVYYCARPQY NLGRDPLDVW GLGTMVTVSS  120
ASTKG                                                              125

SEQ ID NO: 263         moltype = AA  length = 124
FEATURE                Location/Qualifiers
source                 1..124
                       mol_type = protein
                       organism = Homo sapiens
SEQUENCE: 263
EVQLVESGGG LVKPGGSLRL SCADSGFTFR SYSMHWVRQA PGKGLAWVSS ISSTSNYIYY  60
ADSVKGRFTI SRDNAKNSLY LQMNSLRAED TAVYYCARTF ITASWFDSWG QGTLVTVSSA  120
STKG                                                               124

SEQ ID NO: 264         moltype = AA  length = 104
FEATURE                Location/Qualifiers
source                 1..104
                       mol_type = protein
                       organism = Homo sapiens
SEQUENCE: 264
VSGGRFSNYG LSWVRQAPGQ GLEWMGRIVP AINRAKYAQK FQGRVILTAD KITDTAYMEL  60
RSLRSEDTAI FYCARDPQIE IRGNAFDIWG QGTVVTVSSA STKG                   104

SEQ ID NO: 265         moltype = AA  length = 128
FEATURE                Location/Qualifiers
source                 1..128
                       mol_type = protein
                       organism = Homo sapiens
SEQUENCE: 265
QVQLQESGPG LVKPSGTLSL TCNVYGGSMI SYYWSWIRQP PGKGLEWIGH VYNSGNTKYS  60
PSLKNRVTIS MDTSRNLFSL KVTSVTPADT AVYYCARADY DNIWDSRGGF DLWGQGTLVT  120
VSSASTKG                                                           128

SEQ ID NO: 266         moltype = AA  length = 130
FEATURE                Location/Qualifiers
source                 1..130
                       mol_type = protein
                       organism = Homo sapiens
SEQUENCE: 266
QVQLVQLLQS GAEVKKPGSS VKVSCQISGY GFSNYAISWV RQAPGQGLEW LGRIVPAVGM  60
TEYAQKFQGR VTFTADRSTI TAYMDLRGLR SDDTAVYYCV RDPQVEVRGN AFDIWGQGTM  120
VTVSSASTKG                                                         130

SEQ ID NO: 267         moltype = AA  length = 126
FEATURE                Location/Qualifiers
source                 1..126
                       mol_type = protein
                       organism = Homo sapiens
SEQUENCE: 267
QVQLVQSGAE MKKPGASVKV SCKASGHTFT NYYMHWVRQA PGQGLEWMGM INPTGDSTRY  60
AQRFQGRVTM TRDTSTRTVY MELSSLRSDD TAVYYCARAH HDFWRAPVDV WGKGTTVTVS  120
SASTKG                                                             126

SEQ ID NO: 268         moltype = AA  length = 130
```

-continued

```
FEATURE                Location/Qualifiers
source                 1..130
                       mol_type = protein
                       organism = Homo sapiens
SEQUENCE: 268
EVQLVQSGAE VKKPGESLRI SCKTSGYNFN DDWIAWVRQR PDKGPEWMGI FYPGDSQATY  60
SPSFQGHVTF SADTSISTAY LQWTSLKASD TAIYYCARTR CFGANCFNFM DVWGKGTALT  120
VTVSSASTKG                                                        130

SEQ ID NO: 269         moltype = AA  length = 125
FEATURE                Location/Qualifiers
source                 1..125
                       mol_type = protein
                       organism = Homo sapiens
SEQUENCE: 269
QVQLQESGPG PVKPSETLSL TCTVSGGSMI SYYWSWIRQP PGKGLEWIGY IFTNGRTTYS  60
PSLRSRVTIS LDTSTNHFSL RLKSVTAADT AIYYCARLDG EAFRYYLDLW GQGNLVTVSS  120
ASTKG                                                             125

SEQ ID NO: 270         moltype = AA  length = 99
FEATURE                Location/Qualifiers
source                 1..99
                       mol_type = protein
                       organism = Homo sapiens
SEQUENCE: 270
IRSFYWHWIR QSPGKGLEWL GSVFDNGLTT HNPSLKSRLT ISEDPSRNQI SLKLRSMTAA  60
DTAVYYCARG DYDILTSSYQ FDYWGQGTLV AVSSASTKG                        99

SEQ ID NO: 271         moltype = AA  length = 127
FEATURE                Location/Qualifiers
source                 1..127
                       mol_type = protein
                       organism = Homo sapiens
SEQUENCE: 271
QVQLQESGPG LVKPSETLSL TCTVFGASIR SFYWHWIRQS PGKGLEWLGS VFDNGLTTYN  60
PSLKNRLSIS EDPSRNQISL NLRSMTAADT AVYYCARADY DLLTSSYHFD SWGQGTLVTV  120
SSASTKG                                                           127

SEQ ID NO: 272         moltype = AA  length = 125
FEATURE                Location/Qualifiers
source                 1..125
                       mol_type = protein
                       organism = Homo sapiens
SEQUENCE: 272
QVQLQESGPG LVKPSETLSL TCTVSGGSIS YYYWSWIRQP PGKGLEWIGD IYYSGTTDYN  60
PSLKSRVTIS VDTSKNQFSL KLSSVTAADT AVYYCARRRG QRLLAYFDYW GQGSLVTVSS  120
ASTKG                                                             125

SEQ ID NO: 273         moltype = AA  length = 127
FEATURE                Location/Qualifiers
source                 1..127
                       mol_type = protein
                       organism = Homo sapiens
SEQUENCE: 273
QVQLVQSGAE VKKPGASVKV SCKAPGYTFI GHYMHWIRQA PGQGLEWMGW INPNSGDTNY  60
AQTFQGRVTM TRDTSISTAY MELTRLRSDD TAVYYCARDL RPMRGNWAMH VWGEGTTVTV  120
SSASTKG                                                           127

SEQ ID NO: 274         moltype = AA  length = 106
FEATURE                Location/Qualifiers
source                 1..106
                       mol_type = protein
                       organism = Homo sapiens
SEQUENCE: 274
CTVSGGSISS AGYYWTWIRQ HPGKGLEFIG YIYYIGTTYY NPSLKSRLTI SIDTSKNQFS  60
LKLSSVTAAD TAIYYCARDY TARGRHFFDY WGQGALVTVS SASTKG                106

SEQ ID NO: 275         moltype = AA  length = 98
FEATURE                Location/Qualifiers
source                 1..98
                       mol_type = protein
                       organism = Homo sapiens
SEQUENCE: 275
SSFAISWVRQ APGQGLEWMG GIIPIFEATS YAQKFQDRLT ITTDESTTTA YMDLSSLRSE  60
DTAVYYCARA QGDILTEGYF DYWGQGTLVT VSSASTKG                         98

SEQ ID NO: 276         moltype = AA  length = 125
FEATURE                Location/Qualifiers
source                 1..125
```

```
                        mol_type = protein
                        organism = Homo sapiens
SEQUENCE: 276
QVQLVQSGAE VKKPGSSVKV SCKVSFFSNY GISWVRQRPG QGLEWMGRII PAIDDMTYAQ  60
TFRGRVTFSA DKFTTTAYME LTGLTFEDTA TYFCARDPQV NRRGNCFDHW GQGTLVTVSS  120
ASTKG                                                              125

SEQ ID NO: 277          moltype = AA  length = 83
FEATURE                 Location/Qualifiers
source                  1..83
                        mol_type = protein
                        organism = Homo sapiens
SEQUENCE: 277
LEWMGRIIPA IDDVTYAQTF RGRVTFSADK FTTTAYMDLT GLRSEDTATY FCARDPQVNR  60
RGNCFDHWGQ GTLVTVSSAS TKG                                          83

SEQ ID NO: 278          moltype = AA  length = 126
FEATURE                 Location/Qualifiers
source                  1..126
                        mol_type = protein
                        organism = Homo sapiens
SEQUENCE: 278
QVQLVQSGAE VKKPGAAVKI SCKASRFTFS SYYIHWVRQA PGQGLEWMGI INPSGGSTSN  60
AQKFQDRVTL TRDMSTGTVY MELSRLTSED TAVYYCATPE PSSIVAPLYY WGQGTLVTVS  120
SASTKG                                                             126

SEQ ID NO: 279          moltype = AA  length = 125
FEATURE                 Location/Qualifiers
source                  1..125
                        mol_type = protein
                        organism = Homo sapiens
SEQUENCE: 279
EVQLLESGGG LVQPGGSLRL SCAVSGFTFG GHAVSWVRQA PGKGLEWLSQ ISGTGSRTDY  60
ADAVKGRFTV SRDNSKKTVY LQMNSLRVED TALFYCATRS PGGGYAFDIW GQGAMVTVSS  120
ASTKG                                                              125

SEQ ID NO: 280          moltype = AA  length = 127
FEATURE                 Location/Qualifiers
source                  1..127
                        mol_type = protein
                        organism = Homo sapiens
SEQUENCE: 280
QVQLQESGPG LVKPSETLSL TCTVSGGSIS SAGYYWSWIR QHPEKGLEFI GYIYYLGTTY  60
YNPSLKSRVS ISIDTSNNQF SLELSSVSAA DTAIYYCARD YTASGRHFFD YWGQGTLVTV  120
SSASTKG                                                            127

SEQ ID NO: 281          moltype = AA  length = 124
FEATURE                 Location/Qualifiers
source                  1..124
                        mol_type = protein
                        organism = Homo sapiens
SEQUENCE: 281
EVQLLESGGA LVQPGGSLRL SCAASGFTFS TSSMSWVRQA PGKGLEWVSA IGSGRGSTFY  60
ADSVKGRFTI SRDNSKNTLS LQMNSLTAED TATYYCTKTG GLLRFPEVWG KGTTVTVSSA  120
STKG                                                               124

SEQ ID NO: 282          moltype = AA  length = 127
FEATURE                 Location/Qualifiers
source                  1..127
                        mol_type = protein
                        organism = Homo sapiens
SEQUENCE: 282
QVQLVQSGAE VKKPGSSVKV SCKASGGTFS NYAISWVRQA PGQGLEWMGG IIPIFEAASY  60
AQKFQDRLTI TTDESTTTAY MDLSSLRSED TAIYYCARAQ GDILTEGYFD YWGQGTLVTV  120
SSASTKG                                                            127

SEQ ID NO: 283          moltype = AA  length = 126
FEATURE                 Location/Qualifiers
source                  1..126
                        mol_type = protein
                        organism = Homo sapiens
SEQUENCE: 283
QVQLQESGPG LVKPSETLSL TCTVSGGSIS TYYWSWIRQP PGKGLEWIGY ISYSGSTNYN  60
PSLKSRVTIS VDTSKNQFSL KLSSVTAADT AVYYCARHKS VLLWFRELDY WGQGTLVTVS  120
SASTKG                                                             126

SEQ ID NO: 284          moltype = AA  length = 126
FEATURE                 Location/Qualifiers
source                  1..126
```

```
                         mol_type = protein
                         organism = Homo sapiens
SEQUENCE: 284
QVQLVQSGAE VKKPGSSVKV SCKTSGVRFS SNAISWVRQA PGQGLEWMGR TTPMLGGANH  60
APSFKGRVTI SADESTRTVY MEMSSLRYED TAVYYCASGR REGLNFLLDY WGQGTLVTVS  120
SASTKG                                                             126

SEQ ID NO: 285           moltype = AA  length = 128
FEATURE                  Location/Qualifiers
source                   1..128
                         mol_type = protein
                         organism = Homo sapiens
SEQUENCE: 285
QVQLVQSGAE VRKPGASVKV SCKTSGYTFT NSYIHWVRQA PGQGLEWMGI INPPGGNTYY  60
AQKFHGRVTL TRDTSTSTVY MELNSLRSED TAVYFCARPH SPTNIPSRPL DYWGQGTLVT  120
VSSASTKG                                                           128

SEQ ID NO: 286           moltype = AA  length = 130
FEATURE                  Location/Qualifiers
source                   1..130
                         mol_type = protein
                         organism = Homo sapiens
SEQUENCE: 286
QVQLVQSGAE VKKPGASVKV SCKVSGYPLA ELSVHWVRQV PGKGLEWVGG FDPEEGKTVY  60
AQKFQGRVTM TEDRSTDTVY MELISLRYED TAVYYCATDN PVLQLGELSS SLDYWGQGTL  120
VTVSSASTKG                                                         130

SEQ ID NO: 287           moltype = AA  length = 115
FEATURE                  Location/Qualifiers
source                   1..115
                         mol_type = protein
                         organism = Homo sapiens
SEQUENCE: 287
PSETLSLTCR VSGASISNFY WTWIRQPAGK GLEWIGRLYS SDKTNYNPSL NGRVTMSLDT  60
SKNQFSLRLT SMTDADTAIY YCAREKGQWV TLPPYYFDSW GQGILVTVSS ASTKG       115

SEQ ID NO: 288           moltype = AA  length = 99
FEATURE                  Location/Qualifiers
source                   1..99
                         mol_type = protein
                         organism = Homo sapiens
SEQUENCE: 288
NTFTSHYVHW VRQAPGQGLE WMGMINPGGT TRYAPKFQDR VTLTRDTSTR TVYMELRSLR  60
SEDTAVYYCA RPQYNLGREP LNVWGQGTMV TVSSASTKG                         99

SEQ ID NO: 289           moltype = AA  length = 128
FEATURE                  Location/Qualifiers
source                   1..128
                         mol_type = protein
                         organism = Homo sapiens
SEQUENCE: 289
QVQLQESGPG LVKPSETLSL TCSVSGASIS NFYWTWIRQP AGKGLEWVGR LYSSDRTNYN  60
PSLNGRVTMS LDTSKNQFSL RLTSMTDADT AIYFCAREKG QWLTVPPYYF DSWGQGILVT  120
VSSASTKG                                                           128

SEQ ID NO: 290           moltype = AA  length = 104
FEATURE                  Location/Qualifiers
source                   1..104
                         mol_type = protein
                         organism = Homo sapiens
SEQUENCE: 290
CTVSGGSIIS YYWNWIRQSP GKGLEWLGYI FDGGRANYNP SLRSRLTMSV DTSKNQISLK  60
VKSVTAADSA IYYCARLDGE AFRYYFDSWG QGTLVTVSSA STKG                   104

SEQ ID NO: 291           moltype = AA  length = 112
FEATURE                  Location/Qualifiers
source                   1..112
                         mol_type = protein
                         organism = Homo sapiens
SEQUENCE: 291
QTLSLTCSVS GGSISSAGYY WGWIRQHPGK GLEWIGHIYY SGNTNYNPSL KSRLSMSVET  60
SKNQFSLNLA SVTAADTAVY FCARDYSAAG RHLFDSWGQG ILVTVSSAST KG          112

SEQ ID NO: 292           moltype = AA  length = 115
FEATURE                  Location/Qualifiers
source                   1..115
                         mol_type = protein
                         organism = Homo sapiens
SEQUENCE: 292
```

-continued

```
KPSQTLSLTC TVSGGSISSA GYYWTWIRHH PGKGLEFIGY IYHIGTPYYN PSLKSRLTIS  60
IDTSKNQFSL KLSSVTAADT AIYYCARDYT ARGRHFFDYW GQGALVTVSS ASTKG       115

SEQ ID NO: 293          moltype = AA  length = 128
FEATURE                 Location/Qualifiers
source                  1..128
                        mol_type = protein
                        organism = Homo sapiens
SEQUENCE: 293
QVQLVQSGAD VKKPGASVTV SCKTDEDEDD FRAHLVQWMR QAPGQRLEWV GWIKPQTGQP  60
SYAQKFQGRV TLTREVSTST VFLQLRNLRS DDTAVYYCAR PRGGRDNWSF HVWGRGTLVT  120
VSSASTKG                                                           128

SEQ ID NO: 294          moltype = AA  length = 126
FEATURE                 Location/Qualifiers
source                  1..126
                        mol_type = protein
                        organism = Homo sapiens
SEQUENCE: 294
QVQLVQSGAA VKKPGASVKV SCETYGYTFT DHFMHWWRQA PGQGLEWMGW INPYSSAVSY  60
SPRYQGRVTM TRDTFLETVY MELRGLKFDD TAIYYCATPK SGRDYWSFDL WGQGTLVTVS  120
SASTKG                                                             126

SEQ ID NO: 295          moltype = AA  length = 126
FEATURE                 Location/Qualifiers
source                  1..126
                        mol_type = protein
                        organism = Homo sapiens
SEQUENCE: 295
QVQLVQSGAA VKKPGASVKV SCETYGYKFT DHFMHWWRQA PGQGLEWMGW INPYSSAVSY  60
SPRYQGRVTM TRDTFLETVY MELRGLRFDD TAIYYCATPK SGRDYWSFDL WGQGTLVTVS  120
SASTKG                                                             126

SEQ ID NO: 296          moltype = AA  length = 126
FEATURE                 Location/Qualifiers
source                  1..126
                        mol_type = protein
                        organism = Homo sapiens
SEQUENCE: 296
QVQLVQSGAA VKKPGASVKV SCEAYGYKFT DHFMHWWRQA PGQGLEWMGW INPYTSAVNY  60
SPKYQGRVTM TRDTFLETVY MELRGLRVDD TAIYYCATPK SGRDYWSFDL WGQGTLVTVS  120
SASTKG                                                             126

SEQ ID NO: 297          moltype = AA  length = 125
FEATURE                 Location/Qualifiers
source                  1..125
                        mol_type = protein
                        organism = Homo sapiens
SEQUENCE: 297
QVQLQESGPG LVKPSETLSL TCSVSNGSIS SGGYYWSWLR QFPGKGLEWI GSIHYTGRTM  60
YNPSLMGRPA LSMDTSNNQF SLKLRSVTAA DTALYFCARD LQWIFVVDPW GQGTLVTVSS  120
ASTKG                                                              125

SEQ ID NO: 298          moltype = AA  length = 144
FEATURE                 Location/Qualifiers
source                  1..144
                        mol_type = protein
                        organism = Homo sapiens
SEQUENCE: 298
LQQLQVPRLS MWRVFKVAAA TGAQTLTVEE PGSSVKVSCK ASGGSSTAYG YSWVRQAPGQ  60
GFEWMGRIIP FYGIITYAPK FQGRVTITAD RSTSTVYMEL TSLTFADTAL FFCARDFGDP  120
RNGYYFDSWD QGLWLTVSSA STKG                                         144

SEQ ID NO: 299          moltype = AA  length = 132
FEATURE                 Location/Qualifiers
source                  1..132
                        mol_type = protein
                        organism = Homo sapiens
SEQUENCE: 299
QVHLVQSGAE VKKPGSSVRV SCKASGWTFG DSVNSAITWV RQAPGQGLEW MGRFIPILGL  60
SNYAQKFQDR VTINVDRSTN TAYMELSGLR SEDTAVYYCA RLITGMNAPW FYYMDVWGKG  120
TTITVSSAST KG                                                      132

SEQ ID NO: 300          moltype = AA  length = 138
FEATURE                 Location/Qualifiers
source                  1..138
                        mol_type = protein
                        organism = Homo sapiens
SEQUENCE: 300
```

```
FICFSVVVRL LEFGGRLVQP GGSLRLSCSA SGFTFSNSAM SWVRQAPGKG LEWVSSILSS  60
GVGTFYADSV KGRFTVSRDN SRNTLYLQMK SLRAEDTALY YCAKVQIQQL NFGVITDAGL  120
DVWGKGTTLI VSSASTKG                                                138

SEQ ID NO: 301          moltype = AA  length = 127
FEATURE                 Location/Qualifiers
source                  1..127
                        mol_type = protein
                        organism = Homo sapiens
SEQUENCE: 301
QVQLGQSGTE VKKPGFSVKV SCKASGGSST AYGYSWVRQA PGQGFEWMGR IIPFYGIITY  60
APKFQGRVTI TADRSTSTVY MELTSLTFAD TALFFCARDF GDPRNGYYFD SWDQGLWLTV  120
SSASTKG                                                            127

SEQ ID NO: 302          moltype = AA  length = 127
FEATURE                 Location/Qualifiers
source                  1..127
                        mol_type = protein
                        organism = Homo sapiens
SEQUENCE: 302
QVQLVQSGGE VRKPGSSVKV PCKISGNAFS NYGVNWVRQA PGQGLEWVGR IIPVIGVAQH  60
APKFQGRVTI TADKSTTTAY LELSSLRSDD TAVYFCAKDH GDPRTGYYFD YWGQGALVTV  120
SSASTKG                                                            127

SEQ ID NO: 303          moltype = AA  length = 132
FEATURE                 Location/Qualifiers
source                  1..132
                        mol_type = protein
                        organism = Homo sapiens
SEQUENCE: 303
QVQLLQSGTE VKKPGSSVKV SCRASGWTLG NSPNSAIGWV RQAPGQGLEW IGRIIPILDV  60
TNYAQKFQGR VTISADKSTN IAYMEISSLG SEDTAFYYCA RVITGMTSPW YFYMDVWGEG  120
TTVIVSSAST KG                                                      132

SEQ ID NO: 304          moltype = AA  length = 134
FEATURE                 Location/Qualifiers
source                  1..134
                        mol_type = protein
                        organism = Homo sapiens
SEQUENCE: 304
VQSQVYLVQS GGEVKKPGSS VKVSCKASGD SFSSSVITWV RQAPGQGPEW MGRIIPVLGV  60
AAYAQNFYGR VTISADTSSN TAYMELSSLR FEDTAVFYCA RETGRGGNLA LRQYFFDSWG  120
QGTLVTVSSP STKG                                                    134

SEQ ID NO: 305          moltype = AA  length = 123
FEATURE                 Location/Qualifiers
source                  1..123
                        mol_type = protein
                        organism = Homo sapiens
SEQUENCE: 305
EVQLVESGGG LVQPGGSLRI SCSATGFTFS THAMHWVRQA PGKGLEYVSA INSNGRSAFY  60
ADSVKGRVTI SRDNSKNTLF LQMTSLRAED TAVYYCVKGP LLRYLDSWGQ GTLVTVSSAS  120
TKG                                                                123

SEQ ID NO: 306          moltype = AA  length = 130
FEATURE                 Location/Qualifiers
source                  1..130
                        mol_type = protein
                        organism = Homo sapiens
SEQUENCE: 306
QVQLVESGGG LVKPGGSLRL SCAASGFSFN EYYMSWIRQA PGQGLEWVAN IGSSDAYTIY  60
ADSVKGRFTI SRDNAENTVY LQMNSLRGED TAVYYCARIE GYCSNSRCSN YFDPWGQGAL  120
VTVSSASTKG                                                         130

SEQ ID NO: 307          moltype = AA  length = 145
FEATURE                 Location/Qualifiers
source                  1..145
                        mol_type = protein
                        organism = Homo sapiens
SEQUENCE: 307
MFLFLVAGAT GVQSQVYLVP FGPEVKKPGS SVKVSCKASG DSFTSSVITW VRQAPGQGPE  60
WMGRVIPVLG VAAYAQKFYG RVTITADTSS NTAYMEVNSL RFEDTAVYYC ARETGRGGNL  120
ALRQYFFDSW GQGTLVTVSS PSTKG                                        145

SEQ ID NO: 308          moltype = AA  length = 133
FEATURE                 Location/Qualifiers
source                  1..133
                        mol_type = protein
                        organism = Homo sapiens
```

```
SEQUENCE: 308
CQVQLVESGG GVVQPGRSLR LSCVGSGFTF SSSGMHWVRQ APGKGLEWVA VISSDGSDEY  60
YGDSVEGRFT ISRDNSKNTL FLQLDSLEAE DSAVYYCAKT PPHYDALTGY PSSVLEFWGL  120
GTLVTVSSAS TKG                                                     133

SEQ ID NO: 309         moltype = AA  length = 123
FEATURE                Location/Qualifiers
source                 1..123
                       mol_type = protein
                       organism = Homo sapiens
SEQUENCE: 309
EVQLVESGGG LVQPGGSLRI SCSATGFTFS THAMHWVRQA PGKGLEYVSA INSNGRSAFY  60
ADSVKGRVTI SRDNSKNTLF LQMTSLRAED TAVYYCVKGP LLRYLDSWGQ GTLVTVSSAS  120
TKG                                                                123

SEQ ID NO: 310         moltype = AA  length = 132
FEATURE                Location/Qualifiers
source                 1..132
                       mol_type = protein
                       organism = Homo sapiens
SEQUENCE: 310
QVHLVQSGAE VKKPGSSVRV SCKASGWTFG DSVNSAITWV RQAPGQGLEW MGRFIPILGL  60
SNYAQKFQDR VTINVDRSTN TAYMELSGLR SEDTAVYYCA RLITGMNAPW FYYMDVWGKG  120
TTITVSSAST KG                                                      132

SEQ ID NO: 311         moltype = AA  length = 126
FEATURE                Location/Qualifiers
source                 1..126
                       mol_type = protein
                       organism = Homo sapiens
SEQUENCE: 311
SGGRLVQPGG SLRLSCSASG FTLSNSAMSW VRQAPGKGLE WVSSILSSGV GTFYADSVKG  60
RFTVSRDNSR NTLYLQMKSL RAEDTALYYC AKVQIQQLNF GVITDAGLDV WGKGTTLIVS  120
SASTKG                                                             126

SEQ ID NO: 312         moltype = AA  length = 132
FEATURE                Location/Qualifiers
source                 1..132
                       mol_type = protein
                       organism = Homo sapiens
SEQUENCE: 312
EVQLVQSGAE VKKPGSSVKV SCKASGGTFT TYDISWVRQA PGQGLEWIGG ILPDFGAPSY  60
AQKFQDRVTI TTDESSRTAY MELNSLRSED TAIYYCARGR GDDFWSGESP SWYFDYWGQG  120
TQVTVSSAST KG                                                      132

SEQ ID NO: 313         moltype = AA  length = 135
FEATURE                Location/Qualifiers
source                 1..135
                       mol_type = protein
                       organism = Homo sapiens
SEQUENCE: 313
PLVQLEPSGV EVKKRGASVK VSCKVSGYSL TELSMHWVRQ APGKGLEWMG SFDPLDGDTI  60
YAQKFQGRVT MTVDTSTDTA YMDLSSLRFE DTAVYYCATP SKAYYYDSPN YEGDFYMDVW  120
GKGTTVIVSS ASTKG                                                   135

SEQ ID NO: 314         moltype = AA  length = 132
FEATURE                Location/Qualifiers
source                 1..132
                       mol_type = protein
                       organism = Homo sapiens
SEQUENCE: 314
QVQLVESGGG VVQPGRSLRL SCVGSGFTFS SSGMHWVRQA PGKGLEWVAV ISSDGSDEYY  60
GDSVEGRFTI SRDNSKNTLF LQLDSLEAED SAVYYCAKTP PHYDALTGYP SSVLEFWGLG  120
TLVTVSSAST KG                                                      132

SEQ ID NO: 315         moltype = AA  length = 136
FEATURE                Location/Qualifiers
source                 1..136
                       mol_type = protein
                       organism = Homo sapiens
SEQUENCE: 315
EVQLVQSGAE VKKPGASVKV SCKVSGYTLT ELSMHWVRQA PGKGLEWMGV FDPLEGDGVY  60
AEKFRGRVIM TEDTSTDTGY MELTSLRSED TAIYYCATKA KDYYYESSDY SPYYYYYMDV  120
WGKGTTVTVS SASTKG                                                  136

SEQ ID NO: 316         moltype = AA  length = 132
FEATURE                Location/Qualifiers
source                 1..132
                       mol_type = protein
```

-continued

```
                         organism = Homo sapiens
SEQUENCE: 316
EVRLLESGGG LVQPGGSLRL SCSASGFTFS NSALSWVRQA PGKGLEWVSS VVSSGGDTFY  60
ADSVKGRFTI SRDNSRNTLY LQMKSLRAED TALYYCAKVQ IQQLNFGVIT DAGMDVWGKG  120
TTVIVSSAST KG                                                     132

SEQ ID NO: 317           moltype = AA  length = 117
FEATURE                  Location/Qualifiers
source                   1..117
                         mol_type = protein
                         organism = Homo sapiens
SEQUENCE: 317
VEEPGSSVKV SCKASGGSST AYGYSWVRQA PGQGFEWMGR IIPFYGIITY APKFQGRVTI  60
TADRSTSTVY MELTRLTFAD TALFFCARDY GDPRNGYYFD SWDQGLWLTV SSASTKG     117

SEQ ID NO: 318           moltype = AA  length = 123
FEATURE                  Location/Qualifiers
source                   1..123
                         mol_type = protein
                         organism = Homo sapiens
SEQUENCE: 318
QVQLVESGGG LVQPGGSLRI SCSATGFTFS THAMHWVRQA PGKGLEYVSA INSNGRSAFY  60
ADSVKGRVTI SRDNSKNTLF LQMTSLRAED TAVYYCVKGP LLRYLDSWGQ GTLVTVSSAS  120
TKG                                                               123

SEQ ID NO: 319           moltype = AA  length = 125
FEATURE                  Location/Qualifiers
source                   1..125
                         mol_type = protein
                         organism = Homo sapiens
SEQUENCE: 319
QVQLVQSGPG LVKPSETLSL TCSVSNGSIS SGGYYWSWLR QFPGKGLEWI GSIHYTGRTF  60
YNPSLMGRTA LSMDTSNNQF SLKVSSVTAA DTALYYCARE LQWMFVVDPW GQGTLVTVSS  120
ASTKG                                                             125

SEQ ID NO: 320           moltype = AA  length = 132
FEATURE                  Location/Qualifiers
source                   1..132
                         mol_type = protein
                         organism = Homo sapiens
SEQUENCE: 320
QVQLLQSGTE VKKPGSSVKV SCRASGWTLG NSPNSAIGWV RQAPGQGLEW IGRIIPILDV  60
TNYAQKFQGR VTISADKSTN IAYMEISSLG SEDTAFYYCA RVITGMTSPW YFYMDVWGEG  120
TTVIVSSAST KG                                                     132

SEQ ID NO: 321           moltype = AA  length = 136
FEATURE                  Location/Qualifiers
source                   1..136
                         mol_type = protein
                         organism = Homo sapiens
SEQUENCE: 321
QVQLVQSGGE VKKPGASVKV SCKVSGYSLT ELSMHWVRQA PGKGLEWMGV FDPLEGDGVY  60
VQKFRGRVIM TEDTSTDTAY MELTSLRSED TAIYYCATKA KDYYYESSDY SPYYYYYMDV  120
WGKGTTVTVS SASTKG                                                 136

SEQ ID NO: 322           moltype = AA  length = 136
FEATURE                  Location/Qualifiers
source                   1..136
                         mol_type = protein
                         organism = Homo sapiens
SEQUENCE: 322
GSEVQLVESG AEVKKRGASV KVSCKVSGYS LTELSMHWVR QAPGKGLEWM GSFDPLDGDT  60
IYAQKFQGRV TMTVDTSTDT AYMDLSSLRF EDTAVYYCAT PSKAYYYDSP NYEGDFYMDV  120
WGKGTTVIVS SASTKG                                                 136

SEQ ID NO: 323           moltype = AA  length = 126
FEATURE                  Location/Qualifiers
source                   1..126
                         mol_type = protein
                         organism = Homo sapiens
SEQUENCE: 323
SVVQLVESGP GLVKPSETLS LTCSVSNGSI SSGGYYWSWL RQFPGKGLEW IGSIHYTGRT  60
MYNPSLMGRP ALSMDTSNNQ FSLKLRSVTA ADTALYFCAR DLQWIFVVDP WGQGTLVTVS  120
SASTKG                                                            126

SEQ ID NO: 324           moltype = AA  length = 134
FEATURE                  Location/Qualifiers
source                   1..134
                         mol_type = protein
```

```
                          organism = Homo sapiens
SEQUENCE: 324
SVDERLLEFG GRLVQPGGSL RLSCSASGFT FSNSAMSWVR QAPGKGLEWV SSILSSGVGT  60
FYADSVKGRF TVSRDNSRNT LYLQMKSLRA EDTALYYCAK VQIQQLNFGV ITDAGLDVWG  120
KGTTLIVSSA STKG                                                    134

SEQ ID NO: 325            moltype = AA  length = 133
FEATURE                   Location/Qualifiers
source                    1..133
                          mol_type = protein
                          organism = Homo sapiens
SEQUENCE: 325
QLQLKESGPG MVKPSETLSL TCSVSGASVV SANDYWGWIR QAPGKGLECI GIILYTGSTF  60
YNPSLQSRVT ISRDPSKNHV SLTLTSVTAA DSAVYYCARI PYHSESYYNV VIGGFDVWGQ  120
GTRVTVSSAS TKG                                                     133

SEQ ID NO: 326            moltype = AA  length = 132
FEATURE                   Location/Qualifiers
source                    1..132
                          mol_type = protein
                          organism = Homo sapiens
SEQUENCE: 326
QVHLVQSGAE VKKPGSSVRV SCKASGWTFG DSVNSAITWV RQAPGQGLEW MGRFIPILGL  60
SNYAQKFQDR VTINVDRSTN TAYMELSGLR SEDTAVYYCA RLITGMNAPW FYYMDVWGKG  120
TTITVSSAST KG                                                      132

SEQ ID NO: 327            moltype = AA  length = 127
FEATURE                   Location/Qualifiers
source                    1..127
                          mol_type = protein
                          organism = Homo sapiens
SEQUENCE: 327
QVQLGQSGTE VKKPGFSVKV SCKASGGSST AYGYSWVRQA PGQGFEWMGR IIPFYGIITY  60
APKFQGRVTI TADRSTSTVY MELTSLTFAD TALFFCARDF GDPRNGYYFD SWDQGLWLTV  120
SSASTKG                                                            127

SEQ ID NO: 328            moltype = AA  length = 126
FEATURE                   Location/Qualifiers
source                    1..126
                          mol_type = protein
                          organism = Homo sapiens
SEQUENCE: 328
SQVQLVESGP GLVKPSETLS LTCSVSNGSI SSGGYYWSWL RQFPGKGLEW IGSIHYTGRT  60
MYNPSLMGRP ALSMDTSNNQ FSLKLSSVTA ADTALYFCAR DLQWIFVVDP WGQGTLVTVS  120
SASTKG                                                             126

SEQ ID NO: 329            moltype = AA  length = 134
FEATURE                   Location/Qualifiers
source                    1..134
                          mol_type = protein
                          organism = Homo sapiens
SEQUENCE: 329
RVHSQVQLVE SGPGLVKPSQ TLSLTCTVSG GSISNGGHYW NWIRQHPGKG LEWIGHIYNI  60
ATTYYNPSLK SRVSISVDTS KNQFSLKLSS VTAADTAVYY CARGSGRWTI GARIYFDNWG  120
QGALVAVSSA STKG                                                    134

SEQ ID NO: 330            moltype = AA  length = 127
FEATURE                   Location/Qualifiers
source                    1..127
                          mol_type = protein
                          organism = Homo sapiens
SEQUENCE: 330
QVQLVQSGGE VRKPGSSVKV PCKISGNAFS NYGVNWVRQA PGQGLEWVGR IIPVIGVAQH  60
APKFQGRVTI TADKSTTTAY LELSSLRSDD TAVYFCAKDH GDPRTGYYFD YWGQGALVTV  120
SSASTKG                                                            127

SEQ ID NO: 331            moltype = AA  length = 131
FEATURE                   Location/Qualifiers
source                    1..131
                          mol_type = protein
                          organism = Homo sapiens
SEQUENCE: 331
QVHLVQSGAE VKKPGSSVRV SCEASGWTFG SVNSAITWVR QAPGQGLEWM GRTIPFLGIS  60
NYAQKFQGRV TITADKSTNI AYVDVTSLTS QDTAVYYCAR LITGMTAPWF YYMDVWGKGT  120
TVTVSSASTK G                                                       131

SEQ ID NO: 332            moltype = AA  length = 130
FEATURE                   Location/Qualifiers
source                    1..130
```

```
                         mol_type = protein
                         organism = Homo sapiens
SEQUENCE: 332
EVQLVQSGSD VKKPGTTVTI SCKADEDEDD FTAYNYFMHW VRQAPGQGLE WIGWINPRTG  60
QPNHAKQLQG RVTLTRERST STVFMKLTNL RLDDTAVYFC ARPLRGGDTW HYHSWGRGTS  120
LIVSSASTKG                                                        130

SEQ ID NO: 333           moltype = AA  length = 136
FEATURE                  Location/Qualifiers
source                   1..136
                         mol_type = protein
                         organism = Homo sapiens
SEQUENCE: 333
QSQVHLVQSG AEVKKPGSSV KVSCQASGGT FNTFAINWVR QAPGQGLEWV GGIIPVFGTA  60
SYAQKFQGRV TVTTDESRGT AYMELNSLRS EDTAVYYCAR GQTDLNDDLW SDYSTPGFDY  120
WGQGTLVTVS SASTKG                                                  136

SEQ ID NO: 334           moltype = AA  length = 128
FEATURE                  Location/Qualifiers
source                   1..128
                         mol_type = protein
                         organism = Homo sapiens
SEQUENCE: 334
RVQLGQSGAE VKKPGASVKV SCKVSGNSLT EFSIHWVRQA PGKGLEWMGG FDPEEGETVP  60
AQKFKGRVTM TEDTSTNTAY MELSSLRSED TAVYYCSTEP REMGTLTAGF EYWGQGTLVI  120
VSSASTKG                                                          128

SEQ ID NO: 335           moltype = AA  length = 132
FEATURE                  Location/Qualifiers
source                   1..132
                         mol_type = protein
                         organism = Homo sapiens
SEQUENCE: 335
QPQLVQSGSG AEVKKPGASV RISCEASEYN VFDHFMQWVR QAPMEGLEWM GWINPRGGYP  60
SYSPTFQGRL TFTRQPSWDD STITFHMELR GLRHDDTAVY YCARPHSPDD AWSLDVWGRG  120
TLVTVSSAST KG                                                      132

SEQ ID NO: 336           moltype = AA  length = 136
FEATURE                  Location/Qualifiers
source                   1..136
                         mol_type = protein
                         organism = Homo sapiens
SEQUENCE: 336
LQPRVHSEVQ LVESGAEVKK PGASVKVSCK VSGYTLSDLS MHWVRQAPGK GLEWMGGFDE  60
EDGEITYAQK FQGRVSMTED TSRDTAYMEL SSLRSEDTAV YYCATAPRLE LGELSSGFHY  120
WGLGTLVTVS SASTKG                                                  136

SEQ ID NO: 337           moltype = AA  length = 128
FEATURE                  Location/Qualifiers
source                   1..128
                         mol_type = protein
                         organism = Homo sapiens
SEQUENCE: 337
RVQLGQSGAE VKKPGASVKV SCKVSGNSLT EFSIHWVRQA PGKGLEWMGG FDPEEGETVP  60
AQKFKGRVTM TEDTSTNTAY MELSSLRSED TAVYYCSTEP REMGTLTAGF EYWGQGTLVI  120
VSSASTKG                                                          128

SEQ ID NO: 338           moltype = AA  length = 136
FEATURE                  Location/Qualifiers
source                   1..136
                         mol_type = protein
                         organism = Homo sapiens
SEQUENCE: 338
IWAPLIAVTF LVLHCESLGT CCCCQASGGT FNTFAINWVR QAPGQGLEWV GGIIPVFGTA  60
SYAQKFQGRV TVTTDESRGT AYMELNSLRS EDTAVYYCAR GQTDLNDDLW SDYSTPGFDY  120
WGQGTLVTVS SASTKG                                                  136

SEQ ID NO: 339           moltype = AA  length = 129
FEATURE                  Location/Qualifiers
source                   1..129
                         mol_type = protein
                         organism = Homo sapiens
SEQUENCE: 339
EVQLVESGAE VKKPGASVKV SCKVSGYTLS DLSMHWVRQA PGKGLEWMGG FDEEDGEITY  60
AQKFQGRVSM TEDTSRDTAY MELSSLRSED TAVYYCATAP RLELGELSSG FHYWGLGTLV  120
TVSSASTKG                                                         129

SEQ ID NO: 340           moltype = AA  length = 129
FEATURE                  Location/Qualifiers
```

```
source                  1..129
                        mol_type = protein
                        organism = Homo sapiens
SEQUENCE: 340
EVQLVESGAE VKKPGASVKV ACKVSGKKLS DLSIHWVRQA PGKGLEWMGG FDEEDGKISY  60
ERKFQGRVTM TEDTARDTAF MEMSSLRSDD TAVYFCAAAP RLDLGELSSG FHFWGLGTLV  120
SVSSASTKG                                                          129

SEQ ID NO: 341          moltype = AA  length = 136
FEATURE                 Location/Qualifiers
source                  1..136
                        mol_type = protein
                        organism = Homo sapiens
SEQUENCE: 341
CNPRVHSEVQ LVESGAEVKK PGASVKVACK VSGKKLSDLS IHWVRQAPGK GLEWMGGFDE  60
EDGKISYERK FQGRVSMTED TARDTAFMEM SSLRSDDTAV YFCAAAPRLD LGELSSGFHF  120
WGLGTLVTVS SASTKG                                                  136

SEQ ID NO: 342          moltype = AA  length = 128
FEATURE                 Location/Qualifiers
source                  1..128
                        mol_type = protein
                        organism = Homo sapiens
SEQUENCE: 342
EVQLVESGAE VKKPGASVKV SCKVSGNSLT EFSIHWVRQA PGKGLEWMGG FDPEEGETVP  60
AQKFKGRLTM TEDTSTNTAY MELSSLRSED TAVYYCSTEP REMGTLTAGF EYWGQGTLVT  120
VSSASTKG                                                           128

SEQ ID NO: 343          moltype = AA  length = 125
FEATURE                 Location/Qualifiers
VARIANT                 18
                        note = Any naturally occurring amino acid or not present
source                  1..125
                        mol_type = protein
                        organism = Homo sapiens
SEQUENCE: 343
QVQLQESGPG LVKPSETXSL TCSVSNGSIS SGGYYWSWLR QFPGKGLEWI GSIHYTGRTM  60
YNPSLMGRPA LSMDTSNNQF SLKLSSVTAA DTALYFCARD LQWIFVVDPW GQGTLVTVSS  120
ASTKG                                                              125

SEQ ID NO: 344          moltype = AA  length = 132
FEATURE                 Location/Qualifiers
source                  1..132
                        mol_type = protein
                        organism = Homo sapiens
SEQUENCE: 344
QVQLVQSGAE VKKPGSSVKV SCKASGGTFT TYDISWVRQA PGQGLEWMGG ILPDFGAPSY  60
AQKFQDRVTI TTDESSSTAY MELNSLRSED TAIYYCARGR GDDFWSGESP SWYFDYWGQG  120
TLVTVSSAST KG                                                      132

SEQ ID NO: 345          moltype = AA  length = 133
FEATURE                 Location/Qualifiers
source                  1..133
                        mol_type = protein
                        organism = Homo sapiens
SEQUENCE: 345
GYSEVQLVQS GPGLVKPSQT LSLTCTVSGG SISNGGHYWN WIRQHPGKGL EWIGHIYNIA  60
TTYYNPSLKS RVSISVDTSK NQFSLKLSSV TAADTAVYYC ARGSGRWTIG ARIYFDNWGQ  120
GALVAVSSAS TKG                                                     133

SEQ ID NO: 346          moltype = AA  length = 128
FEATURE                 Location/Qualifiers
source                  1..128
                        mol_type = protein
                        organism = Homo sapiens
SEQUENCE: 346
QVQLVQSGAD VKKPGATVTV SCKTDEDEDD FRAHLMQWMR QAPGQRLEWV GWIKPQTGQP  60
SYGQKFQGRV TLTREVSTST VFLQLRNLRS DDTAVYYCAR PRGGRDNWSF HVWGRGTLVT  120
VSSASTKG                                                           128

SEQ ID NO: 347          moltype = AA  length = 128
FEATURE                 Location/Qualifiers
source                  1..128
                        mol_type = protein
                        organism = Homo sapiens
SEQUENCE: 347
QVQLVQSGAD VKKPGASVTV SCKTDEDEDD FRAHLVQWMR QAPGQRLEWV GWIKPQTGQP  60
SYAQKFQGRV TLTREVSTST VFLQLRNLRS DDTAVYYCAR PRGGRDNWSF HVWGRGTLVT  120
VSSASTKG                                                           128
```

```
SEQ ID NO: 348          moltype = AA  length = 126
FEATURE                 Location/Qualifiers
source                  1..126
                        mol_type = protein
                        organism = Homo sapiens
SEQUENCE: 348
QVQLVQSGAA VKKPGASVKV SCETYGYTFT DHFMHWWRQA PGQGLEWMGW INPYSSAVSY  60
SPRYQGRVTM TRDTFLETVY MELRGLKFDD TAIYYCATPK SGRDYWSFDL WGQGTLVTVS  120
SASTKG                                                             126

SEQ ID NO: 349          moltype = AA  length = 126
FEATURE                 Location/Qualifiers
source                  1..126
                        mol_type = protein
                        organism = Homo sapiens
SEQUENCE: 349
QVQLVQSGAA VKKPGASVKV SCETYGYTFT DHFMHWWRQA PGQGLEWMGW INPYSSAVSY  60
SPRYQGRVTM TRDTFLETVY MELRGLKFDD TAIYYCATPK SGRDYWSFDL WGQGTLVTVS  120
SASTKG                                                             126

SEQ ID NO: 350          moltype = AA  length = 126
FEATURE                 Location/Qualifiers
source                  1..126
                        mol_type = protein
                        organism = Homo sapiens
SEQUENCE: 350
QVQLVQSGAA VKKPGASVKV SCETYGYKFT DHFMHWWRQA PGQGLEWMGW INPYSSAVSY  60
SPRYQGRVTM TRDTFLETVY MELRGLRFDD TAIYYCATPK SGRDYWSFDL WGQGTLVTVS  120
SASTKG                                                             126

SEQ ID NO: 351          moltype = AA  length = 126
FEATURE                 Location/Qualifiers
source                  1..126
                        mol_type = protein
                        organism = Homo sapiens
SEQUENCE: 351
QVQLVQSGAA VKKPGASVKV SCETYGYKFT DHFMHWWRQA PGQGLEWMGW INPYSSAVSY  60
SPRYQGRVTM TRDTFLETVY MELRGLRFDD TAIYYCATPK SGRDYWSFDL WGQGTLVTVS  120
SASTKG                                                             126

SEQ ID NO: 352          moltype = AA  length = 126
FEATURE                 Location/Qualifiers
source                  1..126
                        mol_type = protein
                        organism = Homo sapiens
SEQUENCE: 352
QVQLVQSGAA VKKPGASVKV SCETYGYTFT DHFMHWWRQA PGQGLEWMGW INPYSSAVSY  60
SPRYQGRVTM TRDTFLETVY MELRGLKFDD TAIYYCATPK SGRDYWSFDL WGQGTLVTVS  120
SASTKG                                                             126

SEQ ID NO: 353          moltype = AA  length = 126
FEATURE                 Location/Qualifiers
source                  1..126
                        mol_type = protein
                        organism = Homo sapiens
SEQUENCE: 353
QVQLVQSGAA VKKPGASVKV SCEAYGYKFT DHFMHWWRQA PGQGLEWMGW INPYTSAVNY  60
SPKYQGRVTM TRDTFLETVY MELRGLRVDD TAIYYCATPK SGRDYWSFDL WGQGTLVTVS  120
SASTKG                                                             126

SEQ ID NO: 354          moltype = AA  length = 126
FEATURE                 Location/Qualifiers
source                  1..126
                        mol_type = protein
                        organism = Homo sapiens
SEQUENCE: 354
QVQLVQSGGA VKKPGASVKV SCETYGYTFT DHFMHWWRQA PGQGLEWMGW INPYSSAVSY  60
SPRYQGRVTM TRDTFLETVY MELRGLKFDD TAIYYCATPK SGRDYWSFDL WGQGTLVTVS  120
SASTKG                                                             126

SEQ ID NO: 355          moltype = AA  length = 128
FEATURE                 Location/Qualifiers
source                  1..128
                        mol_type = protein
                        organism = Homo sapiens
SEQUENCE: 355
QVQLVQSGAD VKKPGASVTV SCKTDEDEDD FRAHLVQWMR QAPGQRLEWV GWIKPQTGQP  60
SYAQKFQGRV TLTREVSTST VFLQLRNLRS DDTAVYYCAR PRGGRDNWSF HVWGRGTLVT  120
```

-continued

```
VSSASTKG                                                          128

SEQ ID NO: 356         moltype = AA  length = 128
FEATURE                Location/Qualifiers
source                 1..128
                       mol_type = protein
                       organism = Homo sapiens
SEQUENCE: 356
QVQLVQSGAD VKKPGASVTV SCKTDEDEDD FRAHLVQWMR QAPGQRLEWV GWIKPQTGQP  60
SYAQKFQGRV TLTREVSTST VFLQLRNLRS DDTAVYYCAR PRGGRDNWSF HVWGRGTLVT  120
VSSASTKG                                                          128

SEQ ID NO: 357         moltype = AA  length = 128
FEATURE                Location/Qualifiers
source                 1..128
                       mol_type = protein
                       organism = Homo sapiens
SEQUENCE: 357
QVQLLQSGAA VTKPGASVRV SCEASGYNIR DYFIHWWRQA PGQGLQWVGW INPKTGQPNN  60
PRQFQGRVSL TRHASWDFDT FSFYMDLKAL RSDDTAVYFC ARQRSDYWDF DVWGSGTQVI  120
VSSASTKG                                                          128

SEQ ID NO: 358         moltype = AA  length = 127
FEATURE                Location/Qualifiers
source                 1..127
                       mol_type = protein
                       organism = Homo sapiens
SEQUENCE: 358
QVQLLQSGAA VTKPGASVRV SCEASGYNIR DYFIHWWRQA PGQGLQWVGW INPKTGQPNN  60
PCQFQGRVSL TRHASWDFDT FSFYMDLKAL RSDDTAVYFC ARQRSDYWDF DVWGSGTQVT  120
VSSASTK                                                           127

SEQ ID NO: 359         moltype = AA  length = 128
FEATURE                Location/Qualifiers
source                 1..128
                       mol_type = protein
                       organism = Homo sapiens
SEQUENCE: 359
QVQLLQSGAA VTKPGASVRV SCEASGYNIR DYFIHWWRQA PGQGLQWVGW INPKTGQPNN  60
PCQFQGRVSL TRQASWDFDT ISFYMDLKAL RLDDTAVYFC ARQRSDYWDF DVWGSGTQVT  120
VSSASTKG                                                          128

SEQ ID NO: 360         moltype = AA  length = 128
FEATURE                Location/Qualifiers
source                 1..128
                       mol_type = protein
                       organism = Homo sapiens
SEQUENCE: 360
QVRLLQSGAA VTKPGASVRV SCEASGYEIR DYFIHWWRQA PGQGLQWVGW INPKTGQPNN  60
PRQFQGRVSL TRQASWDFDS YSFYMDLKAL RSDDTAVYFC ARQRSDYWDF DVWGSGSQVT  120
VSSASTKG                                                          128

SEQ ID NO: 361         moltype = AA  length = 128
FEATURE                Location/Qualifiers
source                 1..128
                       mol_type = protein
                       organism = Homo sapiens
SEQUENCE: 361
QVRLLQSGAA VTKPGASVRV SCEASGYEIR DYFIHWWRQA PGQGLQWVGW INPKTGQPNN  60
PRQFQGRVSL TRQASWDFDS YSFYMDLKAL RSDDTGVYFC ARQRSDYWDF DVWGSGTQVT  120
VSSASTKG                                                          128

SEQ ID NO: 362         moltype = AA  length = 128
FEATURE                Location/Qualifiers
source                 1..128
                       mol_type = protein
                       organism = Homo sapiens
SEQUENCE: 362
QVRLLQSGAA VTKPGASVRV SCEASGYEIR DYFIHWWRQA PGQGLQWVGW INPKTGQPNN  60
PRQFQGRVSL TRQASWDFDS YSFYMDLKAL RSDDTAVYFC ARQRSDYWDF DVWGSGTQVT  120
VSSASTKG                                                          128

SEQ ID NO: 363         moltype = AA  length = 128
FEATURE                Location/Qualifiers
source                 1..128
                       mol_type = protein
                       organism = Homo sapiens
SEQUENCE: 363
QVHLSQSGAV VTKPGASVRV SCEASGYKIS DHFIHWWRQA PGQGPQWVGW INPKTGQPNN  60
```

-continued

```
PRQFQGRISL TRQASWDFDT FSFYMDLKAL RSDDTAVYFC ARHRSDYWDF DVWGSGTQVT  120
VSSASTKG                                                           128

SEQ ID NO: 364          moltype = AA  length = 128
FEATURE                 Location/Qualifiers
source                  1..128
                        mol_type = protein
                        organism = Homo sapiens
SEQUENCE: 364
QVHLSQSGAA VTKPGASVRV SCEASGYKIS DHFIHWWRQA PGQGLQWVGW INPKTGQPNN  60
PRQFQGRISL TRQASWDFDT FSFYMDLKAL RSDDTAVYFC ARQRSDYRDF DVWGSGTQVT  120
VSSASTKG                                                           128

SEQ ID NO: 365          moltype = AA  length = 128
FEATURE                 Location/Qualifiers
source                  1..128
                        mol_type = protein
                        organism = Homo sapiens
SEQUENCE: 365
QVHLSQSGAA VTKPGASVRV SCEASGYKIR DYSIHWWRQA PGQGLQWVGW INPQTGQPNI  60
PRPFQGRISL TRQASWDFDT FSFYMDLEAL RSDDTAVYFC ARQRSDYWDF DVWGSGTQVT  120
VSSASTKG                                                           128

SEQ ID NO: 366          moltype = AA  length = 128
FEATURE                 Location/Qualifiers
source                  1..128
                        mol_type = protein
                        organism = Homo sapiens
SEQUENCE: 366
QVHLSQSGAV VTKPGASVRV SCEASGYKIS DHFIHWWRQA PGQGLQWVGW INPKTGQPNN  60
PRQFQGRISL TRQASWDFDT FSFYMDLEAL RSDDTAVYFC ARQRSDYWDF DVWGSGTQVT  120
VSSASTKG                                                           128

SEQ ID NO: 367          moltype = AA  length = 128
FEATURE                 Location/Qualifiers
source                  1..128
                        mol_type = protein
                        organism = Homo sapiens
SEQUENCE: 367
QVHLSQSGAV VTKPGASVRV SCEASGYKIS DHFIHWWRQA PGQGLQWVGW INPKTGQPNN  60
PRQFQGRISL TRQASWDFDT FSFYMDLKAL RSDDTAVYFC ARHRSDYWDF DVWGSGTQVT  120
VSSASTKG                                                           128

SEQ ID NO: 368          moltype = AA  length = 128
FEATURE                 Location/Qualifiers
source                  1..128
                        mol_type = protein
                        organism = Homo sapiens
SEQUENCE: 368
QVHLSQSGAA VTKPGASVRV SCEASGYKIS DHFIHWWRQA PGQGLQWVGW INPKTGQPNN  60
PRQFQGRVSL TRQASWDFDT YSFYMGLKAV RSDDTAIYFC ARQRSDFWDF DVWGSGTQVT  120
VSSASTKG                                                           128

SEQ ID NO: 369          moltype = AA  length = 128
FEATURE                 Location/Qualifiers
source                  1..128
                        mol_type = protein
                        organism = Homo sapiens
SEQUENCE: 369
QVHLSQSGAA VTKPGASVRV SCEASGYKIS DHFIHWWRQA PGQGLQWVGW INPKTGQPNN  60
PRQFQGRISL TRQASWDFDT FSFYMDLKAL RSDDTAVYFC ARHRSDYWDF DVWGSGTQVT  120
VSSASTKG                                                           128

SEQ ID NO: 370          moltype = AA  length = 128
FEATURE                 Location/Qualifiers
source                  1..128
                        mol_type = protein
                        organism = Homo sapiens
SEQUENCE: 370
QVHLSQSGAV VTKPGASVRV SCEASGYKIS GHFIHWWRQA PGQGLQWVGW INPKTGQPNN  60
PRQFQGRISL TRQASWDFDT FSFYMDLKAL RSDDTAVYFC ARHRSDYWDF DVWGSGTQVT  120
VSSASTKG                                                           128

SEQ ID NO: 371          moltype = AA  length = 128
FEATURE                 Location/Qualifiers
source                  1..128
                        mol_type = protein
                        organism = Homo sapiens
SEQUENCE: 371
```

-continued

```
QVHLSQSGAV VTKPGASVRV SCEASGYKIS DHFIHWWRQA PGQGLQWVGW INPKTGQPNI  60
PRQFQGRISL TRQASGDFDT FSFYMDLKAL RSDDTAVYFC ARQRSDYWDF GVWGSGTQVT  120
VSSASTKG                                                           128

SEQ ID NO: 372         moltype = AA  length = 128
FEATURE                Location/Qualifiers
source                 1..128
                       mol_type = protein
                       organism = Homo sapiens
SEQUENCE: 372
QVHLSQSGAV VTKPGASVRV SCEASGYKIS DHFIHWWRQA PGQGLQWVGW INPKTGQPNN  60
PRQFQGRISL TRQASWDIDT FSFYMDLKAL RSDDTAVYFC ARHRSDYWDF DVWGSGTQVT  120
VSSASTKG                                                           128

SEQ ID NO: 373         moltype = AA  length = 128
FEATURE                Location/Qualifiers
source                 1..128
                       mol_type = protein
                       organism = Homo sapiens
SEQUENCE: 373
QVHLSQSGAV VTKPGASVRV SCEASGYKIS DHFIHWWRQA PGQGLQWVGW INPKTGQPNN  60
PRQFQGRISL TRQASWDFDT FSFYMDLKAL RSDDTAVYFC ARQRSDYWDF DVWGSGTQVT  120
VSSASTKG                                                           128

SEQ ID NO: 374         moltype = AA  length = 128
FEATURE                Location/Qualifiers
source                 1..128
                       mol_type = protein
                       organism = Homo sapiens
SEQUENCE: 374
QVHLSHSGAA VTKPGASVRV SCEASGYKIS DHFIHWWRQA PGQGLQWVGW INPKTGQPNN  60
PRQFQGRISL TRQASWDFDT FSFYMDLKAL RSDDTAVYFC ARQRSDYWDF DVWGSGTQVT  120
VSSASTKG                                                           128

SEQ ID NO: 375         moltype = AA  length = 128
FEATURE                Location/Qualifiers
source                 1..128
                       mol_type = protein
                       organism = Homo sapiens
SEQUENCE: 375
QVHLSQSGAV VTKPGASVRV SCEASGYKIS DHFIHWWRQA PGQGLQWVGW INPKTGQPNN  60
PRQFQGRISL TRQASWDFDT FSFYMDLKAL RSDDTAVYFC ARHRSDYWDF DVWGSGTQVT  120
VSSASTKG                                                           128

SEQ ID NO: 376         moltype = AA  length = 128
FEATURE                Location/Qualifiers
source                 1..128
                       mol_type = protein
                       organism = Homo sapiens
SEQUENCE: 376
QVHLSQSGAV VTKPGASVRV SCEASGYKIS DHFIHWWRQA PGQGLQWVGW INPKTGQPNN  60
PRQFQGRISL TRQASWDFDT FSFYMDLKAL RSDDTAVYFC ARHRSDYWDF DVWGSGTQVT  120
VSSASTKG                                                           128

SEQ ID NO: 377         moltype = AA  length = 128
FEATURE                Location/Qualifiers
source                 1..128
                       mol_type = protein
                       organism = Homo sapiens
SEQUENCE: 377
QVHLSQSGAA VTKPGASVRV SCEASGYKIS DHFIHWWRQA PGQGLQWVGW INPKTGQPNN  60
PRQFQGRISL TRQASWDFDT FSFYMDLKAL RSDDTAVYFC ARHRSDYWDF DVWGSGTQVT  120
VSSASTKG                                                           128

SEQ ID NO: 378         moltype = AA  length = 130
FEATURE                Location/Qualifiers
source                 1..130
                       mol_type = protein
                       organism = Homo sapiens
SEQUENCE: 378
EVQLVQSGSD VKKPGTTVTI SCKADEDEDD FTAYNYFMHW VRQAPGQGLE WIGWINPRTG  60
QPNHAKQLQG RVTLTRERST STVFMKLTNL RLDDTAVYFC ARPLRGGDTW HYHSWGRGTS  120
LIVSSASTKG                                                         130

SEQ ID NO: 379         moltype = AA  length = 132
FEATURE                Location/Qualifiers
source                 1..132
                       mol_type = protein
                       organism = Homo sapiens
```

```
SEQUENCE: 379
QPQLVQSGSG AEVKKPGASV RISCEASEYN VFDHFMQWVR QAPGQGLEWM GWINPRGGYP  60
SYSPRFQGRL TFTRQPSWDD SSVTFHMELR GLRHDDTAVY YCARPHSPDD AWSLDVWGRG  120
TLVTVSSAST KG                                                      132

SEQ ID NO: 380         moltype = AA  length = 130
FEATURE                Location/Qualifiers
source                 1..130
                       mol_type = protein
                       organism = Homo sapiens
SEQUENCE: 380
EVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                         130

SEQ ID NO: 381         moltype = AA  length = 128
FEATURE                Location/Qualifiers
source                 1..128
                       mol_type = protein
                       organism = Homo sapiens
SEQUENCE: 381
HVQLLQSGAA VTKPGASVRV SCEASGYNIR DYFIHWWRQA PGQGLQWVGW INPKTGQPNN  60
PRQFQGRVSL TRQASWDFDT FSFYMDLKAL RLDDTAIYFC ARQRSDYWDF DVWGSGTQVT  120
VSSASTKG                                                           128

SEQ ID NO: 382         moltype = AA  length = 130
FEATURE                Location/Qualifiers
source                 1..130
                       mol_type = protein
                       organism = Homo sapiens
SEQUENCE: 382
VVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                         130

SEQ ID NO: 383         moltype = AA  length = 124
FEATURE                Location/Qualifiers
source                 1..124
                       mol_type = protein
                       organism = Homo sapiens
SEQUENCE: 383
QVQLVQSGAA LKKPGASLRI SCQAYGYKFT DYLIHWWRQA PGQGLEWIGW IKPETGQPSY  60
SYKFQGRVSL TRDTFEEILF MDLRGLRSDD TAIYFCARRH SDYCDFDVWG GGSQVLVSSA  120
STKG                                                               124

SEQ ID NO: 384         moltype = AA  length = 124
FEATURE                Location/Qualifiers
source                 1..124
                       mol_type = protein
                       organism = Homo sapiens
SEQUENCE: 384
QVQLVQSGTA VKKPGASVRV SCQASGYTFT DYFIYWWRQA PGQGLEWLGW INPRTSQPSY  60
PYRFQGRVTL TRDIFEEMLY MDLRGLRSDD TGIYFCARRH SDYCDFDIWG SGTQIIVSSA  120
STKG                                                               124

SEQ ID NO: 385         moltype = AA  length = 130
FEATURE                Location/Qualifiers
source                 1..130
                       mol_type = protein
                       organism = Homo sapiens
SEQUENCE: 385
EVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                         130

SEQ ID NO: 386         moltype = AA  length = 130
FEATURE                Location/Qualifiers
source                 1..130
                       mol_type = protein
                       organism = Homo sapiens
SEQUENCE: 386
EVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                         130

SEQ ID NO: 387         moltype = AA  length = 128
FEATURE                Location/Qualifiers
source                 1..128
                       mol_type = protein
```

```
                         organism = Homo sapiens
SEQUENCE: 387
QVQLLQSGAA VTKPGASVRV SCEASGYNIR DYFIHWWRQA PGQGLQWVGW INPKTGQPNN  60
PRQFQGRVSL TRHASWDFDT FSFYMDLKAL RSDDTAVYFC ARQRSDYWDF DVWGSGTQVT  120
VSSASTKG                                                          128

SEQ ID NO: 388           moltype = AA  length = 132
FEATURE                  Location/Qualifiers
source                   1..132
                         mol_type = protein
                         organism = Homo sapiens
SEQUENCE: 388
QPQLVQSGSG AEVKKPGASV RISCEASEYN VFDHFMQWVR QAPGQGLEWM GWINPRGGYP  60
SYSPTFQGRL TFTRQPSWDD STITFHMELR GLGHDDTAVY YCARPHSPDD AWSLDVWGRG  120
TLVTVSSAST KG                                                     132

SEQ ID NO: 389           moltype = AA  length = 130
FEATURE                  Location/Qualifiers
source                   1..130
                         mol_type = protein
                         organism = Homo sapiens
SEQUENCE: 389
EVQLVESGSD VRKPGATVTV SCKADEDEDD FTAYNYFMHW VRQAPGQGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 390           moltype = AA  length = 124
FEATURE                  Location/Qualifiers
source                   1..124
                         mol_type = protein
                         organism = Homo sapiens
SEQUENCE: 390
QVQLVQSGAA LKKPGASLRI SCQAYGYKFT DHLIYWWRQA PGQGLEWIGW IKPETGQPSY  60
SYKFQGRVSL TRDTFQEILF MNLRGLRSDD TAIYFCARRH SDYCDFDVWG SGSQILVSSA  120
STKG                                                              124

SEQ ID NO: 391           moltype = AA  length = 130
FEATURE                  Location/Qualifiers
source                   1..130
                         mol_type = protein
                         organism = Homo sapiens
SEQUENCE: 391
EVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 392           moltype = AA  length = 130
FEATURE                  Location/Qualifiers
source                   1..130
                         mol_type = protein
                         organism = Homo sapiens
SEQUENCE: 392
VVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 393           moltype = AA  length = 124
FEATURE                  Location/Qualifiers
source                   1..124
                         mol_type = protein
                         organism = Homo sapiens
SEQUENCE: 393
QVQLVQSGAA LKKPGASVRI SCQAYGYKFT DHLIYWWRQA PGQGLEWIGW IKPETGQPSY  60
SYKFQGRVTL TRDTFEEIHF MDLRGLRYDD TATYFCARRH SDYCDFDVWG SGSQVSVSSA  120
STKG                                                              124

SEQ ID NO: 394           moltype = AA  length = 130
FEATURE                  Location/Qualifiers
source                   1..130
                         mol_type = protein
                         organism = Homo sapiens
SEQUENCE: 394
QVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSRGRGTS  120
LTVSSASTKG                                                        130

SEQ ID NO: 395           moltype = AA  length = 132
FEATURE                  Location/Qualifiers
source                   1..132
```

```
                        mol_type = protein
                        organism = Homo sapiens
SEQUENCE: 395
QPQLVQSGSG AEVKKPGASV RISCEASEYN VFDHFMQWVR QAPMEGLEWM GWINPRGGYP  60
SYSPTFQGRL TFTRQPSWDD STITFHMELR GLRHDDTAVY YCARPHSPDD AWSLDVWGRG  120
TLVTVSSAST KG                                                      132

SEQ ID NO: 396          moltype = AA  length = 124
FEATURE                 Location/Qualifiers
source                  1..124
                        mol_type = protein
                        organism = Homo sapiens
SEQUENCE: 396
QVQLVQSGAT LKKPGASVRI SCQAYGYKFT DHLIHWWRQA PGQGLEWIGW IKPETGQPSY  60
AYKFQGRVSL TRDTFEEILF MDLRGLRSDD TAIYFCARRH SDYCDLDVWG GGTQLLVSSA  120
STKG                                                               124

SEQ ID NO: 397          moltype = AA  length = 124
FEATURE                 Location/Qualifiers
source                  1..124
                        mol_type = protein
                        organism = Homo sapiens
SEQUENCE: 397
QVQLVQSGAA LKKPGASLRI SCLTYGYKFT DHLIYWWRQA PGQGLEWIGW IKPETGQPSY  60
SYRFQGRVSL TRDTFEEIVF MDLRGLRSDD TAIYFCARRH SDYCDFDVWG SGSQVIVSSA  120
STKG                                                               124

SEQ ID NO: 398          moltype = AA  length = 124
FEATURE                 Location/Qualifiers
source                  1..124
                        mol_type = protein
                        organism = Homo sapiens
SEQUENCE: 398
QVQLVQSGAA LKKPGASLRI SCQTYGYKFT DHLIYWWRQA PGQGLEWIGW IKPETGQPSY  60
SYRFQGRVSL TRDTFEEIVF MDLRGLRSDD TAIYFCARRH SDYCDFDVWG GGSQVIVSSA  120
STKG                                                               124

SEQ ID NO: 399          moltype = AA  length = 124
FEATURE                 Location/Qualifiers
source                  1..124
                        mol_type = protein
                        organism = Homo sapiens
SEQUENCE: 399
QVQLVQSGAA LKKPGASLRI SCQTYGYKFT DHLIYWWRQA PGQGLEWIGW IKPETGQPSY  60
SYRFQGRVSL TRDTFEEIVF MDLRGLRSDD TAIYFCARRH SDYCDFDVWG SGSQVIVSSA  120
STKG                                                               124

SEQ ID NO: 400          moltype = AA  length = 124
FEATURE                 Location/Qualifiers
source                  1..124
                        mol_type = protein
                        organism = Homo sapiens
SEQUENCE: 400
QVQLVQSGAA LKKPGASVRI SCQTYGYKFT DHLIHWWRQA PGQGLEWIGW IKPDTGQPSY  60
SSRFQGRVSL TRDTFEEIVF MDLRGLRSDD TAIYFCARRH SDYCDFDVWG SGSQVLVSSA  120
STKG                                                               124

SEQ ID NO: 401          moltype = AA  length = 124
FEATURE                 Location/Qualifiers
source                  1..124
                        mol_type = protein
                        organism = Homo sapiens
SEQUENCE: 401
QVQLVQSGAA LKKPGASLRI SCQTYGYKFT DHLIYWWRQA PGQGLEWIGW IKPETGQPSY  60
SYRFQGRVSL TRDTFEEIVF MDLRGLRSDD TAIYFCARRH SDYCDFDVWG SGSQVLVSSA  120
STKG                                                               124

SEQ ID NO: 402          moltype = AA  length = 130
FEATURE                 Location/Qualifiers
source                  1..130
                        mol_type = protein
                        organism = Homo sapiens
SEQUENCE: 402
QVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                         130

SEQ ID NO: 403          moltype = AA  length = 130
FEATURE                 Location/Qualifiers
```

```
source                  1..130
                        mol_type = protein
                        organism = Homo sapiens
SEQUENCE: 403
EVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 404          moltype = AA  length = 128
FEATURE                 Location/Qualifiers
source                  1..128
                        mol_type = protein
                        organism = Homo sapiens
SEQUENCE: 404
QVQLLQSGAA VTKPGASVRV SCEASGYNIR DYFIHWWRQA PGQGLQWVGW INPKTGQPNN  60
PRQFQGRVSL TRHASWDFDT FSFYMDLKGL RSDDTAIYFC ARQRSDYWDF DVWGSGTQVT  120
VSSASTKG                                                          128

SEQ ID NO: 405          moltype = AA  length = 130
FEATURE                 Location/Qualifiers
source                  1..130
                        mol_type = protein
                        organism = Homo sapiens
SEQUENCE: 405
EVQLVQSGSD VRKPGATVTV SCKADEDEDD FTAYDYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 406          moltype = AA  length = 130
FEATURE                 Location/Qualifiers
source                  1..130
                        mol_type = protein
                        organism = Homo sapiens
SEQUENCE: 406
EVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 407          moltype = AA  length = 130
FEATURE                 Location/Qualifiers
source                  1..130
                        mol_type = protein
                        organism = Homo sapiens
SEQUENCE: 407
EVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 408          moltype = AA  length = 124
FEATURE                 Location/Qualifiers
source                  1..124
                        mol_type = protein
                        organism = Homo sapiens
SEQUENCE: 408
QVQLVQSGTA VKKPGASVRV SCQASGYTFT DYFIYWWRQA PGQGLEWLGW INPRTSQPSY  60
PYRFQGRVTL TRDIFEEMLY MDLRGLRSDD TGIYFCARRH SDYCDFDIWG SGTQIIVSSA  120
STKG                                                              124

SEQ ID NO: 409          moltype = AA  length = 128
FEATURE                 Location/Qualifiers
source                  1..128
                        mol_type = protein
                        organism = Homo sapiens
SEQUENCE: 409
QVQLLQSGAA VTKPGASVRV SCEASGYKIS DHFIHWWRQA PGQGLQWVGW INPKTGQPNN  60
PRQFQGRISL TRQASWDFDT FSFYMDLKAL RSDDTAVYFC ARQRSDYWDF DVWGSGTQVT  120
VSSASTKG                                                          128

SEQ ID NO: 410          moltype = AA  length = 130
FEATURE                 Location/Qualifiers
source                  1..130
                        mol_type = protein
                        organism = Homo sapiens
SEQUENCE: 410
QVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 411          moltype = AA  length = 130
```

```
FEATURE                Location/Qualifiers
source                 1..130
                       mol_type = protein
                       organism = Homo sapiens
SEQUENCE: 411
VVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 412         moltype = AA  length = 124
FEATURE                Location/Qualifiers
source                 1..124
                       mol_type = protein
                       organism = Homo sapiens
SEQUENCE: 412
QVQLVQSGAA LKKPGASVRI SCQTYGYKFT DHLIYWWRQA PGQGLEWIGW IKPETGQPSY  60
SYRFQGRVSL TRDTFEEIVF MDLRGLRSDD TAIYFCARRH SDYCDFDVWG SGSQVLVSSA  120
STKG                                                              124

SEQ ID NO: 413         moltype = AA  length = 130
FEATURE                Location/Qualifiers
source                 1..130
                       mol_type = protein
                       organism = Homo sapiens
SEQUENCE: 413
VVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 414         moltype = AA  length = 125
FEATURE                Location/Qualifiers
source                 1..125
                       mol_type = protein
                       organism = Homo sapiens
SEQUENCE: 414
QVQLVQSGAA LKKPGASVRI SCQAYGYKFT DYLIHWWRQA PGQGLEWIGW IKPETGQPSY  60
SYKFQGRVTL TRDTFEEILF MDLRGLRSDD TAIYFCARRH SDYCDFDVWG SGSQVIVSSA  120
STKGA                                                             125

SEQ ID NO: 415         moltype = AA  length = 130
FEATURE                Location/Qualifiers
source                 1..130
                       mol_type = protein
                       organism = Homo sapiens
SEQUENCE: 415
EVQLVESGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 416         moltype = AA  length = 130
FEATURE                Location/Qualifiers
source                 1..130
                       mol_type = protein
                       organism = Homo sapiens
SEQUENCE: 416
VVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 417         moltype = AA  length = 124
FEATURE                Location/Qualifiers
source                 1..124
                       mol_type = protein
                       organism = Homo sapiens
SEQUENCE: 417
QVQLVQSGAA LKKPGASVRI SCQAYGYKFT DHLIYWWRQA PGQGLEWIGW IKPETGQPSY  60
AYKFQGRVTL TRDTFEEIHF MDLRGVRNDD TATYFCARRH SDYCDFDVWG SGSQVIVSSA  120
STKG                                                              124

SEQ ID NO: 418         moltype = AA  length = 130
FEATURE                Location/Qualifiers
source                 1..130
                       mol_type = protein
                       organism = Homo sapiens
SEQUENCE: 418
EVQLVESGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130
```

```
SEQ ID NO: 419         moltype = AA  length = 124
FEATURE                Location/Qualifiers
source                 1..124
                       mol_type = protein
                       organism = Homo sapiens
SEQUENCE: 419
QVQLVQSGTA VKRPGASVRV SCQASGYTFT DYFIYWWRQA PGQGLEWLGW INPLTSQPSY  60
PSRFQGRLTL TRDTFDEMLY MDLRGLRSDD TGIYFCARRH SDYCDFDIWG SGTQIIVSSA  120
STKG                                                               124

SEQ ID NO: 420         moltype = AA  length = 130
FEATURE                Location/Qualifiers
source                 1..130
                       mol_type = protein
                       organism = Homo sapiens
SEQUENCE: 420
EVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                         130

SEQ ID NO: 421         moltype = AA  length = 128
FEATURE                Location/Qualifiers
source                 1..128
                       mol_type = protein
                       organism = Homo sapiens
SEQUENCE: 421
QVHLSQSGAA VTKPGASVRV SCEASGYKIS DHFIHWWRQA PGQGLQWVGW INPKTGQPNN  60
PRQFQGRVSL TRQASWDFDT YSFYMDLKAV RSDDTAIYFC ARQRSDFWDF DVWGSGTQVT  120
VSSASTKG                                                           128

SEQ ID NO: 422         moltype = AA  length = 128
FEATURE                Location/Qualifiers
source                 1..128
                       mol_type = protein
                       organism = Homo sapiens
SEQUENCE: 422
QVRLLQSGAA VTKPGASVRV SCEASGYEIR DYFIHWWRQA PGQGLQWVGW INPKTGQPNN  60
PRQFQGRVSL TRQASWDFDS YSFYMDLKAL RSDDTGVYFC ARQRSDYWDF DVWGSGTQVT  120
VSSASTKG                                                           128

SEQ ID NO: 423         moltype = AA  length = 128
FEATURE                Location/Qualifiers
source                 1..128
                       mol_type = protein
                       organism = Homo sapiens
SEQUENCE: 423
QVHLSQSGAA VTKPGASVRV SCEASGYKIS DHFIHWWRQA PGQGLQWVGW INPKTGQPNN  60
PRQFQGRVSL TRQASWDFDT YSFYMDLKAL RSDDTAIYFC ARQRSDFWDF DVWGSGTQVT  120
VSSASTKG                                                           128

SEQ ID NO: 424         moltype = AA  length = 128
FEATURE                Location/Qualifiers
source                 1..128
                       mol_type = protein
                       organism = Homo sapiens
SEQUENCE: 424
QVQLLPFGGA VTKPGASVRV SCEASGYNIR DYFIHWWRQA PGQGLQWVGW INPKTGQPNN  60
PCQFQGRVSL TRPASWDFDT ISFYMDLKAL RLDDTAVYFC ARQRSDYWDF DVWGSGTQVT  120
VSSASTKG                                                           128

SEQ ID NO: 425         moltype = AA  length = 124
FEATURE                Location/Qualifiers
source                 1..124
                       mol_type = protein
                       organism = Homo sapiens
SEQUENCE: 425
QVQLVQSGAA LKKPGASLRI SCQTYGYKFT DHLIYWWRQA PGQGLEWIGW IKPETGQPSY  60
SYRFQGRVSL TRDTFEEIAF MDLRGLRSDD TAIYFCARRH TDYCVFDVWG SGSQIIVSSA  120
STKG                                                               124

SEQ ID NO: 426         moltype = AA  length = 130
FEATURE                Location/Qualifiers
source                 1..130
                       mol_type = protein
                       organism = Homo sapiens
SEQUENCE: 426
QVQLVESGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                         130
```

```
SEQ ID NO: 427         moltype = AA  length = 124
FEATURE                Location/Qualifiers
source                 1..124
                       mol_type = protein
                       organism = Homo sapiens
SEQUENCE: 427
QVQLVQSGAA LKKPGASLRI SCQTYGYKFT DHLIYWWRQA PGQGLEWMGW IKPETGQPSY  60
SYRFQGRVSL TRDTFEEIVF MDLRGLRSDD TAIYFCARRH SDYCDFDVWG SGSQVIVSSA  120
STKG                                                               124

SEQ ID NO: 428         moltype = AA  length = 128
FEATURE                Location/Qualifiers
source                 1..128
                       mol_type = protein
                       organism = Homo sapiens
SEQUENCE: 428
QVQLLQSGAA VTKPGASVRV SCEASGYNIR DYFIHWWRQA PGQGLQWVGW INPKTGQPNN  60
PRQFQGRVSL TRHASWDFDT FSFYMDLKAL RSDDTAVYFC ARQRSDYWDF DVWGSGTQVT  120
VYSASTKG                                                           128

SEQ ID NO: 429         moltype = AA  length = 128
FEATURE                Location/Qualifiers
source                 1..128
                       mol_type = protein
                       organism = Homo sapiens
SEQUENCE: 429
QVQLLQSGAA VTKPGASVRV SCEASGYNIR DYFIHWWRQA PGQGLQWVGW INPKTGQPNN  60
PRQFQGRVSL TRQASWDFDT ISFYMDLKAL RLDDTAVYFC ARQRSDYWDF DVWGSGTQVT  120
VSSASTKG                                                           128

SEQ ID NO: 430         moltype = AA  length = 125
FEATURE                Location/Qualifiers
source                 1..125
                       mol_type = protein
                       organism = Homo sapiens
SEQUENCE: 430
RQVQLVQSGA ALKKPGASLR ISCQAYGYKF TDHLIYWWRQ APGQGLEWIG WIKPETGQPS  60
YSYKFQGRVS LTRDTFQEIL FMDLRGLRSD DTAIYFCARR HSDYCDFDVW GSGSQILVSS  120
ASTKG                                                              125

SEQ ID NO: 431         moltype = AA  length = 124
FEATURE                Location/Qualifiers
source                 1..124
                       mol_type = protein
                       organism = Homo sapiens
SEQUENCE: 431
QVQLVQSGAA LKKPGASLRI SCQAYGYKFT DHLIYWWRQA PGQGLEWIGW IKPETGQPSY  60
SYKFQGRVSL TRDTFQEILF MDLRGLRSDD TAIYFCARRH SDYCDFDVWG SGSQVIVSSA  120
STKG                                                               124

SEQ ID NO: 432         moltype = AA  length = 130
FEATURE                Location/Qualifiers
source                 1..130
                       mol_type = protein
                       organism = Homo sapiens
SEQUENCE: 432
QVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                         130

SEQ ID NO: 433         moltype = AA  length = 128
FEATURE                Location/Qualifiers
source                 1..128
                       mol_type = protein
                       organism = Homo sapiens
SEQUENCE: 433
QVQLLQSGAA VTKPGASVRV SCEASGYNIR DYFIHWWRQA PGQGLQWVGW INPKTGQPNN  60
PRQFQGRVSL TRHASWDFDT FSFYMDLKAL RSDDTAVYFC ARQRSDYWDF DVWGSGTQVT  120
VSSASTKG                                                           128

SEQ ID NO: 434         moltype = AA  length = 124
FEATURE                Location/Qualifiers
source                 1..124
                       mol_type = protein
                       organism = Homo sapiens
SEQUENCE: 434
QVQLVQSGTA VKRPGASVRV SCQASGYTFI DHFIYWWRQA PGQGLEWLGW INPLTSQPSY  60
PSRFQGRLTL TRDTFDEMLY MDLRGLRSDD TGIYFCARRH SDYCDFDIWG SGTQIIVSSA  120
```

```
STKG                                                              124

SEQ ID NO: 435         moltype = AA  length = 128
FEATURE                Location/Qualifiers
source                 1..128
                       mol_type = protein
                       organism = Homo sapiens
SEQUENCE: 435
QVQLLQSGAV VTKPGASVRV SCEASGYKIR DYFIHWWRQA PGQGLQWVGW INPQTGQPNI  60
PRPFQGRVTL TRHASWDFDT FSFYMDLKAL RSDDTAIYFC ARRRSDYCDF DVWGSGTHVT  120
VSSASTKG                                                          128

SEQ ID NO: 436         moltype = AA  length = 130
FEATURE                Location/Qualifiers
source                 1..130
                       mol_type = protein
                       organism = Homo sapiens
SEQUENCE: 436
EVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 437         moltype = AA  length = 130
FEATURE                Location/Qualifiers
source                 1..130
                       mol_type = protein
                       organism = Homo sapiens
SEQUENCE: 437
QVQLVQSGSD VRKPGATVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 438         moltype = AA  length = 128
FEATURE                Location/Qualifiers
source                 1..128
                       mol_type = protein
                       organism = Homo sapiens
SEQUENCE: 438
QVQLLQSGAA VTKPGASVRV SCEASGYNIR DYFIHWWRQA PGQGLQWVGW INPKTGQPNN  60
PRLFQGRVSL TRHASWDFDT FSFYMDLKAV RSDDTAVYFC ARQRSDYWDF DVWGSGTQVT  120
VSSASTKG                                                          128

SEQ ID NO: 439         moltype = AA  length = 123
FEATURE                Location/Qualifiers
source                 1..123
                       mol_type = protein
                       organism = Homo sapiens
SEQUENCE: 439
EIVLTQSPAT LSLSPGERAT LSCRASQGLN FVVWYQQKRG QAPRLLIHAP SGRAPGVPDR  60
FSARGSGTEF SLVISSVEPD DFAIYYCQEY SSTPYNFGPG TRVDRKRTVA APSVFIFPPS  120
DEQ                                                               123

SEQ ID NO: 440         moltype = AA  length = 123
FEATURE                Location/Qualifiers
source                 1..123
                       mol_type = protein
                       organism = Homo sapiens
SEQUENCE: 440
EIVLTQSPAT LSLSPGERAT LSCRASQGLN FVVWYQQKGG QAPRLLIHGP TDRAPGVPDR  60
FSARGSGTEF SLVISSVEPD DFALYYCQEY SSTPYNFGPG TRVDRKRTVA APSVFIFPPS  120
DEQ                                                               123

SEQ ID NO: 441         moltype = AA  length = 123
FEATURE                Location/Qualifiers
source                 1..123
                       mol_type = protein
                       organism = Homo sapiens
SEQUENCE: 441
EIVLTQSPAT LSLSPGERAT LSCRASQGLN FVVWYQQKRG QAPRLLIHGP SHRAPGVPDR  60
FSARGSGTEF SLVISSVEPD DFAIYYCQEY SSTPYNFGPG TRVDRKRTVA APSVFIFPPS  120
DEQ                                                               123

SEQ ID NO: 442         moltype = AA  length = 123
FEATURE                Location/Qualifiers
source                 1..123
                       mol_type = protein
                       organism = Homo sapiens
SEQUENCE: 442
EIVLTQSPAT LSLSPGERAT LSCRASQGVN FVVWYQQKRG QAPRLLIYGP SNRAPGVPDR  60
```

```
FSARGSGTEF SLVISSVEPD DFALYYCQEY SSTPYNFGPG TRVDRKRTVA APSVFIFPPS  120
DEQ                                                                123

SEQ ID NO: 443          moltype = AA  length = 123
FEATURE                 Location/Qualifiers
source                  1..123
                        mol_type = protein
                        organism = Homo sapiens
SEQUENCE: 443
EIVLTQSPTT LSLSPGERAT LSCRASQGVN LVVWYQQKRG QAPRLLIYGP SDRAPGVPDR  60
FSARGSGTEF SLVISSVEPD DFALYYCQEY SSTPYNFGTG TRVDRKRTVA APSVFIFPPS  120
DEQ                                                                123

SEQ ID NO: 444          moltype = AA  length = 123
FEATURE                 Location/Qualifiers
source                  1..123
                        mol_type = protein
                        organism = Homo sapiens
SEQUENCE: 444
EIVLTQSPAT LSLSPGERAT LSCRASQGLN FVVWYQQKRG QAPRLLIHAP SDRAPGVPDR  60
FSARGSGTDF SLVISSVEPD DFAIYYCQEY SSTPYNFGPG TRVDRKRTVA APSVFIFPPS  120
DEQ                                                                123

SEQ ID NO: 445          moltype = AA  length = 112
FEATURE                 Location/Qualifiers
source                  1..112
                        mol_type = protein
                        organism = Homo sapiens
SEQUENCE: 445
EIVLTQSPAT LSLSPGERAT LSCRASQGVN FVVWYQQKRG QAPRLLIYGP SDRAPGVPDR  60
FSARGSGTEF SLVISSVEPD DFALYYCQEY SSTPYNFGTG TRVDRKRTVA AP          112

SEQ ID NO: 446          moltype = AA  length = 111
FEATURE                 Location/Qualifiers
source                  1..111
                        mol_type = protein
                        organism = Homo sapiens
SEQUENCE: 446
EIVLTQSPAT LSLSPGERAT LSCRASQGVN FVVWYQQKRG QAPRLLIYGN SDRVPGVPDR  60
FSARGSGTEF SLVISSVEPD DFALYYCQEY SSTPYNFGPG TRVDRKRTVA A           111

SEQ ID NO: 447          moltype = AA  length = 126
FEATURE                 Location/Qualifiers
source                  1..126
                        mol_type = protein
                        organism = Homo sapiens
SEQUENCE: 447
SEIVLTQSPA TLSLSPGERA TLSCRASQSI NNYLAWYQQK PGQAPRLLIY DASNRATGIP  60
ARFSGGGSGT DFTLTISSLE PEDFAVYYCQ QRANWRLLTF GGGTKVEIKR TVAAPSVFIF  120
PPSDEQ                                                             126

SEQ ID NO: 448          moltype = AA  length = 125
FEATURE                 Location/Qualifiers
source                  1..125
                        mol_type = protein
                        organism = Homo sapiens
SEQUENCE: 448
EIVMTQSPDT LSVSPGERAT LSCRASQSVN SNLAWYQQKP GQAPRLLIYG ASTRATAVPA  60
RFSGSGSGTE FTLTISSLQS EDSAVYYCQQ YYQWLSYTFG QGTKLEIKRT VAAPSVFIFP  120
PSDEQ                                                              125

SEQ ID NO: 449          moltype = AA  length = 125
FEATURE                 Location/Qualifiers
source                  1..125
                        mol_type = protein
                        organism = Homo sapiens
SEQUENCE: 449
DIQMTQSPST LAASIGGTVR VSCRASQSIT GNWVAWYQQR PGKAPRLLIY RGAALLGGVP  60
SRFSGSAAGT DFTLTIGNLQ AEDFGTFYCQ QYDTYPGTFG QGTKVEVKRT VAAPSVFIFP  120
PSDEQ                                                              125

SEQ ID NO: 450          moltype = AA  length = 126
FEATURE                 Location/Qualifiers
source                  1..126
                        mol_type = protein
                        organism = Homo sapiens
SEQUENCE: 450
SEIVMTQSPA TLSMSPGERA TLSCRASLSV NTNLAWYQQK PGQAPRLLIY GASTRATGIP  60
ARFSGSGSGT EFTLTISSLQ SEDFALYYCQ QYNHWPQTFG QGTKVEIKRT VAAPSVFIFP  120
```

```
PSDEQK                                                      126

SEQ ID NO: 451          moltype = AA  length = 124
FEATURE                 Location/Qualifiers
source                  1..124
                        mol_type = protein
                        organism = Homo sapiens
SEQUENCE: 451
DIQMTQSPPS LSASVGDRVT ITCQASQDIN NFLNWYQQKP GKAPRLLIYD ASNLESGVSS  60
RFSGSRSGTD FTLTISSLLP EDIATYSCQQ YSNLPYTFSQ GTKLEIKRTV AAPSVFIFPP  120
SDEQ                                                        124

SEQ ID NO: 452          moltype = AA  length = 123
FEATURE                 Location/Qualifiers
source                  1..123
                        mol_type = protein
                        organism = Homo sapiens
SEQUENCE: 452
DIQMTQSPSS LSASVGDRVT ITCQAGQGIG SSLQWYQQKP GKAPKLLVHG ASNLHRGVPS  60
RFSGSGFHTT FSLTISGLQR DDFATYFCAV LEFFGPGTKV EIKRTVAAPS VFIFPPSDEQ  120
LKS                                                         123

SEQ ID NO: 453          moltype = AA  length = 121
FEATURE                 Location/Qualifiers
source                  1..121
                        mol_type = protein
                        organism = Homo sapiens
SEQUENCE: 453
DIQMTQSPSS LSASVGDRVT ITCQAGQGIG SSLQWYQQKP GKAPKLLVHG ASNLHRGVPS  60
RFSGSGFHTT FSLTISGLQR DDFATYFCAV VEFFGPGTKV DIKRTVAAPS VFIFPPSDEQ  120
L                                                           121

SEQ ID NO: 454          moltype = AA  length = 122
FEATURE                 Location/Qualifiers
source                  1..122
                        mol_type = protein
                        organism = Homo sapiens
SEQUENCE: 454
DIQMTQSPSS LSASVGDRVT ITCQASQGIG SSLQWYQQKP GRAPNLLVHG ASKLHRGVPS  60
RFSGSGFHTT FSLTISGLQR DDFATYFCAV LEFFGPGTKV EIKRTVAAPS VFIFPPSDEQ  120
LK                                                          122

SEQ ID NO: 455          moltype = AA  length = 105
FEATURE                 Location/Qualifiers
source                  1..105
                        mol_type = protein
                        organism = Homo sapiens
SEQUENCE: 455
DIQMTQSPSS LSASVGDRVS INCQAGQGLG SSLNWYQQKP GRAPKLLVHG ASNLQRGVPS  60
RFSGSGFHTT FTLTISSLQP DDVATYFCAA FQWFGPGTKV EIKRT           105

SEQ ID NO: 456          moltype = AA  length = 102
FEATURE                 Location/Qualifiers
source                  1..102
                        mol_type = protein
                        organism = Homo sapiens
SEQUENCE: 456
DIQMTQSPSS LSASVGDRVS IHCQAGQGIG SSLNWYQQKP GRAPRLLVHG ASNLQRGVPS  60
RFSGSGFHTT FTLTISSLQP DDVATYWCAA LEFFGPGTKV EI              102

SEQ ID NO: 457          moltype = AA  length = 122
FEATURE                 Location/Qualifiers
source                  1..122
                        mol_type = protein
                        organism = Homo sapiens
SEQUENCE: 457
DIQMTQSPSS LSASVGDRVT INCQAGQGIG SSLNWYQKKP GRAPKLLVHG ASNLQRGVPS  60
RFSGSGFHTT FTLTISSLQP DDVATYFCAV FQWFGPGTKV DIKRTVAAPS VFIFPPSDEQ  120
LK                                                          122

SEQ ID NO: 458          moltype = AA  length = 120
FEATURE                 Location/Qualifiers
source                  1..120
                        mol_type = protein
                        organism = Homo sapiens
SEQUENCE: 458
DIQMTQSPSS LSASVGDRVT ITCQAGQGIG SSLNWYQQKP GRAPKLLVYG ASNLQRGVPS  60
RFSGSGFHTT FTLTISSLQP EDFATYFCSV YEFLGPGTKV EIKRTVAAPS VFIFPPSDEQ  120
```

```
SEQ ID NO: 459         moltype = AA  length = 120
FEATURE                Location/Qualifiers
source                 1..120
                       mol_type = protein
                       organism = Homo sapiens
SEQUENCE: 459
DIQMTQSPSS LSVSVGDRVS ITCRATQGIG NSLNWYQQKP GKAPKVLIYG TTKLHGGVPS  60
RFSGGGSGST GTLTIDSLQP EDIATYFCQL FEFFGPGTKV EIKRTVAAPS VFIFPPSDEQ  120

SEQ ID NO: 460         moltype = AA  length = 120
FEATURE                Location/Qualifiers
source                 1..120
                       mol_type = protein
                       organism = Homo sapiens
SEQUENCE: 460
DIQMTQSPSS LSASVGDRVT ITCQASQGIG SSLQWYQQKP GRAPNLLVHG ASNLHRGVPS  60
RFSGSGFHTT FSLTISGLQR DDFATYFCAV LEFFGPGTKV DIKRTVAAPS VFIFPPSDEQ  120

SEQ ID NO: 461         moltype = AA  length = 120
FEATURE                Location/Qualifiers
source                 1..120
                       mol_type = protein
                       organism = Homo sapiens
SEQUENCE: 461
DIQMTQSPSS LPASVGDTVT ITCQAGQGIG SSLQWYQQRP GRAPNLLVYD ASNLQRGVPS  60
RFTGTGFHTT FTLTIRGLRP EDFGTYFCAS LEFFGPGTKV DIKRTVAAPS VFIFPPSDEQ  120

SEQ ID NO: 462         moltype = AA  length = 120
FEATURE                Location/Qualifiers
source                 1..120
                       mol_type = protein
                       organism = Homo sapiens
SEQUENCE: 462
YIQMTQSPSS LSASIGDRVT ITCQAGQGIG SSLNWYQQKP GKAPKLLVHG ASNLQRGVSS  60
RFSGSGFHTT FTLTISSLRP EDVGTYFCEV YEFIGPGTKV DIKRTVAAPS VFIFPPSDEQ  120

SEQ ID NO: 463         moltype = AA  length = 120
FEATURE                Location/Qualifiers
source                 1..120
                       mol_type = protein
                       organism = Homo sapiens
SEQUENCE: 463
DIQMTQSPSS LSASVGDRVS INCQAGQGIG SSLNWYQQKR GKAPKLLVHG ASTLQRGVPS  60
RFSGSGFHTT FTLTISSLQP DDVATYFCES FQWFGPGTKV EIKRTVAAPS VFIFPPSDEQ  120

SEQ ID NO: 464         moltype = AA  length = 120
FEATURE                Location/Qualifiers
source                 1..120
                       mol_type = protein
                       organism = Homo sapiens
SEQUENCE: 464
DIQMTQSPSS LSASVGDRVT ITCQASQGIG SSLQWYQQKP GRAPKLLVHG ASNLHRGVPS  60
RFSGSGFHTS FTLTISSLQP DDVATYFCAV LEFFGPGTKV EIKRTVAAPS VFIFPPSDEQ  120

SEQ ID NO: 465         moltype = AA  length = 120
FEATURE                Location/Qualifiers
source                 1..120
                       mol_type = protein
                       organism = Homo sapiens
SEQUENCE: 465
DIQMTQSPSS LSASVGDRVS IHCQAGQGIG SSLKWYQQKS GRAPRLLVHG ASNLQRGVPS  60
RFSGSGFHTT FTLTISSLQP DDVATYWCAV LEFFGPGTKV EIKRTVAAPS VFIFPPSDEQ  120

SEQ ID NO: 466         moltype = AA  length = 129
FEATURE                Location/Qualifiers
source                 1..129
                       mol_type = protein
                       organism = Homo sapiens
SEQUENCE: 466
QSVLTQPPSA SGAPGQRVTI SCSGGPSNVG GNYVYWYRQF PGTAPNLLIL RDDQRPSGVP  60
DRFSASKSGN SASLAISGLR PDDEAFYFCA TYDSDGSVRL FGGGTTLTVL SQPKAAPSVT  120
LFPPSNGGR                                                        129

SEQ ID NO: 467         moltype = AA  length = 129
FEATURE                Location/Qualifiers
source                 1..129
                       mol_type = protein
                       organism = Homo sapiens
SEQUENCE: 467
```

```
QSALTQTPSV SGAPGQRVTI SCSGGPSNVG GNYVYWYQQF PGAAPKLLIR RDDQRPSGVP  60
DRFSGSKSGN SASLAISGLR LDDEAYYFCA TYDSGWSIRL FGGGTRLTVL SQPKAAPSVT  120
LFPPSSEEL                                                         129

SEQ ID NO: 468         moltype = AA  length = 125
FEATURE                Location/Qualifiers
source                 1..125
                       mol_type = protein
                       organism = Homo sapiens
SEQUENCE: 468
SQAVVTQPPS VSGAPGQRVT ISCSGGPSNV GGNLVYWYKQ FPGTAPKLLI RRDDQRPSGV  60
PDRFSGSKSG NSASLAISGL RPDDEAFYFC ATYDSHGSIR LFGGGTLLTV LSQPKAAPSV  120
TLFPP                                                             125

SEQ ID NO: 469         moltype = AA  length = 129
FEATURE                Location/Qualifiers
source                 1..129
                       mol_type = protein
                       organism = Homo sapiens
SEQUENCE: 469
QTVVTQPPSA SGTPGQRVTI SCSGGGSNIG GNLVSWYQHF PGAAPKLLIY RNDQRPSGVP  60
DRFSGSKSGT SASLTISGLR SDDEATYFCA AYDCTLSLRL FGGGTTLNVL SQPKAAPSVT  120
LFPPSSEEL                                                         129

SEQ ID NO: 470         moltype = AA  length = 129
FEATURE                Location/Qualifiers
source                 1..129
                       mol_type = protein
                       organism = Homo sapiens
SEQUENCE: 470
QSALTQPPSV SGTPGQNVTI SCSGGGSNVG GNLVSWYQHF PGAAPKLLIH RDNQRPSGVP  60
DRFSVLKSGN SASLAISGPR SDDEAFYFCA VYDSSLSLGL FGGGTKLTVL SQPKAAPSVT  120
LFPPSSEEL                                                         129

SEQ ID NO: 471         moltype = AA  length = 130
FEATURE                Location/Qualifiers
source                 1..130
                       mol_type = protein
                       organism = Homo sapiens
SEQUENCE: 471
QSALTQPPSA SGAPGQRVTI SCSGGPSNVG GNYVYWYRQF PGTAPTLLIL RDDQRPSGVP  60
DRFSASKSGN SASLAISGLR PDDEGFYFCA TYDSDGSIRL FGGGTALTVL SQPKAAPSVT  120
LFPPSSEELK                                                        130

SEQ ID NO: 472         moltype = AA  length = 119
FEATURE                Location/Qualifiers
source                 1..119
                       mol_type = protein
                       organism = Homo sapiens
SEQUENCE: 472
NFMLTQAPSA SGAPGQRVTI SCSGGPSNVG GNYVYWYRQY PGTAPKLLIL RDDQRPSGVP  60
DRFSASKSGN SASLAISELR PDDEAFYFCA TYDSDGSIRL FGGGTALTVL SQPKAAPSV   119

SEQ ID NO: 473         moltype = AA  length = 124
FEATURE                Location/Qualifiers
source                 1..124
                       mol_type = protein
                       organism = Homo sapiens
SEQUENCE: 473
NFMLTQPPSA SGAPGQRVTI SCSGGPSNVG GNYVYWYRQF PGTAPNLLIL RDDQRPSGVP  60
DRFSASKSGN SASLAISGLR PDDEAFYFCA TYDSDGSIRL FGGGTTLTVL SQPKAAPSVT  120
LFPP                                                              124

SEQ ID NO: 474         moltype = AA  length = 118
FEATURE                Location/Qualifiers
source                 1..118
                       mol_type = protein
                       organism = Homo sapiens
SEQUENCE: 474
QSVLTQPPSA SGAPGQRVTI SCSGGPSNVG GNYVYWYRQF PGTAPKLLIL RDDQRPSGVP  60
DRFSASKSGN SASLAISGLR PDDEAFYFCA TYDSDGSIRL FGGGTALTVL SQPKAAPS    118

SEQ ID NO: 475         moltype = AA  length = 120
FEATURE                Location/Qualifiers
source                 1..120
                       mol_type = protein
                       organism = Homo sapiens
SEQUENCE: 475
QLVLTQPPSV SGTPGQNVTI SCSGGGSHVG GNLVSWYQHF PGAAPKLLIH RDNQRPSGVP  60
```

```
DRFSALKSGN SASLAISGLR SDDEAFYFCA VYDSSLSLGL FGGGTKLTVL SQPKAAPSVT  120

SEQ ID NO: 476         moltype = AA  length = 131
FEATURE                Location/Qualifiers
source                 1..131
                       mol_type = protein
                       organism = Homo sapiens
SEQUENCE: 476
RTVVTQPPSV SGAPGQRVTI SCTGSSSNIG AGYDVHWYQQ LPGTAPKLLI YGNSNRPSGV  60
PDRFSGSKSG TSASLAITGL QAEDEADYYC QSYDSSLSGS GVFGTGTKVT VLGQPKANPT  120
VTLFPPSSEE L                                                      131

SEQ ID NO: 477         moltype = AA  length = 128
FEATURE                Location/Qualifiers
source                 1..128
                       mol_type = protein
                       organism = Homo sapiens
SEQUENCE: 477
QSALTQPPSA SGAPGQRVTI SCSGGPSNVG GNYVYWYRQF PGTAPKLLIL RDDQRPSGVP  60
DRFSASKSGN SASLAISGLR PDDEALYFCA TYDSDGSIRL FGGGTALTVL SQPKAAPSVT  120
LFPPGWEE                                                          128

SEQ ID NO: 478         moltype = AA  length = 124
FEATURE                Location/Qualifiers
source                 1..124
                       mol_type = protein
                       organism = Homo sapiens
SEQUENCE: 478
QPVLTQPPSA SGAPGQRVTI SCSGGPSNVG GNYVYWYRQF PGTAPNLLIL RDDQRPSGVP  60
DRFSASKSGN SASLAITGLR PDDEAFYFCA TYDSDGSIRL FGGGTALTVL SQPKAAPSVT  120
LFPP                                                              124

SEQ ID NO: 479         moltype = AA  length = 122
FEATURE                Location/Qualifiers
source                 1..122
                       mol_type = protein
                       organism = Homo sapiens
SEQUENCE: 479
QSALTQPPSA SGAPGQRVTI SCSGGPSNVG GNYVYWYRQF PGTAPNLLIL RDDQRPSGVP  60
DRFSASKSGN SASLAISGLR PDDEAFYFCA TYDSDGSIRL FGGGTTLTVL SQPKAAPSVT  120
LF                                                                122

SEQ ID NO: 480         moltype = AA  length = 129
FEATURE                Location/Qualifiers
source                 1..129
                       mol_type = protein
                       organism = Homo sapiens
SEQUENCE: 480
QSALTQTPSV SGAPGQRVTI SCSGGPSNVG GNYVYWYQQF PGAAPKLLIR RDDQRPSGVP  60
DRFSGSKSGN SASLAISGLR LDDEAYYFCA TYDSGWSIRL FGGGTRLTVL SQPKAAPSVT  120
LFPPSSEEL                                                         129

SEQ ID NO: 481         moltype = AA  length = 129
FEATURE                Location/Qualifiers
source                 1..129
                       mol_type = protein
                       organism = Homo sapiens
SEQUENCE: 481
QLVLTQPPSV SATPGQTVTI SCSGSGSNVG GNHVYWYRQL PGAAPTLVIS KTDHRPSRVP  60
DRFSGSKSGN SASLAISGLR PDDEAAYFCA TYDTGLSLRL FGGGTRLAVL SQPKAAPSVT  120
LFPPSSEEL                                                         129

SEQ ID NO: 482         moltype = AA  length = 129
FEATURE                Location/Qualifiers
source                 1..129
                       mol_type = protein
                       organism = Homo sapiens
SEQUENCE: 482
QSALTQPPAT SGTPGQRVTI SCSGGGSNVG GNLVSWYQQF PGAAPKLILH RDGQRPSGVP  60
DRFSASKSGT SASLTISGLR SDDEATYFCA AFDSALSLPL FGGGTKLTVL SQPKAAPSVT  120
LFPPSSEEL                                                         129

SEQ ID NO: 483         moltype = AA  length = 129
FEATURE                Location/Qualifiers
source                 1..129
                       mol_type = protein
                       organism = Homo sapiens
SEQUENCE: 483
QSVLTQVLSV SGTPGQRVII SCSGTSSNVG GNLVSWYQHL PGAAPRLLIH RDDQRPSGVP  60
```

```
DRFSGSKSGN SASLVISGLR SDDEADYFCG AYDSTFSLPV FGGGTRLTVL SQPKAAPSVT  120
LFPPSSEEL                                                          129

SEQ ID NO: 484         moltype = AA  length = 128
FEATURE                Location/Qualifiers
source                 1..128
                       mol_type = protein
                       organism = Homo sapiens
SEQUENCE: 484
NFMLTQPPSV SATPGQTVTI SCSGSGSNVG GNHVYWYRQL PGAAPTLVIS KTDHRPSRVP  60
DRFSGSKSGN SASLAISGLR PDDEAVYFCA TYDTGLSLRL FGGGTRLTVL SQPKAAPSVT  120
QFPPSSEE                                                           128

SEQ ID NO: 485         moltype = AA  length = 129
FEATURE                Location/Qualifiers
source                 1..129
                       mol_type = protein
                       organism = Homo sapiens
SEQUENCE: 485
QSALTQPPSV SATPGQTVTI SCSGSGSNVG GNHVYWYRQL PGAAPTLLIS KTNHRPSQVP  60
DRFSASKSGN SASLAISGLR PDDEADYFCG TYDTSLSLRL FGGGTRLTVL SQPKAAPSVT  120
LFPPSSEEL                                                          129

SEQ ID NO: 486         moltype = AA  length = 129
FEATURE                Location/Qualifiers
source                 1..129
                       mol_type = protein
                       organism = Homo sapiens
SEQUENCE: 486
QSALTQPPSA SGTPGQRVTI SCSGGGSNIG GNLVSWYQHF PGTAPKLLIY RNDQRPSGVP  60
DRFSGSKSGT SASLTISGLR SDDEATYFCA AYDSSLSLRL FGGGTTLNVL SQPKAAPSVT  120
LFPPSSEEL                                                          129

SEQ ID NO: 487         moltype = AA  length = 129
FEATURE                Location/Qualifiers
source                 1..129
                       mol_type = protein
                       organism = Homo sapiens
SEQUENCE: 487
QSALTQPPSV SGTPGQNVTI SCSGGGSDVG GNLVSWYQHF PGAAPKLLIH RDNQRPSGVP  60
DRFSALKSGN SASLAISGLR SDDEAFYFCA VYDSSLSLGL FGGGTKLTVL SQPKAAPSVT  120
LFPPSSEEL                                                          129

SEQ ID NO: 488         moltype = AA  length = 129
FEATURE                Location/Qualifiers
source                 1..129
                       mol_type = protein
                       organism = Homo sapiens
SEQUENCE: 488
QAVVTQPPSV SATPGQTVTI SCSGSGSNVG GNHVYWYRQL PGAAPTLLIS KTNRRPSQVP  60
DRFSGSKSGN SASLAISGLR PDDEADYFCA TYDTDLSLRL FGGGTRLTVL SQPKAAPSVT  120
LFPPSSEEL                                                          129

SEQ ID NO: 489         moltype = AA  length = 120
FEATURE                Location/Qualifiers
source                 1..120
                       mol_type = protein
                       organism = Homo sapiens
SEQUENCE: 489
QSALTQPPAA SGAPGQRVTI SCSGGGSNVG GNLVSWYQQF PGAAPKLILH RDGQRPSGVP  60
DRFSASKSGT SASLTISGLR SDDEATYFCA AYDSAVSLPV FGGGTKLTVL SQPKAAPLVT  120

SEQ ID NO: 490         moltype = AA  length = 128
FEATURE                Location/Qualifiers
source                 1..128
                       mol_type = protein
                       organism = Homo sapiens
SEQUENCE: 490
NFMLTQPPSA SGTPGQRVTI SCSGGGSNIG GNLVSWYQHF PGAAPKLLIY RNDQRPSGVP  60
DRFSGSKSGT SASLAISGLR SDDKATYFCA AYDSTLSLRL FGGGTTLTVL SQPKAAPSVT  120
LFPPSSEE                                                           128

SEQ ID NO: 491         moltype = AA  length = 127
FEATURE                Location/Qualifiers
source                 1..127
                       mol_type = protein
                       organism = Homo sapiens
SEQUENCE: 491
QSVLTQVLSV SGTPGQRVII SCSGTSSNVG GNLVSWYQHL PGAAPRLLIH RDDQRPSGVP  60
```

```
DRFSGSKSGN SASLVISGLR SDDEADYFCA AYDSTFSLPV FGGGTRLTVL SQPKAAPSVT  120
LFPPSSE                                                            127

SEQ ID NO: 492         moltype = AA  length = 129
FEATURE                Location/Qualifiers
source                 1..129
                       mol_type = protein
                       organism = Homo sapiens
SEQUENCE: 492
QSALTQPPSV SATPGQTVTI SCSGSGSNVG GNHVYWYRQL PGAAPTLLIS KTDHRPSRVP  60
DRFSASKSGN SASLAISGLR PDDEAIYFCA TYDTGLSLRL FGGGTRLTVL SQPKAAPSVT  120
LFPPSSEEL                                                          129

SEQ ID NO: 493         moltype = AA  length = 129
FEATURE                Location/Qualifiers
source                 1..129
                       mol_type = protein
                       organism = Homo sapiens
SEQUENCE: 493
QSALTRTPSV SGAPGQRVTI SCSGGPSNVG GNYVYWYQQF PGAAPKLLIR RDDQRPSGVP  60
DRFSGSKSGN SASLAISGLR LDDEAYYFCA TYDSGWSIRL FGGGTRLTVL SQPKAAPSVT  120
LFPPSSEEL                                                          129

SEQ ID NO: 494         moltype = AA  length = 115
FEATURE                Location/Qualifiers
source                 1..115
                       mol_type = protein
                       organism = Homo sapiens
SEQUENCE: 494
QSALTQAPSA SGTPGQRVTI SCSGGGSNIG GNLVSWYQHF PGAAPKLLIY RNDQRPSGVP  60
DRFSASKSGT SASLAISGLR SDDEATYFCA AYDSTLSLRL FGGGTTLAVL SQPKA        115

SEQ ID NO: 495         moltype = AA  length = 129
FEATURE                Location/Qualifiers
source                 1..129
                       mol_type = protein
                       organism = Homo sapiens
SEQUENCE: 495
NFMLTQPPSV SGAPGQRVTI SCSGGPSNVG GNLVYWYKQF PGTAPKLLIR RDDQRPSGVP  60
DRFSGSKSGN SASLAISGLR PDDEAFYFCA TYDSHGSIRL FGGGTLLTVL SQPKAAPSVT  120
LFPPSSEEL                                                          129

SEQ ID NO: 496         moltype = AA  length = 129
FEATURE                Location/Qualifiers
source                 1..129
                       mol_type = protein
                       organism = Homo sapiens
SEQUENCE: 496
QLVLTQPPSV SGAPGQRVTI SCSGGPSNVG GNLVYWYKQF PGTAPKLLIR RDDQRPSGVP  60
DRFSGSKSGN SASLTISGLR PDDEAFYFCA TYDSQGSTRL FGGGTVLTVL SQPKAAPSVT  120
LFPPSSEEL                                                          129

SEQ ID NO: 497         moltype = AA  length = 128
FEATURE                Location/Qualifiers
source                 1..128
                       mol_type = protein
                       organism = Homo sapiens
SEQUENCE: 497
QSALTQPPSV SGAPGQRVTI SCSGGPSNVG GNYVYWYRQF PGTAPKLLIL RDDQRPSGVP  60
DRFSASKSGN SASLAISGLR PDDEAFYFCA TYDSQGSFRV FGGGTALTVL SQPKAAPSVT  120
LYPPSSEE                                                           128

SEQ ID NO: 498         moltype = AA  length = 129
FEATURE                Location/Qualifiers
source                 1..129
                       mol_type = protein
                       organism = Homo sapiens
SEQUENCE: 498
NFMLTQPPSA SGAPGQRVTI SCSGGPSNVG GNYVYWYRQF PGTAPNLLIL RDDQRPSGVP  60
DRFSASKSGN SASLAISGLR PDDEAFYFCA TYDSDGSIRL FGGGTTLTVL SQPKAAPSVT  120
LFPPSSEEL                                                          129

SEQ ID NO: 499         moltype = AA  length = 123
FEATURE                Location/Qualifiers
source                 1..123
                       mol_type = protein
                       organism = Homo sapiens
SEQUENCE: 499
QVLSVSGTPG QRVIISCSGT SSNVGGNLVS WYQHLPGAAP RLLIHRDDQR PSGVPDRFSG  60
```

-continued

```
SKSGNSASLV ISGLRSDDEA DYFCAAYDST FSLPVFGGGT RLTVLSQPKA APSVTLYAPS  120
SEE                                                                123

SEQ ID NO: 500         moltype = AA  length = 117
FEATURE                Location/Qualifiers
source                 1..117
                       mol_type = protein
                       organism = Homo sapiens
SEQUENCE: 500
PVTLSASVGD RVTITCRASE DISKYLNWYQ HKPGKAPKLL IYTASSLETG VPSRFSGSGS  60
GTDFSLTISS LQPDDFATYY CQQSYTSSVT FGQGTRVEVK RTVAAPSVFI FPPSDEQ     117

SEQ ID NO: 501         moltype = AA  length = 124
FEATURE                Location/Qualifiers
source                 1..124
                       mol_type = protein
                       organism = Homo sapiens
SEQUENCE: 501
PATLAVSPGE RATISCKSSQ NLLYSANNQH SLAWYQQRPG QPPKLLLYWA STRLSGVPDR  60
FSGSGSGTDF TLTISNLQAE DVAVYYCQQY YSPPPTFGQG TKVEIRRTVA APSVFIFPPS  120
DEQL                                                               124

SEQ ID NO: 502         moltype = AA  length = 115
FEATURE                Location/Qualifiers
source                 1..115
                       mol_type = protein
                       organism = Homo sapiens
SEQUENCE: 502
TLSASVGDRV TITCRASQSI NNYLNWYQQK PGKAPKLLIY AASSLQSGVP SRFSGSGSGT  60
DFTLTISSLQ PEDFVTYYCQ QTYSNPRMFG QGTKVEIKRT VAAPSVFIFP PSDEQ       115

SEQ ID NO: 503         moltype = AA  length = 118
FEATURE                Location/Qualifiers
source                 1..118
                       mol_type = protein
                       organism = Homo sapiens
SEQUENCE: 503
KAPATLSLSP GERATLSCRA SQSVGSDLAW YQQKPGQAPR LLIYDASNRA TAIPARFSGS  60
GSGTDFTLSI SSLEPEDFAV YFCQQRYDKI TFGQGTRLEI QRTVAAPSVF IFPPSDEQ    118

SEQ ID NO: 504         moltype = AA  length = 126
FEATURE                Location/Qualifiers
source                 1..126
                       mol_type = protein
                       organism = Homo sapiens
SEQUENCE: 504
RGPVTLAVSL GERATITCKS SQSVLVHSNN KNYLSWYQQK PGQPPKLLIY WASTRESGVP  60
ERFSGSGSGT DFTLSISSLQ AEDVAVYYCH QYFSTPRTFG QGTKVEIKGT VAAPSVFIFP  120
PSDEQL                                                             126

SEQ ID NO: 505         moltype = AA  length = 123
FEATURE                Location/Qualifiers
source                 1..123
                       mol_type = protein
                       organism = Homo sapiens
SEQUENCE: 505
SEIVLTQSPA TLSLSPGESA TLSCRASQSL SSSLAWYQQK PGQAPRLLIY DTSDRATGIP  60
ARFSGRGSGT DFTLTISSLE PEDFAVYYCQ QRSNWAITFG QGTRLEIKRT VAAPSVFIFP  120
PSD                                                                123

SEQ ID NO: 506         moltype = AA  length = 123
FEATURE                Location/Qualifiers
VARIANT                18
                       note = Any naturally occurring amino acid or not present
VARIANT                35
                       note = Any naturally occurring amino acid or not present
source                 1..123
                       mol_type = protein
                       organism = Homo sapiens
SEQUENCE: 506
EIVLTQSPGT LSLSPGEXAT LSCRASQTIS NNYLXWYQQK AGQAPRLLIY GASSGATGIP  60
DRFSGSGSGT DFTLTISRLE PEDFAVYYCQ QYGLSPWTFG RGTKVEIKRT VAAPSVFIFP  120
PSD                                                                123

SEQ ID NO: 507         moltype = AA  length = 129
FEATURE                Location/Qualifiers
source                 1..129
                       mol_type = protein
                       organism = Homo sapiens
```

```
SEQUENCE: 507
QSALTQPRSV SGSPGQSVTI SCTGTSSDVG AYNYVSWYRQ HPGKAPKLMI NDVSKRPSGV  60
PDRFSGSKSG NTASLTISGL QAEDEADYYC CSYAGTYSYV FGTGTKVTVL GQPKANPTVT  120
LFPPSSEEL                                                         129

SEQ ID NO: 508         moltype = AA  length = 116
FEATURE                Location/Qualifiers
source                 1..116
                       mol_type = protein
                       organism = Homo sapiens
SEQUENCE: 508
APVTLSASVG DTVTITCRAS QPIATFLNWY QHKPGQAPKL LIYAASTFQR GAPSRYSGSG  60
SGTDFTLTIN SLQPEDLATY YCQQTFTDPV TFGQGTRLEI KRTVAAPSVF IFPPSD      116

SEQ ID NO: 509         moltype = AA  length = 122
FEATURE                Location/Qualifiers
source                 1..122
                       mol_type = protein
                       organism = Homo sapiens
SEQUENCE: 509
DIQMTQSPAS LSASVGDRVT ITCRASQGIS HYLAWYQQKP GKVPRLLIYA ASRLQSGVTS  60
RFSGSGSGTE FTLTISSLLP EDAAVYFCQK YDTDPMTFGQ GTRLEIKRTV AAPSVFIFPP  120
SD                                                                122

SEQ ID NO: 510         moltype = AA  length = 123
FEATURE                Location/Qualifiers
source                 1..123
                       mol_type = protein
                       organism = Homo sapiens
SEQUENCE: 510
DIQMTQSPSS LSASIGDRVT ITCRANQHIR SFLNWYQQTP GKAPKLLIYA ASTLQRGVPS  60
RFSGSGSGTD FTLTITSLER EDLATYYCQQ TYTSPITFGQ GTRLEIKRTV AAPSVFIFPP  120
SDE                                                               123

SEQ ID NO: 511         moltype = AA  length = 124
FEATURE                Location/Qualifiers
source                 1..124
                       mol_type = protein
                       organism = Homo sapiens
SEQUENCE: 511
EIVLTQSPGT LSLSPGERAT LSCRASQSVS NNYLAWYQQK PGQAPRLLIY GASSRATGIP  60
DRFSGSGSGT DFTLTISRLE PEDFAVYYCQ QYATSSLYTF GQGTKLEIKR TVAAPSVFIF  120
PPSD                                                              124

SEQ ID NO: 512         moltype = AA  length = 118
FEATURE                Location/Qualifiers
source                 1..118
                       mol_type = protein
                       organism = Homo sapiens
SEQUENCE: 512
LSVSLGERAT INCKSSQSIL YSSDKKNYLA WYQQKIGQPP KLLLYWASTR ESGIPDRFSG  60
SGSGSDFTLT ISSLQPEDVA VYYCQQYYIS PFTFGPGTKV DLKRTVAAPS VFIFPPSD    118

SEQ ID NO: 513         moltype = AA  length = 120
FEATURE                Location/Qualifiers
source                 1..120
                       mol_type = protein
                       organism = Homo sapiens
SEQUENCE: 513
NFMLTQPASV SGSPGQSITL SCTGTTSDVR DSNFVSWYQQ VPGKAPKLII YDVSARPSGV  60
SFRFSGSKSG NTASLTISGL QAEDEALYYC SSFTPTNTLV FGGGTKLTVL GQPKAAPSVT  120

SEQ ID NO: 514         moltype = AA  length = 114
FEATURE                Location/Qualifiers
source                 1..114
                       mol_type = protein
                       organism = Homo sapiens
SEQUENCE: 514
SQSVVTQEPS LTVSPGGTVT LTCGPSTGAV TSGFYPHWFQ QKPGQAPRAL IYSTSNKYSW  60
TPARFSGSLL GGKAVLTLSD VQPDDEAEYY CLLLLYYGGP WIFGGGTKLT VLVS        114

SEQ ID NO: 515         moltype = AA  length = 130
FEATURE                Location/Qualifiers
source                 1..130
                       mol_type = protein
                       organism = Homo sapiens
SEQUENCE: 515
QAVVTQEPSL TVSPGGTVTL TCASSTGAVT SGFYPHWFQQ KPGQAPRALI YSTSNRYSWT  60
PARFSGSLLG GKAALTLSGV QPEDEAEYYC LLLPYYGGPW IFGGGTKLTV LGQPKAAPSV  120
```

```
TLFPPSSEEL                                                  130

SEQ ID NO: 516          moltype = AA  length = 122
FEATURE                 Location/Qualifiers
source                  1..122
                        mol_type = protein
                        organism = Homo sapiens
SEQUENCE: 516
EIVMTQSPAT LSVSPGDRAT LSCRASQSVS TNLAWYQQKP GQAPRLLIYG ASTRATGIPA  60
TFSGSGFATE FTLTISSLQS EDFAVYYCQQ YNNWPPAFGQ GTKVEIKRTV AAPSVFIFPP  120
SD                                                          122

SEQ ID NO: 517          moltype = AA  length = 130
FEATURE                 Location/Qualifiers
source                  1..130
                        mol_type = protein
                        organism = Homo sapiens
SEQUENCE: 517
QSVLTQPPSA SGSPGQSITI SCTGTSSDVG GYNYVSWYQQ PPGKAPKVII YEVSKRPSGV  60
PDRFSGSKSG NTASLTVSGL QAEDEADYYC SSYAGSNNFV FGTGTEVTVV GQPKANPTVT  120
LFPPSSEELL                                                  130

SEQ ID NO: 518          moltype = AA  length = 113
FEATURE                 Location/Qualifiers
source                  1..113
                        mol_type = protein
                        organism = Homo sapiens
SEQUENCE: 518
SLSASVGDRV TITCRASESI SFYLNWYQQK PGKAPELLIF ATSTLHSGVP SRFSGSGSGT  60
DFTLTISSLQ LEDFATYYCQ QSSSTPFTFG GGTKVEIKRT VAAPSVFIFP PSD         113

SEQ ID NO: 519          moltype = AA  length = 121
FEATURE                 Location/Qualifiers
source                  1..121
                        mol_type = protein
                        organism = Homo sapiens
SEQUENCE: 519
DIQMTQSPSS LSAYVGDRVT ITCRASQNIN TYLNWYQQRP GKAPKLLIYA ASTLQSGVPS  60
RFSGSGSGTD FTLTISNLET EDFAVYYCQQ TYRSVTFGQG TKLEIKRTVA APSVFIFPPS  120
D                                                           121

SEQ ID NO: 520          moltype = AA  length = 111
FEATURE                 Location/Qualifiers
source                  1..111
                        mol_type = protein
                        organism = Homo sapiens
SEQUENCE: 520
LSAYVGDRVT ITCRASQNIN TYLNWYQQRP GKAPKLLIYA ASTLQSGVPS RFSGSGSGTD  60
FTLTISNLET EDFAVYYCQQ TYSSVTFGQG TKLETRRTVA APSVFIFPPS D           111

SEQ ID NO: 521          moltype = AA  length = 125
FEATURE                 Location/Qualifiers
source                  1..125
                        mol_type = protein
                        organism = Homo sapiens
SEQUENCE: 521
SEIVLTQSPG TLSLSPGERA TLSCRASQSV SSSYLAWYQQ KPVQAPRLLI YGASSRATGI  60
PDRFSGSGSG TDFTLTISRL EPEDFAVYYC QQYGTLHPRT FGQGTKVEIK RTVAAPSVFI  120
FPPSD                                                       125

SEQ ID NO: 522          moltype = AA  length = 122
FEATURE                 Location/Qualifiers
source                  1..122
                        mol_type = protein
                        organism = Homo sapiens
SEQUENCE: 522
EIVLTQSPGT LSLSPGERAT LSCRASQSIS SNYLAWYQQK PGQAPRLLIY GASTRATGIP  60
DRFSGSGSGT DFTLSISRLE PEDIAVYYCH QYGSSQRFGQ GTKVEIKRTV AAPSVFIFPP  120
SD                                                          122

SEQ ID NO: 523          moltype = AA  length = 122
FEATURE                 Location/Qualifiers
source                  1..122
                        mol_type = protein
                        organism = Homo sapiens
SEQUENCE: 523
DIQMTQSPSS LSASVGDRVT ITCRASQSIS RYLNWYQQKP GKAPKLLIYA ASSLQGGVPS  60
RFSGSGSGTD FTLTISSLQP EDFATYYCQQ SSSKPFTFGG GTKVEIKRTV AAPSVFIFPP  120
SD                                                          122
```

```
SEQ ID NO: 524          moltype = AA  length = 129
FEATURE                 Location/Qualifiers
source                  1..129
                        mol_type = protein
                        organism = Homo sapiens
SEQUENCE: 524
NFMLTQPASV SGSPGQSITI SCSGTGSDIG VYNYVSWYQQ HPGKAPRLMI YDVTNRPSGV  60
SNRFSGSKSG FTASLTISGL QGDDEADYYC SSYSSTNTYV FGTGTHVTVL GQPKANPTVT  120
LFPPSSEEL                                                          129

SEQ ID NO: 525          moltype = AA  length = 127
FEATURE                 Location/Qualifiers
source                  1..127
                        mol_type = protein
                        organism = Homo sapiens
SEQUENCE: 525
QSALTQPPSA SGTPGQRVTI SCSGSYHNIG SNAVNWYQQL PGTAPKLLIY SNDQRPSGVP  60
DRFSGSKSGT SASLAISGLQ SEDEADYYCA AWDDSLHVFG TGTKVTVLGQ PKANPTVTLF  120
PPSSEEL                                                            127

SEQ ID NO: 526          moltype = AA  length = 127
FEATURE                 Location/Qualifiers
source                  1..127
                        mol_type = protein
                        organism = Homo sapiens
SEQUENCE: 526
QSALTQPPSA SGTPGQRVTI SCSGSYHNIG SNAVNWYQQL PGTAPKLLIY SNDQRPSGVP  60
DRFSGSKSGT SASLAISGLQ SEDEADYYCA AWDDSLHVFG TGTKVTVLGQ PKANPTVTLF  120
PPSSEEL                                                            127

SEQ ID NO: 527          moltype = AA  length = 123
FEATURE                 Location/Qualifiers
source                  1..123
                        mol_type = protein
                        organism = Homo sapiens
SEQUENCE: 527
DIQMTQSPSS LSASVGDRVT ITCRASQDIT TYLAWLQQKP GKAPKSLIYS ASTVQSGVPS  60
RFSGSGSGTE FTLTISGLQP EDFATYYCQQ YNYYPITFGL GTRLEIKRTV AAPSVFIFPP  120
SDE                                                                123

SEQ ID NO: 528          moltype = AA  length = 117
FEATURE                 Location/Qualifiers
source                  1..117
                        mol_type = protein
                        organism = Homo sapiens
SEQUENCE: 528
IILFLVATAT GSWAQSALTQ PRSVSGSLGQ SVTISCTGSS SDVGRYNYVS WYQHHPGKAP  60
KLMISDVNKR PSGVPDRFSG SKSGNTASLT ISGLQAEDET DYYCCSYAGS YIWVFGG     117

SEQ ID NO: 529          moltype = AA  length = 125
FEATURE                 Location/Qualifiers
source                  1..125
                        mol_type = protein
                        organism = Homo sapiens
SEQUENCE: 529
EIVLTQSPAT LSLSPGERAT LSCRASQSVS SYLAWYQQKP GQAPRLLIYD ASNRATGIPA  60
RFSGSGSDTD FTLTISSLEP EDFAVYYCQQ RGIWPLQITF GQGTRLEIKR TVAAPSVFIF  120
PPSDE                                                              125

SEQ ID NO: 530          moltype = AA  length = 119
FEATURE                 Location/Qualifiers
source                  1..119
                        mol_type = protein
                        organism = Homo sapiens
SEQUENCE: 530
LSASVGDRVT ITCRASQSID RYLNWYQQKP GKAPKLLIYA ASSLHTDVPS RFSGSGAGTY  60
FTLTITSLQP EDFATYYCQQ SHSPSFGQES YSITFGQGTR LEIKRTVAAP SVFIFPPSD   119

SEQ ID NO: 531          moltype = AA  length = 115
FEATURE                 Location/Qualifiers
source                  1..115
                        mol_type = protein
                        organism = Homo sapiens
SEQUENCE: 531
VTLSLSPGER ATLSCRASQT ISNNYLAWYQ QKPGQAPRLL IYGASSGATG LPDRFSGSGS  60
GTDFTLTISR LEPEDFAVYY CHQYALSPWT FGRGTKVEIK RTVAAPSVFI FPPSD       115

SEQ ID NO: 532          moltype = AA  length = 144
```

-continued

```
FEATURE                Location/Qualifiers
source                 1..144
                       mol_type = protein
                       organism = Homo sapiens
SEQUENCE: 532
IILFLVATAT GVHSDIQMTQ SPSSLSASVG DRVTITCRAS QSIDRYLNWY QHKPGKAPKL  60
LIYAASNLHT DVPSRFSGSG AGTYFTLTIT SLQPEDFATY YCQQSHSPSF GQESYSIAFG  120
QGTRLEIKRT VAAPSVFIFP PSDE                                         144

SEQ ID NO: 533         moltype = AA  length = 113
FEATURE                Location/Qualifiers
source                 1..113
                       mol_type = protein
                       organism = Homo sapiens
SEQUENCE: 533
QSVLTQPASV SGSPGQSITI SCTGTNSDVG YSYVSWFQQH PGKVPKLLIY DVSRRSSGVS  60
NRFSGSRSGN TASLTISGLR AEDEADYYCG SFTTSLTLVF GGGTKLAVLV SPS         113

SEQ ID NO: 534         moltype = AA  length = 124
FEATURE                Location/Qualifiers
source                 1..124
                       mol_type = protein
                       organism = Homo sapiens
SEQUENCE: 534
EIVLTQSPGT LSLSPGERAT LSCRASQSVS SRYLAWYQQK PGQAPRLIIY DASSRASGIP  60
DRFSGSGSET DFTLTITRLE PEDFAVYYCQ LYGTSPKFTF GQGTKLEIKR TVAAPSVFIF  120
PPSD                                                               124

SEQ ID NO: 535         moltype = AA  length = 90
FEATURE                Location/Qualifiers
source                 1..90
                       mol_type = protein
                       organism = Homo sapiens
SEQUENCE: 535
DVVMTQSPLS LPVTLGQPAS ISCRSSQSLV YSHGDTYLKC FQQRPGQSPR RPIYKVSNRD  60
SGVPDRFSGS GSGTDFTLKI SRVEAEDVGV                                   90

SEQ ID NO: 536         moltype = AA  length = 116
FEATURE                Location/Qualifiers
source                 1..116
                       mol_type = protein
                       organism = Homo sapiens
SEQUENCE: 536
GPATLSVSPG ERATLSCRAS QSLRNNLAWY QQKTGQSPRL LIYAVSTRAT GIPPRFSGGG  60
SGTEFTLTID SLQSEDFAVY FCQQYDSPQW TFGQGTKVEI KRTVAAPSVF IFPPSD      116

SEQ ID NO: 537         moltype = AA  length = 120
FEATURE                Location/Qualifiers
source                 1..120
                       mol_type = protein
                       organism = Homo sapiens
SEQUENCE: 537
QSVLTQPASV SGSPGQSITI SCTGTSNDVG GQNFVSWYQQ HPGTAPQLLI YDVTNRPAGV  60
SSRFSGSKSG NTASLTISGL RTEDEADYYC ASFTILNGVD YVFGTGTKVT VLLSPSQPYL  120

SEQ ID NO: 538         moltype = AA  length = 124
FEATURE                Location/Qualifiers
source                 1..124
                       mol_type = protein
                       organism = Homo sapiens
SEQUENCE: 538
EIVLTQSPAT LSVSPGERAT LSCRAGQSVS SDLAWYQHKP GQAPRLLIYD ASKRATGIPA  60
RFSGSGSGTD FTLTISSLEP EDFAVYYCQH RTNWPPSITF GQGTRLEIKR TVAAPSVFIF  120
PPSD                                                               124

SEQ ID NO: 539         moltype = AA  length = 119
FEATURE                Location/Qualifiers
source                 1..119
                       mol_type = protein
                       organism = Homo sapiens
SEQUENCE: 539
EIVLTQSPGT LSLSPGERAT LSCRASQSVS SNYLAWYQQK PGQAPRLLIY GASSRATGIP  60
DRFSGSGSGT DFTLSISRLE PEDFAVYYCQ QYGTSSCTFG QGTKLEIKRT VAAPSVFIF   119

SEQ ID NO: 540         moltype = AA  length = 123
FEATURE                Location/Qualifiers
source                 1..123
                       mol_type = protein
                       organism = Homo sapiens
```

SEQUENCE: 540
EIVLTQSPGT LSLSPGDRAA LSCRASETLS GNSLAWYQQK RGQPPRLLIF AASSRATGIP 60
ERFSGGGSGT DFTLTITRLE PEDFAVYFCQ QYVDAPITFG QGTRLEIKRT VAAPSVFIFP 120
PSD 123

SEQ ID NO: 541 moltype = AA length = 121
FEATURE Location/Qualifiers
source 1..121
mol_type = protein
organism = Homo sapiens
SEQUENCE: 541
EIVLTQSPGT LSLSPGERAT LSCRASQSVS SNNLAWYQQK PGQAPRLLMS GASSRATGIP 60
DRFSGSGSGT DFTLTISRLE PEDFAVYHCQ QYGSSPPTFG QGTKVEIKRT VAAPSVFIFP 120
P 121

SEQ ID NO: 542 moltype = AA length = 119
FEATURE Location/Qualifiers
source 1..119
mol_type = protein
organism = Homo sapiens
SEQUENCE: 542
QSVLTQPRSV SGSPGQSVTI SCTGTSSDVG GYNYVSWYQQ HPGKAPKTMI FDVTKRPSGV 60
PDRFSGSKSG NTASLTISGL QAEDEADYYC SSYAGRNTFY VFGTGTTVTV QVSPSQPPP 119

SEQ ID NO: 543 moltype = AA length = 123
FEATURE Location/Qualifiers
source 1..123
mol_type = protein
organism = Homo sapiens
SEQUENCE: 543
EIVLTQSPGT LSLSPGERAT LSCRASQSVS SNLAWYAQKP GQAPRLIIYG ASSRASAIPD 60
RFRGSGSGTD FTLTISRLEP EDFAVYYCQQ YDDAPITFGH GTRLEIKRTV AAPSVFIFPP 120
SDE 123

SEQ ID NO: 544 moltype = AA length = 105
FEATURE Location/Qualifiers
source 1..105
mol_type = protein
organism = Homo sapiens
SEQUENCE: 544
DIQMTQSPSS LSASVGDKVT ITCQTSAGYL NWYQQRRGRA PKLLMYDGSR LVTGVPSRFS 60
GRRWGTQYNL TIGSLQPEDI ATYYCQVYEF FGPGTRLDLK STVAA 105

SEQ ID NO: 545 moltype = AA length = 104
FEATURE Location/Qualifiers
source 1..104
mol_type = protein
organism = Homo sapiens
SEQUENCE: 545
DIQMTQSPSS LSARVGDTVT ITCQANGYLN WYQQRRGKAP KLLIYDGSKL ERGVPARFSG 60
RRWGQEYNLT INNLQPEDVA TYFCQVYEFI VPGTRLDLKR TVAA 104

SEQ ID NO: 546 moltype = AA length = 121
FEATURE Location/Qualifiers
source 1..121
mol_type = protein
organism = Homo sapiens
SEQUENCE: 546
DIQMTQSPSS VSASVGDRVT ITCQASRDTD NSLTWYQQKP GRPPKLLIYH VVNLGPGVPS 60
RFSGSASSAT QSTLIISDFQ PDDVATYFCQ NYEFFGPGTK VEIKRTVAAP SVFIFPPSDE 120
Q 121

SEQ ID NO: 547 moltype = AA length = 114
FEATURE Location/Qualifiers
source 1..114
mol_type = protein
organism = Homo sapiens
SEQUENCE: 547
DIQMTQSPSS LSASVGDTVT ITCQANGYLN WYQQRRGKAP KLLIYDGSKL ERGVPSRFSG 60
RRWGQEYNLT INNLQPEDIA TYFCQVYEFV VPGTRLDLKR TVAAPSVFIF PPSD 114

SEQ ID NO: 548 moltype = AA length = 114
FEATURE Location/Qualifiers
source 1..114
mol_type = protein
organism = Homo sapiens
SEQUENCE: 548
DIQMTQSPSS LSASVGDTVT ITCQANGYLN WYQQRRGKAP KLLIYDGSKL ERGVPSRFSG 60
RRWGQEYNLT INNLQPEDIA TYFCQVYEFV VPGTRLDLKR TVAAPSVFIF PPSD 114

```
SEQ ID NO: 549         moltype = AA  length = 114
FEATURE                Location/Qualifiers
source                 1..114
                       mol_type = protein
                       organism = Homo sapiens
SEQUENCE: 549
DIQMTQSPSS LSARVGDTVT FTCQANGYLN WYQQRRGKAP KLLIYDGSKL ERGVPSRFSG  60
RGWGQEYNLT INNLQPEDIA TYFCQVYEFA VPGTRLDLKR TVAAPSVFIF PPSD        114

SEQ ID NO: 550         moltype = AA  length = 114
FEATURE                Location/Qualifiers
source                 1..114
                       mol_type = protein
                       organism = Homo sapiens
SEQUENCE: 550
DIQMTQSPSS LSARVGDTVT ITCQANGYLN WYQQRRGKAP KLLIYDGSKL ETGVPSRFTG  60
RRWGQEYNLT INNLQPEDIA TYFCQVYEFI VPGTRLDLKR TVAAPSVFIF PPSD        114

SEQ ID NO: 551         moltype = AA  length = 114
FEATURE                Location/Qualifiers
source                 1..114
                       mol_type = protein
                       organism = Homo sapiens
SEQUENCE: 551
DIQMTHSPSS LSASVGDTVT ITCQANGYLN WYQQRRGKAP KLLIYDGSKL ETGVPSRFTG  60
RRWGQEYNLT INNLQPEDIA TYFCQVYEFI VPGTRLDLKR TVAAPSVFIF PPSD        114

SEQ ID NO: 552         moltype = AA  length = 114
FEATURE                Location/Qualifiers
source                 1..114
                       mol_type = protein
                       organism = Homo sapiens
SEQUENCE: 552
DIQMTQSPSS LSARVGDTVT ITCQANGYLN WYQQRRGKAP KLLIYDGSKL ETGVPSRFTG  60
RRWGQEYNLT INNLQPEDIA TYFCQVYEFI VPGTRLDLKR TVAAPSVFIF PPSD        114

SEQ ID NO: 553         moltype = AA  length = 121
FEATURE                Location/Qualifiers
source                 1..121
                       mol_type = protein
                       organism = Homo sapiens
SEQUENCE: 553
DIQMTQSPSS LSASVGDRVT ITCQASQGIS NSLNWYQQKP GKAPRLLIYG TSTLQRGVPS  60
RFSGSGSGTR FTVTINSLQP EDIATYFCQH NEFFGRGTKV DIKRTVAAPS VFIFPPSDEQ  120
L                                                                  121

SEQ ID NO: 554         moltype = AA  length = 120
FEATURE                Location/Qualifiers
source                 1..120
                       mol_type = protein
                       organism = Homo sapiens
SEQUENCE: 554
DIQMTQSPSS LSASIGDRVN ITCQASRDTG SALNWYQQKV GRPPRLLISA VSNLGAGVPS  60
RFSGRRSGTQ STLTINTLQP EDIATYFCQH YEFFGPGTKV DIKRTVAAPS VFIFPPSDEQ  120

SEQ ID NO: 555         moltype = AA  length = 114
FEATURE                Location/Qualifiers
source                 1..114
                       mol_type = protein
                       organism = Homo sapiens
SEQUENCE: 555
DIQMTQSPSS LSASVGDTVT FTCQANGYLN WYQQRRGKAP KLLIYDGSRL ERGVPSRFSG  60
RRWGQEYNLT INNLQPEDIA TYFCQVYEFA VPGTRLDLKR TVAAPSVFIF PPSD        114

SEQ ID NO: 556         moltype = AA  length = 115
FEATURE                Location/Qualifiers
source                 1..115
                       mol_type = protein
                       organism = Homo sapiens
SEQUENCE: 556
DIQMTQSPSS LSASVGDTVT ITCQTNKGYL NWYQQRRGRA PKLLMYDGSK LVTGVPSRFS  60
GRRWGTQYNL TIGSLQPEDI ATYYCQVYEF FGPGTRLDLK RTVAAPSVFI FPPSD       115

SEQ ID NO: 557         moltype = AA  length = 115
FEATURE                Location/Qualifiers
source                 1..115
                       mol_type = protein
                       organism = Homo sapiens
```

```
SEQUENCE: 557
DIQMTQSPSS LSARVGDKVT ITYQTSAGYL NWYQQRRGRA PKLLMYDGSR LVTGAPSRFS  60
GRRWGTQYNL TIGSLQPEDI ATYYCQVYEF FGPGTRLDLK RTVAAPSVFI FPPSD       115

SEQ ID NO: 558         moltype = AA  length = 114
FEATURE                Location/Qualifiers
source                 1..114
                       mol_type = protein
                       organism = Homo sapiens
SEQUENCE: 558
DIQMTQSPSS LSASVGDTVT ITCQANGYLN WYQQRRGKAP KLLIYDGSKL ERGVPSRFSG  60
RRWGQEYNLT INNLQPEDIA TYFCQVYEFV VPGTRLDLKR TVAAPSVFIF PPSD        114

SEQ ID NO: 559         moltype = AA  length = 115
FEATURE                Location/Qualifiers
source                 1..115
                       mol_type = protein
                       organism = Homo sapiens
SEQUENCE: 559
DIQMTQSPSS LSASVGDTVT INCQTNKGYL NWYQQRRGRA PKLLMYDGSK LVTGVPSRFS  60
GRRWGTQYNL TIGSLQPEDI ATYYCQVYEF FGPGTRLDLK RTVAAPSVFI FPPSD       115

SEQ ID NO: 560         moltype = AA  length = 115
FEATURE                Location/Qualifiers
source                 1..115
                       mol_type = protein
                       organism = Homo sapiens
SEQUENCE: 560
DIQMTQSPSS LSASVGDTVT ITCHTNKGYL NWYQQRRGRA PKLLMFDGSK LVTGVPSRFS  60
GRRWGTQYNL TIGSLQPEDI ATYYCQVYEV FGPGTRLDLK RTVAAPSVFI FPPSD       115

SEQ ID NO: 561         moltype = AA  length = 115
FEATURE                Location/Qualifiers
source                 1..115
                       mol_type = protein
                       organism = Homo sapiens
SEQUENCE: 561
DIQMTQSPSS LSASVGDTVT ITCQTNKGYL NWYQQRRGRA PKLLMYDGSK LVTGVPSRFS  60
GRRWGTQYNL TIGSLQPEDI ATYYCQVYEF FGPGTRLDLK RTVAAPSVFI FPPSD       115

SEQ ID NO: 562         moltype = AA  length = 115
FEATURE                Location/Qualifiers
source                 1..115
                       mol_type = protein
                       organism = Homo sapiens
SEQUENCE: 562
DIQMTQSPSS LSASVGDTVT ITCQTNKGYL NWYQQRRGRA PKLLMYDGSK LVTGVPSRLS  60
GRRWGTQYNL TIGSLQPEDI ATYYCQVYEF FGPGTRLDLK RTVAAPSVFI FPPSD       115

SEQ ID NO: 563         moltype = AA  length = 115
FEATURE                Location/Qualifiers
source                 1..115
                       mol_type = protein
                       organism = Homo sapiens
SEQUENCE: 563
DIQMTQSPSS LSASVGDTVT ITCQTNKGYL NWYQQKRGRA PKLLMYDGSK LVTGVPSRLS  60
GRRWGTQYNL TIGSLQPEDI ATYYCQVYEF FGPGTRLDLK RTVAAPSVFI FPPSD       115

SEQ ID NO: 564         moltype = AA  length = 115
FEATURE                Location/Qualifiers
source                 1..115
                       mol_type = protein
                       organism = Homo sapiens
SEQUENCE: 564
DIQMTQSPSS LSASVGDTVT ITCQTNKGYL NWYQQRRGRA PKLLMYDGSK LVTGVPSRLS  60
GRRWGTQYNL TIGSLQPEDI ATYYCQVYEF FGPGTRLDLK RTVAAPSVFI FPPSD       115

SEQ ID NO: 565         moltype = AA  length = 115
FEATURE                Location/Qualifiers
source                 1..115
                       mol_type = protein
                       organism = Homo sapiens
SEQUENCE: 565
DIQMTQSPSS LSASVGDTVT ITCQTNKGYL NWYQQRRGRA PKLLMYDGSK LVTGVPSRFS  60
GRRWGTQYNL TIGSLQPEDI ATYYCQVYEF FGPGTRLDLK RTVAAPSVFI FPPSD       115

SEQ ID NO: 566         moltype = AA  length = 115
FEATURE                Location/Qualifiers
source                 1..115
```

```
                        mol_type = protein
                        organism = Homo sapiens
SEQUENCE: 566
DIQMTQSPSS LSASVGDTVT ITCQTNKGYL NWYQQRRGRA PKLLMYDGSK LVTGVPSRLS  60
GRRWGTQYNL TIGSLQPEDI ATYYCQVYEF FGPGTRLDLK RTVAAPSVFI FPPSD      115

SEQ ID NO: 567          moltype = AA  length = 114
FEATURE                 Location/Qualifiers
source                  1..114
                        mol_type = protein
                        organism = Homo sapiens
SEQUENCE: 567
DIQMTQSPSS LSASVGDTVT ITCQANGYLN WYQQRRGKAP KLLIYDGSKL ERGVPSRFSG  60
RRWGQEYNLT INNLQAEDIA TYFCQVYEFA VPGTRLDLKR TVAAPSVFIF PPSD       114

SEQ ID NO: 568          moltype = AA  length = 115
FEATURE                 Location/Qualifiers
source                  1..115
                        mol_type = protein
                        organism = Homo sapiens
SEQUENCE: 568
DIQMTQSPSS LSARVGDKVT ITCQTSAGYL NWYQQRRGRA PKLLMYDGSR LVTGVPSRFS  60
GRRWGTQYNL TIGSLQPEDI ATYYCQVYEF FGPGTRLDLK RTVAAPSVFI FPPSD      115

SEQ ID NO: 569          moltype = AA  length = 114
FEATURE                 Location/Qualifiers
source                  1..114
                        mol_type = protein
                        organism = Homo sapiens
SEQUENCE: 569
DIQMTQSPSS LSASVGDTVT ITCQANGYLN WYQQRRGKAP KLLMYDGSTL ERGVPARFSG  60
RRWGQEYNLT INNLQPEDVA TYFCQVYEFI VPGTRLDLKR TVAAPSVFIF PPSD       114

SEQ ID NO: 570          moltype = AA  length = 115
FEATURE                 Location/Qualifiers
source                  1..115
                        mol_type = protein
                        organism = Homo sapiens
SEQUENCE: 570
DIQMTQSPSS LSASVGDTVT ITCQTNKGYL NWYQQRRGRA PKLLMCDGSK LVTGVPSRFS  60
GRRWGTQYNL TIGSLQPEDI ATYYCQVYEF FGPGTRLDLK RTVAAPSVFI FPPSD      115

SEQ ID NO: 571          moltype = AA  length = 115
FEATURE                 Location/Qualifiers
source                  1..115
                        mol_type = protein
                        organism = Homo sapiens
SEQUENCE: 571
DIQMTQSPSS LSASVGDTVT ITCQTTKGYL NWYQQRRGRA PKLLMFDGSK LVTGVPSRFS  60
GRRWGTQYNL TIGSLQPEDL ATYYCQVYEF FGPGTRLDLK RTVAAPSVFI FPPSD      115

SEQ ID NO: 572          moltype = AA  length = 115
FEATURE                 Location/Qualifiers
source                  1..115
                        mol_type = protein
                        organism = Homo sapiens
SEQUENCE: 572
DIQMTQSPSS LSASVGDTVT ITCHTNKGYL NWYQQRRGRA PKLLMFDGSK LVTGVPSRFS  60
GRRWGTQYNL TIGSLQPEDI ATYYCQVYEV FGPGTRLDLK RTVAAPSVFI FPPSD      115

SEQ ID NO: 573          moltype = AA  length = 114
FEATURE                 Location/Qualifiers
source                  1..114
                        mol_type = protein
                        organism = Homo sapiens
SEQUENCE: 573
DIQMTQSPSS LSARVGDTVT ITCQANGYLN WYQQRRGKAP KLLIYDGSKL ETGVPSRFTG  60
RRWGQEYNLT INNLQPEDIA TYFCQVYEFI VPGTRLDLKR TVAAPSVFIF PPSD       114

SEQ ID NO: 574          moltype = AA  length = 114
FEATURE                 Location/Qualifiers
source                  1..114
                        mol_type = protein
                        organism = Homo sapiens
SEQUENCE: 574
DIQMTQSPSS LSARVGDTVT FTCQANGYLN WYQQRRGKAP KLLIYDGSKL ERGVPSRFSG  60
RRWGQEYNLT INNLQPEDIA TYFCQVYEFA VPGTRLDLKR TVAAPSVFIF PPSD       114

SEQ ID NO: 575          moltype = AA  length = 115
```

```
FEATURE                Location/Qualifiers
source                 1..115
                       mol_type = protein
                       organism = Homo sapiens
SEQUENCE: 575
DIQMTQSPSS LSASVGDTVT ITCQTNKGYL NWYQQRRGRA PKLLMYDGSK LVTGVPSRLS  60
GRRWGTQYNL TIGSLQPEDI ATYYCQVYEF FGPGTRLDLK RTVAAPSVFI FPPSD       115

SEQ ID NO: 576         moltype = AA  length = 114
FEATURE                Location/Qualifiers
source                 1..114
                       mol_type = protein
                       organism = Homo sapiens
SEQUENCE: 576
DIQMTQSPSS LSARVGDTVT ITCQANGYLN WYQQRRGKAP KLLIYDGSKL ERGVPSRFSG  60
RRWGQEYNLT INNLQPEDIA TYFCQVYEFV VPGTRLDLKR TVAAPSVFIF PPSD        114

SEQ ID NO: 577         moltype = AA  length = 113
FEATURE                Location/Qualifiers
source                 1..113
                       mol_type = protein
                       organism = Homo sapiens
SEQUENCE: 577
DIQMTQSPSS LSARVGDTVT FTCQANGYLN WYQQRRGKAP KLLIYDGSKL ERGVPSRFSG  60
RRWGQEYNLT INNLQPEDIA TYFCQVYEFA VPGTRLDLKR TVAAPSVFIF PSD         113

SEQ ID NO: 578         moltype = AA  length = 108
FEATURE                Location/Qualifiers
source                 1..108
                       mol_type = protein
                       organism = Homo sapiens
SEQUENCE: 578
DIQMTQSPSS LSASVGDTVT INCQTNKGYL NWYQQRRGRA PKLLMYDGSK LVTGVPSRFS  60
GRRWGTQYNL TIGSLQPEDI ATYYCQVYEF FGPGTRLDLK RTVAAPSD               108

SEQ ID NO: 579         moltype = AA  length = 115
FEATURE                Location/Qualifiers
source                 1..115
                       mol_type = protein
                       organism = Homo sapiens
SEQUENCE: 579
DIQMTQSPSS LSASVGDTVT INCQTNKGYL NWYQQRRGRA PKLLMYDGSK LVTGVPSRFS  60
GRRWGTQYNL TIGSLQPEDI ATYYCQVYEF FGPGTRLDLK RTVAAPSVFI FPPSD       115

SEQ ID NO: 580         moltype = AA  length = 114
FEATURE                Location/Qualifiers
source                 1..114
                       mol_type = protein
                       organism = Homo sapiens
SEQUENCE: 580
DIQMTQSPSS LSARVGDTVT ITCQANGYLN WYQQRRGKAP KLLIYDGSKL ERGVPSRFSG  60
RRWGQEYNLT INNLQPEDIA TYFCQVYEFV VPGTRLDLKR TVAAPSVFIF PPSD        114

SEQ ID NO: 581         moltype = AA  length = 115
FEATURE                Location/Qualifiers
source                 1..115
                       mol_type = protein
                       organism = Homo sapiens
SEQUENCE: 581
DIQMTQSPSS LSASVGDKVT ITCQTSAGYL NWYQQRRGRA PKLLMYDGSR LVTGVPSRFS  60
GRRWGTQYNL TIGSLQPEDV ATYYCQVYEF FGPGTRLDLK RTVAAPSVFI FPPSD       115

SEQ ID NO: 582         moltype = AA  length = 114
FEATURE                Location/Qualifiers
source                 1..114
                       mol_type = protein
                       organism = Homo sapiens
SEQUENCE: 582
DIQMTQSPSS LSARVGDTVT ITCQANGYLN WYQQRRGKAP KLLIYDGSKL ERGVPSRFSG  60
RRWGQEYNLT INNLQPEDIA TYFCQVYEFA VPGTRLDLKR TVAAPSVFIF PPSD        114

SEQ ID NO: 583         moltype = AA  length = 114
FEATURE                Location/Qualifiers
source                 1..114
                       mol_type = protein
                       organism = Homo sapiens
SEQUENCE: 583
DIQMTQSPSS LSASVGDTVT ITCQANGYLN WYQQRRGKAP KLLIYDGSKL ERGVPSRFSG  60
RRWGQEYNLT INNLQPEDIA TYFCQVYEFI VPGTRLDLKR TVAAPSVFIF PPSD        114
```

```
SEQ ID NO: 584          moltype = DNA  length = 36
FEATURE                 Location/Qualifiers
misc_feature            1..36
                        note = Description of Artificial Sequence: Synthetic
                         forward primer
source                  1..36
                        mol_type = other DNA
                        organism = synthetic construct
SEQUENCE: 584
ctgcaaccgg tgtacattct caagtgcaac tggtgc                             36

SEQ ID NO: 585          moltype = DNA  length = 38
FEATURE                 Location/Qualifiers
misc_feature            1..38
                        note = Description of Artificial Sequence: Synthetic
                         forward primer
source                  1..38
                        mol_type = other DNA
                        organism = synthetic construct
SEQUENCE: 585
ctgcaaccgg tgtacattct caggtccatt tgtcacag                           38

SEQ ID NO: 586          moltype = DNA  length = 33
FEATURE                 Location/Qualifiers
misc_feature            1..33
                        note = Description of Artificial Sequence: Synthetic
                         reverse primer
source                  1..33
                        mol_type = other DNA
                        organism = synthetic construct
SEQUENCE: 586
tgcgaagtcg acgctgacga gacagtgacc tgc                                33

SEQ ID NO: 587          moltype = DNA  length = 32
FEATURE                 Location/Qualifiers
misc_feature            1..32
                        note = Description of Artificial Sequence: Synthetic
                         reverse primer
source                  1..32
                        mol_type = other DNA
                        organism = synthetic construct
SEQUENCE: 587
tgcgaagtcg acgctgaaga gacaataatt tg                                 32

SEQ ID NO: 588          moltype = DNA  length = 30
FEATURE                 Location/Qualifiers
misc_feature            1..30
                        note = Description of Artificial Sequence: Synthetic
                         reverse primer
source                  1..30
                        mol_type = other DNA
                        organism = synthetic construct
SEQUENCE: 588
tgcgaagtcg acgctgacga gacaataact                                    30

SEQ ID NO: 589          moltype = DNA  length = 35
FEATURE                 Location/Qualifiers
misc_feature            1..35
                        note = Description of Artificial Sequence: Synthetic
                         forward primer
source                  1..35
                        mol_type = other DNA
                        organism = synthetic construct
SEQUENCE: 589
ctgcaaccgg tgtacatttt caggggcact tggtg                              35

SEQ ID NO: 590          moltype = DNA  length = 33
FEATURE                 Location/Qualifiers
misc_feature            1..33
                        note = Description of Artificial Sequence: Synthetic
                         reverse primer
source                  1..33
                        mol_type = other DNA
                        organism = synthetic construct
SEQUENCE: 590
tgcgaagtcg acgctgaggt gacgatgacc gtg                                33

SEQ ID NO: 591          moltype = DNA  length = 20
```

```
FEATURE                Location/Qualifiers
misc_feature           1..20
                       note = Description of Artificial Sequence: Synthetic
                        forward leader primer
source                 1..20
                       mol_type = other DNA
                       organism = synthetic construct
SEQUENCE: 591
atggactgga cctggaggat                                              20

SEQ ID NO: 592         moltype = DNA  length = 20
FEATURE                Location/Qualifiers
misc_feature           1..20
                       note = Description of Artificial Sequence: Synthetic
                        forward leader primer
source                 1..20
                       mol_type = other DNA
                       organism = synthetic construct
SEQUENCE: 592
atggactgga cctggagcat                                              20

SEQ ID NO: 593         moltype = DNA  length = 20
FEATURE                Location/Qualifiers
misc_feature           1..20
                       note = Description of Artificial Sequence: Synthetic
                        forward leader primer
source                 1..20
                       mol_type = other DNA
                       organism = synthetic construct
SEQUENCE: 593
atggactgga cctggacaat                                              20

SEQ ID NO: 594         moltype = DNA  length = 20
FEATURE                Location/Qualifiers
misc_feature           1..20
                       note = Description of Artificial Sequence: Synthetic
                        forward leader primer
source                 1..20
                       mol_type = other DNA
                       organism = synthetic construct
SEQUENCE: 594
ggccttctct ttgtggtggc                                              20

SEQ ID NO: 595         moltype = DNA  length = 20
FEATURE                Location/Qualifiers
misc_feature           1..20
                       note = Description of Artificial Sequence: Synthetic
                        forward leader primer
source                 1..20
                       mol_type = other DNA
                       organism = synthetic construct
SEQUENCE: 595
atggactgga cctggagggt                                              20

SEQ ID NO: 596         moltype = DNA  length = 20
FEATURE                Location/Qualifiers
misc_feature           1..20
                       note = Description of Artificial Sequence: Synthetic
                        forward leader primer
source                 1..20
                       mol_type = other DNA
                       organism = synthetic construct
SEQUENCE: 596
atggactgga tttggaggat                                              20

SEQ ID NO: 597         moltype = DNA  length = 22
FEATURE                Location/Qualifiers
misc_feature           1..22
                       note = Description of Artificial Sequence: Synthetic
                        forward leader primer
source                 1..22
                       mol_type = other DNA
                       organism = synthetic construct
SEQUENCE: 597
aggttcctct ttgtggtggc ag                                           22

SEQ ID NO: 598         moltype = DNA  length = 17
FEATURE                Location/Qualifiers
misc_feature           1..17
```

```
                        note = Description of Artificial Sequence: Synthetic
                         forward leader primer
source                  1..17
                        mol_type = other DNA
                        organism = synthetic construct
SEQUENCE: 598
taaaaggtgt ccagtgt                                                17

SEQ ID NO: 599          moltype = DNA  length = 17
FEATURE                 Location/Qualifiers
misc_feature            1..17
                        note = Description of Artificial Sequence: Synthetic
                         forward leader primer
source                  1..17
                        mol_type = other DNA
                        organism = synthetic construct
SEQUENCE: 599
taagaggtgt ccagtgt                                                17

SEQ ID NO: 600          moltype = DNA  length = 17
FEATURE                 Location/Qualifiers
misc_feature            1..17
                        note = Description of Artificial Sequence: Synthetic
                         forward leader primer
source                  1..17
                        mol_type = other DNA
                        organism = synthetic construct
SEQUENCE: 600
tagaaggtgt ccagtgt                                                17

SEQ ID NO: 601          moltype = DNA  length = 24
FEATURE                 Location/Qualifiers
misc_feature            1..24
                        note = Description of Artificial Sequence: Synthetic
                         forward leader primer
source                  1..24
                        mol_type = other DNA
                        organism = synthetic construct
SEQUENCE: 601
gctattttta aaggtgtcca gtgt                                        24

SEQ ID NO: 602          moltype = DNA  length = 17
FEATURE                 Location/Qualifiers
misc_feature            1..17
                        note = Description of Artificial Sequence: Synthetic
                         forward leader primer
source                  1..17
                        mol_type = other DNA
                        organism = synthetic construct
SEQUENCE: 602
tacaaggtgt ccagtgt                                                17

SEQ ID NO: 603          moltype = DNA  length = 17
FEATURE                 Location/Qualifiers
misc_feature            1..17
                        note = Description of Artificial Sequence: Synthetic
                         forward leader primer
source                  1..17
                        mol_type = other DNA
                        organism = synthetic construct
SEQUENCE: 603
ttaaagctgt ccagtgt                                                17

SEQ ID NO: 604          moltype = DNA  length = 22
FEATURE                 Location/Qualifiers
misc_feature            1..22
                        note = Description of Artificial Sequence: Synthetic
                         forward leader primer
source                  1..22
                        mol_type = other DNA
                        organism = synthetic construct
SEQUENCE: 604
atgaaacacc tgtggttctt cc                                          22

SEQ ID NO: 605          moltype = DNA  length = 18
FEATURE                 Location/Qualifiers
misc_feature            1..18
                        note = Description of Artificial Sequence: Synthetic
                         forward leader primer
```

```
source                  1..18
                        mol_type = other DNA
                        organism = synthetic construct
SEQUENCE: 605
atgaaacacc tgtttctt                                              18

SEQ ID NO: 606          moltype = DNA  length = 20
FEATURE                 Location/Qualifiers
misc_feature            1..20
                        note = Description of Artificial Sequence: Synthetic
                         forward leader primer
source                  1..20
                        mol_type = other DNA
                        organism = synthetic construct
SEQUENCE: 606
atgaagcacc tgtggttctt                                            20

SEQ ID NO: 607          moltype = DNA  length = 20
FEATURE                 Location/Qualifiers
misc_feature            1..20
                        note = Description of Artificial Sequence: Synthetic
                         forward leader primer
source                  1..20
                        mol_type = other DNA
                        organism = synthetic construct
SEQUENCE: 607
atgaaacatc tgtggttctt                                            20

SEQ ID NO: 608          moltype = DNA  length = 17
FEATURE                 Location/Qualifiers
misc_feature            1..17
                        note = Description of Artificial Sequence: Synthetic
                         forward leader primer
source                  1..17
                        mol_type = other DNA
                        organism = synthetic construct
SEQUENCE: 608
ttctccaagg agtctgt                                               17

SEQ ID NO: 609          moltype = DNA  length = 19
FEATURE                 Location/Qualifiers
misc_feature            1..19
                        note = Description of Artificial Sequence: Synthetic
                         forward leader primer
source                  1..19
                        mol_type = other DNA
                        organism = synthetic construct
SEQUENCE: 609
cctccacagt gagagtctg                                             19

SEQ ID NO: 610          moltype = DNA  length = 21
FEATURE                 Location/Qualifiers
misc_feature            1..21
                        note = Description of Artificial Sequence: Synthetic
                         forward leader primer
source                  1..21
                        mol_type = other DNA
                        organism = synthetic construct
SEQUENCE: 610
atgtctgtct ccttcctcat c                                          21

SEQ ID NO: 611          moltype = DNA  length = 21
FEATURE                 Location/Qualifiers
misc_feature            1..21
                        note = Description of Artificial Sequence: Synthetic
                         forward leader primer
source                  1..21
                        mol_type = other DNA
                        organism = synthetic construct
SEQUENCE: 611
ggcagcagca acaggtgccc a                                          21

SEQ ID NO: 612          moltype = DNA  length = 23
FEATURE                 Location/Qualifiers
misc_feature            1..23
                        note = Description of Artificial Sequence: Synthetic
                         reverse constant region primer
source                  1..23
                        mol_type = other DNA
```

```
                        organism = synthetic construct
SEQUENCE: 612
ggaaggtgtg cacgccgctg gtc                                          23

SEQ ID NO: 613          moltype = DNA  length = 22
FEATURE                 Location/Qualifiers
misc_feature            1..22
                        note = Description of Artificial Sequence: Synthetic
                         reverse constant region primer
source                  1..22
                        mol_type = other DNA
                        organism = synthetic construct
SEQUENCE: 613
gttcggggaa gtagtccttg ac                                           22

SEQ ID NO: 614          moltype = AA  length = 10
FEATURE                 Location/Qualifiers
source                  1..10
                        mol_type = protein
                        organism = Homo sapiens
SEQUENCE: 614
RHSDYCDFDV                                                         10

SEQ ID NO: 615          moltype = AA  length = 10
FEATURE                 Location/Qualifiers
source                  1..10
                        mol_type = protein
                        organism = Homo sapiens
SEQUENCE: 615
QRSDFWDFDV                                                         10

SEQ ID NO: 616          moltype = AA  length = 10
FEATURE                 Location/Qualifiers
source                  1..10
                        mol_type = protein
                        organism = Homo sapiens
SEQUENCE: 616
RHSDYCDFDV                                                         10

SEQ ID NO: 617          moltype = AA  length = 10
FEATURE                 Location/Qualifiers
source                  1..10
                        mol_type = protein
                        organism = Homo sapiens
SEQUENCE: 617
RHSDYCDFDV                                                         10

SEQ ID NO: 618          moltype = AA  length = 10
FEATURE                 Location/Qualifiers
source                  1..10
                        mol_type = protein
                        organism = Homo sapiens
SEQUENCE: 618
RHSDYCDFDI                                                         10

SEQ ID NO: 619          moltype = AA  length = 10
FEATURE                 Location/Qualifiers
source                  1..10
                        mol_type = protein
                        organism = Homo sapiens
SEQUENCE: 619
QRSDYWDFDV                                                         10

SEQ ID NO: 620          moltype = AA  length = 10
FEATURE                 Location/Qualifiers
source                  1..10
                        mol_type = protein
                        organism = Homo sapiens
SEQUENCE: 620
QRSDYWDFDV                                                         10

SEQ ID NO: 621          moltype = AA  length = 10
FEATURE                 Location/Qualifiers
source                  1..10
                        mol_type = protein
                        organism = Homo sapiens
SEQUENCE: 621
RHTDYCDFDV                                                         10
```

```
SEQ ID NO: 622          moltype = AA  length = 10
FEATURE                 Location/Qualifiers
source                  1..10
                        mol_type = protein
                        organism = Homo sapiens
SEQUENCE: 622
RHSDYCDFDV                                                            10

SEQ ID NO: 623          moltype = AA  length = 10
FEATURE                 Location/Qualifiers
source                  1..10
                        mol_type = protein
                        organism = Homo sapiens
SEQUENCE: 623
QRSDYWDFDV                                                            10

SEQ ID NO: 624          moltype = AA  length = 10
FEATURE                 Location/Qualifiers
source                  1..10
                        mol_type = protein
                        organism = Homo sapiens
SEQUENCE: 624
RHSDYCDFDV                                                            10

SEQ ID NO: 625          moltype = AA  length = 10
FEATURE                 Location/Qualifiers
source                  1..10
                        mol_type = protein
                        organism = Homo sapiens
SEQUENCE: 625
RHSDYCDFDI                                                            10

SEQ ID NO: 626          moltype = AA  length = 10
FEATURE                 Location/Qualifiers
source                  1..10
                        mol_type = protein
                        organism = Homo sapiens
SEQUENCE: 626
RRSDYCDFDV                                                            10

SEQ ID NO: 627          moltype = AA  length = 10
FEATURE                 Location/Qualifiers
source                  1..10
                        mol_type = protein
                        organism = Homo sapiens
SEQUENCE: 627
QRSDYWDFDV                                                            10

SEQ ID NO: 628          moltype = AA  length = 10
FEATURE                 Location/Qualifiers
source                  1..10
                        mol_type = protein
                        organism = Homo sapiens
SEQUENCE: 628
QRSDYWDFDV                                                            10

SEQ ID NO: 629          moltype = AA  length = 10
FEATURE                 Location/Qualifiers
source                  1..10
                        mol_type = protein
                        organism = Homo sapiens
SEQUENCE: 629
RHSDYCDFDV                                                            10

SEQ ID NO: 630          moltype = AA  length = 10
FEATURE                 Location/Qualifiers
source                  1..10
                        mol_type = protein
                        organism = Homo sapiens
SEQUENCE: 630
RHSDYCDFDI                                                            10

SEQ ID NO: 631          moltype = AA  length = 10
FEATURE                 Location/Qualifiers
source                  1..10
                        mol_type = protein
                        organism = Homo sapiens
SEQUENCE: 631
QRSDYWDFDV                                                            10
```

```
SEQ ID NO: 632          moltype = AA  length = 10
FEATURE                 Location/Qualifiers
source                  1..10
                        mol_type = protein
                        organism = Homo sapiens
SEQUENCE: 632
RHSDYCDFDV                                                                 10

SEQ ID NO: 633          moltype = AA  length = 10
FEATURE                 Location/Qualifiers
source                  1..10
                        mol_type = protein
                        organism = Homo sapiens
SEQUENCE: 633
RHSDYCDFDV                                                                 10

SEQ ID NO: 634          moltype = AA  length = 10
FEATURE                 Location/Qualifiers
source                  1..10
                        mol_type = protein
                        organism = Homo sapiens
SEQUENCE: 634
RHSDYCDLDV                                                                 10

SEQ ID NO: 635          moltype = AA  length = 10
FEATURE                 Location/Qualifiers
source                  1..10
                        mol_type = protein
                        organism = Homo sapiens
SEQUENCE: 635
RHSDYCDFDV                                                                 10

SEQ ID NO: 636          moltype = AA  length = 10
FEATURE                 Location/Qualifiers
source                  1..10
                        mol_type = protein
                        organism = Homo sapiens
SEQUENCE: 636
RHSDYCDFDV                                                                 10

SEQ ID NO: 637          moltype = AA  length = 10
FEATURE                 Location/Qualifiers
source                  1..10
                        mol_type = protein
                        organism = Homo sapiens
SEQUENCE: 637
QRSDYWDFDV                                                                 10

SEQ ID NO: 638          moltype = AA  length = 10
FEATURE                 Location/Qualifiers
source                  1..10
                        mol_type = protein
                        organism = Homo sapiens
SEQUENCE: 638
QRSDYWDFDV                                                                 10

SEQ ID NO: 639          moltype = AA  length = 12
FEATURE                 Location/Qualifiers
source                  1..12
                        mol_type = protein
                        organism = Homo sapiens
SEQUENCE: 639
PLRGGDTWHY HS                                                              12

SEQ ID NO: 640          moltype = AA  length = 12
FEATURE                 Location/Qualifiers
source                  1..12
                        mol_type = protein
                        organism = Homo sapiens
SEQUENCE: 640
PLRGGDTWHY HS                                                              12

SEQ ID NO: 641          moltype = AA  length = 12
FEATURE                 Location/Qualifiers
source                  1..12
                        mol_type = protein
                        organism = Homo sapiens
SEQUENCE: 641
```

```
PHSPDDAWSL DV                                                         12

SEQ ID NO: 642          moltype = AA  length = 12
FEATURE                 Location/Qualifiers
source                  1..12
                        mol_type = protein
                        organism = Homo sapiens
SEQUENCE: 642
PHSPDDAWSL DV                                                         12

SEQ ID NO: 643          moltype = AA  length = 12
FEATURE                 Location/Qualifiers
source                  1..12
                        mol_type = protein
                        organism = Homo sapiens
SEQUENCE: 643
PHSPDDAWSL DV                                                         12

SEQ ID NO: 644          moltype = AA  length = 12
FEATURE                 Location/Qualifiers
source                  1..12
                        mol_type = protein
                        organism = Homo sapiens
SEQUENCE: 644
PRGGRDNWSF HV                                                         12

SEQ ID NO: 645          moltype = AA  length = 12
FEATURE                 Location/Qualifiers
source                  1..12
                        mol_type = protein
                        organism = Homo sapiens
SEQUENCE: 645
PKSGRDYWSF DL                                                         12

SEQ ID NO: 646          moltype = AA  length = 14
FEATURE                 Location/Qualifiers
source                  1..14
                        mol_type = protein
                        organism = Homo sapiens
SEQUENCE: 646
ATGYSYGYLD AFDI                                                       14

SEQ ID NO: 647          moltype = AA  length = 14
FEATURE                 Location/Qualifiers
source                  1..14
                        mol_type = protein
                        organism = Homo sapiens
SEQUENCE: 647
EPREMGTLTA GFEY                                                       14

SEQ ID NO: 648          moltype = AA  length = 20
FEATURE                 Location/Qualifiers
source                  1..20
                        mol_type = protein
                        organism = Homo sapiens
SEQUENCE: 648
GQTDLNDDLW SDYSTPGFDY                                                 20

SEQ ID NO: 649          moltype = AA  length = 20
FEATURE                 Location/Qualifiers
source                  1..20
                        mol_type = protein
                        organism = Homo sapiens
SEQUENCE: 649
GQTDLNDDFW SEYSTPGFDY                                                 20

SEQ ID NO: 650          moltype = AA  length = 20
FEATURE                 Location/Qualifiers
source                  1..20
                        mol_type = protein
                        organism = Homo sapiens
SEQUENCE: 650
GEFDSSGFDY ESWYPYYMDV                                                 20

SEQ ID NO: 651          moltype = AA  length = 15
FEATURE                 Location/Qualifiers
source                  1..15
                        mol_type = protein
                        organism = Homo sapiens
```

-continued

```
SEQUENCE: 651
APRLELGELS SGFHY                                                       15

SEQ ID NO: 652          moltype = AA  length = 15
FEATURE                 Location/Qualifiers
source                  1..15
                        mol_type = protein
                        organism = Homo sapiens
SEQUENCE: 652
APRLDLGELS SGFHF                                                       15

SEQ ID NO: 653          moltype = AA  length = 15
FEATURE                 Location/Qualifiers
source                  1..15
                        mol_type = protein
                        organism = Homo sapiens
SEQUENCE: 653
APRLDLGELS SGFHF                                                       15

SEQ ID NO: 654          moltype = AA  length = 16
FEATURE                 Location/Qualifiers
source                  1..16
                        mol_type = protein
                        organism = Homo sapiens
SEQUENCE: 654
DNPLLQSGEF SSSLDN                                                      16

SEQ ID NO: 655          moltype = AA  length = 16
FEATURE                 Location/Qualifiers
source                  1..16
                        mol_type = protein
                        organism = Homo sapiens
SEQUENCE: 655
DNPLLQSGEF SSSLEN                                                      16

SEQ ID NO: 656          moltype = AA  length = 13
FEATURE                 Location/Qualifiers
source                  1..13
                        mol_type = protein
                        organism = Homo sapiens
SEQUENCE: 656
AQGDILTEGY FDY                                                         13

SEQ ID NO: 657          moltype = AA  length = 5
FEATURE                 Location/Qualifiers
source                  1..5
                        mol_type = protein
                        organism = Homo sapiens
SEQUENCE: 657
QVYEF                                                                  5

SEQ ID NO: 658          moltype = AA  length = 5
FEATURE                 Location/Qualifiers
source                  1..5
                        mol_type = protein
                        organism = Homo sapiens
SEQUENCE: 658
QVYEF                                                                  5

SEQ ID NO: 659          moltype = AA  length = 5
FEATURE                 Location/Qualifiers
source                  1..5
                        mol_type = protein
                        organism = Homo sapiens
SEQUENCE: 659
QVYEF                                                                  5

SEQ ID NO: 660          moltype = AA  length = 5
FEATURE                 Location/Qualifiers
source                  1..5
                        mol_type = protein
                        organism = Homo sapiens
SEQUENCE: 660
QVYEV                                                                  5

SEQ ID NO: 661          moltype = AA  length = 5
FEATURE                 Location/Qualifiers
source                  1..5
                        mol_type = protein
```

```
                        organism = Homo sapiens
SEQUENCE: 661
QVYEF                                                                5

SEQ ID NO: 662          moltype = AA  length = 5
FEATURE                 Location/Qualifiers
source                  1..5
                        mol_type = protein
                        organism = Homo sapiens
SEQUENCE: 662
QVYEF                                                                5

SEQ ID NO: 663          moltype = AA  length = 5
FEATURE                 Location/Qualifiers
source                  1..5
                        mol_type = protein
                        organism = Homo sapiens
SEQUENCE: 663
QVYEF                                                                5

SEQ ID NO: 664          moltype = AA  length = 5
FEATURE                 Location/Qualifiers
source                  1..5
                        mol_type = protein
                        organism = Homo sapiens
SEQUENCE: 664
QVYEF                                                                5

SEQ ID NO: 665          moltype = AA  length = 5
FEATURE                 Location/Qualifiers
source                  1..5
                        mol_type = protein
                        organism = Homo sapiens
SEQUENCE: 665
QVYEF                                                                5

SEQ ID NO: 666          moltype = AA  length = 5
FEATURE                 Location/Qualifiers
source                  1..5
                        mol_type = protein
                        organism = Homo sapiens
SEQUENCE: 666
QVYEF                                                                5

SEQ ID NO: 667          moltype = AA  length = 5
FEATURE                 Location/Qualifiers
source                  1..5
                        mol_type = protein
                        organism = Homo sapiens
SEQUENCE: 667
QVYEF                                                                5

SEQ ID NO: 668          moltype = AA  length = 5
FEATURE                 Location/Qualifiers
source                  1..5
                        mol_type = protein
                        organism = Homo sapiens
SEQUENCE: 668
QVYEF                                                                5

SEQ ID NO: 669          moltype = AA  length = 5
FEATURE                 Location/Qualifiers
source                  1..5
                        mol_type = protein
                        organism = Homo sapiens
SEQUENCE: 669
QVYEF                                                                5

SEQ ID NO: 670          moltype = AA  length = 5
FEATURE                 Location/Qualifiers
source                  1..5
                        mol_type = protein
                        organism = Homo sapiens
SEQUENCE: 670
QVYEF                                                                5

SEQ ID NO: 671          moltype = AA  length = 5
FEATURE                 Location/Qualifiers
source                  1..5
```

```
                        mol_type = protein
                        organism = Homo sapiens
SEQUENCE: 671
QVYEF                                                                    5

SEQ ID NO: 672          moltype = AA  length = 5
FEATURE                 Location/Qualifiers
source                  1..5
                        mol_type = protein
                        organism = Homo sapiens
SEQUENCE: 672
QVYEF                                                                    5

SEQ ID NO: 673          moltype = AA  length = 5
FEATURE                 Location/Qualifiers
source                  1..5
                        mol_type = protein
                        organism = Homo sapiens
SEQUENCE: 673
QVYEF                                                                    5

SEQ ID NO: 674          moltype = AA  length = 5
FEATURE                 Location/Qualifiers
source                  1..5
                        mol_type = protein
                        organism = Homo sapiens
SEQUENCE: 674
QVYEF                                                                    5

SEQ ID NO: 675          moltype = AA  length = 5
FEATURE                 Location/Qualifiers
source                  1..5
                        mol_type = protein
                        organism = Homo sapiens
SEQUENCE: 675
QVYEV                                                                    5

SEQ ID NO: 676          moltype = AA  length = 5
FEATURE                 Location/Qualifiers
source                  1..5
                        mol_type = protein
                        organism = Homo sapiens
SEQUENCE: 676
QVYEF                                                                    5

SEQ ID NO: 677          moltype = AA  length = 5
FEATURE                 Location/Qualifiers
source                  1..5
                        mol_type = protein
                        organism = Homo sapiens
SEQUENCE: 677
QVYEF                                                                    5

SEQ ID NO: 678          moltype = AA  length = 5
FEATURE                 Location/Qualifiers
source                  1..5
                        mol_type = protein
                        organism = Homo sapiens
SEQUENCE: 678
QVYEF                                                                    5

SEQ ID NO: 679          moltype = AA  length = 5
FEATURE                 Location/Qualifiers
source                  1..5
                        mol_type = protein
                        organism = Homo sapiens
SEQUENCE: 679
QVYEF                                                                    5

SEQ ID NO: 680          moltype = AA  length = 5
FEATURE                 Location/Qualifiers
source                  1..5
                        mol_type = protein
                        organism = Homo sapiens
SEQUENCE: 680
QVYEF                                                                    5

SEQ ID NO: 681          moltype = AA  length = 5
FEATURE                 Location/Qualifiers
```

```
source                  1..5
                        mol_type = protein
                        organism = Homo sapiens
SEQUENCE: 681
QHYEF                                                                     5

SEQ ID NO: 682          moltype = AA  length = 5
FEATURE                 Location/Qualifiers
source                  1..5
                        mol_type = protein
                        organism = Homo sapiens
SEQUENCE: 682
QHYEF                                                                     5

SEQ ID NO: 683          moltype = AA  length = 5
FEATURE                 Location/Qualifiers
source                  1..5
                        mol_type = protein
                        organism = Homo sapiens
SEQUENCE: 683
QHYEF                                                                     5

SEQ ID NO: 684          moltype = AA  length = 5
FEATURE                 Location/Qualifiers
source                  1..5
                        mol_type = protein
                        organism = Homo sapiens
SEQUENCE: 684
QQYEF                                                                     5

SEQ ID NO: 685          moltype = AA  length = 9
FEATURE                 Location/Qualifiers
source                  1..9
                        mol_type = protein
                        organism = Homo sapiens
SEQUENCE: 685
AAWDDTLYV                                                                 9

SEQ ID NO: 686          moltype = AA  length = 11
FEATURE                 Location/Qualifiers
source                  1..11
                        mol_type = protein
                        organism = Homo sapiens
SEQUENCE: 686
QHRSIWPLMC T                                                              11

SEQ ID NO: 687          moltype = AA  length = 9
FEATURE                 Location/Qualifiers
source                  1..9
                        mol_type = protein
                        organism = Homo sapiens
SEQUENCE: 687
GAWDDTLYV                                                                 9

SEQ ID NO: 688          moltype = AA  length = 16
FEATURE                 Location/Qualifiers
source                  1..16
                        mol_type = protein
                        organism = Homo sapiens
SEQUENCE: 688
AEAESQSHSR PIMFDF                                                         16

SEQ ID NO: 689          moltype = AA  length = 16
FEATURE                 Location/Qualifiers
source                  1..16
                        mol_type = protein
                        organism = Homo sapiens
SEQUENCE: 689
AEAESQSHSR PIMFDS                                                         16

SEQ ID NO: 690          moltype = AA  length = 19
FEATURE                 Location/Qualifiers
source                  1..19
                        mol_type = protein
                        organism = Homo sapiens
SEQUENCE: 690
QDSDFHDGHG HTLRGMFDS                                                      19

SEQ ID NO: 691          moltype = AA  length = 14
```

```
FEATURE                Location/Qualifiers
source                 1..14
                       mol_type = protein
                       organism = Homo sapiens
SEQUENCE: 691
NEPQYHSLPG MFDY                                                  14

SEQ ID NO: 692         moltype = AA  length = 19
FEATURE                Location/Qualifiers
source                 1..19
                       mol_type = protein
                       organism = Homo sapiens
SEQUENCE: 692
NEPQYHDGNG HSLPGMFDY                                             19

SEQ ID NO: 693         moltype = AA  length = 19
FEATURE                Location/Qualifiers
source                 1..19
                       mol_type = protein
                       organism = Homo sapiens
SEQUENCE: 693
NEPQYYDGSG HSLPGMFDY                                             19

SEQ ID NO: 694         moltype = AA  length = 15
FEATURE                Location/Qualifiers
source                 1..15
                       mol_type = protein
                       organism = Homo sapiens
SEQUENCE: 694
LEADGDDYSP KMVDY                                                 15

SEQ ID NO: 695         moltype = AA  length = 19
FEATURE                Location/Qualifiers
source                 1..19
                       mol_type = protein
                       organism = Homo sapiens
SEQUENCE: 695
READYHDGNG HTLPGMFDF                                             19

SEQ ID NO: 696         moltype = AA  length = 19
FEATURE                Location/Qualifiers
source                 1..19
                       mol_type = protein
                       organism = Homo sapiens
SEQUENCE: 696
NEPQYFDGSG HSLPGMFDY                                             19

SEQ ID NO: 697         moltype = AA  length = 19
FEATURE                Location/Qualifiers
source                 1..19
                       mol_type = protein
                       organism = Homo sapiens
SEQUENCE: 697
NEPQYYDGSG HSLPGMFDY                                             19

SEQ ID NO: 698         moltype = AA  length = 15
FEATURE                Location/Qualifiers
source                 1..15
                       mol_type = protein
                       organism = Homo sapiens
SEQUENCE: 698
LEADGDDYSP KMFDH                                                 15

SEQ ID NO: 699         moltype = AA  length = 16
FEATURE                Location/Qualifiers
source                 1..16
                       mol_type = protein
                       organism = Homo sapiens
SEQUENCE: 699
LEAESDSHSR PIMFDH                                                16

SEQ ID NO: 700         moltype = AA  length = 19
FEATURE                Location/Qualifiers
source                 1..19
                       mol_type = protein
                       organism = Homo sapiens
SEQUENCE: 700
NEPQYHDGNG HSLPGMFDF                                             19
```

-continued

```
SEQ ID NO: 701          moltype = AA  length = 19
FEATURE                 Location/Qualifiers
source                  1..19
                        mol_type = protein
                        organism = Homo sapiens
SEQUENCE: 701
NEPQYYDGSG HSLPGMFDY                                                  19

SEQ ID NO: 702          moltype = AA  length = 16
FEATURE                 Location/Qualifiers
source                  1..16
                        mol_type = protein
                        organism = Homo sapiens
SEQUENCE: 702
AEAESQSHSR PIMFDF                                                     16

SEQ ID NO: 703          moltype = AA  length = 16
FEATURE                 Location/Qualifiers
source                  1..16
                        mol_type = protein
                        organism = Homo sapiens
SEQUENCE: 703
AEAASDSHSR PIMFDH                                                     16

SEQ ID NO: 704          moltype = AA  length = 15
FEATURE                 Location/Qualifiers
source                  1..15
                        mol_type = protein
                        organism = Homo sapiens
SEQUENCE: 704
LEADGSDYSP KMFDF                                                      15

SEQ ID NO: 705          moltype = AA  length = 15
FEATURE                 Location/Qualifiers
source                  1..15
                        mol_type = protein
                        organism = Homo sapiens
SEQUENCE: 705
LEADGDDYSP KMFDY                                                      15

SEQ ID NO: 706          moltype = AA  length = 19
FEATURE                 Location/Qualifiers
source                  1..19
                        mol_type = protein
                        organism = Homo sapiens
SEQUENCE: 706
READYHDGNG HTLPGMFDF                                                  19

SEQ ID NO: 707          moltype = AA  length = 15
FEATURE                 Location/Qualifiers
source                  1..15
                        mol_type = protein
                        organism = Homo sapiens
SEQUENCE: 707
LEADGDDYSP KMFDY                                                      15

SEQ ID NO: 708          moltype = AA  length = 15
FEATURE                 Location/Qualifiers
source                  1..15
                        mol_type = protein
                        organism = Homo sapiens
SEQUENCE: 708
LEADGDNYSP KMVDY                                                      15

SEQ ID NO: 709          moltype = AA  length = 14
FEATURE                 Location/Qualifiers
source                  1..14
                        mol_type = protein
                        organism = Homo sapiens
SEQUENCE: 709
NEPQYHSLPG MFDY                                                       14

SEQ ID NO: 710          moltype = AA  length = 15
FEATURE                 Location/Qualifiers
source                  1..15
                        mol_type = protein
                        organism = Homo sapiens
SEQUENCE: 710
LEADGGDYSP KMFDY                                                      15
```

```
SEQ ID NO: 711          moltype = AA  length = 15
FEATURE                 Location/Qualifiers
source                  1..15
                        mol_type = protein
                        organism = Homo sapiens
SEQUENCE: 711
LEADGADYSP KMFDF                                                15

SEQ ID NO: 712          moltype = AA  length = 16
FEATURE                 Location/Qualifiers
source                  1..16
                        mol_type = protein
                        organism = Homo sapiens
SEQUENCE: 712
AEAESQSHSR PIMFDY                                               16

SEQ ID NO: 713          moltype = AA  length = 16
FEATURE                 Location/Qualifiers
source                  1..16
                        mol_type = protein
                        organism = Homo sapiens
SEQUENCE: 713
AEAASDSHSR PIMFDH                                               16

SEQ ID NO: 714          moltype = AA  length = 16
FEATURE                 Location/Qualifiers
source                  1..16
                        mol_type = protein
                        organism = Homo sapiens
SEQUENCE: 714
LEAESDSHSR PIMFDH                                               16

SEQ ID NO: 715          moltype = AA  length = 19
FEATURE                 Location/Qualifiers
source                  1..19
                        mol_type = protein
                        organism = Homo sapiens
SEQUENCE: 715
NEPQYHDDNG HSLPGMIDY                                            19

SEQ ID NO: 716          moltype = AA  length = 16
FEATURE                 Location/Qualifiers
source                  1..16
                        mol_type = protein
                        organism = Homo sapiens
SEQUENCE: 716
AEAESQSHSR PIMFDS                                               16

SEQ ID NO: 717          moltype = AA  length = 19
FEATURE                 Location/Qualifiers
source                  1..19
                        mol_type = protein
                        organism = Homo sapiens
SEQUENCE: 717
NEPQYHDGNG HSLPGMFDS                                            19

SEQ ID NO: 718          moltype = AA  length = 18
FEATURE                 Location/Qualifiers
source                  1..18
                        mol_type = protein
                        organism = Homo sapiens
SEQUENCE: 718
GRQTFRAIWS GPPVVFDI                                             18

SEQ ID NO: 719          moltype = AA  length = 18
FEATURE                 Location/Qualifiers
source                  1..18
                        mol_type = protein
                        organism = Homo sapiens
SEQUENCE: 719
GRQTFRAIWS GPPAVFDI                                             18

SEQ ID NO: 720          moltype = AA  length = 16
FEATURE                 Location/Qualifiers
source                  1..16
                        mol_type = protein
                        organism = Homo sapiens
SEQUENCE: 720
```

-continued

```
AVAGLWFEDA YNWFGP                                                 16

SEQ ID NO: 721          moltype = AA  length = 16
FEATURE                 Location/Qualifiers
source                  1..16
                        mol_type = protein
                        organism = Homo sapiens
SEQUENCE: 721
AVKGLWFDET YTWFGP                                                 16

SEQ ID NO: 722          moltype = AA  length = 16
FEATURE                 Location/Qualifiers
source                  1..16
                        mol_type = protein
                        organism = Homo sapiens
SEQUENCE: 722
AVKGFWFDEP STWFGP                                                 16

SEQ ID NO: 723          moltype = AA  length = 16
FEATURE                 Location/Qualifiers
source                  1..16
                        mol_type = protein
                        organism = Homo sapiens
SEQUENCE: 723
AVKGFWFDDP YTWFGP                                                 16

SEQ ID NO: 724          moltype = AA  length = 16
FEATURE                 Location/Qualifiers
source                  1..16
                        mol_type = protein
                        organism = Homo sapiens
SEQUENCE: 724
AVKGFWFDEV YNWFGP                                                 16

SEQ ID NO: 725          moltype = AA  length = 11
FEATURE                 Location/Qualifiers
source                  1..11
                        mol_type = protein
                        organism = Homo sapiens
SEQUENCE: 725
AVYDSSLSLG L                                                      11

SEQ ID NO: 726          moltype = AA  length = 11
FEATURE                 Location/Qualifiers
source                  1..11
                        mol_type = protein
                        organism = Homo sapiens
SEQUENCE: 726
ATYDSQRSIR L                                                      11

SEQ ID NO: 727          moltype = AA  length = 11
FEATURE                 Location/Qualifiers
source                  1..11
                        mol_type = protein
                        organism = Homo sapiens
SEQUENCE: 727
ATYDSQGSTR L                                                      11

SEQ ID NO: 728          moltype = AA  length = 11
FEATURE                 Location/Qualifiers
source                  1..11
                        mol_type = protein
                        organism = Homo sapiens
SEQUENCE: 728
AAYDSTFSLP V                                                      11

SEQ ID NO: 729          moltype = AA  length = 11
FEATURE                 Location/Qualifiers
source                  1..11
                        mol_type = protein
                        organism = Homo sapiens
SEQUENCE: 729
AAYDSSLSLR L                                                      11

SEQ ID NO: 730          moltype = AA  length = 11
FEATURE                 Location/Qualifiers
source                  1..11
                        mol_type = protein
                        organism = Homo sapiens
```

```
SEQUENCE: 730
ATYDTDLSLR L                                                    11

SEQ ID NO: 731          moltype = AA  length = 11
FEATURE                 Location/Qualifiers
source                  1..11
                        mol_type = protein
                        organism = Homo sapiens
SEQUENCE: 731
AAYDSAVSLP V                                                    11

SEQ ID NO: 732          moltype = AA  length = 11
FEATURE                 Location/Qualifiers
source                  1..11
                        mol_type = protein
                        organism = Homo sapiens
SEQUENCE: 732
AAYDSTLSLR L                                                    11

SEQ ID NO: 733          moltype = AA  length = 11
FEATURE                 Location/Qualifiers
source                  1..11
                        mol_type = protein
                        organism = Homo sapiens
SEQUENCE: 733
AAYDSTFSLP V                                                    11

SEQ ID NO: 734          moltype = AA  length = 11
FEATURE                 Location/Qualifiers
source                  1..11
                        mol_type = protein
                        organism = Homo sapiens
SEQUENCE: 734
ATYDTGLSLR L                                                    11

SEQ ID NO: 735          moltype = AA  length = 11
FEATURE                 Location/Qualifiers
source                  1..11
                        mol_type = protein
                        organism = Homo sapiens
SEQUENCE: 735
ATYDSGWSIR L                                                    11

SEQ ID NO: 736          moltype = AA  length = 11
FEATURE                 Location/Qualifiers
source                  1..11
                        mol_type = protein
                        organism = Homo sapiens
SEQUENCE: 736
AAYDSTLSLR L                                                    11

SEQ ID NO: 737          moltype = AA  length = 11
FEATURE                 Location/Qualifiers
source                  1..11
                        mol_type = protein
                        organism = Homo sapiens
SEQUENCE: 737
AAYDSTLSLR L                                                    11

SEQ ID NO: 738          moltype = AA  length = 11
FEATURE                 Location/Qualifiers
source                  1..11
                        mol_type = protein
                        organism = Homo sapiens
SEQUENCE: 738
ATYDSQGSTR L                                                    11

SEQ ID NO: 739          moltype = AA  length = 11
FEATURE                 Location/Qualifiers
source                  1..11
                        mol_type = protein
                        organism = Homo sapiens
SEQUENCE: 739
ATYDSDGSIR L                                                    11

SEQ ID NO: 740          moltype = AA  length = 11
FEATURE                 Location/Qualifiers
source                  1..11
                        mol_type = protein
```

```
                        organism = Homo sapiens
SEQUENCE: 740
ATYDTGLSLR L                                                            11

SEQ ID NO: 741          moltype = AA  length = 11
FEATURE                 Location/Qualifiers
source                  1..11
                        mol_type = protein
                        organism = Homo sapiens
SEQUENCE: 741
AAFDSALSLP L                                                            11

SEQ ID NO: 742          moltype = AA  length = 11
FEATURE                 Location/Qualifiers
source                  1..11
                        mol_type = protein
                        organism = Homo sapiens
SEQUENCE: 742
ATYDTGLSLR L                                                            11

SEQ ID NO: 743          moltype = AA  length = 11
FEATURE                 Location/Qualifiers
source                  1..11
                        mol_type = protein
                        organism = Homo sapiens
SEQUENCE: 743
GTYDTSLSLR L                                                            11

SEQ ID NO: 744          moltype = AA  length = 11
FEATURE                 Location/Qualifiers
source                  1..11
                        mol_type = protein
                        organism = Homo sapiens
SEQUENCE: 744
ATYDSHGSIR L                                                            11

SEQ ID NO: 745          moltype = AA  length = 11
FEATURE                 Location/Qualifiers
source                  1..11
                        mol_type = protein
                        organism = Homo sapiens
SEQUENCE: 745
ATYDSDGSIR L                                                            11

SEQ ID NO: 746          moltype = AA  length = 11
FEATURE                 Location/Qualifiers
source                  1..11
                        mol_type = protein
                        organism = Homo sapiens
SEQUENCE: 746
ATYDSGWSIR L                                                            11

SEQ ID NO: 747          moltype = AA  length = 16
FEATURE                 Location/Qualifiers
source                  1..16
                        mol_type = protein
                        organism = Homo sapiens
SEQUENCE: 747
DGLGEVAPAY LYGIDA                                                       16

SEQ ID NO: 748          moltype = AA  length = 16
FEATURE                 Location/Qualifiers
source                  1..16
                        mol_type = protein
                        organism = Homo sapiens
SEQUENCE: 748
DGLGEVAPAY LYGIDA                                                       16

SEQ ID NO: 749          moltype = AA  length = 16
FEATURE                 Location/Qualifiers
source                  1..16
                        mol_type = protein
                        organism = Homo sapiens
SEQUENCE: 749
DGLGEVAPAY LYGIDA                                                       16

SEQ ID NO: 750          moltype = AA  length = 16
FEATURE                 Location/Qualifiers
source                  1..16
```

```
                        mol_type = protein
                        organism = Homo sapiens
SEQUENCE: 750
DGLGELAPAY HYGIDV                                                   16

SEQ ID NO: 751          moltype = AA  length = 16
FEATURE                 Location/Qualifiers
source                  1..16
                        mol_type = protein
                        organism = Homo sapiens
SEQUENCE: 751
DGLGELAPAY QYGIDV                                                   16

SEQ ID NO: 752          moltype = AA  length = 16
FEATURE                 Location/Qualifiers
source                  1..16
                        mol_type = protein
                        organism = Homo sapiens
SEQUENCE: 752
DGLGEVAPDY RYGIDV                                                   16

SEQ ID NO: 753          moltype = AA  length = 16
FEATURE                 Location/Qualifiers
source                  1..16
                        mol_type = protein
                        organism = Homo sapiens
SEQUENCE: 753
DGLGEVAPAY LYGIDA                                                   16

SEQ ID NO: 754          moltype = AA  length = 16
FEATURE                 Location/Qualifiers
source                  1..16
                        mol_type = protein
                        organism = Homo sapiens
SEQUENCE: 754
DGLGEVAPDY RYGIDV                                                   16

SEQ ID NO: 755          moltype = AA  length = 20
FEATURE                 Location/Qualifiers
source                  1..20
                        mol_type = protein
                        organism = Homo sapiens
SEQUENCE: 755
TSTYDQWSGL HHDGVMAFSS                                               20

SEQ ID NO: 756          moltype = AA  length = 11
FEATURE                 Location/Qualifiers
source                  1..11
                        mol_type = protein
                        organism = Homo sapiens
SEQUENCE: 756
SSGNFEFAFE I                                                        11

SEQ ID NO: 757          moltype = AA  length = 11
FEATURE                 Location/Qualifiers
source                  1..11
                        mol_type = protein
                        organism = Homo sapiens
SEQUENCE: 757
SSGNYDFAYD I                                                        11

SEQ ID NO: 758          moltype = AA  length = 11
FEATURE                 Location/Qualifiers
source                  1..11
                        mol_type = protein
                        organism = Homo sapiens
SEQUENCE: 758
SSGNYDFAFD I                                                        11

SEQ ID NO: 759          moltype = AA  length = 18
FEATURE                 Location/Qualifiers
source                  1..18
                        mol_type = protein
                        organism = Homo sapiens
SEQUENCE: 759
ADRFKVAQDE GLFVIFDY                                                 18

SEQ ID NO: 760          moltype = AA  length = 18
FEATURE                 Location/Qualifiers
```

```
source                  1..18
                        mol_type = protein
                        organism = Homo sapiens
SEQUENCE: 760
ADPFKVAQDE GLYVIFDY                                                18

SEQ ID NO: 761          moltype = AA  length = 18
FEATURE                 Location/Qualifiers
source                  1..18
                        mol_type = protein
                        organism = Homo sapiens
SEQUENCE: 761
ADPFKVAQDE GLYVIFDY                                                18

SEQ ID NO: 762          moltype = AA  length = 18
FEATURE                 Location/Qualifiers
source                  1..18
                        mol_type = protein
                        organism = Homo sapiens
SEQUENCE: 762
ADPFKVAQDE GLFVIFDY                                                18

SEQ ID NO: 763          moltype = AA  length = 24
FEATURE                 Location/Qualifiers
source                  1..24
                        mol_type = protein
                        organism = Homo sapiens
SEQUENCE: 763
DRGDTRLLDY GDYEDERYYY GMDV                                         24

SEQ ID NO: 764          moltype = AA  length = 24
FEATURE                 Location/Qualifiers
source                  1..24
                        mol_type = protein
                        organism = Homo sapiens
SEQUENCE: 764
DRGDTRLLDY GDYEDERYYY GMDV                                         24

SEQ ID NO: 765          moltype = AA  length = 24
FEATURE                 Location/Qualifiers
source                  1..24
                        mol_type = protein
                        organism = Homo sapiens
SEQUENCE: 765
DRGDTRLLDY GDYEDERYYY GMDV                                         24

SEQ ID NO: 766          moltype = AA  length = 24
FEATURE                 Location/Qualifiers
source                  1..24
                        mol_type = protein
                        organism = Homo sapiens
SEQUENCE: 766
DRGDTRLLDY GDYEDERYYY GMDV                                         24

SEQ ID NO: 767          moltype = AA  length = 24
FEATURE                 Location/Qualifiers
source                  1..24
                        mol_type = protein
                        organism = Homo sapiens
SEQUENCE: 767
DRGDTRLLDY GDYEDERYYY GMDV                                         24

SEQ ID NO: 768          moltype = AA  length = 24
FEATURE                 Location/Qualifiers
source                  1..24
                        mol_type = protein
                        organism = Homo sapiens
SEQUENCE: 768
DRGDTRLLDY GDYEDERYYY GMDV                                         24

SEQ ID NO: 769          moltype = AA  length = 24
FEATURE                 Location/Qualifiers
source                  1..24
                        mol_type = protein
                        organism = Homo sapiens
SEQUENCE: 769
DRGDTRLLDY GDYEDERYYY GMDV                                         24

SEQ ID NO: 770          moltype = AA  length = 21
```

```
FEATURE                Location/Qualifiers
source                 1..21
                       mol_type = protein
                       organism = Homo sapiens
SEQUENCE: 770
DRSSAIGYCS SISCYKGSFD I                                      21

SEQ ID NO: 771         moltype = AA  length = 14
FEATURE                Location/Qualifiers
source                 1..14
                       mol_type = protein
                       organism = Homo sapiens
SEQUENCE: 771
GGLYCSSISC IMDV                                              14

SEQ ID NO: 772         moltype = AA  length = 14
FEATURE                Location/Qualifiers
source                 1..14
                       mol_type = protein
                       organism = Homo sapiens
SEQUENCE: 772
GGLYCSSISC IMDV                                              14

SEQ ID NO: 773         moltype = AA  length = 5
FEATURE                Location/Qualifiers
source                 1..5
                       mol_type = protein
                       organism = Homo sapiens
SEQUENCE: 773
NGFDV                                                        5

SEQ ID NO: 774         moltype = AA  length = 9
FEATURE                Location/Qualifiers
source                 1..9
                       mol_type = protein
                       organism = Homo sapiens
SEQUENCE: 774
QEYSSTPYN                                                    9

SEQ ID NO: 775         moltype = AA  length = 9
FEATURE                Location/Qualifiers
source                 1..9
                       mol_type = protein
                       organism = Homo sapiens
SEQUENCE: 775
QEYSSTPYN                                                    9

SEQ ID NO: 776         moltype = AA  length = 9
FEATURE                Location/Qualifiers
source                 1..9
                       mol_type = protein
                       organism = Homo sapiens
SEQUENCE: 776
QEYSSTPYN                                                    9

SEQ ID NO: 777         moltype = AA  length = 9
FEATURE                Location/Qualifiers
source                 1..9
                       mol_type = protein
                       organism = Homo sapiens
SEQUENCE: 777
QEYSSTPYN                                                    9

SEQ ID NO: 778         moltype = AA  length = 9
FEATURE                Location/Qualifiers
source                 1..9
                       mol_type = protein
                       organism = Homo sapiens
SEQUENCE: 778
QEYSSTPYN                                                    9

SEQ ID NO: 779         moltype = AA  length = 9
FEATURE                Location/Qualifiers
source                 1..9
                       mol_type = protein
                       organism = Homo sapiens
SEQUENCE: 779
QEYSSTPYN                                                    9
```

```
SEQ ID NO: 780          moltype = AA  length = 9
FEATURE                 Location/Qualifiers
source                  1..9
                        mol_type = protein
                        organism = Homo sapiens
SEQUENCE: 780
QEYSSTPYN                                                        9

SEQ ID NO: 781          moltype = AA  length = 9
FEATURE                 Location/Qualifiers
source                  1..9
                        mol_type = protein
                        organism = Homo sapiens
SEQUENCE: 781
QQYDTYPGT                                                        9

SEQ ID NO: 782          moltype = AA  length = 11
FEATURE                 Location/Qualifiers
source                  1..11
                        mol_type = protein
                        organism = Homo sapiens
SEQUENCE: 782
QSYDRSLRGS V                                                     11

SEQ ID NO: 783          moltype = AA  length = 10
FEATURE                 Location/Qualifiers
source                  1..10
                        mol_type = protein
                        organism = Homo sapiens
SEQUENCE: 783
QQRANWRLLT                                                       10

SEQ ID NO: 784          moltype = AA  length = 9
FEATURE                 Location/Qualifiers
source                  1..9
                        mol_type = protein
                        organism = Homo sapiens
SEQUENCE: 784
QQYSNLPYT                                                        9

SEQ ID NO: 785          moltype = AA  length = 10
FEATURE                 Location/Qualifiers
source                  1..10
                        mol_type = protein
                        organism = Homo sapiens
SEQUENCE: 785
QQYYQWLSYT                                                       10

SEQ ID NO: 786          moltype = AA  length = 9
FEATURE                 Location/Qualifiers
source                  1..9
                        mol_type = protein
                        organism = Homo sapiens
SEQUENCE: 786
QQYNHWPQT                                                        9

SEQ ID NO: 787          moltype = AA  length = 9
FEATURE                 Location/Qualifiers
source                  1..9
                        mol_type = protein
                        organism = Homo sapiens
SEQUENCE: 787
CLKKTSSYV                                                        9

SEQ ID NO: 788          moltype = AA  length = 13
FEATURE                 Location/Qualifiers
source                  1..13
                        mol_type = protein
                        organism = Homo sapiens
SEQUENCE: 788
DGSGDDTSWH LHP                                                   13

SEQ ID NO: 789          moltype = AA  length = 13
FEATURE                 Location/Qualifiers
source                  1..13
                        mol_type = protein
                        organism = Homo sapiens
SEQUENCE: 789
DESGDDLKWH LHP                                                   13
```

```
SEQ ID NO: 790          moltype = AA  length = 13
FEATURE                 Location/Qualifiers
source                  1..13
                        mol_type = protein
                        organism = Homo sapiens
SEQUENCE: 790
DGSGDATSWH LHP                                                            13

SEQ ID NO: 791          moltype = AA  length = 13
FEATURE                 Location/Qualifiers
source                  1..13
                        mol_type = protein
                        organism = Homo sapiens
SEQUENCE: 791
DGSGDARDWH LDP                                                            13

SEQ ID NO: 792          moltype = AA  length = 13
FEATURE                 Location/Qualifiers
source                  1..13
                        mol_type = protein
                        organism = Homo sapiens
SEQUENCE: 792
DRRDDDRAWL LDP                                                            13

SEQ ID NO: 793          moltype = AA  length = 13
FEATURE                 Location/Qualifiers
source                  1..13
                        mol_type = protein
                        organism = Homo sapiens
SEQUENCE: 793
DGSGDDTSWH LDP                                                            13

SEQ ID NO: 794          moltype = AA  length = 13
FEATURE                 Location/Qualifiers
source                  1..13
                        mol_type = protein
                        organism = Homo sapiens
SEQUENCE: 794
DGSGDDTSWY LDP                                                            13

SEQ ID NO: 795          moltype = AA  length = 13
FEATURE                 Location/Qualifiers
source                  1..13
                        mol_type = protein
                        organism = Homo sapiens
SEQUENCE: 795
DGSGDARDWH LHP                                                            13

SEQ ID NO: 796          moltype = AA  length = 13
FEATURE                 Location/Qualifiers
source                  1..13
                        mol_type = protein
                        organism = Homo sapiens
SEQUENCE: 796
DGGGDDRTWL LDA                                                            13

SEQ ID NO: 797          moltype = AA  length = 13
FEATURE                 Location/Qualifiers
source                  1..13
                        mol_type = protein
                        organism = Homo sapiens
SEQUENCE: 797
DRRDDGLDWL LDP                                                            13

SEQ ID NO: 798          moltype = AA  length = 13
FEATURE                 Location/Qualifiers
source                  1..13
                        mol_type = protein
                        organism = Homo sapiens
SEQUENCE: 798
DGSGDDTSWH LHP                                                            13

SEQ ID NO: 799          moltype = AA  length = 12
FEATURE                 Location/Qualifiers
source                  1..12
                        mol_type = protein
                        organism = Homo sapiens
SEQUENCE: 799
```

```
GGGDGRNWHL HP                                                       12

SEQ ID NO: 800          moltype = AA  length = 13
FEATURE                 Location/Qualifiers
source                  1..13
                        mol_type = protein
                        organism = Homo sapiens
SEQUENCE: 800
DGSGDDRNWH LDP                                                      13

SEQ ID NO: 801          moltype = AA  length = 13
FEATURE                 Location/Qualifiers
source                  1..13
                        mol_type = protein
                        organism = Homo sapiens
SEQUENCE: 801
DESGYDLNWH LDS                                                      13

SEQ ID NO: 802          moltype = AA  length = 5
FEATURE                 Location/Qualifiers
source                  1..5
                        mol_type = protein
                        organism = Homo sapiens
SEQUENCE: 802
AVLEF                                                               5

SEQ ID NO: 803          moltype = AA  length = 5
FEATURE                 Location/Qualifiers
source                  1..5
                        mol_type = protein
                        organism = Homo sapiens
SEQUENCE: 803
AVFQW                                                               5

SEQ ID NO: 804          moltype = AA  length = 5
FEATURE                 Location/Qualifiers
source                  1..5
                        mol_type = protein
                        organism = Homo sapiens
SEQUENCE: 804
AVLEF                                                               5

SEQ ID NO: 805          moltype = AA  length = 5
FEATURE                 Location/Qualifiers
source                  1..5
                        mol_type = protein
                        organism = Homo sapiens
SEQUENCE: 805
AVLEF                                                               5

SEQ ID NO: 806          moltype = AA  length = 5
FEATURE                 Location/Qualifiers
source                  1..5
                        mol_type = protein
                        organism = Homo sapiens
SEQUENCE: 806
QLFEF                                                               5

SEQ ID NO: 807          moltype = AA  length = 5
FEATURE                 Location/Qualifiers
source                  1..5
                        mol_type = protein
                        organism = Homo sapiens
SEQUENCE: 807
AVLEF                                                               5

SEQ ID NO: 808          moltype = AA  length = 5
FEATURE                 Location/Qualifiers
source                  1..5
                        mol_type = protein
                        organism = Homo sapiens
SEQUENCE: 808
AVVEF                                                               5

SEQ ID NO: 809          moltype = AA  length = 5
FEATURE                 Location/Qualifiers
source                  1..5
                        mol_type = protein
                        organism = Homo sapiens
```

-continued

```
SEQUENCE: 809
AALEF                                                        5

SEQ ID NO: 810          moltype = AA  length = 5
FEATURE                 Location/Qualifiers
source                  1..5
                        mol_type = protein
                        organism = Homo sapiens
SEQUENCE: 810
SVYEF                                                        5

SEQ ID NO: 811          moltype = AA  length = 5
FEATURE                 Location/Qualifiers
source                  1..5
                        mol_type = protein
                        organism = Homo sapiens
SEQUENCE: 811
QLFEF                                                        5

SEQ ID NO: 812          moltype = AA  length = 5
FEATURE                 Location/Qualifiers
source                  1..5
                        mol_type = protein
                        organism = Homo sapiens
SEQUENCE: 812
AVLEF                                                        5

SEQ ID NO: 813          moltype = AA  length = 5
FEATURE                 Location/Qualifiers
source                  1..5
                        mol_type = protein
                        organism = Homo sapiens
SEQUENCE: 813
ASLEF                                                        5

SEQ ID NO: 814          moltype = AA  length = 5
FEATURE                 Location/Qualifiers
source                  1..5
                        mol_type = protein
                        organism = Homo sapiens
SEQUENCE: 814
EVYEF                                                        5

SEQ ID NO: 815          moltype = AA  length = 5
FEATURE                 Location/Qualifiers
source                  1..5
                        mol_type = protein
                        organism = Homo sapiens
SEQUENCE: 815
ESFQW                                                        5

SEQ ID NO: 816          moltype = AA  length = 10
FEATURE                 Location/Qualifiers
source                  1..10
                        mol_type = protein
                        organism = Homo sapiens
SEQUENCE: 816
QRSDYWDFDV                                                   10

SEQ ID NO: 817          moltype = AA  length = 18
FEATURE                 Location/Qualifiers
source                  1..18
                        mol_type = protein
                        organism = Homo sapiens
SEQUENCE: 817
IPYHSESYYK VVIGGFDV                                          18

SEQ ID NO: 818          moltype = AA  length = 13
FEATURE                 Location/Qualifiers
source                  1..13
                        mol_type = protein
                        organism = Homo sapiens
SEQUENCE: 818
DHGDPRTGYY FDY                                               13

SEQ ID NO: 819          moltype = AA  length = 9
FEATURE                 Location/Qualifiers
source                  1..9
                        mol_type = protein
```

```
                        organism = Homo sapiens
SEQUENCE: 819
GPLLRYLDS                                                         9

SEQ ID NO: 820          moltype = AA  length = 22
FEATURE                 Location/Qualifiers
source                  1..22
                        mol_type = protein
                        organism = Homo sapiens
SEQUENCE: 820
KAKDYYYESS DYSPYYYYYM DV                                          22

SEQ ID NO: 821          moltype = AA  length = 15
FEATURE                 Location/Qualifiers
source                  1..15
                        mol_type = protein
                        organism = Homo sapiens
SEQUENCE: 821
GSGRWTIGAR IYFDN                                                  15

SEQ ID NO: 822          moltype = AA  length = 18
FEATURE                 Location/Qualifiers
source                  1..18
                        mol_type = protein
                        organism = Homo sapiens
SEQUENCE: 822
TPPHYDVLTG YPSSVLEF                                               18

SEQ ID NO: 823          moltype = AA  length = 14
FEATURE                 Location/Qualifiers
source                  1..14
                        mol_type = protein
                        organism = Homo sapiens
SEQUENCE: 823
ATGYSYGYLD AFDI                                                   14

SEQ ID NO: 824          moltype = AA  length = 15
FEATURE                 Location/Qualifiers
source                  1..15
                        mol_type = protein
                        organism = Homo sapiens
SEQUENCE: 824
EKGQWLTVPP YYFDS                                                  15

SEQ ID NO: 825          moltype = AA  length = 14
FEATURE                 Location/Qualifiers
source                  1..14
                        mol_type = protein
                        organism = Homo sapiens
SEQUENCE: 825
TRCFGANCFN FMDV                                                   14

SEQ ID NO: 826          moltype = AA  length = 12
FEATURE                 Location/Qualifiers
source                  1..12
                        mol_type = protein
                        organism = Homo sapiens
SEQUENCE: 826
PEPSSIVAPL YY                                                     12

SEQ ID NO: 827          moltype = AA  length = 13
FEATURE                 Location/Qualifiers
source                  1..13
                        mol_type = protein
                        organism = Homo sapiens
SEQUENCE: 827
DPQVEVRGNA FDI                                                    13

SEQ ID NO: 828          moltype = AA  length = 12
FEATURE                 Location/Qualifiers
source                  1..12
                        mol_type = protein
                        organism = Homo sapiens
SEQUENCE: 828
PQYNLGRDPL DV                                                     12

SEQ ID NO: 829          moltype = AA  length = 14
FEATURE                 Location/Qualifiers
source                  1..14
```

```
                        mol_type = protein
                        organism = Homo sapiens
SEQUENCE: 829
ADYDLLTSSY HFDS                                                      14

SEQ ID NO: 830          moltype = AA  length = 12
FEATURE                 Location/Qualifiers
source                  1..12
                        mol_type = protein
                        organism = Homo sapiens
SEQUENCE: 830
LDGEAFRYYL DL                                                        12

SEQ ID NO: 831          moltype = AA  length = 5
FEATURE                 Location/Qualifiers
source                  1..5
                        mol_type = protein
                        organism = Homo sapiens
SEQUENCE: 831
QVYEF                                                                5

SEQ ID NO: 832          moltype = AA  length = 5
FEATURE                 Location/Qualifiers
source                  1..5
                        mol_type = protein
                        organism = Homo sapiens
SEQUENCE: 832
QQLAT                                                                5

SEQ ID NO: 833          moltype = AA  length = 9
FEATURE                 Location/Qualifiers
source                  1..9
                        mol_type = protein
                        organism = Homo sapiens
SEQUENCE: 833
QQYDDAPIT                                                            9

SEQ ID NO: 834          moltype = AA  length = 11
FEATURE                 Location/Qualifiers
source                  1..11
                        mol_type = protein
                        organism = Homo sapiens
SEQUENCE: 834
QHRTNWPPSI T                                                         11

SEQ ID NO: 835          moltype = AA  length = 9
FEATURE                 Location/Qualifiers
source                  1..9
                        mol_type = protein
                        organism = Homo sapiens
SEQUENCE: 835
QQYGTSSCT                                                            9

SEQ ID NO: 836          moltype = AA  length = 9
FEATURE                 Location/Qualifiers
source                  1..9
                        mol_type = protein
                        organism = Homo sapiens
SEQUENCE: 836
QQYGSSPPT                                                            9

SEQ ID NO: 837          moltype = AA  length = 10
FEATURE                 Location/Qualifiers
source                  1..10
                        mol_type = protein
                        organism = Homo sapiens
SEQUENCE: 837
QQYNNWPPIT                                                           10

SEQ ID NO: 838          moltype = AA  length = 9
FEATURE                 Location/Qualifiers
source                  1..9
                        mol_type = protein
                        organism = Homo sapiens
SEQUENCE: 838
AAWDDTLYV                                                            9

SEQ ID NO: 839          moltype = AA  length = 7
FEATURE                 Location/Qualifiers
```

```
source                1..7
                      mol_type = protein
                      organism = Homo sapiens
SEQUENCE: 839
QQSHSPS                                                        7

SEQ ID NO: 840        moltype = AA  length = 7
FEATURE               Location/Qualifiers
source                1..7
                      mol_type = protein
                      organism = Homo sapiens
SEQUENCE: 840
QQYYISP                                                        7

SEQ ID NO: 841        moltype = AA  length = 10
FEATURE               Location/Qualifiers
source                1..10
                      mol_type = protein
                      organism = Homo sapiens
SEQUENCE: 841
QQYGTLHPRT                                                     10

SEQ ID NO: 842        moltype = AA  length = 9
FEATURE               Location/Qualifiers
source                1..9
                      mol_type = protein
                      organism = Homo sapiens
SEQUENCE: 842
QQTYTSPIT                                                      9

SEQ ID NO: 843        moltype = AA  length = 9
FEATURE               Location/Qualifiers
source                1..9
                      mol_type = protein
                      organism = Homo sapiens
SEQUENCE: 843
QQYGLSPWT                                                      9

SEQ ID NO: 844        moltype = AA  length = 11
FEATURE               Location/Qualifiers
source                1..11
                      mol_type = protein
                      organism = Homo sapiens
SEQUENCE: 844
LLLPYYGGPW I                                                   11

SEQ ID NO: 845        moltype = AA  length = 10
FEATURE               Location/Qualifiers
source                1..10
                      mol_type = protein
                      organism = Homo sapiens
SEQUENCE: 845
SSFTPTNTLV                                                     10

SEQ ID NO: 846        moltype = AA  length = 19
FEATURE               Location/Qualifiers
source                1..19
                      mol_type = protein
                      organism = Homo sapiens
SEQUENCE: 846
NEADYHDGNG HSLRGMFDY                                           19

SEQ ID NO: 847        moltype = AA  length = 18
FEATURE               Location/Qualifiers
source                1..18
                      mol_type = protein
                      organism = Homo sapiens
SEQUENCE: 847
GRQTFRAIWS GPPVVFDI                                            18

SEQ ID NO: 848        moltype = AA  length = 17
FEATURE               Location/Qualifiers
source                1..17
                      mol_type = protein
                      organism = Homo sapiens
SEQUENCE: 848
RYFDWSPFRR DTYGTDV                                             17

SEQ ID NO: 849        moltype = AA  length = 17
```

```
FEATURE                Location/Qualifiers
source                 1..17
                       mol_type = protein
                       organism = Homo sapiens
SEQUENCE: 849
RYLDWSPIGR DTYGTDV                                                    17

SEQ ID NO: 850         moltype = AA  length = 18
FEATURE                Location/Qualifiers
source                 1..18
                       mol_type = protein
                       organism = Homo sapiens
SEQUENCE: 850
GLCRGGNCRL GPSGWLDP                                                   18

SEQ ID NO: 851         moltype = AA  length = 14
FEATURE                Location/Qualifiers
source                 1..14
                       mol_type = protein
                       organism = Homo sapiens
SEQUENCE: 851
VAYVHVVTTR SLDN                                                       14

SEQ ID NO: 852         moltype = AA  length = 20
FEATURE                Location/Qualifiers
source                 1..20
                       mol_type = protein
                       organism = Homo sapiens
SEQUENCE: 852
HEAPRYSYAF RRYYHYGLDV                                                 20

SEQ ID NO: 853         moltype = AA  length = 16
FEATURE                Location/Qualifiers
source                 1..16
                       mol_type = protein
                       organism = Homo sapiens
SEQUENCE: 853
VISGRITIFY YNYIDV                                                     16

SEQ ID NO: 854         moltype = AA  length = 14
FEATURE                Location/Qualifiers
source                 1..14
                       mol_type = protein
                       organism = Homo sapiens
SEQUENCE: 854
GTLWFGESGL RLDH                                                       14

SEQ ID NO: 855         moltype = AA  length = 18
FEATURE                Location/Qualifiers
source                 1..18
                       mol_type = protein
                       organism = Homo sapiens
SEQUENCE: 855
NRRVAMPEAM ILSFYMDV                                                   18

SEQ ID NO: 856         moltype = AA  length = 18
FEATURE                Location/Qualifiers
source                 1..18
                       mol_type = protein
                       organism = Homo sapiens
SEQUENCE: 856
VVPMFSIFGV VKANYFDY                                                   18

SEQ ID NO: 857         moltype = AA  length = 19
FEATURE                Location/Qualifiers
source                 1..19
                       mol_type = protein
                       organism = Homo sapiens
SEQUENCE: 857
AGLDYNFWNG KGRKGAFDV                                                  19

SEQ ID NO: 858         moltype = AA  length = 16
FEATURE                Location/Qualifiers
source                 1..16
                       mol_type = protein
                       organism = Homo sapiens
SEQUENCE: 858
GFRGSPFSSG SLYFDS                                                     16
```

```
SEQ ID NO: 859          moltype = AA  length = 24
FEATURE                 Location/Qualifiers
source                  1..24
                        mol_type = protein
                        organism = Homo sapiens
SEQUENCE: 859
AVITDLHTFG DYELEDPSYY YMDV                                          24

SEQ ID NO: 860          moltype = AA  length = 9
FEATURE                 Location/Qualifiers
source                  1..9
                        mol_type = protein
                        organism = Homo sapiens
SEQUENCE: 860
RGRRQIGDY                                                           9

SEQ ID NO: 861          moltype = AA  length = 16
FEATURE                 Location/Qualifiers
source                  1..16
                        mol_type = protein
                        organism = Homo sapiens
SEQUENCE: 861
SYYDFSIGDG NDAFDV                                                   16

SEQ ID NO: 862          moltype = AA  length = 19
FEATURE                 Location/Qualifiers
source                  1..19
                        mol_type = protein
                        organism = Homo sapiens
SEQUENCE: 862
DTTTFTTFGG GPNMGGFDP                                                19

SEQ ID NO: 863          moltype = AA  length = 11
FEATURE                 Location/Qualifiers
source                  1..11
                        mol_type = protein
                        organism = Homo sapiens
SEQUENCE: 863
AVYDSSLSLG L                                                        11

SEQ ID NO: 864          moltype = AA  length = 9
FEATURE                 Location/Qualifiers
source                  1..9
                        mol_type = protein
                        organism = Homo sapiens
SEQUENCE: 864
QHRSNWPWT                                                           9

SEQ ID NO: 865          moltype = AA  length = 9
FEATURE                 Location/Qualifiers
source                  1..9
                        mol_type = protein
                        organism = Homo sapiens
SEQUENCE: 865
HQYFSTPRT                                                           9

SEQ ID NO: 866          moltype = AA  length = 9
FEATURE                 Location/Qualifiers
source                  1..9
                        mol_type = protein
                        organism = Homo sapiens
SEQUENCE: 866
HQYFNTPRT                                                           9

SEQ ID NO: 867          moltype = AA  length = 9
FEATURE                 Location/Qualifiers
source                  1..9
                        mol_type = protein
                        organism = Homo sapiens
SEQUENCE: 867
QQYEDPPWT                                                           9

SEQ ID NO: 868          moltype = AA  length = 9
FEATURE                 Location/Qualifiers
source                  1..9
                        mol_type = protein
                        organism = Homo sapiens
SEQUENCE: 868
QQTYSNPRM                                                           9
```

```
SEQ ID NO: 869          moltype = AA  length = 11
FEATURE                 Location/Qualifiers
source                  1..11
                        mol_type = protein
                        organism = Homo sapiens
SEQUENCE: 869
ASWDDSLSGW V                                                            11

SEQ ID NO: 870          moltype = AA  length = 11
FEATURE                 Location/Qualifiers
source                  1..11
                        mol_type = protein
                        organism = Homo sapiens
SEQUENCE: 870
ASWDNSLSGP V                                                            11

SEQ ID NO: 871          moltype = AA  length = 9
FEATURE                 Location/Qualifiers
source                  1..9
                        mol_type = protein
                        organism = Homo sapiens
SEQUENCE: 871
QQYNSFPPT                                                               9

SEQ ID NO: 872          moltype = AA  length = 7
FEATURE                 Location/Qualifiers
source                  1..7
                        mol_type = protein
                        organism = Homo sapiens
SEQUENCE: 872
QQYGRSP                                                                 7

SEQ ID NO: 873          moltype = AA  length = 11
FEATURE                 Location/Qualifiers
source                  1..11
                        mol_type = protein
                        organism = Homo sapiens
SEQUENCE: 873
GTWDSSLSAV L                                                            11

SEQ ID NO: 874          moltype = AA  length = 5
FEATURE                 Location/Qualifiers
source                  1..5
                        mol_type = protein
                        organism = Homo sapiens
SEQUENCE: 874
QQYDS                                                                   5

SEQ ID NO: 875          moltype = AA  length = 9
FEATURE                 Location/Qualifiers
source                  1..9
                        mol_type = protein
                        organism = Homo sapiens
SEQUENCE: 875
HQYAYSPRT                                                               9

SEQ ID NO: 876          moltype = AA  length = 9
FEATURE                 Location/Qualifiers
source                  1..9
                        mol_type = protein
                        organism = Homo sapiens
SEQUENCE: 876
QQYKSYSGT                                                               9

SEQ ID NO: 877          moltype = AA  length = 10
FEATURE                 Location/Qualifiers
source                  1..10
                        mol_type = protein
                        organism = Homo sapiens
SEQUENCE: 877
QHSFGSPPWT                                                              10

SEQ ID NO: 878          moltype = AA  length = 10
FEATURE                 Location/Qualifiers
source                  1..10
                        mol_type = protein
                        organism = Homo sapiens
SEQUENCE: 878
```

AAWDDSFDYV 10

SEQ ID NO: 879 moltype = AA length = 5
FEATURE Location/Qualifiers
source 1..5
mol_type = protein
organism = Homo sapiens
SEQUENCE: 879
QQLRT 5

SEQ ID NO: 880 moltype = AA length = 11
FEATURE Location/Qualifiers
source 1..11
mol_type = protein
organism = Homo sapiens
SEQUENCE: 880
QQRTIWPPGC S 11

SEQ ID NO: 881 moltype = AA length = 19
FEATURE Location/Qualifiers
source 1..19
mol_type = protein
organism = Homo sapiens
SEQUENCE: 881
NEADYHDGNG HSLRGMFDY 19

SEQ ID NO: 882 moltype = AA length = 11
FEATURE Location/Qualifiers
source 1..11
mol_type = protein
organism = Homo sapiens
SEQUENCE: 882
GTYDSQGSTR L 11

SEQ ID NO: 883 moltype = AA length = 9
FEATURE Location/Qualifiers
source 1..9
mol_type = protein
organism = Homo sapiens
SEQUENCE: 883
QHRSNWPWT 9

SEQ ID NO: 884 moltype = AA length = 9
FEATURE Location/Qualifiers
source 1..9
mol_type = protein
organism = Homo sapiens
SEQUENCE: 884
QQSFAVPYT 9

SEQ ID NO: 885 moltype = AA length = 16
FEATURE Location/Qualifiers
source 1..16
mol_type = protein
organism = Homo sapiens
SEQUENCE: 885
DGLGEVAPDY RYGIDV 16

SEQ ID NO: 886 moltype = AA length = 13
FEATURE Location/Qualifiers
source 1..13
mol_type = protein
organism = Homo sapiens
SEQUENCE: 886
DESGDDLKWH LHP 13

SEQ ID NO: 887 moltype = AA length = 5
FEATURE Location/Qualifiers
source 1..5
mol_type = protein
organism = Homo sapiens
SEQUENCE: 887
AAFQW 5

SEQ ID NO: 888 moltype = AA length = 24
FEATURE Location/Qualifiers
source 1..24
mol_type = protein
organism = Homo sapiens

```
SEQUENCE: 888
HSDYCDFDVW GSGSQVIVSS ASTK                                         24

SEQ ID NO: 889          moltype = AA  length = 31
FEATURE                 Location/Qualifiers
source                  1..31
                        mol_type = protein
                        organism = Homo sapiens
SEQUENCE: 889
DGLGEVAPAY LYGIDAWGQG TTVIVTSAST K                                 31

SEQ ID NO: 890          moltype = AA  length = 98
FEATURE                 Location/Qualifiers
source                  1..98
                        mol_type = protein
                        organism = Homo sapiens
SEQUENCE: 890
QVQLVQSGAE VKKPGASVKV SCKASGYTFT GYYMHWVRQA PGQGLEWMGW INPNSGGTNY  60
AQKFQGRVTM TRDTSISTAY MELSRLRSDD TAVYYCAR                          98

SEQ ID NO: 891          moltype = AA  length = 98
FEATURE                 Location/Qualifiers
source                  1..98
                        mol_type = protein
                        organism = Homo sapiens
SEQUENCE: 891
QVQLVQSGAE VKKPGASVKV SCKASGYTFN SYYMHWVRQA PGQGLEWMGI INPSGGSTSY  60
AQKFQGRVTM TRDTSTSTVY MELSSLRSED TAVYYCAR                          98

SEQ ID NO: 892          moltype = AA  length = 112
FEATURE                 Location/Qualifiers
source                  1..112
                        mol_type = protein
                        organism = Homo sapiens
SEQUENCE: 892
QVQLLQSGAA VTKPGASVRV SCEASGYNIR DYFIHWWRQA PGQGLQWVGW INPKTGQPNN  60
PRQFQGRVSL TRHASWDFDT FSFYMDLKAL RSDDTAVYFC ARQRSDYWDF DV          112

SEQ ID NO: 893          moltype = AA  length = 112
FEATURE                 Location/Qualifiers
source                  1..112
                        mol_type = protein
                        organism = Homo sapiens
SEQUENCE: 893
QVHLSQSGAA VTKPGASVRV SCEASGYKIS DHFIHWWRQA PGQGLQWVGW INPKTGQPNN  60
PRQFQGRVSL TRQASWDFDT YSFYMDLKAV RSDDTAIYFC ARQRSDFWDF DV          112

SEQ ID NO: 894          moltype = AA  length = 111
FEATURE                 Location/Qualifiers
source                  1..111
                        mol_type = protein
                        organism = Homo sapiens
SEQUENCE: 894
SQHLVQSGTQ VKKPGASVRI SCQASGYSFT DYVLHWWRQA PGQGLEWMGW IKPVYGARNY  60
ARRFQGRINF DRDIYREIAF MDLSGLRSDD TALYFCARDG SGDDTSWHLD P           111

SEQ ID NO: 895          moltype = AA  length = 111
FEATURE                 Location/Qualifiers
source                  1..111
                        mol_type = protein
                        organism = Homo sapiens
SEQUENCE: 895
SQHLVQSGTQ VKKPGASVRV SCQASGYTFT NYILHWWRQA PGQGLEWMGL IKPVFGAVNY  60
ARQFQGRIQL TRDIYREIAF LDLSGLRSDD TAVYYCARDE SGDDLKWHLH P           111

SEQ ID NO: 896          moltype = AA  length = 114
FEATURE                 Location/Qualifiers
source                  1..114
                        mol_type = protein
                        organism = Homo sapiens
SEQUENCE: 896
QVRLSQSGGQ MKKPGESMRL SCRASGYEFL NCPINWIRLA PGRRPEWMGW LKPRGGAVNY  60
ARKFQGRVTM TRDVYSDTAF LELRSLTSDD TAVYFCTRGK YCTARDYYNW DFEH        114

SEQ ID NO: 897          moltype = AA  length = 110
FEATURE                 Location/Qualifiers
source                  1..110
                        mol_type = protein
                        organism = Homo sapiens
```

```
SEQUENCE: 897
QVQLVQSGGQ MKKPGESMRI SCRASGYEFI DCTLNWIRLA PGKRPEWMGW LKPRGGAVNY  60
ARPLQGRVTM TRDVYSDTAF LELRSLTVDD TAVYFCTRGK NCDYNWDFEH            110

SEQ ID NO: 898         moltype = AA  length = 113
FEATURE                Location/Qualifiers
source                 1..113
                       mol_type = protein
                       organism = Homo sapiens
SEQUENCE: 898
QGHLVQSGGG LKKPGTSVTI SCLASEYTFN EFVIHWIRQA PGQGPLWLGL IKRSGRLMTA  60
YNFQDRLSLR RDRSTGTVFM ELRGLRPDDT AVYYCARDGL GEVAPDYRYG IDV         113

SEQ ID NO: 899         moltype = AA  length = 113
FEATURE                Location/Qualifiers
source                 1..113
                       mol_type = protein
                       organism = Homo sapiens
SEQUENCE: 899
QGQLVQSGGG VKKPGTSVTI SCLASEYTFN EFVIHWIRQA PGQGPVWLGL IKRSGRLMTS  60
YKFQDRLSLR RDRSTGTVFM ELRGLRLDDT AVYYCARDGL GEVAPAYLYG IDA         113

SEQ ID NO: 900         moltype = AA  length = 114
FEATURE                Location/Qualifiers
source                 1..114
                       mol_type = protein
                       organism = Homo sapiens
SEQUENCE: 900
QVQLEQSGTA VRKPGASVTL SCQASGYNFV KYIIHWVRQK PGLGFEWVGM IDPYRGRPWS  60
AHKFQGRLSL SRDTSMEILY MTLTSLKSDD TATYFCARAE AASDSHSRPI MFDH        114

SEQ ID NO: 901         moltype = AA  length = 117
FEATURE                Location/Qualifiers
source                 1..117
                       mol_type = protein
                       organism = Homo sapiens
SEQUENCE: 901
QVRLFQSGAQ LKKPGASVTV SCEASGYNFV NYIINWVRQT PGRSFEWVGM IDPRRGRPWS  60
AQKFQGRLTL TRDIDSEKLY MHLSGLRGDD TAVYYCARQD SDFHDGHGHT LRGMFDS     117

SEQ ID NO: 902         moltype = AA  length = 121
FEATURE                Location/Qualifiers
source                 1..121
                       mol_type = protein
                       organism = Homo sapiens
SEQUENCE: 902
QIHLVQSGTE VKKPGSSVTV SCKAYGVNTF GLYAVNWVRQ APGQSLEYIG QIWRWKSSAS  60
HHFRGRVLIS AVDLTGSSPP ISSLEIKNLT SDDTAVYFCT TTSTYDKWSG LHHDGVMAFS  120
S                                                                 121

SEQ ID NO: 903         moltype = AA  length = 95
FEATURE                Location/Qualifiers
source                 1..95
                       mol_type = protein
                       organism = Homo sapiens
SEQUENCE: 903
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWP                            95

SEQ ID NO: 904         moltype = AA  length = 95
FEATURE                Location/Qualifiers
source                 1..95
                       mol_type = protein
                       organism = Homo sapiens
SEQUENCE: 904
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ YDNLP                            95

SEQ ID NO: 905         moltype = AA  length = 98
FEATURE                Location/Qualifiers
source                 1..98
                       mol_type = protein
                       organism = Homo sapiens
SEQUENCE: 905
QSVLTQPPSA SGTPGQRVTI SCSGSSSNIG SNYVYWYQQL PGTAPKLLIY RNNQRPSGVP  60
DRFSGSKSGT SASLAISGLR SEDEADYYCA AWDDSLSG                         98

SEQ ID NO: 906         moltype = AA  length = 91
FEATURE                Location/Qualifiers
```

```
source                  1..91
                        mol_type = protein
                        organism = Homo sapiens
SEQUENCE: 906
DIQMTQSPSS LSASVGDTVT ITCQANGYLN WYQQRRGKAP KLLIYDGSKL ERGVPSRFSG  60
RRWGQEYNLT INNLQPEDIA TYFCQVYEFV V                                 91

SEQ ID NO: 907          moltype = AA  length = 91
FEATURE                 Location/Qualifiers
source                  1..91
                        mol_type = protein
                        organism = Homo sapiens
SEQUENCE: 907
DIQMTQSPSS LSARVGDTVT ITCQANGYLN WYQQRRGKAP KLLIYDGSKL ERGVPARFSG  60
RRWGQEYNLT INNLQPEDVA TYFCQVYEFI V                                 91

SEQ ID NO: 908          moltype = AA  length = 95
FEATURE                 Location/Qualifiers
source                  1..95
                        mol_type = protein
                        organism = Homo sapiens
SEQUENCE: 908
DIQMTQSPSS LSASVGDRVT ITCQAGQGIG SSLQWYQQKP GKAPKLLVHG ASNLHRGVPS  60
RFSGSGFHTT FSLTISGLQR DDFATYFCAV LEFFG                             95

SEQ ID NO: 909          moltype = AA  length = 95
FEATURE                 Location/Qualifiers
source                  1..95
                        mol_type = protein
                        organism = Homo sapiens
SEQUENCE: 909
DIQMTQSPSS LSASVGDRVT INCQAGQGIG SSLNWYQKKP GRAPKLLVHG ASNLQRGVPS  60
RFSGSGFHTT FTLTISSLQP DDVATYFCAV FQWFG                             95

SEQ ID NO: 910          moltype = AA  length = 93
FEATURE                 Location/Qualifiers
source                  1..93
                        mol_type = protein
                        organism = Homo sapiens
SEQUENCE: 910
EIVLTQSPAT LSLSPGETAI ISCRTSQSGS LAWYQQRPGQ APRLVIYSGS TRAAGIPDRF  60
SGSRWGADYN LSISNLESGD FGVYYCQQYE FFG                               93

SEQ ID NO: 911          moltype = AA  length = 95
FEATURE                 Location/Qualifiers
source                  1..95
                        mol_type = protein
                        organism = Homo sapiens
SEQUENCE: 911
EIVLTQSPGT LSLSPGETAI ISCRTSQYGS LAWYQQRPGQ APRLVIYSGS TRAAGIPDRF  60
SGSRWGPDYN LTISNLESGD FGVYYCQQYE FFGQG                             95

SEQ ID NO: 912          moltype = AA  length = 94
FEATURE                 Location/Qualifiers
source                  1..94
                        mol_type = protein
                        organism = Homo sapiens
SEQUENCE: 912
EIVLTQSPAT LSLSPGERAT LSCRASQGLN FVVWYQQKRG QAPRLLIHAP SGRAPGVPDR  60
FSARGSGTEF SLVISSVEPD DFAIYYCQEY SSTP                              94

SEQ ID NO: 913          moltype = AA  length = 94
FEATURE                 Location/Qualifiers
source                  1..94
                        mol_type = protein
                        organism = Homo sapiens
SEQUENCE: 913
EIVLTQSPAT LSLSPGERAT LSCRASQGLN FVVWYQQKGG QAPRLLIHGP TDRAPGVPDR  60
FSARGSGTEF SLVISSVEPD DFALYYCQEY SSTP                              94

SEQ ID NO: 914          moltype = AA  length = 100
FEATURE                 Location/Qualifiers
source                  1..100
                        mol_type = protein
                        organism = Homo sapiens
SEQUENCE: 914
QSALTQPPSA SGAPGQRVTI SCSGGPSNVG GNYVYWYRQF PGTAPTLLIL RDDQRPSGVP  60
DRFSASKSGN SASLAISGLR PDDEGFYFCA TYDSDGSIRL                        100
```

```
SEQ ID NO: 915         moltype = AA  length = 100
FEATURE                Location/Qualifiers
source                 1..100
                       mol_type = protein
                       organism = Homo sapiens
SEQUENCE: 915
NFMLTQVLSV SGTPGQRVII SCSGTSSNVG GNLVSWYQHL PGAAPRLLIH RDDQRPSGVP  60
DRFSGSKSGN SASLVISGLR SDDEADYFCA AYDSTFSLPV                        100

SEQ ID NO: 916         moltype = AA  length = 98
FEATURE                Location/Qualifiers
source                 1..98
                       mol_type = protein
                       organism = Homo sapiens
SEQUENCE: 916
DIQMTQSPST LAASIGGTVR VSCRASQSIT GNWVAWYQQR PGKAPRLLIY RGAALLGGVP  60
SRFSGSAAGT DFTLTIGNLQ AKDFGTFYCQ QYDTYPGT                          98

SEQ ID NO: 917         moltype = AA  length = 16
FEATURE                Location/Qualifiers
source                 1..16
                       mol_type = protein
                       organism = Homo sapiens
SEQUENCE: 917
DGLGEVAPDY RYGIDV                                                  16

SEQ ID NO: 918         moltype = AA  length = 14
FEATURE                Location/Qualifiers
source                 1..14
                       mol_type = protein
                       organism = Homo sapiens
SEQUENCE: 918
QSLSWYRPSG YFES                                                    14

SEQ ID NO: 919         moltype = AA  length = 24
FEATURE                Location/Qualifiers
source                 1..24
                       mol_type = protein
                       organism = Homo sapiens
SEQUENCE: 919
DRGDTRLLDY GDYEDERYYY GMDV                                         24

SEQ ID NO: 920         moltype = AA  length = 20
FEATURE                Location/Qualifiers
source                 1..20
                       mol_type = protein
                       organism = Homo sapiens
SEQUENCE: 920
SINAAVPGLE GVYYYYGMAV                                              20

SEQ ID NO: 921         moltype = AA  length = 24
FEATURE                Location/Qualifiers
source                 1..24
                       mol_type = protein
                       organism = Homo sapiens
SEQUENCE: 921
DRGDTRLLDY GDYEDERYYY GMDV                                         24

SEQ ID NO: 922         moltype = AA  length = 24
FEATURE                Location/Qualifiers
source                 1..24
                       mol_type = protein
                       organism = Homo sapiens
SEQUENCE: 922
DRGDTRLLDY GDYEDERYYY GMDV                                         24

SEQ ID NO: 923         moltype = AA  length = 17
FEATURE                Location/Qualifiers
source                 1..17
                       mol_type = protein
                       organism = Homo sapiens
SEQUENCE: 923
WDYYDSRGYY YGEYFDL                                                 17

SEQ ID NO: 924         moltype = AA  length = 16
FEATURE                Location/Qualifiers
source                 1..16
                       mol_type = protein
                       organism = Homo sapiens
```

```
SEQUENCE: 924
DTKVGAPRQD CYAMDL                                              16

SEQ ID NO: 925          moltype = AA  length = 16
FEATURE                 Location/Qualifiers
source                  1..16
                        mol_type = protein
                        organism = Homo sapiens
SEQUENCE: 925
DGLGEVAPDY RYGIDV                                              16

SEQ ID NO: 926          moltype = AA  length = 18
FEATURE                 Location/Qualifiers
source                  1..18
                        mol_type = protein
                        organism = Homo sapiens
SEQUENCE: 926
ADRFKVAQDE GLFVIFDY                                            18

SEQ ID NO: 927          moltype = AA  length = 21
FEATURE                 Location/Qualifiers
source                  1..21
                        mol_type = protein
                        organism = Homo sapiens
SEQUENCE: 927
DRSSAIGYCS SISCYKGSFD I                                        21

SEQ ID NO: 928          moltype = AA  length = 18
FEATURE                 Location/Qualifiers
source                  1..18
                        mol_type = protein
                        organism = Homo sapiens
SEQUENCE: 928
LAEVPPAIRG SYYYGMDV                                            18

SEQ ID NO: 929          moltype = AA  length = 19
FEATURE                 Location/Qualifiers
source                  1..19
                        mol_type = protein
                        organism = Homo sapiens
SEQUENCE: 929
AYGTGNWRGL YYYYYGMDV                                           19

SEQ ID NO: 930          moltype = AA  length = 8
FEATURE                 Location/Qualifiers
source                  1..8
                        mol_type = protein
                        organism = Homo sapiens
SEQUENCE: 930
SPSYYFDY                                                       8

SEQ ID NO: 931          moltype = AA  length = 16
FEATURE                 Location/Qualifiers
source                  1..16
                        mol_type = protein
                        organism = Homo sapiens
SEQUENCE: 931
DGLGEVAPAY LYGIDA                                              16

SEQ ID NO: 932          moltype = AA  length = 14
FEATURE                 Location/Qualifiers
source                  1..14
                        mol_type = protein
                        organism = Homo sapiens
SEQUENCE: 932
GGLYCSSISC IMDV                                                14

SEQ ID NO: 933          moltype = AA  length = 14
FEATURE                 Location/Qualifiers
source                  1..14
                        mol_type = protein
                        organism = Homo sapiens
SEQUENCE: 933
GGLYCSSISC IMDV                                                14

SEQ ID NO: 934          moltype = AA  length = 16
FEATURE                 Location/Qualifiers
source                  1..16
                        mol_type = protein
```

```
                        organism = Homo sapiens
SEQUENCE: 934
DGLGEVAPAY LYGIDA                                                   16

SEQ ID NO: 935          moltype = AA  length = 18
FEATURE                 Location/Qualifiers
source                  1..18
                        mol_type = protein
                        organism = Homo sapiens
SEQUENCE: 935
ADRFKVAQDE GLFVIFDY                                                 18

SEQ ID NO: 936          moltype = AA  length = 16
FEATURE                 Location/Qualifiers
source                  1..16
                        mol_type = protein
                        organism = Homo sapiens
SEQUENCE: 936
DGLGEVAPAY LYGIDA                                                   16

SEQ ID NO: 937          moltype = AA  length = 11
FEATURE                 Location/Qualifiers
source                  1..11
                        mol_type = protein
                        organism = Homo sapiens
SEQUENCE: 937
EGGLRFLEWL F                                                        11

SEQ ID NO: 938          moltype = AA  length = 12
FEATURE                 Location/Qualifiers
source                  1..12
                        mol_type = protein
                        organism = Homo sapiens
SEQUENCE: 938
SRPPQRLYGM DV                                                       12

SEQ ID NO: 939          moltype = AA  length = 18
FEATURE                 Location/Qualifiers
source                  1..18
                        mol_type = protein
                        organism = Homo sapiens
SEQUENCE: 939
ADPFKVAQDE GLYVIFDY                                                 18

SEQ ID NO: 940          moltype = AA  length = 10
FEATURE                 Location/Qualifiers
source                  1..10
                        mol_type = protein
                        organism = Homo sapiens
SEQUENCE: 940
DSSGSNWFDY                                                          10

SEQ ID NO: 941          moltype = AA  length = 16
FEATURE                 Location/Qualifiers
source                  1..16
                        mol_type = protein
                        organism = Homo sapiens
SEQUENCE: 941
DGLGEVAPAY LYGIDA                                                   16

SEQ ID NO: 942          moltype = AA  length = 5
FEATURE                 Location/Qualifiers
source                  1..5
                        mol_type = protein
                        organism = Homo sapiens
SEQUENCE: 942
NGFDV                                                               5

SEQ ID NO: 943          moltype = AA  length = 18
FEATURE                 Location/Qualifiers
source                  1..18
                        mol_type = protein
                        organism = Homo sapiens
SEQUENCE: 943
ADPFKVAQDE GLYVIFDY                                                 18

SEQ ID NO: 944          moltype = AA  length = 16
FEATURE                 Location/Qualifiers
source                  1..16
```

```
                        mol_type = protein
                        organism = Homo sapiens
SEQUENCE: 944
DGLGEVAPAY LYGIDA                                                   16

SEQ ID NO: 945          moltype = AA  length = 16
FEATURE                 Location/Qualifiers
source                  1..16
                        mol_type = protein
                        organism = Homo sapiens
SEQUENCE: 945
DGLGELAPAY HYGIDV                                                   16

SEQ ID NO: 946          moltype = AA  length = 14
FEATURE                 Location/Qualifiers
source                  1..14
                        mol_type = protein
                        organism = Homo sapiens
SEQUENCE: 946
ARADSHTPID AFDI                                                     14

SEQ ID NO: 947          moltype = AA  length = 16
FEATURE                 Location/Qualifiers
source                  1..16
                        mol_type = protein
                        organism = Homo sapiens
SEQUENCE: 947
DGLGELAPAY HYGIDV                                                   16

SEQ ID NO: 948          moltype = AA  length = 11
FEATURE                 Location/Qualifiers
source                  1..11
                        mol_type = protein
                        organism = Homo sapiens
SEQUENCE: 948
SSGNFEFAFE I                                                        11

SEQ ID NO: 949          moltype = AA  length = 14
FEATURE                 Location/Qualifiers
source                  1..14
                        mol_type = protein
                        organism = Homo sapiens
SEQUENCE: 949
DRWLPQYYYY GMDV                                                     14

SEQ ID NO: 950          moltype = AA  length = 19
FEATURE                 Location/Qualifiers
source                  1..19
                        mol_type = protein
                        organism = Homo sapiens
SEQUENCE: 950
NPESRCIVGR NRGWCRYFD                                                19

SEQ ID NO: 951          moltype = AA  length = 16
FEATURE                 Location/Qualifiers
source                  1..16
                        mol_type = protein
                        organism = Homo sapiens
SEQUENCE: 951
DGLGELAPAY QYGIDV                                                   16

SEQ ID NO: 952          moltype = AA  length = 19
FEATURE                 Location/Qualifiers
source                  1..19
                        mol_type = protein
                        organism = Homo sapiens
SEQUENCE: 952
PKFLPGADIV VVVAATPFD                                                19

SEQ ID NO: 953          moltype = AA  length = 16
FEATURE                 Location/Qualifiers
source                  1..16
                        mol_type = protein
                        organism = Homo sapiens
SEQUENCE: 953
DGLGELAPAY HYGIDV                                                   16

SEQ ID NO: 954          moltype = AA  length = 16
FEATURE                 Location/Qualifiers
```

```
source                  1..16
                        mol_type = protein
                        organism = Homo sapiens
SEQUENCE: 954
DGLGEVAPAY LYGIDA                                                    16

SEQ ID NO: 955          moltype = AA  length = 5
FEATURE                 Location/Qualifiers
source                  1..5
                        mol_type = protein
                        organism = Homo sapiens
SEQUENCE: 955
NGFDV                                                                5

SEQ ID NO: 956          moltype = AA  length = 18
FEATURE                 Location/Qualifiers
source                  1..18
                        mol_type = protein
                        organism = Homo sapiens
SEQUENCE: 956
ADPFKVAQDE GLYVIFDY                                                  18

SEQ ID NO: 957          moltype = AA  length = 12
FEATURE                 Location/Qualifiers
source                  1..12
                        mol_type = protein
                        organism = Homo sapiens
SEQUENCE: 957
EMAVGGTKAL DH                                                        12

SEQ ID NO: 958          moltype = AA  length = 4
FEATURE                 Location/Qualifiers
source                  1..4
                        mol_type = protein
                        organism = Homo sapiens
SEQUENCE: 958
GVSF                                                                 4

SEQ ID NO: 959          moltype = AA  length = 8
FEATURE                 Location/Qualifiers
source                  1..8
                        mol_type = protein
                        organism = Homo sapiens
SEQUENCE: 959
DLLHAHDF                                                             8

SEQ ID NO: 960          moltype = AA  length = 13
FEATURE                 Location/Qualifiers
source                  1..13
                        mol_type = protein
                        organism = Homo sapiens
SEQUENCE: 960
DSVAFVLEGP IDY                                                       13

SEQ ID NO: 961          moltype = AA  length = 15
FEATURE                 Location/Qualifiers
source                  1..15
                        mol_type = protein
                        organism = Homo sapiens
SEQUENCE: 961
YSTRQFFHYY YVTDV                                                     15

SEQ ID NO: 962          moltype = AA  length = 16
FEATURE                 Location/Qualifiers
source                  1..16
                        mol_type = protein
                        organism = Homo sapiens
SEQUENCE: 962
GKVWGITARP RDAGLD                                                    16

SEQ ID NO: 963          moltype = AA  length = 12
FEATURE                 Location/Qualifiers
source                  1..12
                        mol_type = protein
                        organism = Homo sapiens
SEQUENCE: 963
VRDPNYNLHF DS                                                        12

SEQ ID NO: 964          moltype = AA  length = 8
```

```
FEATURE                Location/Qualifiers
source                 1..8
                       mol_type = protein
                       organism = Homo sapiens
SEQUENCE: 964
GLRVYFDL                                                        8

SEQ ID NO: 965         moltype = AA  length = 21
FEATURE                Location/Qualifiers
source                 1..21
                       mol_type = protein
                       organism = Homo sapiens
SEQUENCE: 965
DRSSAIGYCS SISCYKGSFD I                                         21

SEQ ID NO: 966         moltype = AA  length = 10
FEATURE                Location/Qualifiers
source                 1..10
                       mol_type = protein
                       organism = Homo sapiens
SEQUENCE: 966
QKGSGTSLLY                                                      10

SEQ ID NO: 967         moltype = AA  length = 15
FEATURE                Location/Qualifiers
source                 1..15
                       mol_type = protein
                       organism = Homo sapiens
SEQUENCE: 967
DLLESRTYYN DIRDC                                                15

SEQ ID NO: 968         moltype = AA  length = 24
FEATURE                Location/Qualifiers
source                 1..24
                       mol_type = protein
                       organism = Homo sapiens
SEQUENCE: 968
DRGDTRLLDY GDYEDERYYY GMDV                                      24

SEQ ID NO: 969         moltype = AA  length = 9
FEATURE                Location/Qualifiers
source                 1..9
                       mol_type = protein
                       organism = Homo sapiens
SEQUENCE: 969
VRGSWNFDY                                                       9

SEQ ID NO: 970         moltype = AA  length = 22
FEATURE                Location/Qualifiers
source                 1..22
                       mol_type = protein
                       organism = Homo sapiens
SEQUENCE: 970
TYLAVVPDGF DGYSSSWYWF DP                                        22

SEQ ID NO: 971         moltype = AA  length = 21
FEATURE                Location/Qualifiers
source                 1..21
                       mol_type = protein
                       organism = Homo sapiens
SEQUENCE: 971
DRSSAIGYCS SISCYKGSFD I                                         21

SEQ ID NO: 972         moltype = AA  length = 12
FEATURE                Location/Qualifiers
source                 1..12
                       mol_type = protein
                       organism = Homo sapiens
SEQUENCE: 972
CQDGLASRPI DF                                                   12

SEQ ID NO: 973         moltype = AA  length = 13
FEATURE                Location/Qualifiers
source                 1..13
                       mol_type = protein
                       organism = Homo sapiens
SEQUENCE: 973
DSVSKSYSAP PEF                                                  13
```

```
SEQ ID NO: 974          moltype = AA  length = 16
FEATURE                 Location/Qualifiers
source                  1..16
                        mol_type = protein
                        organism = Homo sapiens
SEQUENCE: 974
DGLGEVAPDY RYGIDV                                                  16

SEQ ID NO: 975          moltype = AA  length = 18
FEATURE                 Location/Qualifiers
source                  1..18
                        mol_type = protein
                        organism = Homo sapiens
SEQUENCE: 975
HVRPYDRSGY PERPNWFD                                                18

SEQ ID NO: 976          moltype = AA  length = 11
FEATURE                 Location/Qualifiers
source                  1..11
                        mol_type = protein
                        organism = Homo sapiens
SEQUENCE: 976
NAGAYFYPFD I                                                       11

SEQ ID NO: 977          moltype = AA  length = 22
FEATURE                 Location/Qualifiers
source                  1..22
                        mol_type = protein
                        organism = Homo sapiens
SEQUENCE: 977
EMGTFTLLGV VIDHYDFYPM DV                                           22

SEQ ID NO: 978          moltype = AA  length = 18
FEATURE                 Location/Qualifiers
source                  1..18
                        mol_type = protein
                        organism = Homo sapiens
SEQUENCE: 978
GRGKRCSGAY CFAGYFDS                                                18

SEQ ID NO: 979          moltype = AA  length = 16
FEATURE                 Location/Qualifiers
source                  1..16
                        mol_type = protein
                        organism = Homo sapiens
SEQUENCE: 979
DGLGEVAPAY LYGIDA                                                  16

SEQ ID NO: 980          moltype = AA  length = 112
FEATURE                 Location/Qualifiers
source                  1..112
                        mol_type = protein
                        organism = Homo sapiens
SEQUENCE: 980
QVQLVQSGGQ MKKPGESMRI SCRASGYEFI DCTLNWIRLA PGKRPEWMGW LKPRGGAVNY  60
ARPLQGRVTM TRDVYSDTAF LELRSLTVDD TAVYFCTRGK NCDYNWDFEH WG          112

SEQ ID NO: 981          moltype = AA  length = 112
FEATURE                 Location/Qualifiers
source                  1..112
                        mol_type = protein
                        organism = Homo sapiens
SEQUENCE: 981
QVQLVQSGGQ MKKPGESMRI SCQASGYEFI DCTLNWVRLA PGRRPEWMGW LKPRGGAVNY  60
ARPLQGRVTM TRDVYSDTAF LELRSLTADD TAVYYCTRGK NCDYNWDFEH WG          112

SEQ ID NO: 982          moltype = AA  length = 116
FEATURE                 Location/Qualifiers
source                  1..116
                        mol_type = protein
                        organism = Homo sapiens
SEQUENCE: 982
QVRLSQSGGQ MKKPGESMRL SCRASGYEFL NCPINWIRLA PGRRPEWMGW LKPRGGAVNY  60
ARKFQGRVTM TRDVYSDTAF LELRSLTSDD TAVYFCTRGK YCTARDYYNW DFEHWG      116

SEQ ID NO: 983          moltype = AA  length = 112
FEATURE                 Location/Qualifiers
source                  1..112
                        mol_type = protein
```

-continued

```
                         organism = Homo sapiens
SEQUENCE: 983
QVRLSQSGGQ MKKPGESMRI SCRASGYEFI DCTLNWIRLA PGRRPEWMGW LKPRGGAVNY  60
ARPLQGRVTM TRDVYSDTAF LELRSLTADD TAVYFCTRGK NCNYNWDFEH WG          112

SEQ ID NO: 984           moltype = AA  length = 112
FEATURE                  Location/Qualifiers
source                   1..112
                         mol_type = protein
                         organism = Homo sapiens
SEQUENCE: 984
QVRLSQSGGQ MKKPGESMRI SCRASGYEFI DCTLNWIRLA PGRRPEWMGW LKPRGGAVNY  60
ARSFQGRVTM TRDVYSDTAF LELRSLTADD TAVYFCARGK NCDYNWDFEH WG          112

SEQ ID NO: 985           moltype = AA  length = 94
FEATURE                  Location/Qualifiers
source                   1..94
                         mol_type = protein
                         organism = Homo sapiens
SEQUENCE: 985
EIVLTQSPGT LSLSPGETAI ISCRTSQYGS LAWYQQRPGQ APRLVIYSGS TRAAGIPDRF  60
SGSRWGPDYN LTISNLESGD FGVYYCQQYE FFGQ                              94

SEQ ID NO: 986           moltype = AA  length = 94
FEATURE                  Location/Qualifiers
source                   1..94
                         mol_type = protein
                         organism = Homo sapiens
SEQUENCE: 986
EIVLTQSPGT LSLSPGETAI ISCRTSQYGS LAWYQQRPGQ APRLVIYSGS TRAAGIPDRF  60
SGSRWGPDYN LTIRNLESGD FGLYYCQQYE FFGQ                              94

SEQ ID NO: 987           moltype = AA  length = 94
FEATURE                  Location/Qualifiers
source                   1..94
                         mol_type = protein
                         organism = Homo sapiens
SEQUENCE: 987
EIVLTQSPAT LSLSPGETAI ISCRTSQSGS LAWYQQRPGQ APRLVIYSGS TRAAGIPDRF  60
SGSRWGADYN LSISNLESGD FGVYYCQQYE FFGQ                              94

SEQ ID NO: 988           moltype = AA  length = 94
FEATURE                  Location/Qualifiers
source                   1..94
                         mol_type = protein
                         organism = Homo sapiens
SEQUENCE: 988
EIVLTQSPAT LSLSPGETAI ISCRTSQYGS LAWYQQRPGQ APRLVIYSGS TRAAGIPDRF  60
SGSRWGPDYN LTISNLESGD FGVYYCQQYE FFGQ                              94

SEQ ID NO: 989           moltype = AA  length = 94
FEATURE                  Location/Qualifiers
source                   1..94
                         mol_type = protein
                         organism = Homo sapiens
SEQUENCE: 989
EIVLTQSPAT LSLSPGETAI ISCRTSQYGS LAWYQQRPGQ APRLVIYSGS TRAAGIPDRF  60
SGSRWGPDYN LTISNLESGD FGVYYCQQYE FFGQ                              94

SEQ ID NO: 990           moltype = DNA  length = 294
FEATURE                  Location/Qualifiers
source                   1..294
                         mol_type = unassigned DNA
                         organism = Homo sapiens
CDS                      1..294
SEQUENCE: 990
caggtgcagc tggtgcagtc tggggctgag gtgaagaagc ctggggcctc agtgaaggtc  60
tcctgcaagg cttctggata caccttcacc ggctactata tgcactgggt gcgacaggcc  120
cctggacaag ggcttgagtg gatgggatgg atcaacccta acagtggtgg cacaaactat  180
gcacagaagt ttcagggcag ggtcaccatg accagggaca cgtccatcag cacagcctac  240
atggagctga gcaggctgag atctgacgac acggccgtgt attactgtgc gaga        294

SEQ ID NO: 991           moltype = AA  length = 98
FEATURE                  Location/Qualifiers
source                   1..98
                         mol_type = protein
                         organism = Homo sapiens
SEQUENCE: 991
QVQLVQSGAE VKKPGASVKV SCKASGYTFT GYYMHWVRQA PGQGLEWMGW INPNSGGTNY  60
```

```
AQKFQGRVTM TRDTSISTAY MELSRLRSDD TAVYYCAR                        98

SEQ ID NO: 992          moltype = DNA  length = 306
FEATURE                 Location/Qualifiers
source                  1..306
                        mol_type = unassigned DNA
                        organism = Homo sapiens
SEQUENCE: 992
caggtccatt tgtcacagtc tggggcagcg gtgacgaagc ccggggcctc agtgagagtc  60
tcctgcgagg cttccggata caagattagt gaccacttta ttcattggtg gcgacaggcc  120
ccaggacagg gccttcagtg ggtggggtgg atcaatccta agactggtca gccaaacaat  180
cctcgtcaat ttcagggtag agtcagtctg actcgacagg cgtcgtggga ctttgacaca  240
tattcctttt acatggacct caaggcagta agatcggacg acacggccat ttatttctgt  300
gcgcga                                                            306

SEQ ID NO: 993          moltype = DNA  length = 306
FEATURE                 Location/Qualifiers
source                  1..306
                        mol_type = unassigned DNA
                        organism = Homo sapiens
SEQUENCE: 993
caggtccaat tgttacagtc tggggcagcg gtgacgaagc ccggggcctc agtgagagtc  60
tcctgcgagg cttctggata caacattcgt gactacttta ttcattggtg gcgacaggcc  120
ccaggacagg gccttcagtg ggtgggatgg atcaatccta agacaggtca gccaaacaat  180
cctcgtcaat ttcagggtag agtcagtctg actcgacacg cgtcgtggga ctttgacaca  240
ttttcctttt acatggacct gaaggcacta agatcggacg acacggccgt ttatttctgt  300
gcgcga                                                            306

SEQ ID NO: 994          moltype = DNA  length = 294
FEATURE                 Location/Qualifiers
source                  1..294
                        mol_type = unassigned DNA
                        organism = Homo sapiens
SEQUENCE: 994
caagtgcgac tgtcgcagtc tggaggtcag atgaagaagc ctggcgagtc gatgagactt  60
tcctgtcggg cttccggata tgaatttctg aattgtccaa taaattggat tcgcctggcc  120
cccggaagac ggcctgagtg gatgggatgg ctgaagccta ggggaggggc cgtcaattac  180
gcacgtaaat ttcagggcag agtgaccatg actcgagacg tgtattccga cacagccttt  240
ttggagttgc gctccttgac atcagacgac acggccgtct atttttgtac tagg        294

SEQ ID NO: 995          moltype = DNA  length = 294
FEATURE                 Location/Qualifiers
source                  1..294
                        mol_type = unassigned DNA
                        organism = Homo sapiens
SEQUENCE: 995
caggtgcagc tggtgcagtc tggaggtcag atgaagaagc ctggcgagtc gatgagaatt  60
tcttgtcggg cttctggata tgaatttatt gattgtacgc taaattggat tcgtctggcc  120
cccggaaaaa ggcctgagtg gatgggatgg ctgaagcctc ggggggggc cgtcaactac  180
gcacgtccac ttcagggcag agtgaccatg actcgagacg tttattccga cacagccttt  240
ttggagctgc gctcgttgac agtagacgac acggccgtct acttttgtac tagg        294

SEQ ID NO: 996          moltype = DNA  length = 294
FEATURE                 Location/Qualifiers
source                  1..294
                        mol_type = unassigned DNA
                        organism = Homo sapiens
SEQUENCE: 996
tcccagcatt tggtgcaatc tgggactcag gtgaagaagc ctggggcctc agtgaggatc  60
tcatgccagg cttctggata cagcttcacc gactacgttc tccactggtg gcgacaggcc  120
ccaggccaag ggctggagtg gatggggtgg atcaagcctg tctacggtgc cagaaactac  180
gcgcgcaggt ttcagggcag gataaacttt gatcgggaca tctacaggga gatagccttc  240
atggacttga gtggactgag atctgacgac acggccctat atttttgtgc gaga        294

SEQ ID NO: 997          moltype = DNA  length = 294
FEATURE                 Location/Qualifiers
source                  1..294
                        mol_type = unassigned DNA
                        organism = Homo sapiens
SEQUENCE: 997
tcccagcatt tggtgcaatc tgggactcag gtgaagaagc ctggggcctc agtgcgggtc  60
tcctgccagg cttctggata taccttcacc aattacattc tccactggtg gcgacaggcc  120
cctggacaag ggctggagtg gatgggattg atcaagcctg tctttggtgc cgtaaattac  180
gcgcgccagt ttcagggcag gattcagttg actagggaca tctacaggga gatagccttc  240
ctggacctga gtggcctcag atctgacgac acggccgtct attactgtgc gcga        294

SEQ ID NO: 998          moltype = DNA  length = 294
FEATURE                 Location/Qualifiers
source                  1..294
```

```
                        mol_type = unassigned DNA
                        organism = Homo sapiens
CDS                     1..294
SEQUENCE: 998
caggtgcagc tggtgcagtc tggggctgag gtgaagaagc ctggggcctc agtgaaggtt  60
tcctgcaagg catctggata caccttcaac agctactata tgcactgggt gcgacaggcc  120
cctggacaag ggcttgagtg gatgggaata atcaacccta gtggtggtag cacaagctac  180
gcacagaagt tccagggcag agtcaccatg accagggaca cgtccacgag cacagtctac  240
atggagctga gcagcctgag atctgaggac acggccgtgt attactgtgc gaga        294

SEQ ID NO: 999          moltype = AA  length = 98
FEATURE                 Location/Qualifiers
source                  1..98
                        mol_type = protein
                        organism = Homo sapiens
SEQUENCE: 999
QVQLVQSGAE VKKPGASVKV SCKASGYTFN SYYMHWVRQA PGQGLEWMGI INPSGGSTSY  60
AQKFQGRVTM TRDTSTSTVY MELSSLRSED TAVYYCAR                          98

SEQ ID NO: 1000         moltype = DNA  length = 291
FEATURE                 Location/Qualifiers
source                  1..291
                        mol_type = unassigned DNA
                        organism = Homo sapiens
SEQUENCE: 1000
caggggcact tggtgcagtc cgggggtgga ctgaagaaac ctgggacgtc agtgacgatt  60
tcctgcctgg catctgaata cacattcaac gaattcgtta ttcactggat tcgacaggcc  120
cctggacagg ggcctctgtg gctgggtcta atcaaacgta gcggtcgttt gatgactgcc  180
tataattttc aagacagact cagtctgcga agagaccgtt cgacgggaac agtcttcatg  240
gagttgcggg gtctcagacc tgacgacacg gccgtgtatt attgtgcgag g           291

SEQ ID NO: 1001         moltype = DNA  length = 291
FEATURE                 Location/Qualifiers
source                  1..291
                        mol_type = unassigned DNA
                        organism = Homo sapiens
SEQUENCE: 1001
caggggcagt tggtgcagtc cgggggtgga gtgaagaaac ctgggacgtc agtgacgatt  60
tcctgcctgg catctgagta cacattcaat gaattcgtta ttcactggat tagacaggcc  120
cctggacagg ggcctgtgtg gctgggtcta atcaaacgta gcggtcgttt gatgacttcc  180
tataaattcc aagacagact cagtctgcga agagaccgtt cgacgggaac agtgttcatg  240
gagttgcggg gtctcagact tgacgacacg gccgtctatt actgtgcgag g           291

SEQ ID NO: 1002         moltype = DNA  length = 294
FEATURE                 Location/Qualifiers
source                  1..294
                        mol_type = unassigned DNA
                        organism = Homo sapiens
SEQUENCE: 1002
caggtgcagc tggaacaatc ggggactgcg gtgaggaagc ctggggcctc ggtgacgctt  60
tcctgccagg cgtccggtta caacttcgtc aaatacatca ttcactgggt gcgccagaaa  120
cctggactcg gctttgagtg ggttggcatg atcgacccct accgtggccg gccatggtcc  180
gcgcacaaat ttcagggtcg actctccctg agtcgagaca cttccatgga aatactatat  240
atgaccctga ccagcctgaa atctgacgac acggccacct atttctgtgc gagg        294

SEQ ID NO: 1003         moltype = DNA  length = 294
FEATURE                 Location/Qualifiers
source                  1..294
                        mol_type = unassigned DNA
                        organism = Homo sapiens
SEQUENCE: 1003
caggtgcgat tatttcaatc tggggcacag ttgaagaaac ctggggcctc agtgacggtc  60
tcttgcgagg cgtctggata caacttcgtc aactacatta taaattgggt ccgacagaca  120
cctggacgaa gttttgagtg ggtggggatg atcgacccta gacgcggcag gccatggtcc  180
gcgcagaagt tccagggcag actcactttg acccgggaca tcgactccga gaaactctac  240
atgcatttga gtggcctgag aggtgacgac acggccgtct actattgcgc gagg        294

SEQ ID NO: 1004         moltype = DNA  length = 264
FEATURE                 Location/Qualifiers
source                  1..264
                        mol_type = unassigned DNA
                        organism = Homo sapiens
CDS                     1..264
SEQUENCE: 1004
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgt                                         264
```

```
SEQ ID NO: 1005        moltype = AA  length = 88
FEATURE                Location/Qualifiers
source                 1..88
                       mol_type = protein
                       organism = Homo sapiens
SEQUENCE: 1005
EIVLTQSPAT LSLSPGERAT LSCRASQSVS SYLAWYQQKP GQAPRLLIYD ASNRATGIPA  60
RFSGSGSGTD FTLTISSLEP EDFAVYYC                                     88

SEQ ID NO: 1006        moltype = DNA  length = 258
FEATURE                Location/Qualifiers
source                 1..258
                       mol_type = unassigned DNA
                       organism = Homo sapiens
SEQUENCE: 1006
gaaattgtgt tgacacagtc tccaggcacc ctgtctttgt ctccagggga aacagccatc  60
atctcttgtc ggaccagtca gtatggttcc ttagcctggt atcaacagag gcccggccag  120
gcccccaggc tcgtcatcta ttcgggctct actcgggccg ctggcatccc agacaggttc  180
agcggcagtc ggtgggggcc agactacaat ctcaccatca gcaacctgga gtcgggagat  240
tttggtgttt attattgc                                                258

SEQ ID NO: 1007        moltype = DNA  length = 258
FEATURE                Location/Qualifiers
source                 1..258
                       mol_type = unassigned DNA
                       organism = Homo sapiens
SEQUENCE: 1007
gaaattgtgt tgacacagtc tccagccacc ctgtctttgt ctccagggga aacagccatc  60
atctcttgtc ggaccagtca gtctggttcc ttagcctggt atcaacagag gcccggccag  120
gcccccaggc tcgtcatcta ttcgggttct actcgggccg ctggcatccc agacaggttc  180
agcggcagtc ggtggggggc agactacaat ctcagcatca gcaacctgga gtcgggagat  240
tttggtgttt attattgt                                                258

SEQ ID NO: 1008        moltype = DNA  length = 261
FEATURE                Location/Qualifiers
source                 1..261
                       mol_type = unassigned DNA
                       organism = Homo sapiens
SEQUENCE: 1008
gaaattgtgt tgacgcagtc tccagccacc ctgtctctgt ctccagggga aagagccacc  60
ctttcctgca gggccagtca gggtttgaat ttcgtagtct ggtatcaaca aaagggtggg  120
caggctccca gacttctcat ccacggacct actgataggg cccctggcgt cccagacaga  180
ttcagtgccc gggggtccgg gacagagttc tctctcgtca ttagttcggt ggagcctgat  240
gatttcgcac tatattactg t                                            261

SEQ ID NO: 1009        moltype = DNA  length = 261
FEATURE                Location/Qualifiers
source                 1..261
                       mol_type = unassigned DNA
                       organism = Homo sapiens
SEQUENCE: 1009
gaaattgtgt tgacgcagtc tccagccacc ctgtctctgt ctccagggga aagagccacc  60
ctttcctgca gggccagtca gggtctgaac ttcgtagtct ggtatcaaca aaaacgtggg  120
caggctccca gacttctcat ccacgctcct tctggtaggg cccctggcgt cccagacaga  180
ttcagtgccc gggggtccgg gacagagttc tctctcgtca ttagttcggt ggagcctgat  240
gatttcgcaa tatattactg t                                            261

SEQ ID NO: 1010        moltype = DNA  length = 264
FEATURE                Location/Qualifiers
source                 1..264
                       mol_type = unassigned DNA
                       organism = Homo sapiens
CDS                    1..264
SEQUENCE: 1010
gacatccaga tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcag cctgcagcct  240
gaagatattg caacatatta ctgt                                         264

SEQ ID NO: 1011        moltype = AA  length = 88
FEATURE                Location/Qualifiers
source                 1..88
                       mol_type = protein
                       organism = Homo sapiens
SEQUENCE: 1011
DIQMTQSPSS LSASVGDRVT ITCQASQDIS NYLNWYQQKP GKAPKLLIYD ASNLETGVPS  60
RFSGSGSGTD FTFTISSLQP EDIATYYC                                     88
```

```
SEQ ID NO: 1012        moltype = DNA  length = 252
FEATURE                Location/Qualifiers
source                 1..252
                       mol_type = unassigned DNA
                       organism = Homo sapiens
SEQUENCE: 1012
gacatccaga tgacccagtc tccatcctcc ctgtctgcac gtgtaggcga taccgtcact  60
atcacttgcc aggcaaacgg ctacttaaat tggtatcaac agagacgagg gaaagcccca  120
aaactcctga tctacgatgg gtccaaattg gagagaggcg tcccagcaag gttcagtgga  180
agaagatggg gacaagaata taatctgacc atcaacaatc tgcagcccga agacgttgca  240
acatattttt gt                                                     252

SEQ ID NO: 1013        moltype = DNA  length = 252
FEATURE                Location/Qualifiers
source                 1..252
                       mol_type = unassigned DNA
                       organism = Homo sapiens
SEQUENCE: 1013
gacatccaga tgacccagtc tccatcctcc ctgtctgcct ctgtgggaga taccgtcact  60
atcacttgcc aggcaaacgg ctacttaaat tggtatcaac agaggcgagg gaaagcccca  120
aaactcctga tctacgatgg gtccaaattg gaaagagggg tcccatcaag gttcagtgga  180
agaagatggg ggcaagaata taatctgacc atcaacaatc tgcagcccga agacattgca  240
acatattttt gt                                                     252

SEQ ID NO: 1014        moltype = DNA  length = 264
FEATURE                Location/Qualifiers
source                 1..264
                       mol_type = unassigned DNA
                       organism = Homo sapiens
SEQUENCE: 1014
gacatccaga tgacccagtc tccatcctcc ctgtctgcat ctgtaggaga cagagtcacc  60
ataaactgcc aggcgggtca gggcattggc tcctctttaa attggtatca aaaaaaacca  120
gggagagccc ctaagctcct ggtccacggc gcttccaatc ttcaaagagg ggtcccatcg  180
aggttcagtg gaagtggatt tcacacaact ttcactctca ccatcagcag cctgcagcct  240
gacgatgttg cgacatactt ctgt                                        264

SEQ ID NO: 1015        moltype = DNA  length = 264
FEATURE                Location/Qualifiers
source                 1..264
                       mol_type = unassigned DNA
                       organism = Homo sapiens
SEQUENCE: 1015
gacatccaga tgacccagtc tccatcctcc ctgtctgcat ctgttggaga cagagtcacc  60
atcacctgcc aggcgggtca gggcattggc tcctctctac agtggtatca acaaaaacca  120
gggaaagccc ctaagctcct ggtccacggc gcttccaact tacacagagg ggtcccatca  180
aggttcagtg gaagtggatt ccacacaact ttcagtctca ccatcagcgg cctacagcgt  240
gacgattttg cgacatactt ctgt                                        264

SEQ ID NO: 1016        moltype = DNA  length = 267
FEATURE                Location/Qualifiers
source                 1..267
                       mol_type = unassigned DNA
                       organism = Homo sapiens
CDS                    1..267
SEQUENCE: 1016
cagtctgtgc tgactcagcc accctcagcg tctgggaccc ccgggcagag ggtcaccatc  60
tcttgttctg gaagcagctc caacatcgga agtaattatg tatactggta ccagcagctc  120
ccaggaacgg cccccaaact cctcatctat aggaataatc agcggccctc aggggtccct  180
gaccgattct ctggctccaa gtctggcacc tcagcctccc tggccatcag tgggctccgg  240
tccgaggatg aggctgatta ttactgt                                     267

SEQ ID NO: 1017        moltype = AA  length = 89
FEATURE                Location/Qualifiers
source                 1..89
                       mol_type = protein
                       organism = Homo sapiens
SEQUENCE: 1017
QSVLTQPPSA SGTPGQRVTI SCSGSSSNIG SNYVYWYQQL PGTAPKLLIY RNNQRPSGVP  60
DRFSGSKSGT SASLAISGLR SEDEADYYC                                   89

SEQ ID NO: 1018        moltype = DNA  length = 267
FEATURE                Location/Qualifiers
source                 1..267
                       mol_type = unassigned DNA
                       organism = Homo sapiens
SEQUENCE: 1018
aattttatgc tgactcaggt cctctcagtg tctgggaccc ccggacagag agtcatcatc  60
tcctgctctg gaaccagctc caacgtcggc ggtaacttgg tttcctggta tcaacacttg  120
```

-continued

```
ccaggcgcgg ctcccagact cctcatccat agagatgatc aacggccctc tggggtccct  180
gaccgcttct ccggttccaa gtctggcaat tcagcctccc tggtcatcag tgggctccgg  240
tccgacgatg aggctgatta tttctgt                                       267

SEQ ID NO: 1019        moltype = DNA  length = 267
FEATURE                Location/Qualifiers
source                 1..267
                       mol_type = unassigned DNA
                       organism = Homo sapiens
SEQUENCE: 1019
cagtctgccc tgactcagcc accctcagcg tctggggccc ccgggcagag ggtcaccatc  60
tcctgttccg gaggtccctc caacgtcggc ggcaattatg tctactggta tcggcagttt  120
ccaggcacgg cccccacgct cctcatcctt cgagatgacc agcggccctc aggggtccct  180
gaccgattct ccgcgtctaa gtctggcaat tcagcctccc tggccatcag tgggctccga  240
ccggacgatg agggttttta tttctgt                                       267

SEQ ID NO: 1020        moltype = AA  length = 130
FEATURE                Location/Qualifiers
source                 1..130
                       mol_type = protein
                       organism = Homo sapiens
SEQUENCE: 1020
QVRLEQSGAA MRKPGASVTL SCQASGYNFV KYIIHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                          130

SEQ ID NO: 1021        moltype = AA  length = 130
FEATURE                Location/Qualifiers
source                 1..130
                       mol_type = protein
                       organism = Homo sapiens
SEQUENCE: 1021
QVRLEQSGAA MRKPGASVTL SCQASGYNFV KYIVHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                          130

SEQ ID NO: 1022        moltype = AA  length = 130
FEATURE                Location/Qualifiers
source                 1..130
                       mol_type = protein
                       organism = Homo sapiens
SEQUENCE: 1022
QVRLEQSGTA MRKPGASVTL SCQASGYNFV KYIVHWVRQK PGLGFEWVGM IDPYRGRPWS  60
AHKFQGRLSL SRDTSMEILY MTLTSLKSDD TATYFCARAE AASDSHSRPI MFDHWGQGSR  120
VTVSSASTKG                                                          130

SEQ ID NO: 1023        moltype = AA  length = 130
FEATURE                Location/Qualifiers
source                 1..130
                       mol_type = protein
                       organism = Homo sapiens
SEQUENCE: 1023
QVRLEQSGAA MRKPGASVTL SCQASGYNFV KYIVHWVRQK PGLGFEWVGM IDPYRGRPWS  60
AHKFQGRLSL SRDTSMEILY MTLTSLTSDD TATYFCARAE AASDSHSRPI MFDHWGQGSR  120
VTVSSASTKG                                                          130

SEQ ID NO: 1024        moltype = AA  length = 144
FEATURE                Location/Qualifiers
source                 1..144
                       mol_type = protein
                       organism = Homo sapiens
SEQUENCE: 1024
QVRLEQSGVA MRKPGASVTL SCQASGYNFV KYIIHWVRQK PGLGFEWVGM IDPYRGRPWS  60
AHKFQGRLSL SRDTSMEILY MTLTSLKSDD TATYFCARAE AASDIHSRPI ILTGPGEYGL  120
DLEHMDWTWR ILCLLAVAPG CHSQ                                          144

SEQ ID NO: 1025        moltype = AA  length = 130
FEATURE                Location/Qualifiers
source                 1..130
                       mol_type = protein
                       organism = Homo sapiens
SEQUENCE: 1025
QVRLEQSGGA LRKPGASVTL SCQASGYNFV KYIIHWVRQR PGLGFEWVGM IDPYRGRPWY  60
AHSFAGRLSL SRDTSTETLY MTLSSLKSDD TATYFCARAE AASDSHSRPI MDWTWRILCL  120
LAVVPASTKG                                                          130

SEQ ID NO: 1026        moltype = AA  length = 117
FEATURE                Location/Qualifiers
source                 1..117
```

```
                         mol_type = protein
                         organism = Homo sapiens
SEQUENCE: 1026
QVRLEQSGAA VRTPGASVTL SCQASGYKFV NYIIHWVRQR PGLAFEWVGM IDPYRGRPWS  60
AHSFEGRLSL SRDVSMEILY MTLTSLRSDD TATYFCARAE AESQSHSRPI ISTSGAR     117

SEQ ID NO: 1027          moltype = AA  length = 130
FEATURE                  Location/Qualifiers
source                   1..130
                         mol_type = protein
                         organism = Homo sapiens
SEQUENCE: 1027
QVRLEQSGAA VRKPGASVTL SCQASGYNFV NYIIHWVRQR PGLDFEWVGM IDPYRGRPWS  60
AHKFQGRLSL SRDVSTEILY MTLSSLRSDD TATYFCARAE AESQSHSRPI MFDFWGQGSR  120
VTVSSASTKG                                                         130

SEQ ID NO: 1028          moltype = AA  length = 130
FEATURE                  Location/Qualifiers
source                   1..130
                         mol_type = protein
                         organism = Homo sapiens
SEQUENCE: 1028
QVRLEQSGAA VRKPGASVTL SCQASGYNFV NYIIHWVRQR PGLDFEWVGM IDPYRGRPWS  60
AHKFQGRLSL SRDVSTEILY MTLNSLRSDD TATYFCARAE AESQSHSRPI MFDSWGQGSR  120
VTVSSASTKG                                                         130

SEQ ID NO: 1029          moltype = AA  length = 130
FEATURE                  Location/Qualifiers
source                   1..130
                         mol_type = protein
                         organism = Homo sapiens
SEQUENCE: 1029
QVRLEQSGAA VRKPGASVTL SCQASGYNFV NYIIHWVRQR PGLDFEWVGM IDPYRGRPWS  60
AHKFEGRLSL SRDVSTEVLY MTLSSLRSDD TATYFCARAE AESQSHSRPI MFDYWGQGSR  120
VTVSSASTKG                                                         130

SEQ ID NO: 1030          moltype = AA  length = 130
FEATURE                  Location/Qualifiers
source                   1..130
                         mol_type = protein
                         organism = Homo sapiens
SEQUENCE: 1030
QVRLEQSGAA VRKPGASVTL SCQASGYNFV RYIIHWVRQR PGLDFEWVGM IDPYRGRPWS  60
AHKFGGRLSL TRDVSTEILY MTLTSLRSDD TATYFCARAE AESQSHSRPI MFDSWGQGSR  120
VTVSSASTKG                                                         130

SEQ ID NO: 1031          moltype = AA  length = 130
FEATURE                  Location/Qualifiers
source                   1..130
                         mol_type = protein
                         organism = Homo sapiens
SEQUENCE: 1031
QVRLEQSGTA VRKPGASVTI SCQASGYNFV KFFIHWVRQR PGQGFEWVGM IEPFRGRPWS  60
AGNFQGRLSL SRDVSTETLY MTLNNLRSDD TAVYFCARLE AESDSHSRPI MFDHWGHGSL  120
VTVSSASTKG                                                         130

SEQ ID NO: 1032          moltype = AA  length = 130
FEATURE                  Location/Qualifiers
source                   1..130
                         mol_type = protein
                         organism = Homo sapiens
SEQUENCE: 1032
QVRLEQSGTA VRKPGASVTI SCQASGYNFV KFFIHGVRQR PGQGFEWVGM IEPFRGRPWS  60
AGNFQGRLSL SRDVSTETLY MTLNNLRSDD TAVYFCARLE AESDSHSRPI MFDHWGHGSL  120
VTVSSASTKG                                                         130

SEQ ID NO: 1033          moltype = AA  length = 130
FEATURE                  Location/Qualifiers
source                   1..130
                         mol_type = protein
                         organism = Homo sapiens
SEQUENCE: 1033
QVRLEQSGNA VRKPGASVTI SCQASGYNFV KFFIHWVRQR PGQGFEWVGM IEPFRGRPWS  60
AGNFQGRLSL SRDVSTETLY MTLNNLRSDD TAVYFCARLE AESDSHSRPI MFDHWGHGSL  120
VTVSSASTKG                                                         130

SEQ ID NO: 1034          moltype = AA  length = 130
FEATURE                  Location/Qualifiers
source                   1..130
```

```
                        mol_type = protein
                        organism = Homo sapiens
SEQUENCE: 1034
QVRLEQSGAA VKKPGASVTI SCQASGYNFV KFFIHWVRQR PGQGFEWVGM IEPYRGRPWS  60
AGNFQGRLSL SRDVSTETLY MTLNNLRSDD TAVYFCARLE AESDSHSRPI MFDHWGHGSL  120
VTVSSASTKG                                                        130

SEQ ID NO: 1035         moltype = AA  length = 133
FEATURE                 Location/Qualifiers
source                  1..133
                        mol_type = protein
                        organism = Homo sapiens
SEQUENCE: 1035
QVRLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 1036         moltype = AA  length = 133
FEATURE                 Location/Qualifiers
source                  1..133
                        mol_type = protein
                        organism = Homo sapiens
SEQUENCE: 1036
QVQLFQSGAA MRKPGASVTI SCEASGYNFM NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 1037         moltype = AA  length = 133
FEATURE                 Location/Qualifiers
source                  1..133
                        mol_type = protein
                        organism = Homo sapiens
SEQUENCE: 1037
QVRLFQSGAA MRKPGASVTI SCEASGYNFL NYFVHWVRQR PGRGFEWLGM INPRGGRPWS  60
AQSVQGRLTL TRDTSTEMFY MRLDGLRSDD TATYFCARNE ADYHDGNGHS LRGMFDYWGQ  120
GSLITVSSAS TKG                                                    133

SEQ ID NO: 1038         moltype = AA  length = 133
FEATURE                 Location/Qualifiers
source                  1..133
                        mol_type = protein
                        organism = Homo sapiens
SEQUENCE: 1038
QVRLFQSGAA MKKPGASVTI SCEASGYNFM NYFVHWVRQR PGRGFEWLGM INPRGGRPWS  60
AQSVQGRLTL TRDISTEMFY MRLDGLRSDD TATYFCARNE ADYHDGNGHS LRGMFDYWGQ  120
GSLITVSSAS TKG                                                    133

SEQ ID NO: 1039         moltype = AA  length = 133
FEATURE                 Location/Qualifiers
source                  1..133
                        mol_type = protein
                        organism = Homo sapiens
SEQUENCE: 1039
QVRLSQSGAA IKKPGASVTI SCETEGYTFI NYIIHWVRQP PGRGFEWLGM IDPRNGRPWF  60
GQSVQGRLSL RRDTYTEVVY MTLSGLTSDD AGHYFCARNE PQYHDGNGHS LPGMFDYWGQ  120
GTLVAVSSAS TKG                                                    133

SEQ ID NO: 1040         moltype = AA  length = 133
FEATURE                 Location/Qualifiers
source                  1..133
                        mol_type = protein
                        organism = Homo sapiens
SEQUENCE: 1040
QVRLSQSGAA MKKPGASVTI SCETEGYTFI NYIIHWVRQP PGRGFEWLGM IDPRNGRPWF  60
GQSVQGRLSL RRDTYTEVVY MTLSGLTSDD AGLYFCARNE PQYHDGNGHS LPGMFDYWGQ  120
GTLVAVSSAS TKG                                                    133

SEQ ID NO: 1041         moltype = AA  length = 133
FEATURE                 Location/Qualifiers
source                  1..133
                        mol_type = protein
                        organism = Homo sapiens
SEQUENCE: 1041
QVRLSQSGAA IKKPGASVTI SCETEGYTFI NYIIHWVRQP PGRGFEWLGM IDPRNGRPWF  60
GQSVQGRLSL RRDTYTEVVY MTLSGLTSDD TGLYFCARNE PQYHDGNGHS LPGMFDSWGQ  120
GTLVAVSSAS TKG                                                    133

SEQ ID NO: 1042         moltype = AA  length = 128
FEATURE                 Location/Qualifiers
```

```
source                  1..128
                        mol_type = protein
                        organism = Homo sapiens
SEQUENCE: 1042
QVRLSQSGAA VVKTGASVTI SCETEGYNFV NYIIHWVRRP PGRGFEWLGM IDPRNGHPWF  60
AQTVRGRLSL RRDTFKETVY MTLSGLTSDD TGVYFCARNE PQYHSLPGMF DYWGHGTPVT  120
VSSASTKG                                                           128

SEQ ID NO: 1043         moltype = AA  length = 128
FEATURE                 Location/Qualifiers
source                  1..128
                        mol_type = protein
                        organism = Homo sapiens
SEQUENCE: 1043
QVRLSQSGAA VMKTGASVTI SCETEGFNFV NYIIHWVRRP PGRGFEWLGM IDPRNGHPWF  60
AQTVRGRLSL RRDTFNEIVY MTLSGLTTDD TGLYFCARNE PQYHSLPGMF DYWGQGTPVT  120
VSSASTKG                                                           128

SEQ ID NO: 1044         moltype = AA  length = 133
FEATURE                 Location/Qualifiers
source                  1..133
                        mol_type = protein
                        organism = Homo sapiens
SEQUENCE: 1044
QVRLSQSGAA VMKTGASVTI SCETEGYNFV NYIIHWVRRP PGRGFEWLGM IDPKNGHPWF  60
AQAVRGRLSL RRDTFNEVVY MTLSGLTSDD TGLYFCARNE PQYHDGNGHS LPGMFDFWGQ  120
GTLVTVSSAS TKG                                                     133

SEQ ID NO: 1045         moltype = AA  length = 133
FEATURE                 Location/Qualifiers
source                  1..133
                        mol_type = protein
                        organism = Homo sapiens
SEQUENCE: 1045
QVRLSQSGAA VVKTGASVTI SCETEGYTFV NHIIHWVRQP PGRGFEWLGM IDPRNGHPWF  60
GQRLRGRLSL RRDRSTETVF MTLSGLTSDD IGIYFCARNE PQYFDGSGHS LPGMFDYWGQ  120
GTRVVVSSAS TKG                                                     133

SEQ ID NO: 1046         moltype = AA  length = 133
FEATURE                 Location/Qualifiers
source                  1..133
                        mol_type = protein
                        organism = Homo sapiens
SEQUENCE: 1046
QVRLSQSGAA VVKTGASVTI SCETEGYTFV NYIIHWVRQP PGRGFEWLGM IDPRNGHPWF  60
GQRFRGRLSL RRDRSTETVF MTLSGLTSDD NGIYFCARNE PQYYDGSGHS LPGMFDYWGQ  120
GTRVVVSSAS TKG                                                     133

SEQ ID NO: 1047         moltype = AA  length = 133
FEATURE                 Location/Qualifiers
source                  1..133
                        mol_type = protein
                        organism = Homo sapiens
SEQUENCE: 1047
QVRLSQSGAA VVKTGASVTI SCETEGYTFV NYIIHWVRQP PGRGFEWLGM IDPRNGHPWF  60
GQRLQGRLSL RRDRSTETVF MTLSGLTSDD TGIYFCARNE PQYYDGSGHS LPGMFDYWGQ  120
GTRVVVSSAS TKG                                                     133

SEQ ID NO: 1048         moltype = AA  length = 133
FEATURE                 Location/Qualifiers
source                  1..133
                        mol_type = protein
                        organism = Homo sapiens
SEQUENCE: 1048
QVRLSQSGAA VVKTGASVTI SCETEGYTFV NYIIHWVRQS PGRGFEWLGM IDPRNGHPWF  60
GQRLRGRLSL RRDRSTETVF MTLSGLTSDD TAIYFCARNE PQYYDGSGHS LPGMFDYWGQ  120
GTRVVVSSAS TKG                                                     133

SEQ ID NO: 1049         moltype = AA  length = 133
FEATURE                 Location/Qualifiers
source                  1..133
                        mol_type = protein
                        organism = Homo sapiens
SEQUENCE: 1049
QVRLSQSGAA VKKPGASVTI VCETEGYNFI DYIIHWVRQP PGRGFEWLGM IDPRNGRPWS  60
GQKVHGRLSL WRDTSTEKVY MTLTGLTSDD TGLYFCGRNE PQYHDDNGHS LPGMIDYWGQ  120
GTMVTVSSAS TKG                                                     133

SEQ ID NO: 1050         moltype = AA  length = 133
```

```
FEATURE                Location/Qualifiers
source                 1..133
                       mol_type = protein
                       organism = Homo sapiens
SEQUENCE: 1050
QVHTFQSGSS MKKSGASVTI SCEATGYNIK NYILHWVRQK PGRGFEWVGM IDPINGRPWF  60
GQPFRGRLTL TRDLSTETFY MSLSGLTSDD TATYFCARRE ADYHDGNGHT LPGMFDFWGP  120
GTLITVSSAS TKG                                                    133

SEQ ID NO: 1051        moltype = AA  length = 133
FEATURE                Location/Qualifiers
source                 1..133
                       mol_type = protein
                       organism = Homo sapiens
SEQUENCE: 1051
QVQFFQSGSS MKKSGASVTI SCEATGYNIK NHILHWVRQK PGRGFEWVGM IDPINGRPWF  60
GQAFRGRLTL TRDLSTETFY MSLSGLTSDD TATYFCARRE ADYHDGNGHT LPGMFDFWGP  120
GTLVTVSSAS TKG                                                    133

SEQ ID NO: 1052        moltype = AA  length = 133
FEATURE                Location/Qualifiers
source                 1..133
                       mol_type = protein
                       organism = Homo sapiens
SEQUENCE: 1052
QVRLVQSGAQ LKKPGASVTV SCEASGYNFV NYIINWVRQT PGQGFEWVGM IDPRRGRPWS  60
AQKFQGRLTL TRDIDSEKLY MHLSGLRGDD TAVYYCARQD SDFHDGHGHT LRGMFDSWGQ  120
GSPVTVSSAS TKG                                                    133

SEQ ID NO: 1053        moltype = AA  length = 133
FEATURE                Location/Qualifiers
source                 1..133
                       mol_type = protein
                       organism = Homo sapiens
SEQUENCE: 1053
QVRLVQSGAQ LKKPGASVTV SCEASGYNFV NYIINWVRQT PGRSFEWVGM IDPRRGRPWS  60
AQKFQGRLTL TRDIDSEKLY MHLSGLRGDD TAVYYCARQD SDFHDGHGHT LRGMFDSWGQ  120
GSPVTVSSAS TKG                                                    133

SEQ ID NO: 1054        moltype = AA  length = 129
FEATURE                Location/Qualifiers
source                 1..129
                       mol_type = protein
                       organism = Homo sapiens
SEQUENCE: 1054
QVRLVQSGPQ VKTAGASMRV SCEASGYRFL DYIIVWIRQT HGQHFEYVGM INPRGGTPWP  60
SSKFRDRLTL TRDIYTDTFY LGLNNLGSGD TAIYFCARLE ADGDDYSPKM FDYWGQGTRI  120
IVSAASTKG                                                         129

SEQ ID NO: 1055        moltype = AA  length = 129
FEATURE                Location/Qualifiers
source                 1..129
                       mol_type = protein
                       organism = Homo sapiens
SEQUENCE: 1055
QVSLVQSGPQ VKTPGASMRV SCETSGYRFL DYIIVWIRQT HGQHFEYVGM INPRGGTPWP  60
SSKFRDRLTM TRDIHTDTFY LGLNNLRSDD TAIYFCARLE ADGDDYSPKM FDYWGQGTRI  120
IVSAASTKG                                                         129

SEQ ID NO: 1056        moltype = AA  length = 129
FEATURE                Location/Qualifiers
source                 1..129
                       mol_type = protein
                       organism = Homo sapiens
SEQUENCE: 1056
QVRLVQSGPQ VKTPGASMRV SCEASGYRFL DYIIVWIRQT HGQHFEYVGM INPRGGTPWP  60
SSKFRDRLSL TRDIHTDTFY LGLNNLGSDD TAIYFCARLE ADGDDYSPKM FDHWGQGTRI  120
IVSAASTKG                                                         129

SEQ ID NO: 1057        moltype = AA  length = 129
FEATURE                Location/Qualifiers
source                 1..129
                       mol_type = protein
                       organism = Homo sapiens
SEQUENCE: 1057
QVRLVQSGPQ VKTPGASMRI SCEASGYRFQ DYIIVWIRQT HGQGFEYVGM INPRGGTPWS  60
SSKFRDRLSL TRDIYTDTFY LGLNNLGSDD TAIYFCARLE ADGGDYSPKM FDYWGQGTRI  120
IVSAASTKG                                                         129
```

```
SEQ ID NO: 1058        moltype = AA  length = 129
FEATURE                Location/Qualifiers
source                 1..129
                       mol_type = protein
                       organism = Homo sapiens
SEQUENCE: 1058
QVRLVQSGPQ MKTPGASLRL SCEVSGYRFL DYFIVWVRQT GGQGFEYVGM INPRGGRPWS  60
SWKFRDRLSL TRDIETDTFY LGLNNLRSDD TAIYFCARLE ADGDNYSPKM VDYWGQGTKI  120
IVSPASTKG                                                          129

SEQ ID NO: 1059        moltype = AA  length = 129
FEATURE                Location/Qualifiers
source                 1..129
                       mol_type = protein
                       organism = Homo sapiens
SEQUENCE: 1059
QVRLVQSGPQ VKTPGASIRL SCEASGYRFL DYFIVWVRQT PGQGFEYVGM INPRGGRPWS  60
SWKFRDRLSL TREIDTDTFY LGLSNLRSDD TAIYFCARLE ADGDDYSPKM VDYWGQGTKI  120
IVSAASTKG                                                          129

SEQ ID NO: 1060        moltype = AA  length = 129
FEATURE                Location/Qualifiers
source                 1..129
                       mol_type = protein
                       organism = Homo sapiens
SEQUENCE: 1060
QVRLVQSGPQ VKRPGASIRL SCETSGYRFQ DYIVAWIRQT RGQRFEFVGM VNPRGGRPWP  60
SSKFRDRVTL TRDIESETFH LGLNDLTSDD TATYFCARLE ADGADYSPKM FDFWGQGTKI  120
VVSPASTKG                                                          129

SEQ ID NO: 1061        moltype = AA  length = 129
FEATURE                Location/Qualifiers
source                 1..129
                       mol_type = protein
                       organism = Homo sapiens
SEQUENCE: 1061
QVRLVQSGPQ VKRPGASIRL SCESSGYRFQ DYIVAWIRQT RGQGFEFVGM VNPRGGRPWP  60
SSRFRDRVTL TRDIESETFY LGLNDLTSDD TATYFCARLE ADGSDYSPKM FDFWGQGTKI  120
VVSPASTKG                                                          129

SEQ ID NO: 1062        moltype = AA  length = 128
FEATURE                Location/Qualifiers
source                 1..128
                       mol_type = protein
                       organism = Homo sapiens
SEQUENCE: 1062
QVQLLQSGAA VTKPGASVRV SCEASGYNIR DYFIHWWRQA PGQGLQWVGW INPKTGQPNN  60
PRQFQGRVSL TRHASWDFDT FSFYMDLKAL RSDDTAVYFC ARQRSDYWDF DVWGSGTQVT  120
VSSASTKG                                                           128

SEQ ID NO: 1063        moltype = AA  length = 127
FEATURE                Location/Qualifiers
source                 1..127
                       mol_type = protein
                       organism = Homo sapiens
SEQUENCE: 1063
QVQLLQSGAA VTKPGASVRV SCEASGYNIR DYFIHWWRQA PGQGLQWVGW INPKTGQPNN  60
PCQFQGRVSL TRHASWDFDT FSFYMDLKAL RSDDTAVYFC ARQRSDYWDF DVWGSGTQVT  120
VSSASTK                                                            127

SEQ ID NO: 1064        moltype = AA  length = 128
FEATURE                Location/Qualifiers
source                 1..128
                       mol_type = protein
                       organism = Homo sapiens
SEQUENCE: 1064
QVQLLQSGAA VTKPGASVRV SCEASGYNIR DYFIHWWRQA PGQGLQWVGW INPKTGQPNN  60
PRLFQGRVSL TRHASWDFDT FSFYMDLKAV RSDDTAVYFC ARQRSDYWDF DVWGSGTQVT  120
VSSASTKG                                                           128

SEQ ID NO: 1065        moltype = AA  length = 128
FEATURE                Location/Qualifiers
source                 1..128
                       mol_type = protein
                       organism = Homo sapiens
SEQUENCE: 1065
QVQLLQSGAA VTKPGASVRV SCEASGYNIR DYFIHWWRQA PGQGLQWVGW INPKTGQPNN  60
PRQFQGRVSL TRHASWDFDT FSFYMDLKGL RSDDTAIYFC ARQRSDYWDF DVWGSGTQVT  120
VSSASTKG                                                           128
```

```
SEQ ID NO: 1066        moltype = AA  length = 128
FEATURE                Location/Qualifiers
source                 1..128
                       mol_type = protein
                       organism = Homo sapiens
SEQUENCE: 1066
QAQLLQSGAA VTKPGASVRV SCEASGYNIR DYFIHWWRQA PGQGLQWVGW INPKTGQPNN  60
PRQFQGRVSL TRHASWDFDT FSFYMDLKGL RSDDTAIYFC ARQRSDYWDF DVWGSGTQVT  120
VSSASTKG                                                           128

SEQ ID NO: 1067        moltype = AA  length = 128
FEATURE                Location/Qualifiers
source                 1..128
                       mol_type = protein
                       organism = Homo sapiens
SEQUENCE: 1067
QVQLLQSGAA VTKPGASVRV SCEASGYNIR DYFIHWWRQA PGQGLQWVGW INPKTGQPNN  60
PCQFQGRVSL TRQASWDFDT ISFYMDLKAL RLDDTAVYFC ARQRSDYWDF DVWGSGTQVT  120
VSSASTKG                                                           128

SEQ ID NO: 1068        moltype = AA  length = 128
FEATURE                Location/Qualifiers
source                 1..128
                       mol_type = protein
                       organism = Homo sapiens
SEQUENCE: 1068
QVQLLPFGGA VTKPGASVRV SCEASGYNIR DYFIHWWRQA PGQGLQWVGW INPKTGQPNN  60
PCQFQGRVSL TRPASWDFDT ISFYMDLKAL RLDDTAVYFC ARQRSDYWDF DVWGSGTQVT  120
VSSASTKG                                                           128

SEQ ID NO: 1069        moltype = AA  length = 128
FEATURE                Location/Qualifiers
source                 1..128
                       mol_type = protein
                       organism = Homo sapiens
SEQUENCE: 1069
QVQLLQSGAA VTKPGASVRV SCEASGYNIR DYFIHWWRQA PGQGLQWVGW INPKTGQPNN  60
PRQFQGRVSL TRQASWDFDT ISFYMDLKAL RLDDTAVYFC ARQRSDYWDF DVWGSGTQVT  120
VSSASTKG                                                           128

SEQ ID NO: 1070        moltype = AA  length = 128
FEATURE                Location/Qualifiers
source                 1..128
                       mol_type = protein
                       organism = Homo sapiens
SEQUENCE: 1070
HVQLLQSGAA VTKPGASVRV SCEASGYNIR DYFIHWWRQA PGQGLQWVGW INPKTGQPNN  60
PRQFQGRVSL TRQASWDFDT FSFYMDLKAL RLDDTAIYFC ARQRSDYWDF DVWGSGTQVT  120
VSSASTKG                                                           128

SEQ ID NO: 1071        moltype = AA  length = 128
FEATURE                Location/Qualifiers
source                 1..128
                       mol_type = protein
                       organism = Homo sapiens
SEQUENCE: 1071
QVRLLQSGAA VTKPGASVRV SCEASGYEIR DYFIHWWRQA PGQGLQWVGW INPKTGQPNN  60
PRQFQGRVSL TRQASWDFDS YSFYMDLKAL RSDDTAVYFC ARQRSDYWDF DVWGSGSQVT  120
VSSASTKG                                                           128

SEQ ID NO: 1072        moltype = AA  length = 128
FEATURE                Location/Qualifiers
source                 1..128
                       mol_type = protein
                       organism = Homo sapiens
SEQUENCE: 1072
QVRLLQSGAA VTKPGASVRV SCEASGYEIR DYFIHWWRQA PGQGLQWVGW INPKTGQPNN  60
PRQFQGRVSL TRQASWDFDS YSFYMDLKAL RSDDTAVYFC ARQRSDYWDF DVWGSGTQVT  120
VSSASTKG                                                           128

SEQ ID NO: 1073        moltype = AA  length = 128
FEATURE                Location/Qualifiers
source                 1..128
                       mol_type = protein
                       organism = Homo sapiens
SEQUENCE: 1073
QVRLLQSGAA VTKPGASVRV SCEASGYEIR DYFIHWWRQA PGQGLQWVGW INPKTGQPNN  60
PRQFQGRVSL TRQASWDFDS YSFYMDLKAL RSDDTGVYFC ARQRSDYWDF DVWGSGYQVT  120
```

```
VSSASTKG                                                          128

SEQ ID NO: 1074         moltype = AA  length = 128
FEATURE                 Location/Qualifiers
source                  1..128
                        mol_type = protein
                        organism = Homo sapiens
SEQUENCE: 1074
QVHLSQSGAA VTKPGASVRV SCEASGYKIS DHFIHWWRQA PGQGLQWVGW INPKTGQPNN  60
PRQFQGRVSL TRQASWDFDT YSFYMDLKAL RSDDTAIYFC ARQRSDFWDF DVWGSGTQVT  120
VSSASTKG                                                          128

SEQ ID NO: 1075         moltype = AA  length = 128
FEATURE                 Location/Qualifiers
source                  1..128
                        mol_type = protein
                        organism = Homo sapiens
SEQUENCE: 1075
QVHLSQSGAA VTKPGASVRV SCEASGYKIS DHFIHWWRQA PGQGLQWVGW INPKTGQPNN  60
PRQFQGRVSL TRQASWDFDT YSFYMDLKAV RSDDTAIYFC ARQRSDFWDF DVWGSGTQVT  120
VSSASTKG                                                          128

SEQ ID NO: 1076         moltype = AA  length = 128
FEATURE                 Location/Qualifiers
source                  1..128
                        mol_type = protein
                        organism = Homo sapiens
SEQUENCE: 1076
QVQLLQSGAA VTKPGASVRV SCEASGYKIS DHFIHWWRQA PGQGLQWVGW INPKTGQPNN  60
PRQFQGRISL TRQASWDFDT FSFYMDLKAL RSDDTAVYFC ARQRSDYWDF DVWGSGTQVT  120
VSSASTKG                                                          128

SEQ ID NO: 1077         moltype = AA  length = 128
FEATURE                 Location/Qualifiers
source                  1..128
                        mol_type = protein
                        organism = Homo sapiens
SEQUENCE: 1077
QVQLLQSGAV VTKPGASVRV SCEASGYKIR DYFIHWWRQA PGQGLQWVGW INPQTGQPNI  60
PRPFQGRVTL TRHASWDFDT FSFYMDLKAL RSDDTAIYFC ARRRSDYCDF DVWGSGTHVT  120
VSSASTKG                                                          128

SEQ ID NO: 1078         moltype = AA  length = 124
FEATURE                 Location/Qualifiers
source                  1..124
                        mol_type = protein
                        organism = Homo sapiens
SEQUENCE: 1078
QVQLVQSGAA LKKPGASLRI SCQAYGYKFT DHLIYWWRQA PGQGLEWIGW IKPETGQPSY  60
SYKFQGRVSL TRDTFQEILF MNLRGLRSDD TAIYFCARRH SDYCDFDVWG SGSQILVSSA  120
STKG                                                              124

SEQ ID NO: 1079         moltype = AA  length = 124
FEATURE                 Location/Qualifiers
source                  1..124
                        mol_type = protein
                        organism = Homo sapiens
SEQUENCE: 1079
QVQLVQSGAA LKKPGASLRI SCQAYGYKFT DHLIYWWRQA PGQGLEWIGW IKPETGQPSY  60
SYKFQGRVSL TRDTFQEILF MDLRGLRSDD TAIYFCARRH SDYCDFDVWG SGSQILVSSA  120
STKG                                                              124

SEQ ID NO: 1080         moltype = AA  length = 124
FEATURE                 Location/Qualifiers
source                  1..124
                        mol_type = protein
                        organism = Homo sapiens
SEQUENCE: 1080
QVQLVQSGAA LKKPGASLRI SCQAYGYKFT DHLIYWWRQA PGQGLEWIGW IKPETGQPSY  60
SYKFQGRVSL TRDTFQEILF MDLRGLRSDD TAIYFCARRH SDYCDFDVWG SGSQVIVSSA  120
STKG                                                              124

SEQ ID NO: 1081         moltype = AA  length = 124
FEATURE                 Location/Qualifiers
source                  1..124
                        mol_type = protein
                        organism = Homo sapiens
SEQUENCE: 1081
QVQLVQSGAA LKKPGASLRI SCQAYGYKFT DHLIHWWRQA PGQGLEWIGW IKPETGQPSY  60
```

```
SYKFQGRVSL TRDTFEEILF MDLRGLRSDD TAIYFCARRH SDYCDFDVWG GGSQVLVSSA  120
STKG                                                               124

SEQ ID NO: 1082        moltype = AA  length = 124
FEATURE                Location/Qualifiers
source                 1..124
                       mol_type = protein
                       organism = Homo sapiens
SEQUENCE: 1082
QVQLVQSGAA LKKPGASVRI SCQAYGYKFT DYLIHWWRQA PGQGLEWIGW IKPETGQPSY  60
SYKFQGRVTL TRDTFEEILF MDLRGLRSDD TAIYFCARRH SDYCDFDVWG SGSQVIVSSA  120
STKG                                                               124

SEQ ID NO: 1083        moltype = AA  length = 124
FEATURE                Location/Qualifiers
source                 1..124
                       mol_type = protein
                       organism = Homo sapiens
SEQUENCE: 1083
QVQLVQSGAA LKKPGASVRI SCQAYGYKFT DHLIYWWRQA PGQGLEWIGW IKPETGQPSY  60
SYKFQGRVTL TRDTFEEIHF MDLRGLRYDD TATYFCARRH SDYCDFDVWG SGSQVSVSSA  120
STKG                                                               124

SEQ ID NO: 1084        moltype = AA  length = 124
FEATURE                Location/Qualifiers
source                 1..124
                       mol_type = protein
                       organism = Homo sapiens
SEQUENCE: 1084
QVQLVQSGAA LKKPGASVRI SCQAYGYKFT DHLIYWWRQA PGQGLEWIGW IKPETGQPSY  60
AYKFQGRVTL TRDTFEEIHF MDLRGVRNDD TATYFCARRH SDYCDFDVWG SGSQVIVSSA  120
STKG                                                               124

SEQ ID NO: 1085        moltype = AA  length = 124
FEATURE                Location/Qualifiers
source                 1..124
                       mol_type = protein
                       organism = Homo sapiens
SEQUENCE: 1085
QVQLVQSGAA LKKPGASVRI SCQTYGYKFT DHLIYWWRQA PGQGLEWIGW IKPETGQPSY  60
SYRFQGRVSL TRDTFEEIVF MDLRGLRSDD TAIYFCARRH SDYCDFDVWG SGSQVLVSSA  120
STKG                                                               124

SEQ ID NO: 1086        moltype = AA  length = 124
FEATURE                Location/Qualifiers
source                 1..124
                       mol_type = protein
                       organism = Homo sapiens
SEQUENCE: 1086
QVQLVQSGAA LKKPGASLRI SCLTYGYKFT DHLIYWWRQA PGQGLEWIGW IKPETGQPSY  60
SYRFQGRVSL TRDTFEEIVF MDLRGLRSDD TAIYFCARRH SDYCDFDVWG SGSQVIVSSA  120
STKG                                                               124

SEQ ID NO: 1087        moltype = AA  length = 124
FEATURE                Location/Qualifiers
source                 1..124
                       mol_type = protein
                       organism = Homo sapiens
SEQUENCE: 1087
QVQLVQSGAA LKKPGASLRI SCQTYGYKFT DHLIYWWRQA PGQGLEWIGW IKPETGQPSY  60
SYRFQGRVSL TRDTFEEIVF MDLRGLRSDD TAIYFCARRH SDYCDFDVWG GPSQVIVSSA  120
STKG                                                               124

SEQ ID NO: 1088        moltype = AA  length = 124
FEATURE                Location/Qualifiers
source                 1..124
                       mol_type = protein
                       organism = Homo sapiens
SEQUENCE: 1088
QVQLVQSGAA LKKPGASLRI SCQTYGYKFT DHLIYWWRQA PGQGLEWMGW IKPETGQPSY  60
SYRFQGRVSL TRDTFEEIVF MDLRGLRSDD TAIYFCARRH SDYCDFDVWG SGSQVIVSSA  120
STKG                                                               124

SEQ ID NO: 1089        moltype = AA  length = 124
FEATURE                Location/Qualifiers
source                 1..124
                       mol_type = protein
                       organism = Homo sapiens
SEQUENCE: 1089
```

```
QVQLVQSGAA LKKPGASLRI SCQTYGYKFT DHLIYWWRQA PGQGLEWIGW IKPETGQPSY  60
SYRFQGRVSL TRDTFEEIVF MDLRGLRSDD TAIYFCARRH SDYCDFDVWG SGSQVLVSSA  120
STKG                                                               124

SEQ ID NO: 1090        moltype = AA  length = 124
FEATURE                Location/Qualifiers
source                 1..124
                       mol_type = protein
                       organism = Homo sapiens
SEQUENCE: 1090
QVQLVQSGAA LKKPGASLRI SCQTYGYKFT DHLIYWWRQA PGQGLEWIGW IKPETGQPSY  60
SYRFQGRVSL TRDTFEEIAF MDLRGLRSDD TAIYFCARRH TDYCVFDVWG SGSQIIVSSA  120
STKG                                                               124

SEQ ID NO: 1091        moltype = AA  length = 124
FEATURE                Location/Qualifiers
source                 1..124
                       mol_type = protein
                       organism = Homo sapiens
SEQUENCE: 1091
QVQLVQSGAA LKKPGASVRI SCQTYGYKFT DHLIHWWRQA PGQGLEWIGW IKPDTGQPSY  60
SSRFQGRVSL TRDTFEEIVF MDLRGLRSDD TAIYFCARRH SDYCDFDVWG SGSQVLVSSA  120
STKG                                                               124

SEQ ID NO: 1092        moltype = AA  length = 124
FEATURE                Location/Qualifiers
source                 1..124
                       mol_type = protein
                       organism = Homo sapiens
SEQUENCE: 1092
QVQLVQSGAT LKKPGASVRI SCQAYGYKFT DHLIHWWRQA PGQGLEWIGW IKPETGQPSY  60
AYKFQGRVSL TRDTFEEILF MDLRGLRSDD TAIYFCARRH SDYCDLDVWG GGTQLLVSSA  120
STKG                                                               124

SEQ ID NO: 1093        moltype = AA  length = 124
FEATURE                Location/Qualifiers
source                 1..124
                       mol_type = protein
                       organism = Homo sapiens
SEQUENCE: 1093
QVQLVQSGTA VKKPGASVRV SCQASGYTFT DYFIYWWRQA PGQGLEWLGW INPRTSQPSY  60
PYRFQGRVTL TRDIFEEMLY MDLRGLRSDD TGIYFCARRH SDYCDFDIWG SGTQIIVSSA  120
STKG                                                               124

SEQ ID NO: 1094        moltype = AA  length = 124
FEATURE                Location/Qualifiers
source                 1..124
                       mol_type = protein
                       organism = Homo sapiens
SEQUENCE: 1094
QVQLVQSGTA VKRPGASVRV SCQASGYTFT DYFIYWWRQA PGQGLEWLGW INPLTSQPSY  60
PSRFQGRLTL TRDTFDEMLY MDLRGLRSDD TGIYFCARRH SDYCDFDIWG SGTQIIVSSA  120
STKG                                                               124

SEQ ID NO: 1095        moltype = AA  length = 124
FEATURE                Location/Qualifiers
source                 1..124
                       mol_type = protein
                       organism = Homo sapiens
SEQUENCE: 1095
QVQLVQSGTA VKRPGASVRV SCQASGYTFI DHFIYWWRQA PGQGLEWLGW INPLTSQPSY  60
PSRFQGRLTL TRDTFDEMLY MDLRGLRSDD TGIYFCARRH SDYCDFDIWG SGTQIIVSSA  120
STKG                                                               124

SEQ ID NO: 1096        moltype = AA  length = 126
FEATURE                Location/Qualifiers
source                 1..126
                       mol_type = protein
                       organism = Homo sapiens
SEQUENCE: 1096
QVQLVQSGAA VKKPGASVKV SCETYGYTFT DHFMHWWRQA PGQGLEWMGW INPYSSAVSY  60
SPRYQGRVTM TRDTFLETVY MELRGLKFDD TAIYYCATPK SGRDYWSFDL WGQGTLVTVS  120
SASTKG                                                             126

SEQ ID NO: 1097        moltype = AA  length = 126
FEATURE                Location/Qualifiers
source                 1..126
                       mol_type = protein
                       organism = Homo sapiens
```

```
SEQUENCE: 1097
QVQLVQSGGA VKKPGASVKV SCETYGYTFT DHFMHWWRQA PGQGLEWMGW INPYSSAVSY  60
SPRYQGRVTM TRDTFLETVY MELRGLKFDD TAIYYCATPK SGRDYWSFDL WGQGTLVTVS  120
SASTKG                                                             126

SEQ ID NO: 1098        moltype = AA  length = 126
FEATURE                Location/Qualifiers
source                 1..126
                       mol_type = protein
                       organism = Homo sapiens
SEQUENCE: 1098
QVQLVQSGAA VKKPGASVKV SCETYGYKFT DHFMHWWRQA PGQGLEWMGW INPYSSAVSY  60
SPRYQGRVTM TRDTFLETVY MELRGLRFDD TAIYYCATPK SGRDYWSFDL WGQGTLVTVS  120
SASTKG                                                             126

SEQ ID NO: 1099        moltype = AA  length = 126
FEATURE                Location/Qualifiers
source                 1..126
                       mol_type = protein
                       organism = Homo sapiens
SEQUENCE: 1099
QVQLVQSGAA VKKPGASVKV SCEAYGYKFT DHFMHWWRQA PGQGLEWMGW INPYTSAVNY  60
SPKYQGRVTM TRDTFLETVY MELRGLRVDD TAIYYCATPK SGRDYWSFDL WGQGTLVTVS  120
SASTKG                                                             126

SEQ ID NO: 1100        moltype = AA  length = 132
FEATURE                Location/Qualifiers
source                 1..132
                       mol_type = protein
                       organism = Homo sapiens
SEQUENCE: 1100
QPQLVQSGSG AEVKKPGASV RISCEASEYN VFDHFMQWVR QAPGQGLEWM GWINPRGGYP  60
SYSPTFQGRL TFTRQPSWDD STITFHMELR GLGHDDTAVY YCARPHSPDD AWSLDVWGRG  120
TLVTVSSAST KG                                                      132

SEQ ID NO: 1101        moltype = AA  length = 132
FEATURE                Location/Qualifiers
source                 1..132
                       mol_type = protein
                       organism = Homo sapiens
SEQUENCE: 1101
QPQLVQSGSG AEVKKPGASV RISCEASEYN VFDHFMQWVR QAPMEGLEWM GWINPRGGYP  60
SYSPTFQGRL TFTRQPSWDD STITFHMELR GLRHDDTAVY YCARPHSPDD AWSLDVWGRG  120
TLVTVSSAST KG                                                      132

SEQ ID NO: 1102        moltype = AA  length = 132
FEATURE                Location/Qualifiers
source                 1..132
                       mol_type = protein
                       organism = Homo sapiens
SEQUENCE: 1102
QPQLVQSGSG AEVKKPGASV RISCEASEYN VFDHFMQWVR QAPGQGLEWM GWINPRGGYP  60
SYSPRFQGRL TFTRQPSWDD SSVTFHMELR GLRHDDTAVY YCARPHSPDD AWSLDVWGRG  120
TLVTVSSAST KG                                                      132

SEQ ID NO: 1103        moltype = AA  length = 128
FEATURE                Location/Qualifiers
source                 1..128
                       mol_type = protein
                       organism = Homo sapiens
SEQUENCE: 1103
QVQLVQSGAD VKKPGASVTV SCKTDEDEDD FRAHLVQWMR QAPGQRLEWV GWIKPQTGQP  60
SYAQKFQGRV TLTREVSTST VFLQLRNLRS DDTAVYYCAR PRGGRDNWSF HVWGRGTLVT  120
VSSASTKG                                                           128

SEQ ID NO: 1104        moltype = AA  length = 128
FEATURE                Location/Qualifiers
source                 1..128
                       mol_type = protein
                       organism = Homo sapiens
SEQUENCE: 1104
QVQLVQSGAD VKKPGAAVTV SCKTDEDEDD FRAHLMQWMR QAPGQRLEWV GWIKPQTGQP  60
SYGQKFQGRV TLTREVSTST VFLQLRNLRS DDTAVYYCAR PRGGRDNWSF HVWGRGTLVT  120
VSSASTKG                                                           128

SEQ ID NO: 1105        moltype = AA  length = 130
FEATURE                Location/Qualifiers
source                 1..130
                       mol_type = protein
```

```
                       organism = Homo sapiens
SEQUENCE: 1105
EVQLVQSGSD VRKPGAAVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 1106        moltype = AA  length = 130
FEATURE                Location/Qualifiers
source                 1..130
                       mol_type = protein
                       organism = Homo sapiens
SEQUENCE: 1106
VVQLVQSGSD VRKPGAAVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 1107        moltype = AA  length = 130
FEATURE                Location/Qualifiers
source                 1..130
                       mol_type = protein
                       organism = Homo sapiens
SEQUENCE: 1107
EVQLVESGSD VRKPGAAVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 1108        moltype = AA  length = 130
FEATURE                Location/Qualifiers
source                 1..130
                       mol_type = protein
                       organism = Homo sapiens
SEQUENCE: 1108
EVQLVESGSD VRKPGAAVTV SCKADEDEDD FTAYNYFMHW VRQAPGQGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 1109        moltype = AA  length = 130
FEATURE                Location/Qualifiers
source                 1..130
                       mol_type = protein
                       organism = Homo sapiens
SEQUENCE: 1109
QVQLVESGSD VRKPGAAVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 1110        moltype = AA  length = 130
FEATURE                Location/Qualifiers
source                 1..130
                       mol_type = protein
                       organism = Homo sapiens
SEQUENCE: 1110
QVQLVQSGSD VRKPGAAVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSRGRGTS  120
LTVSSASTKG                                                        130

SEQ ID NO: 1111        moltype = AA  length = 130
FEATURE                Location/Qualifiers
source                 1..130
                       mol_type = protein
                       organism = Homo sapiens
SEQUENCE: 1111
QVQLVQSGSD VRKPGAAVTV SCKADEDEDD FTAYNYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 1112        moltype = AA  length = 130
FEATURE                Location/Qualifiers
source                 1..130
                       mol_type = protein
                       organism = Homo sapiens
SEQUENCE: 1112
EVQLVQSGSD VRKPGAAVTV SCKADEDEDD FTAYDYFMHW VRQAPGHGLE WIGWINPRTG  60
QPNHAKQFQG RVTLTRERST STVFMKLTNL RLDDTAVYFC ARPLRGGDTW HYHSWGRGTS  120
LTVSSASTKG                                                        130

SEQ ID NO: 1113        moltype = AA  length = 130
FEATURE                Location/Qualifiers
source                 1..130
```

```
                         mol_type = protein
                         organism = Homo sapiens
SEQUENCE: 1113
EVQLVQSGSD VKKPGTTVTI SCKADEDEDD FTAYNYFMHW VRQAPGQGLE WIGWINPRTG  60
QPNHAKQLQG RVTLTRERST STVFMKLTNL RLDDTAVYFC ARPLRGGDTW HYHSWGRGTS  120
LIVSSASTKG                                                        130

SEQ ID NO: 1114          moltype = AA  length = 127
FEATURE                  Location/Qualifiers
VARIANT                  10
                         note = Any naturally occurring amino acid or not present
source                   1..127
                         mol_type = protein
                         organism = Homo sapiens
SEQUENCE: 1114
GHLVQSGGGX KKPGTSVTIS CLASEYTFTE FTIHRIRQAP GQGPLWLGLI KGSGRLMTSY  60
GFQDRLSLRR DRSTGTVFME LRSLRTDDTA VYYCARDGLG ELAPAYHYGI DVWGQGTTVI  120
VTSASTS                                                           127

SEQ ID NO: 1115          moltype = AA  length = 128
FEATURE                  Location/Qualifiers
source                   1..128
                         mol_type = protein
                         organism = Homo sapiens
SEQUENCE: 1115
QGQLVQSGGG VKKPGSSVTI SCLASEYTFT EFTIHWIRQA PGQGPLWLGL IKRSGRLMTS  60
YGFQDRLSVR RDRSTGTVFM ELRSLRTDDT AVYYCARDGL GELAPAYHYG IDVWGQGTTV  120
IVTSASTS                                                          128

SEQ ID NO: 1116          moltype = AA  length = 128
FEATURE                  Location/Qualifiers
source                   1..128
                         mol_type = protein
                         organism = Homo sapiens
SEQUENCE: 1116
QGHLVQSGGG VKKPGTSVTL SCLASEYTFT EFTIHWIRQA PGQGPLWLGL IKRSGRLMTS  60
YRFQDRLSLR RDRSTGTVFM ELRSLRTDDT AVYYCARDGL GELAPAYHYG IDAWGQGTTV  120
IVTSASTS                                                          128

SEQ ID NO: 1117          moltype = AA  length = 129
FEATURE                  Location/Qualifiers
source                   1..129
                         mol_type = protein
                         organism = Homo sapiens
SEQUENCE: 1117
QGQLVQSGGG LKKPGTSVTI SCLASEYTFN EFVIHWIRQA PGQGPLWLGL IKRSGRLMTA  60
YNFQDRLSLR RDRSTGTVFM ELRGLRPDDT AVYYCARDGL GEVAPDYRYG IDVWGQGSTV  120
IVTAASTKG                                                         129

SEQ ID NO: 1118          moltype = AA  length = 129
FEATURE                  Location/Qualifiers
source                   1..129
                         mol_type = protein
                         organism = Homo sapiens
SEQUENCE: 1118
QGQLVQSGGG LKKPGTSVTI SCLASEYTFN EFVIHWIRQA PGQGPLWLGL IKRSGRLMTA  60
YNFQDRLRLR RDRSTGTVFM ELRGLRPDDT AVYYCARDGL GEVAPDYRYG IDVWGQGSTV  120
IVTAASTKG                                                         129

SEQ ID NO: 1119          moltype = AA  length = 129
FEATURE                  Location/Qualifiers
source                   1..129
                         mol_type = protein
                         organism = Homo sapiens
SEQUENCE: 1119
QGQLVQSGGG VKKPGASVTI SCLASEYTFN EFVIHWIRQA PGQGPLWLGL IKRSGRLMTA  60
YKFQDRLSLR RDRSTGTVFM ELRGLRPEDT AVYYCARDGL GEVAPDYRYG IDVWGQGSTV  120
IVSAASTKG                                                         129

SEQ ID NO: 1120          moltype = AA  length = 129
FEATURE                  Location/Qualifiers
source                   1..129
                         mol_type = protein
                         organism = Homo sapiens
SEQUENCE: 1120
QGQLVQSGGG VKKPGTSVTI SCLASEYTFN EFVIHWIRQA PGQGPLWLGL IKRSGRLMTS  60
YKFQDRLNLR RDRSTGTVFM ELRGLRPDDT AVYYCARDGL GEVAPDYRYG IDVWGQGSTV  120
IVTAASTKG                                                         129
```

```
SEQ ID NO: 1121         moltype = AA  length = 129
FEATURE                 Location/Qualifiers
source                  1..129
                        mol_type = protein
                        organism = Homo sapiens
SEQUENCE: 1121
QGQLVQSGGG VKKPGTSVTI SCLASEYTFN EFVIHWIRQA PGQGPVWLGL IKRSGRLMTS  60
YKFQDRLSLR RDRSTGTVFM ELRGLRLDDT AVYYCARDGL GEVAPAYHYG IDAWGQGSTV  120
IVTSASTKG                                                          129

SEQ ID NO: 1122         moltype = AA  length = 129
FEATURE                 Location/Qualifiers
source                  1..129
                        mol_type = protein
                        organism = Homo sapiens
SEQUENCE: 1122
QGQLVQSGGG VKKPGTSVTI SCLASEYTFN EFVIHWIRQA PGQGPVWLGL IKRSGRLMTS  60
YKFQDRLSLR RDRSTGTVFM ELRGLRLDDT AVYYCARDGL GEVAPAYLYG IDAWGQGSKV  120
IVTPASTKG                                                          129

SEQ ID NO: 1123         moltype = AA  length = 129
FEATURE                 Location/Qualifiers
source                  1..129
                        mol_type = protein
                        organism = Homo sapiens
SEQUENCE: 1123
QGHLVQSGGG VKKLGTSVTI SCLVSEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 1124         moltype = AA  length = 129
FEATURE                 Location/Qualifiers
source                  1..129
                        mol_type = protein
                        organism = Homo sapiens
SEQUENCE: 1124
QGHLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 1125         moltype = AA  length = 128
FEATURE                 Location/Qualifiers
source                  1..128
                        mol_type = protein
                        organism = Homo sapiens
SEQUENCE: 1125
QGHLVQSGGG VKKLGTSVTI SCLASEDTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTS                                                           128

SEQ ID NO: 1126         moltype = AA  length = 129
FEATURE                 Location/Qualifiers
source                  1..129
                        mol_type = protein
                        organism = Homo sapiens
SEQUENCE: 1126
QGHLVQSGGG VKKLGTSVTI SCLASEDTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 1127         moltype = AA  length = 127
FEATURE                 Location/Qualifiers
source                  1..127
                        mol_type = protein
                        organism = Homo sapiens
SEQUENCE: 1127
QGHLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSAST                                                            127

SEQ ID NO: 1128         moltype = AA  length = 129
FEATURE                 Location/Qualifiers
source                  1..129
                        mol_type = protein
                        organism = Homo sapiens
SEQUENCE: 1128
QGLLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129
```

```
SEQ ID NO: 1129        moltype = AA  length = 129
FEATURE                Location/Qualifiers
source                 1..129
                       mol_type = protein
                       organism = Homo sapiens
SEQUENCE: 1129
QGQLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVSSASTKG                                                          129

SEQ ID NO: 1130        moltype = AA  length = 129
FEATURE                Location/Qualifiers
source                 1..129
                       mol_type = protein
                       organism = Homo sapiens
SEQUENCE: 1130
QGQLVQSGGG GKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVSSASTKG                                                          129

SEQ ID NO: 1131        moltype = AA  length = 129
FEATURE                Location/Qualifiers
source                 1..129
                       mol_type = protein
                       organism = Homo sapiens
SEQUENCE: 1131
QGQLVQSGGG VKKLGTSVTI PCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTKG                                                          129

SEQ ID NO: 1132        moltype = AA  length = 129
FEATURE                Location/Qualifiers
source                 1..129
                       mol_type = protein
                       organism = Homo sapiens
SEQUENCE: 1132
QGQLVQSGGG VKKLGTSVTI SCLASEYTFN EFVIHWIRQA LGQGLLWLGL IKRSGRLMTS  60
YQFQDRLSLR RDRSTGTVFM ELRGLRVDDT AVYYCARDGL GEVALAYLYG IDAWGQGTTV  120
IVTSASTKG                                                          129

SEQ ID NO: 1133        moltype = AA  length = 128
FEATURE                Location/Qualifiers
source                 1..128
                       mol_type = protein
                       organism = Homo sapiens
SEQUENCE: 1133
QGQLVQSGGG VKKLGTSVTI SCLASEYTFN EFVIHWIRQA PGQGPLWLGL IKRSGRLMTS  60
YQFQDRLSLR RDRSTGTVFM ELRGLRVDDT AVYYCARDGL GEVAPAYLYG IDAWGQGTTV  120
IVTSASTS                                                           128

SEQ ID NO: 1134        moltype = AA  length = 128
FEATURE                Location/Qualifiers
source                 1..128
                       mol_type = protein
                       organism = Homo sapiens
SEQUENCE: 1134
QGHLVQSGGG VKKPGSSVTI SCLASEYTFT EFTIHWIRQA PGQGPLWLGL IKRSGRLMTS  60
YRFQDRLSLR RDRSTGTVFM ELRGLRIDDT AVYYCARDGL GEVAPAYLYG IDVWGQGTTV  120
IVTSASTS                                                           128

SEQ ID NO: 1135        moltype = AA  length = 128
FEATURE                Location/Qualifiers
source                 1..128
                       mol_type = protein
                       organism = Homo sapiens
SEQUENCE: 1135
QGHLVQSGGG VKKPGSSVTI SCLASEYTFT EFTIHWIRQA PGQGPLWLGL IKRSGRLMTS  60
YRFQDRLSLR RDRSTGTVFM ELRGLRIDDT AVYYCARDGL GEVAPAYLYG IDVWGQGSTV  120
IVTSASTS                                                           128

SEQ ID NO: 1136        moltype = AA  length = 129
FEATURE                Location/Qualifiers
source                 1..129
                       mol_type = protein
                       organism = Homo sapiens
SEQUENCE: 1136
QGQLVQSGGG VKKPGTSVTI SCLASEYTFT EFTIHWIRQA PGQGPLWLGL IKRSGRLMTA  60
YRFQDRLSLR RDRSTGTVFM ELRNLRMDDT AVYYCARDGL GELAPAYQYG IDVWGQGTTV  120
```

```
IVSSASTKG                                                           129

SEQ ID NO: 1137        moltype = AA  length = 129
FEATURE                Location/Qualifiers
source                 1..129
                       mol_type = protein
                       organism = Homo sapiens
SEQUENCE: 1137
QGQLVQSGGG VKKTGTSVTI SCLASEYTFT EFTIHWIRQA PGQGPLWLGL IKRSGRLMTA  60
NRFQDRLSLR RDRSTGTVFM ELRSLRIDDT AVYYCARDGL GELAPAYHYG IDVWGQGTTI  120
IVTSASTKG                                                           129

SEQ ID NO: 1138        moltype = AA  length = 130
FEATURE                Location/Qualifiers
VARIANT                9
                       note = Any naturally occurring amino acid or not present
VARIANT                31
                       note = Any naturally occurring amino acid or not present
source                 1..130
                       mol_type = protein
                       organism = Homo sapiens
SEQUENCE: 1138
QGHLVQSGXE VKKPGSSVKV SCKASGGTFS XYAIGWVRQA PGQGLEWMGG IIPILGTTNY  60
AQRFQGGVTI TADESTNTAY MDVSSLRSDD TAVYYCAKAP YRPRGSGNYY YAMDVWGQGT  120
TVIVSSASTS                                                          130

SEQ ID NO: 1139        moltype = AA  length = 5
FEATURE                Location/Qualifiers
source                 1..5
                       mol_type = protein
                       organism = Homo sapiens
SEQUENCE: 1139
DYFIH                                                               5

SEQ ID NO: 1140        moltype = AA  length = 17
FEATURE                Location/Qualifiers
source                 1..17
                       mol_type = protein
                       organism = Homo sapiens
SEQUENCE: 1140
WINPKTGQPN NPRQFQG                                                  17

SEQ ID NO: 1141        moltype = AA  length = 10
FEATURE                Location/Qualifiers
source                 1..10
                       mol_type = protein
                       organism = Homo sapiens
SEQUENCE: 1141
QRSDYWDFDV                                                          10

SEQ ID NO: 1142        moltype = AA  length = 7
FEATURE                Location/Qualifiers
source                 1..7
                       mol_type = protein
                       organism = Homo sapiens
SEQUENCE: 1142
QANGYLN                                                             7

SEQ ID NO: 1143        moltype = AA  length = 7
FEATURE                Location/Qualifiers
source                 1..7
                       mol_type = protein
                       organism = Homo sapiens
SEQUENCE: 1143
DGSKLER                                                             7

SEQ ID NO: 1144        moltype = AA  length = 5
FEATURE                Location/Qualifiers
source                 1..5
                       mol_type = protein
                       organism = Homo sapiens
SEQUENCE: 1144
QVYEF                                                               5

SEQ ID NO: 1145        moltype = AA  length = 5
FEATURE                Location/Qualifiers
source                 1..5
                       mol_type = protein
                       organism = Homo sapiens
```

```
SEQUENCE: 1145
NCPIN                                                              5

SEQ ID NO: 1146        moltype = AA  length = 17
FEATURE                Location/Qualifiers
source                 1..17
                       mol_type = protein
                       organism = Homo sapiens
SEQUENCE: 1146
WLKPRGGAVN YARKFQG                                                17

SEQ ID NO: 1147        moltype = AA  length = 16
FEATURE                Location/Qualifiers
source                 1..16
                       mol_type = protein
                       organism = Homo sapiens
SEQUENCE: 1147
GKYCTARDYY NWDFEH                                                 16

SEQ ID NO: 1148        moltype = AA  length = 8
FEATURE                Location/Qualifiers
source                 1..8
                       mol_type = protein
                       organism = Homo sapiens
SEQUENCE: 1148
RTSQSGSL                                                           8

SEQ ID NO: 1149        moltype = AA  length = 7
FEATURE                Location/Qualifiers
source                 1..7
                       mol_type = protein
                       organism = Homo sapiens
SEQUENCE: 1149
SGSTRAA                                                            7

SEQ ID NO: 1150        moltype = AA  length = 5
FEATURE                Location/Qualifiers
source                 1..5
                       mol_type = protein
                       organism = Homo sapiens
SEQUENCE: 1150
QQYEF                                                              5

SEQ ID NO: 1151        moltype = AA  length = 5
FEATURE                Location/Qualifiers
source                 1..5
                       mol_type = protein
                       organism = Homo sapiens
SEQUENCE: 1151
DHFIH                                                              5

SEQ ID NO: 1152        moltype = AA  length = 17
FEATURE                Location/Qualifiers
source                 1..17
                       mol_type = protein
                       organism = Homo sapiens
SEQUENCE: 1152
WINPKTGQPN NPRQFQG                                                17

SEQ ID NO: 1153        moltype = AA  length = 10
FEATURE                Location/Qualifiers
source                 1..10
                       mol_type = protein
                       organism = Homo sapiens
SEQUENCE: 1153
QRSDFWDFDV                                                        10

SEQ ID NO: 1154        moltype = AA  length = 7
FEATURE                Location/Qualifiers
source                 1..7
                       mol_type = protein
                       organism = Homo sapiens
SEQUENCE: 1154
QANGYLN                                                            7

SEQ ID NO: 1155        moltype = AA  length = 7
FEATURE                Location/Qualifiers
source                 1..7
                       mol_type = protein
```

```
                        organism = Homo sapiens
SEQUENCE: 1155
DGSKLER                                                                 7

SEQ ID NO: 1156         moltype = AA  length = 5
FEATURE                 Location/Qualifiers
source                  1..5
                        mol_type = protein
                        organism = Homo sapiens
SEQUENCE: 1156
QVYEF                                                                   5

SEQ ID NO: 1157         moltype = AA  length = 5
FEATURE                 Location/Qualifiers
source                  1..5
                        mol_type = protein
                        organism = Homo sapiens
SEQUENCE: 1157
DYVLH                                                                   5

SEQ ID NO: 1158         moltype = AA  length = 17
FEATURE                 Location/Qualifiers
source                  1..17
                        mol_type = protein
                        organism = Homo sapiens
SEQUENCE: 1158
WIKPVYGARN YARRFQG                                                      17

SEQ ID NO: 1159         moltype = AA  length = 13
FEATURE                 Location/Qualifiers
source                  1..13
                        mol_type = protein
                        organism = Homo sapiens
SEQUENCE: 1159
DGSGDDTSWH LDP                                                          13

SEQ ID NO: 1160         moltype = AA  length = 11
FEATURE                 Location/Qualifiers
source                  1..11
                        mol_type = protein
                        organism = Homo sapiens
SEQUENCE: 1160
QAGQGIGSSL Q                                                            11

SEQ ID NO: 1161         moltype = AA  length = 7
FEATURE                 Location/Qualifiers
source                  1..7
                        mol_type = protein
                        organism = Homo sapiens
SEQUENCE: 1161
GASNLHR                                                                 7

SEQ ID NO: 1162         moltype = AA  length = 5
FEATURE                 Location/Qualifiers
source                  1..5
                        mol_type = protein
                        organism = Homo sapiens
SEQUENCE: 1162
AVLEF                                                                   5

SEQ ID NO: 1163         moltype = AA  length = 5
FEATURE                 Location/Qualifiers
source                  1..5
                        mol_type = protein
                        organism = Homo sapiens
SEQUENCE: 1163
NYILH                                                                   5

SEQ ID NO: 1164         moltype = AA  length = 17
FEATURE                 Location/Qualifiers
source                  1..17
                        mol_type = protein
                        organism = Homo sapiens
SEQUENCE: 1164
LIKPVFGAVN YARQFQG                                                      17

SEQ ID NO: 1165         moltype = AA  length = 13
FEATURE                 Location/Qualifiers
source                  1..13
```

```
                         mol_type = protein
                         organism = Homo sapiens
SEQUENCE: 1165
DESGDDLKWH LHP                                                             13

SEQ ID NO: 1166          moltype = AA  length = 11
FEATURE                  Location/Qualifiers
source                   1..11
                         mol_type = protein
                         organism = Homo sapiens
SEQUENCE: 1166
QAGQGIGSSL N                                                               11

SEQ ID NO: 1167          moltype = AA  length = 7
FEATURE                  Location/Qualifiers
source                   1..7
                         mol_type = protein
                         organism = Homo sapiens
SEQUENCE: 1167
GASNLQR                                                                    7

SEQ ID NO: 1168          moltype = AA  length = 5
FEATURE                  Location/Qualifiers
source                   1..5
                         mol_type = protein
                         organism = Homo sapiens
SEQUENCE: 1168
AVFQW                                                                      5

SEQ ID NO: 1169          moltype = AA  length = 5
FEATURE                  Location/Qualifiers
source                   1..5
                         mol_type = protein
                         organism = Homo sapiens
SEQUENCE: 1169
EFVIH                                                                      5

SEQ ID NO: 1170          moltype = AA  length = 16
FEATURE                  Location/Qualifiers
source                   1..16
                         mol_type = protein
                         organism = Homo sapiens
SEQUENCE: 1170
LIKRSGRLMT AYNFQD                                                          16

SEQ ID NO: 1171          moltype = AA  length = 16
FEATURE                  Location/Qualifiers
source                   1..16
                         mol_type = protein
                         organism = Homo sapiens
SEQUENCE: 1171
DGLGEVAPDY RYGIDV                                                          16

SEQ ID NO: 1172          moltype = AA  length = 10
FEATURE                  Location/Qualifiers
source                   1..10
                         mol_type = protein
                         organism = Homo sapiens
SEQUENCE: 1172
RASQGLNFVV                                                                 10

SEQ ID NO: 1173          moltype = AA  length = 7
FEATURE                  Location/Qualifiers
source                   1..7
                         mol_type = protein
                         organism = Homo sapiens
SEQUENCE: 1173
APSGRAP                                                                    7

SEQ ID NO: 1174          moltype = AA  length = 5
FEATURE                  Location/Qualifiers
source                   1..5
                         mol_type = protein
                         organism = Homo sapiens
SEQUENCE: 1174
QEYSS                                                                      5

SEQ ID NO: 1175          moltype = AA  length = 5
FEATURE                  Location/Qualifiers
```

```
source                 1..5
                       mol_type = protein
                       organism = Homo sapiens
SEQUENCE: 1175
EFVIH                                                             5

SEQ ID NO: 1176        moltype = AA  length = 16
FEATURE                Location/Qualifiers
source                 1..16
                       mol_type = protein
                       organism = Homo sapiens
SEQUENCE: 1176
LIKRSGRLMT SYKFQD                                                 16

SEQ ID NO: 1177        moltype = AA  length = 16
FEATURE                Location/Qualifiers
source                 1..16
                       mol_type = protein
                       organism = Homo sapiens
SEQUENCE: 1177
DGLGEVAPAY LYGIDA                                                 16

SEQ ID NO: 1178        moltype = AA  length = 10
FEATURE                Location/Qualifiers
source                 1..10
                       mol_type = protein
                       organism = Homo sapiens
SEQUENCE: 1178
RASQGLNFVV                                                        10

SEQ ID NO: 1179        moltype = AA  length = 7
FEATURE                Location/Qualifiers
source                 1..7
                       mol_type = protein
                       organism = Homo sapiens
SEQUENCE: 1179
GPTDRAP                                                           7

SEQ ID NO: 1180        moltype = AA  length = 5
FEATURE                Location/Qualifiers
source                 1..5
                       mol_type = protein
                       organism = Homo sapiens
SEQUENCE: 1180
QEYSS                                                             5

SEQ ID NO: 1181        moltype = AA  length = 5
FEATURE                Location/Qualifiers
source                 1..5
                       mol_type = protein
                       organism = Homo sapiens
SEQUENCE: 1181
KYIIH                                                             5

SEQ ID NO: 1182        moltype = AA  length = 49
FEATURE                Location/Qualifiers
source                 1..49
                       mol_type = protein
                       organism = Homo sapiens
SEQUENCE: 1182
MIDPYRGRPW SAHKFQGSEQ AAHOMOSAPI ENSAEAASDS HSRPIMFDH             49

SEQ ID NO: 1183        moltype = AA  length = 13
FEATURE                Location/Qualifiers
source                 1..13
                       mol_type = protein
                       organism = Homo sapiens
SEQUENCE: 1183
SGGPSNVGGN YVY                                                    13

SEQ ID NO: 1184        moltype = AA  length = 9
FEATURE                Location/Qualifiers
source                 1..9
                       mol_type = protein
                       organism = Homo sapiens
SEQUENCE: 1184
RDDQRPSGV                                                         9

SEQ ID NO: 1185        moltype = AA  length = 5
```

```
FEATURE                 Location/Qualifiers
source                  1..5
                        mol_type = protein
                        organism = Homo sapiens
SEQUENCE: 1185
ATYDS                                                                   5

SEQ ID NO: 1186         moltype = AA  length = 5
FEATURE                 Location/Qualifiers
source                  1..5
                        mol_type = protein
                        organism = Homo sapiens
SEQUENCE: 1186
NYIIN                                                                   5

SEQ ID NO: 1187         moltype = AA  length = 17
FEATURE                 Location/Qualifiers
source                  1..17
                        mol_type = protein
                        organism = Homo sapiens
SEQUENCE: 1187
MIDPRRGRPW SAQKFQG                                                      17

SEQ ID NO: 1188         moltype = AA  length = 19
FEATURE                 Location/Qualifiers
source                  1..19
                        mol_type = protein
                        organism = Homo sapiens
SEQUENCE: 1188
QDSDFHDGHG HTLRGMFDS                                                    19

SEQ ID NO: 1189         moltype = AA  length = 13
FEATURE                 Location/Qualifiers
source                  1..13
                        mol_type = protein
                        organism = Homo sapiens
SEQUENCE: 1189
SGTSSNVGGN LVS                                                          13

SEQ ID NO: 1190         moltype = AA  length = 9
FEATURE                 Location/Qualifiers
source                  1..9
                        mol_type = protein
                        organism = Homo sapiens
SEQUENCE: 1190
RDDQRPSGV                                                               9

SEQ ID NO: 1191         moltype = AA  length = 5
FEATURE                 Location/Qualifiers
source                  1..5
                        mol_type = protein
                        organism = Homo sapiens
SEQUENCE: 1191
AAYDS                                                                   5

SEQ ID NO: 1192         moltype = AA  length = 5
FEATURE                 Location/Qualifiers
source                  1..5
                        mol_type = protein
                        organism = Homo sapiens
SEQUENCE: 1192
LYAVN                                                                   5

SEQ ID NO: 1193         moltype = AA  length = 15
FEATURE                 Location/Qualifiers
source                  1..15
                        mol_type = protein
                        organism = Homo sapiens
SEQUENCE: 1193
QIWRWKSSAS HHFRG                                                        15

SEQ ID NO: 1194         moltype = AA  length = 20
FEATURE                 Location/Qualifiers
source                  1..20
                        mol_type = protein
                        organism = Homo sapiens
SEQUENCE: 1194
TSTYDKWSGL HHDGVMAFSS                                                   20
```

-continued

```
SEQ ID NO: 1195         moltype = AA  length = 12
FEATURE                 Location/Qualifiers
source                  1..12
                        mol_type = protein
                        organism = Homo sapiens
SEQUENCE: 1195
RASQSITGNW VA                                                      12

SEQ ID NO: 1196         moltype = AA  length = 7
FEATURE                 Location/Qualifiers
source                  1..7
                        mol_type = protein
                        organism = Homo sapiens
SEQUENCE: 1196
RGAALLG                                                            7

SEQ ID NO: 1197         moltype = AA  length = 5
FEATURE                 Location/Qualifiers
source                  1..5
                        mol_type = protein
                        organism = Homo sapiens
SEQUENCE: 1197
QQYDT                                                              5
```

What is claimed is:

1. A non-naturally occurring anti-HIV gp120 antibody or antigen binding fragment thereof, comprising a heavy chain variable region (VH) comprising the amino acid sequence of SEQ ID NO: 892, and a light chain variable region (VL) comprising the amino acid sequence of SEQ ID NO: 906.

2. The anti-HIV antibody or antigen binding fragment thereof of claim 1, wherein the antigen binding fragment is selected from the group consisting of Fab, Fab', F(ab')2, Fv, sFv and scFv.

3. The anti-HIV antibody or antigen binding fragment thereof of claim 1, wherein the antibody is a recombinant antibody.

4. The anti-HIV antibody or antigen binding fragment thereof of claim 1, wherein the antibody or antigen binding fragment thereof is formatted for prolonged serum half life.

5. The anti-HIV antibody of claim 1, wherein the antibody is an immunoglobulin class or isotype selected from the group consisting of IgG1, IgG2, IgG3, IgG4, IgA, IgD, IgE and IgM.

6. A nucleic acid molecule comprising a sequence encoding the anti-HIV antibody or antigen binding fragment thereof of claim 1.

7. A vector comprising the nucleic acid molecule of claim 6.

8. A cultured cell comprising the vector of claim 7.

9. A method for making an anti-HIV antibody or a fragment thereof, comprising:

obtaining the cultured cell of claim 8;

culturing the cell in a medium under conditions permitting expression of a polypeptide encoded by the vector and assembling of an antibody or fragment thereof; and purifying the antibody or fragment from the cultured cell or the medium of the cell.

10. A pharmaceutical composition comprising (i) the anti-HIV antibody or antigen binding fragment thereof of claim 1 and (ii) a pharmaceutically acceptable carrier.

11. The pharmaceutical composition of claim 10, further comprising a second therapeutic agent.

12. The pharmaceutical composition of claim 11, wherein the second therapeutic agent comprises a second anti-HIV antibody or antigen binding fragment thereof.

13. The pharmaceutical composition of claim 12, wherein the second therapeutic agent comprises an antiviral agent.

14. The pharmaceutical composition of claim 13, wherein the antiviral agent is selected from the group consisting of a non-nucleoside reverse transcriptase inhibitor, a protease inhibitor, an entry or fusion inhibitor, and an integrase inhibitor.

15. A method of treating an HIV infection or an HIV-related disease comprising the steps of:

identifying a patient in need of such treatment, and administering to said patient the pharmaceutical composition of claim 10.

16. A method of treating an HIV infection or an HIV-related disease comprising the steps of:

identifying a patient in need of such treatment, and administering to said patient a therapeutically effective amount of at least one isolated anti-HIV antibody or antigen binding fragment thereof of claim 1.

17. The method of claim 16, further comprising administering to said patient a second therapeutic agent.

18. The method of claim 17, wherein the second therapeutic agent comprises a second anti-HIV antibody or antigen binding fragment thereof.

19. The method of claim 18, wherein said second therapeutic agent comprises an antiviral agent.

20. The method of claim 19, wherein the antiviral agent is selected from the group consisting of a non-nucleoside reverse transcriptase inhibitor, a protease inhibitor, an entry or fusion inhibitor, and an integrase inhibitor.

21. A kit comprising:

a pharmaceutically acceptable dose unit of a pharmaceutically effective amount of the anti-HIV antibody of claim 1, and a pharmaceutically acceptable dose unit of a pharmaceutically effective amount of an anti-HIV agent.

22. The kit of claim 21, wherein the two pharmaceutically acceptable dose units take the form of a single pharmaceutically acceptable dose unit.

23. The kit of claim 22, wherein the anti-HIV agent is selected from the group consisting of a non-nucleoside reverse transcriptase inhibitor, a protease inhibitor, an entry or fusion inhibitor, and an integrase inhibitor.

* * * * *